US011085049B2

(12) United States Patent
Couture et al.

(10) Patent No.: US 11,085,049 B2
(45) Date of Patent: Aug. 10, 2021

(54) INFLUENZA VIRUS-LIKE PARTICLE PRODUCTION IN PLANTS

(71) Applicant: MEDICAGO INC., Quebec (CA)

(72) Inventors: Manon Couture, St-Augustin-de-Desmaures (CA); Marc-Andre D'Aoust, Quebec (CA); Louis-Philippe Vezina, Neuville (CA)

(73) Assignee: MEDICAGO INC., Quebec (CA)

( * ) Notice: Subject to any disclaimer, the term of this patent is extended or adjusted under 35 U.S.C. 154(b) by 17 days.

(21) Appl. No.: 16/516,802

(22) Filed: Jul. 19, 2019

(65) Prior Publication Data

US 2020/0255849 A1 Aug. 13, 2020

Related U.S. Application Data

(63) Continuation of application No. 14/779,423, filed as application No. PCT/CA2014/050326 on Mar. 28, 2014, now Pat. No. 10,358,652.

(Continued)

(51) Int. Cl.
*C07K 14/005* (2006.01)
*A61K 39/12* (2006.01)
(Continued)

(52) U.S. Cl.
CPC .......... *C12N 15/8258* (2013.01); *A61K 39/12* (2013.01); *A61K 39/145* (2013.01);
(Continued)

(58) Field of Classification Search
None
See application file for complete search history.

(56) References Cited

U.S. PATENT DOCUMENTS 5,232,833 A 8/1993 Sanders et al.
6,392,121 B1 5/2002 Mason et al.
(Continued)

FOREIGN PATENT DOCUMENTS

CN 101883856 A 11/2010
WO 2000/20557 A2 4/2000
(Continued)

OTHER PUBLICATIONS

GenBank: AET22022.1 (Year: 2011).*
(Continued)

*Primary Examiner* — Michelle S Horning
(74) *Attorney, Agent, or Firm* — J.A. Lindeman & Co., PLLC

(57) ABSTRACT

A method of producing a virus like particle (VLP) in a plant comprising modified hemagglutinin is provided. The method comprises introducing a nucleic acid comprising a regulatory region active in the plant and operatively linked to a nucleotide sequence encoding a modified influenza hemagglutinin (HA) protein into the plant, or portion of the plant, the modified HA protein comprises a modified proteolytic loop. Followed by incubating the plant or portion of the plant under conditions that permit the expression of the nucleic acids, thereby producing the VLP. The modified proteolytic loop may comprise one or more protease cleavage sites exhibiting reduced or abolished cleavage by a protease. The nucleotide sequence encoding the HA may be selected from the group consisting of B HA, C, H1, H2, H3, H4, H5, H6, H7, H8, H9, H10, H11, H12, H13, H14, H15, and H16. Also described is a virus like particle (VLP) produced by the method, and plants expressing the VLP. The virus like particle (VLP) may comprise plant-specific N-glycans, or modified N-glycans.

15 Claims, 154 Drawing Sheets

Specification includes a Sequence Listing.

IF-H5A-I-05.s1+3c SEQ ID NO: 2

AAATTTGTCGGGCCCATGGAGAAAATAGTGCTTCTTCTTGC

IF-H5dTm.r SEQ ID NO: 3

ACTAAAGAAAATAGGCCTTTAAATGCAAATTCTGCATTGTAACGATCCAT

Related U.S. Application Data

(60) Provisional application No. 61/806,227, filed on Mar. 28, 2013, provisional application No. 61/925,852, filed on Jan. 10, 2014, provisional application No. 61/971,274, filed on Mar. 27, 2014.

(51) Int. Cl.

| | |
|---|---|
| ***C12N 15/82*** | (2006.01) |
| ***C12N 7/00*** | (2006.01) |
| ***A61K 39/145*** | (2006.01) |
| *A61K 39/00* | (2006.01) |

(52) U.S. Cl.

CPC .............. *C07K 14/005* (2013.01); *C12N 7/00* (2013.01); *C12N 15/8257* (2013.01); *A61K 2039/5258* (2013.01); *A61K 2039/54* (2013.01); *C07K 2319/02* (2013.01); *C12N 2760/16122* (2013.01); *C12N 2760/16123* (2013.01); *C12N 2760/16134* (2013.01); *C12N 2760/16151* (2013.01); *C12N 2760/16171* (2013.01); *C12N 2760/16222* (2013.01); *C12N 2760/16223* (2013.01); *C12N 2760/16234* (2013.01); *C12N 2760/16251* (2013.01); *C12N 2760/16271* (2013.01)

(56) References Cited

U.S. PATENT DOCUMENTS

| | | | | |
|---|---|---|---|---|
| 7,132,291 | B2 | 11/2006 | Cardineau et al. | |
| 7,618,815 | B2 | 11/2009 | Ghabrial et al. | |
| 8,519,113 | B2 | 8/2013 | Lomonossoff et al. | |
| 8,697,088 | B2 | 4/2014 | Smith et al. | |
| 9,017,987 | B2 | 4/2015 | Williamson et al. | |
| 9,056,901 | B2 | 6/2015 | Song | |
| 9,505,806 | B2 * | 11/2016 | Sirko ................... | A61K 39/145 |
| 9,546,375 | B2 | 1/2017 | Couture et al. | |
| 9,555,094 | B2 | 1/2017 | Kuroda et al. | |
| 2003/0079248 | A1 | 4/2003 | Mason et al. | |
| 2004/0268442 | A1 * | 12/2004 | Miller ..................... | A61P 37/04 800/288 |
| 2005/0091706 | A1 | 4/2005 | Klimyuk et al. | |
| 2008/0069821 | A1 | 3/2008 | Yang et al. | |
| 2010/0287670 | A1 | 11/2010 | Sainsbury et al. | |
| 2012/0207786 | A1 | 8/2012 | Smith et al. | |
| 2015/0104480 | A1 | 4/2015 | D'Aoust | |
| 2015/0218579 | A1 | 8/2015 | D'Aoust | |

FOREIGN PATENT DOCUMENTS

| | | | |
|---|---|---|---|
| WO | 01/48145 | A2 | 7/2001 |
| WO | 2007/047831 | A2 | 4/2007 |
| WO | 2007/100584 | A2 | 9/2007 |
| WO | 2007/135480 | A1 | 11/2007 |
| WO | 2008/148104 | A1 | 12/2008 |
| WO | 2008/151440 | A1 | 12/2008 |
| WO | 2009/009876 | A1 | 1/2009 |
| WO | 2009009876 | A1 | 1/2009 |
| WO | 2009/076778 | A1 | 6/2009 |
| WO | 2009/087391 | A1 | 7/2009 |
| WO | 2010/003225 | A1 | 1/2010 |
| WO | 2010/003235 | A1 | 1/2010 |
| WO | 2010/006452 | A1 | 1/2010 |
| WO | 2010/025285 | A1 | 3/2010 |
| WO | 2010/011786 | A1 | 10/2010 |
| WO | 2010/148511 | A1 | 12/2010 |
| WO | 2011/011390 | A1 | 1/2011 |
| WO | 2011/028914 | A1 | 3/2011 |
| WO | 2011/035422 | A1 | 3/2011 |
| WO | 2011/102900 | A1 | 8/2011 |
| WO | 2012/047941 | A2 | 4/2012 |
| WO | 2012058762 | A1 | 5/2012 |
| WO | 2012/083445 | A1 | 6/2012 |
| WO | 2012/126123 | A8 | 9/2012 |
| WO | 2012/171104 | A1 | 12/2012 |
| WO | 2013/043067 | A2 | 3/2013 |
| WO | 2013/044390 | A1 | 4/2013 |
| WO | 2013068593 | A1 | 5/2013 |
| WO | 2014/153674 | A1 | 10/2014 |

OTHER PUBLICATIONS

Bianchi et al. Universal influenza B vaccine based on the maturational cleavage site of the hemagglutinin precursor. J Virol Jun. 2005; 79(12):7380-8. (Year: 2005).*

GenBank Accession ABU99194, Jul. 26, 2016.

GenBank Accession ACN29380, Feb. 28, 2009.

GenBank Accession ACS71642, Jun. 29, 2009.

Harvey, R., et al. Restrictions to the Adaptation of Influenza A Virus H5 Hemagglutinin to the Human Host. Journal of Virology, 2004, pp. 502-507, vol. 78:1.

Hatta, M., et al. Molecular Basis for High Virulence of Hong Kong H5N1 Influenza A Viruses. Science 2001 vol. 293, pp. 1840-1842.

Joshi, An inspection of the domain between putative TATA box and translation start site in 79 plant genes. Nucleic Acids Research. vol. 15:16, 1987.

Kalthoff, D., et al. Immunicaionm with Plant-Expressed Hemagglutinin Protects Chickens from Lethal Highly Pathogenic Avian Influenza Virus H5N1 Challenge Infection. Journal of Virology, vol. 84:22, 2010, pp. 12002-12010.

Klenk, Hans-Dieter, et al. Host cell proteases controlling virus pathogenicity. Trends in Microbiology, vol. 2:2, 1994, pp. 39-43.

Sakaguchi, T., et al. The Ion Channel Activity of the Influenza Virus M2 Protein Affects Transport through the Golgi Apparatus. J of Cell Bio, vol. 133:4, 1996, pp. 733-747.

Office Action in CA Application No. 2,651,907, dated Dec. 15, 2011.

Extended European Search Report in EP Application No. 15769248.4, dated Oct. 30, 2017.

Communication pursuant to Article 94(3) EPC in EP Application No. 14773061.8, dated Jan. 8, 2018.

Gleba et al., "Engineering viral expression vectors for plants: the 'full virus' and the 'deconstructed virus' strategies", Current Opinion in Plant Biology, 2004, 7:182-188.

English translation Office Action in JP Application No. 2016-504431, dated Jan. 16, 2018.

Lomonossoff and Porta "Cowpea mosaic virus as a versatile system for the expression of foreign peptides and proteins in legumes", Department of Virus Research, John Innes Centre, Norwich, UK, pp. 151-165.

English translation Office Action in MX Application No. MX/a/2014/003776, dated Aug. 30, 2017.

Substantive Examination Adverse Report in MY Application No. PI 2014700716, dated Nov. 30, 2017.

Substantive Examination Report in PH Application No. 1/2014/500640, dated Feb. 6, 2018.

Serizawa et al., "Custom-Designed MLPA Using Multiple Short Synthetic Probes. Application to Methylation Analysis of Five Promoter CpG Islands in Tumor and Urine Specimens from Patients with Bladder Cancer", Journal of Molecular Diagnostics, 2010, vol. 12, No. 4, pp. 402-408.

Verver et al., "Studies on the Movement of Cowpea Mosaic Virus Using the Jellyfish Green Fluorescent Protein", Virology, 1998, 242, pp. 22-27.

Yusibov et al., "Antigens produced in plants by infection with chimeric plant viruses immunize against rabies virus and HIV-1", Proc. Natl. Acad. Sci., 1997, vol. 94, pp. 5784-5788.

Notice of Allowance in U.S. Appl. No. 12/300,922, dated Jun. 11, 2013.

Office Action in U.S. Appl. No. 12/300,922, dated Feb. 16, 2012.

Office Action in U.S. Appl. No. 12/300,922, dated Jul. 20, 2011.

Office Action in U.S. Appl. No. 12/300,922, dated Nov. 15, 2012.

Office Action in U.S. Appl. No. 15/110,696, dated Jan. 29, 2018.

Office Action in U.S. Appl. No. 14/605,504, dated Dec. 14, 2017.

Restriction Requirement in U.S. Appl. No. 12/300,922, dated Apr. 21, 2011.

(56) References Cited

OTHER PUBLICATIONS

GenBank: GQ497237.1 (2009) Binary vector pEAQ-HT-DEST3, complete sequence.
BLAST alignments, search results for instant SEQ ID No: 17; searched Oct. 30, 2016.
Song et al. Protective immunity against H5N 1 influenza virus by a single dose vaccination with virus-like particles. Virology. Sep. 15, 2010; 405(1): 165-175.
Lu et al., Insights into avian influenza virus pathogenicity: the hemagglutinin precursor HAO of subtype H 16 has an alpha-helix structure in its cleavage site with inefficient HA1/HA2 cleavage. J Viral. Dec. 2012 ;86(23):12861-70. (Year: 2012).
International Search Report and Written Opinion in corresponding International Application No. PCT/CA2015/050009, dated Apr. 17, 2015.
International Search Report and Written Opinion in corresponding International Application No. PCT/CA2015/050240, dated Jun. 25, 2015.
Extended European Search Report in corresponding EP Application No. 14773061.8, dated Oct. 18, 2016.
Australian Patent Examination Report No. 1 in Patent Application No. 2012315421, dated Oct. 12, 2016.
Canadian Office Action in Application No. 2,850,407, dated Jul. 12, 2016.
English translation of Chinese Second Office Action in Application No. 201280047819.2, dated Mar. 2, 2016.
English translation of Chinese Third Office Action in Application No. 201280047819.2, dated Nov. 8, 2016.
English translation of Japanese Office Action in Application No. 2014-532198, dated Aug. 4, 2016.
Kanagarajan, S., et al. Transient expression of hemagglutinin antigen from low pathogenic avian influenza A (H7N7) in Nicotiana benthamiana. PLoS ONE, 7/3, pp. 1-10, 2012.
Kang, Sang-Moo, et al., Influenza vaccines based on virus-like particles. Virus Res. (2009) 143, pp. 140-146.
English translation of Mexican Office Action in Application No. MX/a/2014/003776, dated Jun. 11, 2016.
New Zealand Letters Patent No. 622731, dated Aug. 2, 2016.
Sainsbury, Frank, et al. Cowpea Mosaic Virus: The Plant Virus-Based Biotechnology Workhorse. Ann. Rev. Phytopathol. 48, pp. 437-455, 2010.
English translation of Thailand Office Action in Application No. 1401001699, dated Feb. 22, 2016.
English translation of Taiwan Office Action in Application No. 101135891, dated Jul. 15, 2016.
Restriction Requirement in U.S. Appl. No. 14/347,804, dated Nov. 3, 2016.
English translation of Israeli Office Action in Application No. 231587, dated Feb. 16, 2017.
English translation of Mexican Office Action in Application No. MX/a/2014/003776, dated Feb. 1, 2017.
English translation of Russian Office Action in Application No. 2014116371, dated Jul. 15, 2016.
English translation of Russian Office Action in Application No. 2014116371, dated Jan. 11, 2017.
Written Opinion and Search Report in Singapore Application No. 11201507928Q, dated Dec. 15, 2016.
English translation of Taiwan Rejection Decision Notification in Application No. 101135891, dated Feb. 23, 2017.
De Amicis, F., et al. Improvement of the pBI121 plant expression vector by leader replacement with a sequence combining a poly (CAA) and a CT motif. Transgenic Res (2007) 16, pp. 731-738.
GenBank Accession AGX20074.1; accessed on Oct. 30, 2016.
GenBank Accession BAO45161; accessed on Nov. 26, 2019.
Stech, J. et al. A new approach to an influenza live vaccine: modification of the cleavage site of hemagglutinin. Nature Medicine, vol. 11:6, 2005 pp. 683-689.
Stech, J., et al. Influenza B Virus with Modified Hemagglutinin Cleavage Site as a Novel Attenuated Live Vaccine. Journal of Infectious Diseases, vol. 204:10, 2011, pp. 1483-1490.
Sun, X., et al. Modification to the Hemagglutinin Cleavage Site Control the Virulence of a Neurotropic H1N1 Influenza Virus. Journal of Virology, 2010, pp. 8683-8690.
Canadian Office Action in Application No. 2,850,407 dated Jul. 4, 2017.
English translation of Notification of First Office Action in CN Application No. 201480029001.7, dated Jul. 24, 2017.
English translation of Fourth Office Action in CN Application No. 201280047819.2, dated Jun. 14, 2017.
Extended European Search Report in EP Application No. 15735364.0, dated May 26, 2017.
Office Action in EP Application No. 12836545.9, dated Jul. 21, 2017.
English translation Office Action in JP Application No. 2014-532198, dated Jun. 28, 2017.
English translation Office Action in RU Application No. 2014116371, dated Jul. 3, 2017.
Office Action in U.S. Appl. No. 14/347,804, dated May 9, 2017.
Betakova, T. et al., "Comparison of the activities of BM2 protein and its H19 and W23 mutants of influenza B virus with activities of M2 protein and its H37 and W41 mutants of influenza A virus", Arch. Virol (2009) vol. 154, pp. 1619-1624.
Canizares, M., et al., "A bipartite system for the constitutive an inducible expression of high levels of foreign proteins in plants", Plant Biotechnology Journal (2006), vol. 4, pp. 183-193.
GenBank Accession AXV41427, Jan. 2010.
GenBank FJ766840, Influenza B virus, Feb. 2009 (Komadina), accessed on May 12, 2017.
Leikina, E., et al., "Reversible stages of the low-pH-triggered conformational change in influenza virus hemagglutinin", The EMBO Journal, 2002 vol. 21:21, pp. 5701-5710.
Li Liu and George P. Lomonossoff "Agroinfection as a rapid method for propagating Cowpea mosaic virus-based constructs", Journal of Virological Methods. (2002) vol. 105, pp. 343-348.
Robinson, D., et al., "The V-ATPase inhibitors concanamycin A and bafilomycin A lead to Golgi swelling in tobacco BY-2 cells", Protoplasma (2004) vol. 224, pp. 255-260.
Verch et al., "Expression and assembly of a full-length monoclonal antibody in plants using a plant virus vector", J. Immunol. Methods 220, 1998, pp. 69-75.
International Search Report and Written Opinion in International Application No. PCT/CA2014/050326, dated Jul. 16, 2014.
Chen, J. et al., Structure of the Hemagglutinin Precursor Cleavage Site, a Determinant of Influenza Pathogenicity and the Origin of the Labile Conformation. Cell (1998), vol. 95, pp. 409-417.
D'Aoust et al., "Influenza virus-like particles produced by transient expression in Nicotiana benthamiana induce a protective immune response against a lethal viral challenge in mice," Plant Biotechnology J., vol. 6, No. 9, Dec. 2008, pp. 930-940.
D'Aoust et al., "The production of hemagglutinin-based virus-like particles in plaints: a rapid, efficient and safe response to pandemic influenza," Plant Biotechnology J., vol. 8, No. 5, Jun. 2010, pp. 607-619.
Gomez-Puertas, P. et al., Influenza Virus matrix protein is the major driving force in virus budding. J Virol. (2000), 74:24 pp. 11538-11547.
Horimoto, T. et al., The development and characterization of H5 influenza virus vaccines derived from a 2003 human isolate. Vaccine (2006), vol. 24, pp. 3669-3676.
Hoffmann, E et al., Eight-plasmid system for rapid generation of influenza virus vaccines. Vaccine (2002), vol. 20, pp. 3165-3170.
Ha, Y. et al., H5 avian and H9 swine influenza virus haemagglutinin structures: possible origin of influenza subtypes. The EMBO Journal (2002), 21(5): pp. 865-875.
Huang et al., "A DNA Replicon System for Rapid High-Level Production of Full-Sized Monoclonal Antibodies in Pants by a Single-vector DNA Replicon System", Biotechnolo. Bioeng. (2009), vol. 103:4, pp. 706-714.
Huang et al., "High-Level Rapid Production of Full-Size Monoclonal Antibodies in Plants by a Single-Vector DNA Replicon System", Biotechnol. Bioeng. (2010), vol. 106:1, pp. 9-17.

(56) References Cited

OTHER PUBLICATIONS

Landry et al., "Preclinical and clinical development of plant-made virus-like particle vaccine against avian H5N1 Influenza," PLOS One, vol. 5, No. 12, Dec. 22, 2010, pp. 1-12.
Latham, T. et al., Formation of wild-type and chimeric influenza virus-like particles following simultaneous expression of only four structural proteins, J. Virol. (2001), 75:13, pp. 6154-6165.
Medeiros, Hemagglutinin Residues of recent human A(H3N2) Influenza viruses that contribute to the inability to agglutinate chick erythrocytes, Virology (2001), vol. 289, pp. 74-85.
Mongrand, S. et al., Lipid rafts in higher plant cells. The Journal of Biological Chemistry (2004), 279(35): pp. 36277-36286.
Mortimer et al., "Setting up a platform for plant-based influenza virus vaccine production in South Africa," BMC Biotechnology, vol. 12, No. 14, Apr. 26, 2012, pp. 1-10.
Nemchinov, L.G. et al., Transient expression of the ectodomain of matrix protein (M2e) of avian influenza A virus in plants. Protein Expression and Purification (2007), 56: pp. 153-159.
Neumann, G. et al., Plasmid-driven formation of virus-like particles. J. Virol. (2000), 74(1): pp. 547-551.
Noad, R. et al., Virus-like particles as immunogens. Trends in Microbiology (2003), vol. 11, No. 9, pp. 438-444.
Beyer, W.E.P. et al., Influenza Virus Strains with a Fusion Threshold of pH 5.5 or lower are Inhibited by Amantadine, 1986, Archives of Virology, 90, pp. 173-181.
Bianchi, E. et al., Universal Influenza B Vaccine Based on the Maturational Cleavage Site of the Hemagglutinin precursor. J. of Virology (2005), pp. 7380-7388.
Bullough, P. et al., Structure of influenza haemagglutinin at the pH of membrane fusion. Nature (1994), vol. 371:1, pp. 37-43.
Frugis, MsJ1, an alfalfa DnaJ-like gene, is tissue specific and transcriptionally regulated during cell cycle. Plant Molecular Biology (1999), vol. 40, pp. 397-408.
Hartl, F. Ulrich, Molecular chaperones in cellular protein folding. Nature (1996), vol. 381, Jun. 13, pp. 571-580.
Ito, Receptor Specificity of Influenza A viruses correlates with the agglutination of erythrocytes from different animal species. Virology (1997), vol. 227, pp. 493-499.
Lin, Genomic analysis of the Hsp70 superfamily in *Arabidopsis thaliana*. Cell Stress & Chaperones (2001), pp. 201-208.
Macario, Heat-shock proteins and molecular chaperones, implications for pathogenesis, diagnostics and therapeutics. Int. J. Clin Lab Res. (1995), vol. 25, pp. 59-70.
Parsell, The function of heat-shock proteins in stress tolerance: degradation and reactivation of damages proteins. Annu. Rev. Genet. (1993), vol. 27, pp. 437-496.
Paul, M. et al., Mutational Analysis of the Human Immunodeficiency Virus Type 1 Vpu Transmembrane Domain that Promotes the Enhanced Release of Virus-Like Particles from the Plasma Membrane of Mammalian Cells. Journal of Virology (1998), pp. 1270-1279.
Rangan, L. et al., Analysis of Context Sequence Surrounding Translation Initiation Site from Complete Genome of Model Plants. Mol. Biotechnol. (2008), vol. 39, pp. 207-213.
Rott, Rudolf et al., Influenza Viruses, Cell Enzymes and Pathogenicity. Am J. Respir Crit Care Med (1995), vol. 152, pp. 516-519.
Sainsbury, F. et al., Expression of multiple proteins using full-length and deleted versions of cowpea mosaic virus RNA-2. Plant Biotechnology Journal (2008), vol. 6, pp. 82-92.
Sainsbury, F. et al., pEAQ: versatile expression vectors for easy and quick transient expression of heterologous proteins in plants. Plant Biotechnology Journal (2009), vol. 7, pp. 682-693.
Sainsbury F. et al., Cowpea mosaic virus-based systems for the expression of antigens and antibodies in plants. Methods in Molecular Biology (2009), Recombinant Proteins From Plants, vol. 483: pp. 25-39.
Sainsbury, Extremely high-level and rapid transient protein production in plants without the use of viral replication. Plant Physiology (2008), vol. 148, pp. 1212-1218.
Shoji, Y., et al., A plant-produced H1N1 trimeric hemagglutinin protects mice from a lethal influenza virus challenge. Human Vaccines and Immunotherapeutics (2013), vol. 9, pp. 553-560.
Song, J. et al., Influenza Virus-Like Particles Containing M2 Induce Broadly Cross Protective Immunity. PlosS One, Jan. 2011, vol. 6:1, pp. 1-11.
Wang, K. et al., Viral proteins function as ion channels. Biochimica et Biophysica Acta. vol. 1808:2, Feb. 2011, pp. 510-515.
Zhang, X. et al., Bean Yellow Dwarf Virus Replicons for High-Level Transgene Expression in Transgenic Plants and Cell Cultures. Biotechnology and Bioengineering (2005), vol. 93, pp. 271-279.
International Search Report and Written Opinion in International Application No. PCT/CA2012/050681, dated Jan. 3, 2013.
Extended European Search Report in EP Application No. 12836545.9, dated May 12, 2015.
First Examination Report in NZ Application No. 622731, dated Jan. 30, 2015.
Office Action in CA Application No. 2,850,407, dated Jun. 1, 2015.
English Translation of Office Action in CN Application No. 201280047819.2, dated Jun. 24, 2015.
Fischetti, V. Streptococcal M Protein: Molecular Design and Biological Behavior. Clinical Microbiology Reviews, 1989, pp. 285-314.
GenBank Accession AFD32428.2, dated Apr. 2012.
GenBank Accession ACU12738.1, dated Aug. 2017.
Huang et al., "A DNA Replicon System for Rapid High-Level Production of Full-Sized Monoclonal Antibodies in Plants by a Single-vector DNA Replicon System", Biotechnolo. Bioeng. (2009), vol. 103:4, pp. 706-714.
Banerjee, Indranil, et al. High-content analysis of sequential events during the early phase of Influenza A virus infection. PLOS one, 2013, vol. 8:7, pp. 109.
GenBank Accession AFN19371; accessed on Jul. 4, 2012.
Reed, M.L, et al. The pH of Activation of the Hemagglutinin Protein Regulates H5N1 Influenza Virus Pathogenicity and Transmissibility in Ducks. Jour of Virol 2010, vol. 84:3, pp. 1527-1535.
Shoji, Yoko et al. Immunogenicity of H1N1 influenza virus-like particles produced in Nicotiana benthamiana. Human Vccine & Immunotherapeutics 11:1, pp. 118-123.
Skeik, N., et al. Influenza viruses and the evolution of avian influenza virus H5N1. Int. Journal of Infectious diseases, 2008, vol. 12, pp. 233-238.

* cited by examiner

Figure 1: A-2X35S/CPMV-HT/H5 Indonesia/NOS (Construct number 489)

Figure 1A

IF-H5A-I-05.s1+3c SEQ ID NO: 2

AAATTTGTCGGGCCCATGGAGAAAATAGTGCTTCTTCTTGC

Figure 1B

IF-H5dTm.r SEQ ID NO: 3

ACTAAAGAAAATAGGCCTTTAAATGCAAATTCTGCATTGTAACGATCCAT

Schematic representation of construct 1191. SacII and StuI restriction enzyme sites used for plasmid linearization are annotated on the representation.

Figure 1D

Construct 1191 from left to right t-DNA borders (underlined). 2X35S/CPMV-HT/NOS with Plastocyanine-P19-Plastocyanine silencing inhibitor expression cassette (SEQ ID NO: 4)

TGGCAGGATATATTGTGGTGTAAACAAATTGACGCTTAGACAACTTAATAACACATTGCGGACG
TTTTTAATGTACTGAATTAACGCCGAATCCCGGGCTGGTATATTTATATGTTGTCAAATAACTC
AAAAACCATAAAAGTTTAAGTTAGCAAGTGTGTACATTTTTACTTGAACAAAAATATTCACCTA
CTACTGTTATAAATCATTATTAAACATTAGAGTAAAGAAATATGGATGATAAGAACAAGAGTAG
TGATATTTTGACAACAATTTTGTTGCAACATTTGAGAAAATTTTGTTGTTCTCTCTTTTCATTG
GTCAAAAACAATAGAGAGAGAAAAAGGAAGAGGGAGAATAAAAACATAATGTGAGTATGAGAGA
GAAAGTTGTACAAAAGTTGTACCAAAATAGTTGTACAAATATCATTGAGGAATTTGACAAAAGC
TACACAAATAAGGGTTAATTGCTGTAAATAAATAAGGATGACGCATTAGAGAGATGTACCATTA
GAGAATTTTTGGCAAGTCATTAAAAAGAAAGAATAAATTATTTTTAAAATTAAAAGTTGAGTCA
TTTGATTAAACATGTGATTATTTAATGAATTGATGAAAGAGTTGGATTAAAGTTGTATTAGTAA
TTAGAATTTGGTGTCAAATTTAATTTGACATTTGATCTTTTCCTATATATTGCCCCATAGAGTC
AGTTAACTCATTTTTATATTTCATAGATCAAATAAGAGAAATAACGGTATATTAATCCCTCCAA
AAAAAAAAAACGGTATATTTACTAAAAAATCTAAGCCACGTAGGAGGATAACAGGATCCCCGTA
GGAGGATAACATCCAATCCAACCAATCACAACAATCCTGATGAGATAACCCACTTTAAGCCCAC
GCATCTGTGGCACATCTACATTATCTAAATCACACATTCTTCCACACATCTGAGCCACACAAAA
ACCAATCCACATCTTTATCACCCATTCTATAAAAAATCACACTTTGTGAGTCTACACTTTGATT
CCCTTCAAACACATACAAAGAGAAGAGACTAATTAATTAATTAATCATCTTGAGAGAAAATGGA
ACGAGCTATACAAGGAAACGACGCTAGGGAACAAGCTAACAGTGAACGTTGGGATGGAGGATCA
GGAGGTACCACTTCTCCCTTCAAACTTCCTGACGAAAGTCCGAGTTGGACTGAGTGGCGGCTAC
ATAACGATGAGACGAATTCGAATCAAGATAATCCCCTTGGTTTCAAGGAAAGCTGGGGTTTCGG
GAAAGTTGTATTTAAGAGATATCTCAGATACGACAGGACGGAAGCTTCACTGCACAGAGTCCTT
GGATCTTGGACGGGAGATTCGGTTAACTATGCAGCATCTCGATTTTTCGGTTTCGACCAGATCG
GATGTACCTATAGTATTCGGTTTCGAGGAGTTAGTATCACCGTTTCTGGAGGGTCGCGAACTCT
TCAGCATCTCTGTGAGATGGCAATTCGGTCTAAGCAAGAACTGCTACAGCTTGCCCCAATCGAA
GTGGAAAGTAATGTATCAAGAGGATGCCCTGAAGGTACTCAAACCTTCGAAAAAGAAAGCGAGT
AAGTTAAAATGCTTCTTCGTCTCCTATTTATAATATGGTTTGTTATTGTTAATTTTGTTCTTGT
AGAAGAGCTTAATTAATCGTTGTTGTTATGAAATACTATTTGTATGAGATGAACTGGTGTAATG
TAATTCATTTACATAAGTGGAGTCAGAATCAGAATGTTTCCTCCATAACTAACTAGACATGAAG
ACCTGCCGCGTACAATTGTCTTATATTTGAACAACTAAAATTGAACATCTTTTGCCACAACTTT
ATAAGTGGTTAATATAGCTCAAATATATGGTCAAGTTCAATAGATTAATAATGGAAATATCAGT
TATCGAAATTCATTAACAATCAACTTAACGTTATTAACTACTAATTTTATATCATCCCCTTTGA
TAAATGATAGTACACCAATTAGGAAGGAGCATGCTCGCCTAGGAGATTGTCGTTTCCCGCCTTC
AGTTTGCAAGCTGCTCTAGCCGTGTAGCCAATACGCAAACCGCCTCTCCCCGCGCGTTGGAAT
TACTAGCGCGTGTCGACAAGCTTGCATGCCGGTCAACATGGTGGAGCACGACACACTTGTCTAC
TCCAAAAATATCAAAGATACAGTCTCAGAAGACCAAAGGGCAATTGAGACTTTTCAACAAAGGG
TAATATCCGGAAACCTCCTCGGATTCCATTGCCCAGCTATCTGTCACTTTATTGTGAAGATAGT
GGAAAAGGAAGGTGGCTCCTACAAATGCCATCATTGCGATAAAGGAAAGGCCATCGTTGAAGAT
GCCTCTGCCGACAGTGGTCCCAAAGATGGACCCCCACCCACGAGGAGCATCGTGGAAAAAGAAG
ACGTTCCAACCACGTCTTCAAAGCAAGTGGATTGATGTGATAACATGGTGGAGCACGACACACT
TGTCTACTCCAAAAATATCAAAGATACAGTCTCAGAAGACCAAAGGGCAATTGAGACTTTTCAA
CAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGT

Figure 1D continued

TGAAGATGCCTCTGCCGACAGTGGTCCCAAAGATGGACCCCCACCCACGAGGAGCATCGTGGAA
AAAGAAGACGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGTTCATTTCA
TTTGGAGAGGTATTAAAATCTTAATAGGTTTTGATAAAAGCGAACGTGGGGAAACCCGAACCAA
ACCTTCTTCTAAACTCTCTCTCATCTCTCTTAAAGCAAACTTCTCTCTTGTCTTTCTTGCGTGA
GCGATCTTCAACGTTGTCAGATCGTGCTTCGGCACCAGTACAACGTTTTCTTTCACTGAAGCGA
AATCAAAGATCTCTTTGTGGACACGTAGTGCGGCGCCATTAAATAACGTGTACTTGTCCTATTC
TTGTCGGTGTGGTCTTGGGAAAAGAAAGCTTGCTGGAGGCTGCTGTTCAGCCCCATACATTACT
TGTTACGATTCTGCTGACTTTCGGCGGGTGCAATATCTCTACTTCTGCTTGACGAGGTATTGTT
GCCTGTACTTCTTTCTTCTTCTTCTTGCTGATTGGTTCTATAAGAAATCTAGTATTTTCTTTGA
AACAGAGTTTTCCCGTGGTTTTCGAACTTGGAGAAAGATTGTTAAGCTTCTGTATATTCTGCCC
AAATTTGTCGGGCCCGCGGATGGCGAAAAACGTTGCGATTTTCGGCTTATTGTTTTCTCTTCTT
GTGTTGGTTCCTTCTCAGATCTTCGCCTGCAGGCTCCTCAGCCAAAACGACACCCCCATCTGTC
TATCCACTGGCCCCTGGATCTGCTGCCCAAACTAACTCCATGGTGACCCTGGGATGCCTGGTCA
AGGGCTATTTCCCTGAGCCAGTGACAGTGACCTGGAACTCTGGATCCCTGTCCAGCGGTGTGCA
CACCTTCCCAGCTGTCCTGCAGTCTGACCTCTACACTCTGAGCAGCTCAGTGACTGTCCCCTCC
AGCACCTGGCCCAGCGAGACCGTCACCTGCAACGTTGCCCACCCGGCCAGCAGCACCAAGGTGG
ACAAGAAAATTGTGCCCAGGGATTGTGGTTGTAAGCCTTGCATATGTACAGTCCCAGAAGTATC
ATCTGTCTTCATCTTCCCCCCAAAGCCCAAGGATGTGCTCACCATTACTCTGACTCCTAAGGTC
ACGTGTGTTGTGGTAGACATCAGCAAGGATGATCCCGAGGTCCAGTTCAGCTGGTTTGTAGATG
ATGTGGAGGTGCACACAGCTCAGACGCAACCCCGGGAGGAGCAGTTCAACAGCACTTTCCGCTC
AGTCAGTGAACTTCCCATCATGCACCAGGACTGGCTCAATGGCAAGGAGCGATCGCTCACCATC
ACCATCACCATCACCATCACCATTAAAGGCCTATTTTCTTTAGTTTGAATTTACTGTTATTCGG
TGTGCATTTCTATGTTTGGTGAGCGGTTTTCTGTGCTCAGAGTGTGTTTATTTTATGTAATTTA
ATTTCTTTGTGAGCTCCTGTTTAGCAGGTCGTCCCTTCAGCAAGGACACAAAAAGATTTTAATT
TTATTAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCA
TATAATTTCTGTTGAATTACGTTAAGCATGTAATAATTAACATGTAATGCATGACGTTATTTAT
GAGATGGGTTTTTATGATTAGAGTCCCGCAATTATACATTTAATACGCGATAGAAAACAAAATA
TAGCGCGCAAACTAGGATAAATTATCGCGCGCGGTGTCATCTATGTTACTAGATCTCTAGAGTC
TCAAGCTTGGCGCGCCCACGTGACTAGTGGCACTGGCCGTCGTTTTACAACGTCGTGACTGGGA
AAACCCTGGCGTTACCCAACTTAATCGCCTTGCAGCACATCCCCCTTTCGCCAGCTGGCGTAAT
AGCGAAGAGGCCCGCACCGATCGCCCTTCCCAACAGTTGCGCAGCCTGAATGGCGAATGCTAGA
GCAGCTTGAGCTTGGATCAGATTGTCGTTTCCCGCCTTCAGTTTAAACTATCAGTGTTTGACAG
GATATATTGGCGGGTAAACCTAAGAGAAAAGAGCGTTTA

Figure 1E

Expression cassette number 489 from 2X35S promoter to NOS terminator. H5 from influenza A/Indonesia/5/2005 (H5N1) is underlined. SEQ ID NO: 5

GTCAACATGGTGGAGCACGACACACTTGTCTACTCCAAAAATATCAAAGATACAGTCTCAGAAG
ACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCAT
CATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGA
TTGATGTGATAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCTCCTCGGAT
TCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAA
GATGGACCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTT
AAAGCAAACTTCTCTCTTGTCTTTCTTGCGTGAGCGATCTTCAACGTTGTCAGATCGTGCTTCG
GCACCAGTACAACGTTTTCTTTCACTGAAGCGAAATCAAAGATCTCTTTGTGGACACGTAGTGC
GGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGA
TTGGTTCTATAAGAAATCTAGTATTTTCTTTGAAACAGAGTTTTCCCGTGGTTTTCGAACTTGG
AGAAAGATTGTTAAGCTTCTGTATATTCTGCCCAAATTTGTCGGGCCCATGGAGAAAATAGTGC
TTCTTCTTGCAATAGTCAGTCTTGTTAAAAGTGATCAGATTTGCATTGGTTACCATGCAAACAA
TTCAACAGAGCAGGTTGACACAATCATGGAAAAGAACGTTACTGTTACACATGCCCAAGACATA
CTGGAAAAGACACACAACGGGAAGCTCTGCGATCTAGATGGAGTGAAGCCTCTAATTTTAAGAG
ATTGTAGTGTAGCTGGATGGCTCCTCGGGAACCCAATGTGTGACGAATTCATCAATGTACCGGA
ATGGTCTTACATAGTGGAGAAGGCCAATCCAACCAATGACCTCTGTTACCCAGGGAGTTTCAAC
GACTATGAAGAACTGAAACACCTATTGAGCAGAATAAACCATTTTGAGAAAATTCAAATCATCC
CCAAAAGTTCTTGGTCCGATCATGAAGCCTCATCAGGAGTTAGCTCAGCATGTCCATACCTGGG
AAGTCCCTCCTTTTTTAGAAATGTGGTATGGCTTATCAAAAAGAACAGTACATACCCAACAATA
AAGAAAAGCTACAATAATACCAACCAAGAGGATCTTTTGGTACTGTGGGGAATTCACCATCCTA
ATGATGCGGCAGAGCAGACAAGGCTATATCAAAACCCAACCACCTATATTTCCATTGGGACATC
AACACTAAACCAGAGATTGGTACCAAAAATAGCTACTAGATCCAAAGTAAACGGGCAAAGTGGA
AGGATGGAGTTCTTCTGGACAATTTTAAAACCTAATGATGCAATCAACTTCGAGAGTAATGGAA
ATTTCATTGCTCCAGAATATGCATACAAAATTGTCAAGAAAGGGGACTCAGCAATTATGAAAAG
TGAATTGGAATATGGTAACTGCAACACCAAGTGTCAAACTCCAATGGGGGCGATAAACTCTAGT
ATGCCATTCCACAACATACACCCTCTCACCATCGGGGAATGCCCCAAATATGTGAAATCAAACA
GATTAGTCCTTGCAACAGGGCTCAGAAATAGCCCTCAAAGAGAGAGCAGAAGAAAAAGAGAGG
ACTATTTGGAGCTATAGCAGGTTTTATAGAGGGAGGATGGCAGGGAATGGTAGATGGTTGGTAT
GGGTACCACCATAGCAATGAGCAGGGGAGTGGGTACGCTGCAGACAAAGAATCCACTCAAAAGG
CAATAGATGGAGTCACCAATAAGGTCAACTCAATCATTGACAAAATGAACACTCAGTTTGAGGC
CGTTGGAAGGGAATTTAATAACTTAGAAAGGAGAATAGAGAATTTAAACAAGAAGATGGAAGAC
GGGTTTCTAGATGTCTGGACTTATAATGCCGAACTTCTGGTTCTCATGGAAAATGAGAGAACTC
TAGACTTTCATGACTCAAATGTTAAGAACCTCTACGACAAGGTCCGACTACAGCTTAGGGATAA

Figure 1E continued

TGCAAAGGAGCTGGGTAACGGTTGTTTCGAGTTCTATCACAAATGTGATAATGAATGTATGGAA
AGTATAAGAAACGGAACGTACAACTATCCGCAGTATTCAGAAGAAGCAAGATTAAAAGAGAGG
AAATAAGTGGGGTAAAATTGGAATCAATAGGAACTTACCAAATACTGTCAATTTATTCAACAGT
GGCGAGTTCCCTAGCACTGGCAATCATGATGGCTGGTCTATCTTTATGGATGTGCTCCAATGGA
TCGTTACAATGCAGAATTTGCATTTAAAGGCCTATTTTCTTTAGTTTGAATTTACTGTTATTCG
GTGTGCATTTCTATGTTTGGTGAGCGGTTTTCTGTGCTCAGAGTGTGTTTATTTTATGTAATTT
AATTTCTTTGTGAGCTCCTGTTTAGCAGGTCGTCCCTTCAGCAAGGACACAAAAAGATTTTAAT
TTTATTAAAAAAAAAAAAAAAAAAGACCGGGAATTCGATATCAAGCTTATCGACCTGCAGATCG
TTCAAACATTTGGCAATAAAGTTTCTTAAGATTGAATCCTGTTGCCGGTCTTGCGATGATTATC
ATATAATTTCTGTTGAATTACGTTAAGCATGTAATAATTAACATGTAATGCATGACGTTATTTA
TGAGATGGGTTTTTATGATTAGAGTCCCGCAATTATACATTTAATACGCGATAGAAAACAAAAT
ATAGCGCGCAAACTAGGATAAATTATCGCGCGCGGTGTCATCTATGTTACTAGAT

Figure 1F

Amino acid sequence of H5 from influenza A/Indonesia/5/2005 (H5N1) SEQ ID NO: 6

MEKIVLLLAIVSLVKSDQICIGYHANNSTEQVDTIMEKNVTVTHAQDILEKTHNGKLCDLDGVK
PLILRDCSVAGWLLGNPMCDEFINVPEWSYIVEKANPTNDLCYPGSFNDYEELKHLLSRINHFE
KIQIIPKSSWSDHEASSGVSSACPYLGSPSFFRNVVWLIKKNSTYPTIKKSYNNTNQEDLLVLW
GIHHPNDAAEQTRLYQNPTTYISIGTSTLNQRLVPKIATRSKVNGQSGRMEFFWTILKPNDAIN
FESNGNFIAPEYAYKIVKKGDSAIMKSELEYGNCNTKCQTPMGAINSSMPFHNIHPLTIGECPK
YVKSNRLVLATGLRNSPQRESRRKKRGLFGAIAGFIEGGWQGMVDGWYGYHHSNEQGSGYAADK
ESTQKAIDGVTNKVNSIIDKMNTQFEAVGREFNNLERRIENLNKKMEDGFLDVWTYNAELLVLM
ENERTLDFHDSNVKNLYDKVRLQLRDNAKELGNGCFEFYHKCDNECMESIRNGTYNYPQYSEEA
RLKREEISGVKLESIGTYQILSIYSTVASSLALAIMMAGLSLWMCSNGSLQCRICI

Figure 1G nucleotide sequence encoding H5 from influenza A/Indonesia/5/2005 (H5N1) SEQ ID NO: 42)

ATGGAGAAAATAGTGCTTCTTCTTGCAATAGTCAGTCTTGTTAAAAGTGATCAGATTTGCATTG
GTTACCATGCAAACAATTCAACAGAGCAGGTTGACACAATCATGGAAAAGAACGTTACTGTTAC
ACATGCCCAAGACATACTGGAAAAGACACACAACGGGAAGCTCTGCGATCTAGATGGAGTGAAG
CCTCTAATTTTAAGAGATTGTAGTGTAGCTGGATGGCTCCTCGGGAACCCAATGTGTGACGAAT
TCATCAATGTACCGGAATGGTCTTACATAGTGGAGAAGGCCAATCCAACCAATGACCTCTGTTA
CCCAGGGAGTTTCAACGACTATGAAGAACTGAAACACCTATTGAGCAGAATAAACCATTTTGAG
AAAATTCAAATCATCCCCAAAAGTTCTTGGTCCGATCATGAAGCCTCATCAGGAGTTAGCTCAG
CATGTCCATACCTGGGAAGTCCCTCCTTTTTTAGAAATGTGGTATGGCTTATCAAAAAGAACAG
TACATACCCAACAATAAAGAAAAGCTACAATAATACCAACCAAGAGGATCTTTTGGTACTGTGG
GGAATTCACCATCCTAATGATGCGGCAGAGCAGACAAGGCTATATCAAAACCCAACCACCTATA
TTTCCATTGGGACATCAACACTAAACCAGAGATTGGTACCAAAAATAGCTACTAGATCCAAAGT
AAACGGGCAAAGTGGAAGGATGGAGTTCTTCTGGACAATTTTAAAACCTAATGATGCAATCAAC
TTCGAGAGTAATGGAAATTTCATTGCTCCAGAATATGCATACAAAATTGTCAAGAAAGGGGACT
CAGCAATTATGAAAAGTGAATTGGAATATGGTAACTGCAACACCAAGTGTCAAACTCCAATGGG
GGCGATAAACTCTAGTATGCCATTCCACAACATACACCCTCTCACCATCGGGGAATGCCCCAAA
TATGTGAAATCAAACAGATTAGTCCTTGCAACAGGGCTCAGAAATAGCCCTCAAAGAGAGAGCA
GAAGAAAAAAGAGAGGACTATTTGGAGCTATAGCAGGTTTTATAGAGGGAGGATGGCAGGGAAT
GGTAGATGGTTGGTATGGGTACCACCATAGCAATGAGCAGGGGAGTGGGTACGCTGCAGACAAA
GAATCCACTCAAAAGGCAATAGATGGAGTCACCAATAAGGTCAACTCAATCATTGACAAAATGA
ACACTCAGTTTGAGGCCGTTGGAAGGGAATTTAATAACTTAGAAAGGAGAATAGAGAATTTAAA
CAAGAAGATGGAAGACGGGTTTCTAGATGTCTGGACTTATAATGCCGAACTTCTGGTTCTCATG
GAAAATGAGAGAACTCTAGACTTTCATGACTCAAATGTTAAGAACCTCTACGACAAGGTCCGAC
TACAGCTTAGGGATAATGCAAAGGAGCTGGGTAACGGTTGTTTCGAGTTCTATCACAAATGTGA
TAATGAATGTATGGAAAGTATAAGAAACGGAACGTACAACTATCCGCAGTATTCAGAAGAAGCA
AGATTAAAAAGAGAGGAAATAAGTGGGGTAAAATTGGAATCAATAGGAACTTACCAAATACTGT
CAATTTATTCAACAGTGGCGAGTTCCCTAGCACTGGCAATCATGATGGCTGGTCTATCTTTATG
GATGTGCTCCAATGGATCGTTACAATGCAGAATTTGCATTTAA

Figure 2: B-2X35S/CPMV HT/M2 New Caledonia/NOS (Construct number 1261)

Figure 2A

IF-S1-M1+M2ANC.c (SEQ ID NO:7)

AAATTTGTCGGGCCCATGAGTCTTCTAACCGAGGTCGAAACG

Figure 2B

IF-S1-4-M2ANC.r (SEQ ID NO: 8)

ACTAAAGAAAATAGGCCTTTACTCCAGCTCTATGCTGACAAAA

Figure 2C

Synthesized M2 gene (corresponding to nt 1-26 joined to 715-982 from Genbank accession number DQ508860) (SEQ ID NO: 9)

ATGAGTCTTCTAACCGAGGTCGAAACGCCTATCAGAAACGAATGGGGGTGCAGATGCAACGATT
CAAGTGATCCTCTTGTTGTTGCCGCAAGTATAATTGGGATTGTGCACCTGATATTGTGGATTAT
TGATCGCCTTTTTTTCCAAAAGCATTTATCGTATCTTTAAACACGGTTTAAAAAGAGGGCCTTCT
ACGGAAGGAGTACCAGAGTCTATGAGGGAAGAATATCGAGAGGAACAGCAGAATGCTGTGGATG
CTGACGATGGTCATTTTGTCAGCATAGAGCTGGAGTAA

Figure 2D

Expression cassette number 1261 from 2X35S promoter to NOS terminator. M2 from influenza A/New Caledonia/20/1999 (H1N1) is underlined. (SEQ ID NO: 10)

GTCAACATGGTGGAGCACGACACACTTGTCTACTCCAAAAATATCAAAGATACAGTCTCAGAAG
ACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCAT
CATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGA
TTGATGTGATAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCTCCTCGGAT
TCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAA
GATGGACCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCTTCGCA

Figure 2D continued

AGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTT
AAAGCAAACTTCTCTCTTGTCTTTCTTGCGTGAGCGATCTTCAACGTTGTCAGATCGTGCTTCG
GCACCAGTACAACGTTTTCTTTCACTGAAGCGAAATCAAAGATCTCTTTGTGGACACGTAGTGC
GGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGA
TTGGTTCTATAAGAAATCTAGTATTTTCTTTGAAACAGAGTTTTCCCGTGGTTTTCGAACTTGG
AGAAAGATTGTTAAGCTTCTGTATATTCTGCCCAAATTTGTCGGGCCCATGAGTCTTCTAACCG
AGGTCGAAACGCCTATCAGAAACGAATGGGGGTGCAGATGCAACGATTCAAGTGATCCTCTTGT
TGTTGCCGCAAGTATAATTGGGATTGTGCACCTGATATTGTGGATTATTGATCGCCTTTTTTCC
AAAAGCATTTATCGTATCTTTAAACACGGTTTAAAAAGAGGGCCTTCTACGGAAGGAGTACCAG
AGTCTATGAGGGAAGAATATCGAGAGGAACAGCAGAATGCTGTGGATGCTGACGATGGTCATTT
TGTCAGCATAGAGCTGGAGTAAAGGCCTATTTTCTTTAGTTTGAATTTACTGTTATTCGGTGTG
CATTTCTATGTTTGGTGAGCGGTTTTCTGTGCTCAGAGTGTGTTTATTTTATGTAATTTAATTT
CTTTGTGAGCTCCTGTTTAGCAGGTCGTCCCTTCAGCAAGGACACAAAAAGATTTTAATTTTAT
TAAAAAAAAAAAAAAAAAGACCGGGAATTCGATATCAAGCTTATCGACCTGCAGATCGTTCAA
ACATTTGGCAATAAAGTTTCTTAAGATTGAATCCTGTTGCCGGTCTTGCGATGATTATCATATA
ATTTCTGTTGAATTACGTTAAGCATGTAATAATTAACATGTAATGCATGACGTTATTTATGAGA
TGGGTTTTTATGATTAGAGTCCCGCAATTATACATTTAATACGCGATAGAAAACAAAATATAGC
GCGCAAACTAGGATAAATTATCGCGCGCGGTGTCATCTATGTTACTAGAT

Figure 2E

Amino acid sequence of M2 from influenza A/New Caledonia/20/1999 (H1N1) (SEQ ID NO: 11)

MSLLTEVETPIRNEWGCRCNDSSDPLVVAASIIGIVHLILWIIDRLFSKSIYRIFKHGLKRGPS
TEGVPESMREEYREEQQNAVDADDGHFVSIELE

Figure 3: C-2X35S/CPMV-HT/M2 Puerto Rico/NOS (Construct number 859)

Figure 3A

Synthesized M2 gene (corresponding to nt 26-51 joined to nt 740-1007 from Genebank accession number EF467824) (SEQ ID NO: 12)

ATGAGTCTTCTAACCGAGGTCGAAACGCCTATCAGAAACGAATGGGGGTGCAGATGCAACGGTT
CAAGTGATCCTCTCACTATTGCCGCAAATATCATTGGGATCTTGCACTTGACATTGTGGATTCT
TGATCGTCTTTTTTTCAAATGCATTTACCGTCGCTTTAAATACGGACTGAAAGGAGGGCCTTCT
ACGGAAGGAGTGCCAAAGTCTATGAGGGAAGAATATCGAAAGGAACAGCAGAGTGCTGTGGATG
CTGACGATGGTCATTTTGTCAGCATAGAGCTGGAGTAA

Figure 3B

Expression cassette number 859 from 2X35S promoter to NOS terminator. M2 from Influenza A/Puerto Rico/8/1934 (H1N1) is underlined. (SEQ ID NO: 13)

GTCAACATGGTGGAGCACGACACACTTGTCTACTCCAAAAATATCAAAGATACAGTCTCAGAAG
ACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCAT
CATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGA
TTGATGTGATAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCTCCTCGGAT
TCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAA
GATGGACCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTT
AAAGCAAACTTCTCTCTTGTCTTTCTTGCGTGAGCGATCTTCAACGTTGTCAGATCGTGCTTCG
GCACCAGTACAACGTTTTCTTTCACTGAAGCGAAATCAAAGATCTCTTTGTGGACACGTAGTGC
GGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGA
TTGGTTCTATAAGAAATCTAGTATTTTCTTTGAAACAGAGTTTTCCCGTGGTTTTCGAACTTGG
AGAAAGATTGTTAAGCTTCTGTATATTCTGCCCAAATTTGTCGGGCCCATGAGTCTTCTAACCG
AGGTCGAAACGCCTATCAGAAACGAATGGGGGTGCAGATGCAACGGTTCAAGTGATCCTCTCAC
TATTGCCGCAAATATCATTGGGATCTTGCACTTGACATTGTGGATTCTTGATCGTCTTTTTTTC
AAATGCATTTACCGTCGCTTTAAATACGGACTGAAAGGAGGGCCTTCTACGGAAGGAGTGCCAA
AGTCTATGAGGGAAGAATATCGAAAGGAACAGCAGAGTGCTGTGGATGCTGACGATGGTCATTT
TGTCAGCATAGAGCTGGAGTAAAGGCCTATTTTCTTTAGTTTGAATTTACTGTTATTCGGTGTG
CATTTCTATGTTTGGTGAGCGGTTTTCTGTGCTCAGAGTGTGTTTATTTTATGTAATTTAATTT

Figure 3B continued

CTTTGTGAGCTCCTGTTTAGCAGGTCGTCCCTTCAGCAAGGACACAAAAAGATTTTAATTTTAT
TAAAAAAAAAAAAAAAAAAGACCGGGAATTCGATATCAAGCTTATCGACCTGCAGATCGTTCAA
ACATTTGGCAATAAAGTTTCTTAAGATTGAATCCTGTTGCCGGTCTTGCGATGATTATCATATA
ATTTCTGTTGAATTACGTTAAGCATGTAATAATTAACATGTAATGCATGACGTTATTTATGAGA
TGGGTTTTTATGATTAGAGTCCCGCAATTATACATTTAATACGCGATAGAAAACAAAATATAGC
GCGCAAACTAGGATAAATTATCGCGCGCGGTGTCATCTATGTTACTAGAT

Figure 3C

Amino acid sequence of M2 from influenza A/Puerto Rico/8/1934 (H1N1) (SEQ ID NO:14)

MSLLTEVETPIRNEWGCRCNGSSDPLTIAANIIGILHLTLWILDRLFFKCIYRRFKYGLKGGPS
TEGVPKSMREEYRKEQQSAVDADDGHFVSIELE

Figure 4: G-2X35S/CPMV-HT/PDISP/HA B Brisbane/NOS into BeYDV+Replicase amplification system (Construct number 1008)

Figure 4A

Schematic representation of construct 1194. SacII and StuI restriction enzyme sites used for plasmid linearization are annotated on the representation.

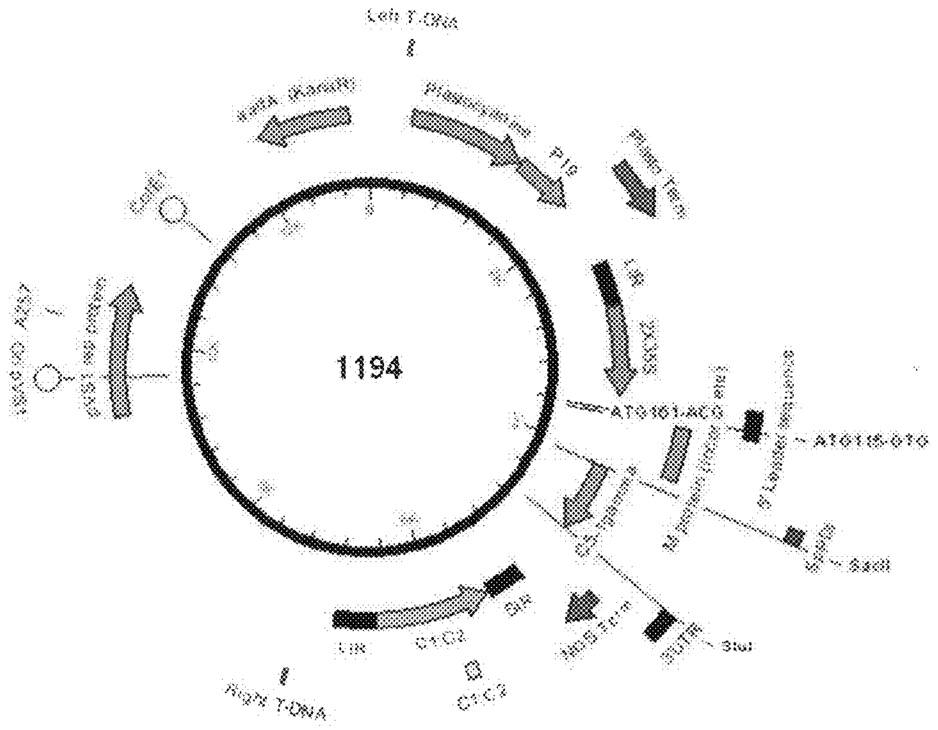

Figure 4B

Construct 1194 from left to right t-DNA borders (underlined). 2X35S/CPMV-HT/PDISP/NOS into BeYDV+Replicase amplification system with Plastocyanine-P19-Plastocyanine silencing inhibitor expression cassette (SEQ ID NO: 31)

TGGCAGGATATATTGTGGTGTAAACAAATTGACGCTTAGACAACTTAATAACACATTGCG
GACGTTTTTAATGTACTGAATTAACGCCGAATCCCGGGCTGGTATATTTATATGTTGTCAA
ATAACTCAAAAACCATAAAAGTTTAAGTTAGCAAGTGTGTACATTTTTACTTGAACAAAA
ATATTCACCTACTACTGTTATAAATCATTATTAAACATTAGAGTAAAGAAATATGGATGAT
AAGAACAAGAGTAGTGATATTTTGACAACAATTTTGTTGCAACATTTGAGAAAATTTTGTT
GTTCTCTCTTTTCATTGGTCAAAAACAATAGAGAGAGAAAAAGGAAGAGGGAGAATAAA
AACATAATGTGAGTATGAGAGAGAAAGTTGTACAAAAGTTGTACCAAAATAGTTGTACAA
ATATCATTGAGGAATTTGACAAAAGC

Figure 4B continued

TACACAAATAAGGGTTAATTGCTGTAAATAAATAAGGATGACGCATTAGAGAGATGTACCATTA
GAGAATTTTTGGCAAGTCATTAAAAAGAAAGAATAAATTATTTTTAAAATTAAAAGTTGAGTCA
TTTGATTAAACATGTGATTATTTAATGAATTGATGAAAGAGTTGGATTAAAGTTGTATTAGTAA
TTAGAATTTGGTGTCAAATTTAATTTGACATTTGATCTTTTCCTATATATTGCCCCATAGAGTC
AGTTAACTCATTTTTATATTTCATAGATCAAATAAGAGAAATAACGGTATATTAATCCCTCCAA
AAAAAAAAAACGGTATATTTACTAAAAAATCTAAGCCACGTAGGAGGATAACAGGATCCCCGTA
GGAGGATAACATCCAATCCAACCAATCACAACAATCCTGATGAGATAACCCACTTTAAGCCCAC
GCATCTGTGGCACATCTACATTATCTAAATCACACATTCTTCCACACATCTGAGCCACACAAAA
ACCAATCCACATCTTTATCACCCATTCTATAAAAAATCACACTTTGTGAGTCTACACTTTGATT
CCCTTCAAACACATACAAAGAGAAGAGACTAATTAATTAATTAATCATCTTGAGAGAAAATGGA
ACGAGCTATACAAGGAAACGACGCTAGGGAACAAGCTAACAGTGAACGTTGGGATGGAGGATCA
GGAGGTACCACTTCTCCCTTCAAACTTCCTGACGAAAGTCCGAGTTGGACTGAGTGGCGGCTAC
ATAACGATGAGACGAATTCGAATCAAGATAATCCCCTTGGTTTCAAGGAAAGCTGGGGTTTCGG
GAAAGTTGTATTTAAGAGATATCTCAGATACGACAGGACGGAAGCTTCACTGCACAGAGTCCTT
GGATCTTGGACGGGAGATTCGGTTAACTATGCAGCATCTCGATTTTTCGGTTTCGACCAGATCG
GATGTACCTATAGTATTCGGTTTCGAGGAGTTAGTATCACCGTTTCTGGAGGGTCGCGAACTCT
TCAGCATCTCTGTGAGATGGCAATTCGGTCTAAGCAAGAACTGCTACAGCTTGCCCCAATCGAA
GTGGAAAGTAATGTATCAAGAGGATGCCCTGAAGGTACTCAAACCTTCGAAAAAGAAAGCGAGT
AAGTTAAAATGCTTCTTCGTCTCCTATTTATAATATGGTTTGTTATTGTTAATTTTGTTCTTGT
AGAAGAGCTTAATTAATCGTTGTTGTTATGAAATACTATTTGTATGAGATGAACTGGTGTAATG
TAATTCATTTACATAAGTGGAGTCAGAATCAGAATGTTTCCTCCATAACTAACTAGACATGAAG
ACCTGCCGCGTACAATTGTCTTATATTTGAACAACTAAAATTGAACATCTTTTGCCACAACTTT
ATAAGTGGTTAATATAGCTCAAATATATGGTCAAGTTCAATAGATTAATAATGGAAATATCAGT
TATCGAAATTCATTAACAATCAACTTAACGTTATTAACTACTAATTTTATATCATCCCCTTTGA
TAAATGATAGTACACCAATTAGGAAGGAGCATGCTCGCCTAGGAGATTGTCGTTTCCCGCCTTC
AGTTTGCAAGCTGCTCTAGCCGTGTAGCCAATACGCAAACCGCCTCTCCCCGCGCGTTGGGAAT
TACTAGCGCGTGTCGACACGCGTGGCGCGCCCTAGCAGAAGGCATGTTGTTGTGACTCCGAGGG
GTTGCCTCAAACTCTATCTTATAACCGGCGTGGAGGCATGGAGGCAAGGGCATTTTGGTAATTT
AAGTAGTTAGTGGAAAATGACGTCATTTACTTAAAGACGAAGTCTTGCGACAAGGGGGGCCCAC
GCCGAATTTTAATATTACCGGCGTGGCCCCACCTTATCGCGAGTGCTTTAGCACGAGCGGTCCA
GATTTAAAGTAGAAAAGTTCCCGCCCACTAGGGTTAAAGGTGTTCACACTATAAAAGCATATAC
GATGTGATGGTATTTGATAAAGCGTATATTGTATCAGGTATTTCCGTCGGATACGAATTATTCG
TACAAGCTTCTTAAGCCGGTCAACATGGTGGAGCACGACACACTTGTCTACTCCAAAAATATCA
AAGATACAGTCTCAGAAGACCAAAGGGCAATTGAGACTTTTCAACAAAGGGTAATATCCGGAAA
CCTCCTCGGATTCCATTGCCCAGCTATCTGTCACTTTATTGTGAAGATAGTGGAAAAGGAAGGT
GGCTCCTACAAATGCCATCATTGCGATAAAGGAAAGGCCATCGTTGAAGATGCCTCTGCCGACA
GTGGTCCCAAAGATGGACCCCCACCCACGAGGAGCATCGTGGAAAAAGAAGACGTTCCAACCAC
GTCTTCAAAGCAAGTGGATTGATGTGATAACATGGTGGAGCACGACACACTTGTCTACTCCAAA
AATATCAAAGATACAGTCTCAGAAGACCAAAGGGCAATTGAGACTTTTCAACAAAGGGTAATAT
CCGGAAACCTCCTCGGATTCCATTGCCCAGCTATCTGTCACTTTATTGTGAAGATAGTGGAAAA
GGAAGGTGGCTCCTACAAATGCCATCATTGCGATAAAGGAAAGGCCATCGTTGAAGATGCCTCT
GCCGACAGTGGTCCCAAAGATGGACCCCCACCCACGAGGAGCATCGTGGAAAAAGAAGACGTTC
CAACCACGTCTTCAAAGCAAGTGGATTGATGTGATATCTCCACTGACGTAAGGGATGACGCACA
ATCCCACTATCCTTCGCAAGACCCTTCCTCTATATAAGGAAGTTCATTTCATTTGGAGAGGTAT
TAAAATCTTAATAGGTTTTGATAAAAGCGAACGTGGGGAAACCCGAACCAAACCTTCTTCTAAA
CTCTCTCTCATCTCTCTTAAAGCAAACTTCTCTCTTGTCTTTCTTGCGTGAGCGATCTTCAACG
TTGTCAGATCGTGCTTCGGCACCAGTACAACGTTTTCTTTCACTGAAGCGAAATCAAAGATCTC

Figure 4B continued

TTTGTGGACACGTAGTGCGGCGCCATTAAATAACGTGTACTTGTCCTATTCTTGTCGGTGTGGT
CTTGGGAAAAGAAAGCTTGCTGGAGGCTGCTGTTCAGCCCCATACATTACTTGTTACGATTCTG
CTGACTTTCGGCGGGTGCAATATCTCTACTTCTGCTTGACGAGGTATTGTTGCCTGTACTTCTT
TCTTCTTCTTCTTGCTGATTGGTTCTATAAGAAATCTAGTATTTTCTTTGAAACAGAGTTTTCC
CGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCA
GATCTTCGCCGCGGCTCCTCAGCCAAAACGACACCCCCATCTGTCTATCCACTGGCCCCTGGAT
CTGCTGCCCAAACTAACTCCATGGTGACCCTGGGATGCCTGGTCAAGGGCTATTTCCCTGAGCC
AGTGACAGTGACCTGGAACTCTGGATCCCTGTCCAGCGGTGTGCACACCTTCCCAGCTGTCCTG
CAGTCTGACCTCTACACTCTGAGCAGCTCAGTGACTGTCCCCTCCAGCACCTGGCCCAGCGAGA
CCGTCACCTGCAACGTTGCCCACCCGGCCAGCAGCACCAAGGTGGACAAGAAAATTGTGCCCAG
GGATTGTGGTTGTAAGCCTTGCATATGTACAGTCCCAGAAGTATCATCTGTCTTCATCTTCCCC
CCAAAGCCCAAGGATGTGCTCACCATTACTCTGACTCCTAAGGTCACGTGTGTTGTGGTAGACA
TCAGCAAGGATGATCCCGAGGTCCAGTTCAGCTGGTTTGTAGATGATGTGGAGGTGCACACAGC
TCAGACGCAACCCCGGGAGGAGCAGTTCAACAGCACTTTCCGCTCAGTCAGTGAACTTCCCATC
ATGCACCAGGACTGGCTCAATGGCAAGGAAGGCCTATTTCTTTAGTTTGAATTTACTGTTATT
CGGTGTGCATTTCTATGTTTGGTGAGCGGTTTTCTGTGCTCAGAGTGTGTTTATTTTATGTAAT
TTAATTTCTTTGTGAGCTCCTGTTTAGCAGGTCGTCCCTTCAGCAAGGACACAAAAAGATTTTA
ATTTTATTAAAAAAAAAAAAAAAAAGACCGGGAATTCGATATCAAGCTTATCGACCTGCAGAT
CGTTCAAACATTTGGCAATAAAGTTTCTTAAGATTGAATCCTGTTGCCGGTCTTGCGATGATTA
TCATATAATTTCTGTTGAATTACGTTAAGCATGTAATAATTAACATGTAATGCATGACGTTATT
TATGAGATGGGTTTTTATGATTAGAGTCCCGCAATTATACATTTAATACGCGATAGAAAACAAA
ATATAGCGCGCAAACTAGGATAAATTATCGCGCGCGGTGTCATCTATGTTACTAGATCTCTAGA
GTCTCAAGCTTGGCGCGGGGTACCGAGCTCGAATTCCGAGTGTACTTCAAGTCAGTTGGAAATC
AATAAAATGATTATTTTATGAATATATTTCATTGTGCAAGTAGATAGAAATTACATATGTTACA
TAACACACGAAATAAACAAAAAAACACAATCCAAAACAAACACCCCAAACAAAATAACACTATA
TATATCCTCGTATGAGGAGAGGCACGTTCAGTGACTCGACGATTCCCGAGCAAAAAAAGTCTCC
CCGTCACACATATAGTGGGTGACGCAATTATCTTCAAAGTAATCCTTCTGTTGACTTGTCATTG
ATAACATCCAGTCTTCGTCAGGATTGCAAAGAATTATAGAAGGGATCCCACCTTTTATTTTCTT
CTTTTTTCCATATTTAGGGTTGACAGTGAAATCAGACTGGCAACCTATTAATTGCTTCCACAAT
GGGACGAACTTGAAGGGGATGTCGTCGATGATATTATAGGTGGCGTGTTCATCGTAGTTGGTGA
AGTCGATGGTCCCGTTCCAGTAGTTGTGTCGCCCGAGACTTCTAGCCCAGGTGGTCTTTCCGGT
ACGAGTTGGTCCGCAGATGTAGAGGCTGGGGTGTCTGACCCCAGTCCTTCCCTCATCCTGGTTA
GATCGGCCATCCACTCAAGGTCAGATTGTGCTTGATCGTAGGAGACAGGATGTATGAAAGTGTA
GGCATCGATGCTTACATGATATAGGTGCGTCTCTCTCCAGTTGTGCAGATCTTCGTGGCAGCGG
AGATCTGATTCTGTGAAGGGCGACACGTACTGCTCAGGTTGTGGAGGAAATAATTTGTTGGCTG
AATATTCCAGCCATTGAAGCTTTGTTGCCCATTCATGAGGGAATTCTTCTTTGATCATGTCAAG
ATACTCCTCCTTAGACGTTGCAGTCTGGATAATAGTTCGCCATCGTGCGTCAGATTTGCGAGGA
GAGACCTTATGATCTCGGAAATCTCCTCTGGTTTTAATATCTCCGTCCTTTGATATGTAATCAA
GGACTTGTTTAGAGTTTCTAGCTGGCTGGATATTAGGGTGATTTCCTTCAAAATCGAAAAAGA
AGGATCCCTAATACAAGGTTTTTTATCAAGCTGGATAAGAGCATGATAGTGGGTAGTGCCATCT
TGATGAAGCTCAGAAGCAACACCAAGGAAGAAAATAAGAAAAGGTGTGAGTTTCTCCCAGAGAA
ACTGGAATAAATCATCTCTTTGAGATGAGCACTTGGGGTAGGTAAGGAAAACATATTTAGATTG
GAGTCTGAAGTTCTTGCTAGCAGAAGGCATGTTGTTGTGACTCCGAGGGGTTGCCTCAAACTCT
ATCTTATAACCGGCGTGGAGGCATGGAGGCAAGGGCATTTTGGTAATTTAAGTAGTTAGTGGAA
AATGACGTCATTTACTTAAAGACGAAGTCTTGCGACAAGGGGGGCCCACGCCGAATTTTAATAT
TACCGGCGTGGCCCCACCTTATCGCGAGTGCTTTAGCACGAGCGGTCCAGATTTAAAGTAGAAA

Figure 4B continued

```
AGTTCCCGCCCACTAGGGTTAAAGGTGTTCACACTATAAAAGCATATACGATGTGATGGTATTT
GATGGAGCGTATATTGTATCAGGTATTTCCGTCGGATACGAATTATTCGTACGGCCGGCCACTA
GTGGCACTGGCCGTCGTTTTACAACGTCGTGACTGGGAAAACCCTGGCGTTACCCAACTTAATC
GCCTTGCAGCACATCCCCCTTTCGCCAGCTGGCGTAATAGCGAAGAGGCCCGCACCGATCGCCC
TTCCCAACAGTTGCGCAGCCTGAATGGCGAATGCTAGAGCAGCTTGAGCTTGGATCAGATTGTC
GTTTCCCGCCTTCAGTTTAAACTATCAGTGTTTGACAGGATATATTGGCGGGTAAACCTAAGAG
AAAAGAGCGTTTA
```

Figure 4C

Expression cassette number 1008 from BeYDV left LIR to BeYDV right LIR. PDISP/HA from influenza B/Brisbane/60/2008 is underlined (SEQ ID NO: 32)

CTAGCAGAAGGCATGTTGTTGTGACTCCGAGGGGTTGCCTCAAACTCTATCTTATAACCGGCGT
GGAGGCATGGAGGCAAGGGCATTTTGGTAATTTAAGTAGTTAGTGGAAAATGACGTCATTTACT
TAAAGACGAAGTCTTGCGACAAGGGGGGCCCACGCCGAATTTTAATATTACCGGCGTGGCCCCA
CCTTATCGCGAGTGCTTTAGCACGAGCGGTCCAGATTTAAAGTAGAAAAGTTCCCGCCCACTAG
GGTTAAAGGTGTTCACACTATAAAAGCATATACGATGTGATGGTATTTGATAAAGCGTATATTG
TATCAGGTATTTCCGTCGGATACGAATTATTCGTACAAGCTTCTTAAGCCGGTCAACATGGTGG
AGCACGACACACTTGTCTACTCCAAAAATATCAAAGATACAGTCTCAGAAGACCAAAGGGCAAT
TGAGACTTTTCAACAAAGGGTAATATCCGGAAACCTCCTCGGATTCCATTGCCCAGCTATCTGT
CACTTTATTGTGAAGATAGTGGAAAAGGAAGGTGGCTCCTACAAATGCCATCATTGCGATAAAG
GAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATAAC
ATGGTGGAGCACGACACACTTGTCTACTCCAAAAATATCAAAGATACAGTCTCAGAAGACCAAA
GGGCAATTGAGACTTTTCAACAAAGGGTAATATCCGGAAACCTCCTCGGATTCCATTGCCCAGC
TATCTGTCACTTTATTGTGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGACCCCCAC
CCACGAGGAGCATCGTGGAAAAAGAAGACGTTCCAACCACGTCTTCAAAGCAAGTGGATTGATG
TGATATCTCCACTGACGTAAGGGATGACGCACAATCCCACTATCCTTCGCAAGACCCTTCCTCT
ATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCT
CTCTTGTCTTTCTTGCGTGAGCGATCTTCAACGTTGTCAGATCGTGCTTCGGCACCAGTACAAC
GTTTTCTTTCACTGAAGCGAAATCAAAGATCTCTTTGTGGACACGTAGTGCGGCGCCATTAAAT
AACGTGTACTTGTCCTATTCTTGTCGGTGTGGTCTTGGGAAAAGAAAGCTTGCTGGAGGCTGCT
GTTCAGCCCCATACATTACTTGTTACGATTCTGCTGACTTTCGGCGGGTGCAATATCTCTACTT
CTGCTTGACGAGGTATTGTTGCCTGTACTTCTTTCTTCTTCTTCTTGCTGATTGGTTCTATAAG
AAATCTAGTATTTTCTTTGAAACAGAGTTTTCCCGTGGTTTTCGAACTTGGAGAAAGATTGTTA
AGCTTCTGTATATTCTGCCCAAATTTGTCGGGCCCATGGCGAAAAACGTTGCGATTTTCGGCTT
ATTGTTTTCTCTTCTTGTGTTGGTTCCTTCTCAGATCTTCGCCGATCGAATCTGCACTGGAATA
ACATCGTCAAACTCACCACATGTCGTCAAAACTGCTACTCAAGGGGAGGTCAATGTGACTGGTG
TAATACCACTGACAACAACACCCACCAAATCTCATTTTGCAAATCTCAAAGGAACAGAAACCAG
GGGGAAACTATGCCCAAAATGCCTCAACTGCACAGATCTGGACGTAGCCTTGGGCAGACCAAAA
TGCACGGGGAAAATACCCTCGGCAAGAGTTTCAATACTCCATGAAGTCAGACCTGTTACATCTG
GGTGCTTTCCTATAATGCACGACAGAACAAAAATTAGACAGCTGCCTAACCTTCTCCGAGGATA
CGAACATATCAGGTTATCAACCCATAACGTTATCAATGCAGAAAATGCACCAGGAGGACCCTAC

Figure 4C continued

AAAATTGGAACCTCAGGGTCTTGCCCTAACATTACCAATGGAAACGGATTTTTCGCAACAATGG
CTTGGGCCGTCCCAAAAAACGACAAAAACAAAACAGCAACAAATCCATTAACAATAGAAGTACC
ATACATTTGTACAGAAGGAGAAGACCAAATTACCGTTTGGGGGTTCCACTCTGACAACGAGACC
CAAATGGCAAAGCTCTATGGGGACTCAAAGCCCCAGAAGTTCACCTCATCTGCCAACGGAGTGA
CCACACATTACGTTTCACAGATTGGTGGCTTCCCAAATCAAACAGAAGACGGAGGACTACCACA
AAGTGGTAGAATTGTTGTTGATTACATGGTGCAAAAATCTGGGAAAACAGGAACAATTACCTAT
CAAAGGGGTATTTTATTGCCTCAAAAGGTGTGGTGCGCAAGTGGCAGGAGCAAGGTAATAAAAG
GATCCTTGCCTTTAATTGGAGAAGCAGATTGCCTCCACGAAAAATACGGTGGATTAAACAAAAG
CAAGCCTTACTACACAGGGGAACATGCAAAGGCCATAGGAAATTGCCCAATATGGGTGAAAACA
CCCTTGAAGCTGGCCAATGGAACCAAATATAGACCTCCTGCAAAACTATTAAAGGAAAGGGGTT
TCTTCGGAGCTATTGCTGGTTTCTTAGAAGGAGGATGGGAAGGAATGATTGCAGGTTGGCACGG
ATACACATCCCATGGGGCACATGGAGTAGCGGTGGCAGCAGACCTTAAGAGCACTCAAGAGGCC
ATAAACAAGATAACAAAAAATCTCAACTCTTTGAGTGAGCTGGAAGTAAAGAATCTTCAAAGAC
TAAGCGGTGCCATGGATGAACTCCACAACGAAATACTAGAACTAGATGAGAAAGTGGATGATCT
CAGAGCTGATACAATAAGCTCACAAATAGAACTCGCAGTCCTGCTTTCCAATGAAGGAATAATA
AACAGTGAAGATGAACATCTCTTGGCGCTTGAAAGAAAGCTGAAGAAAATGCTGGGCCCCTCTG
CTGTAGAGATAGGGAATGGATGCTTTGAAACCAAACACAAGTGCAACCAGACCTGTCTCGACAG
AATAGCTGCTGGTACCTTTGATGCAGGAGAATTTTCTCTCCCCACCTTTGATTCACTGAATATT
ACTGCTGCATCTTTAAATGACGATGGATTGGATAATCATACTATACTGCTTTACTACTCAACTG
CTGCCTCCAGTTTGGCTGTAACACTGATGATAGCTATCTTTGTTGTTTATATGGTCTCCAGAGA
CAATGTTTCTTGCTCCATCTGTCTATAAAGGCCTATTTTCTTTAGTTTGAATTTACTGTTATTC
GGTGTGCATTTCTATGTTTGGTGAGCGGTTTTCTGTGCTCAGAGTGTGTTTATTTTATGTAATT
TAATTTCTTTGTGAGCTCCTGTTTAGCAGGTCGTCCCTTCAGCAAGGACACAAAAAGATTTTAA
TTTTATTAAAAAAAAAAAAAAAAAAAGACCGGGAATTCGATATCAAGCTTATCGACCTGCAGATC
GTTCAAACATTTGGCAATAAAGTTTCTTAAGATTGAATCCTGTTGCCGGTCTTGCGATGATTAT
CATATAATTTCTGTTGAATTACGTTAAGCATGTAATAATTAACATGTAATGCATGACGTTATTT
ATGAGATGGGTTTTTATGATTAGAGTCCCGCAATTATACATTTAATACGCGATAGAAAACAAAA
TATAGCGCGCAAACTAGGATAAATTATCGCGCGCGGTGTCATCTATGTTACTAGATCTCTAGAG
TCTCAAGCTTGGCGCGGGGTACCGAGCTCGAATTCCGAGTGTACTTCAAGTCAGTTGGAAATCA
ATAAAATGATTATTTTATGAATATATTTCATTGTGCAAGTAGATAGAAATTACATATGTTACAT
AACACACGAAATAAACAAAAAAACACAATCCAAAACAAACACCCCAAACAAAATAACACTATAT
ATATCCTCGTATGAGGAGAGGCACGTTCAGTGACTCGACGATTCCCGAGCAAAAAAAGTCTCCC
CGTCACACATATAGTGGGTGACGCAATTATCTTCAAAGTAATCCTTCTGTTGACTTGTCATTGA
TAACATCCAGTCTTCGTCAGGATTGCAAAGAATTATAGAAGGGATCCCACCTTTTATTTTCTTC
TTTTTTCCATATTTAGGGTTGACAGTGAAATCAGACTGGCAACCTATTAATTGCTTCCACAATG
GGACGAACTTGAAGGGGATGTCGTCGATGATATTATAGGTGGCGTGTTCATCGTAGTTGGTGAA
GTCGATGGTCCCGTTCCAGTAGTTGTGTCGCCCGAGACTTCTAGCCCAGGTGGTCTTTCCGGTA
CGAGTTGGTCCGCAGATGTAGAGGCTGGGGTGTCTGACCCCAGTCCTTCCCTCATCCTGGTTAG
ATCGGCCATCCACTCAAGGTCAGATTGTGCTTGATCGTAGGAGACAGGATGTATGAAAGTGTAG
GCATCGATGCTTACATGATATAGGTGCGTCTCTCTCCAGTTGTGCAGATCTTCGTGGCAGCGGA
GATCTGATTCTGTGAAGGGCGACACGTACTGCTCAGGTTGTGGAGGAAATAATTTGTTGGCTGA
ATATTCCAGCCATTGAAGCTTTGTTGCCCATTCATGAGGGAATTCTTCTTTGATCATGTCAAGA
TACTCCTCCTTAGACGTTGCAGTCTGGATAATAGTTCGCCATCGTGCGTCAGATTTGCGAGGAG
AGACCTTATGATCTCGGAAATCTCCTCTGGTTTTAATATCTCCGTCCTTTGATATGTAATCAAG
GACTTGTTTAGAGTTTCTAGCTGGCTGGATATTAGGGTGATTTCCTTCAAAATCGAAAAAAGAA
GGATCCCTAATACAAGGTTTTTTATCAAGCTGGATAAGAGCATGATAGTGGGTAGTGCCATCTT
GATGAAGCTCAGAAGCAACACCAAGGAAGAAAATAAGAAAAGGTGTGAGTTTCTCCCAGAGAAA

Figure 4C continued

CTGGAATAAATCATCTCTTTGAGATGAGCACTTGGGGTAGGTAAGGAAAACATATTTAGATTGG
AGTCTGAAGTTCTTGCTAGCAGAAGGCATGTTGTTGTGACTCCGAGGGGTTGCCTCAAACTCTA
TCTTATAACCGGCGTGGAGGCATGGAGGCAAGGGCATTTTGGTAATTTAAGTAGTTAGTGGAAA
ATGACGTCATTTACTTAAAGACGAAGTCTTGCGACAAGGGGGGCCCACGCCGAATTTTAATATT
ACCGGCGTGGCCCCACCTTATCGCGAGTGCTTTAGCACGAGCGGTCCAGATTTAAAGTAGAAAA
GTTCCCGCCCACTAGGGTTAAAGGTGTTCACACTATAAAAGCATATACGATGTGATGGTATTTG
ATGGAGCGTATATTGTATCAGGTATTTCCGTCGGATACGAATTATTCGTAC

Figure 5: I-2X35S/CPMV-HT/PDISP/HA B Brisbane with deleted proteolytic loop/NOS into BeYDV+Replicase amplification system (Construct number 1059)

Figure 5A,

1039+1059.r (SEQ ID NO: 38)

CTTCCCATCCTCCACCAGGAGGTCTATATTTGGTTCCATTGGCCAGCTTCAA

Figure 5B

1039+1059.c (SEQ ID NO: 39)

CAAATATAGACCTCCTGGTGGAGGATGGGAAGGAATGATTGCAGGTTGGCAC

Figure 5C,

Expression cassette number 1059 from BeYDV left LIR to BeYDV right LIR. PDISP/HA from influenza B/Brisbane/60/2008 with deleted proteolytic loop is underlined. (SEQ ID NO: 40)

CTAGCAGAAGGCATGTTGTTGTGACTCCGAGGGGTTGCCTCAAACTCTATCTTATAACCGGCGT
GGAGGCATGGAGGCAAGGGCATTTTGGTAATTTAAGTAGTTAGTGGAAAATGACGTCATTTACT
TAAAGACGAAGTCTTGCGACAAGGGGGGCCCACGCCGAATTTTAATATTACCGGCGTGGCCCCA
CCTTATCGCGAGTGCTTTAGCACGAGCGGTCCAGATTTAAAGTAGAAAAGTTCCCGCCCACTAG
GGTTAAAGGTGTTCACACTATAAAAGCATATACGATGTGATGGTATTTGATAAAGCGTATATTG
TATCAGGTATTTCCGTCGGATACGAATTATTCGTACAAGCTTCTTAAGCCGGTCAACATGGTGG
AGCACGACACACTTGTCTACTCCAAAAATATCAAAGATACAGTCTCAGAAGACCAAAGGGCAAT
TGAGACTTTTCAACAAAGGGTAATATCCGGAAACCTCCTCGGATTCCATTGCCCAGCTATCTGT
CACTTTATTGTGAAGATAGTGGAAAAGGAAGGTGGCTCCTACAAATGCCATCATTGCGATAAAG
GAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATAAC

Figure 5C continued

ATGGTGGAGCACGACACACTTGTCTACTCCAAAAATATCAAAGATACAGTCTCAGAAGACCAAA
GGGCAATTGAGACTTTTCAACAAAGGGTAATATCCGGAAACCTCCTCGGATTCCATTGCCCAGC
TATCTGTCACTTTATTGTGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGACCCCCAC
CCACGAGGAGCATCGTGGAAAAAGAAGACGTTCCAACCACGTCTTCAAAGCAAGTGGATTGATG
TGATATCTCCACTGACGTAAGGGATGACGCACAATCCCACTATCCTTCGCAAGACCCTTCCTCT
ATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCT
CTCTTGTCTTTCTTGCGTGAGCGATCTTCAACGTTGTCAGATCGTGCTTCGGCACCAGTACAAC
GTTTTCTTTCACTGAAGCGAAATCAAAGATCTCTTTGTGGACACGTAGTGCGGCGCCATTAAAT
AACGTGTACTTGTCCTATTCTTGTCGGTGTGGTCTTGGGAAAAGAAAGCTTGCTGGAGGCTGCT
GTTCAGCCCCATACATTACTTGTTACGATTCTGCTGACTTTCGGCGGGTGCAATATCTCTACTT
CTGCTTGACGAGGTATTGTTGCCTGTACTTCTTTCTTCTTCTTCTTGCTGATTGGTTCTATAAG
AAATCTAGTATTTTCTTTGAAACAGAGTTTTCCCGTGGTTTTCGAACTTGGAGAAAGATTGTTA
AGCTTCTGTATATTCTGCCCAAATTTGTCGGGCCCATGGCGAAAAACGTTGCGATTTTCGGCTT
ATTGTTTTCTCTTCTTGTGTTGGTTCCTTCTCAGATCTTCGCCGATCGAATCTGCACTGGAATA
ACATCGTCAAACTCACCACATGTCGTCAAAACTGCTACTCAAGGGGAGGTCAATGTGACTGGTG
TAATACCACTGACAACAACACCCACCAAATCTCATTTTGCAAATCTCAAAGGAACAGAAACCAG
GGGGAAACTATGCCCAAAATGCCTCAACTGCACAGATCTGGACGTAGCCTTGGGCAGACCAAAA
TGCACGGGGAAAATACCCTCGGCAAGAGTTTCAATACTCCATGAAGTCAGACCTGTTACATCTG
GGTGCTTTCCTATAATGCACGACAGAACAAAAATTAGACAGCTGCCTAACCTTCTCCGAGGATA
CGAACATATCAGGTTATCAACCCATAACGTTATCAATGCAGAAAATGCACCAGGAGGACCCTAC
AAAATTGGAACCTCAGGGTCTTGCCCTAACATTACCAATGGAAACGGATTTTTCGCAACAATGG
CTTGGGCCGTCCCAAAAAACGACAAAAACAAAACAGCAACAAATCCATTAACAATAGAAGTACC
ATACATTTGTACAGAAGGAGAAGACCAAATTACCGTTTGGGGGTTCCACTCTGACAACGAGACC
CAAATGGCAAAGCTCTATGGGGACTCAAAGCCCCAGAAGTTCACCTCATCTGCCAACGGAGTGA
CCACACATTACGTTTCACAGATTGGTGGCTTCCCAAATCAAACAGAAGACGGAGGACTACCACA
AAGTGGTAGAATTGTTGTTGATTACATGGTGCAAAAATCTGGGAAAACAGGAACAATTACCTAT
CAAAGGGGTATTTTATTGCCTCAAAAGGTGTGGTGCGCAAGTGGCAGGAGCAAGGTAATAAAAG
GATCCTTGCCTTTAATTGGAGAAGCAGATTGCCTCCACGAAAAATACGGTGGATTAAACAAAAG
CAAGCCTTACTACACAGGGGAACATGCAAAGGCCATAGGAAATTGCCCAATATGGGTGAAAACA
CCCTTGAAGCTGGCCAATGGAACCAAATATAGACCTCCTGGTGGAGGATGGGAAGGAATGATTG
CAGGTTGGCACGGATACACATCCCATGGGGCACATGGAGTAGCGGTGGCAGCAGACCTTAAGAG
CACTCAAGAGGCCATAAACAAGATAACAAAAAATCTCAACTCTTTGAGTGAGCTGGAAGTAAAG
AATCTTCAAAGACTAAGCGGTGCCATGGATGAACTCCACAACGAAATACTAGAACTAGATGAGA
AAGTGGATGATCTCAGAGCTGATACAATAAGCTCACAAATAGAACTCGCAGTCCTGCTTTCCAA
TGAAGGAATAATAAACAGTGAAGATGAACATCTCTTGGCGCTTGAAAGAAAGCTGAAGAAAATG
CTGGGCCCCTCTGCTGTAGAGATAGGGAATGGATGCTTTGAAACCAAACACAAGTGCAACCAGA
CCTGTCTCGACAGAATAGCTGCTGGTACCTTTGATGCAGGAGAATTTTCTCTCCCCACCTTTGA
TTCACTGAATATTACTGCTGCATCTTTAAATGACGATGGATTGGATAATCATACTATACTGCTT
TACTACTCAACTGCTGCCTCCAGTTTGGCTGTAACACTGATGATAGCTATCTTTGTTGTTTATA
TGGTCTCCAGAGACAATGTTTCTTGCTCCATCTGTCTATAAAGGCCTATTTTCTTTAGTTTGAA
TTTACTGTTATTCGGTGTGCATTTCTATGTTTGGTGAGCGGTTTTCTGTGCTCAGAGTGTGTTT
ATTTTATGTAATTTAATTTCTTTGTGAGCTCCTGTTTAGCAGGTCGTCCCTTCAGCAAGGACAC
AAAAAGATTTTAATTTTATTAAAAAAAAAAAAAAAAAAGACCGGGAATTCGATATCAAGCTTAT
CGACCTGCAGATCGTTCAAACATTTGGCAATAAAGTTTCTTAAGATTGAATCCTGTTGCCGGTC
TTGCGATGATTATCATATAATTTCTGTTGAATTACGTTAAGCATGTAATAATTAACATGTAATG

Figure 5C continued

CATGACGTTATTTATGAGATGGGTTTTTATGATTAGAGTCCCGCAATTATACATTTAATACGCG
ATAGAAAACAAAATATAGCGCGCAAACTAGGATAAATTATCGCGCGCGGTGTCATCTATGTTAC
TAGATCTCTAGAGTCTCAAGCTTGGCGCGGGGTACCGAGCTCGAATTCCGAGTGTACTTCAAGT
CAGTTGGAAATCAATAAAATGATTATTTTATGAATATATTTCATTGTGCAAGTAGATAGAAATT
ACATATGTTACATAACACACGAAATAAACAAAAAAACACAATCCAAAACAAACACCCCAAACAA
AATAACACTATATATATCCTCGTATGAGGAGAGGCACGTTCAGTGACTCGACGATTCCCGAGCA
AAAAAGTCTCCCCGTCACACATATAGTGGGTGACGCAATTATCTTCAAAGTAATCCTTCTGTT
GACTTGTCATTGATAACATCCAGTCTTCGTCAGGATTGCAAAGAATTATAGAAGGGATCCCACC
TTTTATTTTCTTCTTTTTTCCATATTTAGGGTTGACAGTGAAATCAGACTGGCAACCTATTAAT
TGCTTCCACAATGGGACGAACTTGAAGGGGATGTCGTCGATGATATTATAGGTGGCGTGTTCAT
CGTAGTTGGTGAAGTCGATGGTCCCGTTCCAGTAGTTGTGTCGCCCGAGACTTCTAGCCCAGGT
GGTCTTTCCGGTACGAGTTGGTCCGCAGATGTAGAGGCTGGGGTGTCTGACCCCAGTCCTTCCC
TCATCCTGGTTAGATCGGCCATCCACTCAAGGTCAGATTGTGCTTGATCGTAGGAGACAGGATG
TATGAAAGTGTAGGCATCGATGCTTACATGATATAGGTGCGTCTCTCTCCAGTTGTGCAGATCT
TCGTGGCAGCGGAGATCTGATTCTGTGAAGGGCGACACGTACTGCTCAGGTTGTGGAGGAAATA
ATTTGTTGGCTGAATATTCCAGCCATTGAAGCTTTGTTGCCCATTCATGAGGGAATTCTTCTTT
GATCATGTCAAGATACTCCTCCTTAGACGTTGCAGTCTGGATAATAGTTCGCCATCGTGCGTCA
GATTTGCGAGGAGAGACCTTATGATCTCGGAAATCTCCTCTGGTTTTAATATCTCCGTCCTTTG
ATATGTAATCAAGGACTTGTTTAGAGTTTCTAGCTGGCTGGATATTAGGGTGATTTCCTTCAAA
ATCGAAAAAGAAGGATCCCTAATACAAGGTTTTTTATCAAGCTGGATAAGAGCATGATAGTGG
GTAGTGCCATCTTGATGAAGCTCAGAAGCAACACCAAGGAAGAAAATAAGAAAAGGTGTGAGTT
TCTCCCAGAGAAACTGGAATAAATCATCTCTTTGAGATGAGCACTTGGGGTAGGTAAGGAAAAC
ATATTTAGATTGGAGTCTGAAGTTCTTGCTAGCAGAAGGCATGTTGTTGTGACTCCGAGGGGTT
GCCTCAAACTCTATCTTATAACCGGCGTGGAGGCATGGAGGCAAGGGCATTTTGGTAATTTAAG
TAGTTAGTGGAAAATGACGTCATTTACTTAAAGACGAAGTCTTGCGACAAGGGGGGCCCACGCC
GAATTTAATATTACCGGCGTGGCCCCACCTTATCGCGAGTGCTTTAGCACGAGCGGTCCAGAT
TTAAAGTAGAAAAGTTCCCGCCCACTAGGGTTAAAGGTGTTCACACTATAAAAGCATATACGAT
GTGATGGTATTTGATGGAGCGTATATTGTATCAGGTATTTCCGTCGGATACGAATTATTCGTAC

Figure 5D

Amino acid sequence of PDISP/HA from influenza B/Brisbane/60/2008 with deleted proteolytic loop (SEQ ID NO: 41)

MAKNVAIFGLLFSLLVLVPSQIFADRICTGITSSNSPHVVKTATQGEVNVTGVIPLTTTPTKSH
FANLKGTETRGKLCPKCLNCTDLDVALGRPKCTGKIPSARVSILHEVRPVTSGCFPIMHDRTKI
RQLPNLLRGYEHIRLSTHNVINAENAPGGPYKIGTSGSCPNITNGNGFFATMAWAVPKNDKNKT
ATNPLTIEVPYICTEGEDQITVWGFHSDNETQMAKLYGDSKPQKFTSSANGVTTHYVSQIGGFP
NQTEDGGLPQSGRIVVDYMVQKSGKTGTITYQRGILLPQKVWCASGRSKVIKGSLPLIGEADCL
HEKYGGLNKSKPYYTGEHAKAIGNCPIWVKTPLKLANGTKYRPPGGGWEGMIAGWHGYTSHGAH
GVAVAADLKSTQEAINKITKNLNSLSELEVKNLQRLSGAMDELHNEILELDEKVDDLRADTISS
QIELAVLLSNEGIINSEDEHLLALERKLKKMLGPSAVEIGNGCFETKHKCNQTCLDRIAAGTFD
AGEFSLPTFDSLNITAASLNDDGLDNHTILLYYSTAASSLAVTLMIAIFVVYMVSRDNVSCSIC
L

Figure 5E nucleotide sequence of PDISP/HA from influenza B/Brisbane/60/2008 with deleted proteolytic loop (SEQ ID NO: 43)

ATGGCGAAAAACGTTGCGATTTTCGGCTTATTGTTTTCTCTTCTTGTGTTGGTTCCTTCTCAGA
TCTTCGCCGATCGAATCTGCACTGGAATAACATCGTCAAACTCACCACATGTCGTCAAAACTGC
TACTCAAGGGGAGGTCAATGTGACTGGTGTAATACCACTGACAACAACACCCACCAAATCTCAT
TTTGCAAATCTCAAAGGAACAGAAACCAGGGGGAAACTATGCCCAAAATGCCTCAACTGCACAG
ATCTGGACGTAGCCTTGGGCAGACCAAAATGCACGGGGAAAATACCCTCGGCAAGAGTTTCAAT
ACTCCATGAAGTCAGACCTGTTACATCTGGGTGCTTTCCTATAATGCACGACAGAACAAAAATT
AGACAGCTGCCTAACCTTCTCCGAGGATACGAACATATCAGGTTATCAACCCATAACGTTATCA
ATGCAGAAAATGCACCAGGAGGACCCTACAAAATTGGAACCTCAGGGTCTTGCCCTAACATTAC
CAATGGAAACGGATTTTTCGCAACAATGGCTTGGGCCGTCCCAAAAAACGACAAAAACAAAACA
GCAACAAATCCATTAACAATAGAAGTACCATACATTTGTACAGAAGGAGAAGACCAAATTACCG
TTTGGGGGTTCCACTCTGACAACGAGACCCAAATGGCAAAGCTCTATGGGGACTCAAAGCCCCA
GAAGTTCACCTCATCTGCCAACGGAGTGACCACACATTACGTTTCACAGATTGGTGGCTTCCCA
AATCAAACAGAAGACGGAGGACTACCACAAAGTGGTAGAATTGTTGTTGATTACATGGTGCAAA
AATCTGGGAAAACAGGAACAATTACCTATCAAAGGGGTATTTTATTGCCTCAAAAGGTGTGGTG
CGCAAGTGGCAGGAGCAAGGTAATAAAAGGATCCTTGCCTTTAATTGGAGAAGCAGATTGCCTC
CACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACC
TCCTGGTGGAGGATGGGAAGGAATGATTGCAGGTTGGCACGGATACACATCCCATGGGGCACAT
GGAGTAGCGGTGGCAGCAGACCTTAAGAGCACTCAAGAGGCCATAAACAAGATAACAAAAAATC
TCAACTCTTTGAGTGAGCTGGAAGTAAAGAATCTTCAAAGACTAAGCGGTGCCATGGATGAACT
CCACAACGAAATACTAGAACTAGATGAGAAAGTGGATGATCTCAGAGCTGATACAATAAGCTCA
CAAATAGAACTCGCAGTCCTGCTTTCCAATGAAGGAATAATAAACAGTGAAGATGAACATCTCT
TGGCGCTTGAAAGAAAGCTGAAGAAAATGCTGGGCCCCTCTGCTGTAGAGATAGGGAATGGATG
CTTTGAAACCAAACACAAGTGCAACCAGACCTGTCTCGACAGAATAGCTGCTGGTACCTTTGAT
GCAGGAGAATTTTCTCTCCCCACCTTTGATTCACTGAATATTACTGCTGCATCTTTAAATGACG
ATGGATTGGATAATCATACTATACTGCTTTACTACTCAACTGCTGCCTCCAGTTTGGCTGTAAC
ACTGATGATAGCTATCTTTGTTGTTTATATGGTCTCCAGAGACAATGTTTCTTGCTCCATCTGT
CTATAA

Figure 6: B-2X35S/CPMV-HT/HA B Wisconsin/NOS into BeYDV(m)+Replicase amplification system (Construct number 1462)

Figure 6A, SEQ ID NO: 49
IF-HAB110.S1+3c

AAATTTGTCGGGCCCATGAAGGCAATAATTGTACTACTCATGGTAG

Figure 6B, SEQ ID NO: 50
IF-HAB110.s1-4r

ACTAAAGAAAATAGGCCTTTATAGACAGATGGAGCATGAAACGTTGTCTCTG

Figure 6C, SEQ ID NO: 51
Synthesized HA B Wisconsin (Genbank accession number JN993010)

ATGAAGGCAATAATTGTACTACTCATGGTAGTAACATCCAATGCAGATCGAATCTGCACTGGGA
TAACATCTTCAAACTCACCTCATGTGGTCAAAACAGCTACTCAAGGGGAGGTCAATGTGACTGG
CGTGATACCACTGACAACAACACCAACAAAATCTTATTTTGCAAATCTCAAAGGAACAAGGACC
AGAGGGAAACTATGCCCGGACTGTCTCAACTGTACAGATCTGGATGTGGCCTTGGGCAGGCCAA
TGTGTGTGGGGACCACACCTTCTGCTAAAGCTTCAATACTCCACGAGGTCAGACCTGTTACATC
CGGGTGCTTTCCTATAATGCACGACAGAACAAAAATCAGGCAACTACCCAATCTTCTCAGAGGA
TATGAAAATATCAGGTTATCAACCCAAAACGTTATCGATGCAGAAAAAGCACCAGGAGGACCCT
ACAGACTTGGAACCTCAGGATCTTGCCCTAACGCTACCAGTAAAATCGGATTTTTTGCAACAAT
GGCTTGGGCTGTCCCAAAGGACAACTACAAAAATGCAACGAACCCACTAACAGTAGAAGTACCA
TACATTTGTACAGAAGGGGAAGACCAAATTACTGTTTGGGGGTTCCATTCAGATAACAAAACCC
AAATGAAGAGCCTCTATGGAGACTCAAATCCTCAAAAGTTCACCTCATCTGCTAATGGAGTAAC
CACACATTATGTTTCTCAGATTGGCGACTTCCCAGATCAAACAGAAGACGGAGGACTACCACAA
AGCGGCAGAATTGTTGTTGATTACATGATGCAAAAACCTGGGAAAACAGGAACAATTGTCTATC
AAAGAGGTGTTTTGTTGCCTCAAAAGGTGTGGTGCGCGAGTGGCAGGAGCAAAGTAATAAAAGG
GTCATTGCCTTTAATTGGTGAAGCAGATTGCCTTCATGAAAAATACGGTGGATTAAACAAAAGC
AAGCCTTACTACACAGGAGAACATGCAAAAGCCATAGGAAATTGCCCAATATGGGTAAAAACAC
CTTTGAAGCTTGCCAATGGAACCAAATATAGACCTCCTGCAAAACTATTGAAGGAAAGGGGTTT
CTTCGGAGCTATTGCTGGTTTCCTAGAAGGAGGATGGGAAGGAATGATTGCAGGTTGGCACGGA
TACACATCTCACGGAGCACATGGAGTGGCAGTGGCGGCAGACCTTAAGAGTACACAAGAAGCTA
TAAATAAGATAACAAAAAATCTCAATTCTTTGAGTGAGCTAGAAGTAAAGAACCTTCAAAGACT
AAGTGGTGCCATGGATGAACTCCACAACGAAATACTCGAGCTGGATGAGAAAGTGGATGATCTC
AGAGCTGACACTATAAGCTCACAAATAGAACTTGCAGTCTTGCTTTCCAACGAAGGAATAATAA
ACAGTGAAGACGAGCATCTATTGGCACTTGAGAGAAAACTAAAGAAAATGCTGGGTCCCTCTGC
TGTAGACATAGGAAACGGATGCTTCGAAACCAAACACAAATGCAACCAGACCTGCTTAGACAGG
ATAGCTGCTGGCACCTTTAATGCAGGAGAATTTTCTCTCCCCACTTTTGATTCATTGAACATTA
CTGCTGCATCTTTAAATGATGATGGATTGGATAACCATACTATACTGCTCTATTACTCAACTGC
TGCTTCTAGTTTGGCTGTAACATTAATGCTAGCTATTTTTATTGTTTATATGGTCTCCAGAGAC
AACGTTTCATGCTCCATCTGTCTATAA

Schematic representation of construct 193. SacII and StuI restriction enzyme sites used for plasmid linearization are annotated on the representation.

Figure 6E:
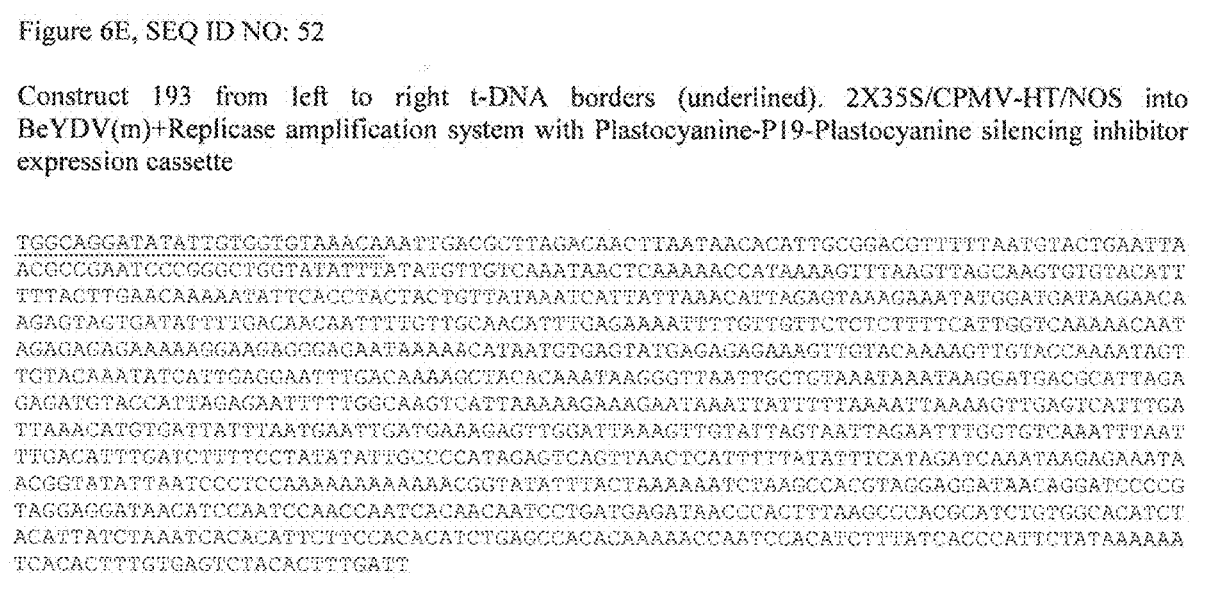

Figure 6E, SEQ ID NO: 52

Construct 193 from left to right t-DNA borders (underlined). 2X35S/CPMV-HT/NOS into BeYDV(m)+Replicase amplification system with Plastocyanine-P19-Plastocyanine silencing inhibitor expression cassette TGGCAGGATATATTGTGGTGTAAACAAATTGACGCTTAGACAACTTAATAACACATTGCGGACGTTTTTAATGTACTGAATTA
ACGCCGAATCCCGGGCTGGTATATTTATATGTTGTCAAATAACTCAAAAACCATAAAAGTTTAAGTTAGCAAGTGTGTACATT
TTTACTTGAACAAAAATATTCACCTACTACTGTTATAAATCATTATTAAACATTAGAGTAAAGAAATATGGATGATAAGAACA
AGAGTAGTGATATTTTGACAACAATTTTGTTGCAACATTTGAGAAAATTTTGTTGTTCTCTCTTTTCATTGGTCAAAAACAAT
AGAGAGAGAAAAAGGAAGAGGGAGAATAAAAACATAATGTGAGTATGAGAGAGAAAGTTGTACAAAAGTTGTACCAAAATAGT
TGTACAAATATCATTGAGGAATTTGACAAAAGCTACACAAATAAGGGTTAATTGCTGTAAATAAATAAGGATGACGCATTAGA
GAGATGTACCATTAGAGAATTTTTGGCAAGTCATTAAAAAGAAAGAATAAATTATTTTTAAAATTAAAAGTTGAGTCATTTGA
TTAAACATGTGATTATTTAATGAATTGATGAAAGAGTTGGATTAAAGTTGTATTAGTAATTAGAATTTGGTGTCAAATTTAAT
TTGACATTTGATCTTTTCCTATATATTGCCCCATAGAGTCAGTTAACTCATTTTTATATTTCATAGATCAAATAAGAGAAATA
ACGGTATATTAATCCCTCCAAAAAAAAAAAACGGTATATTTACTAAAAAATCTAAGCCACGTAGGAGGATAACAGGATCCCCG
TAGGAGGATAACATCCAATCCAACCAATCACAACAATCCTGATGAGATAACCCACTTTAAGCCCACGCATCTGTGGCACATCT
ACATTATCTAAATCACACATTCTTCCACACATCTGAGCCACACAAAAACCAATCCACATCTTTATCACCCATTCTATAAAAAA
TCACACTTTGTGAGTCTACACTTTGATT

Figure 6E continued

CCCTTCAAACACATACAAAGAGAAGAGACTAATTAATTAATTAATCATCTTGAGAGAAAATGGA
ACGAGCTATACAAGGAAACGACGCTAGGGAACAAGCTAACAGTGAACGTTGGGATGGAGGATCA
GGAGGTACCACTTCTCCCTTCAAACTTCCTGACGAAAGTCCGAGTTGGACTGAGTGGCGGCTAC
ATAACGATGAGACGAATTCGAATCAAGATAATCCCCTTGGTTTCAAGGAAAGCTGGGGTTTCGG
GAAAGTTGTATTTAAGAGATATCTCAGATACGACAGGACGGAAGCTTCACTGCACAGAGTCCTT
GGATCTTGGACGGGAGATTCGGTTAACTATGCAGCATCTCGATTTTTCGGTTTCGACCAGATCG
GATGTACCTATAGTATTCGGTTTCGAGGAGTTAGTATCACCGTTTCTGGAGGGTCGCGAACTCT
TCAGCATCTCTGTGAGATGGCAATTCGGTCTAAGCAAGAACTGCTACAGCTTGCCCCAATCGAA
GTGGAAAGTAATGTATCAAGAGGATGCCCTGAAGGTACTCAAACCTTCGAAAAAGAAAGCGAGT
AAGTTAAAATGCTTCTTCGTCTCCTATTTATAATATGGTTTGTTATTGTTAATTTTGTTCTTGT
AGAAGAGCTTAATTAATCGTTGTTGTTATGAAATACTATTTGTATGAGATGAACTGGTGTAATG
TAATTCATTTACATAAGTGGAGTCAGAATCAGAATGTTTCCTCCATAACTAACTAGACATGAAG
ACCTGCCGCGTACAATTGTCTTATATTTGAACAACTAAAATTGAACATCTTTTGCCACAACTTT
ATAAGTGGTTAATATAGCTCAAATATATGGTCAAGTTCAATAGATTAATAATGGAAATATCAGT
TATCGAAATTCATTAACAATCAACTTAACGTTATTAACTACTAATTTTATATCATCCCCTTTGA
TAAATGATAGTACACCAATTAGGAAGGAGCATGCTCGCCTAGGAGATTGTCGTTTCCCGCCTTC
AGTTTGCAAGCTGCTCTAGCCGTGTAGCCAATACGCAAACCGCCTCTCCCCGCGCGTTGGGAAT
TACTAGCGCGTGTCGAGACGCGTTGTTGTTGTGACTCCGAGGGGTTGCCTCAAACTCTATCTTA
TAACCGGCGTGGAGGCATGGAGGCAGGGGTATTTTGGTCATTTTAATAGATAGTGGAAAATGAC
GTGGAATTTACTTAAAGACGAAGTCTTTGCGACAAGGGGGGGCCCACGCCGAATTTAATATTAC
CGGCGTGGCCCCCCCTTATCGCGAGTGCTTTAGCACGAGCGGTCCAGATTTAAAGTAGAAAATT
TCCCGCCCACTAGGGTTAAAGGTGTTCACACTATAAAAGCATATACGATGTGATGGTATTTGGT
CGACAAGCTTGCATGCCGGTCAACATGGTGGAGCACGACACACTTGTCTACTCCAAAAATATCA
AAGATACAGTCTCAGAAGACCAAAGGGCAATTGAGACTTTTCAACAAAGGGTAATATCCGGAAA
CCTCCTCGGATTCCATTGCCCAGCTATCTGTCACTTTATTGTGAAGATAGTGGAAAAGGAAGGT
GGCTCCTACAAATGCCATCATTGCGATAAAGGAAAGGCCATCGTTGAAGATGCCTCTGCCGACA
GTGGTCCCAAAGATGGACCCCCACCCACGAGGAGCATCGTGGAAAAAGAAGACGTTCCAACCAC
GTCTTCAAAGCAAGTGGATTGATGTGATAACATGGTGGAGCACGACACACTTGTCTACTCCAAA
AATATCAAAGATACAGTCTCAGAAGACCAAAGGGCAATTGAGACTTTTCAACAAAGGGTAATAT
CCGGAAACCTCCTCGGATTCCATTGCCCAGCTATCTGTCACTTTATTGTGAAGATAGTGGAAAA
GGAAGGTGGCTCCTACAAATGCCATCATTGCGATAAAGGAAAGGCCATCGTTGAAGATGCCTCT
GCCGACAGTGGTCCCAAAGATGGACCCCCACCCACGAGGAGCATCGTGGAAAAAGAAGACGTTC
CAACCACGTCTTCAAAGCAAGTGGATTGATGTGATATCTCCACTGACGTAAGGGATGACGCACA
ATCCCACTATCCTTCGCAAGACCCTTCCTCTATATAAGGAAGTTCATTTCATTTGGAGAGGTAT
TAAAATCTTAATAGGTTTTGATAAAAGCGAACGTGGGGAAACCCGAACCAAACCTTCTTCTAAA
CTCTCTCTCATCTCTCTTAAAGCAAACTTCTCTCTTGTCTTTCTTGCGTGAGCGATCTTCAACG
TTGTCAGATCGTGCTTCGGCACCAGTACAACGTTTTCTTTCACTGAAGCGAAATCAAAGATCTC
TTTGTGGACACGTAGTGCGGCGCCATTAAATAACGTGTACTTGTCCTATTCTTGTCGGTGTGGT
CTTGGGAAAAGAAAGCTTGCTGGAGGCTGCTGTTCAGCCCCATACATTACTTGTTACGATTCTG
CTGACTTTCGGCGGGTGCAATATCTCTACTTCTGCTTGACGAGGTATTGTTGCCTGTACTTCTT
TCTTCTTCTTCTTGCTGATTGGTTCTATAAGAAATCTAGTATTTTCTTTGAAACAGAGTTTTCC
CGTGGTTTTCGAACTTGGAGAAAGATTGTTAAGCTTCTGTATATTCTGCCCAAATTTGTCGGGC
CCGCGGATGGCGAAAAACGTTGCGATTTTCGGCTTATTGTTTTCTCTTCTTGTGTTGGTTCCTT
CTCAGATCTTCGCCTGCAGGCTCCTCAGCCAAAACGACACCCCCATCTGTCTATCCACTGGCCC
CTGGATCTGCTGCCCAAACTAACTCCATGGTGACCCTGGGATGCCTGGTCAAGGGCTATTTCCC
TGAGCCAGTGACAGTGACCTGGAACTCTGGATCCCTGTCCAGCGGTGTGCACACCTTCCCAGCT
GTCCTGCAGTCTGACCTCTACACTCTGAGCAGCTCAGTGACTGTCCCCTCCAGCACCTGGCCCA

Figure 6E continued

GCGAGACCGTCACCTGCAACGTTGCCCACCCGGCCAGCAGCACCAAGGTGGACAAGAAAATTGT
GCCCAGGGATTGTGGTTGTAAGCCTTGCATATGTACAGTCCCAGAAGTATCATCTGTCTTCATC
TTCCCCCCAAAGCCCAAGGATGTGCTCACCATTACTCTGACTCCTAAGGTCACGTGTGTTGTGG
TAGACATCAGCAAGGATGATCCCGAGGTCCAGTTCAGCTGGTTTGTAGATGATGTGGAGGTGCA
CACAGCTCAGACGCAACCCCGGGAGGAGCAGTTCAACAGCACTTTCCGCTCAGTCAGTGAACTT
CCCATCATGCACCAGGACTGGCTCAATGGCAAGGAGCGATCGCTCACCATCACCATCACCATCA
CCATCACCATTAAAGGCCTATTTTCTTTAGTTTGAATTTACTGTTATTCGGTGTGCATTTCTAT
GTTTGGTGAGCGGTTTTCTGTGCTCAGAGTGTGTTTATTTTATGTAATTTAATTTCTTTGTGAG
CTCCTGTTTAGCAGGTCGTCCCTTCAGCAAGGACACAAAAAGATTTTAATTTTATTAAAAAAAA
AAAAAAAAAAGACCGGGAATTCGATATCAAGCTTATCGACCTGCAGATCGTTCAAACATTTGGC
AATAAAGTTTCTTAAGATTGAATCCTGTTGCCGGTCTTGCGATGATTATCATATAATTTCTGTT
GAATTACGTTAAGCATGTAATAATTAACATGTAATGCATGACGTTATTTATGAGATGGGTTTTT
ATGATTAGAGTCCCGCAATTATACATTTAATACGCGATAGAAAACAAAATATAGCGCGCAAACT
AGGATAAATTATCGCGCGCGGTGTCATCTATGTTACTAGATCTCTAGAGTCTCAAGCTTGGCGC
GCCATAAAATGATTATTTTATGAATATATTTCATTGTGCAAGTAGATAGAAATTACATATGTTA
CATAACACACGAAATAAACAAAAAAAGACAATCCAAAAACAAACACCCCAAAAAAAATAATCAC
TTTAGATAAACTCGTATGAGGAGAGGCACGTTCAGTGACTCGACGATTCCCGAGCAAAAAAAGT
CTCCCCGTCACACATATAGTGGGTGACGCAATTATCTTTAAAGTAATCCTTCTGTTGACTTGTC
ATTGATAACATCCAGTCTTCGTCAGGATTGCAAAGAATTATAGAAGGGATCCCACCTTTTATTT
TCTTCTTTTTTCCATATTTAGGGTTGACAGTGAAATCAGACTGGCAACCTATTAATTGCTTCCA
CAATGGGACGAACTTGAAGGGGATGTCGTCGATGATATTATAGGTGGCGTGTTCATCGTAGTTG
GTGAAATCGATGGTACCGTTCCAATAGTTGTGTCGTCCGAGACTTCTAGCCCAGGTGGTCTTTC
CGGTACGAGTTGGTCCGCAGATGTAGAGGCTGGGGTGTCGGATTCCATTCCTTCCATTGTCCTG
GTTAAATCGGCCATCCATTCAAGGTCAGATTGAGCTTGTTGGTATGAGACAGGATGTATGTAAG
TATAAGCGTCTATGCTTACATGGTATAGATGGGTTTCCCTCCAGGAGTGTAGATCTTCGTGGCA
GCGAAGATCTGATTCTGTGAAGGGCGACACATACGGTTCAGGTTGTGGAGGGAATAATTTGTTG
GCTGAATATTCCAGCCATTGAAGTTTTGTTGCCCATTCATGAGGGAATTCTTCCTTGATCATGT
CAAGATATTCCTCCTTAGACGTTGCAGTCTGGATAATAGTTCTCCATCGTGCGTCAGATTTGCG
AGGAGAGACCTTATGATCTCGGAAATCTCCTCTGGTTTTAATATCTCCGTCCTTTGATATGTAA
TCAAGGACTTGTTTAGAGTTTCTAGCTGGCTGGATATTAGGGTGATTTCCTTCAAAATCGAAAA
AAGAAGGATCCCTAATACAAGGTTTTTTATCAAGCTGGAGAAGAGCATGATAGTGGGTAGTGCC
ATCTTGATGAAGCTCAGAAGCAACACCAAGGAAGAAAATAAGAAAAGGTGTGAGTTTCTCCCAG
AGAAACTGGAATAAATCATCTCTTTGAGATGAGCACTTGGGATAGGTAAGGAAAACATATTTAG
ATTGGAGTCTGAAGTTCTTACTAGCAGAAGGCATGTTGTTGTGACTCCGAGGGGTTGCCTCAAA
CTCTATCTTATAACCGGCGTGGAGGCATGGAGGCAGGGGTATTTTGGTCATTTTAATAGATAGT
GGAAAATGACGTGGAATTTACTTAAAGACGAAGTCTTTGCGACAAGGGGGGGCCCACGCCGAAT
TTAATATTACCGGCGTGGCCCCCCCTTATCGCGAGTGCTTTAGCACGAGCGGTCCAGATTTAAA
GTAGAAAATTTCCCGCCCACTAGGGTTAAAGGTGTTCACACTATAAAAGCATATACGATGTGAT
GGTATTTGACTAGTGGCACTGGCCGTCGTTTTACAACGTCGTGACTGGGAAAACCCTGGCGTTA
CCCAACTTAATCGCCTTGCAGCACATCCCCCTTTCGCCAGCTGGCGTAATAGCGAAGAGGCCCG
CACCGATCGCCCTTCCCAACAGTTGCGCAGCCTGAATGGCGAATGCTAGAGCAGCTTGAGCTTG
GATCAGATTGTCGTTTCCCGCCTTCAGTTTAAACTATCAGTGTTTGACAGGATATATTGGCGGG
TAAACCTAAGAGAAAAGAGCGTTTA

Figure 6F, SEQ ID NO: 53

Expression cassette number 1462 from 2X35S promoter to NOS terminator. HA from influenza B/Wisconsin/1/2010 is underlined.

GTCAACATGGTGGAGCACGACACACTTGTCTACTCCAAAAATATCAAAGATACAGTCTCAGAAG
ACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCAT
CATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGA
TTGATGTGATAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCTCCTCGGAT
TCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAA
GATGGACCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTT
AAAGCAAACTTCTCTCTTGTCTTTCTTGCGTGAGCGATCTTCAACGTTGTCAGATCGTGCTTCG
GCACCAGTACAACGTTTTCTTTCACTGAAGCGAAATCAAAGATCTCTTTGTGGACACGTAGTGC
GGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGA
TTGGTTCTATAAGAAATCTAGTATTTTCTTTGAAACAGAGTTTTCCCGTGGTTTTCGAACTTGG
AGAAAGATTGTTAAGCTTCTGTATATTCTGCCCAAATTTGTCGGGCCCATGAAGGCAATAATTG
TACTACTCATGGTAGTAACATCCAATGCAGATCGAATCTGCACTGGGATAACATCTTCAAACTC
ACCTCATGTGGTCAAAACAGCTACTCAAGGGGAGGTCAATGTGACTGGCGTGATACCACTGACA
ACAACACCAACAAAATCTTATTTTGCAAATCTCAAAGGAACAAGGACCAGAGGGAAACTATGCC
CGGACTGTCTCAACTGTACAGATCTGGATGTGGCCTTGGGCAGGCCAATGTGTGTGGGGACCAC
ACCTTCTGCTAAAGCTTCAATACTCCACGAGGTCAGACCTGTTACATCCGGGTGCTTTCCTATA
ATGCACGACAGAACAAAAATCAGGCAACTACCCAATCTTCTCAGAGGATATGAAAATATCAGGT
TATCAACCCAAAACGTTATCGATGCAGAAAAAGCACCAGGAGGACCCTACAGACTTGGAACCTC
AGGATCTTGCCCTAACGCTACCAGTAAAATCGGATTTTTTGCAACAATGGCTTGGGCTGTCCCA
AAGGACAACTACAAAAATGCAACGAACCCACTAACAGTAGAAGTACCATACATTTGTACAGAAG
GGGAAGACCAAATTACTGTTTGGGGGTTCCATTCAGATAACAAAACCCAAATGAAGAGCCTCTA
TGGAGACTCAAATCCTCAAAAGTTCACCTCATCTGCTAATGGAGTAACCACACATTATGTTTCT
CAGATTGGCGACTTCCCAGATCAAACAGAAGACGGAGGACTACCACAAAGCGGCAGAATTGTTG
TTGATTACATGATGCAAAAACCTGGGAAAACAGGAACAATTGTCTATCAAAGAGGTGTTTTGTT
GCCTCAAAAGGTGTGGTGCGCGAGTGGCAGGAGCAAAGTAATAAAGGGTCATTGCCTTTAATT
GGTGAAGCAGATTGCCTTCATGAAAAATACGGTGGATTAAACAAAAGCAAGCCTTACTACACAG
GAGAACATGCAAAAGCCATAGGAAATTGCCCAATATGGGTAAAAACACCTTTGAAGCTTGCCAA
TGGAACCAAATATAGACCTCCTGCAAAACTATTGAAGGAAAGGGGTTTCTTCGGAGCTATTGCT
GGTTTCCTAGAAGGAGGATGGGAAGGAATGATTGCAGGTTGGCACGGATACACATCTCACGGAG
CACATGGAGTGGCAGTGGCGGCAGACCTTAAGAGTACACAAGAAGCTATAAATAAGATAACAAA
AAATCTCAATTCTTTGAGTGAGCTAGAAGTAAAGAACCTTCAAAGACTAAGTGGTGCCATGGAT
GAACTCCACAACGAAATACTCGAGCTGGATGAGAAAGTGGATGATCTCAGAGCTGACACTATAA
GCTCACAAATAGAACTTGCAGTCTTGCTTTCCAACGAAGGAATAATAAACAGTGAAGACGAGCA
TCTATTGGCACTTGAGAGAAAACTAAAGAAAATGCTGGGTCCCTCTGCTGTAGACATAGGAAAC

Figure 6F continued

GGATGCTTCGAAACCAAACACAAATGCAACCAGACCTGCTTAGACAGGATAGCTGCTGGCACCT
TTAATGCAGGAGAATTTTCTCTCCCCACTTTTGATTCATTGAACATTACTGCTGCATCTTTAAA
TGATGATGGATTGGATAACCATACTATACTGCTCTATTACTCAACTGCTGCTTCTAGTTTGGCT
GTAACATTAATGCTAGCTATTTTTATTGTTTATATGGTCTCCAGAGACAACGTTTCATGCTCCA
TCTGTCTATAAAGGCCTATTTTCTTTAGTTTGAATTTACTGTTATTCGGTGTGCATTTCTATGT
TTGGTGAGCGGTTTTCTGTGCTCAGAGTGTGTTTATTTTATGTAATTTAATTTCTTTGTGAGCT
CCTGTTTAGCAGGTCGTCCCTTCAGCAAGGACACAAAAAGATTTTAATTTTATTAAAAAAAAAA
AAAAAAAAGACCGGGAATTCGATATCAAGCTTATCGACCTGCAGATCGTTCAAACATTTGGCAA
TAAAGTTTCTTAAGATTGAATCCTGTTGCCGGTCTTGCGATGATTATCATATAATTTCTGTTGA
ATTACGTTAAGCATGTAATAATTAACATGTAATGCATGACGTTATTTATGAGATGGGTTTTTAT
GATTAGAGTCCCGCAATTATACATTTAATACGCGATAGAAAACAAAATATAGCGCGCAAACTAG
GATAAATTATCGCGCGCGGTGTCATCTATGTTACTAGAT

Figure 6G, SEQ ID NO: 54
Amino acid sequence of HA from influenza B/Wisconsin/1/2010

MKAIIVLLMVVTSNADRICTGITSSNSPHVVKTATQGEVNVTGVIPLTTTPTKSYFANLKGTRT
RGKLCPDCLNCTDLDVALGRPMCVGTTPSAKASILHEVRPVTSGCFPIMHDRTKIRQLPNLLRG
YENIRLSTQNVIDAEKAPGGPYRLGTSGSCPNATSKIGFFATMAWAVPKDNYKNATNPLTVEVP
YICTEGEDQITVWGFHSDNKTQMKSLYGDSNPQKFTSSANGVTTHYVSQIGDFPDQTEDGGLPQ
SGRIVVDYMMQKPGKTGTIVYQRGVLLPQKVWCASGRSKVIKGSLPLIGEADCLHEKYGGLNKS
KPYYTGEHAKAIGNCPIWVKTPLKLANGTKYRPPAKLLKERGFFGAIAGFLEGGWEGMIAGWHG
YTSHGAHGVAVAADLKSTQEAINKITKNLNSLSELEVKNLQRLSGAMDELHNEILELDEKVDDL
RADTISSQIELAVLLSNEGIINSEDEHLLALERKLKKMLGPSAVDIGNGCFETKHKCNQTCLDR
IAAGTFNAGEFSLPTFDSLNITAASLNDDGLDNHTILLYYSTAASSLAVTLMLAIFIVYMVSRD
NVSCSICL*

Schematic representation of construct number 1462

Figure 7: C-2X35S/CPMV-HT/HA B Wisconsin with deleted proteolytic loop/NOS into BeYDV(m)+Replicase amplification system (Construct number 1467)

Figure 7A, SEQ ID NO: 55
HAB110(PrL-).r

TCCTTCCCATCCTCCACCAGGAGGTCTATATTTGGTTCCATTGGCAAGCTTCAAAG

Figure 7B, SEQ ID NO: 56
HAB110(PrL-).c

ATATAGACCTCCTGGTGGAGGATGGGAAGGAATGATTGCAGGTTGGCACGGA

Figure 7C, SEQ ID NO: 57
Expression cassette number 1467 from 2X35S promoter to NOS terminator. HA from influenza B/Wisconsin/1/2010 with deleted proteolytic loop is underlined.

GTCAACATGGTGGAGCACGACACACTTGTCTACTCCAAAAATATCAAAGATACAGTCTCAGAAG
ACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCAT
CATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGA
TTGATGTGATAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCTCCTCGGAT
TCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAA
GATGGACCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTT
AAAGCAAACTTCTCTCTTGTCTTTCTTGCGTGAGCGATCTTCAACGTTGTCAGATCGTGCTTCG
GCACCAGTACAACGTTTTCTTTCACTGAAGCGAAATCAAAGATCTCTTTGTGGACACGTAGTGC
GGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGA
TTGGTTCTATAAGAAATCTAGTATTTTCTTTGAAACAGAGTTTTCCCGTGGTTTTCGAACTTGG
AGAAAGATTGTTAAGCTTCTGTATATTCTGCCCAAATTTGTCGGGCCCATGAAGGCAATAATTG
TACTACTCATGGTAGTAACATCCAATGCAGATCGAATCTGCACTGGGATAACATCTTCAAACTC
ACCTCATGTGGTCAAAACAGCTACTCAAGGGGAGGTCAATGTGACTGGCGTGATACCACTGACA
ACAACACCAACAAAATCTTATTTTGCAAATCTCAAAGGAACAAGGACCAGAGGGAAACTATGCC
CGGACTGTCTCAACTGTACAGATCTGGATGTGGCCTTGGGCAGGCCAATGTGTGTGGGGACCAC
ACCTTCTGCTAAAGCTTCAATACTCCACGAGGTCAGACCTGTTACATCCGGGTGCTTTCCTATA
ATGCACGACAGAACAAAAATCAGGCAACTACCCAATCTTCTCAGAGGATATGAAAATATCAGGT
TATCAACCCAAAACGTTATCGATGCAGAAAAAGCACCAGGAGGACCCTACAGACTTGGAACCTC
AGGATCTTGCCCTAACGCTACCAGTAAAATCGGATTTTTTGCAACAATGGCTTGGGCTGTCCCA
AAGGACAACTACAAAAATGCAACGAACCCACTAACAGTAGAAGTACCATACATTTGTACAGAAG
GGGAAGACCAAATTACTGTTTGGGGGTTCCATTCAGATAACAAAACCCAAATGAAGAGCCTCTA

Figure 7C continued

TGGAGACTCAAATCCTCAAAAGTTCACCTCATCTGCTAATGGAGTAACCACACATTATGTTTCT
CAGATTGGCGACTTCCCAGATCAAACAGAAGACGGAGGACTACCACAAAGCGGCAGAATTGTTG
TTGATTACATGATGCAAAAACCTGGGAAAACAGGAACAATTGTCTATCAAAGAGGTGTTTTGTT
GCCTCAAAAGGTGTGGTGCGCGAGTGGCAGGAGCAAAGTAATAAAAGGGTCATTGCCTTTAATT
GGTGAAGCAGATTGCCTTCATGAAAAATACGGTGGATTAAACAAAAGCAAGCCTTACTACACAG
GAGAACATGCAAAAGCCATAGGAAATTGCCCAATATGGGTAAAAACACCTTTGAAGCTTGCCAA
TGGAACCAAATATAGACCTCCTGGTGGAGGATGGGAAGGAATGATTGCAGGTTGGCACGGATAC
ACATCTCACGGAGCACATGGAGTGGCAGTGGCGGCAGACCTTAAGAGTACACAAGAAGCTATAA
ATAAGATAACAAAAAATCTCAATTCTTTGAGTGAGCTAGAAGTAAAGAACCTTCAAAGACTAAG
TGGTGCCATGGATGAACTCCACAACGAAATACTCGAGCTGGATGAGAAAGTGGATGATCTCAGA
GCTGACACTATAAGCTCACAAATAGAACTTGCAGTCTTGCTTTCCAACGAAGGAATAATAAACA
GTGAAGACGAGCATCTATTGGCACTTGAGAGAAAACTAAAGAAAATGCTGGGTCCCTCTGCTGT
AGACATAGGAAACGGATGCTTCGAAACCAAACACAAATGCAACCAGACCTGCTTAGACAGGATA
GCTGCTGGCACCTTTAATGCAGGAGAATTTTCTCTCCCCACTTTTGATTCATTGAACATTACTG
CTGCATCTTTAAATGATGATGGATTGGATAACCATACTATACTGCTCTATTACTCAACTGCTGC
TTCTAGTTTGGCTGTAACATTAATGCTAGCTATTTTTATTGTTTATATGGTCTCCAGAGACAAC
GTTTCATGCTCCATCTGTCTATAAAGGCCTATTTTCTTTAGTTTGAATTTACTGTTATTCGGTG
TGCATTTCTATGTTTGGTGAGCGGTTTTCTGTGCTCAGAGTGTGTTTATTTTATGTAATTTAAT
TTCTTTGTGAGCTCCTGTTTAGCAGGTCGTCCCTTCAGCAAGGACACAAAAAGATTTTAATTTT
ATTAAAAAAAAAAAAAAAAAAGACCGGGAATTCGATATCAAGCTTATCGACCTGCAGATCGTTC
AAACATTTGGCAATAAAGTTTCTTAAGATTGAATCCTGTTGCCGGTCTTGCGATGATTATCATA
TAATTTCTGTTGAATTACGTTAAGCATGTAATAATTAACATGTAATGCATGACGTTATTTATGA
GATGGGTTTTTATGATTAGAGTCCCGCAATTATACATTTAATACGCGATAGAAAACAAAATATA
GCGCGCAAACTAGGATAAATTATCGCGCGCGGTGTCATCTATGTTACTAGAT

Figure 7D, SEQ ID NO: 58
Amino acid sequence of HA from influenza B/Wisconsin/1/2010 with deleted proteolytic loop MKAIIVLLMVVTSNADRICTGITSSNSPHVVKTATQGEVNVTGVIPLTTTPTKSYFANLKGTRT
RGKLCPDCLNCTDLDVALGRPMCVGTTPSAKASILHEVRPVTSGCFPIMHDRTKIRQLPNLLRG
YENIRLSTQNVIDAEKAPGGPYRLGTSGSCPNATSKIGFFATMAWAVPKDNYKNATNPLTVEVP
YICTEGEDQITVWGFHSDNKTQMKSLYGDSNPQKFTSSANGVTTHYVSQIGDFPDQTEDGGLPQ
SGRIVVDYMMQKPGKTGTIVYQRGVLLPQKVWCASGRSKVIKGSLPLIGEADCLHEKYGGLNKS
KPYYTGEHAKAIGNCPIWVKTPLKLANGTKYRPPGGGWEGMIAGWHGYTSHGAHGVAVAADLKS
TQEAINKITKNLNSLSELEVKNLQRLSGAMDELHNEILELDEKVDDLRADTISSQIELAVLLSN
EGIINSEDEHLLALERKLKKMLGPSAVDIGNGCFETKHKCNQTCLDRIAAGTFNAGEFSLPTFD
SLNITAASLNDDGLDNHTILLYYSTAASSLAVTLMLAIFIVYMVSRDNVSCSICL*

Schematic representation of construct number 1467

Figure 8: A-2X35S/CPMV-HT/PDISP/HA B Brisbane with deleted proteolytic loop/NOS (Construct number 1039)

Figure 8A (SEQ ID NO: 15)

Expression cassette number 1039 from 2X35S promoter to Nos terminator. PDISP/HA from influenza B/Brisbane/60/2008 with deleted proteolytic loop is underlined.

GTCAACATGGTGGAGCACGACACACTTGTCTACTCCAAAAATATCAAAGATACAGTCTCAGAAG
ACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCAT
CATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGA
TTGATGTGATAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCTCCTCGGAT
TCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAA
GATGGACCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTT
AAAGCAAACTTCTCTCTTGTCTTTCTTGCGTGAGCGATCTTCAACGTTGTCAGATCGTGCTTCG
GCACCAGTACAACGTTTTCTTTCACTGAAGCGAAATCAAAGATCTCTTTGTGGACACGTAGTGC
GGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGA
TTGGTTCTATAAGAAATCTAGTATTTTCTTTGAAACAGAGTTTTCCCGTGGTTTTCGAACTTGG
AGAAAGATTGTTAAGCTTCTGTATATTCTGCCCAAATTTGTCGGGCCCATGGCGAAAAACGTTG
CGATTTTCGGCTTATTGTTTTCTCTTCTTGTGTTGGTTCCTTCTCAGATCTTCGCCGATCGAAT
CTGCACTGGAATAACATCGTCAAACTCACCACATGTCGTCAAAACTGCTACTCAAGGGGAGGTC
AATGTGACTGGTGTAATACCACTGACAACAACACCCACCAAATCTCATTTTGCAAATCTCAAAG
GAACAGAAACCAGGGGGAAACTATGCCCAAAATGCCTCAACTGCACAGATCTGGACGTAGCCTT
GGGCAGACCAAAATGCACGGGGAAAATACCCTCGGCAAGAGTTTCAATACTCCATGAAGTCAGA
CCTGTTACATCTGGGTGCTTTCCTATAATGCACGACAGAACAAAAATTAGACAGCTGCCTAACC
TTCTCCGAGGATACGAACATATCAGGTTATCAACCCATAACGTTATCAATGCAGAAAATGCACC
AGGAGGACCCTACAAAATTGGAACCTCAGGGTCTTGCCCTAACATTACCAATGGAAACGGATTT
TTCGCAACAATGGCTTGGGCCGTCCCAAAAAACGACAAAAACAAAACAGCAACAAATCCATTAA
CAATAGAAGTACCATACATTTGTACAGAAGGAGAAGACCAAATTACCGTTTGGGGGTTCCACTC
TGACAACGAGACCCAAATGGCAAAGCTCTATGGGGACTCAAAGCCCCAGAAGTTCACCTCATCT
GCCAACGGAGTGACCACACATTACGTTTCACAGATTGGTGGCTTCCCAAATCAAACAGAAGACG
GAGGACTACCACAAAGTGGTAGAATTGTTGTTGATTACATGGTGCAAAAATCTGGGAAAACAGG
AACAATTACCTATCAAAGGGGTATTTTATTGCCTCAAAAGGTGTGGTGCGCAAGTGGCAGGAGC
AAGGTAATAAAAGGATCCTTGCCTTTAATTGGAGAAGCAGATTGCCTCCACGAAAAATACGGTG
GATTAAACAAAAGCAAGCCTTACTACACAGGGGAACATGCAAAGGCCATAGGAAATTGCCCAAT
ATGGGTGAAAACACCCTTGAAGCTGGCCAATGGAACCAAATATAGACCTCCTGGTGGAGGATGG
GAAGGAATGATTGCAGGTTGGCACGGATACACATCCCATGGGGCACATGGAGTAGCGGTGGCAG
CAGACCTTAAGAGCACTCAAGAGGCCATAAACAAGATAACAAAAAATCTCAACTCTTTGAGTGA

Figure 8A continued

GCTGGAAGTAAAGAATCTTCAAAGACTAAGCGGTGCCATGGATGAACTCCACAACGAAATACTA
GAACTAGATGAGAAAGTGGATGATCTCAGAGCTGATACAATAAGCTCACAAATAGAACTCGCAG
TCCTGCTTTCCAATGAAGGAATAATAAACAGTGAAGATGAACATCTCTTGGCGCTTGAAAGAAA
GCTGAAGAAAATGCTGGGCCCCTCTGCTGTAGAGATAGGGAATGGATGCTTTGAAACCAAACAC
AAGTGCAACCAGACCTGTCTCGACAGAATAGCTGCTGGTACCTTTGATGCAGGAGAATTTTCTC
TCCCCACCTTTGATTCACTGAATATTACTGCTGCATCTTTAAATGACGATGGATTGGATAATCA
TACTATACTGCTTTACTACTCAACTGCTGCCTCCAGTTTGGCTGTAACACTGATGATAGCTATC
TTTGTTGTTTATATGGTCTCCAGAGACAATGTTTCTTGCTCCATCTGTCTATAAAGGCCTATTT
TCTTTAGTTTGAATTTACTGTTATTCGGTGTGCATTTCTATGTTTGGTGAGCGGTTTTCTGTGC
TCAGAGTGTGTTTATTTTATGTAATTTAATTTCTTTGTGAGCTCCTGTTTAGCAGGTCGTCCCT
TCAGCAAGGACACAAAAAGATTTTAATTTTATTAAAAAAAAAAAAAAAAAAGACCGGGAATTCG
ATATCAAGCTTATCGACCTGCAGATCGTTCAAACATTTGGCAATAAAGTTTCTTAAGATTGAAT
CCTGTTGCCGGTCTTGCGATGATTATCATATAATTTCTGTTGAATTACGTTAAGCATGTAATAA
TTAACATGTAATGCATGACGTTATTTATGAGATGGGTTTTTATGATTAGAGTCCCGCAATTATA
CATTTAATACGCGATAGAAAACAAAATATAGCGCGCAAACTAGGATAAATTATCGCGCGCGGTG
TCATCTATGTTACTAGAT

Figure 8B,
Schematic representation of construct number 1039
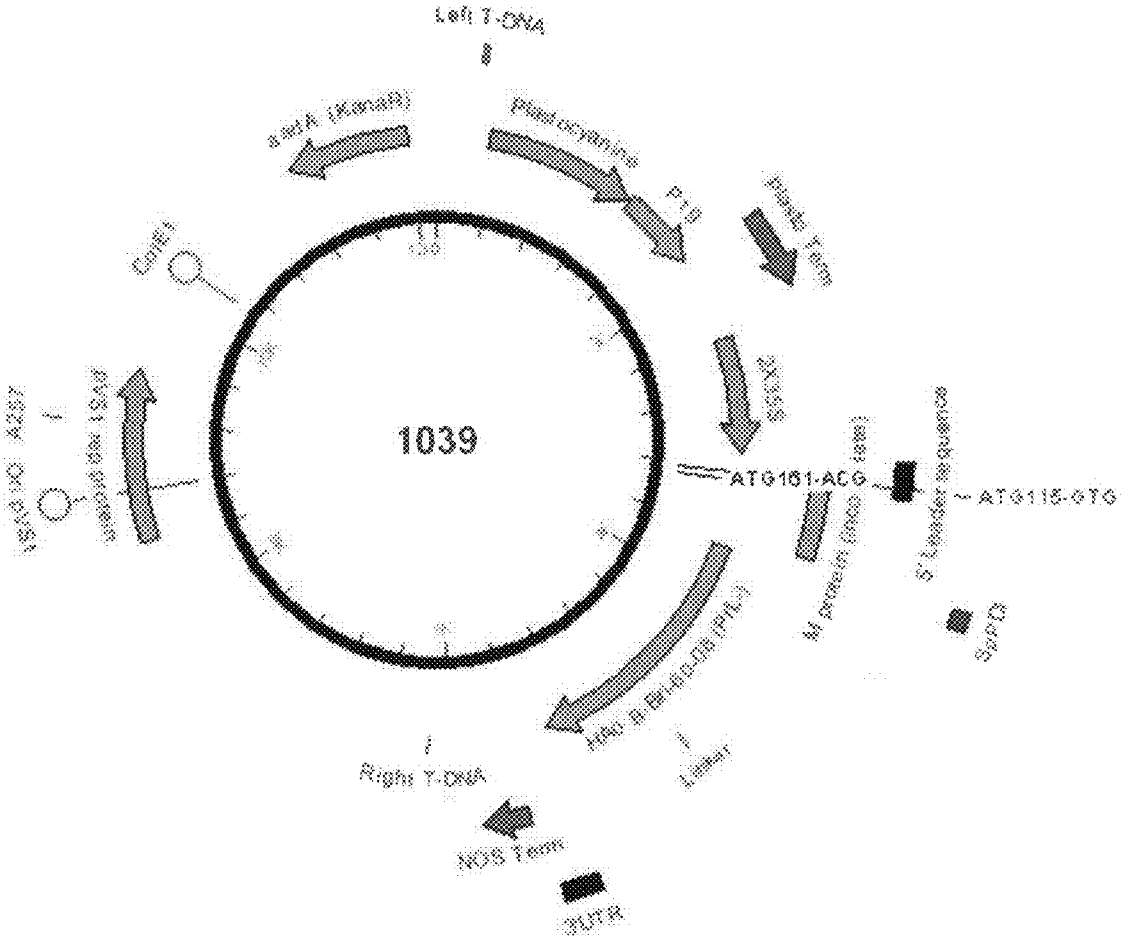

| Construct number | Hemagglutination capacity (HA units / mg protein)[a] |
|---|---|
| 1008 | 533 |
| 1008 + 1261 (4:1) | 3200 |
| 1059 | 4267 |
| 1059 + 1261 (4:1) | 34133 |

[a] Inverse of the smallest amount of total protein required for positive hemagglutination reaction in a final volume of 200 µl.

Fusion peptide

| | | | | | | | | | | | | | 370 | | | | | | | | | 380 | | | | | | | | | 390 | | | | | | | | | 400 |
|---|---|---|---|---|---|---|---|---|---|---|---|---|---|---|---|---|---|---|---|---|---|---|---|---|---|---|---|---|---|---|---|---|---|---|---|---|---|---|---|---|
| H1 New Cal | - | - | - | - | - | - | - | - | - | - | - | - | I | P | S | I | Q | S | R | G | L | F | G | A | I | A | G | F | I | E | G | G | W | T | G | M | V | D | G | W | Y |
| H1 Brisbane | - | - | - | - | - | - | - | - | - | - | - | - | I | P | S | I | Q | S | R | G | L | F | G | A | I | A | G | F | I | E | G | G | W | T | G | M | V | D | G | W | Y |
| H1 Sol Islands | - | - | - | - | - | - | - | - | - | - | - | - | I | P | S | I | Q | S | R | G | L | F | G | A | I | A | G | F | I | E | G | G | W | T | G | M | V | D | G | W | Y |
| H2A_Singapore | - | - | - | - | - | - | - | - | - | - | - | V | P | Q | I | E | S | R | G | L | F | G | A | I | A | G | F | I | E | G | G | W | Q | G | M | V | D | G | W | Y | |
| H3A_Brisbane | - | - | - | - | - | - | - | - | - | - | - | V | P | E | K | Q | T | R | G | I | F | G | A | I | A | G | F | I | E | N | G | W | E | G | M | V | D | G | W | Y | |
| H3A_WCN | - | - | - | - | - | - | - | - | - | - | - | V | P | E | K | Q | T | R | G | I | F | G | A | I | A | G | F | I | E | N | G | W | E | G | M | V | D | G | W | Y | |
| H5 Anhui | - | - | - | - | - | - | - | - | S | P | L | R | E | R | R | R | K | - | R | G | L | F | G | A | I | A | G | F | I | E | G | G | W | Q | G | M | V | D | G | W | Y |
| H5 Indo | - | - | - | - | - | - | - | - | S | P | Q | R | E | S | R | R | K | K | R | G | L | F | G | A | I | A | G | F | I | E | G | G | W | Q | G | M | V | D | G | W | Y |
| H5 Viet Nam | - | - | - | - | - | - | - | - | S | P | Q | R | E | R | R | R | K | K | R | G | L | F | G | A | I | A | G | F | I | E | G | G | W | Q | G | M | V | D | G | W | Y |
| H6 Teal_HK | - | - | - | - | - | - | - | - | - | - | - | V | P | Q | I | E | T | R | G | L | F | G | A | I | A | G | F | I | E | G | G | W | T | G | M | I | D | G | W | Y | |
| H7 Eq_Prague | - | V | P | E | A | P | A | H | K | Q | L | T | H | H | M | R | K | K | R | G | L | F | G | A | I | A | G | F | I | E | N | G | W | E | G | L | I | D | G | W | Y |
| H9A_HK | - | - | - | - | - | - | - | - | - | - | - | V | P | A | R | S | S | R | G | L | F | G | A | I | A | G | F | I | E | G | G | W | P | G | L | V | A | G | W | Y | |
| B_Florida | L | K | L | A | N | G | T | K | Y | R | P | P | A | K | L | L | K | E | R | G | F | F | G | A | I | A | G | F | L | E | G | G | W | E | G | M | I | A | G | W | H |
| B_Malaysia | L | K | L | A | N | G | T | K | Y | R | P | P | A | K | L | L | K | E | R | G | F | F | G | A | I | A | G | F | L | E | G | G | W | E | G | M | I | A | G | W | H |

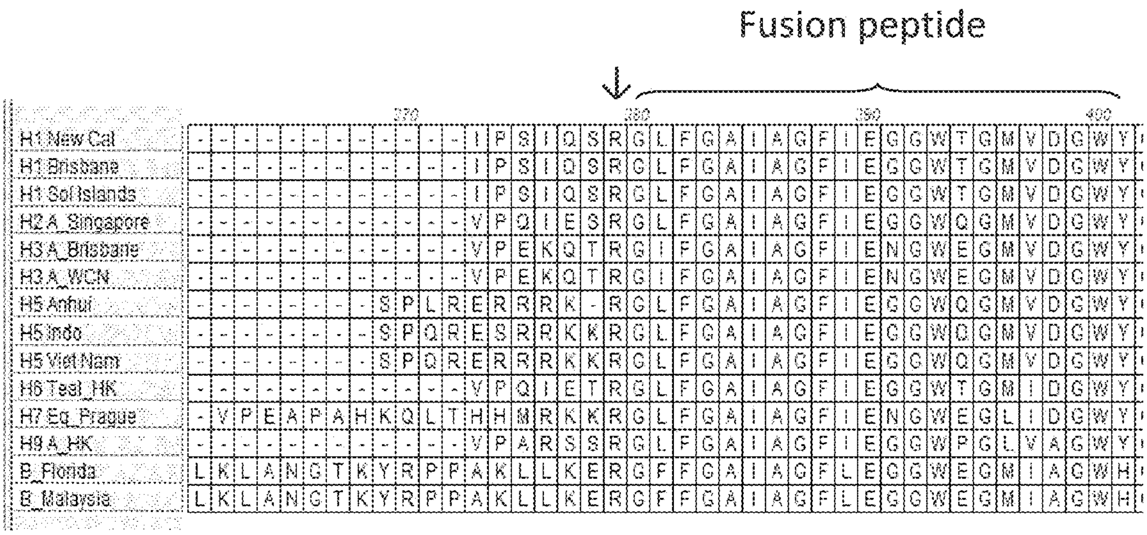

Figure 15

| Construct number | Hemagglutination capacity (HA titer)[a] |
|---|---|
| 1462 (0.8) | 136 ± 48 |
| 1467 (0.8) | 2660 ± 384 |
| 1462 + 1261 (0.8:0.2) | 941 ± 192 |
| 1467 + 1261 (0.8:0.2) | 4344 ± 1536 |

[a] Inverse of the highest dilution capable of agglutinating red blood cells.

| Construct number | Regulatory elements | BeYDV | Proteolytic loop | M2 co-expression | Hemagglutination capacity (HA unit/ml) |
|---|---|---|---|---|---|
| 1008 | CPMV-HT | Yes | Present | No | 1216 |
| 1008 + 1261 | CPMV-HT | Yes | Present | Yes | 5696 |
| 1039 | CPMV-HT | No | Removed | No | 141 |
| 1039 + 1261 | CPMV-HT | No | Removed | Yes | 2944 |
| 1059 | CPMV-HT | Yes | Removed | No | 10197 |
| 1059 + 1261 | CPMV-HT | Yes | Removed | Yes | 43008 |

Figure 18A

Figure 18B

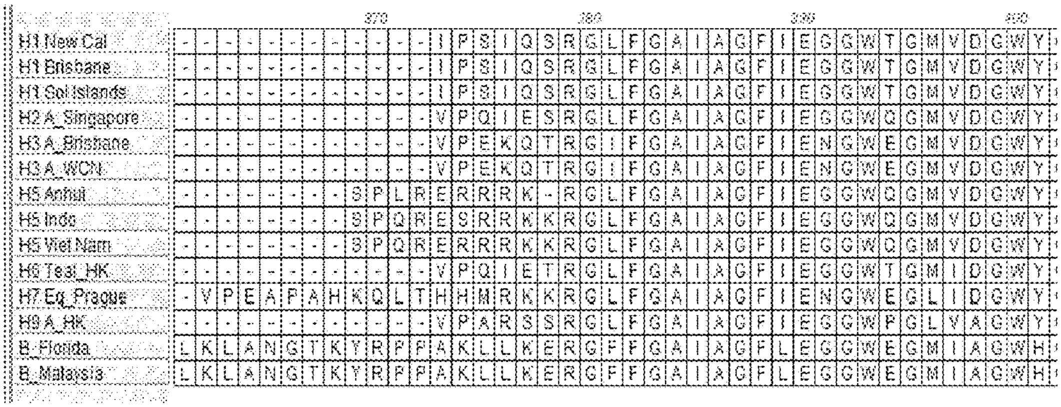

Figure 18C

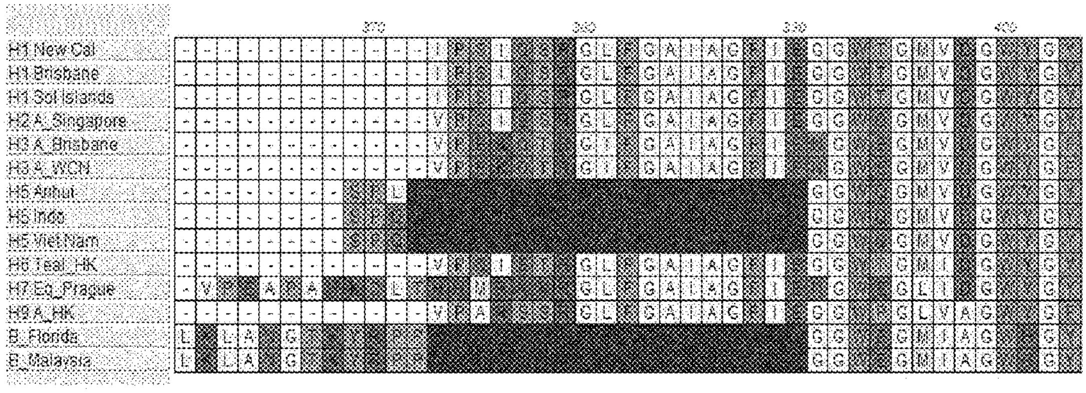

HA0 →(Clara-like / Furin-like)→ HA1-HA2

| | | | | | | | | | | | 370 | | | | | | | | | 380 | | | | | | | | | 390 | | | | | | | | | 400 |
|---|---|---|---|---|---|---|---|---|---|---|---|---|---|---|---|---|---|---|---|---|---|---|---|---|---|---|---|---|---|---|---|---|---|---|---|---|---|---|
| H1 New Cal | - | - | - | - | - | - | - | - | - | - | I | P | S | I | Q | S | R | G | L | F | G | A | I | A | G | F | I | E | G | G | W | T | G | M | V | D | G | W | Y |
| H1 Brisbane | - | - | - | - | - | - | - | - | - | - | I | P | S | I | Q | S | R | G | L | F | G | A | I | A | G | F | I | E | G | G | W | T | G | M | V | D | G | W | Y |
| H1 Sol Islands | - | - | - | - | - | - | - | - | - | - | I | P | S | I | Q | S | R | G | L | F | G | A | I | A | G | F | I | E | G | G | W | T | G | M | V | D | G | W | Y |
| H2 A_Singapore | - | - | - | - | - | - | - | - | - | - | V | P | Q | I | E | S | R | G | L | F | G | A | I | A | G | F | I | E | G | G | W | Q | G | M | V | D | G | W | Y |
| H3 A_Brisbane | - | - | - | - | - | - | - | - | - | - | V | P | E | K | Q | T | R | G | I | F | G | A | I | A | G | F | I | E | N | G | W | E | G | M | V | D | G | W | Y |
| H3 A_WCN | - | - | - | - | - | - | - | - | - | - | V | P | E | K | Q | T | R | G | I | F | G | A | I | A | G | F | I | E | N | G | W | E | G | M | V | D | G | W | Y |
| H5 Anhui | - | - | - | - | - | - | - | S | P | L | R | E | R | R | R | K | - | R | G | L | F | G | A | I | A | G | F | I | E | G | G | W | Q | G | M | V | D | G | W | Y |
| H5 Indo | - | - | - | - | - | - | - | S | P | Q | R | E | S | R | R | K | K | R | G | L | F | G | A | I | A | G | F | I | E | G | G | W | Q | G | M | V | D | G | W | Y |
| H5 VietNam | - | - | - | - | - | - | - | S | P | Q | R | E | R | R | R | K | K | R | G | L | F | G | A | I | A | G | F | I | E | G | G | W | Q | G | M | V | D | G | W | Y |
| H6 Teal_HK | - | - | - | - | - | - | - | - | - | - | V | P | Q | I | E | T | R | G | L | F | G | A | I | A | G | F | I | E | G | G | W | T | G | M | I | D | G | W | Y |
| H7 Eq_Prague | - | V | P | E | A | P | A | H | K | Q | L | T | H | H | M | R | K | K | R | G | L | F | G | A | I | A | G | F | I | E | N | G | W | E | G | L | I | D | G | W | Y |
| H9 A_HK | - | - | - | - | - | - | - | - | - | - | V | P | A | R | S | S | R | G | L | F | G | A | I | A | G | F | I | E | G | G | W | P | G | L | V | A | G | W | Y |
| B_Florida | L | K | L | A | N | G | T | K | Y | R | P | P | A | K | L | L | K | E | R | G | F | F | G | A | I | A | G | F | L | E | G | G | W | E | G | M | I | A | G | W | H |
| B_Malaysia | L | K | L | A | N | G | T | K | Y | R | P | P | A | K | L | L | K | E | R | G | F | F | G | A | I | A | G | F | L | E | G | G | W | E | G | M | I | A | G | W | H |

Figure 19
HA0
HA1-HA2
Clara-like
Furin-like

| Strain | Natural sequence | Abolition of precursor cleavage site |
|---|---|---|
| H5/Indo | TGLRNSPQ**RESRRKKR**↓GLF | TGLRNSPQTETR↓GLF<br>TGLRNSPQTETQGLF |

Figure 21: Deletions/replacement approaches for type B HA

Figure 21 A

Primary sequence of the native B/Brisbane/60/2008 (SEQ ID NO: 16)

DRICTGITSSNSPHVVKTATQGEVNVTGVIPLTTTPTKSHFANLKGTETRGKLCPKCLNCTDLD
VALGRPKCTGKIPSARVSILHEVRPVTSGCFPIMHDRTKIRQLPNLLRGYEHIRLSTHNVINAE
NAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSG
KTGTITYQRGILLPQKVWCASGRSKVIKGSLPLIGEADCLHEKYGGLNKSKPYYTGEHAKAIGN
CPIWVKTPLKLANGTKYRPPAKLLKERGFFGAIAGFLEGGWEGMIAGWHGYTSHGAHGVAVAAD
LKSTQEAINKITKNLNSLSELEVKNLQRLSGAMDELHNEILELDEKVDDLRADTISSQIELAVL
LSNEGIINSEDEHLLALERKLKKMLGPSAVEIGNGCFETKHKCNQTCLDRIAAGTFDAGEFSLP
TFDSLNITAASLNDDGLDNHTILLYYSTAASSLAVTLMIAIFVVYMVSRDNVSCSICL

Figure 21 B

Δ proteolytic loop of type B HA (SEQ ID NO:17)

DRICTGITSSNSPHVVKTATQGEVNVTGVIPLTTTPTKSHFANLKGTETRGKLCPKCLNCTDLD
VALGRPKCTGKIPSARVSILHEVRPVTSGCFPIMHDRTKIRQLPNLLRGYEHIRLSTHNVINAE
NAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSG
KTGTITYQRGILLPQKVWCASGRSKVIKGSLPLIGEADCLHEKYGGLNKSKPYYTGEHAKAIGN
CPIWVKTPLKLANGTKYRPP-*GG*-
GWEGMIAGWHGYTSHGAHGVAVAADLKSTQEAINKITKNLNSLSELEVKNLQRLSGAMDELHNE
ILELDEKVDDLRADTISSQIELAVLLSNEGIINSEDEHLLALERKLKKMLGPSAVEIGNGCFET
KHKCNQTCLDRIAAGTFDAGEFSLPTFDSLNITAASLNDDGLDNHTILLYYSTAASSLAVTLMI
AIFVVYMVSRDNVSCSICL

Figure 21 C

Replacement of cleavage site of type B HA by a linker (SEQ ID NO:18)

DRICTGITSSNSPHVVKTATQGEVNVTGVIPLTTTPTKSHFANLKGTETRGKLCPKCLNCTDLD
VALGRPKCTGKIPSARVSILHEVRPVTSGCFPIMHDRTKIRQLPNLLRGYEHIRLSTHNVINAE
NAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSG
KTGTITYQRGILLPQKVWCASGRSKVIKGSLPLIGEADCLHEKYGGLNKSKPYYTGEHAKAIGN
CPIWVKTPLKLANGTKYR *-GSSSGSSSG-*
GFFGAIAGFLEGGWEGMIAGWHGYTSHGAHGVAVAADLKSTQEAINKITKNLNSLSELEVKNLQ
RLSGAMDELHNEILELDEKVDDLRADTISSQIELAVLLSNEGIINSEDEHLLALERKLKKMLGP
SAVEIGNGCFETKHKCNQTCLDRIAAGTFDAGEFSLPTFDSLNITAASLNDDGLDNHTILLYYS
TAASSLAVTLMIAIFVVYMVSRDNVSCSICL

Figure 21 D

Deletions/replacement approaches for H3

Primary sequence of the native H3 A/Perth/16/2009 (SEQ ID NO:19

QKLPGNDNSTATLCLGHHAVPNGTIVKTITNDQIEVTNATELVQSSSTGEICDSPHQILDGKNC
TLIDALLGDPQCDGFQNKKWDLFVERSKAYSNCYPYDVPDYASLRSLVASSGTLEFNNESFNWT
GVTQNGTSSACIRRSKNSFFSRLNWLTHLNFKYPALNVTMPNNEQFDKLYIWGVHHPGTDKDQI
FLYAQASGRITVSTKRSQQTVSPNIGSRPRVRNIPSRISIYWTIVKPGDILLINSTGNLIAPRG
YFKIRSGKSSIMRSDAPIGKCNSECITPNGSIPNDKPFQNVNRITYGACPRYVKQNTLKLATGM
RNVPEKQTRGIFGAIAGFIENGWEGMVDGWYGFRHQNSEGRGQAADLKSTQAAIDQINGKLNRL
IGKTNEKFHQIEKEFSEVEGRIQDLEKYVEDTKIDLWSYNAELLVALENQHTIDLTDSEMNKLF
EKTKKQLRENAEDMGNGCFKIYHKCDNACIGSIRNGTYDHDVYRDEALNNRFQIKGVELKSGYK
DWILWISFAISCFLLCVALLGFIMWACQKGNIRCNICI

Figure 21 E

Δ proteolytic loop H3 (in BeYDV, 1096) (SEQ ID NO:20)

QKLPGNDNSTATLCLGHHAVPNGTIVKTITNDQIEVTNATELVQSSSTGEICDSPHQILDGKNC
TLIDALLGDPQCDGFQNKKWDLFVERSKAYSNCYPYDVPDYASLRSLVASSGTLEFNNESFNWT
GVTQNGTSSACIRRSKNSFFSRLNWLTHLNFKYPALNVTMPNNEQFDKLYIWGVHHPGTDKDQI
FLYAQASGRITVSTKRSQQTVSPNIGSRPRVRNIPSRISIYWTIVKPGDILLINSTGNLIAPRG
YFKIRSGKSSIMRSDAPIGKCNSECITPNGSIPNDKPFQNVNRITYGACPRYVKQNTLKLATGM
*-GS-*
GAIAGFIENGWEGMVDGWYGFRHQNSEGRGQAADLKSTQAAIDQINGKLNRLIGKTNEKFHQIE
KEFSEVEGRIQDLEKYVEDTKIDLWSYNAELLVALENQHTIDLTDSEMNKLFEKTKKQLRENAE
DMGNGCFKIYHKCDNACIGSIRNGTYDHDVYRDEALNNRFQIKGVELKSGYKDWILWISFAISC
FLLCVALLGFIMWACQKGNIRCNICI

Figure 21 F

Replacement of cleavage site of H3 by a linker (in BeYDV, 1097) (SEQ ID NO:21)

QKLPGNDNSTATLCLGHHAVPNGTIVKTITNDQIEVTNATELVQSSSTGEICDSPHQILDGKNC
TLIDALLGDPQCDGFQNKKWDLFVERSKAYSNCYPYDVPDYASLRSLVASSGTLEFNNESFNWT
GVTQNGTSSACIRRSKNSFFSRLNWLTHLNFKYPALNVTMPNNEQFDKLYIWGVHHPGTDKDQI
FLYAQASGRITVSTKRSQQTVSPNIGSRPRVRNIPSRISIYWTIVKPGDILLINSTGNLIAPRG
YFKIRSGKSSIMRSDAPIGKCNSECITPNGSIPNDKPFQNVNRITYGACPRYVKQNTLKLATGM
*-GSSGSSGSS-*
GIFGAIAGFIENGWEGMVDGWYGFRHQNSEGRGQAADLKSTQAAIDQINGKLNRLIGKTNEKFH
QIEKEFSEVEGRIQDLEKYVEDTKIDLWSYNAELLVALENQHTIDLTDSEMNKLFEKTKKQLRE
NAEDMGNGCFKIYHKCDNACIGSIRNGTYDHDVYRDEALNNRFQIKGVELKSGYKDWILWISFA
ISCFLLCVALLGFIMWACQKGNIRCNICI

| Ligne # | No Échantillon | Description |
|---|---|---|
| 1 | 496-59-001A | H5/Indo CTRL (# 489) |
| 2 | 496-59-001B | H5/Indo CTRL (# 489) |
| 3 | 496-59-002A | H5/Indo PRL- (# 928) |
| 4 | 496-59-002B | H5/Indo PRL- (# 928) |
| 5 | 496-59-003A | H5/Indo TETR (# 676) |
| 6 | 496-59-003B | H5/Indo TETR (# 676) |
| 7 | 496-59-004A | H5/Indo TETQ (# 766) |
| 8 | 496-59-004B | H5/Indo TETQ (# 766) |
| 9 | MW | |
| 10 | C+ | H5 25 ng |

Figure 23: A-2X35S/CPMV-HT/H5 from A/Indonesia/5/2005 with TETR cleavage site mutation (Construct number 676)

Figure 23A, SEQ ID NO : 74 MutCleavage-H5(Indo).r

TAGTCCTCTTGTCTCTGTTTGAGGGCTATTTCTGAGCCCTGTTGC

Figure 23B, SEQ ID NO : 75 MutCleavage-H5(Indo).c

TAGCCCTCAAACAGAGACAAGAGGACTATTTGGAGCTATAGCAGG

Figure 23C, SEQ ID NO : 76

Expression cassette number 676 from 2X35S promoter to NOS terminator. H5 from influenza A/Indonesia/5/2005 (H5N1) TETR cleavage site mutant is underlined.

GTCAACATGGTGGAGCACGACACACTTGTCTACTCCAAAAATATCAAAGATACAGTCTC
AGAAGACCAAAGGGCAATTGAGACTTTTCAACAAAGGGTAATATCCGGAAACCTCCTCG
GATTCCATTGCCCAGCTATCTGTCACTTTATTGTGAAGATAGTGGAAAAGGAAGGTGGC
TCCTACAAATGCCATCATTGCGATAAAGGAAAGGCCATCGTTGAAGATGCCTCTGCCGA
CAGTGGTCCCAAAGATGGACCCCCACCCACGAGGAGCATCGTGGAAAAAGAAGACGTTC
CAACCACGTCTTCAAAGCAAGTGGATTGATGTGATAACATGGTGGAGCACGACACACTT
GTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACT
TTATTGTGAAGATAGTGGAAAAGGAAGGTGGCTCCTACAAATGCCATCATTGCGATAAA
GGAAAGGCCATCGTTGAAGATGCCTCTGCCGACAGTGGTCCCAAAGATGGACCCCCACC
CACGAGGAGCATCGTGGAAAAAGAAGACGTTCCAACCACGTCTTCAAAGCAAGTGGATT
GATGTGATATCTCCACTGACGTAAGGGATGACGCACAATCCCACTATCCTTCGCAAGAC
CCTTCCTCTATATAAGGAAGTTCATTTCATTTGGAGAGGTATTAAAATCTTAATAGGTT
TTGATAAAAGCGAACGTGGGGAAACCCGAACCAAACCTTCTTCTAAACTCTCTCTCATC
TCTCTTAAAGCAAACTTCTCTCTTGTCTTTCTTGCGTGAGCGATCTTCAACGTTGTCAG
ATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGT
GGTCTTGGGAAAAGAAAGCTTGCTGGAGGCTGCTGTTCAGCCCCATACATTACTTGTTA
CGATTCTGCTGACTTTCGGCGGGTGCAATATCTCTACTTCTGCTTGACGAGGTATTGTT
GCCTGTACTTCTTTCTTCTTCTTCTTGCTGATTGGTTCTATAAGAAATCTAGTATTTTC
TTTGAAACAGAGTTTTCCCGTGGTTTTCGAACTTGGAGAAAGATTGTTAAGCTTCTGTA
TATTCTGCCCAAATTTGTCGGGCCCATGGAGAAAATAGTGCTTCTTCTTGCAATAGTCA
GTCTTGTTAAAAGTGATCAGATTTGCATTGGTTACCATGCAAACAATTCAACAGAGCAG

Figure 23C continued

GTTGACACAATCATGGAAAAGAACGTTACTGTTACACATGCCCAAGACATACTGGAAAA
GACACACAACGGGAAGCTCTGCGATCTAGATGGAGTGAAGCCTCTAATTTTAAGAGATT
GTAGTGTAGCTGGATGGCTCCTCGGGAACCCAATGTGTGACGAATTCATCAATGTACCG
GAATGGTCTTACATAGTGGAGAAGGCCAATCCAACCAATGACCTCTGTTACCCAGGGAG
TTTCAACGACTATGAAGAACTGAAACACCTATTGAGCAGAATAAACCATTTTGAGAAAA
TTCAAATCATCCCCAAAAGTTCTTGGTCCGATCATGAAGCCTCATCAGGAGTTAGCTCA
GCATGTCCATACCTGGGAAGTCCCTCCTTTTTTAGAAATGTGGTATGGCTTATCAAAAA
GAACAGTACATACCCAACAATAAAGAAAAGCTACAATAATACCAACCAAGAGGATCTTT
TGGTACTGTGGGGAATTCACCATCCTAATGATGCGGCAGAGCAGACAAGGCTATATCAA
AACCCAACCACCTATATTTCCATTGGGACATCAACACTAAACCAGAGATTGGTACCAAA
AATAGCTACTAGATCCAAAGTAAACGGGCAAAGTGGAAGGATGGAGTTCTTCTGGACAA
TTTTAAAACCTAATGATGCAATCAACTTCGAGAGTAATGGAAATTTCATTGCTCCAGAA
TATGCATACAAAATTGTCAAGAAAGGGGACTCAGCAATTATGAAAAGTGAATTGGAATA
TGGTAACTGCAACACCAAGTGTCAAACTCCAATGGGGGCGATAAACTCTAGTATGCCAT
TCCACAACATACACCCTCTCACCATCGGGGAATGCCCCAAATATGTGAAATCAAACAGA
TTAGTCCTTGCAACAGGGCTCAGAAATAGCCCTCAAACAGAGACAAGAGGACTATTTGG
AGCTATAGCAGGTTTTATAGAGGGAGGATGGCAGGGAATGGTAGATGGTTGGTATGGGT
ACCACCATAGCAATGAGCAGGGGAGTGGGTACGCTGCAGACAAAGAATCCACTCAAAAG
GCAATAGATGGAGTCACCAATAAGGTCAACTCAATCATTGACAAAATGAACACTCAGTT
TGAGGCCGTTGGAAGGGAATTTAATAACTTAGAAAGGAGAATAGAGAATTTAAACAAGA
AGATGGAAGACGGGTTTCTAGATGTCTGGACTTATAATGCCGAACTTCTGGTTCTCATG
GAAAATGAGAGAACTCTAGACTTTCATGACTCAAATGTTAAGAACCTCTACGACAAGGT
CCGACTACAGCTTAGGGATAATGCAAAGGAGCTGGGTAACGGTTGTTTCGAGTTCTATC
ACAAATGTGATAATGAATGTATGGAAAGTATAAGAAACGGAACGTACAACTATCCGCAG
TATTCAGAAGAAGCAAGATTAAAAAGAGAGGAAATAAGTGGGGTAAAATTGGAATCAAT
AGGAACTTACCAAATACTGTCAATTTATTCAACAGTGGCGAGTTCCCTAGCACTGGCAA
TCATGATGGCTGGTCTATCTTTATGGATGTGCTCCAATGGATCGTTACAATGCAGAATT
TGCATTTAAAGGCCTATTTTCTTTAGTTTGAATTTACTGTTATTCGGTGTGCATTTCTA
TGTTTGGTGAGCGGTTTTCTGTGCTCAGAGTGTGTTTATTTTATGTAATTTAATTTCTT
TGTGAGCTCCTGTTTAGCAGGTCGTCCCTTCAGCAAGGACACAAAAAGATTTTAATTTT
ATTAAAAAAAAAAAAAAAAAAGACCGGGAATTCGATATCAAGCTTATCGACCTGCAGAT
CGTTCAAACATTTGGCAATAAAGTTTCTTAAGATTGAATCCTGTTGCCGGTCTTGCGAT
GATTATCATATAATTTCTGTTGAATTACGTTAAGCATGTAATAATTAACATGTAATGCA
TGACGTTATTTATGAGATGGGTTTTTATGATTAGAGTCCCGCAATTATACATTTAATAC
GCGATAGAAAACAAAATATAGCGCGCAAACTAGGATAAATTATCGCGCGCGGTGTCATC
TATGTTACTAGAT

Figure 23D, SEQ ID NO : 77

Amino acid sequence of H5 from influenza A/Indonesia/5/2005 (H5N1) TETR cleavage site mutant.

MEKIVLLLAIVSLVKSDQICIGYHANNSTEQVDTIMEKNVTVTHAQDILEKTHNGKLCDLDGVKPLILRDCSVAGWLLGNPMC
DEFINVPEWSYIVEKANPTNDLCYPGSFNDYEELKHLLSRINHFEKIQIIPKSSWSDHEASSGVSSACPYLGSPSFFRNVVWL
IKKNSTYPTIKKSYNNTNQEDLLVLWGIHHPNDAAEQTRLYQNPTTYISIGTSTLNQRLVPKIATRSKVNGQSGRMEFFWTIL
KPNDAINFESNGNFIAPEYAYKIVKKGDSAIMKSELEYGNCNTKCQTPMGAINSSMPFHNIHPLTIGECPKYVKSNRLVLATG
LRNSPQTETRGLFGAIAGFIEGGWQGMVDGWYGYHHSNEQGSGYAADKESTQKAIDGVTNKVNSIIDKMNTQFEAVGREFNNL
ERRIENLNKKMEDGFLDVWTYNAELLVLMENERTLDFHDSNVKNLYDKVRLQLRDNAKELGNGCFEFYHKCDNECMESIRNGT
YNYPQYSEEARLKREEISGVKLESIGTYQILSIYSTVASSLALAIMMAGLSLWMCSNGSLQCRICI

Figure 23E

Schematic representation of construct number 676.

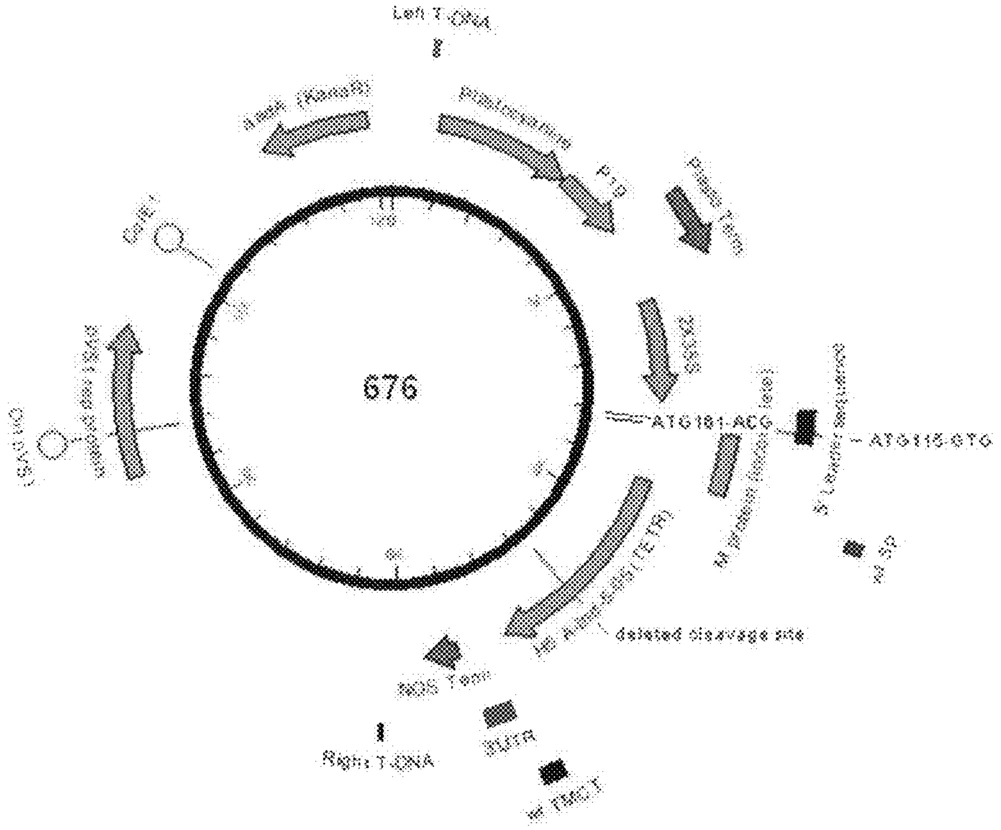

Figure 24: B-2X35S/CPMV-HT/H5 from A/Indonesia/5/2005 with TETQ cleavage site mutation (Construct number 766)

Figure 24A, SEQ ID NO : 78 H5I505_TETQ.r

TCCAAATAGTCCTTGTGTCTCTGTTTGAGGGCTATTTCTGAGCCCTGT

Figure 24B, SEQ ID NO : 79 H5I505_TETQ.c

AAATAGCCCTCAAACAGAGACACAAGGACTATTTGGAGCTATAGCAGG

Figure 24C, SEQ ID NO : 80

Expression cassette number 766 from 2X35S promoter to NOS terminator. H5 from influenza A/Indonesia/5/2005 (H5N1) TETQ cleavage site mutant is underlined.

GTCAACATGGTGGAGCACGACACACTTGTCTACTCCAAAAATATCAAAGATACAGTCTC
AGAAGACCAAAGGGCAATTGAGACTTTTCAACAAAGGGTAATATCCGGAAACCTCCTCG
GATTCCATTGCCCAGCTATCTGTCACTTTATTGTGAAGATAGTGGAAAAGGAAGGTGGC
TCCTACAAATGCCATCATTGCGATAAAGGAAAGGCCATCGTTGAAGATGCCTCTGCCGA
CAGTGGTCCCAAAGATGGACCCCCACCCACGAGGAGCATCGTGGAAAAAGAAGACGTTC
CAACCACGTCTTCAAAGCAAGTGGATTGATGTGATAACATGGTGGAGCACGACACACTT
GTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACT
TTATTGTGAAGATAGTGGAAAAGGAAGGTGGCTCCTACAAATGCCATCATTGCGATAAA
GGAAAGGCCATCGTTGAAGATGCCTCTGCCGACAGTGGTCCCAAAGATGGACCCCCACC
CACGAGGAGCATCGTGGAAAAAGAAGACGTTCCAACCACGTCTTCAAAGCAAGTGGATT
GATGTGATATCTCCACTGACGTAAGGGATGACGCACAATCCCACTATCCTTCGCAAGAC
CCTTCCTCTATATAAGGAAGTTCATTTCATTTGGAGAGGTATTAAAATCTTAATAGGTT
TTGATAAAAGCGAACGTGGGGAAACCCGAACCAAACCTTCTTCTAAACTCTCTCTCATC
TCTCTTAAAGCAAACTTCTCTCTTGTCTTTCTTGCGTGAGCGATCTTCAACGTTGTCAG
ATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGT
GGTCTTGGGAAAAGAAAGCTTGCTGGAGGCTGCTGTTCAGCCCCATACATTACTTGTTA
CGATTCTGCTGACTTTCGGCGGGTGCAATATCTCTACTTCTGCTTGACGAGGTATTGTT
GCCTGTACTTCTTTCTTCTTCTTCTTGCTGATTGGTTCTATAAGAAATCTAGTATTTTC
TTTGAAACAGAGTTTTCCCGTGGTTTTCGAACTTGGAGAAAGATTGTTAAGCTTCTGTA
TATTCTGCCCAAATTTGTCGGGCCCATGGAGAAAATAGTGCTTCTTCTTGCAATAGTCA
GTCTTGTTAAAAGTGATCAGATTTGCATTGGTTACCATGCAAACAATTCAACAGAGCAG

Figure 24C continued

GTTGACACAATCATGGAAAAGAACGTTACTGTTACACATGCCCAAGACATACTGGAAAA
GACACACAACGGGAAGCTCTGCGATCTAGATGGAGTGAAGCCTCTAATTTTAAGAGATT
GTAGTGTAGCTGGATGGCTCCTCGGGAACCCAATGTGTGACGAATTCATCAATGTACCG
GAATGGTCTTACATAGTGGAGAAGGCCAATCCAACCAATGACCTCTGTTACCCAGGGAG
TTTCAACGACTATGAAGAACTGAAACACCTATTGAGCAGAATAAACCATTTTGAGAAAA
TTCAAATCATCCCCAAAAGTTCTTGGTCCGATCATGAAGCCTCATCAGGAGTTAGCTCA
GCATGTCCATACCTGGGAAGTCCCTCCTTTTTAGAAATGTGGTATGGCTTATCAAAAA
GAACAGTACATACCCAACAATAAAGAAAAGCTACAATAATACCAACCAAGAGGATCTTT
TGGTACTGTGGGGAATTCACCATCCTAATGATGCGGCAGAGCAGACAAGGCTATATCAA
AACCCAACCACCTATATTTCCATTGGGACATCAACACTAAACCAGAGATTGGTACCAAA
AATAGCTACTAGATCCAAAGTAAACGGGCAAAGTGGAAGGATGGAGTTCTTCTGGACAA
TTTTAAAACCTAATGATGCAATCAACTTCGAGAGTAATGGAAATTTCATTGCTCCAGAA
TATGCATACAAAATTGTCAAGAAAGGGGACTCAGCAATTATGAAAAGTGAATTGGAATA
TGGTAACTGCAACACCAAGTGTCAAACTCCAATGGGGGCGATAAACTCTAGTATGCCAT
TCCACAACATACACCCTCTCACCATCGGGGAATGCCCCAAATATGTGAAATCAAACAGA
TTAGTCCTTGCAACAGGGCTCAGAAATAGCCCTCAAACAGAGACACAAGGACTATTTGG
AGCTATAGCAGGTTTTATAGAGGGAGGATGGCAGGGAATGGTAGATGGTTGGTATGGGT
ACCACCATAGCAATGAGCAGGGGAGTGGGTACGCTGCAGACAAAGAATCCACTCAAAAG
GCAATAGATGGAGTCACCAATAAGGTCAACTCAATCATTGACAAAATGAACACTCAGTT
TGAGGCCGTTGGAAGGGAATTTAATAACTTAGAAAGGAGAATAGAGAATTTAAACAAGA
AGATGGAAGACGGGTTTCTAGATGTCTGGACTTATAATGCCGAACTTCTGGTTCTCATG
GAAAATGAGAGAACTCTAGACTTTCATGACTCAAATGTTAAGAACCTCTACGACAAGGT
CCGACTACAGCTTAGGGATAATGCAAAGGAGCTGGGTAACGGTTGTTTCGAGTTCTATC
ACAAATGTGATAATGAATGTATGGAAAGTATAAGAAACGGAACGTACAACTATCCGCAG
TATTCAGAAGAAGCAAGATTAAAAGAGAGGAAATAAGTGGGGTAAAATTGGAATCAAT
AGGAACTTACCAAATACTGTCAATTTATTCAACAGTGGCGAGTTCCCTAGCACTGGCAA
TCATGATGGCTGGTCTATCTTTATGGATGTGCTCCAATGGATCGTTACAATGCAGAATT
TGCATTTAAAGGCCTATTTTCTTTAGTTTGAATTTACTGTTATTCGGTGTGCATTTCTA
TGTTTGGTGAGCGGTTTTCTGTGCTCAGAGTGTGTTTATTTTATGTAATTTAATTTCTT
TGTGAGCTCCTGTTTAGCAGGTCGTCCCTTCAGCAAGGACACAAAAAGATTTTAATTTT
ATTAAAAAAAAAAAAAAAAAAAGACCGGGAATTCGATATCAAGCTTATCGACCTGCAGAT
CGTTCAAACATTTGGCAATAAAGTTTCTTAAGATTGAATCCTGTTGCCGGTCTTGCGAT
GATTATCATATAATTTCTGTTGAATTACGTTAAGCATGTAATAATTAACATGTAATGCA
TGACGTTATTTATGAGATGGGTTTTTATGATTAGAGTCCCGCAATTATACATTTAATAC
GCGATAGAAAACAAAATATAGCGCGCAAACTAGGATAAATTATCGCGCGCGGTGTCATC
TATGTTACTAGAT

Figure 24D, SEQ ID NO : 81

Amino acid sequence of H5 from influenza A/Indonesia/5/2005 (H5N1) TETQ cleavage site mutant.

MEKIVLLLAIVSLVKSDQICIGYHANNSTEQVDTIMEKNVTVTHAQDILEKTHNGKLCDLDGVKPLILRDCSVAGWLLGNPMC
DEFINVPEWSYIVEKANPTNDLCYPGSFNDYEELKHLLSRINHFEKIQIIPKSSWSDHEASSGVSSACPYLGSPSFFRNVVWL
IKKNSTYPTIKKSYNNTNQEDLLVLWGIHHPNDAAEQTRLYQNPTTYISIGTSTLNQRLVPKIATRSKVNGQSGRMEFFWTIL
KPNDAINFESNGNFIAPEYAYKIVKKGDSAIMKSELEYGNCNTKCQTPMGAINSSMPFHNIHPLTIGECPKYVKSNRLVLATG
LRNSPQTETQGLFGAIAGFIEGGWQGMVDGWYGYHHSNEQGSGYAADKESTQKAIDGVTNKVNSIIDKMNTQFEAVGREFNNL
ERRIENLNKKMEDGFLDVWTYNAELLVLMENERTLDFHDSNVKNLYDKVRLQLRDNAKELGNGCFEFYHKCDNECMESIRNGT
YNYPQYSEEARLKREEISGVKLESIGTYQILSIYSTVASSLALAIMMAGLSLWMCSNGSLQCRICI

Figure 24E,

Schematic representation of construct number 766.

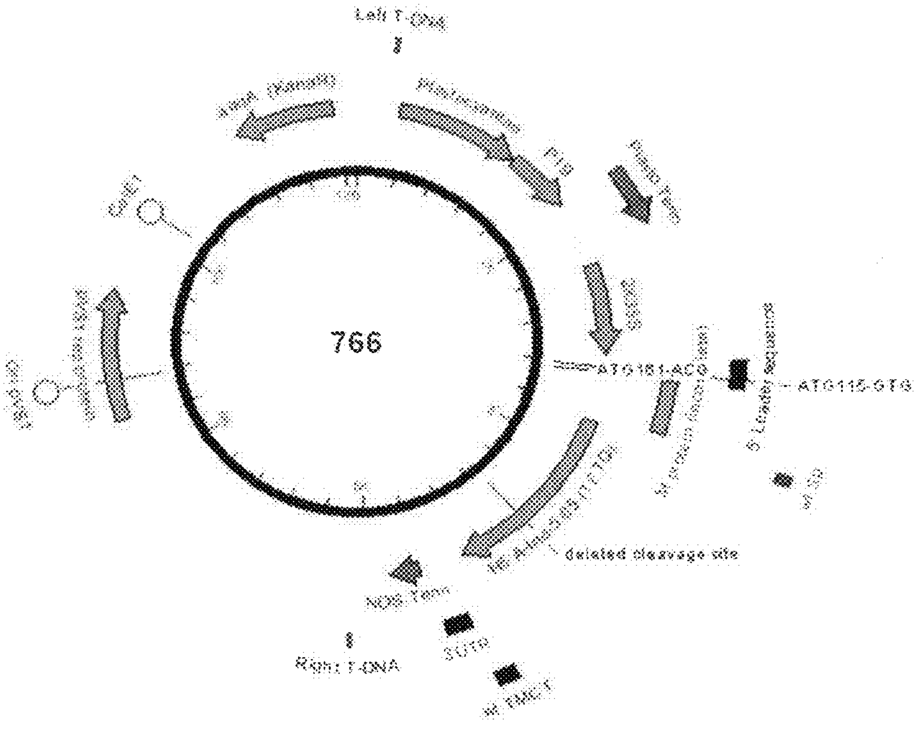

Figure 25: C-2X35S/CPMV-HT/H5 from A/Indonesia/5/2005 with deleted proteolytic loop (Construct number 928)

Figure 25A, SEQ ID NO : 82 H5I505(PrL-).r

CTGCCATCCTCCGCCAGGGCTATTTCTGAGCCCTGTTGCAAGGACTAATC

Figure 25B, SEQ ID NO : 83 H5I505(PrL-).c

GAAATAGCCCTGGCGGAGGATGGCAGGGAATGGTAGATGGTTGGTATGGGTA

Figure 25C, SEQ ID NO : 84

Expression cassette number 928 from 2X35S promoter to NOS terminator. H5 from influenza A/Indonesia/5/2005 (H5N1) with deleted proteolytic loop is underlined.

GTCAACATGGTGGAGCACGACACACTTGTCTACTCCAAAAATATCAAAGATACAGTCTC
AGAAGACCAAAGGGCAATTGAGACTTTTCAACAAAGGGTAATATCCGGAAACCTCCTCG
GATTCCATTGCCCAGCTATCTGTCACTTTATTGTGAAGATAGTGGAAAAGGAAGGTGGC
TCCTACAAATGCCATCATTGCGATAAAGGAAAGGCCATCGTTGAAGATGCCTCTGCCGA
CAGTGGTCCCAAAGATGGACCCCCACCCACGAGGAGCATCGTGGAAAAAGAAGACGTTC
CAACCACGTCTTCAAAGCAAGTGGATTGATGTGATAACATGGTGGAGCACGACACACTT
GTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACT
TTATTGTGAAGATAGTGGAAAAGGAAGGTGGCTCCTACAAATGCCATCATTGCGATAAA
GGAAAGGCCATCGTTGAAGATGCCTCTGCCGACAGTGGTCCCAAAGATGGACCCCCACC
CACGAGGAGCATCGTGGAAAAAGAAGACGTTCCAACCACGTCTTCAAAGCAAGTGGATT
GATGTGATATCTCCACTGACGTAAGGGATGACGCACAATCCCACTATCCTTCGCAAGAC
CCTTCCTCTATATAAGGAAGTTCATTTCATTTGGAGAGGTATTAAAATCTTAATAGGTT
TTGATAAAAGCGAACGTGGGGAAACCCGAACCAAACCTTCTTCTAAACTCTCTCTCATC
TCTCTTAAAGCAAACTTCTCTCTTGTCTTTCTTGCGTGAGCGATCTTCAACGTTGTCAG
ATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGT
GGTCTTGGGAAAAGAAAGCTTGCTGGAGGCTGCTGTTCAGCCCCATACATTACTTGTTA
CGATTCTGCTGACTTTCGGCGGGTGCAATATCTCTACTTCTGCTTGACGAGGTATTGTT
GCCTGTACTTCTTTCTTCTTCTTCTTGCTGATTGGTTCTATAAGAAATCTAGTATTTTC
TTTGAAACAGAGTTTTCCCGTGGTTTTCGAACTTGGAGAAAGATTGTTAAGCTTCTGTA
TATTCTGCCCAAATTTGTCGGGCCCATGGAGAAAATAGTGCTTCTTCTTGCAATAGTCA
GTCTTGTTAAAAGTGATCAGATTTGCATTGGTTACCATGCAAACAATTCAACAGAGCAG

Figure 25C continued

GTTGACACAATCATGGAAAAGAACGTTACTGTTACACATGCCCAAGACATACTGGAAAA
GACACACAACGGGAAGCTCTGCGATCTAGATGGAGTGAAGCCTCTAATTTTAAGAGATT
GTAGTGTAGCTGGATGGCTCCTCGGGAACCCAATGTGTGACGAATTCATCAATGTACCG
GAATGGTCTTACATAGTGGAGAAGGCCAATCCAACCAATGACCTCTGTTACCCAGGGAG
TTTCAACGACTATGAAGAACTGAAACACCTATTGAGCAGAATAAACCATTTTGAGAAAA
TTCAAATCATCCCCAAAAGTTCTTGGTCCGATCATGAAGCCTCATCAGGAGTTAGCTCA
GCATGTCCATACCTGGGAAGTCCCTCCTTTTTAGAAATGTGGTATGGCTTATCAAAAA
GAACAGTACATACCCAACAATAAAGAAAAGCTACAATAATACCAACCAAGAGGATCTTT
TGGTACTGTGGGGAATTCACCATCCTAATGATGCGGCAGAGCAGACAAGGCTATATCAA
AACCCAACCACCTATATTTCCATTGGGACATCAACACTAAACCAGAGATTGGTACCAAA
AATAGCTACTAGATCCAAAGTAAACGGGCAAAGTGGAAGGATGGAGTTCTTCTGGACAA
TTTTAAAACCTAATGATGCAATCAACTTCGAGAGTAATGGAAATTTCATTGCTCCAGAA
TATGCATACAAAATTGTCAAGAAAGGGGACTCAGCAATTATGAAAAGTGAATTGGAATA
TGGTAACTGCAACACCAAGTGTCAAACTCCAATGGGGGCGATAAACTCTAGTATGCCAT
TCCACAACATACACCCTCTCACCATCGGGGAATGCCCCAAATATGTGAAATCAAACAGA
TTAGTCCTTGCAACAGGGCTCAGAAATAGCCCTGGCGGAGGATGGCAGGGAATGGTAGA
TGGTTGGTATGGGTACCACCATAGCAATGAGCAGGGGAGTGGGTACGCTGCAGACAAAG
AATCCACTCAAAAGGCAATAGATGGAGTCACCAATAAGGTCAACTCAATCATTGACAAA
ATGAACACTCAGTTTGAGGCCGTTGGAAGGGAATTTAATAACTTAGAAAGGAGAATAGA
GAATTTAAACAAGAAGATGGAAGACGGGTTTCTAGATGTCTGGACTTATAATGCCGAAC
TTCTGGTTCTCATGGAAAATGAGAGAACTCTAGACTTTCATGACTCAAATGTTAAGAAC
CTCTACGACAAGGTCCGACTACAGCTTAGGGATAATGCAAAGGAGCTGGGTAACGGTTG
TTTCGAGTTCTATCACAAATGTGATAATGAATGTATGGAAAGTATAAGAAACGGAACGT
ACAACTATCCGCAGTATTCAGAAGAAGCAAGATTAAAAAGAGAGGAAATAAGTGGGGTA
AAATTGGAATCAATAGGAACTTACCAAATACTGTCAATTTATTCAACAGTGGCGAGTTC
CCTAGCACTGGCAATCATGATGGCTGGTCTATCTTTATGGATGTGCTCCAATGGATCGT
TACAATGCAGAATTTGCATTTAAAGGCCTATTTTCTTTAGTTTGAATTTACTGTTATTC
GGTGTGCATTTCTATGTTTGGTGAGCGGTTTTCTGTGCTCAGAGTGTGTTTATTTTATG
TAATTTAATTTCTTTGTGAGCTCCTGTTTAGCAGGTCGTCCCTTCAGCAAGGACACAAA
AAGATTTTAATTTTATTAAAAAAAAAAAAAAAAAAGACCGGGAATTCGATATCAAGCTT
ATCGACCTGCAGATCGTTCAAACATTTGGCAATAAAGTTTCTTAAGATTGAATCCTGTT
GCCGGTCTTGCGATGATTATCATATAATTTCTGTTGAATTACGTTAAGCATGTAATAAT
TAACATGTAATGCATGACGTTATTTATGAGATGGGTTTTTATGATTAGAGTCCCGCAAT
TATACATTTAATACGCGATAGAAAACAAAATATAGCGCGCAAACTAGGATAAATTATCG
CGCGCGGTGTCATCTATGTTACTAGAT

Figure 25D, SEQ ID NO : 85

Amino acid sequence of H5 from influenza A/Indonesia/5/2005 (H5N1) with deleted proteolytic loop.

MEKIVLLLAIVSLVKSDQICIGYHANNSTEQVDTIMEKNVTVTHAQDILEKTHNGKLCDLDGVKPLILRDCSVAGWLLGNPMC
DEFINVPEWSYIVEKANPTNDLCYPGSFNDYEELKHLLSRINHFEKIQIIPKSSWSDHEASSGVSSACPYLGSPSFFRNVVWL
IKKNSTYPTIKKSYNNTNQEDLLVLWGIHHPNDAAEQTRLYQNPTTYISIGTSTLNQRLVPKIATRSKVNGQSGRMEFFWTIL
KPNDAINFESNGNFIAPEYAYKIVKKGDSAIMKSELEYGNCNTKCQTPMGAINSSMPFHNIHPLTIGECPKYVKSNRLVLATG
LRNSPGGGWQGMVDGWYGYHHSNEQGSGYAADKESTQKAIDGVTNKVNSIIDKMNTQFEAVGREFNNLERRIENLNKKMEDGF
LDVWTYNAELLVLMENERTLDFHDSNVKNLYDKVRLQLRDNAKELGNGCFEFYHKCDNECMESIRNGTYNYPQYSEEARLKRE
EISGVKLESIGTYQILSIYSTVASSLALAIMMAGLSLWMCSNGSLQCRICI

Figure 25E

Schematic representation of construct number 928.

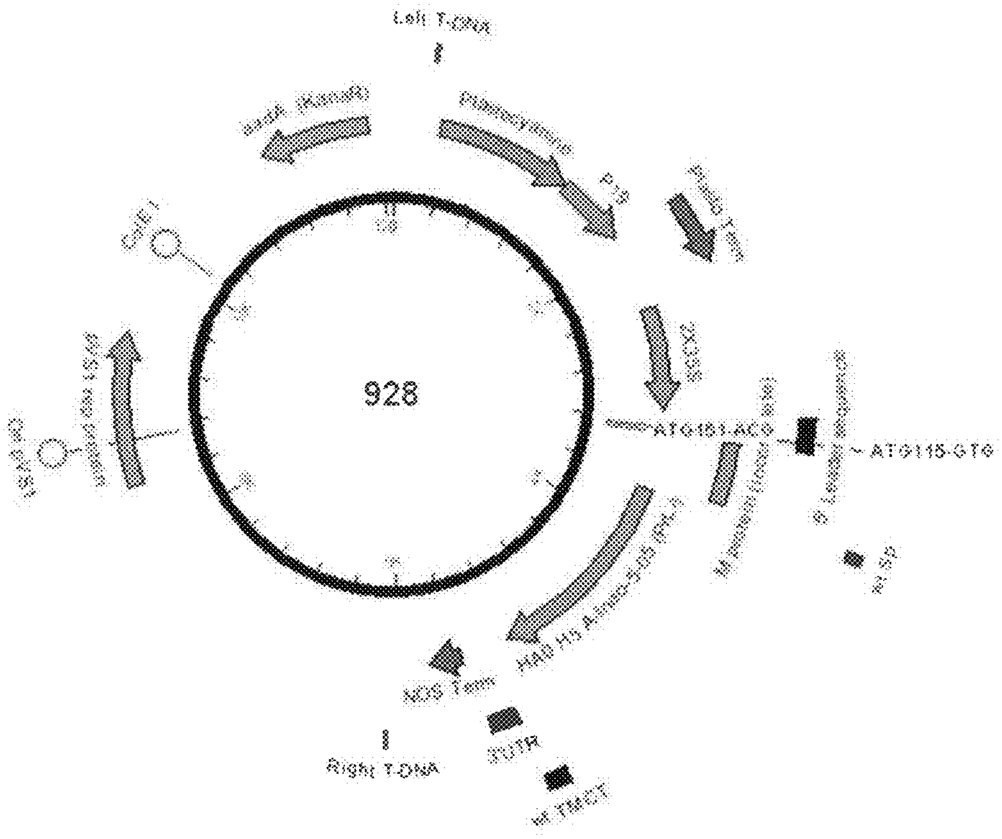

Figure 30

F-2X35S/CPMV-HT/PDISP/HA B Brisbane/NOS (Construct number 1029)

Figure 30A

IF-S2+S4-B Bris.c (SEQ ID NO: 86)

TCTCAGATCTTCGCCGATCGAATCTGCACTGGAATAACAT

Figure 30B

IF-S1a4-B Bris.r (SEQ ID NO: 87)

ACTAAAGAAAATAGGCCTTTATAGACAGATGGAGCAAGAAACA

Figure 30C

Synthesized HA B Brisbane gene (corresponding to nt 34-1791 from Genbank accession number FJ766840) (SEQ ID NO: 88)

ATGAAGGCAATAATTGTACTACTCATGGTAGTAACATCCAATGCAGATCGAATCTGCACTGGAA
TAACATCGTCAAACTCACCACATGTCGTCAAAACTGCTACTCAAGGGGAGGTCAATGTGACTGG
TGTAATACCACTGACAACAACACCCACCAAATCTCATTTTGCAAATCTCAAAGGAACAGAAACC
AGGGGGAAACTATGCCCAAAATGCCTCAACTGCACAGATCTGGACGTAGCCTTGGGCAGACCAA
AATGCACGGGGAAAATACCCTCGGCAAGAGTTTCAATACTCCATGAAGTCAGACCTGTTACATC
TGGGTGCTTTCCTATAATGCACGACAGAACAAAAATTAGACAGCTGCCTAACCTTCTCCGAGGA
TACGAACATATCAGGTTATCAACCCATAACGTTATCAATGCAGAAAATGCACCAGGAGGACCCT
ACAAAATTGGAACCTCAGGGTCTTGCCCTAACATTACCAATGGAAACGGATTTTTCGCAACAAT
GGCTTGGGCCGTCCCAAAAAACGACAAAAACAAAACAGCAACAAATCCATTAACAATAGAAGTA
CCATACATTTGTACAGAAGGAGAAGACCAAATTACCGTTTGGGGGTTCCACTCTGACAACGAGA
CCCAAATGGCAAAGCTCTATGGGGACTCAAAGCCCCAGAAGTTCACCTCATCTGCCAACGGAGT
GACCACACATTACGTTTCACAGATTGGTGGCTTCCCAAATCAAACAGAAGACGGAGGACTACCA
CAAAGTGGTAGAATTGTTGTTGATTACATGGTGCAAAAATCTGGGAAAACAGGAACAATTACCT
ATCAAAGGGGTATTTTATTGCCTCAAAAGGTGTGGTGCGCAAGTGGCAGGAGCAAGGTAATAAA
AGGATCCTTGCCTTTAATTGGAGAAGCAGATTGCCTCCACGAAAAATACGGTGGATTAAACAAA
AGCAAGCCTTACTACACAGGGGAACATGCAAAGGCCATAGGAAATTGCCCAATATGGGTGAAAA
CACCCTTGAAGCTGGCCAATGGAACCAAATATAGACCTCCTGCAAAACTATTAAAGGAAAGGGG
TTTCTTCGGAGCTATTGCTGGTTTCTTAGAAGGAGGATGGGAAGGAATGATTGCAGGTTGGCAC
GGATACACATCCCATGGGGCACATGGAGTAGCGGTGGCAGCAGACCTTAAGAGCACTCAAGAGG
CCATAAACAAGATAACAAAAAATCTCAACTCTTTGAGTGAGCTGGAAGTAAAGAATCTTCAAAG
ACTAAGCGGTGCCATGGATGAACTCCACAACGAAATACTAGAACTAGATGAGAAAGTGGATGAT
CTCAGAGCTGATACAATAAGCTCACAAATAGAACTCGCAGTCCTGCTTTCCAATGAAGGAATAA
TAAACAGTGAAGATGAACATCTCTTGGCGCTTGAAAGAAAGCTGAAGAAAATGCTGGGCCCCTC
TGCTGTAGAGATAGGGAATGGATGCTTTGAAACCAAACACAAGTGCAACCAGACCTGTCTCGAC
AGAATAGCTGCTGGTACCTTTGATGCAGGAGAATTTTCTCTCCCCACCTTTGATTCACTGAATA

Figure 30C continued

TTACTGCTGCATCTTTAAATGACGATGGATTGGATAATCATACTATACTGCTTTACTACTCAAC
TGCTGCCTCCAGTTTGGCTGTAACACTGATGATAGCTATCTTTGTTGTTTATATGGTCTCCAGA
GACAATGTTTCTTGCTCCATCTGTCTATAA

Figure 30D

Expression cassette number 1029 from 2X35S promoter to NOS terminator. PDISP/HA from influenza B/Brisbane/60/2008 is underlined. (SEQ ID NO: 89)

GTCAACATGGTGGAGCACGACACACTTGTCTACTCCAAAAATATCAAAGATACAGTCTCAGAAG
ACCAAAGGGCAATTGAGACTTTTCAACAAAGGGTAATATCCGGAAACCTCCTCGGATTCCATTG
CCCAGCTATCTGTCACTTTATTGTGAAGATAGTGGAAAAGGAAGGTGGCTCCTACAAATGCCAT
CATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGA
TTGATGTGATAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCTCCTCGGAT
TCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAA
GATGGACCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTT
AAAGCAAACTTCTCTCTTGTCTTTCTTGCGTGAGCGATCTTCAACGTTGTCAGATCGTGCTTCG
GCACCAGTACAACGTTTTCTTTCACTGAAGCGAAATCAAAGATCTCTTTGTGGACACGTAGTGC
GGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGA
TTGGTTCTATAAGAAATCTAGTATTTTCTTTGAAACAGAGTTTTCCCGTGGTTTTCGAACTTGG
AGAAAGATTGTTAAGCTTCTGTATATTCTGCCCAAATTTGTCGGGCCCATGGCGAAAAACGTTG
CGATTTTCGGCTTATTGTTTTCTCTTCTTGTGTTGGTTCCTTCTCAGATCTTCGCCGATCGAAT
CTGCACTGGAATAACATCGTCAAACTCACCACATGTCGTCAAAACTGCTACTCAAGGGGAGGTC
AATGTGACTGGTGTAATACCACTGACAACAACACCCACCAAATCTCATTTTGCAAATCTCAAAG
GAACAGAAACCAGGGGAAACTATGCCCAAAATGCCTCAACTGCACAGATCTGGACGTAGCCTT
GGGCAGACCAAAATGCACGGGGAAAATACCCTCGGCAAGAGTTTCAATACTCCATGAAGTCAGA
CCTGTTACATCTGGGTGCTTTCCTATAATGCACGACAGAACAAAAATTAGACAGCTGCCTAACC
TTCTCCGAGGATACGAACATATCAGGTTATCAACCCATAACGTTATCAATGCAGAAAATGCACC
AGGAGGACCCTACAAAATTGGAACCTCAGGGTCTTGCCCTAACATTACCAATGGAAACGGATTT
TTCGCAACAATGGCTTGGGCCGTCCCAAAAAACGACAAAAACAAAACAGCAACAAATCCATTAA
CAATAGAAGTACCATACATTTGTACAGAAGGAGAAGACCAAATTACCGTTTGGGGGTTCCACTC
TGACAACGAGACCCAAATGGCAAAGCTCTATGGGGACTCAAAGCCCCAGAAGTTCACCTCATCT
GCCAACGGAGTGACCACACATTACGTTTCACAGATTGGTGGCTTCCCAAATCAAACAGAAGACG
GAGGACTACCACAAAGTGGTAGAATTGTTGTTGATTACATGGTGCAAAAATCTGGAAAACAGG
AACAATTACCTATCAAAGGGGTATTTTATTGCCTCAAAAGGTGTGGTGCGCAAGTGGCAGGAGC
AAGGTAATAAAAGGATCCTTGCCTTTAATTGGAGAAGCAGATTGCCTCCACGAAAAATACGGTG
GATTAAACAAAAGCAAGCCTTACTACACAGGGGAACATGCAAAGGCCATAGGAAATTGCCCAAT
ATGGGTGAAAACACCCTTGAAGCTGGCCAATGGAACCAAATATAGACCTCCTGCAAAACTATTA
AAGGAAAGGGGTTTCTTCGGAGCTATTGCTGGTTTCTTAGAAGGAGGATGGGAAGGAATGATTG

Figure 30D continued

CAGGTTGGCACGGATACACATCCCATGGGGCACATGGAGTAGCGGTGGCAGCAGACCTTAAGAG
CACTCAAGAGGCCATAAACAAGATAACAAAAAATCTCAACTCTTTGAGTGAGCTGGAAGTAAAG
AATCTTCAAAGACTAAGCGGTGCCATGGATGAACTCCACAACGAAATACTAGAACTAGATGAGA
AAGTGGATGATCTCAGAGCTGATACAATAAGCTCACAAATAGAACTCGCAGTCCTGCTTTCCAA
TGAAGGAATAATAAACAGTGAAGATGAACATCTCTTGGCGCTTGAAAGAAAGCTGAAGAAAATG
CTGGGCCCCTCTGCTGTAGAGATAGGGAATGGATGCTTTGAAACCAAACACAAGTGCAACCAGA
CCTGTCTCGACAGAATAGCTGCTGGTACCTTTGATGCAGGAGAATTTTCTCTCCCCACCTTTGA
TTCACTGAATATTACTGCTGCATCTTTAAATGACGATGGATTGGATAATCATACTATACTGCTT
TACTACTCAACTGCTGCCTCCAGTTTGGCTGTAACACTGATGATAGCTATCTTTGTTGTTTATA
TGGTCTCCAGAGACAATGTTTCTTGCTCCATCTGTCTATAAAGGCCTATTTTCTTTAGTTTGAA
TTTACTGTTATTCGGTGTGCATTTCTATGTTTGGTGAGCGGTTTTCTGTGCTCAGAGTGTGTTT
ATTTTATGTAATTTAATTTCTTTGTGAGCTCCTGTTTAGCAGGTCGTCCCTTCAGCAAGGACAC
AAAAAGATTTTAATTTTATTAAAAAAAAAAAAAAAAAAGACCGGGAATTCGATATCAAGCTTAT
CGACCTGCAGATCGTTCAAACATTTGGCAATAAAGTTTCTTAAGATTGAATCCTGTTGCCGGTC
TTGCGATGATTATCATATAATTTCTGTTGAATTACGTTAAGCATGTAATAATTAACATGTAATG
CATGACGTTATTTATGAGATGGGTTTTTATGATTAGAGTCCCGCAATTATACATTTAATACGCG
ATAGAAAACAAAATATAGCGCGCAAACTAGGATAAATTATCGCGCGCGGTGTCATCTATGTTAC
TAGAT

Figure 30E,

Amino acid sequence of PDISP/HA from influenza
B/Brisbane/60/2008 SEQ ID NO: 90

MAKNVAIFGLLFSLLVLVPSQIFADRICTGITSSNSPHVVKTATQGEVNVTGVIPLTTTPTKSH
FANLKGTETRGKLCPKCLNCTDLDVALGRPKCTGKIPSARVSILHEVRPVTSGCFPIMHDRTKI
RQLPNLLRGYEHIRLSTHNVINAENAPGGPYKIGTSGSCPNITNGNGFFATMAWAVPKNDKNKT
ATNPLTIEVPYICTEGEDQITVWGFHSDNETQMAKLYGDSKPQKFTSSANGVTTHYVSQIGGFP
NQTEDGGLPQSGRIVVDYMVQKSGKTGTITYQRGILLPQKVWCASGRSKVIKGSLPLIGEADCL
HEKYGGLNKSKPYYTGEHAKAIGNCPIWVKTPLKLANGTKYRPPAKLLKERGFFGAIAGFLEGG
WEGMIAGWHGYTSHGAHGVAVAADLKSTQEAINKITKNLNSLSELEVKNLQRLSGAMDELHNEI
LELDEKVDDLRADTISSQIELAVLLSNEGIINSEDEHLLALERKLKKMLGPSAVEIGNGCFETK
HKCNQTCLDRIAAGTFDAGEFSLPTFDSLNITAASLNDDGLDNHTILLYYSTAASSLAVTLMIA
IFVVYMVSRDNVSCSICL

Fig 31

**K- 2X35S/CPMV HT (construct no 1039) and HT* (construct no 1829) for PDISP/HA B Brisbane (PrL-)**

Figure 31A, SEQ ID NO : 91 Nucleotide sequence of PDISP/HA B Brisbane (PrL-).

ATGGCGAAAAACGTTGCGATTTTCGGCTTATTGTTTTCTCTTCTTGTGTTGGTTCCTTCTCAGA
TCTTCGCCGATCGAATCTGCACTGGAATAACATCGTCAAACTCACCACATGTCGTCAAAACTGC
TACTCAAGGGGAGGTCAATGTGACTGGTGTAATACCACTGACAACAACACCCACCAAATCTCAT
TTTGCAAATCTCAAAGGAACAGAAACCAGGGGGAAACTATGCCCAAAATGCCTCAACTGCACAG
ATCTGGACGTAGCCTTGGGCAGACCAAAATGCACGGGGAAAATACCCTCGGCAAGAGTTTCAAT
ACTCCATGAAGTCAGACCTGTTACATCTGGGTGCTTTCCTATAATGCACGACAGAACAAAAATT
AGACAGCTGCCTAACCTTCTCCGAGGATACGAACATATCAGGTTATCAACCCATAACGTTATCA
ATGCAGAAAATGCACCAGGAGGACCCTACAAAATTGGAACCTCAGGGTCTTGCCCTAACATTAC
CAATGGAAACGGATTTTTCGCAACAATGGCTTGGGCCGTCCCAAAAAACGACAAAAACAAAACA
GCAACAAATCCATTAACAATAGAAGTACCATACATTTGTACAGAAGGAGAAGACCAAATTACCG
TTTGGGGGTTCCACTCTGACAACGAGACCCAAATGGCAAAGCTCTATGGGGACTCAAAGCCCCA
GAAGTTCACCTCATCTGCCAACGGAGTGACCACACATTACGTTTCACAGATTGGTGGCTTCCCA
AATCAAACAGAAGACGGAGGACTACCACAAAGTGGTAGAATTGTTGTTGATTACATGGTGCAAA
AATCTGGGAAAACAGGAACAATTACCTATCAAAGGGGTATTTTATTGCCTCAAAAGGTGTGGTG
CGCAAGTGGCAGGAGCAAGGTAATAAAAGGATCCTTGCCTTTAATTGGAGAAGCAGATTGCCTC
CACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACC
TCCTGGTGGAGGATGGGAAGGAATGATTGCAGGTTGGCACGGATACACATCCCATGGGGCACAT
GGAGTAGCGGTGGCAGCAGACCTTAAGAGCACTCAAGAGGCCATAAACAAGATAACAAAAAATC
TCAACTCTTTGAGTGAGCTGGAAGTAAAGAATCTTCAAAGACTAAGCGGTGCCATGGATGAACT
CCACAACGAAATACTAGAACTAGATGAGAAAGTGGATGATCTCAGAGCTGATACAATAAGCTCA
CAAATAGAACTCGCAGTCCTGCTTTCCAATGAAGGAATAATAAACAGTGAAGATGAACATCTCT
TGGCGCTTGAAAGAAAGCTGAAGAAAATGCTGGGCCCCTCTGCTGTAGAGATAGGGAATGGATG
CTTTGAAACCAAACACAAGTGCAACCAGACCTGTCTCGACAGAATAGCTGCTGGTACCTTTGAT
GCAGGAGAATTTTCTCTCCCCACCTTTGATTCACTGAATATTACTGCTGCATCTTTAAATGACG
ATGGATTGGATAATCATACTATACTGCTTTACTACTCAACTGCTGCCTCCAGTTTGGCTGTAAC
ACTGATGATAGCTATCTTTGTTGTTTATATGGTCTCCAGAGACAATGTTTCTTGCTCCATCTGT
CTATAA

Figure 31B, SEQ ID NO :92

Amino acid sequence of PDISP/HA B Brisbane (PrL-).

MAKNVAIFGLLFSLLVLVPSQIFADRICTGITSSNSPHVVKTATQGEVNVTGVIPLTTTPTKSH
FANLKGTETRGKLCPKCLNCTDLDVALGRPKCTGKIPSARVSILHEVRPVTSGCFPIMHDRTKI
RQLPNLLRGYEHIRLSTHNVINAENAPGGPYKIGTSGSCPNITNGNGFFATMAWAVPKNDKNKT
ATNPLTIEVPYICTEGEDQITVWGFHSDNETQMAKLYGDSKPQKFTSSANGVTTHYVSQIGGFP
NQTEDGGLPQSGRIVVDYMVQKSGKTGTITYQRGILLPQKVWCASGRSKVIKGSLPLIGEADCL

Figure 31B continued

HEKYGGLNKSKPYYTGEHAKAIGNCPIWVKTPLKLANGTKYRPPGGGWEGMIAGWHGYTSHGAHGVAVA
ADLKSTQEAINKITKNLNSLSELEVKNLQRLSGAMDELHNEILELDEKVDDLRADTISSQIELAVLLSN
EGIINSEDEHLLALERKLKKMLGPSAVEIGNGCFETKHKCNQTCLDRIAAGTFDAGEFSLPTFDSLNIT
AASLNDDGLDNHTILLYYSTAASSLAVTLMIAIFVVYMVSRDNVSCSICL*

Figure 31C

Schematic representation of construct number 1829 (2X35S/CPMV HT*)

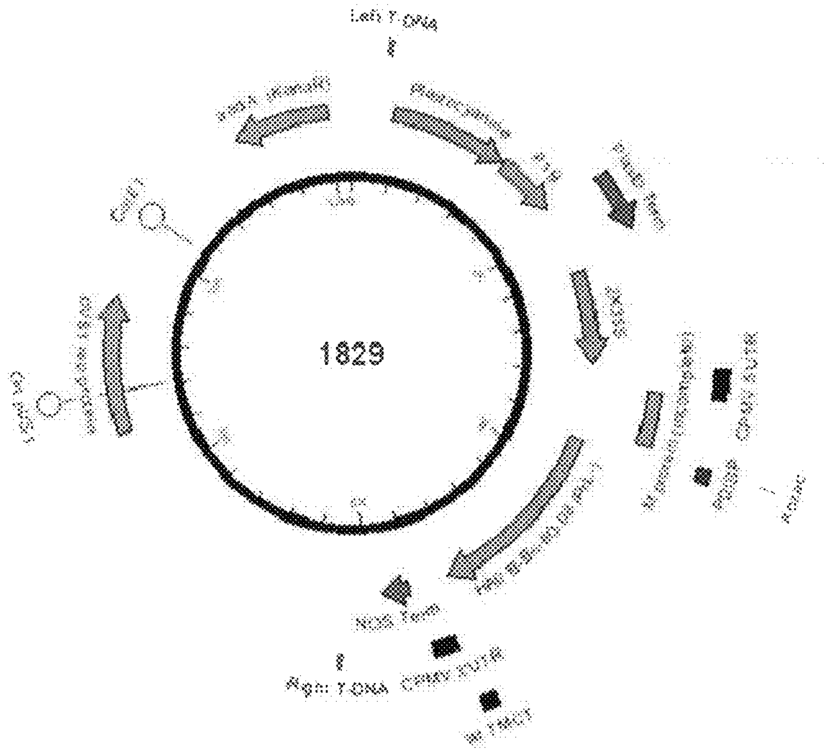

2X35S/CPMV HT (construct no 1039) and HT*(-Mprot) (construct no 1937) for PDISP/HA B Brisbane (PrL-)

Schematic representation of construct number 1937 (2X35S/CPMV HT*(-Mprot))

Figure 33

2X35S/CPMV HT (construct no 1067) and HT*(-Mprot) (construct no 1977) for PDISP/HA B Brisbane (PrL-)+H1 California TMCT

Figure 33A, SEQ ID NO :95

Nucleotide sequence of PDISP/HA B Brisbane (PrL-)+H1 California TMCT.

ATGGCGAAAAACGTTGCGATTTTCGGCTTATTGTTTTCTCTTCTTGTGTTGGTTCCTTCTCAGATCTTCGCCGATCGA
ATCTGCACTGGAATAACATCGTCAAACTCACCACATGTCGTCAAAACTGCTACTCAAGGGGAGGTCAATGTGACTG
GTGTAATACCACTGACAACAACACCCACCAAATCTCATTTTGCAAATCTCAAAGGAACAGAAACCAGGGGGAAAC
TATGCCCAAAATGCCTCAACTGCACAGATCTGGACGTAGCCTTGGGCAGACCAAAATGCACGGGGAAAATACCCT
CGGCAAGAGTTTCAATACTCCATGAAGTCAGACCTGTTACATCTGGGTGCTTTCCTATAATGCACGACAGAACAAA
AATTAGACAGCTGCCTAACCTTCTCCGAGGATACGAACATATCAGGTTATCAACCCATAACGTTATCAATGCAGAA
AATGCACCAGGAGGACCCTACAAAATTGGAACCTCAGGGTCTTGCCCTAACATTACCAATGGAAACGGATTTTTCG
CAACAATGGCTTGGGCCGTCCCAAAAAACGACAAAAACAAAACAGCAACAAATCCATTAACAATAGAAGTACCA
TACATTTGTACAGAAGGAGAAGACCAAATTACCGTTTGGGGGTTCCACTCTGACAACGAGACCCAAATGGCAAAG
CTCTATGGGGACTCAAAGCCCCAGAAGTTCACCTCATCTGCCAACGGAGTGACCACACATTACGTTTCACAGATTG
GTGGCTTCCCAAATCAAACAGAAGACGGAGGACTACCACAAAGTGGTAGAATTGTTGTTGATTACATGGTGCAAA
AATCTGGGAAAACAGGAACAATTACCTATCAAAGGGGTATTTTATTGCCTCAAAAGGTGTGGTGCGCAAGTGGCA
GGAGCAAGGTAATAAAAGGATCCTTGCCTTTAATTGGAGAAGCAGATTGCCTCCACGAAAAATACGGTGGATTAA
ACAAAAGCAAGCCTTACTACACAGGGGAACATGCAAAGGCCATAGGAAATTGCCCAATATGGGTGAAAACACCCT
TGAAGCTGGCCAATGGAACCAAATATAGACCTCCTGGTGGAGGATGGGAAGGAATGATTGCAGGTTGGCACGGAT
ACACATCCCATGGGGCACATGGAGTAGCGGTGGCAGCAGACCTTAAGAGCACTCAAGAGGCCATAAACAAGATA
ACAAAAAATCTCAACTCTTTGAGTGAGCTGGAAGTAAAGAATCTTCAAAGACTAAGCGGTGCCATGGATGAACTC
CACAACGAAATACTAGAACTAGATGAGAAAGTGGATGATCTCAGAGCTGATACAATAAGCTCACAAATAGAACTC
GCAGTCCTGCTTTCCAATGAAGGAATAATAAACAGTGAAGATGAACATCTCTTGGCGCTTGAAAGAAAGCTGAAG
AAAATGCTGGGCCCCTCTGCTGTAGAGATAGGGAATGGATGCTTTGAAACCAAACACAAGTGCAACCAGACCTGT
CTCGACAGAATAGCTGCTGGTACCTTTGATGCAGGAGAATTTTCTCTCCCCACCTTTGATTCACTGAATATTACTGC
TGCATCTTTAAATGACGATGGATTGGATAATTACCAGATTTTGGCGATCTATTCAACTGTCGCCAGTTCATTGGTAC
TGGTAGTCTCCCTGGGGGCAATCAGTTTCTGGATGTGCTCTAATGGGTCTCTACAGTGTAGAATATGTATTTAA

Figure 33B, SEQ ID NO : 96

Amino acid sequence of PDISP/HA B Brisbane (PrL-)+H1 California TMCT.

MAKNVAIFGLLFSLLVLVPSQIFADRICTGITSSNSPHVVKTATQGEVNVTGVIPLTTTPTKSHFANLKGTETRGKLCPKC
LNCTDLDVALGRPKCTGKIPSARVSILHEVRPVTSGCFPIMHDRTKIRQLPNLLRGYEHIRLSTHNVINAENAPGGPYKIG
TSGSCPNITNGNGFFATMAWAVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCASGRSKVIKGSLPLIGEADCL
HEKYGGLNKSKPYYTGEHAKAIGNCPIWVKTPLKLANGTKYRPPGGGWEGMIAGWHGYTSHGAHGVAVAADLKSTQ
EAINKITKNLNSLSELEVKNLQRLSGAMDELHNEILELDEKVDDLRADTISSQIELAVLLSNEGIINSEDEHLLALERKLKK
MLGPSAVEIGNGCFETKHKCNQTCLDRIAAGTFDAGEFSLPTFDSLNITAASLNDDGLDNYQILAIYSTVASSLVLVVSL
GAISFWMCSNGSLQCRICI*

Schematic representation of construct number 1067 (2X35S/CPMV HT)

Schematic representation of construct number 1977 (2X35S/CPMV HT*(-Mprot))

Figure 34

2X35S/CPMV HT (construct no 2072) and HT*(-Mprot) (construct no 2050) for PDISP/HA B Massachussetts (PrL-)

Figure 34A SEQ ID NO : 97

Nucleotide sequence of PDISP/HA B Massachussetts (PrL-).

ATGGCGAAAAACGTTGCGATTTTCGGCTTATTGTTTTCTCTTCTTGTGTTGGTTCCTTCTCAGATCTTCGCCGATCG
AATCTGCACTGGGATAACATCTTCAAACTCACCTCATGTGGTCAAAACAGCTACTCAAGGGGAGGTCAATGTGACTG
GTGTGATACCACTAACAACAACACCAACAAAATCTTATTTTGCAAATCTCAAAGGAACAAAGACCAGAGGGAAACTA
TGCCCAGACTGTCTCAACTGTACAGATCTGGATGTGGCCCTGGGCAGGCCAATGTGTGTGGGAACTACACCTTCTGC
GAAAGCTTCAATACTTCACGAAGTCAGACCTGTTACATCCGGGTGCTTCCCTATAATGCACGACAGAACAAAAATCA
GGCAACTAGCCAATCTTCTCAGAGGATATGAAAATATCAGGTTATCAACCCAAAACGTTATCGATGCAGAAAAGGCA
CCAGGAGGACCCTACAGACTTGGAACCTCAGGATCTTGCCCTAACGCTACCAGTAAAAGCGGATTTTTCGCAACAAT
GGCTTGGGCTGTCCCAAAGGACAACAACAAAAATGCAACGAACCCATTAACAGTAGAAGTACCATACATTTGTGCAG
AAGGGGAAGACCAAATTACTGTTTGGGGGTTCCATTCAGATAACAAAACCCAAATGAAGAACCTCTATGGAGACTCA
AATCCTCAAAAGTTCACCTCATCTGCTAATGGAGTAACCACACATTATGTTTCTCAGATTGGCGGCTTCCCAGATCA
AACAGAAGACGGAGGACTACCACAAAGCGGCAGAATTGTCGTTGATTACATGATGCAAAAACCTGGGAAAACAGGAA
CAATTGTCTATCAAAGAGGTGTTTTGTTGCCTCAAAAGGTGTGGTGCGCGAGTGGCAGGAGCAAAGTAATAAAAGGG
TCCTTGCCTTTAATTGGTGAAGCAGATTGCCTTCATGAAAAATACGGTGGATTAAACAAAAGCAAGCCTTACTACAC
AGGAGAACATGCAAAAGCCATAGGAAATTGCCCAATATGGGTGAAAACACCTTTGAAGCTTGCCAATGGAACCAAAT
ATAGACCTCCTGGTGGAGGATGGGAAGGAATGATTGCAGGTTGGCACGGATACACATCTCACGGAGCACATGGAGTG
GCAGTTGCTGCAGACCTTAAGAGCACACAAGAAGCTATAAACAAGATAACAAAAAATCTCAACTCTTTGAGTGAGCT
AGAAGTAAAGAATCTTCAAAGGCTAAGTGGTGCCATGGATGAACTCCACAACGAAATACTCGAGCTGGATGAGAAAG
TGGATGACCTCAGAGCTGACACTATAAGTTCACAAATAGAACTTGCAGTCTTGCTTTCCAACGAAGGAATAATAAAC
AGTGAAGACGAGCATCTATTGGCACTTGAGAGAAAACTAAAGAAAATGCTGGGTCCCTCTGCTGTAGACATAGGAAA
TGGATGCTTCGAAACCAAACACAAATGCAACCAGACCTGCTTAGACAGGATAGCTGCTGGCACCTTTAATGCAGGAG
AGTTTTCTCTCCCCACTTTTGATTCATTGAACATTACTGCTGCATCTTTAAATGATGATGGATTGGATAACCATACT
ATACTGCTCTATTACTCAACTGCTGCTTCTAGTTTGGCTGTAACATTGATGCTAGCTATTTTTATTGTTTATATGGT
CTCCAGAGACAACGTTTCATGCTCCATCTGTCTATAA

Figure 34B, SEQ ID NO : 98

Amino acid sequence of PDISP/HA B Massachussetts (PrL-).

MAKNVAIFGLLFSLLVLVPSQIFADRICTGITSSNSPHVVKTATQGEVNVTGVIPLTTTPTKSYFANLKGTKTRGKL
CPDCLNCTDLDVALGRPMCVGTTPSAKASILHEVRPVTSGCFPIMHDRTKIRQLANLLRGYENIRLSTQNVIDAEKA
PGGPYRLGTSGSCPNATSKSGFFATMAWAVPKDNNKNATNPLTVEVPYICAEGEDQITVWGFHSDNKTQMKNLYGDS
NPQKFTSSANGVTTHYVSQIGGFPDQTEDGGLPQSGRIVVDYMMQKPGKTGTIVYQRGVLLPQKVWCASGRSKVIKG
SLPLIGEADCLHEKYGGLNKSKPYYTGEHAKAIGNCPIWVKTPLKLANGTKYRPPGGGWEGMIAGWHGYTSHGAHGV
AVAADLKSTQEAINKITKNLNSLSELEVKNLQRLSGAMDELHNEILELDEKVDDLRADTISSQIELAVLLSNEGIIN
SEDEHLLALERKLKKMLGPSAVDIGNGCFETKHKCNQTCLDRIAAGTFNAGEFSLPTFDSLNITAASLNDDGLDNHT
ILLYYSTAASSLAVTLMLAIFIVYMVSRDNVSCSICL*

Schematic representation of construct number 2072 (2X35S/CPMV HT)

Schematic representation of construct number 2050 (2X35S/CPMV HT*(-Mprot))

Figure 35

2X35S/CPMV HT (construct no 2074) and HT*(-Mprot) (construct no 2060) for PDISP/HA B Massachussetts (PrL-)+H1 California TMCT

Figure 35A SEQ ID NO : 99

Nucleotide sequence of PDISP/HA B Massachussetts (PrL-)+H1 California TMCT.

ATGGCGAAAAACGTTGCGATTTTCGGCTTATTGTTTTCTCTTCTTGTGTTGGTTCCTTCTCAGATCTTCGCCGATCG
AATCTGCACTGGGATAACATCTTCAAACTCACCTCATGTGGTCAAAACAGCTACTCAAGGGGAGGTCAATGTGACTG
GTGTGATACCACTAACAACAACACCAACAAAATCTTATTTTGCAAATCTCAAAGGAACAAAGACCAGAGGGAAACTA
TGCCCAGACTGTCTCAACTGTACAGATCTGGATGTGGCCCTGGGCAGGCCAATGTGTGTGGGAACTACACCTTCTGC
GAAAGCTTCAATACTTCACGAAGTCAGACCTGTTACATCCGGGTGCTTCCCTATAATGCACGACAGAACAAAAATCA
GGCAACTAGCCAATCTTCTCAGAGGATATGAAAATATCAGGTTATCAACCCAAAACGTTATCGATGCAGAAAAGGCA
CCAGGAGGACCCTACAGACTTGGAACCTCAGGATCTTGCCCTAACGCTACCAGTAAAAGCGGATTTTTCGCAACAAT
GGCTTGGGCTGTCCCAAAGGACAACAACAAAAATGCAACGAACCCATTAACAGTAGAAGTACCATACATTTGTGCAG
AAGGGGAAGACCAAATTACTGTTTGGGGGTTCCATTCAGATAACAAAACCCAAATGAAGAACCTCTATGGAGACTCA
AATCCTCAAAAGTTCACCTCATCTGCTAATGGAGTAACCACACATTATGTTTCTCAGATTGGCGGCTTCCCAGATCA
AACAGAAGACGGAGGACTACCACAAAGCGGCAGAATTGTCGTTGATTACATGATGCAAAAACCTGGGAAAACAGGAA
CAATTGTCTATCAAAGAGGTGTTTTGTTGCCTCAAAAGGTGTGGTGCGCGAGTGGCAGGAGCAAAGTAATAAAAGGG
TCCTTGCCTTTAATTGGTGAAGCAGATTGCCTTCATGAAAAATACGGTGGATTAAACAAAAGCAAGCCTTACTACAC
AGGAGAACATGCAAAAGCCATAGGAAATTGCCCAATATGGGTGAAAACACCTTTGAAGCTTGCCAATGGAACCAAAT
ATAGACCTCCTGGTGGAGGATGGGAAGGAATGATTGCAGGTTGGCACGGATACACATCTCACGGAGCACATGGAGTG
GCAGTTGCTGCAGACCTTAAGAGCACACAAGAAGCTATAAACAAGATAACAAAAAATCTCAACTCTTTGAGTGAGCT
AGAAGTAAAGAATCTTCAAAGGCTAAGTGGTGCCATGGATGAACTCCACAACGAAATACTCGAGCTGGATGAGAAAG
TGGATGACCTCAGAGCTGACACTATAAGTTCACAAATAGAACTTGCAGTCTTGCTTTCCAACGAAGGAATAATAAAC
AGTGAAGACGAGCATCTATTGGCACTTGAGAGAAAACTAAAGAAAATGCTGGGTCCCTCTGCTGTAGACATAGGAAA
TGGATGCTTCGAAACCAAACACAAATGCAACCAGACCTGCTTAGACAGGATAGCTGCTGGCACCTTTAATGCAGGAG
AGTTTTCTCTCCCCACTTTTGATTCATTGAACATTACTGCTGCATCTTTAAATGATGATGGATTGGATAACTACCAG
ATTTTGGCGATCTATTCAACTGTCGCCAGTTCATTGGTACTGGTAGTCTCCCTGGGGGCAATCAGTTTCTGGATGTG
CTCTAATGGGTCTCTACAGTGTAGAATATGTATTTAA

Figure 35B, SEQ ID NO :100

Amino acid sequence of PDISP/HA B Massachussetts (PrL-)+H1 California TMCT.

MAKNVAIFGLLFSLLVLVPSQIFADRICTGITSSNSPHVVKTATQGEVNVTGVIPLTTTPTKSYFANLKGTKTRGKL
CPDCLNCTDLDVALGRPMCVGTTPSAKASILHEVRPVTSGCFPIMHDRTKIRQLANLLRGYENIRLSTQNVIDAEKA
PGGPYRLGTSGSCPNATSKSGFFATMAWAVPKDNNKNATNPLTVEVPYICAEGEDQITVWGFHSDNKTQMKNLYGDS
NPQKFTSSANGVTTHYVSQIGGFPDQTEDGGLPQSGRIVVDYMMQKPGKTGTIVYQRGVLLPQKVWCASGRSKVIKG
SLPLIGEADCLHEKYGGLNKSKPYYTGEHAKAIGNCPIWVKTPLKLANGTKYRPPGGGWEGMIAGWHGYTSHGAHGV
AVAADLKSTQEAINKITKNLNSLSELEVKNLQRLSGAMDELHNEILELDEKVDDLRADTISSQIELAVLLSNEGIIN
SEDEHLLALERKLKKMLGPSAVDIGNGCFETKHKCNQTCLDRIAAGTFNAGEFSLPTFDSLNITAASLNDDGLDNYQ
ILAIYSTVASSLVLVVSLGAISFWMCSNGSLQCRICI*

Schematic representation of construct number 2074 (2X35S/CPMV HT)

Schematic representation of construct number 2060 (2X35S/CPMV HT*(-Mprot))

Figure 36

2X35S/CPMV HT (construct no 1445), HT*(-Mprot) (construct no 1820) and HT(fl5'UTR) (construct no 1975) for HA B Wisconsin (PrL-)

Figure 36A, SEQ ID NO : 101

Nucleotide sequence of HA B Wisconsin (PrL-).

ATGAAGGCAATAATTGTACTACTCATGGTAGTAACATCCAATGCAGATCGAATCTGCACTGGGATAACATCTTCAAA
CTCACCTCATGTGGTCAAAACAGCTACTCAAGGGGAGGTCAATGTGACTGGCGTGATACCACTGACAACAACACCAA
CAAAATCTTATTTTGCAAATCTCAAAGGAACAAGGACCAGAGGGAAACTATGCCCGGACTGTCTCAACTGTACAGAT
CTGGATGTGGCCTTGGGCAGGCCAATGTGTGTGGGGACCACACCTTCTGCTAAAGCTTCAATACTCCACGAGGTCAG
ACCTGTTACATCCGGGTGCTTTCCTATAATGCACGACAGAACAAAAATCAGGCAACTACCCAATCTTCTCAGAGGAT
ATGAAAATATCAGGTTATCAACCCAAAACGTTATCGATGCAGAAAAAGCACCAGGAGGACCCTACAGACTTGGAACC
TCAGGATCTTGCCCTAACGCTACCAGTAAAATCGGATTTTTTGCAACAATGGCTTGGGCTGTCCCAAAGGACAACTA
CAAAAATGCAACGAACCCACTAACAGTAGAAGTACCATACATTTGTACAGAAGGGGAAGACCAAATTACTGTTTGGG
GGTTCCATTCAGATAACAAAACCCAAATGAAGAGCCTCTATGGAGACTCAAATCCTCAAAAGTTCACCTCATCTGCT
AATGGAGTAACCACACATTATGTTTCTCAGATTGGCGACTTCCCAGATCAAACAGAAGACGGAGGACTACCACAAAG
CGGCAGAATTGTTGTTGATTACATGATGCAAAAACCTGGGAAAACAGGAACAATTGTCTATCAAAGAGGTGTTTTGT
TGCCTCAAAAGGTGTGGTGCGCGAGTGGCAGGAGCAAAGTAATAAAAGGGTCATTGCCTTTAATTGGTGAAGCAGAT
TGCCTTCATGAAAAATACGGTGGATTAAACAAAAGCAAGCCTTACTACACAGGAGAACATGCAAAAGCCATAGGAAA
TTGCCCAATATGGGTAAAAACACCTTTGAAGCTTGCCAATGGAACCAAATATAGACCTCCTGGTGGAGGATGGGAAG
GAATGATTGCAGGTTGGCACGGATACACATCTCACGGAGCACATGGAGTGGCAGTGGCGGCAGACCTTAAGAGTACA
CAAGAAGCTATAAATAAGATAACAAAAAATCTCAATTCTTTGAGTGAGCTAGAAGTAAAGAACCTTCAAAGACTAAG
TGGTGCCATGGATGAACTCCACAACGAAATACTCGAGCTGGATGAGAAAGTGGATGATCTCAGAGCTGACACTATAA
GCTCACAAATAGAACTTGCAGTCTTGCTTTCCAACGAAGGAATAATAAACAGTGAAGACGAGCATCTATTGGCACTT
GAGAGAAAACTAAAGAAAATGCTGGGTCCCTCTGCTGTAGACATAGGAAACGGATGCTTCGAAACCAAACACAAATG
CAACCAGACCTGCTTAGACAGGATAGCTGCTGGCACCTTTAATGCAGGAGAATTTTCTCTCCCCACTTTTGATTCAT
TGAACATTACTGCTGCATCTTTAAATGATGATGGATTGGATAACCATACTATACTGCTCTATTACTCAACTGCTGCT
TCTAGTTTGGCTGTAACATTAATGCTAGCTATTTTTATTGTTTATATGGTCTCCAGAGACAACGTTTCATGCTCCAT
CTGTCTATAA

Figure 36B, SEQ ID NO : 102

Amino acid sequence of HA B Wisconsin (PrL-).

MKAIIVLLMVVTSNADRICTGITSSNSPHVVKTATQGEVNVTGVIPLTTTPTKSYFANLKGTRTRGKLCPDCLNCTD
LDVALGRPMCVGTTPSAKASILHEVRPVTSGCFPIMHDRTKIRQLPNLLRGYENIRLSTQNVIDAEKAPGGPYRLGT
SGSCPNATSKIGFFATMAWAVPKDNYKNATNPLTVEVPYICTEGEDQITVWGFHSDNKTQMKSLYGDSNPQKFTSSA
NGVTTHYVSQIGDFPDQTEDGGLPQSGRIVVDYMMQKPGKTGTIVYQRGVLLPQKVWCASGRSKVIKGSLPLIGEAD
CLHEKYGGLNKSKPYYTGEHAKAIGNCPIWVKTPLKLANGTKYRPPGGGWEGMIAGWHGYTSHGAHGVAVAADLKST
QEAINKITKNLNSLSELEVKNLQRLSGAMDELHNEILELDEKVDDLRADTISSQIELAVLLSNEGIINSEDEHLLAL
ERKLKKMLGPSAVDIGNGCFETKHKCNQTCLDRIAAGTFNAGEFSLPTFDSLNITAASLNDDGLDNHTILLYYSTAA
SSLAVTLMLAIFIVYMVSRDNVSCSICL*

Schematic representation of construct number 1445 (2X35S/CPMV HT)

Schematic representation of construct number 1820 (2X35S/CPMV HT*(-Mprot))

Schematic representation of construct number 1975 (2X35S/CPMV HT*(fl5'UTR))

Figure 37

2X35S/CPMV HT (construct no 1454) and HT*(-Mprot) (construct no 1893) for HA B Wisconsin (PrL-)+H1 California TMCT

Figure 37A, SEQ ID NO : 103

Nucleotide sequence of HA B Wisconsin (PrL-)+H1 California TMCT

ATGAAGGCAATAATTGTACTACTCATGGTAGTAACATCCAATGCAGATCGAATCTGCACTGGGATAACATCTTCAAA
CTCACCTCATGTGGTCAAAACAGCTACTCAAGGGGAGGTCAATGTGACTGGCGTGATACCACTGACAACAACACCAA
CAAAATCTTATTTTGCAAATCTCAAAGGAACAAGGACCAGAGGGAAACTATGCCCGGACTGTCTCAACTGTACAGAT
CTGGATGTGGCCTTGGGCAGGCCAATGTGTGTGGGGACCACACCTTCTGCTAAAGCTTCAATACTCCACGAGGTCAG
ACCTGTTACATCCGGGTGCTTTCCTATAATGCACGACAGAACAAAAATCAGGCAACTACCCAATCTTCTCAGAGGAT
ATGAAAATATCAGGTTATCAACCCAAAACGTTATCGATGCAGAAAAAGCACCAGGAGGACCCTACAGACTTGGAACC
TCAGGATCTTGCCCTAACGCTACCAGTAAAATCGGATTTTTTGCAACAATGGCTTGGGCTGTCCCAAAGGACAACTA
CAAAAATGCAACGAACCCACTAACAGTAGAAGTACCATACATTTGTACAGAAGGGGAAGACCAAATTACTGTTTGGG
GGTTCCATTCAGATAACAAAACCCAAATGAAGAGCCTCTATGGAGACTCAAATCCTCAAAAGTTCACCTCATCTGCT
AATGGAGTAACCACACATTATGTTTCTCAGATTGGCGACTTCCCAGATCAAACAGAAGACGGAGGACTACCACAAAG
CGGCAGAATTGTTGTTGATTACATGATGCAAAAACCTGGAAAAACAGGAACAATTGTCTATCAAAGAGGTGTTTTGT
TGCCTCAAAAGGTGTGGTGCGCGAGTGGCAGGAGCAAAGTAATAAAAGGGTCATTGCCTTTAATTGGTGAAGCAGAT
TGCCTTCATGAAAAATACGGTGGATTAAACAAAAGCAAGCCTTACTACACAGGAGAACATGCAAAAGCCATAGGAAA
TTGCCCAATATGGGTAAAAACACCTTTGAAGCTTGCCAATGGAACCAAATATAGACCTCCTGGTGGAGGATGGGAAG
GAATGATTGCAGGTTGGCACGGATACACATCTCACGGAGCACATGGAGTGGCAGTGGCGGCAGACCTTAAGAGTACA
CAAGAAGCTATAAATAAGATAACAAAAAATCTCAATTCTTTGAGTGAGCTAGAAGTAAAGAACCTTCAAAGACTAAG
TGGTGCCATGGATGAACTCCACAACGAAATACTCGAGCTGGATGAGAAAGTGGATGATCTCAGAGCTGACACTATAA
GCTCACAAATAGAACTTGCAGTCTTGCTTTCCAACGAAGGAATAATAAACAGTGAAGACGAGCATCTATTGGCACTT
GAGAGAAAACTAAAGAAAATGCTGGGTCCCTCTGCTGTAGACATAGGAAACGGATGCTTCGAAACCAAACACAAATG
CAACCAGACCTGCTTAGACAGGATAGCTGCTGGCACCTTTAATGCAGGAGAATTTTCTCTCCCCACTTTTGATTCAT
TGAACATTACTGCTGCATCTTTAAATGATGATGGATTGGATAACTACCAGATTTTGGCGATCTATTCAACTGTCGCC
AGTTCATTGGTACTGGTAGTCTCCCTGGGGGCAATCAGTTTCTGGATGTGCTCTAATGGGTCTCTACAGTGTAGAAT
ATGTATTTAA

Figure 37B, SEQ ID NO : 104

Amino acid sequence of HA B Wisconsin (PrL-)+H1 California TMC.

MKAIIVLLMVVTSNADRICTGITSSNSPHVVKTATQGEVNVTGVIPLTTTPTKSYFANLKGTRTRGKLCPDCLNCTD
LDVALGRPMCVGTTPSAKASILHEVRPVTSGCFPIMHDRTKIRQLPNLLRGYENIRLSTQNVIDAEKAPGGPYRLGT
SGSCPNATSKIGFFATMAWAVPKDNYKNATNPLTVEVPYICTEGEDQITVWGFHSDNKTQMKSLYGDSNPQKFTSSA
NGVTTHYVSQIGDFPDQTEDGGLPQSGRIVVDYMMQKPGKTGTIVYQRGVLLPQKVWCASGRSKVIKGSLPLIGEAD
CLHEKYGGLNKSKPYYTGEHAKAIGNCPIWVKTPLKLANGTKYRPPGGGWEGMIAGWHGYTSHGAHGVAVAADLKST
QEAINKITKNLNSLSELEVKNLQRLSGAMDELHNEILELDEKVDDLRADTISSQIELAVLLSNEGIINSEDEHLLAL
ERKLKKMLGPSAVDIGNGCFETKHKCNQTCLDRIAAGTFNAGEFSLPTFDSLNITAASLNDDGLDNYQILAIYSTVA
SSLVLVVSLGAISFWMCSNGSLQCRICI*

Schematic representation of construct number 1454 (2X35S/CPMV HT)

Schematic representation of construct number 1893 (2X35S/CPMV HT*(-Mprot))

Figure 38

L- 2X35S/CPMV HT (construct no 1067) and HT* (construct no 1875) for PDISP/HA B Brisbane (PrL-)+H1 California TMCT

Figure 38A, SEQ ID NO : 105

Nucleotide sequence of PDISP/HA B Brisbane (PrL-)+H1 California TMCT.
ATGGCGAAAAACGTTGCGATTTTCGGCTTATTGTTTTCTCTTCTTGTGTTGGTTCCTTCTCAGATCTTCGCCGATCGA
ATCTGCACTGGAATAACATCGTCAAACTCACCACATGTCGTCAAAACTGCTACTCAAGGGGAGGTCAATGTGACTG
GTGTAATACCACTGACAACAACACCCACCAAATCTCATTTTGCAAATCTCAAAGGAACAGAAACCAGGGGGAAAC
TATGCCCAAAATGCCTCAACTGCACAGATCTGGACGTAGCCTTGGGCAGACCAAAATGCACGGGGAAAATACCCT
CGGCAAGAGTTTCAATACTCCATGAAGTCAGACCTGTTACATCTGGGTGCTTTCCTATAATGCACGACAGAACAAA
AATTAGACAGCTGCCTAACCTTCTCCGAGGATACGAACATATCAGGTTATCAACCCATAACGTTATCAATGCAGAA
AATGCACCAGGAGGACCCTACAAAATTGGAACCTCAGGGTCTTGCCCTAACATTACCAATGGAAACGGATTTTTCG
CAACAATGGCTTGGGCCGTCCCAAAAAACGACAAAAACAAAACAGCAACAAATCCATTAACAATAGAAGTACCA
TACATTTGTACAGAAGGAGAAGACCAAATTACCGTTTGGGGGTTCCACTCTGACAACGAGACCCAAATGGCAAAG
CTCTATGGGGACTCAAAGCCCCAGAAGTTCACCTCATCTGCCAACGGAGTGACCACACATTACGTTTCACAGATTG
GTGGCTTCCCAAATCAAACAGAAGACGGAGGACTACCACAAAGTGGTAGAATTGTTGTTGATTACATGGTGCAAA
AATCTGGGAAAACAGGAACAATTACCTATCAAAGGGGTATTTTATTGCCTCAAAAGGTGTGGTGCGCAAGTGGCA
GGAGCAAGGTAATAAAAGGATCCTTGCCTTTAATTGGAGAAGCAGATTGCCTCCACGAAAAATACGGTGGATTAA
ACAAAAGCAAGCCTTACTACACAGGGGAACATGCAAAGGCCATAGGAAATTGCCCAATATGGGTGAAAACACCCT
TGAAGCTGGCCAATGGAACCAAATATAGACCTCCTGGTGGAGGATGGGAAGGAATGATTGCAGGTTGGCACGGAT
ACACATCCCATGGGGCACATGGAGTAGCGGTGGCAGCAGACCTTAAGAGCACTCAAGAGGCCATAAACAAGATA
ACAAAAAATCTCAACTCTTTGAGTGAGCTGGAAGTAAAGAATCTTCAAAGACTAAGCGGTGCCATGGATGAACTC
CACAACGAAATACTAGAACTAGATGAGAAAGTGGATGATCTCAGAGCTGATACAATAAGCTCACAAATAGAACTC
GCAGTCCTGCTTTCCAATGAAGGAATAATAAACAGTGAAGATGAACATCTCTTGGCGCTTGAAAGAAAGCTGAAG
AAAATGCTGGGCCCCTCTGCTGTAGAGATAGGGAATGGATGCTTTGAAACCAAACACAAGTGCAACCAGACCTGT
CTCGACAGAATAGCTGCTGGTACCTTTGATGCAGGAGAATTTTCTCTCCCCACCTTTGATTCACTGAATATTACTGC
TGCATCTTTAAATGACGATGGATTGGATAATTACCAGATTTTGGCGATCTATTCAACTGTCGCCAGTTCATTGGTAC
TGGTAGTCTCCCTGGGGGCAATCAGTTTCTGGATGTGCTCTAATGGGTCTCTACAGTGTAGAATATGTATTTAA

Figure 38B, SEQ ID NO : 106

Amino acid sequence of PDISP/HA B Brisbane (PrL-)+H1 California TMCT.
MAKNVAIFGLLFSLLVLVPSQIFADRICTGITSSNSPHVVKTATQGEVNVTGVIPLTTTPTKSHFANLKGTETRGKLCPKC
LNCTDLDVALGRPKCTGKIPSARVSILHEVRPVTSGCFPIMHDRTKIRQLPNLLRGYEHIRLSTHNVINAENAPGGPYKIG
TSGSCPNITNGNGFFATMAWAVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCASGRSKVIKGSLPLIGEADCL
HEKYGGLNKSKPYYTGEHAKAIGNCPIWVKTPLKLANGTKYRPPGGGWEGMIAGWHGYTSHGAHGVAVAADLKSTQ
EAINKITKNLNSLSELEVKNLQRLSGAMDELHNEILELDEKVDDLRADTISSQIELAVLLSNEGIINSEDEHLLALERKLKK
MLGPSAVEIGNGCFETKHKCNQTCLDRIAAGTFDAGEFSLPTFDSLNITAASLNDDGLDNYQILAIYSTVASSLVLVVSL
GAISFWMCSNGSLQCRICI*

Schematic representation of construct number 1875 (2X35S/CPMV HT*)

Figure 39

M- 2X35S/CPMV HT (construct no 2072) and HT* (construct no 2052) for PDISP/HA B Massachussetts (PrL-)

Figure 39A, SEQ ID NO : 107

Nucleotide sequence of PDISP/HA B Massachussetts (PrL-).
ATGGCGAAAAACGTTGCGATTTTCGGCTTATTGTTTTCTCTTCTTGTGTTGGTTCCTTCTCAGATCTTCGCCGATCGA
ATCTGCACTGGGATAACATCTTCAAACTCACCTCATGTGGTCAAAACAGCTACTCAAGGGGAGGTCAATGTGACTG
GTGTGATACCACTAACAACAACACCAACAAAATCTTATTTTGCAAATCTCAAAGGAACAAAGACCAGAGGGAAAC
TATGCCCAGACTGTCTCAACTGTACAGATCTGGATGTGGCCCTGGGCAGGCCAATGTGTGTGGGAACTACACCTTC
TGCGAAAGCTTCAATACTTCACGAAGTCAGACCTGTTACATCCGGGTGCTTCCCTATAATGCACGACAGAACAAAA
ATCAGGCAACTAGCCAATCTTCTCAGAGGATATGAAAATATCAGGTTATCAACCCAAAACGTTATCGATGCAGAA
AAGGCACCAGGAGGACCCTACAGACTTGGAACCTCAGGATCTTGCCCTAACGCTACCAGTAAAAGCGGATTTTTC
GCAACAATGGCTTGGGCTGTCCCAAAGGACAACAACAAAAATGCAACGAACCCATTAACAGTAGAAGTACCATAC
ATTTGTGCAGAAGGGGAAGACCAAATTACTGTTTGGGGGTTCCATTCAGATAACAAAACCCAAATGAAGAACCTC
TATGGAGACTCAAATCCTCAAAAGTTCACCTCATCTGCTAATGGAGTAACCACACATTATGTTTCTCAGATTGGCG
GCTTCCCAGATCAAACAGAAGACGGAGGACTACCACAAAGCGGCAGAATTGTCGTTGATTACATGATGCAAAAAC
CTGGGAAAACAGGAACAATTGTCTATCAAAGAGGTGTTTTGTTGCCTCAAAAGGTGTGGTGCGCGAGTGGCAGGA
GCAAAGTAATAAAAGGGTCCTTGCCTTTAATTGGTGAAGCAGATTGCCTTCATGAAAAATACGGTGGATTAAACA
AAAGCAAGCCTTACTACACAGGAGAACATGCAAAAGCCATAGGAAATTGCCCAATATGGGTGAAAACACCTTTGA
AGCTTGCCAATGGAACCAAATATAGACCTCCTGGTGGAGGATGGGAAGGAATGATTGCAGGTTGGCACGGATACA
CATCTCACGGAGCACATGGAGTGGCAGTTGCTGCAGACCTTAAGAGCACACAAGAAGCTATAAACAAGATAACAA
AAAATCTCAACTCTTTGAGTGAGCTAGAAGTAAAGAATCTTCAAAGGCTAAGTGGTGCCATGGATGAACTCCACA
ACGAAATACTCGAGCTGGATGAGAAAGTGGATGACCTCAGAGCTGACACTATAAGTTCACAAATAGAACTTGCAG
TCTTGCTTTCCAACGAAGGAATAATAAACAGTGAAGACGAGCATCTATTGGCACTTGAGAGAAAACTAAAGAAAA
TGCTGGGTCCCTCTGCTGTAGACATAGGAAATGGATGCTTCGAAACCAAACACAAATGCAACCAGACCTGCTTAG
ACAGGATAGCTGCTGGCACCTTTAATGCAGGAGAGTTTTCTCTCCCCACTTTTGATTCATTGAACATTACTGCTGCA
TCTTTAAATGATGATGGATTGGATAACCATACTATACTGCTCTATTACTCAACTGCTGCTTCTAGTTTGGCTGTAAC
ATTGATGCTAGCTATTTTTATTGTTTATATGGTCTCCAGAGACAACGTTTCATGCTCCATCTGTCTATAA

Figure 39B, SEQ ID NO :108

Amino acid sequence of PDISP/HA B Massachussetts (PrL-).
MAKNVAIFGLLFSLLVLVPSQIFADRICTGITSSNSPHVVKTATQGEVNVTGVIPLTTTPTKSYFANLKGTKTRGKLCPDC
LNCTDLDVALGRPMCVGTTPSAKASILHEVRPVTSGCFPIMHDRTKIRQLANLLRGYENIRLSTQNVIDAEKAPGGPYRL
GTSGSCPNATSKSGFFATMAWAVPKDNNKNATNPLTVEVPYICAEGEDQITVWGFHSDNKTQMKNLYGDSNPQKFTSS
ANGVTTHYVSQIGGFPDQTEDGGLPQSGRIVVDYMMQKPGKTGTIVYQRGVLLPQKVWCASGRSKVIKGSLPLIGEAD
CLHEKYGGLNKSKPYYTGEHAKAIGNCPIWVKTPLKLANGTKYRPPGGGWEGMIAGWHGYTSHGAHGVAVAADLKS
TQEAINKITKNLNSLSELEVKNLQRLSGAMDELHNEILELDEKVDDLRADTISSQIELAVLLSNEGIINSEDEHLLALERKL
KKMLGPSAVDIGNGCFETKHKCNQTCLDRIAAGTFNAGEFSLPTFDSLNITAASLNDDGLDNHTILLYYSTAASSLAVTL
MLAIFIVYMVSRDNVSCSICL*

Schematic representation of construct number 2052 (2X35S/CPMV HT*)

Figure 40

N- 2X35S/CPMV HT (construct no 2074) and HT* (construct no 2062) for PDISP/HA B Massachussetts (PrL-)+H1 California TMCT

Figure 40A, SEQ ID NO : 109

Nucleotide sequence of PDISP/HA B Massachussetts (PrL-)+H1 California TMCT.

ATGGCGAAAAACGTTGCGATTTTCGGCTTATTGTTTTCTCTTCTTGTGTTGGTTCCTTCTCAGATCTTCGCCGATCGA
ATCTGCACTGGGATAACATCTTCAAACTCACCTCATGTGGTCAAAACAGCTACTCAAGGGGAGGTCAATGTGACTG
GTGTGATACCACTAACAACAACACCAACAAAATCTTATTTTGCAAATCTCAAAGGAACAAAGACCAGAGGGAAAC
TATGCCCAGACTGTCTCAACTGTACAGATCTGGATGTGGCCCTGGGCAGGCCAATGTGTGTGGGAACTACACCTTC
TGCGAAAGCTTCAATACTTCACGAAGTCAGACCTGTTACATCCGGGTGCTTCCCTATAATGCACGACAGAACAAAA
ATCAGGCAACTAGCCAATCTTCTCAGAGGATATGAAAATATCAGGTTATCAACCCAAAACGTTATCGATGCAGAA
AAGGCACCAGGAGGACCCTACAGACTTGGAACCTCAGGATCTTGCCCTAACGCTACCAGTAAAAGCGGATTTTTC
GCAACAATGGCTTGGGCTGTCCCAAAGGACAACAACAAAAATGCAACGAACCCATTAACAGTAGAAGTACCATAC
ATTTGTGCAGAAGGGGAAGACCAAATTACTGTTTGGGGGTTCCATTCAGATAACAAAACCCAAATGAAGAACCTC
TATGGAGACTCAAATCCTCAAAAGTTCACCTCATCTGCTAATGGAGTAACCACACATTATGTTTCTCAGATTGGCG
GCTTCCCAGATCAAACAGAAGACGGAGGACTACCACAAAGCGGCAGAATTGTCGTTGATTACATGATGCAAAAAC
CTGGGAAAACAGGAACAATTGTCTATCAAAGAGGTGTTTTGTTGCCTCAAAAGGTGTGGTGCGCGAGTGGCAGGA
GCAAAGTAATAAAAGGGTCCTTGCCTTTAATTGGTGAAGCAGATTGCCTTCATGAAAAATACGGTGGATTAAACA
AAAGCAAGCCTTACTACACAGGAGAACATGCAAAAGCCATAGGAAATTGCCCAATATGGGTGAAAACACCTTTGA
AGCTTGCCAATGGAACCAAATATAGACCTCCTGGTGGAGGATGGGAAGGAATGATTGCAGGTTGGCACGGATACA
CATCTCACGGAGCACATGGAGTGGCAGTTGCTGCAGACCTTAAGAGCACACAAGAAGCTATAAACAAGATAACAA
AAAATCTCAACTCTTTGAGTGAGCTAGAAGTAAAGAATCTTCAAAGGCTAAGTGGTGCCATGGATGAACTCCACA
ACGAAATACTCGAGCTGGATGAGAAAGTGGATGACCTCAGAGCTGACACTATAAGTTCACAAATAGAACTTGCAG
TCTTGCTTTCCAACGAAGGAATAATAAACAGTGAAGACGAGCATCTATTGGCACTTGAGAGAAAACTAAAGAAAA
TGCTGGGTCCCTCTGCTGTAGACATAGGAAATGGATGCTTCGAAACCAAACACAAATGCAACCAGACCTGCTTAG
ACAGGATAGCTGCTGGCACCTTTAATGCAGGAGAGTTTTCTCTCCCCACTTTTGATTCATTGAACATTACTGCTGCA
TCTTTAAATGATGATGGATTGGATAACTACCAGATTTTGGCGATCTATTCAACTGTCGCCAGTTCATTGGTACTGGT
AGTCTCCCTGGGGGCAATCAGTTTCTGGATGTGCTCTAATGGGTCTCTACAGTGTAGAATATGTATTTAA

Figure 40B, SEQ ID NO : 110

Amino acid sequence of PDISP/HA B Massachussetts (PrL-)+H1 California TMCT.

MAKNVAIFGLLFSLLVLVPSQIFADRICTGITSSNSPHVVKTATQGEVNVTGVIPLTTTPTKSYFANLKGTKTRGKLCPDC
LNCTDLDVALGRPMCVGTTPSAKASILHEVRPVTSGCFPIMHDRTKIRQLANLLRGYENIRLSTQNVIDAEKAPGGPYRL
GTSGSCPNATSKSGFFATMAWAVPKDNNKNATNPLTVEVPYICAEGEDQITVWGFHSDNKTQMKNLYGDSNPQKFTSS
ANGVTTHYVSQIGGFPDQTEDGGLPQSGRIVVDYMMQKPGKTGTIVYQRGVLLPQKVWCASGRSKVIKGSLPLIGEAD
CLHEKYGGLNKSKPYYTGEHAKAIGNCPIWVKTPLKLANGTKYRPPGGGWEGMIAGWHGYTSHGAHGVAVAADLKS
TQEAINKITKNLNSLSELEVKNLQRLSGAMDELHNEILELDEKVDDLRADTISSQIELAVLLSNEGIINSEDEHLLALERKL
KKMLGPSAVDIGNGCFETKHKCNQTCLDRIAAGTFNAGEFSLPTFDSLNITAASLNDDGLDNYQILAIYSTVASSLVLVV
SLGAISFWMCSNGSLQCRICI*

Figure 40C Schematic representation of construct number 2062 (2X35S/CPMV HT*)
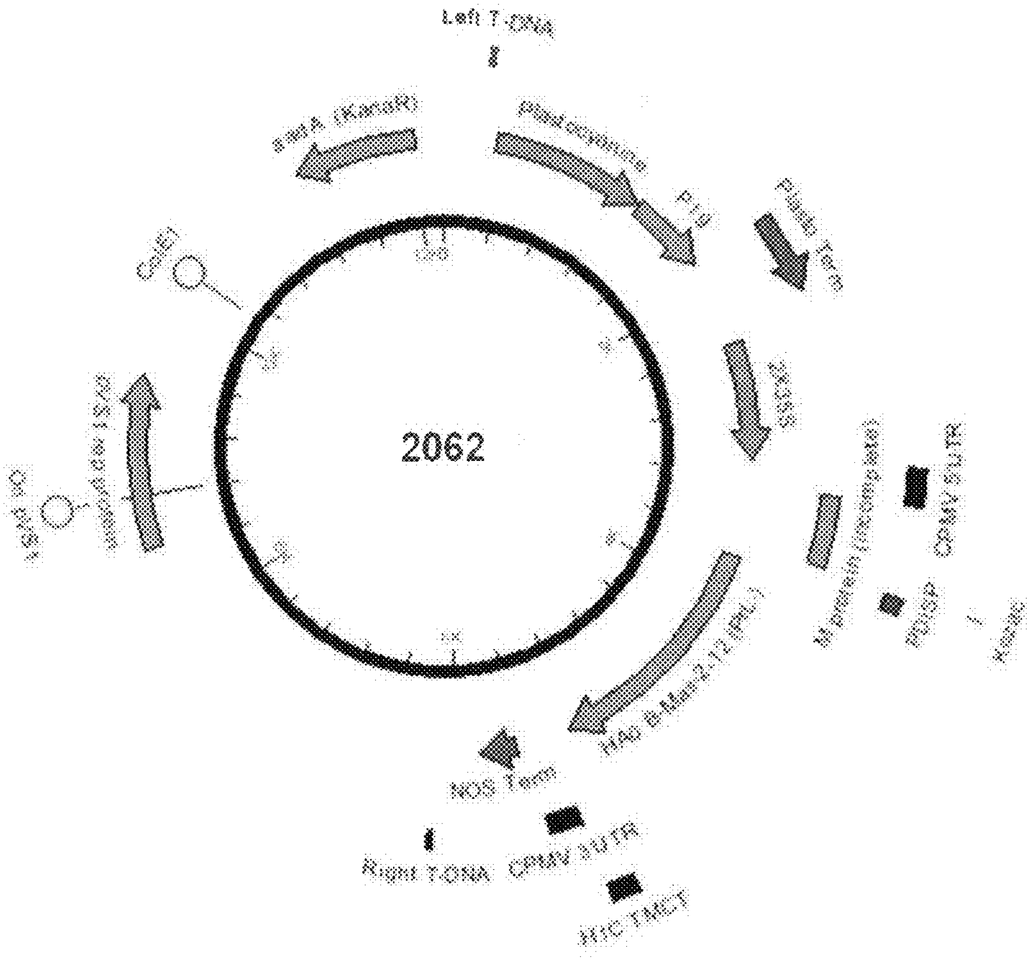

Figure 41

O- 2X35S/CPMV HT (construct no 1445), HT* (construct no 1839), HT*(-Mprot) (construct no 1820) and HT(fl5'UTR) (construct no 1975) for HA B Wisconsin (PrL-)

Figure 41A, SEQ ID NO :111

Nucleotide sequence of HA B Wisconsin (PrL-).

ATGAAGGCAATAATTGTACTACTCATGGTAGTAACATCCAATGCAGATCGAATCTGCACTGGGATAACATCTTCAA
ACTCACCTCATGTGGTCAAAACAGCTACTCAAGGGGAGGTCAATGTGACTGGCGTGATACCACTGACAACAACAC
CAACAAAATCTTATTTTGCAAATCTCAAAGGAACAAGGACCAGAGGGAAACTATGCCCGGACTGTCTCAACTGTA
CAGATCTGGATGTGGCCTTGGGCAGGCCAATGTGTGTGGGGACCACACCTTCTGCTAAAGCTTCAATACTCCACGA
GGTCAGACCTGTTACATCCGGGTGCTTTCCTATAATGCACGACAGAACAAAAATCAGGCAACTACCCAATCTTCTC
AGAGGATATGAAAATATCAGGTTATCAACCCAAAACGTTATCGATGCAGAAAAAGCACCAGGAGGACCCTACAGA
CTTGGAACCTCAGGATCTTGCCCTAACGCTACCAGTAAAATCGGATTTTTTGCAACAATGGCTTGGGCTGTCCCAA
AGGACAACTACAAAAATGCAACGAACCCACTAACAGTAGAAGTACCATACATTTGTACAGAAGGGGAAGACCAA
ATTACTGTTTGGGGGTTCCATTCAGATAACAAAACCCAAATGAAGAGCCTCTATGGAGACTCAAATCCTCAAAAGT
TCACCTCATCTGCTAATGGAGTAACCACACATTATGTTTCTCAGATTGGCGACTTCCCAGATCAAACAGAAGACGG
AGGACTACCACAAAGCGGCAGAATTGTTGTTGATTACATGATGCAAAAACCTGGGAAAACAGGAACAATTGTCTA
TCAAAGAGGTGTTTTGTTGCCTCAAAAGGTGTGGTGCGCGAGTGGCAGGAGCAAAGTAATAAAAGGGTCATTGCC
TTTAATTGGTGAAGCAGATTGCCTTCATGAAAAATACGGTGGATTAAACAAAAGCAAGCCTTACTACACAGGAGA
ACATGCAAAAGCCATAGGAAATTGCCCAATATGGGTAAAAACACCTTTGAAGCTTGCCAATGGAACCAAATATAG
ACCTCCTGGTGGAGGATGGGAAGGAATGATTGCAGGTTGGCACGGATACACATCTCACGGAGCACATGGAGTGGC
AGTGGCGGCAGACCTTAAGAGTACACAAGAAGCTATAAATAAGATAACAAAAAATCTCAATTCTTTGAGTGAGCT
AGAAGTAAAGAACCTTCAAAGACTAAGTGGTGCCATGGATGAACTCCACAACGAAATACTCGAGCTGGATGAGAA
AGTGGATGATCTCAGAGCTGACACTATAAGCTCACAAATAGAACTTGCAGTCTTGCTTTCCAACGAAGGAATAATA
AACAGTGAAGACGAGCATCTATTGGCACTTGAGAGAAAACTAAAGAAAATGCTGGGTCCCTCTGCTGTAGACATA
GGAAACGGATGCTTCGAAACCAAACACAAATGCAACCAGACCTGCTTAGACAGGATAGCTGCTGGCACCTTTAAT
GCAGGAGAATTTTCTCTCCCCACTTTTGATTCATTGAACATTACTGCTGCATCTTTAAATGATGATGGATTGGATAA
CCATACTATACTGCTCTATTACTCAACTGCTGCTTCTAGTTTGGCTGTAACATTAATGCTAGCTATTTTTATTGTTTA
TATGGTCTCCAGAGACAACGTTTCATGCTCCATCTGTCTATAA

Figure 41B, SEQ ID NO : 112

Amino acid sequence of HA B Wisconsin (PrL-).

MKAIIVLLMVVTSNADRICTGITSSNSPHVVKTATQGEVNVTGVIPLTTTPTKSYFANLKGTRTRGKLCPDCLNCTDLDV
ALGRPMCVGTTPSAKASILHEVRPVTSGCFPIMHDRTKIRQLPNLLRGYENIRLSTQNVIDAEKAPGGPYRLGTSGSCPN
ATSKIGFFATMAWAVPKDNYKNATNPLTVEVPYICTEGEDQITVWGFHSDNKTQMKSLYGDSNPQKFTSSANGVTTHY
VSQIGDFPDQTEDGGLPQSGRIVVDYMMQKPGKTGTIVYQRGVLLPQKVWCASGRSKVIKGSLPLIGEADCLHEKYGG
LNKSKPYYTGEHAKAIGNCPIWVKTPLKLANGTKYRPPGGGWEGMIAGWHGYTSHGAHGVAVAADLKSTQEAINKIT
KNLNSLSELEVKNLQRLSGAMDELHNEILELDEKVDDLRADTISSQIELAVLLSNEGIINSEDEHLLALERKLKKMLGPSA
VDIGNGCFETKHKCNQTCLDRIAAGTFNAGEFSLPTFDSLNITAASLNDDGLDNHTILLYYSTAASSLAVTLMLAIFIVY
MVSRDNVSCSICL*

Schematic representation of construct number 1839 (2X35S/CPMV HT*)

Figure 42

P- 2X35S/CPMV HT (construct no 1454) and HT* (construct no 1860) for HA B Wisconsin (PrL-)+H1 California TMCT

Figure 42A, SEQ ID NO : 113

Nucleotide sequence of HA B Wisconsin (PrL-)+H1 California TMCT

ATGAAGGCAATAATTGTACTACTCATGGTAGTAACATCCAATGCAGATCGAATCTGCACTGGGATAACATCTTCAA
ACTCACCTCATGTGGTCAAAACAGCTACTCAAGGGGAGGTCAATGTGACTGGCGTGATACCACTGACAACAACAC
CAACAAAATCTTATTTTGCAAATCTCAAAGGAACAAGGACCAGAGGGAAACTATGCCCGGACTGTCTCAACTGTA
CAGATCTGGATGTGGCCTTGGGCAGGCCAATGTGTGTGGGGACCACACCTTCTGCTAAAGCTTCAATACTCCACGA
GGTCAGACCTGTTACATCCGGGTGCTTTCCTATAATGCACGACAGAACAAAAATCAGGCAACTACCCAATCTTCTC
AGAGGATATGAAAATATCAGGTTATCAACCCAAAACGTTATCGATGCAGAAAAAGCACCAGGAGGACCCTACAGA
CTTGGAACCTCAGGATCTTGCCCTAACGCTACCAGTAAAATCGGATTTTTTGCAACAATGGCTTGGGCTGTCCCAA
AGGACAACTACAAAAATGCAACGAACCCACTAACAGTAGAAGTACCATACATTTGTACAGAAGGGGAAGACCAA
ATTACTGTTTGGGGGTTCCATTCAGATAACAAAACCCAAATGAAGAGCCTCTATGGAGACTCAAATCCTCAAAAGT
TCACCTCATCTGCTAATGGAGTAACCACACATTATGTTTCTCAGATTGGCGACTTCCCAGATCAAACAGAAGACGG
AGGACTACCACAAAGCGGCAGAATTGTTGTTGATTACATGATGCAAAAACCTGGGAAAACAGGAACAATTGTCTA
TCAAAGAGGTGTTTTGTTGCCTCAAAAGGTGTGGTGCGCGAGTGGCAGGAGCAAAGTAATAAAAGGGTCATTGCC
TTTAATTGGTGAAGCAGATTGCCTTCATGAAAAATACGGTGGATTAAACAAAAGCAAGCCTTACTACACAGGAGA
ACATGCAAAAGCCATAGGAAATTGCCCAATATGGGTAAAAACACCTTTGAAGCTTGCCAATGGAACCAAATATAG
ACCTCCTGGTGGAGGATGGGAAGGAATGATTGCAGGTTGGCACGGATACACATCTCACGGAGCACATGGAGTGGC
AGTGGCGGCAGACCTTAAGAGTACACAAGAAGCTATAAATAAGATAACAAAAAATCTCAATTCTTTGAGTGAGCT
AGAAGTAAAGAACCTTCAAAGACTAAGTGGTGCCATGGATGAACTCCACAACGAAATACTCGAGCTGGATGAGAA
AGTGGATGATCTCAGAGCTGACACTATAAGCTCACAAATAGAACTTGCAGTCTTGCTTTCCAACGAAGGAATAATA
AACAGTGAAGACGAGCATCTATTGGCACTTGAGAGAAAACTAAAGAAAATGCTGGGTCCCTCTGCTGTAGACATA
GGAAACGGATGCTTCGAAACCAAACACAAATGCAACCAGACCTGCTTAGACAGGATAGCTGCTGGCACCTTTAAT
GCAGGAGAATTTTCTCTCCCCACTTTTGATTCATTGAACATTACTGCTGCATCTTTAAATGATGATGGATTGGATAA
CTACCAGATTTTGGCGATCTATTCAACTGTCGCCAGTTCATTGGTACTGGTAGTCTCCCTGGGGGCAATCAGTTTCT
GGATGTGCTCTAATGGGTCTCTACAGTGTAGAATATGTATTTAA

Figure 42B, SEQ ID NO : 114

Amino acid sequence of HA B Wisconsin (PrL-)+H1 California TMC.

MKAIIVLLMVVTSNADRICTGITSSNSPHVVKTATQGEVNVTGVIPLTTTPTKSYFANLKGTRTRGKLCPDCLNCTDLDV
ALGRPMCVGTTPSAKASILHEVRPVTSGCFPIMHDRTKIRQLPNLLRGYENIRLSTQNVIDAEKAPGGPYRLGTSGSCPN
ATSKIGFFATMAWAVPKDNYKNATNPLTVEVPYICTEGEDQITVWGFHSDNKTQMKSLYGDSNPQKFTSSANGVTTHY
VSQIGDFPDQTEDGGLPQSGRIVVDYMMQKPGKTGTIVYQRGVLLPQKVWCASGRSKVIKGSLPLIGEADCLHEKYGG
LNKSKPYYTGEHAKAIGNCPIWVKTPLKLANGTKYRPPGGGWEGMIAGWHGYTSHGAHGVAVAADLKSTQEAINKIT
KNLNSLSELEVKNLQRLSGAMDELHNEILELDEKVDDLRADTISSQIELAVLLSNEGIINSEDEHLLALERKLKKMLGPSA
VDIGNGCFETKHKCNQTCLDRIAAGTFNAGEFSLPTFDSLNITAASLNDDGLDNYQILAIYSTVASSLVLVVSLGAISFW
MCSNGSLQCRICI*

Schematic representation of construct number 1860 (2X35S/CPMV HT*)

Figure 43

2X35S/CPMV HT (construct no 489), HT*(-Mprot) (construct no 1880) and HT(fl5'UTR) (construct no 1885) for H5 Indonesia

Figure 43A

Nucleotide sequence of native H5 Indonesia. (SEQ ID NO: 115)

ATGGAGAAAATAGTGCTTCTTCTTGCAATAGTCAGTCTTGTTAAAAGTGATCAGATTTGCATTGGTTACCATGCAAA
CAATTCAACAGAGCAGGTTGACACAATCATGGAAAAGAACGTTACTGTTACACATGCCCAAGACATACTGGAAAAGA
CACACAACGGGAAGCTCTGCGATCTAGATGGAGTGAAGCCTCTAATTTTAAGAGATTGTAGTGTAGCTGGATGGCTC
CTCGGGAACCCAATGTGTGACGAATTCATCAATGTACCGGAATGGTCTTACATAGTGGAGAAGGCCAATCCAACCAA
TGACCTCTGTTACCCAGGGAGTTTCAACGACTATGAAGAACTGAAACACCTATTGAGCAGAATAAACCATTTTGAGA
AAATTCAAATCATCCCCAAAAGTTCTTGGTCCGATCATGAAGCCTCATCAGGAGTTAGCTCAGCATGTCCATACCTG
GGAAGTCCCTCCTTTTTTAGAAATGTGGTATGGCTTATCAAAAAGAACAGTACATACCCAACAATAAAGAAAAGCTA
CAATAATACCAACCAAGAGGATCTTTTGGTACTGTGGGGAATTCACCATCCTAATGATGCGGCAGAGCAGACAAGGC
TATATCAAAACCCAACCACCTATATTTCCATTGGGACATCAACACTAAACCAGAGATTGGTACCAAAAATAGCTACT
AGATCCAAAGTAAACGGGCAAAGTGGAAGGATGGAGTTCTTCTGGACAATTTTAAAACCTAATGATGCAATCAACTT
CGAGAGTAATGGAAATTTCATTGCTCCAGAATATGCATACAAAATTGTCAAGAAAGGGGACTCAGCAATTATGAAAA
GTGAATTGGAATATGGTAACTGCAACACCAAGTGTCAAACTCCAATGGGGGCGATAAACTCTAGTATGCCATTCCAC
AACATACACCCTCTCACCATCGGGGAATGCCCCAAATATGTGAAATCAAACAGATTAGTCCTTGCAACAGGGCTCAG
AAATAGCCCTCAAAGAGAGAGCAGAAGAAAAAAGAGAGGACTATTTGGAGCTATAGCAGGTTTTATAGAGGGAGGAT
GGCAGGGAATGGTAGATGGTTGGTATGGGTACCACCATAGCAATGAGCAGGGGAGTGGGTACGCTGCAGACAAAGAA
TCCACTCAAAAGGCAATAGATGGAGTCACCAATAAGGTCAACTCAATCATTGACAAAATGAACACTCAGTTTGAGGC
CGTTGGAAGGGAATTTAATAACTTAGAAAGGAGAATAGAGAATTTAAACAAGAAGATGGAAGACGGGTTTCTAGATG
TCTGGACTTATAATGCCGAACTTCTGGTTCTCATGGAAAATGAGAGAACTCTAGACTTTCATGACTCAAATGTTAAG
AACCTCTACGACAAGGTCCGACTACAGCTTAGGGATAATGCAAAGGAGCTGGGTAACGGTTGTTTCGAGTTCTATCA
CAAATGTGATAATGAATGTATGGAAAGTATAAGAAACGGAACGTACAACTATCCGCAGTATTCAGAAGAAGCAAGAT
TAAAAAGAGAGGAAATAAGTGGGGTAAAATTGGAATCAATAGGAACTTACCAAATACTGTCAATTTATTCAACAGTG
GCGAGTTCCCTAGCACTGGCAATCATGATGGCTGGTCTATCTTTATGGATGTGCTCCAATGGATCGTTACAATGCAG
AATTTGCATTTAA

Figure 43B

Amino acid sequence of native H5 Indonesia. (SEQ ID NO: 116)

MEKIVLLLAIVSLVKSDQICIGYHANNSTEQVDTIMEKNVTVTHAQDILEKTHNGKLCDLDGVKPLILRDCSVAGWL
LGNPMCDEFINVPEWSYIVEKANPTNDLCYPGSFNDYEELKHLLSRINHFEKIQIIPKSSWSDHEASSGVSSACPYL
GSPSFFRNVVWLIKKNSTYPTIKKSYNNTNQEDLLVLWGIHHPNDAAEQTRLYQNPTTYISIGTSTLNQRLVPKIAT
RSKVNGQSGRMEFFWTILKPNDAINFESNGNFIAPEYAYKIVKKGDSAIMKSELEYGNCNTKCQTPMGAINSSMPFH
NIHPLTIGECPKYVKSNRLVLATGLRNSPQRESRRKKRGLFGAIAGFIEGGWQGMVDGWYGYHHSNEQGSGYAADKE
STQKAIDGVTNKVNSIIDKMNTQFEAVGREFNNLERRIENLNKKMEDGFLDVWTYNAELLVLMENERTLDFHDSNVK
NLYDKVRLQLRDNAKELGNGCFEFYHKCDNECMESIRNGTYNYPQYSEEARLKREEISGVKLESIGTYQILSIYSTV
ASSLALAIMMAGLSLWMCSNGSLQCRICI*

Schematic representation of construct number 489 (2X35S/CPMV HT)

Figure 44

2X35S/CPMV-HT*(-Mprot)/ PDISP/H3 Victoria/ NOS (Construct number 1800)

Figure 44A

IF**(SacII)-PDI.s1+4c

ACAGGGCCCAATACCGCGGAGAAAATGGCGAAAAACGTTGCGATTTTCGGCT (SEQ ID NO: 117)

ACTAAAGAAAATAGGCCTTCAAATGCAAATGTTGCACCTAATGTTGCCCTT (SEQ ID NO: 118)

Figure 44C

Nucleotide sequence of PDISP/H3 Victoria. (SEQ ID NO: 119)

ATGGCGAAAAACGTTGCGATTTTCGGCTTATTGTTTTCTCTTCTTGTGTTGGTTCCTTCTCAGATCTTCGCCCAAAA
ACTTCCTGGAAATGACAACAGCACGGCAACGCTGTGCCTTGGGCACCATGCAGTACCAAACGGAACGATAGTGAAAA
CAATCACGAATGACCAAATTGAAGTTACTAATGCTACTGAGCTGGTTCAGAATTCCTCAATAGGTGAAATATGCGAC
AGTCCTCATCAGATCCTTGATGGAGAAAACTGCACACTAATAGATGCTCTATTGGGAGACCCTCAGTGTGATGGCTT
CCAAAATAAGAAATGGGACCTTTTTGTTGAACGAAGCAAAGCCTACAGCAACTGTTACCCTTATGATGTGCCGGATT
ATGCCTCCCTTAGGTCACTAGTTGCCTCATCCGGCACACTGGAGTTTAACAATGAAAGCTTCAATTGGACTGGAGTC
ACTCAAAACGGAACAAGTTCTGCTTGCATAAGGAGATCTAATAATAGTTTCTTTAGTAGATTAAATTGGTTGACCCA
CTTAAACTTCAAATACCCAGCATTGAACGTGACTATGCCAAACAATGAACAATTTGACAAATTGTACATTTGGGGG
TTCACCACCCGGGTACGGACAAGGACCAAATCTTCCTGTATGCTCAATCATCAGGAAGAATCACAGTATCTACCAAA
AGAAGCCAACAAGCTGTAATCCCGAATATCGGATCTAGACCCAGAATAAGGAATATCCCTAGCAGAATAAGCATCTA
TTGGACAATAGTAAAACCGGGAGACATACTTTTGATTAACAGCACAGGGAATCTAATTGCTCCTAGGGGTTACTTCA
AAATACGAAGTGGGAAAAGCTCAATAATGAGATCAGATGCACCCATTGGCAAATGCAATTCTGAATGCATCACTCCA
AATGGAAGCATTCCCAATGACAAACCATTCCAAAATGTAAACAGGATCACATACGGGGCCTGTCCCAGATATGTTAA
GCAAAGCACTCTGAAATTGGCAACAGGAATGCGAAATGTACCAGAGAAACAAACTAGAGGCATATTTGGCGCAATAG
CGGGTTTCATAGAAAATGGTTGGGAGGGAATGGTGGATGGTTGGTACGGTTTCAGGCATCAAAATTCTGAGGGAAGA
GGACAAGCAGCAGATCTCAAAAGCACTCAAGCAGCAATCGATCAAATCAATGGGAAGCTGAATCGATTGATCGGGAA
AACCAACGAGAAATTCCATCAGATTGAAAAAGAATTCTCAGAAGTCGAAGGGAGAATTCAGGACCTTGAGAAATATG
TTGAGGACACTAAAATAGATCTCTGGTCATACAACGCGGAGCTTCTTGTTGCCCTGGAGAACCAACATACAATTGAT
CTAACTGACTCAGAAATGAACAAACTGTTTGAAAAAACAAAGAAGCAACTAAGGGAAAATGCTGAGGATATGGGCAA
TGGTTGTTTCAAAATATACCACAAATGTGACAATGCCTGCATAGGATCAATCAGAAATGGAACTTATGACCACGATG
TATACAGAGATGAAGCATTAAACAACCGGTTCCAGATCAAGGGAGTTGAGCTGAAGTCAGGGTACAAAGATTGGATC
CTATGGATTTCCTTTGCCATATCATGTTTTTTGCTTTGTGTTGCTTTGTTGGGGTTCATCATGTGGGCCTGCCAAAA
GGGCAACATTAGGTGCAACATTTGCATTTGA

Schematic representation of construct 2171. SacII and StuI restriction enzyme sites used for plasmid linearization are annotated on the representation.

Figure 44E

Construct 2171 from left to right t-DNA borders (underlined). 2X35S/CPMV-HT*(-Mprot)/NOS with Plastocyanine-P19-Plastocyanine silencing inhibitor expression cassette (SEQ ID NO: 120)

TGGCAGGATATATTGTGGTGTAAACAAATTGACGCTTAGACAACTTAATAACACATTGCGGACGTTTTTAATGTACT
GAATTAACGCCGAATCCCGGGCTGGTATATTTATATGTTGTCAAATAACTCAAAAACCATAAAAGTTTAAGTTAGCA
AGTGTGTACATTTTTACTTGAACAAAAATATTCACCTACTACTGTTATAAATCATTATTAAACATTAGAGTAAAGAA
ATATGGATGATAAGAACAAGAGTAGTGATATTTTGACAACAATTTTGTTGCAACATTTGAGAAAATTTTGTTGTTCT
CTCTTTTCATTGGTCAAAAACAATAGAGAGAGAAAAAGGAAGAGGGAGAATAAAAACATAATGTGAGTATGAGAGAG
AAAGTTGTACAAAAGTTGTACCAAAATAGTTGTACAAATATCATTGAGGAATTTGACAAAAGCTACACAAATAAGGG
TTAATTGCTGTAAATAAATAAGGATGACGCATTAGAGAGATGTACCATTAGAGAATTTTTGGCAAGTCATTAAAAAG
AAAGAATAAATTATTTTTAAAATTAAAAGTTGAGTCATTTGATTAAACATGTGATTATTTAATGAATTGATGAAAGA
GTTGGATTAAAGTTGTATTAGTAATTAGAATTTGGTGTCAAATTTAATTTGACATTTGATCTTTTCCTATATATTGC
CCCATAGAGTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGATAACATCCA
ATCCAACCAATCACAACAATCCTGATGAGATAACCCACTTTAAGCCCACGCATCTGTGGCACATCTACATTATCTAA
ATCACACATTCTTCCACACATCTGAGCCACACAAAAACCAATCCACATCTTTATCACCCATTCTATAAAAAATCACA
CTTTGTGAGTCTACACTTTGATTCCCTTCAAACACATACAAAGAGAAGAGACTAATTAATTAATTAATCATCTTGAG
AGAAAATGGAACGAGCTATACAAGGAAACGACGCTAGGGAACAAGCTAACAGTGAACGTTGGGATGGAGGATCAGGA
GGTACCACTTCTCCCTTCAAACTTCCTGACGAAAGTCCGAGTTGGACTGAGTGGCGGCTACATAACGATGAGACGAA
TTCGAATCAAGATAATCCCCTTGGTTTCAAGGAAAGCTGGGGTTTCGGGAAAGTTGTATTTAAGAGATATCTCAGAT
ACGACAGGACGGAAGCTTCACTGCACAGAGTCCTTGGATCTTGGACGGGAGATTCGGTTAACTATGCAGCATCTCGA
TTTTTCGGTTTCGACCAGATCGGATGTACCTATAGTATTCGGTTTCGAGGAGTTAGTATCACCGTTTCTGGAGGGTC
GCGAACTCTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAATGCTTCTT
CGTCTCCTATTTATAATATGGTTTGTTATTGTTAATTTTGTTCTTGTAGAAGAGCTTAATTAATCGTTGTTGTTATG
AAATACTATTTGTATGAGATGAACTGGTGTAATGTAATTCATTTACATAAGTGGAGTCAGAATCAGAATGTTTCCTC
CATAACTAACTAGACATGAAGACCTGCCGCGTACAATTGTCTTATATTTGAACAACTAAAATTGAACATCTTTTGCC
ACAACTTTATAAGTGGTTAATATAGCTCAAATATATGGTCAAGTTCAATAGATTAATAATGGAAATATCAGTTATCG
AAATTCATTAACAATCAACTTAACGTTATTAACTACTAATTTTATATCATCCCCTTTGATAAATGATAGTACACCAA
TTAGGAAGGAGCATGCTCGCCTAGGAGATTGTCGTTTCCCGCCTTCAGTTTGCAAGCTGCTCTAGCCGTGTAGCCAA
TACGCAAACCGCCTCTCCCCGCGCGTTGGGAATTACTAGCGCGTGTCGACAAGCTTGCATGCCGGTCAACATGGTGG
AGCACGACACACTTGTCTACTCCAAAAATATCAAAGATACAGTCTCAGAAGACCAAAGGGCAATTGAGACTTTTCAA
CAAAGGGTAATATCCGGAAACCTCCTCGGATTCCATTGCCCAGCTATCTGTCACTTTATTGTGAAGATAGTGGAAAA
GGAAGGTGGCTCCTACAAATGCCATCATTGCGATAAAGGAAAGGCCATCGTTGAAGATGCCTCTGCCGACAGTGGTC
CCAAAGATGGACCCCCACCCACGAGGAGCATCGTGGAAAAAGAAGACGTTCCAACCACGTCTTCAAAGCAAGTGGAT
TGATGTGATAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTCACTTTA
TTGTGAAGATAGTGGAAAAGGAAGGTGGCTCCTACAAATGCCATCATTGCGATAAAGGAAAGGCCATCGTTGAAGAT
GCCTCTGCCGACAGTGGTCCCAAAGATGGACCCCCACCCACGAGGAGCATCGTGGAAAAAGAAGACGTTCCAACCAC
GTCTTCAAAGCAAGTGGATTGATGTGATATCTCCACTGACGTAAGGGATGACGCACAATCCCACTATCCTTCGCAAG
ACCCTTCCTCTATATAAGGAAGTTCATTTCATTTGGAGAGGTATTAAAATCTTAATAGGTTTTGATAAAAGCGAACG
TGGGGAAACCCGAACCAAACCTTCTTCTAAACTCTCTCTCATCTCTCTTAAAGCAAACTTCTCTCTTGTCTTTCTTG
CGTGAGCGATCTTCAACGTTGTCAGATCGTGCTTCGGCACCAGTACAGGGCCCAATACCGCGGAGAAAATGGCGAAA
AACGTTGCGATTTTCGGCTTATTGTTTTCTCTTCTTGTGTTGGTTCCTTCTCAGATCTTCGCGACGTCACTCCTCAG
CCAAAACGACACCCCCATCTGTCTATCCACTGGCCCCTGGATCTGCTGCCCAAACTAACTCCATGGTGACCCTGGGA
TGCCTGGTCAAGGGCTATTTCCCTGAGCCAGTGACAGTGACCTGGAACTCTGGATCCCTGTCCAGCGGTGTGCACAC
CTTCCCAGCTGTCCTGCAGTCTGACCTCTACACTCTGAGCAGCTCAGTGACTGTCCCCTCCAGCACCTGGCCCAGCG
AGACCGTCACCTGCAACGTTGCCCACCCGGCCAGCAGCACCAAGGTGGACAAGAAAATTGTGCCCAGGGATTGTGGT
TGTAAGCCTTGCATATGTACAGTCCCAGAAGTATCATCTGTCTTCATCTTCCCCCCAAAGCCCAAGGATGTGCTCAC
CATTACTCTGACTCCTAAGGTCACGTGTGTTGTGGTAGACATCAGCAAGGATGATCCCGAGGTCCAGTTCAGCTGGT
TTGTAGATGATGTGGAGGTGCACACAGCTCAGACGCAACCCCGGGAGGAGCAGTTCAACAGCACTTTCCGCTCAGTC
AGTGAACTTCCCATCATGCACCAGGACTGGCTCAATGGCAAGGAGACGTCCAGATTTTGGCGATCTATTCAACTGTC
GCCAGTTCATTGGTACTGGTAGTCTCCCTGGGGGCAATCAGTTTCTGGATGTGCTCTAATGGGTCTCTACAGTGTAG
AATATGTATTTAAAGGCCTATTTTCTTTAGTTTGAATTTACTGTTATTCGGTGTGCATTTCTATGTTTGGTGAGCGG
TTTTCTGTGCTCAGAGTGTGTTTATTTTATGTAATTTAATTTCTTTGTGAGCTCCTGTTTAGCAGGTCGTCCCTTCA

Figure 44E continued

GCAAGGACACAAAAAGATTTTAATTTTATTAAAAAAAAAAAAAAAAAAAAGACCGGGAATTCGATATCAAGCTTATCGA
CCTGCAGATCGTTCAAACATTTGGCAATAAAGTTTCTTAAGATTGAATCCTGTTGCCGGTCTTGCGATGATTATCAT
ATAATTTCTGTTGAATTACGTTAAGCATGTAATAATTAACATGTAATGCATGACGTTATTTATGAGATGGGTTTTTA
TGATTAGAGTCCCGCAATTATACATTTAATACGCGATAGAAAACAAAATATAGCGCGCAAACTAGGATAAATTATCG
CGCGCGGTGTCATCTATGTTACTAGATCTCTAGAGTCTCAAGCTTGGCGCGCCCACGTGACTAGTGGCACTGGCCGT
CGTTTTACAACGTCGTGACTGGGAAAACCCTGGCGTTACCCAACTTAATCGCCTTGCAGCACATCCCCCTTTCGCCA
GCTGGCGTAATAGCGAAGAGGCCCGCACCGATCGCCCTTCCCAACAGTTGCGCAGCCTGAATGGCGAATGCTAGAGC
AGCTTGAGCTTGGATCAGATTGTCGTTTCCCGCCTTCAGTTTAAACTATCAGTGTTTGACAGGATATATTGGCGGGT
AAACCTAAGAGAAAAGAGCGTTTA

Figure 44F

Expression cassette number 1800 from 2X35S promoter to NOS terminator. PDISP/H3 Victoria nucleotide sequence is underlined. SEQ ID NO: 121

GTCAACATGGTGGAGCACGACACACTTGTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACTTTATTGTGAAGATAGTGGAAAAGGAAG
GTGGCTCCTACAAATGCCATCATTGCGATAAAGGAAAGGCCATCGTTGAAGATGCCTCTGCCGACAGTGGTCCCAAAGATGGACCC
CCACCCACGAGGAGCATCGTGGAAAAAGAAGACGTTCCAACCACGTCTTCAAAGCAAGTGGATTGATGTGATAACATGGTGGAGCA
CGACACACTTGTCTACTCCAAAAATATCAAAGATACAGTCTCAGAAGACCAAAGGGCAATTGAGACTTTTCAACAAAGGGTAATAT
CCGGAAACCTCCTCGGATTCCATTGCCCAGCTATCTGTCACTTTATTGTGAAGATAGTGGAAAAGGAAGGTGGCTCCTACAAATGC
CATCATTGCGATAAAGGAAAGGCCATCGTTGAAGATGCCTCTGCCGACAGTGGTCCCAAAGATGGACCCCCACCCACGAGGAGCAT
CGTGGAAAAAGAAGACGTTCCAACCACGTCTTCAAAGCAAGTGGATTGATGTGATATCTCCACTGACGTAAGGGATGACGCACAAT
CCCACTATCCTTCGCAAGACCCTTCCTCTATATAAGGAAGTTCATTTCATTTGGAGAGGTATTAAAATCTTAATAGGTTTTGATAA
AAGCGAACGTGGGGAAACCCGAACCAAACCTTCTTCTAAACTCTCTCTCATCTCTCTTAAAGCAAACTTCTCTCTTGTCTTTCTTG
CGTGAGCGATCTTCAACGTTGTCAGATCGTGCTTCGGCACCAGTACAGGGCCCAATACCGCGGAGAAAATGGCGAAAAACGTTGCG
ATTTTCGGCTTATTGTTTTCTCTTCTTGTGTTGGTTCCTTCTCAGATCTTCGCCCAAAAACTTCCTGGAAATGACAACAGCACGGC
AACGCTGTGCCTTGGGCACCATGCAGTACCAAACGGAACGATAGTGAAAACAATCACGAATGACCAAATTGAAGTTACTAATGCTA
CTGAGCTGGTTCAGAATTCCTCAATAGGTGAAATATGCGACAGTCCTCATCAGATCCTTGATGGAGAAAACTGCACACTAATAGAT
GCTCTATTGGGAGACCCTCAGTGTGATGGCTTCCAAAATAAGAAATGGGACCTTTTTGTTGAACGAAGCAAAGCCTACAGCAACTG
TTACCCTTATGATGTGCCGGATTATGCCTCCCTTAGGTCACTAGTTGCCTCATCCGGCACACTGGAGTTTAACAATGAAAGCTTCA
ATTGGACTGGAGTCACTCAAAACGGAACAAGTTCTGCTTGCATAAGGAGATCTAATAATAGTTTCTTTAGTAGATTAAATTGGTTG
ACCCACTTAAACTTCAAATACCCAGCATTGAACGTGACTATGCCAAACAATGAACAATTTGACAAATTGTACATTTGGGGGGTTCA
CCACCCGGGTACGGACAAGGACCAAATCTTCCTGTATGCTCAATCATCAGGAAGAATCACAGTATCTACCAAAAGAAGCCAACAAG
CTGTAATCCCGAATATCGGATCTAGACCCAGAATAAGGAATATCCCTAGCAGAATAAGCATCTATTGGACAATAGTAAAACCGGGA
GACATACTTTTGATTAACAGCACAGGGAATCTAATTGCTCCTAGGGGTTACTTCAAAATACGAAGTGGGAAAAGCTCAATAATGAG
ATCAGATGCACCCATTGGCAAATGCAATTCTGAATGCATCACTCCAAATGGAAGCATTCCCAATGACAAACCATTCCAAAATGTAA
ACAGGATCACATACGGGGCCTGTCCCAGATATGTTAAGCAAAGCACTCTGAAATTGGCAACAGGAATGCGAAATGTACCAGAGAAA
CAAACTAGAGGCATATTTGGCGCAATAGCGGGTTTCATAGAAAATGGTTGGGAGGGAATGGTGGATGGTTGGTACGGTTTCAGGCA
TCAAAATTCTGAGGGAAGAGGACAAGCAGCAGATCTCAAAAGCACTCAAGCAGCAATCGATCAAATCAATGGGAAGCTGAATCGAT
TGATCGGGAAAACCAACGAGAAATTCCATCAGATTGAAAAAGAATTCTCAGAAGTCGAAGGGAGAATTCAGGACCTTGAGAAATAT
GTTGAGGACACTAAAATAGATCTCTGGTCATACAACGCGGAGCTTCTTGTTGCCCTGGAGAACCAACATACAATTGATCTAACTGA
CTCAGAAATGAACAAACTGTTTGAAAAAACAAAGAAGCAACTAAGGGAAAATGCTGAGGATATGGGCAATGGTTGTTTCAAAATAT
ACCACAAATGTGACAATGCCTGCATAGGATCAATCAGAAATGGAACTTATGACCACGATGTATACAGAGATGAAGCATTAAACAAC
CGGTTCCAGATCAAGGGAGTTGAGCTGAAGTCAGGGTACAAAGATTGGATCCTATGGATTTCCTTTGCCATATCATGTTTTTTGCT
TTGTGTTGCTTTGTTGGGGTTCATCATGTGGGCCTGCCAAAAGGGCAACATTAGGTGCAACATTTGCATTTGAAGGCCTATTTTCT
TTAGTTTGAATTTACTGTTATTCGGTGTGCATTTCTATGTTTGGTGAGCGGTTTTCTGTGCTCAGAGTGTGTTTATTTTATGTAAT
TTAATTTCTTTGTGAGCTCCTGTTTAGCAGGTCGTCCCTTCAGCAAGGACACAAAAAGATTTTAATTTTATTAAAAAAAAAAAAAA
AAAAGACCGGGAATTCGATATCAAGCTTATCGACCTGCAGATCGTTCAAACATTTGGCAATAAAGTTTCTTAAGATTGAATCCTGT
TGCCGGTCTTGCGATGATTATCATATAATTTCTGTTGAATTACGTTAAGCATGTAATAATTAACATGTAATGCATGACGTTATTTA
TGAGATGGGTTTTTATGATTAGAGTCCCGCAATTATACATTTAATACGCGATAGAAAACAAAATATAGCGCGCAAACTAGGATAAA
TTATCGCGCGCGGTGTCATCTATGTTACTAGAT

Figure 44G

Amino acid sequence of PDISP/H3 Victoria (SEQ ID NO: 122)

MAKNVAIFGLLFSLLVLVPSQIFAQKLPGNDNSTATLCLGHHAVPNGTIVKTITNDQIEVTNATELVQNSSIGEICDSPHQILDGE
NCTLIDALLGDPQCDGFQNKKWDLFVERSKAYSNCYPYDVPDYASLRSLVASSGTLEFNNESFNWTGVTQNGTSSACIRRSNNSFF
SRLNWLTHLNFKYPALNVTMPNNEQFDKLYIWGVHHPGTDKDQIFLYAQSSGRITVSTKRSQQAVIPNIGSRPRIRNIPSRISIYW
TIVKPGDILLINSTGNLIAPRGYFKIRSGKSSIMRSDAPIGKCNSECITPNGSIPNDKPFQNVNRITYGACPRYVKQSTLKLATGM
RNVPEKQTRGIFGAIAGFIENGWEGMVDGWYGFRHQNSEGRGQAADLKSTQAAIDQINGKLNRLIGKTNEKFHQIEKEFSEVEGRI
QDLEKYVEDTKIDLWSYNAELLVALENQHTIDLTDSEMNKLFEKTKKQLRENAEDMGNGCFKIYHKCDNACIGSIRNGTYDHDVYR
DEALNNRFQIKGVELKSGYKDWILWISFAISCFLLCVALLGFIMWACQKGNIRCNICI*

Schematic representation of construct number 1800

Figure 45

2X35-2X35S/CPMV-HT*/ PDISP/H3 Victoria/ NOS (Construct number 1819)

Figure 45A

IF(SacII)-Kozac_PDI.c

GTCGGGCCCAATACCGCGGAGAAAATGGCGAAAAACGTTGCGATTTTC (SEQ ID NO.: 123)

ACTAAAGAAAATAGGCCTTCAAATGCAAATGTTGCACCTAATGTTGCCCTT (SEQ ID NO: 124)

Figure 45C

Schematic representation of construct 2181. SacII and StuI restriction enzyme sites used for plasmid linearization are annotated on the representation.

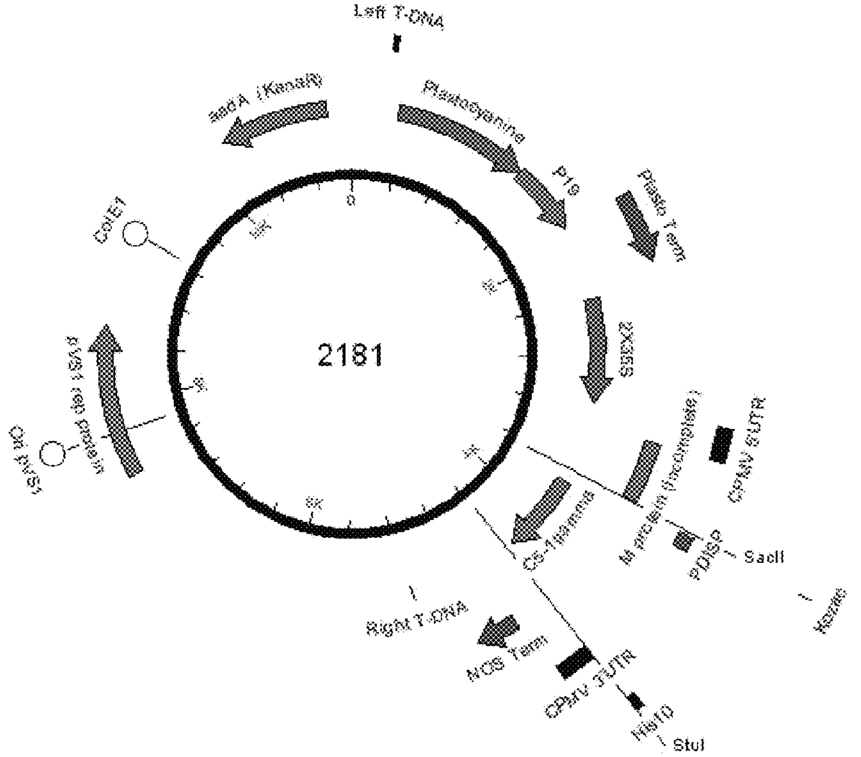

Figure 45D,

Construct 2181 from left to right t-DNA borders (underlined). 2X35S/CPMV-HT*/NOS with Plastocyanine-P19-Plastocyanine silencing inhibitor expression cassette (SEQ ID NO: 125)

<u>TGGCAGGATATATTGTGGTGTAAACA</u>AATTGACGCTTAGACAACTTAATAACACATTGCGGACGTTTTTAATGTACTGAATTAACG
CCGAATCCCGGGCTGGTATATTTATATGTTGTCAAATAACTCAAAAACCATAAAAGTTTAAGTTAGCAAGTGTGTACATTTTTACT
TGAACAAAAATATTCACCTACTACTGTTATAAATCATTATTAAACATTAGAGTAAAGAAATATGGATGATAAGAACAAGAGTAGTG
ATATTTTGACAACAATTTTGTTGCAACATTTGAGAAAATTTTGTTGTTCTCTCTTTTCATTGGTCAAAAACAATAGAGAGAGAAAA
AGGAAGAGGGAGAATAAAAACATAATGTGAGTATGAGAGAGAAAGTTGTACAAAAGTTGTACCAAAATAGTTGTACAAATATCATT
GAGGAATTTGACAAAAGCTACACAAATAAGGGTTAATTGCTGTAAATAAATAAGGATGACGCATTAGAGAGATGTACCATTAGAGA
ATTTTTGGCAAGTCATTAAAAAGAAAGAATAAATTATTTTTAAAATTAAAAGTTGAGTCATTTGATTAAACATGTGATTATTTAAT
GAATTGATGAAAGAGTTGGATTAAAGTTGTATTAGTAATTAGAATTTGGTGTCAAATTTAATTTGACATTTGATCTTTTCCTATAT

Figure 45D continued

ATTGCCCCATAGAGTCAGTTAACTCATTTTTATATTTCATAGATCAAATAAGAGAAATAACGGTATATTAATCCCTCCAAAAAAA
AAAACGGTATATTTACTAAAAAATCTAAGCCACGTAGGAGGATAACAGGATCCCCGTAGGAGGATAACATCCAATCCAACCAATCA
CAACAATCCTGATGAGATAACCCACTTTAAGCCCACGCATCTGTGGCACATCTACATTATCTAAATCACACATTCTTCCACACATC
TGAGCCACACAAAAACCAATCCACATCTTTATCACCCATTCTATAAAAAATCACACTTTGTGAGTCTACACTTTGATTCCCTTCAA
ACACATACAAAGAGAAGAGACTAATTAATTAATTAATCATCTTGAGAGAAAATGGAACGAGCTATACAAGGAAACGACGCTAGGGA
ACAAGCTAACAGTGAACGTTGGGATGGAGGATCAGGAGGTACCACTTCTCCCTTCAAACTTCCTGACGAAAGTCCGAGTTGGACTG
AGTGGCGGCTACATAACGATGAGACGAATTCGAATCAAGATAATCCCCTTGGTTTCAAGGAAAGCTGGGGTTTCGGGAAAGTTGTA
TTTAAGAGATATCTCAGATACGACAGGACGGAAGCTTCACTGCACAGAGTCCTTGGATCTTGGACGGGAGATTCGGTTAACTATGC
AGCATCTCGATTTTTCGGTTTCGACCAGATCGGATGTACCTATAGTATTCGGTTTCGAGGAGTTAGTATCACCGTTTCTGGAGGGT
CGCGAACTCTTCAGCATCTCTGTGAGATGGCAATTCGGTCTAAGCAAGAACTGCTACAGCTTGCCCCAATCGAAGTGGAAAGTAAT
GTATCAAGAGGATGCCCTGAAGGTACTCAAACCTTCGAAAAAGAAAGCGAGTAAGTTAAAATGCTTCTTCGTCTCCTATTTATAAT
ATGGTTTGTTATTGTTAATTTTGTTCTTGTAGAAGAGCTTAATTAATCGTTGTTGTTATGAAATACTATTTGTATGAGATGAACTG
GTGTAATGTAATTCATTTACATAAGTGGAGTCAGAATCAGAATGTTTCCTCCATAACTAACTAGACATGAAGACCTGCCGCGTACA
ATTGTCTTATATTTGAACAACTAAAATTGAACATCTTTTGCCACAACTTTATAAGTGGTTAATATAGCTCAAATATATGGTCAAGT
TCAATAGATTAATAATGGAAATATCAGTTATCGAAATTCATTAACAATCAACTTAACGTTATTAACTACTAATTTTATATCATCCC
CTTTGATAAATGATAGTACACCAATTAGGAAGGAGCATGCTCGCCTAGGAGATTGTCGTTTCCCGCCTTCAGTTTGCAAGCTGCTC
TAGCCGTGTAGCCAATACGCAAACCGCCTCTCCCCGCGCGTTGGGAATTACTAGCGCGTGTCGACAAGCTTGCATGCCGGTCAACA
TGGTGGAGCACGACACACTTGTCTACTCCAAAAATATCAAAGATACAGTCTCAGAAGACCAAAGGGCAATTGAGACTTTTCAACAA
AGGGTAATATCCGGAAACCTCCTCGGATTCCATTGCCCAGCTATCTGTCACTTTATTGTGAAGATAGTGGAAAAGGAAGGTGGCTC
CTACAAATGCCATCATTGCGATAAAGGAAAGGCCATCGTTGAAGATGCCTCTGCCGACAGTGGTCCCAAAGATGGACCCCCACCCA
CGAGGAGCATCGTGGAAAAAGAAGACGTTCCAACCACGTCTTCAAAGCAAGTGGATTGATGTGATAACATGGTGGAGCACGACACA
CTTGTCTACTCCAAAAATATCAAAGATACAGTCTCAGAAGACCAAAGGGCAATTGAGACTTTTCAACAAAGGGTAATATCCGGAAA
CCTCCTCGGATTCCATTGCCCAGCTATCTGTCACTTTATTGTGAAGATAGTGGAAAAGGAAGGTGGCTCCTACAAATGCCATCATT
GCGATAAAGGAAAGGCCATCGTTGAAGATGCCTCTGCCGACAGTGGTCCCAAAGATGGACCCCCACCCACGAGGAGCATCGTGGAA
AAAGAAGACGTTCCAACCACGTCTTCAAAGCAAGTGGATTGATGTGATATCTCCACTGACGTAAGGGATGACGCACAATCCCACTA
TCCTTCGCAAGACCCTTCCTCTATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCTCTCTTGTCTTTCTTGCGTGAGC
GATCTTCAACGTTGTCAGATCGTGCTTCGGCACCAGTACAACGTTTTCTTTCACTGAAGCGAAATCAAAGATCTCTTTGTGGACAC
GTAGTGCGGCGCCATTAAATAACGTGTACTTGTCCTATTCTTGTCGGTGTGGTCTTGGGAAAAGAAAGCTTGCTGGAGGCTGCTGT
TCAGCCCCATACATTACTTGTTACGATTCTGCTGACTTTCGGCGGGTGCAATATCTCTACTTCTGCTTGACGAGGTATTGTTGCCT
GTACTTCTTTCTTCTTCTTCTTGCTGATTGGTTCTATAAGAAATCTAGTATTTTCTTTGAAACAGAGTTTTCCCGTGGTTTTCGAA
CTTGGAGAAAGATTGTTAAGCTTCTGTATATTCTGCCCAAATTTGTCGGGCCCAATACCGCGGAGAAAATGGCGAAAAACGTTGCG
ATTTTCGGCTTATTGTTTTCTCTTCTTGTGTTGGTTCCTTCTCAGATCTTCGCGACGTCACTCCTCAGCCAAAACGACACCCCCAT
CTGTCTATCCACTGGCCCCTGGATCTGCTGCCCAAACTAACTCCATGGTGACCCTGGGATGCCTGGTCAAGGGCTATTTCCCTGAG
CCAGTGACAGTGACCTGGAACTCTGGATCCCTGTCCAGCGGTGTGCACACCTTCCCAGCTGTCCTGCAGTCTGACCTCTACACTCT
GAGCAGCTCAGTGACTGTCCCCTCCAGCACCTGGCCCAGCGAGACCGTCACCTGCAACGTTGCCCACCCGGCCAGCAGCACCAAGG
TGGACAAGAAAATTGTGCCCAGGGATTGTGGTTGTAAGCCTTGCATATGTACAGTCCCAGAAGTATCATCTGTCTTCATCTTCCCC
CCAAAGCCCAAGGATGTGCTCACCATTACTCTGACTCCTAAGGTCACGTGTGTTGTGGTAGACATCAGCAAGGATGATCCCGAGGT
CCAGTTCAGCTGGTTTGTAGATGATGTGGAGGTGCACACAGCTCAGACGCAACCCCGGGAGGAGCAGTTCAACAGCACTTTCCGCT
CAGTCAGTGAACTTCCCATCATGCACCAGGACTGGCTCAATGGCAAGGAGCGATCCTCACCATCACCATCACCATCACCATCACC
ATTAAAGGCCTATTTTCTTTAGTTTGAATTTACTGTTATTCGGTGTGCATTTCTATGTTTGGTGAGCGGTTTTCTGTGCTCAGAGT
GTGTTTATTTTATGTAATTTAATTTCTTTGTGAGCTCCTGTTTAGCAGGTCGTCCCTTCAGCAAGGACACAAAAAGATTTTAATTT
TATTAAAAAAAAAAAAAAAAAAGACCGGGAATTCGATATCAAGCTTATCGACCTGCAGATCGTTCAAACATTTGGCAATAAAGTTT
CTTAAGATTGAATCCTGTTGCCGGTCTTGCGATGATTATCATATAATTTCTGTTGAATTACGTTAAGCATGTAATAATTAACATGT
AATGCATGACGTTATTTATGAGATGGGTTTTTATGATTAGAGTCCCGCAATTATACATTTAATACGCGATAGAAAACAAAATATAG
CGCGCAAACTAGGATAAATTATCGCGCGCGGTGTCATCTATGTTACTAGATCTCTAGAGTCTCAAGCTTGGCGCGCCCACGTGACT
AGTGGCACTGGCCGTCGTTTTACAACGTCGTGACTGGGAAAACCCTGGCGTTACCCAACTTAATCGCCTTGCAGCACATCCCCCTT
TCGCCAGCTGGCGTAATAGCGAAGAGGCCCGCACCGATCGCCCTTCCCAACAGTTGCGCAGCCTGAATGGCGAATGCTAGAGCAGC
TTGAGCTTGGATCAGATTGTCGTTTCCCGCCTTCAGTTTAAACTATCAGTGTTTGACAGGATATATTGGCGGGTAAACCTAAGAGA
AAAGAGCGTTTA

Figure 45E

Expression cassette number 1819 from 2X35S promoter to NOS terminator. PDISP/H3 Victoria nucleotide sequence is underlined. (SEQ ID NO: 126)

GTCAACATGGTGGAGCACGACACACTTGTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACTTTATTGTGAAGATAGTGGAAAAGGAAG
GTGGCTCCTACAAATGCCATCATTGCGATAAAGGAAAGGCCATCGTTGAAGATGCCTCTGCCGACAGTGGTCCCAAAGATGGACCC
CCACCCACGAGGAGCATCGTGGAAAAAGAAGACGTTCCAACCACGTCTTCAAAGCAAGTGGATTGATGTGATAACATGGTGGAGCA
CGACACACTTGTCTACTCCAAAAATATCAAAGATACAGTCTCAGAAGACCAAAGGGCAATTGAGACTTTTCAACAAAGGGTAATAT
CCGGAAACCTCCTCGGATTCCATTGCCCAGCTATCTGTCACTTTATTGTGAAGATAGTGGAAAAGGAAGGTGGCTCCTACAAATGC
CATCATTGCGATAAAGGAAAGGCCATCGTTGAAGATGCCTCTGCCGACAGTGGTCCCAAAGATGGACCCCCACCCACGAGGAGCAT
CGTGGAAAAAGAAGACGTTCCAACCACGTCTTCAAAGCAAGTGGATTGATGTGATATCTCCACTGACGTAAGGGATGACGCACAAT

Figure 45E continued

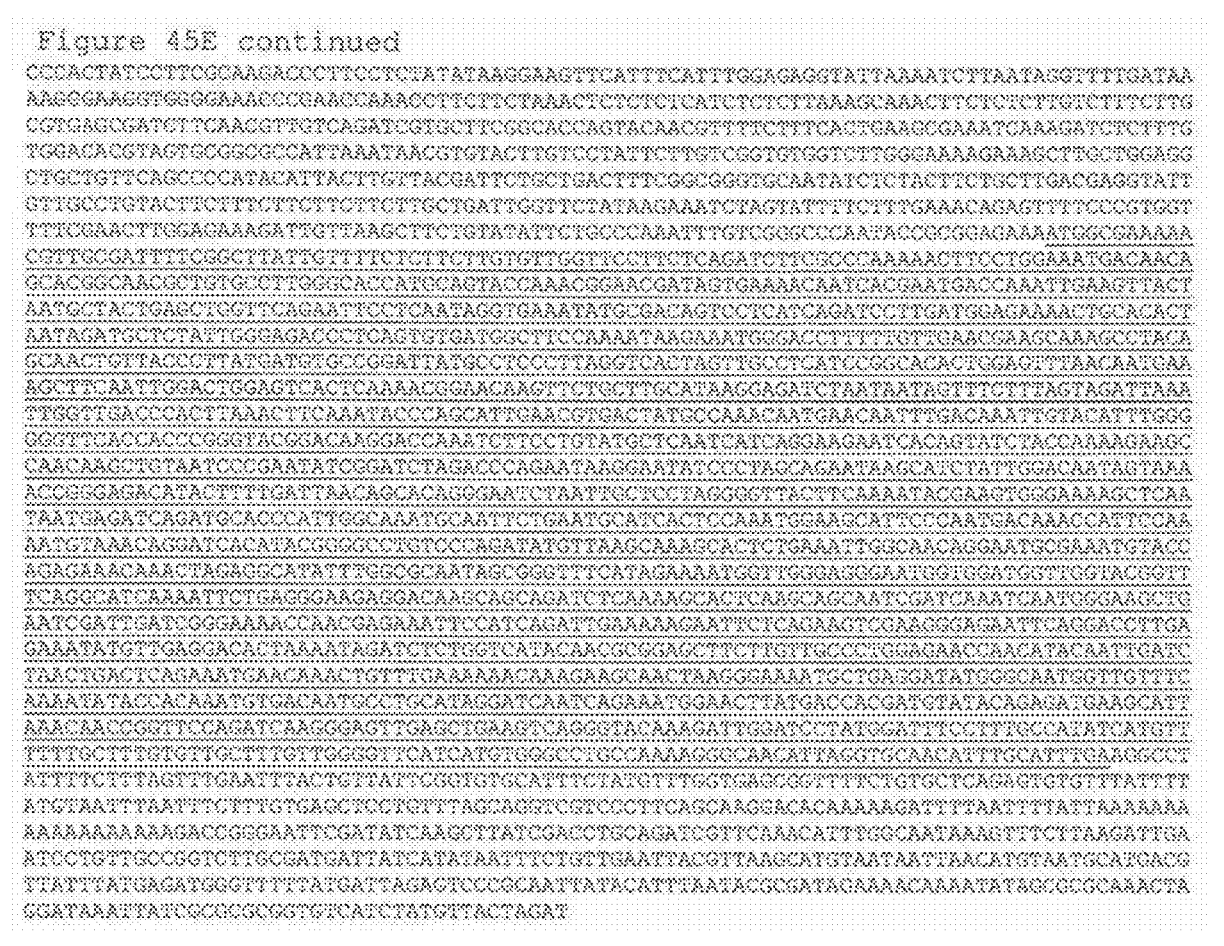

CCCACTATCCTTCGCAAGACCCTTCCTCTATATAAGGAAGTTCATTTCATTTGGAGAGGTATTAAAATCTTAATAGGTTTTGATAA
AAGGGAAGGTGGGGAAACCCGAACCAAACCTTCTTCTAAACTCTCTCTCATCTCTCTTAAAGCAAACTTCTCTCTTGTCTTTCTTG
CGTGAGCGATCTTCAAGCTTGTCAGATCGTGCTTCGGCACCAGTACAACGTTTTCTTTCACTGAAGCGAAATCAAAGATCTCTTTG
TGGACACGTAGTGCGGCGCCATTAAATAACGTGTACTTGTCCTATTCTTGTCGGTGTGGTCTTGGGAAAAGAAAGCTTGCTGGAGG
CTGCTGTTCAGCCCCATACATTACTTGTTACGATTCTGCTGACTTTCGGCGGGTGCAATATCTCTACTTCTGCTTGACGAGGTATT
GTTGCCTGTACTTCTTTCTTCTTGTTCTTGCTGATTGGTTCTATAAGAAATCTAGTATTTTCTTTGAAACAGAGTTTTCCCGTGGT
TTTCGAACTTGGAGAAAGATTGTTAAGCTTCTGTATATTCTGCCCAAATTTGTCGGGCCCAATACCCGCGGAGAAAATGGCGAAAAA
CGTTGCGATTTTCGGCTTATTGTTTTCTCTTCTTGTGTTGGTTCCTTCTCAGATCTTCGCCCAAAAACTTCCTGGAAATGACAACA
GCACGGCAACGCTGTGCCTTGGGCACCATGCAGTACCAAACGGAACGATAGTGAAAACAATCACGAATGACCAAATTGAAGTTACT
AATGCTACTGAGCTGGTTCAGAATTCCTCAATAGGTGAAATATGCGACAGTCCTCATCAGATCCTTGATGGAGAAAACTGCACACT
AATAGATGCTCTATTGGGAGACCCTCAGTGTGATGGCTTCCAAAATAAGAAATGGGACCTTTTTGTTGAACGAAGCAAAGCCTACA
GCAACTGTTACCCTTATGATGTGCCGGATTATGCCTCCCTTAGGTCACTAGTTGCCTCATCCGGCACACTGGAGTTTAACAATGAA
AGCTTCAATTGGACTGGAGTCACTCAAAACGGAACAAGTTCTGCTTGCATAAGGAGATCTAATAATAGTTTCTTTAGTAGATTAAA
TTGGTTGACCCACTTAAACTTCAAATACCCAGCATTGAACGTGACTATGCCAAACAATGAACAATTTGACAAATTGTACATTTGGG
GGGTTCACCACCCGGGTACGGACAAGGACCAAATCTTCCTGTATGCTCAATCATCAGGAAGAATCACAGTATCTACCAAAAGAAGC
CAACAAGCTGTAATCCCGAATATCGGATCTAGACCCAGAATAAGGAATATCCCTAGCAGAATAAGCATCTATTGGACAATAGTAAA
ACCGGGAGACATACTTTTGATTAACAGCACAGGGAATCTAATTGCTCCTAGGGGTTACTTCAAAATACGAAGTGGGAAAAGCTCAA
TAATGAGATCAGATGCACCCATTGGCAAATGCAATTCTGAATGCATCACTCCAAATGGAAGCATTCCCAATGACAAACCATTCCAA
AATGTAAACAGGATCACATACGGGGCCTGTCCCAGATATGTTAAGCAAAGCACTCTGAAATTGGCAACAGGAATGCGAAATGTACC
AGAGAAACAAACTAGAGGCATATTTGGCGCAATAGCGGGTTTCATAGAAAATGGTTGGGAGGGAATGGTGGATGGTTGGTACGGTT
TCAGGCATCAAAATTCTGAGGGAAGAGGACAAGCAGCAGATCTCAAAAGCACTCAAGCAGCAATCGATCAAATCAATGGAAAGCTG
AATCGATTGATCGGGAAAACCAACGAGAAATTCCATCAGATTGAAAAAGAATTCTCAGAAGTCGAAGGGAGAATTCAGGACCTTGA
GAAATATGTTGAGGACACTAAAATAGATCTCTGGTCATACAACGCGGAGCTTCTTGTTGCCCTGGAGAACCAACATACAATTGATC
TAACTGACTCAGAAATGAACAAACTGTTTGAAAAAACAAAGAAGCAACTAAGGGAAAATGCTGAGGATATGGGCAATGGTTGTTTC
AAAATATACCACAAATGTGACAATGCCTGCATAGGATCAATCAGAAATGGAACTTATGACCACGATGTATACAGAGATGAAGCATT
AAACAACCGGTTCCAGATCAAGGGAGTTGAGCTGAAGTCAGGGTACAAAGATTGGATCCTATGGATTTCCTTTGCCATATCATGTT
TTTTGCTTTGTGTTGCTTTGTTGGGGTTCATCATGTGGGCCTGCCAAAAGGGCAACATTAGGTGCAACATTTGCATTTGAAGGCCT
ATTTTCTTTAGTTTGAATTTACTGTTATTCGGTGTGCATTTCTATGTTTGGTGAGCGGTTTTCTGTGCTCAGAGTGTGTTTATTTT
ATGTAATTTAATTTCTTTGTGAGCTCCTGTTTAGCAGGTCGTCCCTTCAGCAAGGACACAAAAAGATTTTAATTTTATTAAAAAA
AAAAAAAAAAAGACCGGGAATTCGATATCAAGCTTATCGACCTGCAGATCGTTCAAACATTTGGCAATAAAGTTTCTTAAGATTGA
ATCCTGTTGCCGGTCTTGCGATGATTATCATATAATTTCTGTTGAATTACGTTAAGCATGTAATAATTAACATGTAATGCATGACG
TTATTTATGAGATGGGTTTTTATGATTAGAGTCCCGCAATTATACATTTAATACGCGATAGAAAACAAAATATAGCGCGCAAACTA
GGATAAATTATCGCGCGCGGTGTCATCTATGTTACTAGAT

Schematic representation of construct number 1819

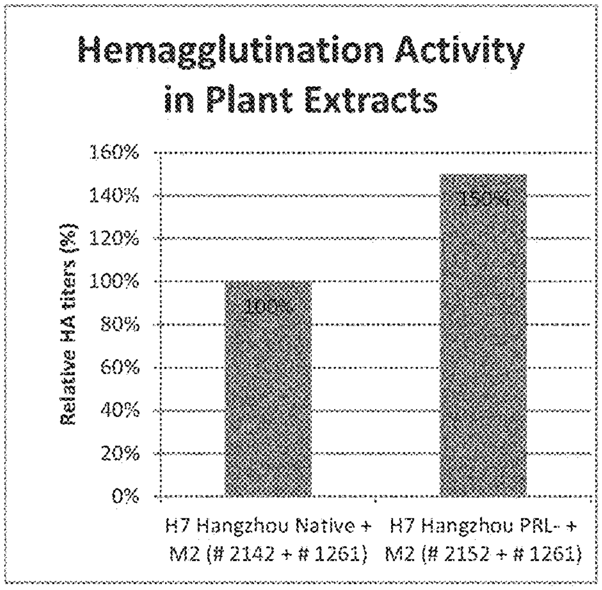
Figure 46A
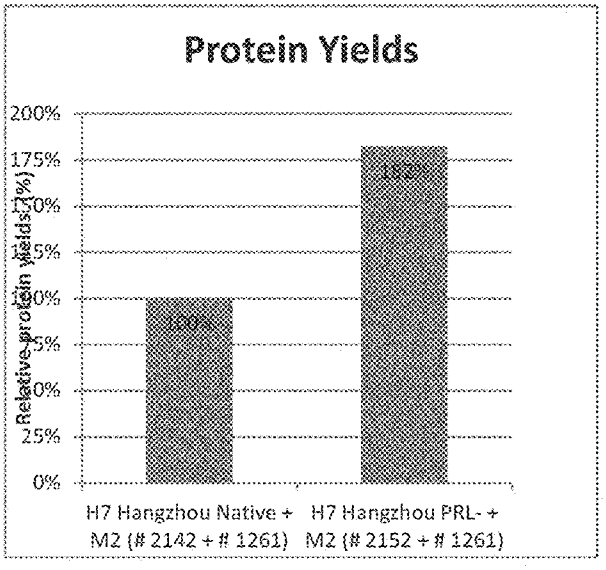
Figure 46B
Figure 46C
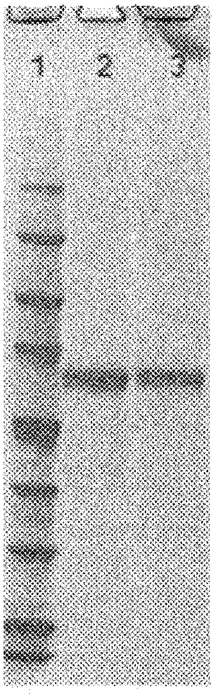

Figure 48

2X35S/CPMV HT+/ PDISP/H2 Singapore/ NOS (Construct number 2220)

Figure 48A, SEQ ID NO: 127

IF**-H2S157.s1-6r

ACTAAAGAAAATAGGCCTTCATATGCAGATCCTGCACTGCAGAGACCCGT

Figure 48B, SEQ ID NO: 128

Nucleotide sequence of PDISP/H2 Singapore.

ATGGCGAAAAACGTTGCGATTTTCGGCTTATTGTTTTCTCTTCTTGTGTTGGTTCCTTCTCAGATCTTCGCGGACCAAA
TATGCATTGGATACCATGCCAATAATTCCACAGAGAAGGTCGACACAATTCTAGAGCGGAACGTCACTGTGACTCATGC
CAAGGACATTCTTGAGAAGACCCATAACGGAAAGTTATGCAAACTAAACGGAATCCCTCCACTTGAACTAGGGGACTGT
AGCATTGCCGGATGGCTCCTTGGAAATCCAGAATGTGATAGGCTTCTAAGTGTGCCAGAATGGTCCTATATAATGGAGA
AAGAAAACCCGAGAGACGGTTTGTGTTATCCAGGCAGCTTCAATGATTATGAAGAATTGAAACATCTCCTCAGCAGCGT
GAAACATTTCGAGAAAGTAAAGATTCTGCCCAAAGATAGATGGACACAGCATACAACAACTGGAGGTTCACGGGCCTGC
GCGGTGTCTGGTAATCCATCATTCTTCAGGAACATGGTCTGGCTGACAAAGAAAGAATCAAATTATCCGGTTGCCAAAG
GATCGTACAACAATACAAGCGGAGAACAAATGCTAATAATTTGGGGGGTGCACCATCCCAATGATGAGACAGAACAAAG
AACATTGTACCAGAATGTGGGAACCTATGTTTCCGTAGGCACATCAACATTGAACAAAAGGTCAACCCCAGACATAGCA
ACAAGGCCTAAAGTGAATGGACTAGGAAGTAGAATGGAGTTCTCTTGGACCCTATTGGATATGTGGGACACCATAAATT
TTGAGAGTACTGGTAATCTAATTGCACCAGAGTATGGATTCAAAATATCGAAAAGAGGTAGTTCAGGGATCATGAAAAC
AGAAGGAACACTTGAGAACTGTGAGACCAAATGCCAAACTCCTTTGGGAGCAATAAATACAACATTGCCTTTTCACAAT
GTCCACCCACTGACAATAGGTGAGTGCCCCAAATATGTAAAATCGGAGAAGTTGGTCTTAGCAACAGGACTAAGGAATG
TTCCCCAGATTGAATCAAGAGGATTGTTTGGGGCAATAGCTGGTTTTATAGAAGGAGGATGGCAAGGAATGGTTGATGG
TTGGTATGGATACCATCACAGCAATGACCAGGGATCAGGGTATGCAGCAGACAAAGAATCCACTCAAAAGGCATTTGAT
GGAATCACCAACAAGGTAAATTCTGTGATTGAAAAGATGAACACCCAATTTGAAGCTGTTGGGAAAGAGTTCAGTAACT
TAGAGAGAAGACTGGAGAACTTGAACAAAAAGATGGAAGACGGGTTTCTAGATGTGTGGACATACAATGCTGAGCTTCT
AGTTCTGATGGAAAATGAGAGGACACTTGACTTTCATGATTCTAATGTCAAGAATCTGTATGATAAAGTCAGAATGCAG
CTGAGAGACAACGTCAAAGAACTAGGAAATGGATGTTTTGAATTTTATCACAAATGTGATGATGAATGCATGAATAGTG
TGAAAAACGGGACGTATGATTATCCCAAGTATGAAGAAGAGTCTAAACTAAATAGAAATGAAATCAAAGGGGTAAAATT
GAGCAGCATGGGGGTTTATCAAATCCTTGCCATTTATGCTACAGTAGCAGGTTCTCTGTCACTGGCAATCATGATGGCT
GGGATCTCTTTCTGGATGTGCTCCAACGGGTCTCTGCAGTGCAGGATCTGCATATGA

Figure 48C, SEQ ID NO: 129

Expression cassette number 2220 from 2X35S promoter to NOS terminator. PDISP/H2 Singapore nucleotide sequence is underlined.

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAACGTTTTCTTTCACTGAAGCGAAATCAAAGATCTCTTTGTG
GACACGTAGTGCGGCGCCATTAAATAACGTGTACTTGTCCTATTCTTGTCGGTGTGGTCTTGGGAAAAGAAAGCTTGCT
GGAGGCTGCTGTTCAGCCCCATACATTACTTGTTACGATTCTGCTGACTTTCGGCGGGTGCAATATCTCTACTTCTGCT
TGACGAGGTATTGTTGCCTGTACTTCTTTCTTCTTCTTCTTGCTGATTGGTTCTATAAGAAATCTAGTATTTTCTTTGA

Figure 48C continued

AACAGAGTTTTCCCGTGGTTTTCGAACTTGGAGAAAGATTGTTAAGCTTCTGTATATTCTGCCCAAATTTGTCGGGCCC
AATACCGGCGGAGAAAATGGCGAAAAACGTTGCGATTTTCGGCTTATTGTTTTCTCTTCTTGTGTTGGTTCCTTCTCAGA
TCTTCGCGGACCAAATATATGCATTGGATACCATGCCAATAATTCCACAGAGAAGGTCGACACAATTCTAGAGCGGAACGT
CACTGTGACTCATGCCAAGGACATTCTTGAGAAGACCCATAACGGAAAGTTATGCAAACTAAACGGAATCCCTCCACTT
GAACTAGGGGACTGTAGCATTGCCGGATGGCTCCTTGGAAATCCAGAATGTGATAGGCTTCTAAGTGTGCCAGAATGGT
CCTATATAATGGAGAAAGAAAACCCGAGAGACGGTTTGTGTTATCCAGGCAGCTTCAATGATTATGAAGAATTGAAACA
TCTCCTCAGCAGCGTGAAACATTTCGAGAAAGTAAAGATTCTGCCCAAAGATAGATGGACACAGCATACAACAACTGGA
GGTTCACGGGCCTGCGCGGTGTCTGGTAATCCATCATTCTTCAGGAACATGGTCTGGCTGACAAAGAAAGGATCAAATT
ATCCGGTTGCCAAAGGATCGTACAACAATACAAGCGGAGAACAAATGCTAATAATTTGGGGGGTGCACCATCCCAATGA
TGAGACAGAACAAAGGAACATTGTACCAGAATGTGGGAACCTATGTTTCCGTAGGCACATCAACATTGAACAAAAGGTCA
ACCCCAGACATAGCAACAAGGCCTAAAGTGAATGGACTAGGAAGTAGAATGGAGTTCTCTTGGACCCTATTGGATATGT
GGGACACCATAAATTTTGAGAGTACTGGTAATCTAATTGCACCAGAGTATGGATTCAAAATATCGAAAAGAGGTAGTTC
AGGGATCATGAAAACAGAAGGAACACTTGAGAACTGTGAGACCAAATGCCAAACTCCTTTGGGAGCAATAAATACAACA
TTGCCTTTTCACAATGTCCACCCACTGACAATAGGTGAGTGCCCCAAATATGTAAAATCGGAGAAGTTGGTCTTAGCAA
CAGGACTAAGGAATGTTCCCCAGATTGAATCAAGAGGATTGTTTGGGGCAATAGCTGGTTTTATAGAAGGAGGATGGCA
AGGAATGGTTGATGGTTGGTATGGATACCATCACAGCAATGACCAGGGATCAGGGTATGCAGCAGACAAAGAATCCACT
CAAAAGGCATTTGATGGAATCACCAACAAGGTAAATTCTGTGATTGAAAAGATGAACACCCAATTTGAAGCTGTTGGGA
AAGAGTTCAGTAACTTAGAGAGAAGACTGGAGAACTTGAACAAAAAGATGGAAGACGGGTTTCTAGATGTGTGGACATA
CAATGCTGAGCTTCTAGTTCTGATGGAAAATGAGAGGACACTTGACTTTCATGATTCTAATGTCAAGAATCTGTATGAT
AAAGTCAGAATGCAGCTGAGAGACAACGTCAAAGAACTAGGAAATGGATGTTTTGAATTTTATCACAAATGTGATGATG
AATGCATGAATAGTGTGAAAAACGGGACGTATGATTATCCCAAGTATGAAGAAGAGTCTAAACTAAATAGAAATGAAAT
CAAAGGGGTAAAATTGAGCAGCATGGGGGTTTATCAAATCCTTGCCATTTATGCTACAGTAGCAGGTTCTCTGTCACTG
GCAATCATGATGGCTGGGATCTCTTTTTGGATGTGCTCCAACGGGTCTCTGCAGTGCAGGATCTGCATATGAAGGCCTA
TTTTCTTTAGTTTGAATTTACTGTTATTCGGTGTGCATTTCTATGTTTGGTGAGCGGTTTTCTGTGCTCAGAGTGTGTT
TATTTTATGTAATTTAATTTCTTTGTGAGCTCCTGTTTAGCAGGTCGTCCCTTCAGCAAGGACACAAAAAGATTTTAAT
TTTATTAAAAAAAAAAAAAAAAAAAAAGACCGGGAATTCGATATCAAGCTTATCGACCTGCAGATCGTTCAAACATTTGGCA
ATAAAGTTTCTTAAGATTGAATCCTGTTGCCGGTCTTGCGATGATTATCATATAATTTCTGTTGAATTACGTTAAGCAT
GTAATAATTAACATGTAATGCATGACGTTATTTATGAGATGGGTTTTTATGATTAGAGTCCCGCAATTATACATTTAAT
ACGCGATAGAAAACAAAATATAGCGCGCAAACTAGGATAAATTATCGCGCGCGGTGTCATCTATGTTACTAGAT

Figure 48D, SEQ ID NO: 130

Amino acid sequence of PDISP/H2 Singapore

MAKNVAIFGLLFSLLVLVPSQIFADQICIGYHANNSTEKVDTILERNVTVTHAKDILEKTHNGKLCKLNGIPPLELGDC
SIAGWLLGNPECDRLLSVPEWSYIMEKENPRDGLCYPGSFNDYEELKHLLSSVKHFEKVKILPKDRWTQHTTTGGSRAC
AVSGNPSFFRNMVWLTKKGSNYPVAKGSYNNTSGEQMLIIWGVHHPNDETEQRTLYQNVGTYVSVGTSTLNKRSTPDIA
TRPKVNGLGSRMEFSWTLLDMWDTINFESTGNLIAPEYGFKISKRGSSGIMKTEGTLENCETKCQTPLGAINTTLPFHN
VHPLTIGECPKYVKSEKLVLATGLRNVPQIESRGLFGAIAGFIEGGWQGMVDGWYGYHHSNDQGSGYAADKESTQKAFD
GITNKVNSVIEKMNTQFEAVGKEFSNLERRLENLNKKMEDGFLDVWTYNAELLVLMENERTLDFHDSNVKNLYDKVRMQ
LRDNVKELGNGCFEFYHKCDDECMNSVKNGTYDYPKYEEESKLNRNEIKGVKLSSMGVYQILAIYATVAGSLSLAIMMA
GISFWMCSNGSLQCRICI*

Figure 48E

Schematic representation of construct number 2220

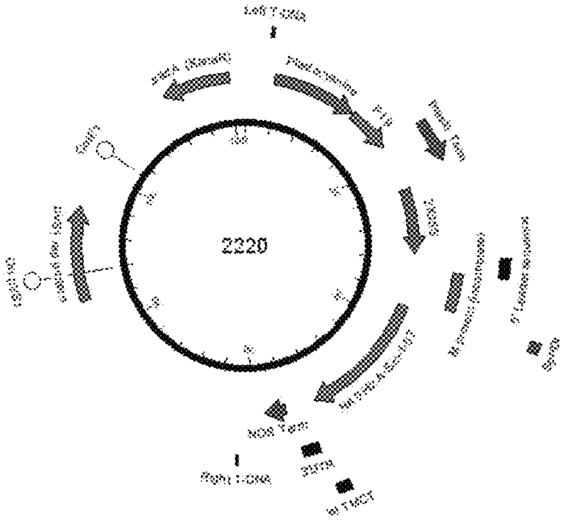

Figure 49

2X35S/CPMV HT+/ PDISP/H2 Singapore with deleted proteolytic loop/ NOS (Construct number 2221)

Figure 49A, SEQ ID NO: 131

H2S157(Prl-).r

TGCCATCCTCCGCCGGGAACATTCCTTAGTCCTGTTGCTAAGACCAAC

Figure 49B, SEQ ID NO: 132

H2S157(Prl-).c

AGGAATGTTCCCGGCGGAGGATGGCAAGGAATGGTTGATGGTTGGTATGG

Figure 49C, SEQ ID NO: 133

Expression cassette number 2221 from 2X35S promoter to NOS terminator. PDISP/H2 Singapore with deleted proteolytic loop nucleotide sequence is underlined.

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA

Figure 49C continued

TCTTCAACGTTGTCAGATCGTGCTTCGGCACCAGTACAACGTTTTCTTTCACTGAAGCGAAATCAAAGATCTCTTTGTG
GACACGTAGTGCGGCGCCATTAAATAACGTGTACTTGTCCTATTCTTGTCGGTGTGGTCTTGGGAAAAGAAAGCTTGCT
GGAGGCTGCTGTTCAGCCCCATACATTACTTGTTACGATTCTGCTGACTTTCGGCGGGTGCAATATCTCTACTTCTGCT
TGACGAGGTATTGTTGCCTGTACTTCTTTCTTCTTCTTCTTGCTGATTGGTTCTATAAGAAATCTAGTATTTTCTTTGA
AACAGAGTTTTCCCGTGGTTTTCGAACTTGGAGAAAGATTGTTAAGCTTCTGTATATTCTGCCCAAATTTGTCGGGCCC
AATACCGCGGAGAAAATGGCGAAAAACGTTGCGATTTTCGGCTTATTGTTTTCTCTTCTTGTGTTGGTTCCTTCTCAGA
TCTTCGCGGACCAAATATGCATTGGATACCATGCCAATAATTCCACAGAGAAGGTCGACACAATTCTAGAGCGGAACGT
CACTGTGACTCATGCCAAGGACATTCTTGAGAAGACCCATAACGGAAAGTTATGCAAACTAAACGGAATCCCTCCACTT
GAACTAGGGGACTGTAGCATTGCCGGATGGCTCCTTGGAAATCCAGAATGTGATAGGCTTCTAAGTGTGCCAGAATGGT
CCTATATAATGGAGAAAGAAAACCCGAGAGACGGTTTGTGTTATCCAGGCAGCTTCAATGATTATGAAGAATTGAAACA
TCTCCTCAGCAGCGTGAAACATTTCGAGAAAGTAAAGATTCTGCCCAAAGATAGATGGACACAGCATACAACAACTGGA
GGTTCACGGGCCTGCGCGGTGTCTGGTAATCCATCATTCTTCAGGAACATGGTCTGGCTGACAAAGAAAGAATCAAATT
ATCCGGTTGCCAAAGGATCGTACAACAATACAAGCGGAGAACAAATGCTAATAATTTGGGGTGCACCATCCCAATGA
TGAGACAGAACAAAGAACATTGTACCAGAATGTGGGAACCTATGTTTCCGTAGGCACATCAACATTGAACAAAAGGTCA
ACCTCAGACATAGCAACAAGGCCTAAAGTGAATGGACTAGGAAGTAGAATGGAGTTCTCTTGGACCCTATTGGATATGT
GGGACACCATAAATTTTGAGAGTACTGGTAATCTAATTGCACCAGAGTATGGATTCAAAATATCGAAAAGAGGTAGTTC
AGGGATCATGAAAACAGAAGGAACACTTGAGAACTGTGAGACCAAATGCCAAACTCCTTTGGGAGCAATAAATACAACA
TTGCCTTTTCACAATGTCCACCCACTGACAATAGGTGAGTGCCCCAAATATGTAAAATCGGAGAAGTTGGTCTTAGCAA
CAGGACTAAGGAATGTTCCCGGGGGAGGATGGCAAGGAATGGTTGATGGTTGGTATGGATACCATCACAGCAATGACCA
GGGATCAGGGTATGCAGCAGACAAAGAATCCACTCAAAAGGCATTTGATGGAATCACCAACAAGGTAAATTCTGTGATT
GAAAAGATGAACACCCAATTTGAAGCTGTTGGGAAAGAGTTCAGTAACTTAGAGAGAAGACTGGAGAACTTGAACAAAA
AGATGGAAGACGGGTTTCTAGATGTGTGGACATACAATGCTGAGCTTCTAGTTCTGATGGAAAATGAGAGGACACTTGA
CTTTCATGATTCTAATGTCAAGAATCTGTATGATAAAGTCAGAATGCAGCTGAGAGACAACGTCAAAGAACTAGGAAAT
GGATGTTTTGAATTTTATCACAAATGTGATGATGAATGCATGAATAGTGTGAAAAACGGGACGTATGATTATCCCAAGT
ATGAAGAAGAGTCTAAACTAAATAGAAATGAAATCAAAGGGGTAAAATTGAGCAGCATGGGGGTTTATCAAATCCTTGC
CATTTATGCTACAGTAGCAGGTTCTCTGTCACTGGCAATCATGATGGCTGGGATCTCTTTCTGGATGTGCTCCAACGGG
TCTCTGCAGTGCAGGATCTGCATATGAAGGCCTATTTTCTTTAGTTTGAATTTACTGTTATTCGGTGTGCATTTCTATG
TTTGGTGAGCGGTTTTCTGTGCTCAGAGTGTGTTTATTTTATGTAATTTAATTTCTTTGTGAGCTCCTGTTTAGCAGGT
CGTCCCTTCAGCAAGGACACAAAAAGATTTTAATTTTATTAAAAAAAAAAAAAAAAAAAAGACCGGGAATTCGATATCAAG
CTTATCGACCTGCAGATCGTTCAAACATTTGGCAATAAAGTTTCTTAAGATTGAATCCTGTTGCCGGTCTTGCGATGAT
TATCATATAATTTCTGTTGAATTACGTTAAGCATGTAATAATTAACATGTAATGCATGACGTTATTTATGAGATGGGTT
TTTATGATTAGAGTCCCGCAATTATACATTTAATACGCGATAGAAAACAAAATATAGCGCGCAAACTAGGATAAATTAT
CGCGCGCGGTGTCATCTATGTTACTAGAT

Figure 49D, SEQ ID NO: 134

Amino acid sequence of PDISP/H2 Singapore with deleted proteolytic loop

MAKNVAIFGLLFSLLVLVPSQIFADQICIGYHANNSTEKVDTILERNVTVTHAKDILEKTHNGKLCKLNGIPPLELGDCSIAGWLLGNPECD
RLLSVPEWSYIMEKENPRDGLCYPGSFNDYEELKHLLSSVKHFEKVKILPKDRWTQHTTTGGSRACAVSGNPSFFRNMVWLTKKESNYP
VAKGSYNNTSGEQMLIIWGVHHPNDETEQRTLYQNVGTYVSVGTSTLNKRSTPDIATRPKVNGLGSRMEFSWTLLDMWDTINFESTG
NLIAPEYGFKISKRGSSGIMKTEGTLENCETKCQTPLGAINTTLPFHNVHPLTIGECPKYVKSEKLVLATGLRNVPGGGWQGMVDGWYG
YHHSNDQGSGYAADKESTQKAFDGITNKVNSVIEKMNTQFEAVGKEFSNLERRLENLNKKMEDGFLDVWTYNAELLVLMENEKTLDF
HDSNVKNLYDKVRMQLRDNVKELGNGCFEFYHKCDDECMNSVKNGTYDYPKYEEESKLNRNEIKGVKLSSMGVYQILAIYATVAGSLSL
AIMMAGISFWMCSNGSLQCRICI*

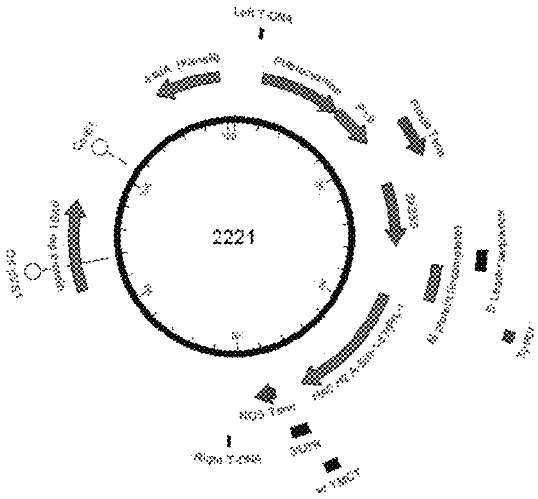

Figure 50

PDISP/H2 Singapore (Construct number 2222) and PDISP/H2 Singapore with deleted proteolytic loop (Construct number 2223) in 2X35S/CPMV 160+/NOS expression system

Figure 50A, SEQ ID NO: 135

Expression cassette number 2222 from 2X35S promoter to NOS terminator. PDISP/H2 Singapore nucleotide sequence is underlined.

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAGGGCCCAATACCGCGGAGAAAATGGCGAAAAACGTTGCGAT
TTTCGGCTTATTGTTTTCTCTTCTTGTGTTGGTTCCTTCTCAGATCTTCGCGGACCAAATATGCATTGGATACCATGCC
AATAATTCCACAGAGAAGGTCGACACAATTCTAGAGCGGAACGTCACTGTGACTCATGCCAAGGACATTCTTGAGAAGA
CCCATAACGGAAAGTTATGCAAACTAAACGGAATCCCTCCACTTGAACTAGGGGACTGTAGCATTGCCGGATGGCTCCT
TGGAAATCCAGAATGTGATAGGCTTCTAAGTGTGCCAGAATGGTCCTATATAATGGAGAAAGAAAACCCGAGAGACGGT
TTGTGTTATCCAGGCAGCTTCAATGATTATGAAGAATTGAAACATCTCCTCAGCAGCGTGAAACATTTCGAGAAAGTAA
AGATTCTGCCCAAAGATAGATGGACACAGCATACAACAACTGGAGGTTCACGGGCCTGCGCGGTGTCTGGTAATCCATC
ATTCTTCAGGAACATGGTCTGGCTGACAAAGAAAGAATCAAATTATCCGGTTGCCAAAGGATCGTACAACAATACAAGC
GGAGAACAAATGCTAATAATTTGGGGGGTGCACCATCCCAATGATGAGACAGAACAAAGAACATTGTACCAGAATGTGG
GAACCTATGTTTCCGTAGGCACATCAACATTGAACAAAAGGTCAACCCCAGACATAGCAACAAGGCCTAAAGTGAATGG
ACTAGGAAGTAGAATGGAGTTCTCTTGGACCCTATTGGATATGTGGGACACCATAAATTTTGAGAGTACTGGTAATCTA

Figure 50A continued

ATTGCACCAGAGTATGGATTCAAAATATCGAAAAAGAGGTAGTTCAGGGATCATGAAAACAGAAGGAACACTTGAGAACT
GTGAGACCAAATGCCAAACTCCTTTGGGAGCAATAAATACAACATTGCCTTTTCACAATGTCCACCCACTGACAATAGG
TGAGTGCCCCAAATATGTAAAATCGGAGAAGTTGGTCTTAGCAACAGGACTAAGGAATGTTCCCCAGATTGAATCAAGA
GGATTGTTTGGGGCAATAGCTGGTTTTATAGAAGGAGGATGGCAAGGAATGGTTGATGGTTGGTATGGATACCATCACA
GCAATGACCAGGGATCAGGGTATGCAGCAGACAAAGAATCCACTCAAAAGGCATTTGATGGAATCACCAACAAGGTAAA
TTCTGTGATTGAAAAGATGAACACCCAATTTGAAGCTGTTGGGAAAGAGTTCAGTAACTTAGAGAGAAGACTGGAGAAC
TTGAACAAAAAGATGGAAGACGGGTTTCTAGATGTGTGGACATACAATGCTGAGCTTCTAGTTCTGATGGAAAATGAGA
GGACACTTGACTTTCATGATTCTAATGTCAAGAATCTGTATGATAAAGTCAGAATGCAGCTGAGAGACAACGTCAAAGA
ACTAGGAAATGGATGTTTTGAATTTTATCACAAATGTGATGATGAATGCATGAATAGTGTGAAAAACGGGACGTATGAT
TATCCCAAGTATGAAGAAGAGTCTAAACTAAATAGAAATGAAATCAAAGGGGTAAAATTGAGCAGCATGGGGGTTTATC
AAATCCTTGCCATTTATGCTACAGTAGCAGGTTCTCTGTCACTGGCAATCATGATGGCTGGGATCTCTTTCTGGATGTG
CTCCAACGGGTCTCTGCAGTGCAGGATCTGCATATGAAGGCCTATTTTCTTTAGTTTGAATTTACTGTTATTCGGTGTG
CATTTCTATGTTTGGTGAGCGGTTTTCTGTGCTCAGAGTGTGTTTATTTTATGTAATTTAATTTCTTTGTGAGCTCCTG
TTTAGCAGGTCGTCCCTTCAGCAAGGACACAAAAAGATTTTAATTTTATTAAAAAAAAAAAAAAAAAAAAGACCGGGAATT
CGATATCAAGCTTATCGACCTGCAGATCGTTCAAACATTTGGCAATAAAGTTTCTTAAGATTGAATCCTGTTGCCGGTC
TTGCGATGATTATCATATAATTTCTGTTGAATTACGTTAAGCATGTAATAATTAACATGTAATGCATGACGTTATTTAT
GAGATGGGTTTTTATGATTAGAGTCCCGCAATTATACATTTAATACGCGATAGAAAACAAAATATAGCGCGCAAACTAG
GATAAATTATCGCGCGCGGTGTCATCTATGTTACTAGAT

Figure 50B, SEQ ID NO: 136

Expression cassette number 2223 from 2X35S promoter to NOS terminator. PDISP/H2 Singapore with deleted proteolytic loop nucleotide sequence is underlined.

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAGGGCCCAATACCGCGGAGAAAATGGCGAAAAACGTTGCGAT
TTTCGGCTTATTGTTTTCTCTTCTTGTGTTGGTTCCTTCTCAGATCTTCGCGGACAAAATATGCATTGGATACCATGCC
AATAATTCCACAGAGAAGGTCGACACAATTCTAGAGCGGAACGTCACTGTGACTCATGCCAAGGACATTCTTGAGAAGA
CCCATAACGGAAAGTTATGCAAACTAAACGGAATCCCTCCACTTGAACTAGGGGACTGTAGCATTGCCGGATGGCTCCT
TGGAAATCCAGAATGTGATAGGCTTCTAAGTGTGCCAGAATGGTCCTATATAATGGAGAAAGAAAACCCGAGAGACGGT
TTGTGTTATCCAGGCAGCTTCAATGATTATGAAGAATTGAAACATCTCCTCAGCAGCGTGAAACATTTCGAGAAAGTAA
AGATTCTGCCCAAAGATAGATGGACACAGCATACAACAACTGGAGGTTCACGGGCCTGCGCGGTGTCTGGTAATCCATC
ATTCTTCAGGAACATGGTCTGGCTGACAAAGAAAGAATCAAATTATCCGGTTGCCAAGGGATCGTACAACAATACAAGC
GGAGAACAAATGCTAATAATTTGGGGGGTGCACCATCCCAATGATGAGACAGAACAAAGAACATTGTACCAGAATGTGG
GAACCTATGTTTCCGTAGGCACATCAACATTGAACAAAAGGTCAACCCCAGACATAGCAACAAGGCCTAAAGTGAATGG
ACTAGGAAGTAGAATGGAGTTCTCTTGGACCCTATTGGATATATGGGACACCATAAATTTTGAGAGTACTGGTAATCTA
ATTGCACCAGAGTATGGATTCAAAATATCGAAAAAGAGGTAGTTCAGGGATCATGAAAACAGAAGGAACACTTGAGAACT
GTGAGACCAAATGCCAAACTCCTTTGGGAGCAATAAATACAACATTGCCTTTTCACAATGTCCACCCACTGACAATAGG
TGAGTGCCCCAAATATGTAAAATCGGAGAAGTTGGTCTTAGCAACAGGACTAAGGAATGTTCCCGGCGGAGGATGGCAA
GGAATGGTTGATGGTTGGTATGGATACCATCACAGCAATGACCAGGGATCAGGGTATGCAGCAGACAAAGAATCCACTC
AAAAGGCATTTGATGGAATCACCAACAAGGTAAATTCTGTGATTGAAAAGATGAACACCCAATTTGAAGCTGTTGGGAA
AGAGTTCAGTAACTTAGAGAGAAGACTGGAGAACTTGAACAAAAAGATGGAAGACGGGTTTCTAGATGTGTGGACATAC
AATGCTGAGCTTCTAGTTCTGATGGAAAATGAGAGGACACTTGACTTTCATGATTCTAATGTCAAGAATCTGTATGATA
AAGTCAGAATGCAGCTGAGAGACAACGTCAAAGAACTAGGAAATGGATGTTTTGAATTTTATCACAAATGTGATGATGA
ATGCATGAATAGTGTGAAAAACGGGACGTATGATTATCCCAAGTATGAAGAAGAGTCTAAACTAAATAGAAATGAAATC

Figure 50B continued

AAAGGGGTAAAATTGAGCAGCATGGGGGTTTATCAAATCCTTGCCATTTATGCTACAGTAGCAGGTTCTCTGTCACTGG
CAATCATGATGGCTGGGATCTCTTTCTGGATGTGCTCCAACGGGTCTCTGCAGTGCAGGATCTGCATATGAAGGCCTAT
TTTCTTTAGTTTGAATTTACTGTTATTCGGTGTGCATTTCTATGTTTGGTGAGCGGTTTTCTGTGCTCAGAGTGTGTTT
ATTTTATGTAATTTAATTTCTTTGTGAGCTCCTGTTTAGCAGGTCGTCCCTTCAGCAACGACACAAAAAGATTTTAATT
TTATTAAAAAAAAAAAAAAAAAAAGACCGGGAATTCGATATCAAGCTTATCGACCTGCAGATCGTTCAAACATTTGGCAA
TAAAGTTTCTTAAGATTGAATCCTGTTGCCGGTCTTGCGATGATTATCATATAATTTCTGTTGAATTACGTTAAGCATG
TAATAATTAACATGTAATGCATGACGTTATTTATGAGATGGGTTTTTATGATTAGAGTCCCGCAATTATACATTTAATA
CGCGATAGAAAACAAAATATAGCGCGCAAACTAGGATAAATTATCGCGCGCGGTGTCATCTATGTTACTAGAT

Schematic representation of construct number 2222

Schematic representation of construct number 2223

Figure 51

2X35S/CPMV HT+ (construct no 2019) and 160+ (construct no 2139) for PDISP/H3 Perth

Figure 51A, SEQ ID NO: 137

Nucleotide sequence of PDISP/H3 Perth

ATGGCGAAAAACGTTGCGATTTTCGGCTTATTGTTTTCTCTTCTTGTGTTGGTTCCTTCTCAGATCTTCGCGCAAAAAC
TTCCTGGAAATGACAACAGCACGGCAACGCTGTGCCTTGGGCACCATGCAGTACCAAACGGAACGATAGTGAAAACAAT
CACGAATGACCAAATTGAAGTTACTAATGCTACTGAGCTGGTTCAGAGTTCCTCAACAGGTGAAATATGCGACAGTCCT
CATCAGATCCTTGATGGAAAAAACTGCACACTAATAGATGCTCTATTGGGAGACCCTCAGTGTGATGGCTTCCAAAATA
AGAAATGGGACCTTTTTGTTGAACGCAGCAAAGCCTACAGCAACTGTTACCCTTATGATGTGCCGGATTATGCCTCCCT
TAGGTCACTAGTTGCCTCATCCGGCACACTGGAGTTTAACAATGAAAGCTTCAATTGGACTGGAGTCACTCAAAACGGA
ACAAGCTCTGCTTGCATAAGGAGATCTAAAAACAGTTTCTTTAGTAGATTGAATTGGTTGACCCACTTAAACTTCAAAT
ACCCAGCATTGAACGTGACTATGCCAAACAATGAACAATTTGACAAATTGTACATTTGGGGGGTTCACCACCCGGGTAC
GGACAAAGACCAAATCTTCCTGTATGCTCAAGCATCAGGAAGAATCACAGTCTCTACCAAAAGAAGCCAACAAACCGTA
AGCCCGAATATCGGATCTAGACCCAGAGTAAGGAATATCCCTAGCAGAATAAGCATCTATTGGACAATAGTAAAACCGG
GAGACATACTTTTGATTAACAGCACAGGGAATCTAATTGCTCCTAGGGGTTACTTCAAAATACGAAGTGGGAAAAGCTC
AATAATGAGATCAGATGCACCCATTGGCAAATGCAATTCTGAATGCATCACTCCAAATGGAAGCATTCCCAATGACAAA
CCATTCCAAAATGTAAACAGGATCACATACGGGGCCTGTCCCAGATATGTTAAGCAAAACACTCTGAAATTGGCAACAG
GGATGCGAAATGTACCAGAGAAACAAACTAGAGGCATATTTGGCGCAATCGCGGGTTTCATAGAAAATGGTTGGGAGGG
AATGGTGGATGGTTGGTACGGTTTCAGGCATCAAAATTCTGAGGGAAGAGGACAAGCAGCAGATCTCAAAAGCACTCAA
GCAGCAATCGATCAAATCAATGGGAAGCTGAATAGATTGATCGGGAAAACCAACGAGAAATTCCATCAGATTGAAAAAG
AATTCTCAGAAGTCGAAGGGAGAATTCAGGACCTTGAGAAATATGTTGAGGACACTAAAATAGATCTCTGGTCATACAA
CGCGGAGCTTCTTGTTGCCCTGGAGAACCAACATACAATTGATCTAACTGACTCAGAAATGAACAAACTGTTTGAAAAA
ACAAAGAAGCAACTGAGGGAAAATGCTGAGGATATGGGCAATGGTTGTTTCAAAATATACCACAAATGTGACAATGCCT
GCATAGGATCAATCAGAAATGGAACTTATGACCACGATGTATACAGAGATGAAGCATTAAACAACCGGTTTCAGATCAA
GGGAGTTGAGCTGAAGTCAGGGTACAAAGATTGGATCCTATGGATTTCCTTTGCCATATCATGTTTTTTGCTTTGTGTT
GCTTTGTTGGGGTTCATCATGTGGGCCTGCCAAAAAGGCAACATTAGGTGCAACATTTGCATTTGA

Figure 51B, SEQ ID NO: 138

IF**-H3P1609.S1-6r

ACTAAAGAAAATAGGCCTTCAAATGCAAATGTTGCACCTAATGTTGCCTT

Figure 51C, SEQ ID NO: 139

Amino acid sequence of PDISP/H3 Perth

MAKNVAIFGLLFSLLVLVPSQIFAQKLPGNDNSTATLCLGHHAVPNGTIVKTITNDQIEVTNATELVQSSSTGEICDSP
HQILDGKNCTLIDALLGDPQCDGFQNKKWDLFVERSKAYSNCYPYDVPDYASLRSLVASSGTLEFNNESFNWTGVTQNG
TSSACIRRSKNSFFSRLNWLTHLNFKYPALNVTMPNNEQFDKLYIWGVHHPGTDKDQIFLYAQASGRITVSTKRSQQTV
SPNIGSRPRVRNIPSRISIYWTIVKPGDILLINSTGNLIAPRGYFKIRSGKSSIMRSDAPIGKCNSECITPNGSIPNDK
PFQNVNRITYGACPRYVKQNTLKLATGMRNVPEKQTRGIFGAIAGFIENGWEGMVDGWYGFRHQNSEGRGQAADLKSTQ
AAIDQINGKLNRLIGKTNEKFHQIEKEFSEVEGRIQDLEKYVEDTKIDLWSYNAELLVALENQHTIDLTDSEMNKLFEK
TKKQLRENAEDMGNGCFKIYHKCDNACIGSIRNGTYDHDVYRDEALNNRFQIKGVELKSGYKDWILWISFAISCFLLCV
ALLGFIMWACQKGNIRCNICI*

Schematic representation of construct number 2019

Schematic representation of construct number 2139

Figure 52

2X35S/CPMV HT+ (construct no 2039) and 160+ (construct no 2159) for PDISP/H3 Perth with deleted proteolytic loop

Figure 52A, SEQ ID NO: 140

Nucleotide sequence of PDISP/H3 Perth with deleted proteolytic loop

ATGGCGAAAAACGTTGCGATTTTCGGCTTATTGTTTTCTCTTCTTGTGTTGGTTCCTTCTCAGATCTTCGCGCAAAAAC
TTCCTGGAAATGACAACAGCACGGCAACGCTGTGCCTTGGGCACCATGCAGTACCAAACGGAACGATAGTGAAAACAAT
CACGAATGACCAAATTGAAGTTACTAATGCTACTGAGCTGGTTCAGAGTTCCTCAACAGGTGAAATATGCGACAGTCCT
CATCAGATCCTTGATGGAAAAAACTGCACACTAATAGATGCTCTATTGGGAGACCCTCAGTGTGATGGCTTCCAAAATA
AGAAATGGGACCTTTTTGTTGAACGCAGCAAAGCCTACAGCAACTGTTACCCTTATGATGTGCCGGATTATGCCTCCCT
TAGGTCACTAGTTGCCTCATCCGGCACACTGGAGTTTAACAATGAAAGCTTCAATTGGACTGGAGTCACTCAAAACGGA
ACAAGCTCTGCTTGCATAAGGAGATCTAAAAACAGTTTCTTTAGTAGATTGAATTGGTTGACCCACTTAAACTTCAAAT
ACCCAGCATTGAACGTGACTATGCCAAACAATGAACAATTTGACAAATTGTACATTTGGGGGGTTCACCACCCGGGTAC
GGACAAAGACCAAATCTTCCTGTATGCTCAAGCATCAGGAAGAATCACAGTCTCTACCAAAAGAAGCCAACAAACCGTA
AGCCCGAATATCGGATCTAGACCCAGAGTAAGGAATATCCCTAGCAGAATAAGCATCTATTGGACAATAGTAAAACCGG
GAGACATACTTTTGATTAACAGCACAGGGAATCTAATTGCTCCTAGGGGTTACTTCAAAATACGAAGTGGGAAAAGCTC
AATAATGAGATCAGATGCACCCATTGGCAAATGCAATTCTGAATGCATCACTCCAAATGGAAGCATTCCCAATGACAAA
CCATTCCAAAATGTAAACAGGATCACATACGGGGCCTGTCCCAGATATGTTAAGCAAAACACTCTGAAATTGGCAACAG
GGATGCGAAATGTACCAGGCGGAGGTTGGGAGGGAATGGTGGATGGTTGGTACGGTTTCAGGCATCAAAATTCTGAGGG
AAGAGGACAAGCAGCAGATCTCAAAAGCACTCAAGCAGCAATCGATCAAATCAATGGGAAGCTGAATAGATTGATCGGG
AAAACCAACGAGAAATTCCATCAGATTGAAAAAGAATTCTCAGAAGTCGAAGGGAGAATTCAGGACCTTGAGAAATATG
TTGAGGACACTAAAATAGATCTCTGGTCATACAACGCGGAGCTTCTTGTTGCCCTGGAGAACCAACATACAATTGATCT
AACTGACTCAGAAATGAACAAACTGTTTGAAAAAACAAAGAAGCAACTGAGGGAAAATGCTGAGGATATGGGCAATGGT
TGTTTCAAAATATACCACAAATGTGACAATGCCTGCATAGGATCAATCAGAAATGGAACTTATGACCACGATGTATACA
GAGATGAAGCATTAAACAACCGGTTTCAGATCAAGGGAGTTGAGCTGAAGTCAGGGTACAAAGATTGGATCCTATGGAT
TTCCTTTGCCATATCATGTTTTTTGCTTTGTGTTGCTTTGTTGGGGTTCATCATGTGGGCCTGCCAAAAAGGCAACATT
AGGTGCAACATTTGCATTTGA

Figure 52B, SEQ ID NO: 141

H3P1609(Prl-)#2.r

CCCTCCCAACCTCCGCCTGGTACATTTCGCATCCCTGTTGCCAATTTC

Figure 52C, SEQ ID NO: 142

H3P1609(Prl-)#2.c

AATGTACCAGGCGGAGGTTGGGAGGGAATGGTGGATGGTTGGTACGGT

Figure 52D, SEQ ID NO: 143

Amino acid sequence of PDISP/H3 Perth with deleted proteolytic loop

MAKNVAIFGLLFSLLVLVPSQIFAQKLPGNDNSTATLCLGHHAVPNGTIVKTITNDQIEVTNATELVQSSSTGEICDSP
HQILDGKNCTLIDALLGDPQCDGFQNKKWDLFVERSKAYSNCYPYDVPDYASLRSLVASSGTLEFNNESFNWTGVTQNG
TSSACIRRSKNSFFSRLNWLTHLNFKYPALNVTMPNNEQFDKLYIWGVHHPGTDKDQIFLYAQASGRITVSTKRSQQTV
SPNIGSRPRVRNIPSRISIYWTIVKPGDILLINSTGNLIAPRGYFKIRSGKSSIMRSDAPIGKCNSECITPNGSIPNDK
PFQNVNRITYGACPRYVKQNTLKLATGMRNVPGGGWEGMVDGWYGFRHQNSEGRGQAADLKSTQAAIDQINGKLNRLIG
KTNEKFHQIEKEFSEVEGRIQDLEKYVEDTKIDLWSYNAELLVALENQHTIDLTDSEMNKLFEKTKKQLRENAEDMGNG
CFKIYHKCDNACIGSIRNGTYDHDVYRDEALNNRFQIKGVELKSGYKDWILWISFAISCFLLCVALLGFIMWACQKGNI
RCNICI*

Schematic representation of construct number 2039

Schematic representation of construct number 2159

Figure 53

<u>2X35S/CPMV HT+ (construct no 2230) and 160+ (construct no 2250) for PDISP/H3 Victoria with deleted proteolytic loop</u>

Figure 53A, SEQ ID NO: 144

Nucleotide sequence of PDISP/H3 Victoria with deleted proteolytic loop

ATGGCGAAAAACGTTGCGATTTTCGGCTTATTGTTTTCTCTTCTTGTGTTGGTTCCTTCTCAGATCTTCGCGCAAAAACTTCCTGGAA
ATGACAACAGCACGGCAACGCTGTGCCTTGGGCACCATGCAGTACCAAACGGAACGATAGTGAAAACAATCACGAATGACCAAA
TTGAAGTTACTAATGCTACTGAGCTGGTTCAGAATTCCTCAATAGGTGAAATATGCGACAGTCCTCATCAGATCCTTGATGGAGAA
AACTGCACACTAATAGATGCTCTATTGGGAGACCCTCAGTGTGATGGCTTCCAAAATAAGAAATGGGACCTTTTTGTTGAACGAAG
CAAAGCCTACAGCAACTGTTACCCTTATGATGTGCCGGATTATGCCTCCCTTAGGTCACTAGTTGCCTCATCCGGCACACTGGAGTT
TAACAATGAAAGCTTCAATTGGACTGGAGTCACTCAAAACGGAACAAGTTCTGCTTGCATAAGGAGATCTAATAATAGTTTCTTTA
GTAGATTAAATTGGTTGACCCACTTAAACTTCAAATACCCAGCATTGAACGTGACTATGCCAAACAATGAACAATTTGACAAATTG
TACATTTGGGGGGTTCACCACCCGGGTACGGACAAGGACCAAATCTTCCTGTATGCTCAATCATCAGGAAGAATCACAGTATCTAC
CAAAAGAAGCCAACAAGCTGTAATCCCGAATATCGGATCTAGACCCAGAATAAGGAATATCCCTAGCAGAATAAGCATCTATTGG
ACAATAGTAAAACCGGGAGACATACTTTTGATTAACAGCACAGGGAATCTAATTGCTCCTAGGGGTTACTTCAAAATACGAAGTG
GGAAAAGCTCAATAATGAGATCAGATGCACCCATTGGCAAATGCAATTCTGAATGCATCACTCCAAATGGAAGCATTCCCAATGA
CAAACCATTCCAAAATGTAAACAGGATCACATACGGGGCCTGTCCCAGATATGTTAAGCAAAGCACTCTGAAATTGGCAACAGGA
ATGCGAAATGTACCAGGCGGAGGTTGGGAGGGAATGGTGGATGGTTGGTACGGTTTCAGGCATCAAAATTCTGAGGGAAGAGG
ACAAGCAGCAGATCTCAAAAGCACTCAAGCAGCAATCGATCAAATCAATGGGAAGCTGAATCGATTGATCGGGAAAACCAACGA
GAAATTCCATCAGATTGAAAAAGAATTCTCAGAAGTCGAAGGGAGAATTCAGGACCTTGAGAAATATGTTGAGGACACTAAAATA
GATCTCTGGTCATACAACGCGGAGCTTCTTGTTGCCCTGGAGAACCAACATACAATTGATCTAACTGACTCAGAAATGAACAAACT
GTTTGAAAAAACAAAGAAGCAACTAAGGGAAAATGCTGAGGATATGGGCAATGGTTGTTTCAAAATATACCACAAATGTGACAAT
GCCTGCATAGGATCAATCAGAAATGGAACTTATGACCACGATGTATACAGAGATGAAGCATTAAACAACCGGTTCCAGATCAAGG
GAGTTGAGCTGAAGTCAGGGTACAAAGATTGGATCCTATGGATTTCCTTTGCCATATCATGTTTTTTGCTTTGTGTTGCTTTGTTGG
GGTTCATCATGTGGGCCTGCCAAAAGGGCAACATTAGGTGCAACATTTGCATTTGA

Figure 53B, SEQ ID NO: 145

H3V36111(Prl-).r

CCCTCCCAACCTCCGCCTGGTACATTTCGCATTCCTGTTGCCAATTTC

Figure 53C, SEQ ID NO: 146

H3V36111(Prl-).c

AATGTACCAGGCGGAGGTTGGGAGGGAATGGTGGATGGTTGGTACGGT

Figure 53D, SEQ ID NO: 147

Amino acid sequence of PDISP/H3 Victoria with deleted proteolytic loop

MAKNVAIFGLLFSLLVLVPSQIFAQKLPGNDNSTATLCLGHHAVPNGTIVKTITNDQIEVTNATELVQNSSIGEICDSPHQILDGENCTLID
ALLGDPQCDGFQNKKWDLFVERSKAYSNCYPYDVPDYASLRSLVASSGTLEFNNESFNWTGVTQNGTSSACIRRSNNSFFSRLNWLTH
LNFKYPALNVTMPNNEQFDKLYIWGVHHPGTDKDQIFLYAQSSGRITVSTKRSQQAVIPNIGSRPRIRNIPSRISIYWTIVKPGDILLINST
GNLIAPRGYFKIRSGKSSIMRSDAPIGKCNSECITPNGSIPNDKPFQNVNRITYGACPRYVKQSTLKLATGMRNVPGGGWEGMVDGWY
GFRHQNSEGRGQAADLKSTQAAIDQINGKLNRLIGKTNEKFHQIEKEFSEVEGRIQDLEKYVEDTKIDLWSYNAELLVALENQHTIDLTDS
EMNKLFEKTKKQLRENAEDMGNGCFKIYHKCDNACIGSIRNGTYDHDVYRDEALNNRFQIKGVELKSGYKDWILWISFAISCFLLCVALL
GFIMWACQKGNIRCNICI*

Schematic representation of construct number 2230

Schematic representation of construct number 2250

Figure 54

2X35S/CPMV HT+/PDISP/H7 Hangzhou/NOS (Construct no 2142)

Figure 54A, SEQ ID NO: 148

Nucleotide sequence of PDISP/H7 Hangzhou

ATGGCGAAAAACGTTGCGATTTTCGGCTTATTGTTTTCTCTTCTTGTGTTGGTTCCTTCTCAGATCTTCGCGGACAAAATCTGCCTCG
GACATCATGCCGTGTCAAACGGAACCAAAGTAAACACATTAACTGAAAGAGGAGTGGAAGTCGTCAATGCAACTGAAACAGTGG
AACGAACAAACATCCCCAGGATCTGCTCAAAAGGGAAAAGGACAGTTGACCTCGGTCAATGTGGACTCCTGGGGACAATCACTG
GACCACCTCAATGTGACCAATTCCTAGAATTTTCAGCCGATTTAATTATTGAGAGGCGAGAAGGAAGTGATGTCTGTTATCCTGGG
AAATTCGTGAATGAAGAAGCTCTGAGGCAAATTCTCAGAGAATCAGGCGGAATTGACAAGGAAGCAATGGGATTCACATACAGT
GGAATAAGAACTAATGGAGCAACCAGTGCATGTAGGAGATCAGGATCTTCATTCTATGCAGAAATGAAATGGCTCCTGTCAAACA
CAGATAATGCTGCATTCCCGCAGATGACTAAGTCATATAAAAATACAAGAAAAAGCCCAGCTCTAATAGTATGGGGGATCCATCA
TTCCGTATCAACTGCAGAGCAAACCAAGCTATATGGGAGTGGAAACAAACTGGTGACAGTTGGGAGTTCTAATTATCAACAATCT
TTTGTACCGAGTCCAGGAGCGAGACCACAAGTTAATGGTATATCTGGAAGAATTGACTTTCATTGGCTAATGCTAAATCCCAATGA
TACAGTCACTTTCAGTTTCAATGGGGCTTTCATAGCTCCAGACCGTGCAAGCTTCCTGAGAGGAAAATCTATGGGAATCCAGAGTG
GAGTACAGGTTGATGCCAATTGTGAAGGGGACTGCTATCATAGTGGAGGGACAATAATAAGTAACTTGCCATTTCAGAACATAGA
TAGCAGGGCAGTTGGAAAATGTCCGAGATATGTTAAGCAAAGGAGTCTGCTGCTAGCAACAGGGATGAAGAATGTTCCTGAGAT
TCCAAAGGGAAGAGGCCTATTTGGTGCTATAGCGGGTTTCATTGAAAATGGATGGGAAGGCCTAATTGATGGTTGGTATGGTTTC
AGACACCAGAATGCACAGGGAGAGGGAACTGCTGCAGATTACAAAAGCACTCAATCGGCAATTGATCAAATAACAGGAAAATTA
AACCGGCTTATAGAAAAAACCAACCAACAATTTGAGTTGATCGACAATGAATTCAATGAGGTAGAGAAGCAAATCGGTAATGTGA
TAAATTGGACCAGAGATTCTATAACAGAAGTGTGGTCATACAATGCTGAACTCTTGGTAGCAATGGAGAACCAGCATACAATTGA
TCTGGCTGATTCAGAAATGGACAAACTGTACGAACGAGTGAAAAGACAGCTGAGAGAGAATGCTGAAGAAGATGGCACTGGTTG
CTTTGAAATATTTCACAAGTGTGATGATGACTGTATGGCCAGTATTAGAAATAACACCTATGATCACAGCAAATACAGGGAAGAG
GCAATGCAAAATAGAATACAGATTGACCCAGTCAAACTAAGCAGCGGCTACAAAGATGTGATACTTTGGTTTAGCTTCGGGGCAT
CATGTTTCATACTTCTAGCCATTGTAATGGGCCTTGTCTTCATATGTGTAAAGAATGGAAACATGCGGTGCACTATTTGTATATAA

Figure 54B, SEQ ID NO: 149

IF*-H7H113.s1-6r

ACTAAAGAAAATAGGCCTTTATATACAAATAGTGCACCGCATGTTTCCAT

Figure 54C, SEQ ID NO: 150

Amino acid sequence of PDISP/H7 Hangzhou

MAKNVAIFGLLFSLLVLVPSQIFADKICLGHHAVSNGTKVNTLTERGVEVVNATETVERTNIPRICSKGKRTVDLGQCGLLGTITGPPQCD
QFLEFSADLIIERREGSDVCYPGKFVNEEALRQILRESGGIDKEAMGFTYSGIRTNGATSACRRSGSSFYAEMKWLLSNTDNAAFPQMTK
SYKNTRKSPALIVWGIHHSVSTAEQTKLYGSGNKLVTVGSSNYQQSFVPSPGARPQVNGISGRIDFHWLMLNPNDTVTFSFNGAFIAPD
RASFLRGKSMGIQSGVQVDANCEGDCYHSGGTIISNLPFQNIDSRAVGKCPRYVKQRSLLLATGMKNVPEIPKGRGLFGAIAGFIENGW
EGLIDGWYGFRHQNAQGEGTAADYKSTQSAIDQITGKLNRLIEKTNQQFELIDNEFNEVEKQIGNVINWTRDSITEVWSYNAELLVAME
NQHTIDLADSEMDKLYERVKRQLRENAEEDGTGCFEIFHKCDDDCMASIRNNTYDHSKYREEAMQNRIQIDPVKLSSGYKDVILWFSFG
ASCFILLAIVMGLVFICVKNGNMRCTICI*

Figure 54D

Schematic representation of construct number 2142

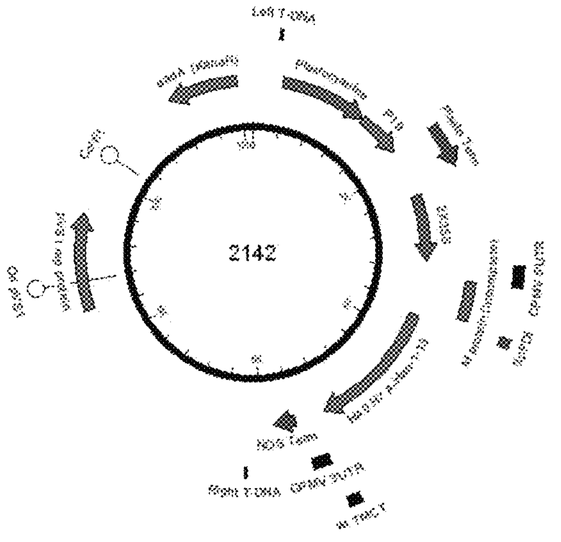

Figure 55

2X35S/CPMV HT+/PDISP/H7 Hangzhou with deleted proteolytic loop/NOS (Construct no 2152)

Figure 55A, SEQ ID NO: 151

Nucleotide sequence of PDISP/H7 Hangzhou with deleted proteolytic loop

ATGGCGAAAAACGTTGCGATTTTCGGCTTATTGTTTTCTCTTCTTGTGTTGGTTCCTTCTCAGATCTTCGCGGACAAAATCTGCCTCG
GACATCATGCCGTGTCAAACGGAACCAAAGTAAACACATTAACTGAAAGAGGAGTGGAAGTCGTCAATGCAACTGAAACAGTGG
AACGAACAAACATCCCCAGGATCTGCTCAAAAGGGAAAAGGACAGTTGACCTCGGTCAATGTGGACTCCTGGGGACAATCACTG
GACCACCTCAATGTGACCAATTCCTAGAATTTTCAGCCGATTTAATTATTGAGAGGCGAGAAGGAAGTGATGTCTGTTATCCTGGG
AAATTCGTGAATGAAGAAGCTCTGAGGCAAATTCTCAGAGAATCAGGCGGAATTGACAAGGAAGCAATGGGATTCACATACAGT
GGAATAAGAACTAATGGAGCAACCAGTGCATGTAGGAGATCAGGATCTTCATTCTATGCAGAAATGAAATGGCTCCTGTCAAACA
CAGATAATGCTGCATTCCCGCAGATGACTAAGTCATATAAAAATACAAGAAAAAGCCCAGCTCTAATAGTATGGGGGATCCATCA
TTCCGTATCAACTGCAGAGCAAACCAAGCTATATGGGAGTGGAAACAAACTGGTGACAGTTGGGAGTTCTAATTATCAACAATCT
TTTGTACCGAGTCCAGGAGCGAGACCACAAGTTAATGGTATATCTGGAAGAATTGACTTTCATTGGCTAATGCTAAATCCCAATGA
TACAGTCACTTTCAGTTTCAATGGGGCTTTCATAGCTCCAGACCGTGCAAGCTTCCTGAGAGGAAAATCTATGGGAATCCAGAGTG
GAGTACAGGTTGATGCCAATTGTGAAGGGGACTGCTATCATAGTGGAGGGACAATAATAAGTAACTTGCCATTTCAGAACATAGA
TAGCAGGGCAGTTGGAAAATGTCCGAGATATGTTAAGCAAAGGAGTCTGCTGCTAGCAACAGGGATGAAGAATGTTCCTGGCGG
ATGGGAAGGCCTAATTGATGGTTGGTATGGTTTCAGACACCAGAATGCACAGGGAGAGGGAACTGCTGCAGATTACAAAAGCAC
TCAATCGGCAATTGATCAAATAACAGGAAAATTAAACCGGCTTATAGAAAAAACCAACCAACAATTTGAGTTGATCGACAATGAA
TTCAATGAGGTAGAGAAGCAAATCGGTAATGTGATAAATTGGACCAGAGATTCTATAACAGAAGTGTGGTCATACAATGCTGAAC
TCTTGGTAGCAATGGAGAACCAGCATACAATTGATCTGGCTGATTCAGAAATGGACAAACTGTACGAACGAGTGAAAAGACAGCT
GAGAGAGAATGCTGAAGAAGATGGCACTGGTTGCTTTGAAATATTTCACAAGTGTGATGATGACTGTATGGCCAGTATTAGAAAT
AACACCTATGATCACAGCAAATACAGGGAAGAGGCAATGCAAAATAGAATACAGATTGACCCAGTCAAACTAAGCAGCGGCTAC
AAAGATGTGATACTTTGGTTTAGCTTCGGGGCATCATGTTTCATACTTCTAGCCATTGTAATGGGCCTTGTCTTCATATGTGTAAAG
AATGGAAACATGCGGTGCACTATTTGTATATAA

Figure 55B, SEQ ID NO: 152

H7H113(PrL-).r

CCTTCCCATCCGCCAGGAACATTCTTCATCCCTGTTGCTAGCAGCAGAC

Figure 55C, SEQ ID NO: 153

H7H113(PrL-).c

AGAATGTTCCTGGCGGATGGGAAGGCCTAATTGATGGTTGGTATGGTT

Figure 55D, SEQ ID NO: 154

Amino acid sequence of PDISP/H7 Hangzhou with deleted proteolytic loop

MAKNVAIFGLLFSLLVLVPSQIFADKICLGHHAVSNGTKVNTLTERGVEVVNATETVERTNIPRICSKGKRTVDLGQCGLLGTITGPPQCDQFLEFSADLIIERRE
GSDVCYPGKFVNEEALRQILRESGGIDKEAMGFTYSGIRTNGATSACRRSGSSFYAEMKWLLSNTDNAAFPQMTKSYKNTRKSPALIVWGIHHSVSTAEQTKL
YGSGNKLVTVGSSNYQQSFVPSPGARPQVNGISGRIDFHWLMLNPNDTVTFSFNGAFIAPDRASFLRGKSMGIQSGVQVDANCEGDCYHSGGTIISNLPFQ
NIDSRAVGKCPRYVKQRSLLLATGMKNVPGGWEGLIDGWYGFRHQNAQGEGTAADYKSTQSAIDQITGKLNRLIEKTNQQFELIDNEFNEVEKQIGNVINW
TRDSITEVWSYNAELLVAMENQHTIDLADSEMDKLYERVKRQLRENAEEDGTGCFEIFHKCDDDCMASIRNNTYDHSKYREEAMQNRIQIDPVKLSSGYKDV
ILWFSFGASCFILLAIVMGLVFICVKNGNMRCTICI*

Schematic representation of construct number 2152

Figure 56

2X35S/CPMV HT+ (construct no 2224) and 160+ (construct no 2226) for PDISP/H9 Hong Kong

Figure 56A, SEQ ID NO: 155

Nucleotide sequence of PDISP/H9 Hong Kong

ATGGCGAAAAACGTTGCGATTTTCGGCTTATTGTTTTCTCTTCTTGTGTTGGTTCCTTCTCAGATCTTCGCGGATAAAATCTGCATCG
GCCACCAGTCAACAAACTCCACAGAAACTGTGGACACGCTAACAGAAACCAATGTTCCTGTGACACATGCCAAAGAATTGCTCCAC
ACAGAGCATAATGGAATGCTGTGTGCAACAAGCCTGGGACATCCCCTCATTCTAGACACATGCACTATTGAAGGACTAGTCTATG
GCAACCCTTCTTGTGACCTGCTGTTGGGAGGAAGAGAATGGTCCTACATCGTCGAAAGATCATCAGCTGTAAATGGAACGTGTTA
CCCTGGGAATGTAGAAAACCTAGAGGAACTCAGGACACTTTTTAGTTCCGCTAGTTCCTACCAAAGAATCCAAATCTTCCCAGACA
CAACCTGGAATGTGACTTACACTGGAACAAGCAGAGCATGTTCAGGTTCATTCTACAGGAGTATGAGATGGCTGACTCAAAAGAG
CGGTTTTTACCCTGTTCAAGACGCCCAATACACAAATAACAGGGGAAAGAGCATTCTTTTCGTGTGGGGCATACATCACCCACCCA
CCTATACCGAGCAAACAAATTTGTACATAAGAAACGACACAACAACAAGCGTGACAACAGAAGATTTGAATAGGACCTTCAAACC
AGTGATAGGGCCAAGGCCCCTTGTCAATGGTCTGCAGGGAAGAATTGATTATTATTGGTCGGTACTAAAACCAGGCCAAACATTG
CGAGTACGATCCAATGGGAATCTAATTGCTCCATGGTATGGACACGTTCTTTCAGGAGGGAGCCATGGAAGAATCCTGAAGACTG
ATTTAAAAGGTGGTAATTGTGTAGTGCAATGTCAGACTGAAAAAGGTGGCTTAAACAGTACATTGCCATTCCACAATATCAGTAAA
TATGCATTTGGAACCTGCCCCAAATATGTAAGAGTTAATAGTCTCAAACTGGCAGTCGGTCTGAGGAACGTGCCTGCTAGATCAA
GTAGAGGACTATTTGGAGCCATAGCTGGATTCATAGAAGGAGGTTGGCCAGGACTAGTCGCTGGCTGGTATGGTTTCCAGCATTC
AAATGATCAAGGGGTTGGTATGGCTGCAGATAGGGATTCAACTCAAAAGGCAATTGATAAAATAACATCCAAGGTGAATAATATA
GTCGACAAGATGAACAAGCAATATGAAATAATTGATCATGAATTTAGTGAGGTTGAAACTAGACTCAATATGATCAATAATAAGA
TTGATGACCAAATACAAGACGTATGGGCATATAATGCAGAATTGCTAGTACTACTTGAAAATCAAAAAACACTCGATGAGCATGA
TGCGAACGTGAACAATCTATATAACAAGGTGAAGAGGGCACTGGGCTCCAATGCTATGGAAGATGGGAAAGGCTGTTTCGAGCT
ATACCATAAATGTGATGATCAGTGCATGGAAACAATTCGGAACGGGACCTATAATAGGAGAAAGTATAGAGAGGAATCAAGACT
AGAAAGGCAGAAAATAGAGGGGGTTAAGCTGGAATCTGAGGGAACTTACAAAATCCTCACCATTTATTCGACTGTCGCCTCATCT
CTTGTGCTTGCAATGGGGTTTGCTGCCTTCCTGTTCTGGGCCATGTCCAATGGATCTTGCAGATGCAACATTTGTATATAA

Figure 56B, SEQ ID NO: 156

IF**-H9HK107399.S1-6r

ACTAAAGAAAATAGGCCTTTATATACAAATGTTGCATCTGCAAGATCCAT

Figure 56C, SEQ ID NO: 157

Amino acid sequence of PDISP/H9 Hong Kong

MAKNVAIFGLLFSLLVLVPSQIFADKICIGHQSTNSTETVDTLTETNVPVTHAKELLHTEHNGMLCATSLGHPLILDTCTIEGLVYGNPSCD
LLLGGREWSYIVERSSAVNGTCYPGNVENLEELRTLFSSASSYQRIQIFPDTTWNVTYTGTSRACSGSFYRSMRWLTQKSGFYPVQDAQ
YTNNRGKSILFVWGIHHPPTYTEQTNLYIRNDTTTSVTTEDLNRTFKPVIGPRPLVNGLQGRIDYYWSVLKPGQTLRVRSNGNLIAPWYG
HVLSGGSHGRILKTDLKGGNCVVQCQTEKGGLNSTLPFHNISKYAFGTCPKYVRVNSLKLAVGLRNVPARSSRGLFGAIAGFIEGGWPGL
VAGWYGFQHSNDQGVGMAADRDSTQKAIDKITSKVNNIVDKMNKQYEIIDHEFSEVETRLNMINNKIDDQIQDVWAYNAELLVLLEN
QKTLDEHDANVNNLYNKVKRALGSNAMEDGKGCFELYHKCDDQCMETIRNGTYNRRKYREESRLERQKIEGVKLESEGTYKILTIYSTVA
SSLVLAMGFAAFLFWAMSNGSCRCNICI*

Schematic representation of construct number 2224

Schematic representation of construct number 2226

Figure 57

2X35S/CPMV HT+ (construct no 2225) and 160+ (construct no 2227) for PDISP/H9 Hong Kong with deleted proteolytic loop

Figure 57A, SEQ ID NO: 158

Nucleotide sequence of PDISP/H9 Hong Kong with deleted proteolytic loop

ATGGCGAAAAACGTTGCGATTTTCGGCTTATTGTTTTCTCTTCTTGTGTTGGTTCCTTCTCAGATCTTCGCGGATAAAATCTGCATCG
GCCACCAGTCAACAAACTCCACAGAAACTGTGGACACGCTAACAGAAACCAATGTTCCTGTGACACATGCCAAAGAATTGCTCCAC
ACAGAGCATAATGGAATGCTGTGTGCAACAAGCCTGGGACATCCCCTCATTCTAGACACATGCACTATTGAAGGACTAGTCTATG
GCAACCCTTCTTGTGACCTGCTGTTGGGAGGAAGAGAATGGTCCTACATCGTCGAAAGATCATCAGCTGTAAATGGAACGTGTTA
CCCTGGGAATGTAGAAAACCTAGAGGAACTCAGGACACTTTTTAGTTCCGCTAGTTCCTACCAAAGAATCCAAATCTTCCCAGACA
CAACCTGGAATGTGACTTACACTGGAACAAGCAGAGCATGTTCAGGTTCATTCTACAGGAGTATGAGATGGCTGACTCAAAAGAG
CGGTTTTTACCCTGTTCAAGACGCCCAATACACAAATAACAGGGGAAAGAGCATTCTTTTCGTGTGGGGCATACATCACCCACCCA
CCTATACCGAGCAAACAAATTTGTACATAAGAAACGACACAACAACAAGCGTGACAACAGAAGATTTGAATAGGACCTTCAAACC
AGTGATAGGGCCAAGGCCCCTTGTCAATGGTCTGCAGGGAAGAATTGATTATTATTGGTCGGTACTAAAACCAGGCCAAACATTG
CGAGTACGATCCAATGGGAATCTAATTGCTCCATGGTATGGACACGTTCTTTCAGGAGGGAGCCATGGAAGAATCCTGAAGACTG
ATTTAAAAGGTGGTAATTGTGTAGTGCAATGTCAGACTGAAAAAGGTGGCTTAAACAGTACATTGCCATTCCACAATATCAGTAAA
TATGCATTTGGAACCTGCCCCAAATATGTAAGAGTTAATAGTCTCAAACTGGCAGTCGGTCTGAGGAACGTGCCTGGCGGAGGTT
GGCCAGGACTAGTCGCTGGCTGGTATGGTTTCCAGCATTCAAATGATCAAGGGGTTGGTATGGCTGCAGATAGGGATTCAACTCA
AAAGGCAATTGATAAAATAACATCCAAGGTGAATAATATAGTCGACAAGATGAACAAGCAATATGAAATAATTGATCATGAATTT
AGTGAGGTTGAAACTAGACTCAATATGATCAATAATAAGATTGATGACCAAATACAAGACGTATGGGCATATAATGCAGAATTGC
TAGTACTACTTGAAAATCAAAAAACACTCGATGAGCATGATGCGAACGTGAACAATCTATATAACAAGGTGAAGAGGGCACTGG
GCTCCAATGCTATGGAAGATGGGAAAGGCTGTTTCGAGCTATACCATAAATGTGATGATCAGTGCATGGAAACAATTCGGAACGG
GACCTATAATAGGAGAAAGTATAGAGAGGAATCAAGACTAGAAAGGCAGAAAATAGAGGGGGTTAAGCTGGAATCTGAGGGAA
CTTACAAAATCCTCACCATTTATTCGACTGTCGCCTCATCTCTTGTGCTTGCAATGGGGTTTGCTGCCTTCCTGTTCTGGGCCATGTC
CAATGGATCTTGCAGATGCAACATTTGTATATAA

Figure 57B, SEQ ID NO: 159

H9HK107399(Prl-).r

GTCCTGGCCAACCTCCGCCAGGCACGTTCCTCAGACCGACTGCCAGTT

Figure 57C, SEQ ID NO: 160

H9HK107399(Prl-).c

GGAACGTGCCTGGCGGAGGTTGGCCAGGACTAGTCGCTGGCTGGTATG

Figure 57D, SEQ ID NO: 161

Amino acid sequence of PDISP/H9 Hong Kong with deleted proteolytic loop

MAKNVAIFGLLFSLLVLVPSQIFADKICIGHQSTNSTETVDTLTETNVPVTHAKELLHTEHNGMLCATSLGHPLILDTCTIEGLVYGNPSCD
LLLGGREWSYIVERSSAVNGTCYPGNVENLEELRTLFSSASSYQRIQIFPDTTWNVTYTGTSRACSGSFYRSMRWLTQKSGFYPVQDAQ
YTNNRGKSILFVWGIHHPPTYTEQTNLYIRNDTTTSVTTEDLNRTFKPVIGPRPLVNGLQGRIDYYWSVLKPGQTLRVRSNGNLIAPWYG
HVLSGGSHGRILKTDLKGGNCVVQCQTEKGGLNSTLPFHNISKYAFGTCPKYVRVNSLKLAVGLRNVPGGGWPGLVAGWYGFQHSND
QGVGMAADRDSTQKAIDKITSKVNNIVDKMNKQYEIIDHEFSEVETRLNMINNKIDDQIQDVWAYNAELLVLLENQKTLDEHDANVN
NLYNKVKRALGSNAMEDGKGCFELYHKCDDQCMETIRNGTYNRRKYREESRLERQKIEGVKLESEGTYKILTIYSTVASSLVLAMGFAAF
LFWAMSNGSCRCNICI*

Schematic representation of construct number 2225

Schematic representation of construct number 2227

Figure 58

2X35S/CPMV 160+/PDISP/HA B Malaysia/NOS (Construct no 2013)

Figure 58A, SEQ ID NO: 162

Nucleotide sequence of PDISP/HA B Malaysia

ATGGCGAAAAACGTTGCGATTTTCGGCTTATTGTTTTCTCTTCTTGTGTTGGTTCCTTCTCAGATCTTCGCGGATCGAATCTGCACTG
GGATAACATCGTCAAACTCACCACATGTTGTCAAAACTGCTACTCAAGGGGAGGTCAATGTGACTGGTGTAATACCACTGACAAC
AACACCCACCAAATCTCATTTTGCAAATCTCAAAGGAACAGAAACCAGAGGGAAACTATGCCCAAAATGCCTCAACTGCACAGATC
TGGACGTGGCCTTGGGCAGACCAAAATGCACGGGGAACATACCCTCGGCAAGAGTTTCAATACTCCATGAAGTCAGACCTGTTAC
ATCTGGGTGCTTTCCTATAATGCACGACAGAACAAAAATTAGACAGCTGCCTAAACTTCTCAGAGGATACGAACATATCAGGTTAT
CAACTCATAACGTTATCAATGCAGAAAATGCACCAGGAGGACCCTACAAAATTGGAACCTCAGGGTCTTGCCCTAACGTTACCAAT
GGAAACGGATTTTTCGCAACAATGGCTTGGGCCGTCCCAAAAAACGACAACAACAAAACAGCAACAAATTCATTAACAATAGAAG
TACCATACATTTGTACAGAAGGAGAAGACCAAATTACCGTTTGGGGGTTCCACTCTGATAACGAAACCCAAATGGCAAAGCTCTAT
GGGGACTCAAAGCCCCAGAAGTTCACCTCATCTGCCAACGGAGTGACCACACATTACGTTTCACAGATTGGTGGCTTCCCAAATCA
AACAGAAGACGGAGGACTACCACAAAGCGGTAGAATTGTTGTTGATTACATGGTGCAAAAATCTGGGAAAACAGGAACAATTAC
CTATCAAAGAGGTATTTTATTGCCTCAAAAAGTGTGGTGCGCAAGTGGCAGGAGCAAGGTAATAAAAGGATCGTTGCCTTTAATT
GGAGAAGCAGATTGCCTCCACGAAAAATACGGTGGATTAAACAAAAGCAAGCCTTACTACACAGGGGAACATGCAAAGGCCATA
GGAAATTGCCCAATATGGGTGAAAACACCCTTGAAGCTGGCCAATGGAACCAAATATAGACCTCCTGCAAAACTATTAAAGGAAA
GGGGTTTCTTCGGAGCTATTGCTGGTTTCTTAGAAGGAGGATGGGAAGGAATGATTGCAGGTTGGCACGGATACACATCCCATG
GGGCACATGGAGTAGCGGTGGCAGCAGACCTTAAGAGCACTCAAGAGGCCATAAACAAGATAACAAAAAATCTCAACTCTTTGA
GTGAGCTGGAAGTAAAGAATCTTCAAAGACTAAGCGGTGCCATGGATGAACTCCACAACGAAATACTAGAACTAGACGAGAAAG
TGGATGATCTCAGAGCTGATACAATAAGCTCACAAATAGAACTCGCAGTCCTGCTTTCCAATGAAGGAATAATAAACAGTGAAGA
TGAGCATCTCTTGGCGCTTGAAAGAAAGCTGAAGAAAATGCTGGGCCCCTCTGCTGTAGAGATAGGGAATGGATGCTTTGAAACC
AAACACAAGTGCAACCAGACCTGTCTCGACAGAATAGCTGCTGGTACCTTTGATGCAGGAGAATTTTCTCTCCCCACTTTTGATTCA
CTGAATATTACTGCTGCATCTTTAAATGACGATGGATTGGATAATCATACTATACTGCTTTACTACTCAACTGCTGCCTCCAGTTTG
GCTGTAACATTGATGATAGCTATCTTTGTTGTTTATATGGTCTCCAGAGACAATGTTTCTTGCTCCATCTGTCTATAA

Figure 58B, SEQ ID NO: 163

IF**-HBM250604.S1-6r

ACTAAAGAAAATAGGCCTTTATAGACAGATGGAGCAAGAAACATTGTCTC

Figure 58C, SEQ ID NO: 164

Amino acid sequence of PDISP/HA B Malaysia

MAKNVAIFGLLFSLLVLVPSQIFADRICTGITSSNSPHVVKTATQGEVNVTGVIPLTTTPTKSHFANLKGTETRGKLCPKCLNCTDLDVALG
RPKCTGNIPSARVSILHEVRPVTSGCFPIMHDRTKIRQLPKLLRGYEHIRLSTHNVINAENAPGGPYKIGTSGSCPNVTNGNGFFATMAW
AVPKNDNNKTATNSLTIEVPYICTEGEDQITVWGFHSDNETQMAKLYGDSKPQKFTSSANGVTTHYVSQIGGFPNQTEDGGLPQSGRI
VVDYMVQKSGKTGTITYQRGILLPQKVWCASGRSKVIKGSLPLIGEADCLHEKYGGLNKSKPYYTGEHAKAIGNCPIWVKTPLKLANGTK
YRPPAKLLKERGFFGAIAGFLEGGWEGMIAGWHGYTSHGAHGVAVAADLKSTQEAINKITKNLNSLSELEVKNLQRLSGAMDELHNEIL
ELDEKVDDLRADTISSQIELAVLLSNEGIINSEDEHLLALERKLKKMLGPSAVEIGNGCFETKHKCNQTCLDRIAAGTFDAGEFSLPTFDSLN
ITAASLNDDGLDNHTILLYYSTAASSLAVTLMIAIFVVYMVSRDNVSCSICL*

Figure 58D

Schematic representation of construct number 2013

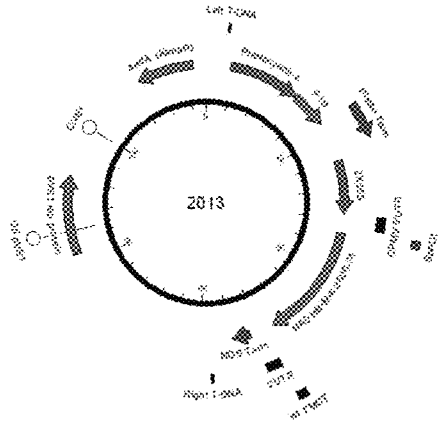

Figure 59

2X35S/CPMV 160+/PDISP/HA B Malaysia with deleted proteolytic loop/NOS (Construct no 2014)

Figure 59A, SEQ ID NO: 165

Nucleotide sequence of PDISP/HA B Malaysia with deleted proteolytic loop

ATGGCGAAAAACGTTGCGATTTTCGGCTTATTGTTTTCTCTTCTTGTGTTGGTTCCTTCTCAGATCTTCGCGGATCGAA
TCTGCACTGGGATAACATCGTCAAACTCACCACATGTTGTCAAAACTGCTACTCAAGGGGAGGTCAATGTGACTGGTGT
AATACCACTGACAACAACACCCACCAAATCTCATTTTGCAAATCTCAAAGGAACAGAAACCAGAGGGAAACTATGCCCA
AAATGCCTCAACTGCACAGATCTGGACGTGGCCTTGGGCAGACCAAAATGCACGGGGAACATACCCTCGGCAAGAGTTT
CAATACTCCATGAAGTCAGACCTGTTACATCTGGGTGCTTTCCTATAATGCACGACAGAACAAAAATTAGACAGCTGCC
TAAACTTCTCAGAGGATACGAACATATCAGGTTATCAACTCATAACGTTATCAATGCAGAAAATGCACCAGGAGGACCC
TACAAAATTGGAACCTCAGGGTCTTGCCCTAACGTTACCAATGGAAACGGATTTTTCGCAACAATGGCTTGGGCCGTCC
CAAAAAACGACAACAACAAAACAGCAACAAATTCATTAACAATAGAAGTACCATACATTTGTACAGAAGGAGAAGACCA
AATTACCGTTTGGGGGTTCCACTCTGATAACGAAACCCAAATGGCAAAGCTCTATGGGGACTCAAAGCCCCAGAAGTTC
ACCTCATCTGCCAACGGAGTGACCACACATTACGTTTCACAGATTGGTGGCTTCCCAAATCAAACAGAAGACGGAGGAC
TACCACAAAGCGGTAGAATTGTTGTTGATTACATGGTGCAAAAATCTGGGAAAACAGGAACAATTACCTATCAAAGAGG
TATTTTATTGCCTCAAAAAGTGTGGTGCGCAAGTGGCAGGAGCAAGGTAATAAAAGGATCGTTGCCTTTAATTGGAGAA
GCAGATTGCCTCCACGAAAAATACGGTGGATTAAACAAAAGCAAGCCTTACTACACAGGGGAACATGCAAAGGCCATAG
GAAATTGCCCAATATGGGTGAAAACACCCTTGAAGCTGGCCAATGGAACCAAATATAGACCTCCTGGTGGAGGATGGGA
AGGAATGATTGCAGGTTGGCACGGATACACATCCCATGGGGCACATGGAGTAGCGGTGGCAGCAGACCTTAAGAGCACT
CAAGAGGCCATAAACAAGATAACAAAAAATCTCAACTCTTTGAGTGAGCTGGAAGTAAAGAATCTTCAAAGACTAAGCG
GTGCCATGGATGAACTCCACAACGAAATACTAGAACTAGACGAGAAAGTGGATGATCTCAGAGCTGATACAATAAGCTC
ACAAATAGAACTCGCAGTCCTGCTTTCCAATGAAGGAATAATAAACAGTGAAGATGAGCATCTCTTGGCGCTTGAAAGA
AAGCTGAAGAAAATGCTGGGCCCCTCTGCTGTAGAGATAGGGAATGGATGCTTTGAAACCAAACACAAGTGCAACCAGA
CCTGTCTCGACAGAATAGCTGCTGGTACCTTTGATGCAGGAGAATTTTCTCTCCCCACTTTTGATTCACTGAATATTAC
TGCTGCATCTTTAAATGACGATGGATTGGATAATCATACTATACTGCTTTACTACTCAACTGCTGCCTCCAGTTTGGCT
GTAACATTGATGATAGCTATCTTTGTTGTTTATATGGTCTCCAGAGACAATGTTTCTTGCTCCATCTGTCTATAA

Figure 59B, SEQ ID NO: 166

HBM250604(PrL-).r

CATTCCTTCCCATCCTCCACCAGGAGGTCTATATTTGGTTCCATTGGC

Figure 59C, SEQ ID NO: 167

HBM250604(PrL-).c

AGACCTCCTGGTGGAGGATGGGAAGGAATGATTGCAGGTTGGCACGGA

Figure 59D, SEQ ID NO: 168

Amino acid sequence of PDISP/HA B Malaysia with deleted proteolytic loop

MAKNVAIFGLLFSLLVLVPSQIFADRICTGITSSNSPHVVKTATQGEVNVTGVIPLTTTPTKSHFANLKGTETRGKLCPKCLNCTDLDVALG
RPKCTGNIPSARVSILHEVRPVTSGCFPIMHDRTKIRQLPKLLRGYEHIRLSTHNVINAENAPGGPYKIGTSGSCPNVTNGNGFFATMAW
AVPKNDNNKTATNSLTIEVPYICTEGEDQITVWGFHSDNETQMAKLYGDSKPQKFTSSANGVTTHYVSQIGGFPNQTEDGGLPQSGRI
VVDYMVQKSGKTGTITYQRGILLPQKVWCASGRSKVIKGSLPLIGEADCLHEKYGGLNKSKPYYTGEHAKAIGNCPIWVKTPLKLANGTK
YRPPGGGWEGMIAGWHGYTSHGAHGVAVAADLKSTQEAINKITKNLNSLSELEVKNLQRLSGAMDELHNEILELDEKVDDLRADTISS
QIELAVLLSNEGIINSEDEHLLALERKLKKMLGPSAVEIGNGCFETKHKCNQTCLDRIAAGTFDAGEFSLPTFDSLNITAASLNDDGLDNHT
ILLYYSTAASSLAVTLMIAIFVVYMVSRDNVSCSICL*

Figure 59E

Schematic representation of construct number 2014

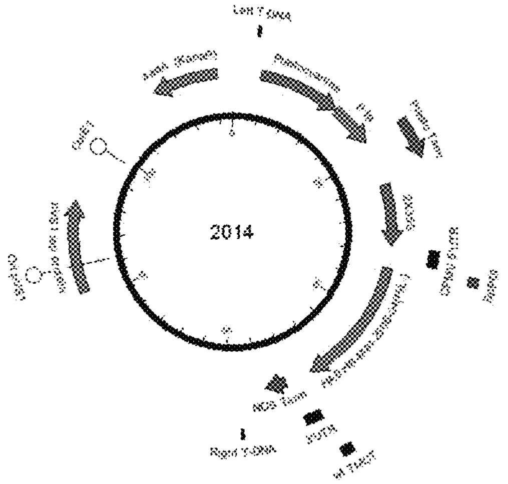

Figure 60

2X35S/CPMV HT (construct no 2070), HT+ (construct no 2080) and 160+ (-Mprot) (construct no 2090) for PDISP/HA B Massachusetts

Figure 60A, SEQ ID NO: 169

Nucleotide sequence of PDISP/HA B Massachusetts

ATGGCGAAAAACGTTGCGATTTTCGGCTTATTGTTTTCTCTTCTTGTGTTGGTTCCTTCTCAGATCTTCGCCGATCGAATCTGCACTG
GGATAACATCTTCAAACTCACCTCATGTGGTCAAAACAGCTACTCAAGGGGAGGTCAATGTGACTGGTGTGATACCACTAACAAC
AACACCAACAAAATCTTATTTTGCAAATCTCAAAGGAACAAAGACCAGAGGGAAACTATGCCCAGACTGTCTCAACTGTACAGATC
TGGATGTGGCCCTGGGCAGGCCAATGTGTGTGGGAACTACACCTTCTGCGAAAGCTTCAATACTTCACGAAGTCAGACCTGTTAC
ATCCGGGTGCTTCCCTATAATGCACGACAGAACAAAAATCAGGCAACTAGCCAATCTTCTCAGAGGATATGAAAATATCAGGTTAT

Figure 60A continued

CAACCCAAAACGTTATCGATGCAGAAAAGGCACCAGGAGGACCCTACAGACTTGGAACCTCAGGATCTTGCCCTAACGCTACCAGTAAAAGCGGATTT
TTCGCAACAATGGCTTGGGCTGTCCCAAAGGACAACAACAAAAATGCAACGAACCCATTAACAGTAGAAGTACCATACATTTGTGCAGAAGGGGAAGA
CCAAATTACTGTTTGGGGGTTCCATTCAGATAACAAAACCCAAATGAAGAACCTCTATGGAGACTCAAATCCTCAAAAGTTCACCTCATCTGCTAATGGA
GTAACCACACATTATGTTTCTCAGATTGGCGGCTTCCCAGATCAAACAGAAGACGGAGGACTACCACAAAGCGGCAGAATTGTCGTTGATTACATGAT
GCAAAAACCTGGGAAAACAGGAACAATTGTCTATCAAAGAGGTGTTTTGTTGCCTCAAAAGGTGTGGTGCGCGAGTGGCAGGAGCAAAGTAATAAAA
GGGTCCTTGCCTTTAATTGGTGAAGCAGATTGCCTTCATGAAAAATACGGTGGATTAAACAAAAGCAAGCCTTACTACACAGGAGAACATGCAAAAGC
CATAGGAAATTGCCCAATATGGGTGAAAACACCTTTGAAGCTTGCCAATGGAACCAAATATAGACCTCCTGCAAAACTATTAAAGGAAAGGGGTTTCTT
CGGAGCTATTGCTGGTTTCCTAGAAGGAGGATGGGAAGGAATGATTGCAGGTTGGCACGGATACACATCTCACGGAGCACATGGAGTGGCAGTTGCT
GCAGACCTTAAGAGCACACAAGAAGCTATAAACAAGATAACAAAAAATCTCAACTCTTTGAGTGAGCTAGAAGTAAAGAATCTTCAAAGGCTAAGTGG
TGCCATGGATGAACTCCACAACGAAATACTCGAGCTGGATGAGAAAGTGGATGACCTCAGAGCTGACACTATAAGTTCACAAATAGAACTTGCAGTCT
TGCTTTCCAACGAAGGAATAATAAACAGTGAAGACGAGCATCTATTGGCACTTGAGAGAAAACTAAAGAAAATGCTGGGTCCCTCTGCTGTAGACATA
GGAAATGGATGCTTCGAAACCAAACACAAATGCAACCAGACCTGCTTAGACAGGATAGCTGCTGGCACCTTTAATGCAGGAGAGTTTTCTCTCCCCACT
TTTGATTCATTGAACATTACTGCTGCATCTTTAAATGATGATGGATTGGATAACCATACTATACTGCTCTATTACTCAACTGCTGCTTCTAGTTTGGCTGT
AACATTGATGCTAGCTATTTTTATTGTTTATATGGTCTCCAGAGACAACGTTTCATGCTCCATCTGTCTATAA

Figure 60B, SEQ ID NO: 170

Amino acid sequence of PDISP/HA B Massachusetts

MAKNVAIFGLLFSLLVLVPSQIFADRICTGITSSNSPHVVKTATQGEVNVTGVIPLTTTPTKSYFANLKGTKTRGKLCPDCLNCTDLDVALGRPMCVGTTPSAKA
SILHEVRPVTSGCFPIMHDRTKIRQLANLLRGYENIRLSTQNVIDAEKAPGGPYRLGTSGSCPNATSKSGFFATMAWAVPKDNNKNATNPLTVEVPYICAEGE
DQITVWGFHSDNKTQMKNLYGDSNPQKFTSSANGVTTHYVSQIGGFPDQTEDGGLPQSGRIVVDYMMQKPGKTGTIVYQRGVLLPQKVWCASGRSKVIK
GSLPLIGEADCLHEKYGGLNKSKPYYTGEHAKAIGNCPIWVKTPLKLANGTKYRPPAKLLKERGFFGAIAGFLEGGWEGMIAGWHGYTSHGAHGVAVAADLK
STQEAINKITKNLNSLSELEVKNLQRLSGAMDELHNEILELDEKVDDLRADTISSQIELAVLLSNEGIINSEDEHLLALERKLKKMLGPSAVDIGNGCFETKHKCNQ
TCLDRIAAGTFNAGEFSLPTFDSLNITAASLNDDGLDNHTILLYYSTAASSLAVTLMLAIFIVYMVSRDNVSCSICL*

Schematic representation of construct number 2070

Schematic representation of construct number 2080

Schematic representation of construct number 2090

Figure 61

2X35S/CPMV HT+/ PDISP/B Florida with proteolytic loop deleted/ NOS (Construct number 2102) and 2X35S/CPMV HT+/ BeYDV/PDISP/B Florida with proteolytic loop deleted/ NOS (Construct number 2104)

Fig 61A SEQ ID NO: 190

HBF406(PrL-).r (construct 2102 and 2104)

TCCTTCCCATCCTCCACCAGGAGGTCTATATTTGGTTCCATTGGCGAGCTTCAAAG

Fig 61B SEQ ID NO: 191

HBF406(PrL-).c (construct 2102 and 2104)

ATATAGACCTCCTGGTGGAGGATGGGAAGGAATGATTGCAGGCTGGCACGGA

Fig 61C SEQ ID NO: 192

IF*-HBF406.s1-6r (construct 2102 and 2104)

ACTAAAGAAAATAGGCCTTTATAGACAGATGGAGCATGAAACGTTGTCTC

Fig 61D SEQ ID NO: 193

Nucleotide sequence of PDISP/HA B Florida with deleted proteolytic loop (construct 2102 and 2104)

ATGGCGAAAAACGTTGCGATTTTCGGCTTATTGTTTTCTCTTCTTGTGTTGGTTCCTTCTCAGATCTTCGCGGATCGAA
TCTGCACTGGAATAACATCTTCAAACTCACCTCATGTGGTCAAAACAGCCACTCAAGGGGAGGTCAATGTGACTGGTGT
GATACCACTAACAACAACACCAACAAAATCTTATTTTGCAAATCTCAAAGGAACAAGGACCAGAGGGAAACTATGCCCA
GACTGTCTCAACTGCACAGATCTGGATGTGGCTTTGGGCAGACCAATGTGTGTGGGGACCACACCTTCGGCGAAGGCTT
CAATACTCCACGAAGTCAAACCTGTTACATCCGGGTGCTTTCCTATAATGCACGACAGAACAAAAATCAGGCAACTACC
CAATCTTCTCAGAGGATATGAAAATATCAGGCTATCAACCCAAAACGTCATCGATGCGGAAAAGGCACCAGGAGGACCC
TACAGACTTGGAACCTCAGGATCTTGCCCTAACGCTACCAGTAAGAGCGGATTTTTCGCAACAATGGCTTGGGCTGTCC
CAAAGGACAACAACAAAAATGCAACGAACCCACTAACAGTAGAAGTACCATACATTTGTACAGAAGGGGAAGACCAAAT
CACTGTTTGGGGGTTCCATTCAGATAACAAAACCCAAATGAAGAACCTCTATGGAGACTCAAATCCTCAAAAGTTCACC
TCATCTGCTAATGGAGTAACCACACACTATGTTTCTCAGATTGGCAGCTTCCCAGATCAAACAGAAGACGGAGGACTAC
CACAAAGCGGCAGGATTGTTGTTGATTACATGATGCAAAAACCTGGGAAAACAGGAACAATTGTCTACCAAAGAGGTGT
TTTGTTGCCTCAAAAGGTGTGGTGCGCGAGTGGCAGGAGCAAAGTAATAAAAGGGTCCTTGCCTTTAATTGGTGAAGCA
GATTGCCTTCATGAAAAATACGGTGGATTAAACAAAAGCAAGCCTTACTACACAGGAGAACATGCAAAAGCCATAGGAA
ATTGCCCAATATGGGTGAAAACACCTTTGAAGCTCGCCAATGGAACCAAATATAGACCTCCTGGTGGAGGATGGGAAGG
AATGATTGCAGGCTGGCACGGATACACATCTCACGGAGCACATGGAGTGGCAGTGGCGGCGGACCTTAAGAGTACGCAA
GAAGCTATAAACAAGATAACAAAAAATCTCAATTCTTTGAGTGAGCTAGAAGTAAAGAATCTTCAAAGACTAAGTGGTG
CCATGGATGAACTCCACAACGAAATACTCGAGCTGGATGAGAAAGTGGATGATCTCAGAGCTGACACTATAAGCTCGCA
AATAGAACTTGCAGTCTTGCTTTCCAACGAAGGAATAATAAACAGTGAAGATGAGCATCTATTGGCACTTGAGAGAAAA
CTAAAGAAAATGCTGGGTCCCTCTGCTGTAGAGATAGGAAATGGATGCTTCGAAACCAAACACAAGTGCAACCAGACCT
GCTTAGACAGGATAGCTGCTGGCACCTTTAATGCAGGAGAATTTTCTCTCCCCACTTTTGATTCACTGAACATTACTGC
TGCATCTTTAAATGATGATGGATTGGATAACCATACTATACTGCTCTATTACTCAACTGCTGCTTCTAGTTTGGCTGTA
ACATTGATGCTAGCTATTTTTATTGTTTATATGGTCTCCAGAGACAACGTTTCATGCTCCATCTGTCTATAA

Fig 61E SEQ ID NO: 194

Amino acid sequence of PDISP/HA B Florida with deleted proteolytic loop (construct 2102 and 2104)

MAKNVAIFGLLFSLLVLVPSQIFADRICTGITSSNSPHVVKTATQGEVNVTGVIPLTTTPTKSYFANLKGTRTRGKLCP
DCLNCTDLDVALGRPMCVGTTPSAKASILHEVKPVTSGCFPIMHDRTKIRQLPNLLRGYENIRLSTQNVIDAEKAPGGP
YRLGTSGSCPNATSKSGFFATMAWAVPKDNNKNATNPLTVEVPYICTEGEDQITVWGFHSDNKTQMKNLYGDSNPQKFT
SSANGVTTHYVSQIGSFPDQTEDGGLPQSGRIVVDYMMQKPGKTGTIVYQRGVLLPQKVWCASGRSKVIKGSLPLIGEA

Figure 61E continued

DCLHEKYGGLNKSKPYYTGEHAKAIGNCPIWVKTPLKLANGTKYRPPGGWEGMIAGWHGYTSHGAHGVAVAADLKSTQ
EAINKITKNLNSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFNAGEFSLPTFDSLNITAASLNDDGLDNHTILLYYSTAASSLAV
TLMLAIFIVYMVSRDNVSCSICL*

Fig 61F SEQ ID NO: 195

Expression cassette number 2102 from 2X35S promoter to NOS terminator. PDISP/ HA B Florida with deleted proteolytic loop nucleotide sequence is underlined.

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAACGTTTTCTTTCACTGAAGCGAAATCAAAGATCTCTTTGTG
GACACGTAGTGCGGCGCCATTAAATAACGTGTACTTGTCCTATTCTTGTCGGTGTGGTCTTGGGAAAAGAAAGCTTGCT
GGAGGCTGCTGTTCAGCCCCATACATTACTTGTTACGATTCTGCTGACTTTCGGCGGGTGCAATATCTCTACTTCTGCT
TGACGAGGTATTGTTGCCTGTACTTCTTTCTTCTTCTTCTTGCTGATTGGTTCTATAAGAAATCTAGTATTTTCTTTGA
AACAGAGTTTTCCCGTGGTTTTCGAACTTGGAGAAAGATTGTTAAGCTTCTGTATATTCTGCCCAAATTTGTCGGGCCC
AATACCGCGGAGAAAATGGCGAAAAACGTTGCGATTTTCGGCTTATTGTTTTCTCTTCTTGTGTTGGTTCCTTCTCAGA
TCTTCGCGATCGAATCTGCACTGGAATAACATCTTCAAACTCACCTCATGTGGTCAAAACAGCCACTCAAGGGGAGGT
CAATGTGACTGGTGTGATACCACTAACAACAACACCAACAAAATCTTATTTTGCAAATCTCAAAGGAACAAGGACCAGA
GGGAAACTATGCCCAGACTGTCTCAACTGCACAGATCTGGATGTGGCTTTGGGCAGACCAATGTGTGTGGGGACCACAC
CTTCGGCGAAGGCTTCAATACTCCACGAAGTCAAACCTGTTACATCCGGGTGCTTTCCTATAATGCACGACAGAACAAA
AATCAGGCAACTACCCAATCTTCTCAGAGGATATGAAAATATCAGGCTATCAACTCAAAACGTCATCGATGCGGAAAAG
GCACCAGGAGGACCCTACAGACTTGGAACCTCAGGATCTTGCCCTAACGCTACCAGTAAGAGCGGATTTTTCGCAACAA
TGGCTTGGGCTGTCCCAAAGGACAACAACAAAAATGCAACGAACCCACTAACAGTAGAAGTACCATACATTTGTACAGA
AGGGGAAGACCAAATCACTGTTTGGGGGTTCCATTCAGATAACAAAACCCAAATGAAGAACCTCTATGGAGACTCAAAT
CCTCAAAAGTTCACCTCATCTGCTAATGGAGTAACCACACACTATGTTTCTCAGATTGGCAGCTTCCCAGATCAAACAG
AAGACGGAGGACTACCACAAAGCGGCAGGATTGTTGTTGATTACATGATGCAAAAACCTGGGAAAACAGGAACAATTGT
CTACCAAAGAGGTGTTTTGTTGCCTCAAAAGGTGTGGTGCGCGAGTGGCAGGAGCAAAGTAATAAAAGGGTCCTTGCCT
TTAATTGGTGAAGCAGATTGCCTTCATGAAAAATACGGTGGATTAAACAAAAGCAAGCCTTACTACACAGGAGAACATG
CAAAAGCCATAGGAAATTGCCCAATATGGGTGAAAACACCTTTGAAGCTCGCCAATGGAACCAAATATAGACCTCCTGG
TGGAGGATGGGAAGGAATGATTGCAGGCTGGCACGGATACACATCTCACGGAGCACATGGAGTGGCAGTGGCGGCGGAC
CTTAAGAGTACGCAAGAAGCTATAAACAAGATAACAAAAAATCTCAATTCTTTGAGTGAGCTAGAAGTAAAGAATCTTC
AAAGACTAAGTGGTGCCATGGATGAACTCCACAACGAAATACTCGAGCTGGATGAGAAAGTGGATGATCTCAGAGCTGA
CACTATAAGCTCGCAAATAGAACTTGCAGTCTTGCTTTCCAACGAAGGAATAATAAACAGTGAAGATGAGCATCTATTG
GCACTTGAGAGAAAACTAAAGAAAATGCTGGGTCCCTCTGCTGTAGAGATAGGAAATGGATGCTTCGAAACCAAACACA
AGTGCAACCAGACCTGCTTAGACAGGATAGCTGCTGGCACCTTTAATGCAGGAGAATTTTCTCTCCCCACTTTTGATTC
ACTGAACATTACTGCTGCATCTTTAAATGATGATGGATTGGATAACCATACTATACTGCTCTATTACTCAACTGCTGCT
TCTAGTTTGGCTGTAACATTGATGCTAGCTATTTTTATTGTTTATATGGTCTCCAGAGACAACGTTTCATGCTCCATCT
GTCTATAAAGGCCTATTTTCTTTAGTTTGAATTTACTGTTATTCGGTGTGCATTTCTATGTTTGGTGAGCGGTTTTCTG
TGCTCAGAGTGTGTTTATTTTATGTAATTTAATTTCTTTGTGAGCTCCTGTTTAGCAGGTCGTCCCTTCAGCAAGGACA
CAAAAAGATTTTAATTTTATTAAAAAAAAAAAAAAAAAAAGACCGGGAATTCGATATCAAGCTTATCGACCTGCAGATCG
TTCAAACATTTGGCAATAAAGTTTCTTAAGATTGAATCCTGTTGCCGGTCTTGCGATGATTATCATATAATTTCTGTTG
AATTACGTTAAGCATGTAATAATTAACATGTAATGCATGACGTTATTTATGAGATGGGTTTTTATGATTAGAGTCCCGC
AATTATACATTTAATACGCGATAGAAAACAAAATATAGCGCGCAAACTAGGATAAATTATCGCGCGCGGTGTCATCTAT
GTTACTAGAT

Schematic representation of construct number 2102

Fig 61H SEQ ID NO: 196

Expression cassette number 2104 from left to right LIR. PDISP/ HA B Florida with deleted proteolytic loop nucleotide sequence is underlined.

TGTTGTTGTGACTCCGAGGGGTTGCCTCAAACTCTATCTTATAACCGGCGTGGAGGCATGGAGGCAGGGGTATTTTGGTCATT
TTAATAGATAGTGGAAAATGACGTGGAATTTACTTAAAGACGAAGTCTTTGCGACAAGGGGGGGCCCACGCCGAATTTAATAT
TACCGGCGTGGCCCCCCCTTATCGCGAGTGCTTTAGCACGAGCGGTCCAGATTTAAAGTAGAAAATTTCCCGCCCACTAGGGT
TAAAGGTGTTCACACTATAAAAGCATATACGATGTGATGGTATTTGGTCGACAAGCTTGCATGCCGGTCAACATGGTGGAGCA
CGACACACTTGTCTACTCCAAAAATATCAAAGATACAGTCTCAGAAGACCAAAGGGCAATTGAGACTTTTCAACAAAGGGTAA
TATCCGGAAACCTCCTCGGATTCCATTGCCCAGCTATCTGTCACTTTATTGTGAAGATAGTGGAAAAGGAAGGTGGCTCCTAC
AAATGCCATCATTGCGATAAAGGAAAGGCCATCGTTGAAGATGCCTCTGCCGACAGTGGTCCCAAAGATGGACCCCCACCCAC
GAGGAGCATCGTGGAAAAAGAAGACGTTCCAACCACGTCTTCAAAGCAAGTGGATTGATGTGATAACATGGTGGAGCACGACA
CACTTGTCTACTCCAAAAATATCAAAGATACAGTCTCAGAAGACCAAAGGGCAATTGAGACTTTTCAACAAAGGGTAATATCC
GGAAACCTCCTCGGATTCCATTGCCCAGCTATCTGTCACTTTATTGTGAAGATAGTGGAAAAGGAAGGTGGCTCCTACAAATG
CCATCATTGCGATAAAGGAAAGGCCATCGTTGAAGATGCCTCTGCCGACAGTGGTCCCAAAGATGGACCCCCACCCACGAGGA
GCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAG
GTTTTGATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAACGTTTTCTTTCACTGAAGCGAA
ATCAAAGATCTCTTTGTGGACACGTAGTGCGGCGCCATTAAATAACGTGTACTTGTCCTATTCTTGTCGGTGTGGTCTTGGGA
AAAGAAAGCTTGCTGGAGGCTGCTGTTCAGCCCCATACATTACTTGTTACGATTCTGCTGACTTTCGGCGGGTGCAATATCTC
TACTTCTGCTTGACGAGGTATTGTTGCCTGTACTTCTTTCTTCTTCTTCTTGCTGATTGGTTCTATAAGAAATCTAGTATTTT
CTTTGAAACAGAGTTTTCCCGTGGTTTTCGAACTTGGAGAAAGATTGTTAAGCTTCTGTATATTCTGCCCAAATTTGTCGGGC
CCAATACCGCGGAGAAAATGGCGAAAAACGTTGCGATTTTCGGCTTATTGTTTTCTCTTCTTGTGTTGGTTCCTTCTCAGATC
TTCGCGGATCGAATCTGCACTGGAATAACATCTTCAAACTCACCTCATGTGGTCAAAACAGCCACTCAAGGGGAGGTCAATGT
GACTGGTGTGATACCACTAACAACAACACCAACAAAATCTTATTTTGCAAATCTCAAAGGAACAAGGACCAGAGGGAAACTAT
GCCCAGACTGTCTCAACTGCACAGATCTGGATGTGGCTTTGGGCAGACCAATGTGTGTGGGGACCACACCTTCGGCGAAGGCT
TCAATACTCCACGAAGTCAAACCTGTTACATCCGGGTGCTTTCCTATAATGCACGACAGAACAAAA

Figure 61H continued

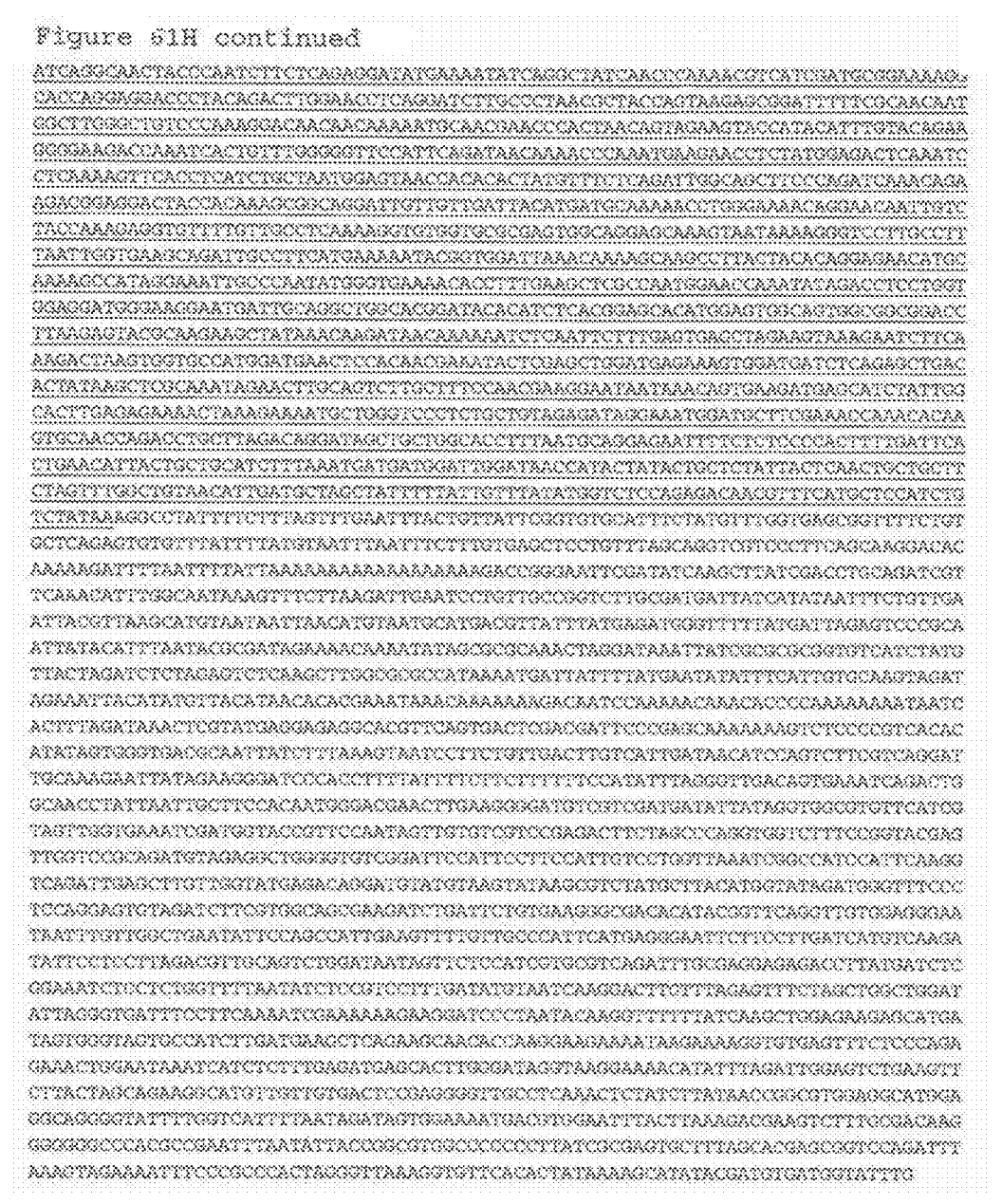

ATCAGGCAACTACCCAATCTTCTCAGAGGATATGAAAATATCAGGCTATCAACCCAAAACGTCATCGATGCGGAAAAG
CACCAGGAGGACCCTACAGACTTGGAACCTCAGGATCTTGCCCTAAGGCTACCAGTAAGAGCGGATTTTTCGCAACAAT
GGCTTGGGCTGTCCCAAAGGACAACAACAAAAATGCAACGAACCCACTAACAGTAGAAGTACCATACATTTGTACAGAA
GGGGAAGACCAAATCACTGTTTGGGGGTTCCATTCAGATAACAAAACCCAAATGAAGAACCTCTATGGAGACTCAAATC
CTCAAAAGTTCACCTCATCTGCTAATGGAGTAACCACACACTATGTTTCTCAGATTGGCAGCTTCCCAGATCAAACAGA
AGACGGAGGACTACCACAAAGCGGCAGGATTGTTGTTGATTACATGATGCAAAAACCTGGGAAAACAGGAACAATTGTC
TACCAAAGAGGTGTTTTGTTGCCTCAAAAGGTGTGGTGCGCGAGTGGCAGGAGCAAAGTAATAAAAGGGTCCTTGCCTT
TAATTGGTGAAGCAGATTGCCTTCATGAAAAATACGGTGGATTAAACAAAAGCAAGCCTTACTACACAGGAGAACATGC
AAAAGCCATAGGAAATTGCCCAATATGGGTGAAAACACCTTTGAAGCTCGCCAATGGAACCAAATACAGACCTCCTGGT
GGAGGATGGGAACGGAATGATTGCAGGCTGGCACGGATACACATCTCACGGAGCACATGGAGTGGCAGTGGCGGCGGACC
TTAAGAGTACGCAAGAAGCTATAAACAAGATAACAAAAAATCTCAATTCTTTGAGTGAGCTAGAAGTAAAGAATCTTCA
AAGACTAAGTGGTGCCATGGATGAACTCCACAACGAAATACTCGAGCTGGATGAGAAAGTGGATGATCTCAGAGCTGAC
ACTATAAGCTCGCAAATAGAACTTGCAGTCTTGCTTTCCAACGAAGGAATAATAAACAGTGAAGATGAGCATCTATTGG
CACTTGAGAGAAAACTAAAGAAAATGCTGGGTCCCTCTGCTGTAGAGATAGGAAATGGATGCTTCGAAACCAAACACAA
GTGCAACCAGACCTGCTTAGACAGGATAGCTGCTGGCACCTTTAATGCAGGAGAATTTTCTCTCCCCACTTTTGATTCA
CTGAACATTACTGCTGCATCTTTAAATGATGATGGATTGGATAACCATACTATACTGCTCTATTACTCAACTGCTGCTT
CTAGTTTGGCTGTAACATTGATGCTAGCTATTTTTATTGTTTATATGGTCTCCAGAGACAACGTTTCATGCTCCATCTG
TCTATAAAGGCCTATTTTCTTTAGTTTGAATTTACTGTTATTCGGTGTGCATTTCTATGTTTGGTGAGCGGTTTTCTGT
GCTCAGAGTGTGTTTATTTTATGTAATTTAATTTCTTTGTGAGCTCCTGTTTAGCAGGTCGTCCCTTCAGCAAGGACAC
AAAAAGATTTTAATTTTATTAAAAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATTTCTGTTGA
ATTACGTTAAGCATGTAATAATTAACATGTAATGCATGACGTTATTTATGAGATGGGTTTTTATGATTAGAGTCCCGCA
ATTATACATTTAATACGCGATAGAAAACAAAATATAGCGCGCAAACTAGGATAAATTATCGCGCGCGGTGTCATCTATG
TTACTAGATCTCTAGAGTCTCAAGCTTGGCGCGCCATAAAAATGATTATTTTATGAATATATTTCATTGTGCAAGTAGAT
AGAAATTACATATGTTACATAACACACGAAATAAACAAAAAAAGACAATCCAAAAACAAACACCCCAAAAAAAAATAATC
ACTTTAGATAAACTCGTATGAGGAGAGGCACGTTCAGTGACTCGACGATTCCCGAGCAAAAAAAGTCTCCCCGTCACAC
ATATAGTGGTGACGCAATTATCTTTAAAGTAATCCTTCTGTTGACTTGTCATTGATAACATCCAGTCTTCGTCAGGAT
TGCAAAGAATTATAGAAGGGATCCCACCTTTTATTTTCTTCTTTTTTCCATATTTAGGGTTGACAGTGAAATCAGACTG
GCAACCTATTAATTGCTTCCACAATGGGACGAACTTGAAGGGGATGTCGTCGATGATATTATAGGTGGCGTGTTCATCG
TAGTTGGTGAAATCGATGGTACCGTTCCAATAGTTGTGTCGTCCGAGACTTCTAGCCCAGGTGGTCTTTCCGGTACGAG
TTGGTCCGCAGATGTAGAGGCTGGGGTGTCGGATTCCATTCCTTCCATTGTCCTGGTTAAATCGGCCATCCATTCAAGG
TCAGATTGAGCTTGTTGGTATGAGACAGGATGTATGTAAGTATAAGCGTCTATGCTTACATGGTATAGATGGGTTTCCC
TCCAGGAGTGTAGATCTTCGTGGCAGCGAAGATCTGATTCTGTGAAGGGCGACACATACGGTTCAGGTTGTGGAGGGAA
TAATTTGTTGGCTGAATATTCCAGCCATTGAAGTTTTGTTGCCCATTCATGAGGGAATTCTTCCTTGATCATGTCAAGA
TATTCCTCCTTAGACGTTGCAGTCTGGATAATAGTTCTCCATCGTGCGTCAGATTTGCGAGGAGAGACCTTATGATCTC
GGAAATCTCCTCTGGTTTTAATATCTCCGTCCTTTGATATGTAATCAAGGACTTGTTTAGAGTTTCTAGCTGGCTGGAT
ATTAGGGTGATTTCCTTCAAAATCGAAAAAAGAAGGATCCCTAATACAAGGTTTTTTATCAAGCTGGAGAAGAGCATGA
TAGTGGGTAGTGCCATCTTGATGAAGCTCAGAAGCAACACCAAGGAAGAAAATAAGAAAAGGTGTGAGTTTCTCCCAGA
GAAACTGGAATAAATCATCTCTTTGAGATGAGCACTTGGGATAGGTAAGGAAAACATATTTAGATTGGAGTCTGAAGTT
CTTACTAGCAGAAGGCATGTTGTTGTGACTCCGAGGGGTTGCCTCAAACTCTATCTTATAACCGGCGTGGAGGCATGGA
GGCAGGGGTATTTTGGTCATTTTAATAGATAGTGGAAAAATGACGTGGAATTTACTTAAAGACGAAGTCTTTGCGACAAG
GGGGGGCCCACGCCGAATTTAATATTACCGGCGTGGCCCCCCCTTATCGCGAGTGCTTTAGCACGAGCGGTCCAGATTT
AAAGTAGAAAATTTCCCGCCCACTAGGGTTAAAGGTGTTCACACTATAAAAGCATATACGATGTGATGGTATTTG

Fig 61I

Schematic representation of construct number 2104

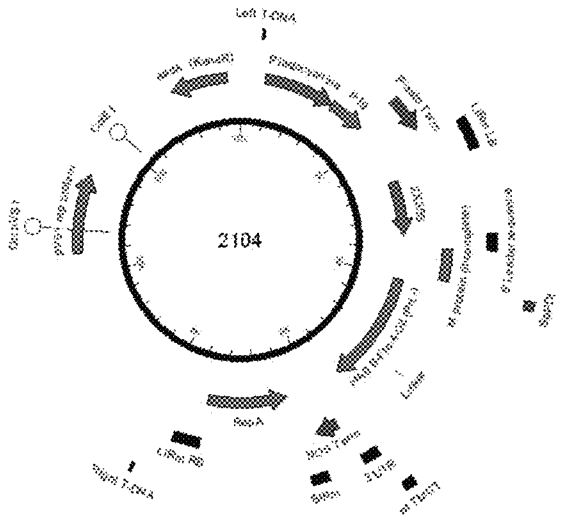

Figure 62

2X35S/CPMV HT+/ PDISP/B Florida +H1 California TMCT with proteolytic loop deleted / NOS (Construct number 2106) and 2X35S/CPMV HT+/ BeYDV/PDISP/B Florida +H1 California TMCT with proteolytic loop deleted/ NOS (Construct number 2108)

FIG 62A SEQ ID NO: 197

IF-H1cTMCT.S1-4r (Construct 2106 and 2108)

ACTAAAGAAAATAGGCCTTTAAATACATATTCTACACTGTAGAGAC

FIG 62B SEQ ID NO: 198

Nucleotide sequence of PDISP/HA B Florida+H1Cal TMCT with deleted proteolytic loop (construct 2106 and 2108)

ATGGCGAAAAACGTTGCGATTTTCGGCTTATTGTTTTCTCTTCTTGTGTTGGTTCCTTCTCAGATCTTCGCGGATCGAA
TCTGCACTGGAATAACATCTTCAAACTCACCTCATGTGGTCAAAACAGCCACTCAAGGGGAGGTCAATGTGACTGGTGT
GATACCACTAACAACAACACCAACAAAATCTTATTTTGCAAATCTCAAAGGAACAAGGACCAGAGGGAAACTATGCCCA
GACTGTCTCAACTGCACAGATCTGGATGTGGCTTTGGGCAGACCAATGTGTGTGGGGACCACACCTTCGGCGAAGGCTT
CAATACTCCACGAAGTCAAACCTGTTACATCCGGGTGCTTTCCTATAATGCACGACAGAACAAAAATCAGGCAACTACC
CAATCTTCTCAGAGGATATGAAAATATCAGGCTATCAACCCAAAACGTCATCGATGCGGAAAAGGCACCAGGAGGACCC
TACAGACTTGGAACCTCAGGATCTTGCCCTAACGCTACCAGTAAGAGCGGATTTTTCGCAACAATGGCTTGGGCTGTCC
CAAAGGACAACAACAAAAATGCAACGAACCCACTAACAGTAGAAGTACCATACATTTGTACAGAAGGGGAAGACCAAAT
CACTGTTTGGGGGTTCCATTCAGATAACAAAACCCAAATGAAGAACCTCTATGGAGACTCAAATCCTCAAAAGTTCACC
TCATCTGCTAATGGAGTAACCACACACTATGTTTCTCAGATTGGCAGCTTCCCAGATCAAACAGAAGACGGAGGACTAC
CACAAAGCGGCAGGATTGTTGTTGATTACATGATGCAAAAACCTGGGAAAACAGGAACAATTGTCTACCAAAGAGGTGT
TTTGTTGCCTCAAAAGGTGTGGTGCGCGAGTGGCAGGAGCAAAGTAATAAAAGGGTCCTTGCCTTTAATTGGTGAAGCA
GATTGCCTTCATGAAAAATACGGTGGATTAAACAAAAGCAAGCCTTACTACACAGGAGAACATGCAAAAGCCATAGGAA
ATTGCCCAATATGGGTGAAAACACCTTTGAAGCTCGCCAATGGAACCAAATATAGACCTCCTGGTGGAGGATGGAAGG
AATGATTGCAGGCTGGCACGGATACACATCTCACGGAGCACATGGAGTGGCAGTGGCGGCGGACCTTAAGAGTACGCAA

Figure 62B continued

GAAGCTATAAACAAGATAACAAAAAATCTCAATTCTTTGAGTGAGCTAGAAGTAAAGAATCTTCAAAGACTAAGTGGTG
CCATGGATGAACTCCACAACGAAATACTCGAGCTGGATGAGAAAGTGGATGATCTCAGAGCTGACACTATAAGCTCGCA
AATAGAACTTGCAGTCTTGCTTTCCAACGAAGGAATAATAAACAGTGAAGATGAGCATCTATTGGCACTTGAGAGAAAA
CTAAAGAAAATGCTGGGTCCCTCTGCTGTAGAGATAGGAAATGGATGCTTCGAAACCAAACACAAGTGCAACCAGACCT
GCTTAGACAGGATAGCTGCTGGCACCTTTAATGCAGGAGAATTTTCTCTCCCCACTTTTGATTCACTGAACATTACTGC
TGCATCTTTAAATGATGATGGATTGGATAACTACCAGATTTTGGCGATCTATTCAACTGTCGCCAGTTCATTGGTACTG
GTAGTCTCCCTGGGGGCAATCAGTTTCTGGATGTGCTCTAATGGGTCTCTACAGTGTAGAATATGTATTTAA

FIG 62C SEQ ID NO: 199

Amino acid sequence of PDISP/HA B Florida+H1Cal TMCT with deleted proteolytic loop (construct 2106 and 2108)

MAKNVAIFGLLFSLLVLVPSQIFADRICTGITSSNSPHVVKTATQGEVNVTGVIPLTTTPTKSYFANLKGTRTRGKLCP
DCLNCTDLDVALGRPMCVGTTPSAKASILHEVKPVTSGCFPIMHDRTKIRQLPNLLRGYENIRLSTQNVIDAEKAPGGP
YRLGTSGSCPNATSKSGFFATMAWAVPKDNNKNATNPLTVEVPYICTEGEDQITVWGFHSDNKTQMKNLYGDSNPQKFT
SSANGVTTHYVSQIGSFPDQTEDGGLPQSGRIVVDYMMQKPGKTGTIVYQRGVLLPQKVWCASGRSKVIKGSLPLIGEA
DCLHEKYGGLNKSKPYYTGEHAKAIGNCPIWVKTPLKLANGTKYRPPGKGWEGMIAGWHGYTSHGAHGVAVAADLKSTQ
EAINKITKNLNSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFNAGEFSLPTFDSLNITAASLNDDGLDNYQILAIYSTVASSLVL
VVSLGAISFWMCSNGSLQCRICI*

FIG 62D SEQ ID NO: 200

Expression cassette number 2106 from 2X35S promoter to NOS terminator. PDISP/ HA B Florida+H1Cal TMCT with deleted proteolytic loop nucleotide sequence is underlined.

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAACGTTTTCTTTCACTGAAGCGAAATCAAAGATCTCTTTGTG
GACACGTAGTGCGGCGCCATTAAATAACGTGTACTTGTCCTATTCTTGTCGGTGTGGTCTTGGGAAAAGAAAGCTTGCT
GGAGGCTGCTGTTCAGCCCCATACATTACTTGTTACGATTCTGCTGACTTTCGGCGGGTGCAATATCTCTACTTCTGCT
TGACGAGGTATTGTTGCCTGTACTTCTTTCTTCTTCTTCTTGCTGATTGGTTCTATAAGAAATCTAGTATTTTCTTTGA
AACAGAGTTTTCCCGTGGTTTTCGAACTTGGAGAAAGATTGTTAAGCTTCTGTATATTCTGCCCAAATTTGTCGGGCCC
AATACCGCGGAGAAAATGGCGAAAAACGTTGCGATTTTCGGCTTATTGTTTTCTCTTCTTGTGTTGGTTCCTTCTCAGA
TCTTCGCGGATCGAATCTGCACTGGAATAACATCTTCAAACTCACCTCATGTGGTCAAAACAGCCACTCAAGGGGAGGT
CAATGTGACTGGTGTGATACCACTAACAACAACACCAACAAAATCTTATTTTGCAAATCTCAAAGGAACAAGGACCAGA
GGGAAACTATGCCCAGACTGTCTCAACTGCACAGATCTGGATGTGGCTTTGGGCAGACCAATGTGTGTGGGGACCACAC
CTTCGGCGAAGGCTTCAATACTCCACGAAGTCAAACCTGTTACATCCGGGTGCTTTCCTATAATGCACGACAGAACAA
AATCAGGCAACTACCCAATCTTCTCAGAGGATATGAAAATATCAGGCTATCAACCCAAAACGTCATCGATGCGGAAAAG
GCACCAGGAGGACCCTACAGACTTGGAACCTCAGGATCTTGCCCTAACGCTACCAGTAAGAGCGGATTTTTCGCAACAA
TGGCTTGGGCTGTCCCAAAGGACAACAACAAAAATGCAACGAACCCACTAACAGTAGAAGTACCATACATTTGTACAGA
AGGGGAAGACCAAATCACTGTTTGGGGGTTCCATTCAGATAACAAAACCCAAATGAAGAACCTCTATGGAGACTCAAAT
CCTCAAAAGTTCACCTCATCTGCTAATGGAGTAACCACACACTATGTTTCTCAGATTGGCAGCTTCCCAGATCAAACAG
AAGACGGAGGACTACCACAAAGCGGCAGGATTGTTGTTGATTACATGATGCAAAAACCTGGGAAAACAGGAACAATTGT
CTACCAAAGAGGTGTTTTGTTGCCTCAAAAGGTGTGGTGCGCGAGTGGCAGGAGCAAAGTAATAAAAGGGTCCTTGCCT
TTAATTGGTGAAGCAGATTGCCTTCATGAAAAATACGGTGGATTAAACAAAAGCAAGCCTTACTACACAGGAGAACATG

Figure 62D continued

CAAAAGCCATAGGAAATTGCCCAATATGGGTGAAAACACCTTTGAAGCTCGCCAATGGAACCAAATATAGACCTCCTGGTGGA
GGATGGCAAGGAATGATTGCAGGCTGGCACGGATACACATCTCACGGAGCACATGGAGTGGCAGTGGCGGCGGACCTTAAGAG
TACGCAAGAAGCTATAAACAAGATAACAAAAAATCTCAATTCTTTGAGTGAGCTAGAAGTAAAGAATCTTCAAAGACTAAGTG
GTGCCATGGATGAACTCCACAACGAAATACTCGAGCTGGATGAGAAAGTGGATGATCTCAGAGCTGACACTATAAGCTCGCAA
ATAGAACTTGCAGTCTTGCTTTCCAACGAAGGAATAATAAACAGTGAAGATGAGCATCTATTGGCACTTGAGAGAAAACTAAA
GAAAATGCTGGGTCCCTCTGCTGTAGAGATAGGAAATGGATGCTTCGAAACCAAACACAAGTGCAACCAGACCTGCTTAGACA
GGATAGCTGCTGGCACCTTTAATGCAGGAGAATTTTCTCTCCCCACTTTTGATTCACTGAACATTACTGCTGCATCTTTAAAT
GATGATGGATTGGATAACTACCAGATTTTGGCGATCTATTCAACTGTCGCCAGTTCATTGGTACTGGTAGTCTCCCTGGGGGC
AATCAGTTTCTGGATGTGCTCTAATGGGTCTCTACAGTGTAGAATATGTATTTAAAGGCCTATTTTCTTTAGTTTGAATTTAC
TGTTATTCGGTGTGCATTTCTATGTTTGGTGAGCGGTTTTCTGTGCTCAGAGTGTGTTTATTTTATGTAATTTAATTTCTTTG
TGAGCTCCTGTTTAGCAGGTCGTCCCTTCAGCAAGGACACAAAAAGATTTAATTTTATTAAAAAAAAAAAAAAAAAAAGACCG
GGAATTCGATATCAAGCTTATCGACCTGCAGATCGTTCAAACATTTGGCAATAAAGTTTCTTAAGATTGAATCCTGTTGCCGG
TCTTGCGATGATTATCATATAATTTCTGTTGAATTACGTTAAGCATGTAATAATTAACATGTAATGCATGACGTTATTTATGA
GATGGGTTTTTATGATTAGAGTCCCGCAATTATACATTTAATACGCGATAGAAAACAAAATATAGCGCGCAAACTAGGATAAA
TTATCGCGCGCGGTGTCATCTATGTTACTAGAT

Schematic representation of construct number 2106

FIG 62F SEQ ID NO: 201

Expression cassette number 2108 from left to right UR. PDISP/ HA B Florida+H1Cal TMCT with deleted proteolytic loop nucleotide sequence is underlined.

TGTTGTTGTGACTCCGAGGGGTTGCCTCAAACTCTATCTTATAACCGGCGTGGAGGCATGGAGGCAGGGGTATTTTGGT
CATTTTAATAGATAGTGGAAAATGACGTGGAATTTACTTAAAGACGAAGTCTTTGCGACAAGGGGGGGCCCACGCCGAA
TTTAATATTACCGGCGTGGCCCCCCCTTATCGCGAGTGCTTTAGCACGAGCGGTCCAGATTTAAAGTAGAAAATTTCCC
GCCCACTAGGGTTAAAGGTGTTCACACTATAAAAGCATATACGATGTGATGGTATTTGGTCGACAAGCTTGCATGCCGG
TCAACATGGTGGAGCACGACACACTTGTCTACTCCAAAAATATCAAAGATACAGTCTCAGAAGACCAAAGGGCAATTGA
GACTTTTCAACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCCTCTGCCGACA
GTGGTCCCAAAGATGGACCCCCACCCACGAGGAGCATCGTGGAAAAAGAAGACGTTCCAACCACGTCTTCAAAGCAAGT
GGATTGATGTGATAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCTGTCACTTTA
TTGTGAAGATAGTGGAAAAGGAAGGTGGCTCCTACAAATGCCATCATTGCGATAAAGGAAAGGCCATCGTTGAAGATGC
CTCTGCCGACAGTGGTCCCAAAGATGGACCCCCACCCACGAGGAGCATCGTGGAAAAAGAAGACGTTCCAACCACGTCT
TCAAAGCAAGTGGATTGATGTGATATCTCCACTGACGTAAGGGATGACGCACAATCCCACTATCCTTCGCAAGACCCTT
CCTCTATATAAGGAAGTTCATTTCATTTGGAGAGGTATTAAAATCTTAATAGGTTTTGATAAAAGCGAACGTGGGGAAA
CCCGAACCAAACCTTCTTCTAAACTCTCTCTCATCTCTCTTAAAGCAAACTTCTCTCTTGTCTTTCTTGCGTGAGCGAT
CTTCAACGTTGTCAGATCGTGCTTCGGCACCAGTACAACGTTTTCTTTCACTGAAGCGAAATCAAAGATCTCTTTGTGG
ACACGTAGTGCGGCGCCATTAAATAACGTGTACTTGTCCTATTCTTGTCGGTGTGGTCTTGGGAAAAGAAAGCTTGCTG
GAGGCTGCTGTTCAGCCCCATACATTACTTGTTACGATTCTGCTGACTTTCGGCGGGTGCAATATCTCTACTTCTGCTT
GACGAGGTATTGTTGCCTGTACTTCTTTCTTCTTCTTCTTGCTGATTGGTTCTATAAGAAATCTAGTATTTTCTTTGAA
ACAGAGTTTTCCCGTGGTTTTCGAACTTGGAGAAAGATTGTTAAGCTTCTGTATATTCTGCCCAAATTTGTCGGGCCCA
ATACCGCGGAGAAAATGGCGAAAAACGTTGCGATTTTCGGCTTATTGTTTTCTCTTCTTGTGTTGGTTCCTTCTCAGAT
CTTCGCGGATCGAATCTGCACTGGAATAACATCTTCAAACTCACCTCATGTGGTCAAAACAGCCACTCAAGGGGAGGTC
AATGTGACTGGTGTGATACCACTAACAACAACACCAACAAAATCTTATTTTGCAAATCTCAAAGGAACAAGGACCAGAG
GGAAACTATGCCCAGACTGTCTCAACTGCACAGATCTGGATGTGGCTTTGGGCAGACCAATGTGTGTGGGGACCACACC
TTCGGCGAAGGCTTCAATACTCCACGAAGTCAAACCTGTTACATCCGGGTGCTTTCCTATAATGCACGACAGAACAAAA
ATCAGGCAACTACCCAATCTTCTCAGAGGATATGAAAATATCAGGCTATCAACCCAAAACGTCATCGATGCGGAAAAGG
CACCAGGAGGACCCTACAGACTTGGAACCTCAGGATCTTGCCCTAACGCTACCAGTAAGAGCGGATTTTTCGCAACAAT
GGCTTGGGCTGTCCCAAAGGACAACAACAAAAATGCAACGAACCCACTAACAGTAGAAGTACCATACATTTGTACAGAA
GGGGAAGACCAAATCACTGTTTGGGGGTTCCATTCAGATAACAAAACCCAAATGAAGAACCTCTATGGAGACTCAAATC
CTCAAAAGTTCACCTCATCTGCTAATGGAGTAACCACACACTATGTTTCTCAGATTGGCAGCTTCCCAGATCAAACAGA
AGACGGAGGACTACCACAAAGCGGCAGGATTGTTGTTGATTACATGATGCAAAAACCTGGGAAAACAGGAACAATTGTC
TACCAAAGAGGTGTTTTGTTGCCTCAAAAGGTGTGGTGCGCGAGTGGCAGGAGCAAAGTAATAAAGGGTCCTTGCCTT
TAATTGGTGAAGCAGATTGCCTTCATGAAAAATACGGTGGATTAAACAAAAGCAAGCCTTACTACACAGGAGAACATGC
AAAAGCCATAGGAAATTGCCCAATATGGGTGAAAACACCTTTGAAGCTCGCCAATGGAACCAAATATAGACCTCCTGGT
GGAGGATGGGAAGGAATGATTGCAGGCTGGCACGGATACACATCTCACGGAGCACATGGAGTGGCAGTGGCGGCGGACC
TTAAGAGTACGCAAGAAGCTATAAACAAGATAACAAAAAATCTCAATTCTTTGAGTGAGCTAGAAGTAAAGAATCTTCA
AAGACTAAGTGGTGCCATGGATGAACTCCACAACGAAATACTCGAGCTGGATGAGAAAGTGGATGATCTCAGAGCTGAC
ACTATAAGCTCGCAAATAGAACTTGCAGTCTTGCTTTCCAACGAAGGAATAATAAACAGTGAAGATGAGCATCTATTGG
CACTTGAGAGAAAACTAAAGAAAATGCTGGGTCCCTCTGCTGTAGAGATAGGAAATGGATGCTTCGAAACCAAACACAA
GTGCAACCAGACCTGCTTAGACAGGATAGCTGCTGGCACCTTTAATGCAGGAGAATTTTCTCTCCCCACTTTTGATTCA
CTGAACATTACTGCTGCATCTTTAAATGATGATGGATTGGATAACTACCAGATTTTGGCGATCTATTCAACTGTCGCCA
GTTCATTGGTACTGGTAGTCTCCCTGGGGGCAATCAGTTTCTGGATGTGCTCTAATGGGTCTCTACAGTGTAGAATATG
TATTTAAAGGCCTATTTTCTTTAGTTTGAATTTACTGTTATTCGGTGTGCATTTCTATGTTTGGTGAGCGGTTTTCTGT
GCTCAGAGTGTGTTTATTTTATGTAATTTAATTTCTTTGTGAGCTCCTGTTTAGCAGGTCGTCCCTTCAGCAAGGACAC
AAAAAGATTTTAATTTTATTAAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATTTCTGTTGA
ATTACGTTAAGCATGTAATAATTAACATGTAATGCATGACGTTATTTATGAGATGGGTTTTTATGATTAGAGTCCCGCA
ATTATACATTTAATACGCGATAGAAAACAAAATATAGCGCGCAAACTAGGATAAATTATCGCGCGCGGTGTCATCTATG
TTACTAGATCTCTAGAGTCTCAAGCTTGGCGCGCCATAAAATGATTATTTTATGAATATATTTCATTGTGCAAGTAGAT
AGAAATTACATATGTTACATAACACACGAAATAAACAAAAAAAGACAATCCAAAAACAAACACCCCAAAAAAAATAATC

Figure 62F continued

ACTTTAGATAAACTCGTATGAGGAGAGGCACGTTCAGTGACTCGACGATTCCCGAGCAAAAAAAGTCTCCCCGTCACACATAT
AGTGGGTGACGCAATTATCTTTAAAGTAATCCTTCTGTTGACTTGTCATTGATAACATCCAGTCTTCGTCAGGATTGCAAAGA
ATTATAGAAGGGATCCCACCTTTTATTTTCTTCTTTTTTCCATATTTAGGCTTGACAGTGAAATCAGACTGGCAACCTATTAA
TTGCTTCCACAATGGGACGAACTTGAAGGGGATGTCGTCGATGATATTATAGGTGGCGTGTTCATCGTAGTTGGTGAAATCGA
TGGTACCGTTCCAATAGTTGTCTCGTCCGAGACTTCTAGCCCAGGTGGTCTTTCCGGTACGAGTTGGTCCGCAGATGTAGAGG
CTGGGGTGTCGGATTCCATTCCTTCCATTGTCCTGGTTAAATCGGCCATCCATTCAAGGTCAGATTGAGCTTGTTGGTATGAG
ACAGGATGTATGTAAGTATAAGCGTCTATGCTTACATGGTATAGATGGGTTTCCCTCCAGGAGTGTAGATCTTCGTGGCAGCG
AAGATCTGATTCTGTGAAGGGCGACACATACGGTTCAGGTTGTGGAGGGAATAATTTGTTGGCTGAATATTCCAGCCATTGAA
GTTTTGTTGCCCATTCATGAGGGAATTCTTCCTTGATCATGTCAAGATATTCCTCCTTAGACGTTGCAGTCTGGATAATAGTT
CTCCATCGTGCGTCAGATTTGCGAGGAGAGACCTTATGATCTCGGAAATCTCCTCTGGTTTTAATATCTCCGTCCTTTGATAT
GTAATCAAGGACTTGTTTAGAGTTTCTAGCTGGCTGGATATTAGGGTGATTTCCTTCAAAATCGAAAAAAGAAGGATCCCTAA
TACAAGCTTTTTTATCAAGCTGGAGAAGAGCATGATAGTGGGTAGTGCCATCTTGATGAAGCTCAGAAGCAACACCAAGGAAG
AAAATAAGAAAAGGTGTGAGTTTCTCCCAGAGAAACTGGAATAAATCATCTCTTTGAGATGAGCACTTGGGATAGGTAAGGAA
AACATATTTAGATTGGAGTCTGAAGTTCTTACTAGCAGAAGGCATGTTGTTGTGACTCCGAGGGGTTGCCTCAAACTCTATCT
TATAACCGGCGTGGAGGCATGGAGGCAGGGGTATTTTGGTCATTTTAATAGATAGTGGAAAATGACGTGGAATTTACTTAAAG
ACGAAGTCTTTGCGACAAGGGGGGCCCACGCCGAATTTAATATTACCGGCGTGGCCCCCCCTTATCGCGAGTGCTTTAGCAC
GAGCGGTCCAGATTTAAAGTAGAAAATTTCCCGCCCACTAGGGTTAAAGGTGTTCACACTATAAAAGCATATACGATGTGATG
GTATTTG

Schematic representation of construct number 2108

SEQUENCE LISTING

<160> NUMBER OF SEQ ID NOS: 201

<210> SEQ ID NO 1
<211> LENGTH: 21
<212> TYPE: PRT
<213> ORGANISM: Artificial sequence
<220> FEATURE:
<223> OTHER INFORMATION: Avian H5 proteolytic loop consensus sequence

<400> SEQUENCE: 1

```
Gln Arg Glu Ser Arg Arg Lys Lys Arg Gly Leu Phe Gly Ala Ile Ala
1               5                   10                  15

Gly Phe Ile Glu Gly
            20
```

<210> SEQ ID NO 2
<211> LENGTH: 41
<212> TYPE: DNA
<213> ORGANISM: Artificial sequence
<220> FEATURE:
<223> OTHER INFORMATION: Primer IF-H5A-I-05.s1+3c

<400> SEQUENCE: 2
aaatttgtcg ggcccatgga gaaaatagtg cttcttcttg c 41

<210> SEQ ID NO 3
<211> LENGTH: 50
<212> TYPE: DNA
<213> ORGANISM: Artificial sequence
<220> FEATURE:
<223> OTHER INFORMATION: Primer IF-H5dTm.r

<400> SEQUENCE: 3
actaaagaaa ataggccttt aaatgcaaat tctgcattgt aacgatccat 50

<210> SEQ ID NO 4
<211> LENGTH: 4903
<212> TYPE: DNA
<213> ORGANISM: Artificial sequence
<220> FEATURE:
<223> OTHER INFORMATION: Construct 1191

<400> SEQUENCE: 4
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840

-continued

```
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccagtaca acgttttctt   3060
tcactgaagc gaaatcaaag atctctttgt ggacacgtag tgcggcgcca ttaaataacg   3120
tgtacttgtc ctattcttgt cggtgtggtc ttgggaaaag aaagcttgct ggaggctgct   3180
```

-continued gttcagcccc atacattact tgttacgatt ctgctgactt tcggcgggtg caatatctct 3240
acttctgctt gacgaggtat tgttgcctgt acttctttct tcttcttctt gctgattggt 3300
tctataagaa atctagtatt ttctttgaaa cagagttttc ccgtggtttt cgaacttgga 3360
gaaagattgt taagcttctg tatattctgc ccaaatttgt cgggcccgcg gatggcgaaa 3420
aacgttgcga ttttcggctt attgttttct cttcttgtgt tggttccttc tcagatcttc 3480
gcctgcaggc tcctcagcca aaacgacacc cccatctgtc tatccactgg cccctggatc 3540
tgctgcccaa actaactcca tggtgaccct gggatgcctg gtcaagggct atttccctga 3600
gccagtgaca gtgacctgga actctggatc cctgtccagc ggtgtgcaca ccttcccagc 3660
tgtcctgcag tctgacctct acactctgag cagctcagtg actgtcccct ccagcacctg 3720
gcccagcgag accgtcacct gcaacgttgc ccacccggcc agcagcacca aggtggacaa 3780
gaaaattgtg cccagggatt gtggttgtaa gccttgcata tgtacagtcc cagaagtatc 3840
atctgtcttc atcttccccc caaagcccaa ggatgtgctc accattactc tgactcctaa 3900
ggtcacgtgt gttgtggtag acatcagcaa ggatgatccc gaggtccagt tcagctggtt 3960
tgtagatgat gtggaggtgc acacagctca gacgcaaccc cgggaggagc agttcaacag 4020
cactttccgc tcagtcagtg aacttcccat catgcaccag gactggctca atggcaagga 4080
gcgatcgctc accatcacca tcaccatcac catcaccatt aaaggcctat tttctttagt 4140
ttgaatttac tgttattcgg tgtgcatttc tatgtttggt gagcggtttt ctgtgctcag 4200
agtgtgttta ttttatgtaa tttaatttct ttgtgagctc ctgtttagca ggtcgtccct 4260
tcagcaagga cacaaaaaga ttttaatttt attaaaaaaa aaaaaaaaaa agaccgggaa 4320
ttcgatatca agcttatcga cctgcagatc gttcaaacat ttggcaataa agtttcttaa 4380
gattgaatcc tgttgccggt cttgcgatga ttatcatata atttctgttg aattacgtta 4440
agcatgtaat aattaacatg taatgcatga cgttatttat gagatgggtt tttatgatta 4500
gagtcccgca attatacatt taatacgcga tagaaaacaa aatatagcgc gcaaactagg 4560
ataaattatc gcgcgcggtg tcatctatgt tactagatct ctagagtctc aagcttggcg 4620
cgcccacgtg actagtggca ctggccgtcg ttttacaacg tcgtgactgg gaaaaccctg 4680
gcgttaccca acttaatcgc cttgcagcac atcccccttt cgccagctgg cgtaatagcg 4740
aagaggcccg caccgatcgc ccttcccaac agttgcgcag cctgaatggc gaatgctaga 4800
gcagcttgag cttggatcag attgtcgttt cccgccttca gtttaaacta tcagtgtttg 4860
acaggatata ttggcgggta aacctaagag aaaagagcgt tta 4903

<210> SEQ ID NO 5
<211> LENGTH: 3447
<212> TYPE: DNA
<213> ORGANISM: Artificial sequence
<220> FEATURE:
<223> OTHER INFORMATION: Cassette 489

<400> SEQUENCE: 5
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360

-continued

```
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggag aaaatagtgc ttcttcttgc aatagtcagt cttgttaaaa gtgatcagat   1320
ttgcattggt taccatgcaa acaattcaac agagcaggtt gacacaatca tggaaaagaa   1380
cgttactgtt acacatgccc aagacatact ggaaaagaca cacaacggga agctctgcga   1440
tctagatgga gtgaagcctc taattttaag agattgtagt gtagctggat ggctcctcgg   1500
gaacccaatg tgtgacgaat tcatcaatgt accggaatgg tcttacatag tggagaaggc   1560
caatccaacc aatgacctct gttacccagg gagtttcaac gactatgaag aactgaaaca   1620
cctattgagc agaataaacc attttgagaa aattcaaatc atccccaaaa gttcttggtc   1680
cgatcatgaa gcctcatcag gagttagctc agcatgtcca tacctgggaa gtccctcctt   1740
ttttagaaat gtggtatggc ttatcaaaaa gaacagtaca tacccaacaa taaagaaaag   1800
ctacaataat accaaccaag aggatctttt ggtactgtgg ggaattcacc atcctaatga   1860
tgcggcagag cagacaaggc tatatcaaaa cccaaccacc tatatttcca ttgggacatc   1920
aacactaaac cagagattgg taccaaaaat agctactaga tccaaagtaa acgggcaaag   1980
tggaaggatg gagttcttct ggacaatttt aaaacctaat gatgcaatca acttcgagag   2040
taatggaaat ttcattgctc cagaatatgc atacaaaatt gtcaagaaag gggactcagc   2100
aattatgaaa agtgaattgg aatatggtaa ctgcaacacc aagtgtcaaa ctccaatggg   2160
ggcgataaac tctagtatgc cattccacaa catacaccct ctcaccatcg ggaatgcccc   2220
caaatatgtg aaatcaaaca gattagtcct tgcaacaggg ctcagaaata gccctcaaag   2280
agagagcaga agaaaaaaga gaggactatt tggagctata gcaggtttta tagagggagg   2340
atggcaggga atggtagatg gttggtatgg gtaccaccat agcaatgagc aggggagtgg   2400
gtacgctgca gacaaagaat ccactcaaaa ggcaatagat ggagtcacca ataaggtcaa   2460
ctcaatcatt gacaaaatga acactcagtt tgaggccgtt ggaagggaat ttaataactt   2520
agaaaggaga atagagaatt taaacaagaa gatggaagac gggtttctag atgtctggac   2580
ttataatgcc gaacttctgg ttctcatgga aaatgagaga actctagact ttcatgactc   2640
aaatgttaag aacctctacg acaaggtccg actacagctt agggataatg caaaggagct   2700
```

-continued

```
gggtaacggt tgtttcgagt tctatcacaa atgtgataat gaatgtatgg aaagtataag   2760

aaacggaacg tacaactatc cgcagtattc agaagaagca agattaaaaa gagaggaaat   2820

aagtggggta aaattggaat caataggaac ttaccaaata ctgtcaattt attcaacagt   2880

ggcgagttcc ctagcactgg caatcatgat ggctggtcta tctttatgga tgtgctccaa   2940

tggatcgtta caatgcagaa tttgcattta aaggcctatt ttctttagtt tgaatttact   3000

gttattcggt gtgcatttct atgtttggtg agcggttttc tgtgctcaga gtgtgtttat   3060

tttatgtaat ttaatttctt tgtgagctcc tgtttagcag gtcgtccctt cagcaaggac   3120

acaaaaagat tttaatttta ttaaaaaaaa aaaaaaaaaa gaccgggaat tcgatatcaa   3180

gcttatcgac ctgcagatcg ttcaaacatt tggcaataaa gtttcttaag attgaatcct   3240

gttgccggtc ttgcgatgat tatcatataa tttctgttga attacgttaa gcatgtaata   3300

attaacatgt aatgcatgac gttatttatg agatgggttt ttatgattag agtcccgcaa   3360

ttatacattt aatacgcgat agaaaacaaa atatagcgcg caaactagga taaattatcg   3420

cgcgcggtgt catctatgtt actagat                                       3447


<210> SEQ ID NO 6
<211> LENGTH: 568
<212> TYPE: PRT
<213> ORGANISM: Influenza H5 A/Indonesia/5/2005 (H5N1)

<400> SEQUENCE: 6

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240
```

-continued

```
Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

<210> SEQ ID NO 7
<211> LENGTH: 42
<212> TYPE: DNA
<213> ORGANISM: Artificial sequence
<220> FEATURE:
<223> OTHER INFORMATION: Primer IF-S1-M1+M2ANC.c

<400> SEQUENCE: 7
aaatttgtcg ggcccatgag tcttctaacc gaggtcgaaa cg 42

<210> SEQ ID NO 8
<211> LENGTH: 43
<212> TYPE: DNA

```
<213> ORGANISM: Artificial sequence
<220> FEATURE:
<223> OTHER INFORMATION: Primer IF-S1-4-M2ANC.r

<400> SEQUENCE: 8

actaaagaaa ataggccttt actccagctc tatgctgaca aaa                     43


<210> SEQ ID NO 9
<211> LENGTH: 294
<212> TYPE: DNA
<213> ORGANISM: Artificial sequence
<220> FEATURE:
<223> OTHER INFORMATION: Synthesized M2 gene

<400> SEQUENCE: 9

atgagtcttc taaccgaggt cgaaacgcct atcagaaacg aatgggggtg cagatgcaac     60

gattcaagtg atcctcttgt tgttgccgca agtataattg ggattgtgca cctgatattg    120

tggattattg atcgcctttt ttccaaaagc atttatcgta tctttaaaca cggtttaaaa    180

agagggcctt ctacggaagg agtaccagag tctatgaggg aagaatatcg agaggaacag    240

cagaatgctg tggatgctga cgatggtcat tttgtcagca tagagctgga gtaa          294


<210> SEQ ID NO 10
<211> LENGTH: 2034
<212> TYPE: DNA
<213> ORGANISM: Artificial sequence
<220> FEATURE:
<223> OTHER INFORMATION: Cassette 1261

<400> SEQUENCE: 10

gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaacg ttttctttca ctgaagcgaa atcaaagatc tctttgtgga cacgtagtgc    960

ggcgccatta aataacgtgt acttgtccta ttcttgtcgg tgtggtcttg ggaaaagaaa   1020

gcttgctgga ggctgctgtt cagccccata cattacttgt tacgattctg ctgactttcg   1080

gcgggtgcaa tatctctact tctgcttgac gaggtattgt tgcctgtact tctttcttct   1140

tcttcttgct gattggttct ataagaaatc tagtattttc tttgaaacag agttttcccg   1200

tggttttcga acttggagaa agattgttaa gcttctgtat attctgccca aatttgtcgg   1260
```

gcccatgagt cttctaaccg aggtcgaaac gcctatcaga aacgaatggg ggtgcagatg 1320
caacgattca agtgatcctc ttgttgttgc cgcaagtata attgggattg tgcacctgat 1380
attgtggatt attgatcgcc ttttttccaa aagcatttat cgtatcttta aacacggttt 1440
aaaaagaggg ccttctacgg aaggagtacc agagtctatg agggaagaat atcgagagga 1500
acagcagaat gctgtggatg ctgacgatgg tcattttgtc agcatagagc tggagtaaag 1560
gcctattttc tttagtttga atttactgtt attcggtgtg catttctatg tttggtgagc 1620
ggttttctgt gctcagagtg tgtttatttt atgtaattta atttctttgt gagctcctgt 1680
ttagcaggtc gtcccttcag caaggacaca aaaagatttt aattttatta aaaaaaaaaa 1740
aaaaaaagac cgggaattcg atatcaagct tatcgacctg cagatcgttc aaacatttgg 1800
caataaagtt tcttaagatt gaatcctgtt gccggtcttg cgatgattat catataattt 1860
ctgttgaatt acgttaagca tgtaataatt aacatgtaat gcatgacgtt atttatgaga 1920
tgggttttta tgattagagt cccgcaatta tacatttaat acgcgataga aaacaaaata 1980
tagcgcgcaa actaggataa attatcgcgc gcggtgtcat ctatgttact agat 2034

<210> SEQ ID NO 11
<211> LENGTH: 97
<212> TYPE: PRT
<213> ORGANISM: Influenza M2 New Caledonia/20/1999 (H1N1)

<400> SEQUENCE: 11

Met Ser Leu Leu Thr Glu Val Glu Thr Pro Ile Arg Asn Glu Trp Gly
1 5 10 15

Cys Arg Cys Asn Asp Ser Ser Asp Pro Leu Val Val Ala Ala Ser Ile
20 25 30

Ile Gly Ile Val His Leu Ile Leu Trp Ile Ile Asp Arg Leu Phe Ser
35 40 45

Lys Ser Ile Tyr Arg Ile Phe Lys His Gly Leu Lys Arg Gly Pro Ser
50 55 60

Thr Glu Gly Val Pro Glu Ser Met Arg Glu Glu Tyr Arg Glu Glu Gln
65 70 75 80

Gln Asn Ala Val Asp Ala Asp Asp Gly His Phe Val Ser Ile Glu Leu
85 90 95

Glu

<210> SEQ ID NO 12
<211> LENGTH: 294
<212> TYPE: DNA
<213> ORGANISM: Artificial sequence
<220> FEATURE:
<223> OTHER INFORMATION: Synthesized M2 gene

<400> SEQUENCE: 12
atgagtcttc taaccgaggt cgaaacgcct atcagaaacg aatgggggtg cagatgcaac 60
ggttcaagtg atcctctcac tattgccgca aatatcattg ggatcttgca cttgacattg 120
tggattcttg atcgtctttt tttcaaatgc atttaccgtc gctttaaata cggactgaaa 180
ggagggcctt ctacggaagg agtgccaaag tctatgaggg aagaatatcg aaaggaacag 240
cagagtgctg tggatgctga cgatggtcat tttgtcagca tagagctgga gtaa 294

<210> SEQ ID NO 13
<211> LENGTH: 2034
<212> TYPE: DNA

<213> ORGANISM: Artificial sequence
<220> FEATURE:
<223> OTHER INFORMATION: Cassette 859

<400> SEQUENCE: 13

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatgagt cttctaaccg aggtcgaaac gcctatcaga aacgaatggg ggtgcagatg   1320
caacggttca agtgatcctc tcactattgc cgcaaatatc attgggatct tgcacttgac   1380
attgtggatt cttgatcgtc ttttttcaa atgcatttac cgtcgcttta aatacggact   1440
gaaaggaggg ccttctacgg aaggagtgcc aaagtctatg agggaagaat atcgaaagga   1500
acagcagagt gctgtggatg ctgacgatgg tcattttgtc agcatagagc tggagtaaag   1560
gcctattttc tttagtttga atttactgtt attcggtgtg catttctatg tttggtgagc   1620
ggttttctgt gctcagagtg tgtttatttt atgtaattta atttctttgt gagctcctgt   1680
ttagcaggtc gtcccttcag caaggacaca aaaagatttt aattttatta aaaaaaaaaa   1740
aaaaaaagac cgggaattcg atatcaagct tatcgacctg cagatcgttc aaacatttgg   1800
caataaagtt tcttaagatt gaatcctgtt gccggtcttg cgatgattat catataattt   1860
ctgttgaatt acgttaagca tgtaataatt aacatgtaat gcatgacgtt atttatgaga   1920
tgggttttta tgattagagt cccgcaatta tacatttaat acgcgataga aaacaaaata   1980
tagcgcgcaa actaggataa attatcgcgc gcggtgtcat ctatgttact agat         2034
```

<210> SEQ ID NO 14
<211> LENGTH: 97
<212> TYPE: PRT
<213> ORGANISM: Influenza M2 A/Puerto Rico/8/1934 (H1N1)

<400> SEQUENCE: 14

Met Ser Leu Leu Thr Glu Val Glu Thr Pro Ile Arg Asn Glu Trp Gly
1 5 10 15

Cys Arg Cys Asn Gly Ser Ser Asp Pro Leu Thr Ile Ala Ala Asn Ile
20 25 30

Ile Gly Ile Leu His Leu Thr Leu Trp Ile Leu Asp Arg Leu Phe Phe
35 40 45

Lys Cys Ile Tyr Arg Arg Phe Lys Tyr Gly Leu Lys Gly Gly Pro Ser
50 55 60

Thr Glu Gly Val Pro Lys Ser Met Arg Glu Glu Tyr Arg Lys Glu Gln
65 70 75 80

Gln Ser Ala Val Asp Ala Asp Asp Gly His Phe Val Ser Ile Glu Leu
85 90 95

Glu

<210> SEQ ID NO 15
<211> LENGTH: 3474
<212> TYPE: DNA
<213> ORGANISM: Artificial sequence
<220> FEATURE:
<223> OTHER INFORMATION: Cassette 1039

<400> SEQUENCE: 15
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccatggcg aaaaacgttg cgattttcgg cttattgttt tctcttcttg tgttggttcc 1320
ttctcagatc ttcgccgatc gaatctgcac tggaataaca tcgtcaaact caccacatgt 1380

```
cgtcaaaact gctactcaag gggaggtcaa tgtgactggt gtaataccac tgacaacaac   1440
acccaccaaa tctcattttg caaatctcaa aggaacagaa accaggggga aactatgccc   1500
aaaatgcctc aactgcacag atctggacgt agccttgggc agaccaaaat gcacggggaa   1560
aataccctcg gcaagagttt caatactcca tgaagtcaga cctgttacat ctgggtgctt   1620
tcctataatg cacgacagaa caaaaattag acagctgcct aaccttctcc gaggatacga   1680
acatatcagg ttatcaaccc ataacgttat caatgcagaa aatgcaccag gaggacccta   1740
caaaattgga acctcagggt cttgccctaa cattaccaat ggaaacggat ttttcgcaac   1800
aatggcttgg gccgtcccaa aaaacgacaa aaacaaaaca gcaacaaatc cattaacaat   1860
agaagtacca tacatttgta cagaaggaga agaccaaatt accgtttggg ggttccactc   1920
tgacaacgag acccaaatgg caaagctcta tggggactca aagccccaga agttcacctc   1980
atctgccaac ggagtgacca cacattacgt ttcacagatt ggtggcttcc caaatcaaac   2040
agaagacgga ggactaccac aaagtggtag aattgttgtt gattacatgg tgcaaaaatc   2100
tgggaaaaca ggaacaatta cctatcaaag ggtatttta ttgcctcaaa aggtgtggtg    2160
cgcaagtggc aggagcaagg taataaaagg atccttgcct ttaattggag aagcagattg   2220
cctccacgaa aaatacggtg gattaaacaa aagcaagcct tactacacag gggaacatgc   2280
aaaggccata ggaaattgcc caatatgggt gaaaacaccc ttgaagctgg ccaatggaac   2340
caaatataga cctcctggtg gaggatggga aggaatgatt gcaggttggc acggatacac   2400
atcccatggg gcacatggag tagcggtggc agcagacctt aagagcactc aagaggccat   2460
aaacaagata acaaaaaatc tcaactcttt gagtgagctg gaagtaaaga atcttcaaag   2520
actaagcggt gccatggatg aactccacaa cgaaatacta gaactagatg agaaagtgga   2580
tgatctcaga gctgatacaa taagctcaca aatagaactc gcagtcctgc tttccaatga   2640
aggaataata aacagtgaag atgaacatct cttggcgctt gaaagaaagc tgaagaaaat   2700
gctgggcccc tctgctgtag agatagggaa tggatgcttt gaaaccaaac acaagtgcaa   2760
ccagacctgt ctcgacagaa tagctgctgg tacctttgat gcaggagaat tttctctccc   2820
cacctttgat tcactgaata ttactgctgc atctttaaat gacgatggat tggataatca   2880
tactatactg ctttactact caactgctgc ctccagtttg gctgtaacac tgatgatagc   2940
tatctttgtt gtttatatgg tctccagaga caatgtttct tgctccatct gtctataaag   3000
gcctattttc tttagtttga atttactgtt attcggtgtg catttctatg tttggtgagc   3060
ggttttctgt gctcagagtg tgtttatttt atgtaattta atttctttgt gagctcctgt   3120
ttagcaggtc gtcccttcag caaggacaca aaaagatttt aattttatta aaaaaaaaaa   3180
aaaaaaagac cgggaattcg atatcaagct tatcgacctg cagatcgttc aaacatttgg   3240
caataaagtt tcttaagatt gaatcctgtt gccggtcttg cgatgattat catataattt   3300
ctgttgaatt acgttaagca tgtaataatt aacatgtaat gcatgacgtt atttatgaga   3360
tgggttttta tgattagagt cccgcaatta tacatttaat acgcgataga aaacaaaata   3420
tagcgcgcaa actaggataa attatcgcgc gcggtgtcat ctatgttact agat         3474
```

<210> SEQ ID NO 16
<211> LENGTH: 570
<212> TYPE: PRT
<213> ORGANISM: Influenza B/Brisbane/60/2008

<400> SEQUENCE: 16

Asp Arg Ile Cys Thr Gly Ile Thr Ser Ser Asn Ser Pro His Val Val

-continued

```
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asn Glu Thr Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
        275                 280                 285

Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg Gly Phe Phe Gly Ala
            340                 345                 350

Ile Ala Gly Phe Leu Glu Gly Gly Trp Glu Gly Met Ile Ala Gly Trp
        355                 360                 365

His Gly Tyr Thr Ser His Gly Ala His Gly Val Ala Val Ala Ala Asp
    370                 375                 380

Leu Lys Ser Thr Gln Glu Ala Ile Asn Lys Ile Thr Lys Asn Leu Asn
385                 390                 395                 400

Ser Leu Ser Glu Leu Glu Val Lys Asn Leu Gln Arg Leu Ser Gly Ala
                405                 410                 415

Met Asp Glu Leu His Asn Glu Ile Leu Glu Leu Asp Glu Lys Val Asp
            420                 425                 430
```

Asp Leu Arg Ala Asp Thr Ile Ser Ser Gln Ile Glu Leu Ala Val Leu
        435                 440                 445

Leu Ser Asn Glu Gly Ile Ile Asn Ser Glu Asp Glu His Leu Leu Ala
    450                 455                 460

Leu Glu Arg Lys Leu Lys Lys Met Leu Gly Pro Ser Ala Val Glu Ile
465                 470                 475                 480

Gly Asn Gly Cys Phe Glu Thr Lys His Lys Cys Asn Gln Thr Cys Leu
                485                 490                 495

Asp Arg Ile Ala Ala Gly Thr Phe Asp Ala Gly Glu Phe Ser Leu Pro
            500                 505                 510

Thr Phe Asp Ser Leu Asn Ile Thr Ala Ala Ser Leu Asn Asp Asp Gly
        515                 520                 525

Leu Asp Asn His Thr Ile Leu Leu Tyr Tyr Ser Thr Ala Ala Ser Ser
    530                 535                 540

Leu Ala Val Thr Leu Met Ile Ala Ile Phe Val Val Tyr Met Val Ser
545                 550                 555                 560

Arg Asp Asn Val Ser Cys Ser Ile Cys Leu
                565                 570

<210> SEQ ID NO 17
<211> LENGTH: 554
<212> TYPE: PRT
<213> ORGANISM: Artificial sequence
<220> FEATURE:
<223> OTHER INFORMATION: Amino acid sequence delta-proteolytic loop of
      type B HA (with linker GG)

<400> SEQUENCE: 17

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asn Glu Thr Gln Met Ala Lys Leu Tyr Gly Asp Ser
        195                 200                 205

Lys Pro Gln Lys Phe Thr Ser Ser Ala Asn Gly Val Thr Thr His Tyr

```
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
        275                 280                 285

Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Gly Gly Gly Trp Glu Gly Met Ile Ala Gly Trp His
            340                 345                 350

Gly Tyr Thr Ser His Gly Ala His Gly Val Ala Val Ala Ala Asp Leu
        355                 360                 365

Lys Ser Thr Gln Glu Ala Ile Asn Lys Ile Thr Lys Asn Leu Asn Ser
    370                 375                 380

Leu Ser Glu Leu Glu Val Lys Asn Leu Gln Arg Leu Ser Gly Ala Met
385                 390                 395                 400

Asp Glu Leu His Asn Glu Ile Leu Glu Leu Asp Glu Lys Val Asp Asp
                405                 410                 415

Leu Arg Ala Asp Thr Ile Ser Ser Gln Ile Glu Leu Ala Val Leu Leu
            420                 425                 430

Ser Asn Glu Gly Ile Ile Asn Ser Glu Asp Glu His Leu Leu Ala Leu
        435                 440                 445

Glu Arg Lys Leu Lys Lys Met Leu Gly Pro Ser Ala Val Glu Ile Gly
    450                 455                 460

Asn Gly Cys Phe Glu Thr Lys His Lys Cys Asn Gln Thr Cys Leu Asp
465                 470                 475                 480

Arg Ile Ala Ala Gly Thr Phe Asp Ala Gly Glu Phe Ser Leu Pro Thr
                485                 490                 495

Phe Asp Ser Leu Asn Ile Thr Ala Ala Ser Leu Asn Asp Asp Gly Leu
            500                 505                 510

Asp Asn His Thr Ile Leu Leu Tyr Tyr Ser Thr Ala Ala Ser Ser Leu
        515                 520                 525

Ala Val Thr Leu Met Ile Ala Ile Phe Val Val Tyr Met Val Ser Arg
    530                 535                 540

Asp Asn Val Ser Cys Ser Ile Cys Leu Pro
545                 550


<210> SEQ ID NO 18
<211> LENGTH: 570
<212> TYPE: PRT
<213> ORGANISM: Artificial sequence
<220> FEATURE:
<223> OTHER INFORMATION: Amino acid sequence replacing cleavage site of
      B HA with linker

<400> SEQUENCE: 18

Asp Arg Ile Cys Thr Gly Ile Thr Ser Ser Asn Ser Pro His Val Val
1               5                   10                  15
```

```
Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asn Glu Thr Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
        275                 280                 285

Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Gly Ser Ser Ser Gly Ser Ser Ser Gly Gly Phe Phe Gly Ala
            340                 345                 350

Ile Ala Gly Phe Leu Glu Gly Gly Trp Glu Gly Met Ile Ala Gly Trp
        355                 360                 365

His Gly Tyr Thr Ser His Gly Ala His Gly Val Ala Val Ala Ala Asp
    370                 375                 380

Leu Lys Ser Thr Gln Glu Ala Ile Asn Lys Ile Thr Lys Asn Leu Asn
385                 390                 395                 400

Ser Leu Ser Glu Leu Glu Val Lys Asn Leu Gln Arg Leu Ser Gly Ala
                405                 410                 415

Met Asp Glu Leu His Asn Glu Ile Leu Glu Leu Asp Glu Lys Val Asp
            420                 425                 430

Asp Leu Arg Ala Asp Thr Ile Ser Ser Gln Ile Glu Leu Ala Val Leu
```

```
        435                 440                 445

Leu Ser Asn Glu Gly Ile Ile Asn Ser Glu Asp Glu His Leu Leu Ala
    450                 455                 460

Leu Glu Arg Lys Leu Lys Lys Met Leu Gly Pro Ser Ala Val Glu Ile
465                 470                 475                 480

Gly Asn Gly Cys Phe Glu Thr Lys His Lys Cys Asn Gln Thr Cys Leu
                485                 490                 495

Asp Arg Ile Ala Ala Gly Thr Phe Asp Ala Gly Glu Phe Ser Leu Pro
            500                 505                 510

Thr Phe Asp Ser Leu Asn Ile Thr Ala Ala Ser Leu Asn Asp Asp Gly
        515                 520                 525

Leu Asp Asn His Thr Ile Leu Leu Tyr Tyr Ser Thr Ala Ala Ser Ser
    530                 535                 540

Leu Ala Val Thr Leu Met Ile Ala Ile Phe Val Val Tyr Met Val Ser
545                 550                 555                 560

Arg Asp Asn Val Ser Cys Ser Ile Cys Leu
                565                 570


<210> SEQ ID NO 19
<211> LENGTH: 550
<212> TYPE: PRT
<213> ORGANISM: Influenza H3 A/Perth/16/2009

<400> SEQUENCE: 19

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Glu Ile Cys Asp Ser Pro His Gln Ile Leu Asp Gly Lys Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Lys
    130                 135                 140

Asn Ser Phe Phe Ser Arg Leu Asn Trp Leu Thr His Leu Asn Phe Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ala Ser Gly Arg Ile Thr Val Ser Thr Lys Arg
        195                 200                 205

Ser Gln Gln Thr Val Ser Pro Asn Ile Gly Ser Arg Pro Arg Val Arg
    210                 215                 220

Asn Ile Pro Ser Arg Ile Ser Ile Tyr Trp Thr Ile Val Lys Pro Gly
225                 230                 235                 240
```

-continued

```
Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550


<210> SEQ ID NO 20
<211> LENGTH: 540
<212> TYPE: PRT
<213> ORGANISM: Artificial sequence
<220> FEATURE:
<223> OTHER INFORMATION: Amino acid sequence delta-proteolytic loop H3
      (with linker GS)

<400> SEQUENCE: 20

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45
```

```
Gly Glu Ile Cys Asp Ser Pro His Gln Ile Leu Asp Gly Lys Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Lys
    130                 135                 140

Asn Ser Phe Phe Ser Arg Leu Asn Trp Leu Thr His Leu Asn Phe Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ala Ser Gly Arg Ile Thr Val Ser Thr Lys Arg
        195                 200                 205

Ser Gln Gln Thr Val Ser Pro Asn Ile Gly Ser Arg Pro Arg Val Arg
    210                 215                 220

Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Gly Ser Gly Ala Ile Ala Gly Phe Ile Glu Asn Gly Trp Glu Gly Met
                325                 330                 335

Val Asp Gly Trp Tyr Gly Phe Arg His Gln Asn Ser Glu Gly Arg Gly
            340                 345                 350

Gln Ala Ala Asp Leu Lys Ser Thr Gln Ala Ala Ile Asp Gln Ile Asn
        355                 360                 365

Gly Lys Leu Asn Arg Leu Ile Gly Lys Thr Asn Glu Lys Phe His Gln
    370                 375                 380

Ile Glu Lys Glu Phe Ser Glu Val Glu Gly Arg Ile Gln Asp Leu Glu
385                 390                 395                 400

Lys Tyr Val Glu Asp Thr Lys Ile Asp Leu Trp Ser Tyr Asn Ala Glu
                405                 410                 415

Leu Leu Val Ala Leu Glu Asn Gln His Thr Ile Asp Leu Thr Asp Ser
            420                 425                 430

Glu Met Asn Lys Leu Phe Glu Lys Thr Lys Lys Gln Leu Arg Glu Asn
        435                 440                 445

Ala Glu Asp Met Gly Asn Gly Cys Phe Lys Ile Tyr His Lys Cys Asp
    450                 455                 460
```

-continued

```
Asn Ala Cys Ile Gly Ser Ile Arg Asn Gly Thr Tyr Asp His Asp Val
465                 470                 475                 480

Tyr Arg Asp Glu Ala Leu Asn Asn Arg Phe Gln Ile Lys Gly Val Glu
                485                 490                 495

Leu Lys Ser Gly Tyr Lys Asp Trp Ile Leu Trp Ile Ser Phe Ala Ile
            500                 505                 510

Ser Cys Phe Leu Leu Cys Val Ala Leu Leu Gly Phe Ile Met Trp Ala
        515                 520                 525

Cys Gln Lys Gly Asn Ile Arg Cys Asn Ile Cys Ile
    530                 535                 540


<210> SEQ ID NO 21
<211> LENGTH: 550
<212> TYPE: PRT
<213> ORGANISM: Artificial sequence
<220> FEATURE:
<223> OTHER INFORMATION: Amino acid sequence Replacing cleavage site of
      H3 with linker

<400> SEQUENCE: 21

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Glu Ile Cys Asp Ser Pro His Gln Ile Leu Asp Gly Lys Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Lys
    130                 135                 140

Asn Ser Phe Phe Ser Arg Leu Asn Trp Leu Thr His Leu Asn Phe Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ala Ser Gly Arg Ile Thr Val Ser Thr Lys Arg
        195                 200                 205

Ser Gln Gln Thr Val Ser Pro Asn Ile Gly Ser Arg Pro Arg Val Arg
    210                 215                 220

Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285
```

```
Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Gly Ser Ser Gly Ser Ser Gly Ser Ser Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550


<210> SEQ ID NO 22
<211> LENGTH: 31
<212> TYPE: PRT
<213> ORGANISM: Influenza H1 New Cal

<400> SEQUENCE: 22

Ile Pro Ser Ile Gln Ser Arg Gly Leu Phe Gly Ala Ile Ala Gly Phe
1               5                   10                  15

Ile Glu Gly Gly Trp Thr Gly Met Val Asp Gly Trp Tyr Gly Tyr
            20                  25                  30


<210> SEQ ID NO 23
<211> LENGTH: 31
<212> TYPE: PRT
<213> ORGANISM: Influenza H1 Brisbane

<400> SEQUENCE: 23

Ile Pro Ser Ile Gln Ser Arg Gly Leu Phe Gly Ala Ile Ala Gly Phe
1               5                   10                  15

Ile Glu Gly Gly Trp Thr Gly Met Val Asp Gly Trp Tyr Gly Tyr
            20                  25                  30
```

<210> SEQ ID NO 24
<211> LENGTH: 31
<212> TYPE: PRT
<213> ORGANISM: Influenza H1 Sol Islands

<400> SEQUENCE: 24

```
Ile Pro Ser Ile Gln Ser Arg Gly Leu Phe Gly Ala Ile Ala Gly Phe
1               5                   10                  15

Ile Glu Gly Gly Trp Thr Gly Met Val Asp Gly Trp Tyr Gly Tyr
            20                  25                  30
```

<210> SEQ ID NO 25
<211> LENGTH: 31
<212> TYPE: PRT
<213> ORGANISM: Influenza H2A Singapore

<400> SEQUENCE: 25

```
Val Pro Gln Ile Glu Ser Arg Gly Leu Phe Gly Ala Ile Ala Gly Phe
1               5                   10                  15

Ile Glu Gly Gly Trp Gln Gly Met Val Asp Gly Trp Tyr Gly Tyr
            20                  25                  30
```

<210> SEQ ID NO 26
<211> LENGTH: 31
<212> TYPE: PRT
<213> ORGANISM: Influenza H3A Brisbane

<400> SEQUENCE: 26

```
Val Pro Glu Lys Gln Thr Arg Gly Ile Phe Gly Ala Ile Ala Gly Phe
1               5                   10                  15

Ile Glu Asn Gly Trp Glu Gly Met Val Asp Gly Trp Tyr Gly Phe
            20                  25                  30
```

<210> SEQ ID NO 27
<211> LENGTH: 31
<212> TYPE: PRT
<213> ORGANISM: Influenza H3A WCN

<400> SEQUENCE: 27

```
Val Pro Glu Lys Gln Thr Arg Gly Ile Phe Gly Ala Ile Ala Gly Phe
1               5                   10                  15

Ile Glu Asn Gly Trp Glu Gly Met Val Asp Gly Trp Tyr Gly Phe
            20                  25                  30
```

<210> SEQ ID NO 28
<211> LENGTH: 34
<212> TYPE: PRT
<213> ORGANISM: Influenza H5 Anhui

<400> SEQUENCE: 28

```
Ser Pro Leu Arg Glu Arg Arg Arg Lys Arg Gly Leu Phe Gly Ala Ile
1               5                   10                  15

Ala Gly Phe Ile Glu Gly Gly Trp Gln Gly Met Val Asp Gly Trp Tyr
            20                  25                  30

Gly Tyr
```

<210> SEQ ID NO 29
<211> LENGTH: 35
<212> TYPE: PRT
<213> ORGANISM: Influenza H5 Indo

<400> SEQUENCE: 29

Ser Pro Gln Arg Glu Ser Arg Arg Lys Lys Arg Gly Leu Phe Gly Ala
1               5                   10                  15

Ile Ala Gly Phe Ile Glu Gly Gly Trp Gln Gly Met Val Asp Gly Trp
            20                  25                  30

Tyr Gly Tyr
        35

<210> SEQ ID NO 30
<211> LENGTH: 35
<212> TYPE: PRT
<213> ORGANISM: Influenza H5 Vietnam

<400> SEQUENCE: 30

Ser Pro Gln Arg Glu Arg Arg Arg Lys Lys Arg Gly Leu Phe Gly Ala
1               5                   10                  15

Ile Ala Gly Phe Ile Glu Gly Gly Trp Gln Gly Met Val Asp Gly Trp
            20                  25                  30

Tyr Gly Tyr
        35

<210> SEQ ID NO 31
<211> LENGTH: 6861
<212> TYPE: DNA
<213> ORGANISM: Artificial sequence
<220> FEATURE:
<223> OTHER INFORMATION: Construct 1194

<400> SEQUENCE: 31
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860
gtggttaata tagctcaaat atatggtcaa gttcaataga ttaataatgg aaatatcagt 1920
tatcgaaatt cattaacaat caacttaacg ttattaacta ctaattttat atcatcccct 1980
ttgataaatg atagtacacc aattaggaag gagcatgctc gcctaggaga ttgtcgtttc 2040
ccgccttcag tttgcaagct gctctagccg tgtagccaat acgcaaaccg cctctccccg 2100
cgcgttggga attactagcg cgtgtcgaca cgcgtggcgc gccctagcag aaggcatgtt 2160
gttgtgactc cgaggggttg cctcaaactc tatcttataa ccggcgtgga ggcatggagg 2220
caagggcatt ttggtaattt aagtagttag tggaaaatga cgtcatttac ttaaagacga 2280
agtcttgcga caagggggc ccacgccgaa ttttaatatt accggcgtgg ccccacctta 2340
tcgcgagtgc tttagcacga gcggtccaga tttaaagtag aaaagttccc gcccactagg 2400
gttaaaggtg ttcacactat aaaagcatat acgatgtgat ggtatttgat aaagcgtata 2460
ttgtatcagg tatttccgtc ggatacgaat tattcgtaca agcttcttaa gccggtcaac 2520
atggtggagc acgacacact tgtctactcc aaaaatatca aagatacagt ctcagaagac 2580
caaagggcaa ttgagacttt tcaacaaagg gtaatatccg gaaacctcct cggattccat 2640
tgcccagcta tctgtcactt tattgtgaag atagtggaaa aggaaggtgg ctcctacaaa 2700
tgccatcatt gcgataaagg aaaggccatc gttgaagatg cctctgccga cagtggtccc 2760
aaagatggac ccccacccac gaggagcatc gtggaaaaag aagacgttcc aaccacgtct 2820
tcaaagcaag tggattgatg tgataacatg gtggagcacg acacacttgt ctactccaaa 2880
aatatcaaag atacagtctc agaagaccaa agggcaattg agacttttca acaaagggta 2940
atatccggaa acctcctcgg attccattgc ccagctatct gtcactttat tgtgaagata 3000
gtggaaaagg aaggtggctc ctacaaatgc catcattgcg ataaaggaaa ggccatcgtt 3060
gaagatgcct ctgccgacag tggtcccaaa gatggacccc cacccacgag gagcatcgtg 3120
gaaaaagaag acgttccaac cacgtcttca aagcaagtgg attgatgtga tatctccact 3180
gacgtaaggg atgacgcaca atcccactat ccttcgcaag acccttcctc tatataagga 3240
agttcatttc atttggagag gtattaaaat cttaataggt tttgataaaa gcgaacgtgg 3300
ggaaacccga accaaacctt cttctaaact ctctctcatc tctcttaaag caaacttctc 3360
tcttgtcttt cttgcgtgag cgatcttcaa cgttgtcaga tcgtgcttcg gcaccagtac 3420
aacgttttct ttcactgaag cgaaatcaaa gatctctttg tggacacgta gtgcggcgcc 3480
attaaataac gtgtacttgt cctattcttg tcggtgtggt cttgggaaaa gaaagcttgc 3540
tggaggctgc tgttcagccc catacattac ttgttacgat tctgctgact ttcggcgggt 3600
gcaatatctc tacttctgct tgacgaggta ttgttgcctg tacttctttc ttcttcttct 3660
tgctgattgg ttctataaga aatctagtat tttctttgaa acagagtttt cccgtggttt 3720
tcgaacttgg agaaagattg ttaagcttct gtatattctg cccaaatttg tcgggcccat 3780
ggcgaaaaac gttgcgattt tcggcttatt gttttctctt cttgtgttgg ttccttctca 3840
gatcttcgcc gcggctcctc agccaaaacg acaccccat ctgtctatcc actggcccct 3900
ggatctgctg cccaaactaa ctccatggtg accctgggat gcctggtcaa gggctatttc 3960
cctgagccag tgacagtgac ctggaactct ggatccctgt ccagcggtgt gcacaccttc 4020
ccagctgtcc tgcagtctga cctctacact ctgagcagct cagtgactgt cccctccagc 4080
acctggccca gcgagaccgt cacctgcaac gttgcccacc cggccagcag caccaaggtg 4140
gacaagaaaa ttgtgcccag ggattgtggt tgtaagcctt gcatatgtac agtcccagaa 4200
gtatcatctg tcttcatctt ccccccaaag cccaaggatg tgctcaccat tactctgact 4260
cctaaggtca cgtgtgttgt ggtagacatc agcaaggatg atcccgaggt ccagttcagc 4320
tggtttgtag atgatgtgga ggtgcacaca gctcagacgc aaccccggga ggagcagttc 4380
aacagcactt tccgctcagt cagtgaactt cccatcatgc accaggactg gctcaatggc 4440
aaggaaggcc tattttcttt agtttgaatt tactgttatt cggtgtgcat ttctatgttt 4500
ggtgagcggt tttctgtgct cagagtgtgt ttattttatg taatttaatt tctttgtgag 4560
ctcctgttta gcaggtcgtc ccttcagcaa ggacacaaaa agattttaat tttattaaaa 4620
aaaaaaaaaa aaaagaccgg gaattcgata tcaagcttat cgacctgcag atcgttcaaa 4680
catttggcaa taaagtttct taagattgaa tcctgttgcc ggtcttgcga tgattatcat 4740
ataatttctg ttgaattacg ttaagcatgt aataattaac atgtaatgca tgacgttatt 4800
tatgagatgg gtttttatga ttagagtccc gcaattatac atttaatacg cgatagaaaa 4860
caaaatatag cgcgcaaact aggataaatt atcgcgcgcg gtgtcatcta tgttactaga 4920
tctctagagt ctcaagcttg gcgcggggta ccgagctcga attccgagtg tacttcaagt 4980
cagttggaaa tcaataaaat gattatttta tgaatatatt tcattgtgca agtagataga 5040
aattacatat gttacataac acacgaaata aacaaaaaaa cacaatccaa aacaaacacc 5100
ccaaacaaaa taacactata tatatcctcg tatgaggaga ggcacgttca gtgactcgac 5160
gattcccgag caaaaaaagt ctccccgtca cacatatagt gggtgacgca attatcttca 5220
aagtaatcct tctgttgact tgtcattgat aacatccagt cttcgtcagg attgcaaaga 5280
attatagaag ggatcccacc ttttattttc ttcttttttc catatttagg gttgacagtg 5340
aaatcagact ggcaacctat taattgcttc cacaatggga cgaacttgaa ggggatgtcg 5400
tcgatgatat tataggtggc gtgttcatcg tagttggtga agtcgatggt cccgttccag 5460
tagttgtgtc gcccgagact tctagcccag gtggtctttc cggtacgagt tggtccgcag 5520
atgtagaggc tggggtgtct gaccccagtc cttccctcat cctggttaga tcggccatcc 5580
actcaaggtc agattgtgct tgatcgtagg agacaggatg tatgaaagtg taggcatcga 5640
tgcttacatg atataggtgc gtctctctcc agttgtgcag atcttcgtgg cagcggagat 5700
ctgattctgt gaagggcgac acgtactgct caggttgtgg aggaaataat ttgttggctg 5760
aatattccag ccattgaagc tttgttgccc attcatgagg gaattcttct ttgatcatgt 5820
caagatactc ctccttagac gttgcagtct ggataatagt tcgccatcgt gcgtcagatt 5880
tgcgaggaga gaccttatga tctcggaaat ctcctctggt tttaatatct ccgtcctttg 5940
atatgtaatc aaggacttgt ttagagtttc tagctggctg gatattaggg tgatttcctt 6000

```
caaaatcgaa aaaagaagga tccctaatac aaggtttttt atcaagctgg ataagagcat   6060

gatagtgggt agtgccatct tgatgaagct cagaagcaac accaaggaag aaaataagaa   6120

aaggtgtgag tttctcccag agaaactgga ataaatcatc tctttgagat gagcacttgg   6180

ggtaggtaag gaaaacatat ttagattgga gtctgaagtt cttgctagca gaaggcatgt   6240

tgttgtgact ccgaggggtt gcctcaaact ctatcttata accggcgtgg aggcatggag   6300

gcaagggcat tttggtaatt taagtagtta gtggaaaatg acgtcattta cttaaagacg   6360

aagtcttgcg acaagggggg cccacgccga attttaatat taccggcgtg gccccacctt   6420

atcgcgagtg ctttagcacg agcggtccag atttaaagta gaaaagttcc cgcccactag   6480

ggttaaaggt gttcacacta taaaagcata tacgatgtga tggtatttga tggagcgtat   6540

attgtatcag gtatttccgt cggatacgaa ttattcgtac ggccggccac tagtggcact   6600

ggccgtcgtt ttacaacgtc gtgactggga aaaccctggc gttacccaac ttaatcgcct   6660

tgcagcacat ccccctttcg ccagctggcg taatagcgaa gaggcccgca ccgatcgccc   6720

ttcccaacag ttgcgcagcc tgaatggcga atgctagagc agcttgagct tggatcagat   6780

tgtcgtttcc cgccttcagt ttaaactatc agtgtttgac aggatatatt ggcgggtaaa   6840

cctaagagaa aagagcgttt a                                             6861
```

<210> SEQ ID NO 32
<211> LENGTH: 5555
<212> TYPE: DNA
<213> ORGANISM: Artificial sequence
<220> FEATURE:
<223> OTHER INFORMATION: Cassette 1008

<400> SEQUENCE: 32

```
ctagcagaag gcatgttgtt gtgactccga ggggttgcct caaactctat cttataaccg     60

gcgtggaggc atggaggcaa gggcattttg gtaatttaag tagttagtgg aaaatgacgt    120

catttactta aagacgaagt cttgcgacaa ggggggccca cgccgaattt taatattacc    180

ggcgtggccc caccttatcg cgagtgcttt agcacgagcg gtccagattt aaagtagaaa    240

agttcccgcc cactagggtt aaaggtgttc acactataaa agcatatacg atgtgatggt    300

atttgataaa gcgtatattg tatcaggtat ttccgtcgga tacgaattat tcgtacaagc    360

ttcttaagcc ggtcaacatg gtggagcacg acacacttgt ctactccaaa aatatcaaag    420

atacagtctc agaagaccaa agggcaattg agacttttca acaaagggta atatccggaa    480

acctcctcgg attccattgc ccagctatct gtcactttat tgtgaagata gtggaaaagg    540

aaggtggctc ctacaaatgc catcattgcg ataaaggaaa ggccatcgtt gaagatgcct    600

ctgccgacag tggtcccaaa gatggacccc cacccacgag gagcatcgtg gaaaaagaag    660

acgttccaac cacgtcttca aagcaagtgg attgatgtga taacatggtg gagcacgaca    720

cacttgtcta ctccaaaaat atcaaagata cagtctcaga agaccaaagg gcaattgaga    780

cttttcaaca aagggtaata tccggaaacc tcctcggatt ccattgccca gctatctgtc    840

actttattgt gaagatagtg gaaaaggaag gtggctccta caaatgccat cattgcgata    900

aaggaaaggc catcgttgaa gatgcctctg ccgacagtgg tcccaaagat ggacccccac    960

ccacgaggag catcgtggaa aaagaagacg ttccaaccac gtcttcaaag caagtggatt   1020

gatgtgatat ctccactgac gtaagggatg acgcacaatc ccactatcct tcgcaagacc   1080

cttcctctat ataaggaagt tcatttcatt tggagaggta ttaaaatctt aataggtttt   1140
```

```
gataaaagcg aacgtgggga aacccgaacc aaaccttctt ctaaactctc tctcatctct   1200
cttaaagcaa acttctctct tgtctttctt gcgtgagcga tcttcaacgt tgtcagatcg   1260
tgcttcggca ccagtacaac gttttctttc actgaagcga aatcaaagat ctctttgtgg   1320
acacgtagtg cggcgccatt aaataacgtg tacttgtcct attcttgtcg gtgtggtctt   1380
gggaaaagaa agcttgctgg aggctgctgt tcagccccat acattacttg ttacgattct   1440
gctgactttc ggcgggtgca atatctctac ttctgcttga cgaggtattg ttgcctgtac   1500
ttctttcttc ttcttcttgc tgattggttc tataagaaat ctagtatttt ctttgaaaca   1560
gagttttccc gtggttttcg aacttggaga aagattgtta agcttctgta tattctgccc   1620
aaatttgtcg ggcccatggc gaaaaacgtt gcgattttcg gcttattgtt ttctcttctt   1680
gtgttggttc cttctcagat cttcgccgat cgaatctgca ctggaataac atcgtcaaac   1740
tcaccacatg tcgtcaaaac tgctactcaa ggggaggtca atgtgactgg tgtaatacca   1800
ctgacaacaa cacccaccaa atctcatttt gcaaatctca aaggaacaga aaccaggggg   1860
aaactatgcc caaaatgcct caactgcaca gatctggacg tagccttggg cagaccaaaa   1920
tgcacgggga aaataccctc ggcaagagtt tcaatactcc atgaagtcag acctgttaca   1980
tctgggtgct ttcctataat gcacgacaga acaaaaatta gacagctgcc taaccttctc   2040
cgaggatacg aacatatcag gttatcaacc cataacgtta tcaatgcaga aaatgcacca   2100
ggaggaccct acaaaattgg aacctcaggg tcttgcccta acattaccaa tggaaacgga   2160
tttttcgcaa caatggcttg ggccgtccca aaaaacgaca aaaacaaaac agcaacaaat   2220
ccattaacaa tagaagtacc atacatttgt acagaaggag aagaccaaat taccgtttgg   2280
gggttccact ctgacaacga gacccaaatg gcaaagctct atggggactc aaagccccag   2340
aagttcacct catctgccaa cggagtgacc acacattacg tttcacagat tggtggcttc   2400
ccaaatcaaa cagaagacgg aggactacca caaagtggta gaattgttgt tgattacatg   2460
gtgcaaaaat ctgggaaaac aggaacaatt acctatcaaa ggggtatttt attgcctcaa   2520
aaggtgtggt gcgcaagtgg caggagcaag gtaataaaag gatccttgcc tttaattgga   2580
gaagcagatt gcctccacga aaaatacggt ggattaaaca aaagcaagcc ttactacaca   2640
ggggaacatg caaaggccat aggaaattgc ccaatatggg tgaaaacacc cttgaagctg   2700
gccaatggaa ccaaatatag acctcctgca aaactattaa aggaaagggg tttcttcgga   2760
gctattgctg gtttcttaga aggaggatgg gaaggaatga ttgcaggttg gcacggatac   2820
acatcccatg gggcacatgg agtagcggtg gcagcagacc ttaagagcac tcaagaggcc   2880
ataaacaaga taacaaaaaa tctcaactct ttgagtgagc tggaagtaaa gaatcttcaa   2940
agactaagcg gtgccatgga tgaactccac aacgaaatac tagaactaga tgagaaagtg   3000
gatgatctca gagctgatac aataagctca caaatagaac tcgcagtcct gctttccaat   3060
gaaggaataa taaacagtga agatgaacat ctcttggcgc ttgaaagaaa gctgaagaaa   3120
atgctgggcc cctctgctgt agagataggg aatggatgct ttgaaaccaa acacaagtgc   3180
aaccagacct gtctcgacag aatagctgct ggtacctttg atgcaggaga attttctctc   3240
cccacctttg attcactgaa tattactgct gcatctttaa atgacgatgg attggataat   3300
catactatac tgctttacta ctcaactgct gcctccagtt tggctgtaac actgatgata   3360
gctatctttg ttgtttatat ggtctccaga gacaatgttt cttgctccat ctgtctataa   3420
aggcctattt tctttagttt gaatttactg ttattcggtg tgcatttcta tgtttggtga   3480
gcggttttct gtgctcagag tgtgtttatt ttatgtaatt taatttcttt gtgagctcct   3540
```

```
gtttagcagg tcgtcccttc agcaaggaca caaaaagatt ttaattttat taaaaaaaaa   3600

aaaaaaaaag accgggaatt cgatatcaag cttatcgacc tgcagatcgt tcaaacattt   3660

ggcaataaag tttcttaaga ttgaatcctg ttgccggtct tgcgatgatt atcatataat   3720

ttctgttgaa ttacgttaag catgtaataa ttaacatgta atgcatgacg ttatttatga   3780

gatgggtttt tatgattaga gtcccgcaat tatacattta atacgcgata gaaaacaaaa   3840

tatagcgcgc aaactaggat aaattatcgc gcgcggtgtc atctatgtta ctagatctct   3900

agagtctcaa gcttggcgcg ggtaccgag ctcgaattcc gagtgtactt caagtcagtt   3960

ggaaatcaat aaaatgatta ttttatgaat atatttcatt gtgcaagtag atagaaatta   4020

catatgttac ataacacacg aaataaacaa aaaaacacaa tccaaaacaa acaccccaaa   4080

caaaataaca ctatatatat cctcgtatga ggagaggcac gttcagtgac tcgacgattc   4140

ccgagcaaaa aaagtctccc cgtcacacat atagtgggtg acgcaattat cttcaaagta   4200

atccttctgt tgacttgtca ttgataacat ccagtcttcg tcaggattgc aaagaattat   4260

agaagggatc ccacctttta ttttcttctt ttttccatat ttagggttga cagtgaaatc   4320

agactggcaa cctattaatt gcttccacaa tgggacgaac ttgaagggga tgtcgtcgat   4380

gatattatag gtggcgtgtt catcgtagtt ggtgaagtcg atggtcccgt tccagtagtt   4440

gtgtcgcccg agacttctag cccaggtggt ctttccggta cgagttggtc cgcagatgta   4500

gaggctgggg tgtctgaccc cagtccttcc ctcatcctgg ttagatcggc catccactca   4560

aggtcagatt gtgcttgatc gtaggagaca ggatgtatga aagtgtaggc atcgatgctt   4620

acatgatata ggtgcgtctc tctccagttg tgcagatctt cgtggcagcg gagatctgat   4680

tctgtgaagg gcgacacgta ctgctcaggt tgtggaggaa ataatttgtt ggctgaatat   4740

tccagccatt gaagctttgt tgcccattca tgagggaatt cttctttgat catgtcaaga   4800

tactcctcct tagacgttgc agtctggata atagttcgcc atcgtgcgtc agatttgcga   4860

ggagagacct tatgatctcg gaaatctcct ctggttttaa tatctccgtc ctttgatatg   4920

taatcaagga cttgtttaga gtttctagct ggctggatat tagggtgatt tccttcaaaa   4980

tcgaaaaaag aaggatccct aatacaaggt tttttatcaa gctggataag agcatgatag   5040

tgggtagtgc catcttgatg aagctcagaa gcaacaccaa ggaagaaaat aagaaaaggt   5100

gtgagtttct cccagagaaa ctggaataaa tcatctcttt gagatgagca cttggggtag   5160

gtaaggaaaa catatttaga ttggagtctg aagttcttgc tagcagaagg catgttgttg   5220

tgactccgag ggttgcctc aaactctatc ttataaccgg cgtggaggca tggaggcaag   5280

ggcattttgg taatttaagt agttagtgga aaatgacgtc atttacttaa agacgaagtc   5340

ttgcgacaag gggggcccac gccgaatttt aatattaccg gcgtggcccc accttatcgc   5400

gagtgcttta gcacgagcgg tccagattta aagtagaaaa gttcccgccc actagggtta   5460

aaggtgttca cactataaaa gcatatacga tgtgatggta tttgatggag cgtatattgt   5520

atcaggtatt tccgtcggat acgaattatt cgtac                              5555
```

<210> SEQ ID NO 33
<211> LENGTH: 31
<212> TYPE: PRT
<213> ORGANISM: Influenza H6 Teal HK

<400> SEQUENCE: 33

```
Val Pro Gln Ile Glu Thr Arg Gly Leu Phe Gly Ala Ile Ala Gly Phe
1               5                   10                  15
```

```
Ile Glu Gly Gly Trp Thr Gly Met Ile Asp Gly Trp Tyr Gly Tyr
            20                  25                  30


<210> SEQ ID NO 34
<211> LENGTH: 42
<212> TYPE: PRT
<213> ORGANISM: Influenza H7 Eq Prague

<400> SEQUENCE: 34

Val Pro Glu Ala Pro Ala His Lys Gln Leu Thr His His Met Arg Lys
1               5                   10                  15

Lys Arg Gly Leu Phe Gly Ala Ile Ala Gly Phe Ile Glu Asn Gly Trp
            20                  25                  30

Glu Gly Leu Ile Asp Gly Trp Tyr Gly Tyr
        35                  40


<210> SEQ ID NO 35
<211> LENGTH: 31
<212> TYPE: PRT
<213> ORGANISM: Influenza H9A HK

<400> SEQUENCE: 35

Val Pro Ala Arg Ser Ser Arg Gly Leu Phe Gly Ala Ile Ala Gly Phe
1               5                   10                  15

Ile Glu Gly Gly Trp Pro Gly Leu Val Ala Gly Trp Tyr Gly Phe
            20                  25                  30


<210> SEQ ID NO 36
<211> LENGTH: 43
<212> TYPE: PRT
<213> ORGANISM: Influenza B Florida

<400> SEQUENCE: 36

Leu Lys Leu Ala Asn Gly Thr Lys Tyr Arg Pro Pro Ala Lys Leu Leu
1               5                   10                  15

Lys Glu Arg Gly Phe Phe Gly Ala Ile Ala Gly Phe Leu Glu Gly Gly
            20                  25                  30

Trp Glu Gly Met Ile Ala Gly Trp His Gly Tyr
        35                  40


<210> SEQ ID NO 37
<211> LENGTH: 43
<212> TYPE: PRT
<213> ORGANISM: Influenza B Malaysia

<400> SEQUENCE: 37

Leu Lys Leu Ala Asn Gly Thr Lys Tyr Arg Pro Pro Ala Lys Leu Leu
1               5                   10                  15

Lys Glu Arg Gly Phe Phe Gly Ala Ile Ala Gly Phe Leu Glu Gly Gly
            20                  25                  30

Trp Glu Gly Met Ile Ala Gly Trp His Gly Tyr
        35                  40


<210> SEQ ID NO 38
<211> LENGTH: 52
<212> TYPE: DNA
<213> ORGANISM: Artificial sequence
<220> FEATURE:
<223> OTHER INFORMATION: Construct 1059 1039 plus 1059.r

<400> SEQUENCE: 38
```

-continued cttcccatcc tccaccagga ggtctatatt tggttccatt ggccagcttc aa 52

<210> SEQ ID NO 39
<211> LENGTH: 52
<212> TYPE: DNA
<213> ORGANISM: Artificial sequence
<220> FEATURE:
<223> OTHER INFORMATION: Construct 1039 plus 1059.c

<400> SEQUENCE: 39
caaatataga cctcctggtg gaggatggga aggaatgatt gcaggttggc ac 52

<210> SEQ ID NO 40
<211> LENGTH: 5504
<212> TYPE: DNA
<213> ORGANISM: Artificial sequence
<220> FEATURE:
<223> OTHER INFORMATION: Cassette 1059

<400> SEQUENCE: 40
ctagcagaag gcatgttgtt gtgactccga ggggttgcct caaactctat cttataaccg 60
gcgtggaggc atggaggcaa gggcattttg gtaatttaag tagttagtgg aaaatgacgt 120
catttactta aagacgaagt cttgcgacaa ggggggccca cgccgaattt taatattacc 180
ggcgtggccc caccttatcg cgagtgcttt agcacgagcg gtccagattt aaagtagaaa 240
agttcccgcc cactagggtt aaaggtgttc acactataaa agcatatacg atgtgatggt 300
atttgataaa gcgtatattg tatcaggtat ttccgtcgga tacgaattat tcgtacaagc 360
ttcttaagcc ggtcaacatg gtggagcacg acacacttgt ctactccaaa aatatcaaag 420
atacagtctc agaagaccaa agggcaattg agacttttca acaaagggta atatccggaa 480
acctcctcgg attccattgc ccagctatct gtcactttat tgtgaagata gtggaaaagg 540
aaggtggctc ctacaaatgc catcattgcg ataaaggaaa ggccatcgtt gaagatgcct 600
ctgccgacag tggtcccaaa gatggacccc cacccacgag gagcatcgtg gaaaaagaag 660
acgttccaac cacgtcttca aagcaagtgg attgatgtga taacatggtg gagcacgaca 720
cacttgtcta ctccaaaaat atcaaagata cagtctcaga agaccaaagg gcaattgaga 780
cttttcaaca aagggtaata tccggaaacc tcctcggatt ccattgccca gctatctgtc 840
actttattgt gaagatagtg gaaaaggaag gtggctccta caaatgccat cattgcgata 900
aaggaaaggc catcgttgaa gatgcctctg ccgacagtgg tcccaaagat ggacccccac 960
ccacgaggag catcgtggaa aaagaagacg ttccaaccac gtcttcaaag caagtggatt 1020
gatgtgatat ctccactgac gtaagggatg acgcacaatc ccactatcct tcgcaagacc 1080
cttcctctat ataaggaagt tcatttcatt tggagaggta ttaaaatctt aataggtttt 1140
gataaaagcg aacgtgggga aacccgaacc aaaccttctt ctaaactctc tctcatctct 1200
cttaaagcaa acttctctct tgtctttctt gcgtgagcga tcttcaacgt tgtcagatcg 1260
tgcttcggca ccagtacaac gttttctttc actgaagcga aatcaaagat ctctttgtgg 1320
acacgtagtg cggcgccatt aaataacgtg tacttgtcct attcttgtcg gtgtggtctt 1380
gggaaaagaa agcttgctgg aggctgctgt tcagccccat acattacttg ttacgattct 1440
gctgactttc ggcgggtgca atatctctac ttctgcttga cgaggtattg ttgcctgtac 1500
ttctttcttc ttcttcttgc tgattggttc tataagaaat ctagtatttt ctttgaaaca 1560
gagttttccc gtggttttcg aacttggaga aagattgtta agcttctgta tattctgccc 1620
aaatttgtcg ggcccatggc gaaaaacgtt gcgattttcg gcttattgtt ttctcttctt 1680

```
gtgttggttc cttctcagat cttcgccgat cgaatctgca ctggaataac atcgtcaaac   1740
tcaccacatg tcgtcaaaac tgctactcaa ggggaggtca atgtgactgg tgtaatacca   1800
ctgacaacaa cacccaccaa atctcatttt gcaaatctca aaggaacaga aaccaggggg   1860
aaactatgcc caaaatgcct caactgcaca gatctggacg tagccttggg cagaccaaaa   1920
tgcacgggga aaataccctc ggcaagagtt tcaatactcc atgaagtcag acctgttaca   1980
tctgggtgct ttcctataat gcacgacaga acaaaaatta gacagctgcc taaccttctc   2040
cgaggatacg aacatatcag gttatcaacc cataacgtta tcaatgcaga aaatgcacca   2100
ggaggaccct acaaaattgg aacctcaggg tcttgcccta acattaccaa tggaaacgga   2160
tttttcgcaa caatggcttg ggccgtccca aaaaacgaca aaaacaaaac agcaacaaat   2220
ccattaacaa tagaagtacc atacatttgt acagaaggag aagaccaaat taccgtttgg   2280
gggttccact ctgacaacga gacccaaatg gcaaagctct atggggactc aaagccccag   2340
aagttcacct catctgccaa cggagtgacc acacattacg tttcacagat tggtggcttc   2400
ccaaatcaaa cagaagacgg aggactacca caaagtggta gaattgttgt tgattacatg   2460
gtgcaaaaat ctgggaaaac aggaacaatt acctatcaaa ggggtatttt attgcctcaa   2520
aaggtgtggt gcgcaagtgg caggagcaag gtaataaaag gatccttgcc tttaattgga   2580
gaagcagatt gcctccacga aaaatacggt ggattaaaca aaagcaagcc ttactacaca   2640
ggggaacatg caaaggccat aggaaattgc ccaatatggg tgaaaacacc cttgaagctg   2700
gccaatggaa ccaaatatag acctcctggt ggaggatggg aaggaatgat tgcaggttgg   2760
cacggataca catcccatgg ggcacatgga gtagcggtgg cagcagacct taagagcact   2820
caagaggcca taaacaagat aacaaaaaat ctcaactctt tgagtgagct ggaagtaaag   2880
aatcttcaaa gactaagcgg tgccatggat gaactccaca acgaaatact agaactagat   2940
gagaaagtgg atgatctcag agctgataca ataagctcac aaatagaact cgcagtcctg   3000
ctttccaatg aaggaataat aaacagtgaa gatgaacatc tcttggcgct tgaaagaaag   3060
ctgaagaaaa tgctgggccc ctctgctgta gagataggga atggatgctt tgaaaccaaa   3120
cacaagtgca accagacctg tctcgacaga atagctgctg gtacctttga tgcaggagaa   3180
ttttctctcc ccacctttga ttcactgaat attactgctg catctttaaa tgacgatgga   3240
ttggataatc atactatact gctttactac tcaactgctg cctccagttt ggctgtaaca   3300
ctgatgatag ctatctttgt tgtttatatg gtctccagag acaatgtttc ttgctccatc   3360
tgtctataaa ggcctatttt ctttagtttg aatttactgt tattcggtgt gcatttctat   3420
gtttggtgag cggttttctg tgctcagagt gtgtttattt tatgtaattt aatttctttg   3480
tgagctcctg tttagcaggt cgtcccttca gcaaggacac aaaaagattt taattttatt   3540
aaaaaaaaaa aaaaaaaaga ccgggaattc gatatcaagc ttatcgacct gcagatcgtt   3600
caaacatttg gcaataaagt ttcttaagat tgaatcctgt tgccggtctt gcgatgatta   3660
tcatataatt tctgttgaat tacgttaagc atgtaataat taacatgtaa tgcatgacgt   3720
tatttatgag atgggttttt atgattagag tcccgcaatt atacatttaa tacgcgatag   3780
aaaacaaaat atagcgcgca aactaggata aattatcgcg cgcggtgtca tctatgttac   3840
tagatctcta gagtctcaag cttggcgcgg ggtaccgagc tcgaattccg agtgtacttc   3900
aagtcagttg gaaatcaata aaatgattat tttatgaata tatttcattg tgcaagtaga   3960
tagaaattac atatgttaca taacacacga aataaacaaa aaaacacaat ccaaaacaaa   4020
```

-continued

```
caccccaaac aaaataacac tatatatatc ctcgtatgag gagaggcacg ttcagtgact   4080

cgacgattcc cgagcaaaaa aagtctcccc gtcacacata tagtgggtga cgcaattatc   4140

ttcaaagtaa tccttctgtt gacttgtcat tgataacatc cagtcttcgt caggattgca   4200

aagaattata gaagggatcc caccttttat tttcttcttt tttccatatt tagggttgac   4260

agtgaaatca gactggcaac ctattaattg cttccacaat gggacgaact tgaaggggat   4320

gtcgtcgatg atattatagg tggcgtgttc atcgtagttg gtgaagtcga tggtcccgtt   4380

ccagtagttg tgtcgcccga gacttctagc ccaggtggtc tttccggtac gagttggtcc   4440

gcagatgtag aggctggggt gtctgacccc agtccttccc tcatcctggt tagatcggcc   4500

atccactcaa ggtcagattg tgcttgatcg taggagacag gatgtatgaa agtgtaggca   4560

tcgatgctta catgatatag gtgcgtctct ctccagttgt gcagatcttc gtggcagcgg   4620

agatctgatt ctgtgaaggg cgacacgtac tgctcaggtt gtggaggaaa taatttgttg   4680

gctgaatatt ccagccattg aagctttgtt gcccattcat gagggaattc ttctttgatc   4740

atgtcaagat actcctcctt agacgttgca gtctggataa tagttcgcca tcgtgcgtca   4800

gatttgcgag gagagacctt atgatctcgg aaatctcctc tggttttaat atctccgtcc   4860

tttgatatgt aatcaaggac ttgtttagag tttctagctg gctggatatt agggtgattt   4920

ccttcaaaat cgaaaaaaga aggatcccta atacaaggtt ttttatcaag ctggataaga   4980

gcatgatagt gggtagtgcc atcttgatga agctcagaag caacaccaag gaagaaaata   5040

agaaaaggtg tgagtttctc ccagagaaac tggaataaat catctctttg agatgagcac   5100

ttggggtagg taaggaaaac atatttagat tggagtctga agttcttgct agcagaaggc   5160

atgttgttgt gactccgagg ggttgcctca aactctatct tataaccggc gtggaggcat   5220

ggaggcaagg gcattttggt aatttaagta gttagtggaa aatgacgtca tttacttaaa   5280

gacgaagtct tgcgacaagg ggggcccacg ccgaatttta atattaccgg cgtggcccca   5340

ccttatcgcg agtgctttag cacgagcggt ccagatttaa agtagaaaag ttcccgccca   5400

ctagggttaa aggtgttcac actataaaag catatacgat gtgatggtat ttgatggagc   5460

gtatattgta tcaggtattt ccgtcggata cgaattattc gtac                    5504
```

<210> SEQ ID NO 41
<211> LENGTH: 577
<212> TYPE: PRT
<213> ORGANISM: Artificial sequence
<220> FEATURE:
<223> OTHER INFORMATION: Amino acid sequence PDISP/HA influenza B/
Brisbane/60/2008 (deleted proteolytic loop)

<400> SEQUENCE: 41

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95
```

-continued

```
Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
```

```
        515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Ser Ile Cys
                565                 570                 575

Leu


<210> SEQ ID NO 42
<211> LENGTH: 1707
<212> TYPE: DNA
<213> ORGANISM: Influenza H5 A/Indonesia/5/2005 (H5N1)

<400> SEQUENCE: 42

atggagaaaa tagtgcttct tcttgcaata gtcagtcttg ttaaaagtga tcagatttgc      60

attggttacc atgcaaacaa ttcaacagag caggttgaca caatcatgga aaagaacgtt     120

actgttacac atgcccaaga catactggaa aagacacaca acgggaagct ctgcgatcta     180

gatggagtga agcctctaat tttaagagat tgtagtgtag ctggatggct cctcgggaac     240

ccaatgtgtg acgaattcat caatgtaccg gaatggtctt acatagtgga gaaggccaat     300

ccaaccaatg acctctgtta cccagggagt ttcaacgact atgaagaact gaaacaccta     360

ttgagcagaa taaaccattt tgagaaaatt caaatcatcc ccaaaagttc ttggtccgat     420

catgaagcct catcaggagt tagctcagca tgtccatacc tgggaagtcc ctcctttttt     480

agaaatgtgg tatggcttat caaaaagaac agtacatacc caacaataaa gaaaagctac     540

aataatacca accaagagga tcttttggta ctgtggggaa ttcaccatcc taatgatgcg     600

gcagagcaga caaggctata tcaaaaccca accacctata tttccattgg gacatcaaca     660

ctaaaccaga gattggtacc aaaaatagct actagatcca aagtaaacgg gcaaagtgga     720

aggatggagt tcttctggac aattttaaaa cctaatgatg caatcaactt cgagagtaat     780

ggaaatttca ttgctccaga atatgcatac aaaattgtca agaaagggga ctcagcaatt     840

atgaaaagtg aattggaata tggtaactgc aacaccaagt gtcaaactcc aatgggggcg     900

ataaactcta gtatgccatt ccacaacata caccctctca ccatcgggga atgccccaaa     960

tatgtgaaat caaacagatt agtccttgca acagggctca gaaatagccc tcaaagagag    1020

agcagaagaa aaaagagagg actatttgga gctatagcag gttttataga gggaggatgg    1080

cagggaatgg tagatggttg gtatgggtac caccatagca atgagcaggg gagtgggtac    1140

gctgcagaca aagaatccac tcaaaaggca atagatggag tcaccaataa ggtcaactca    1200

atcattgaca aaatgaacac tcagtttgag gccgttggaa gggaatttaa taacttagaa    1260

aggagaatag agaatttaaa caagaagatg gaagacgggt ttctagatgt ctggacttat    1320

aatgccgaac ttctggttct catggaaaat gagagaactc tagactttca tgactcaaat    1380

gttaagaacc tctacgacaa ggtccgacta cagcttaggg ataatgcaaa ggagctgggt    1440

aacggttgtt tcgagttcta tcacaaatgt gataatgaat gtatggaaag tataagaaac    1500

ggaacgtaca actatccgca gtattcagaa gaagcaagat taaaaagaga ggaaataagt    1560

ggggtaaaat tggaatcaat aggaacttac caaatactgt caatttattc aacagtggcg    1620

agttccctag cactggcaat catgatggct ggtctatctt tatggatgtg ctccaatgga    1680

tcgttacaat gcagaatttg catttaa                                        1707
```

<210> SEQ ID NO 43
<211> LENGTH: 1734
<212> TYPE: DNA
<213> ORGANISM: Artificial sequence
<220> FEATURE:
<223> OTHER INFORMATION: nucleotide sequence PDISP/HA influenza B/
Brisbane/60/2008 (deleted proteolytic loop)

<400> SEQUENCE: 43
atggcgaaaa acgttgcgat tttcggctta ttgttttctc ttcttgtgtt ggttccttct 60
cagatcttcg ccgatcgaat ctgcactgga ataacatcgt caaactcacc acatgtcgtc 120
aaaactgcta ctcaagggga ggtcaatgtg actggtgtaa taccactgac aacaacaccc 180
accaaatctc attttgcaaa tctcaaagga acagaaacca gggggaaact atgcccaaaa 240
tgcctcaact gcacagatct ggacgtagcc ttgggcagac caaaatgcac ggggaaaata 300
ccctcggcaa gagtttcaat actccatgaa gtcagacctg ttacatctgg gtgctttcct 360
ataatgcacg acagaacaaa aattagacag ctgcctaacc ttctccgagg atacgaacat 420
atcaggttat caacccataa cgttatcaat gcagaaaatg caccaggagg accctacaaa 480
attggaacct cagggtcttg ccctaacatt accaatggaa acggattttt cgcaacaatg 540
gcttgggccg tcccaaaaaa cgacaaaaac aaaacagcaa caaatccatt aacaatagaa 600
gtaccataca tttgtacaga aggagaagac caaattaccg tttgggggtt ccactctgac 660
aacgagaccc aaatggcaaa gctctatggg gactcaaagc cccagaagtt cacctcatct 720
gccaacggag tgaccacaca ttacgtttca cagattggtg gcttcccaaa tcaaacagaa 780
gacggaggac taccacaaag tggtagaatt gttgttgatt acatggtgca aaaatctggg 840
aaaacaggaa caattaccta tcaaaggggt attttattgc ctcaaaaggt gtggtgcgca 900
agtggcagga gcaaggtaat aaaaggatcc ttgcctttaa ttggagaagc agattgcctc 960
cacgaaaaat acggtggatt aaacaaaagc aagccttact acacagggga acatgcaaag 1020
gccataggaa attgcccaat atgggtgaaa acacccttga agctggccaa tggaaccaaa 1080
tatagacctc ctggtggagg atgggaagga atgattgcag gttggcacgg atacacatcc 1140
catggggcac atggagtagc ggtggcagca gaccttaaga gcactcaaga ggccataaac 1200
aagataacaa aaaatctcaa ctctttgagt gagctggaag taaagaatct tcaaagacta 1260
agcggtgcca tggatgaact ccacaacgaa atactagaac tagatgagaa agtggatgat 1320
ctcagagctg atacaataag ctcacaaata gaactcgcag tcctgctttc caatgaagga 1380
ataataaaca gtgaagatga acatctcttg gcgcttgaaa gaaagctgaa gaaaatgctg 1440
ggcccctctg ctgtagagat agggaatgga tgctttgaaa ccaaacacaa gtgcaaccag 1500
acctgtctcg acagaatagc tgctggtacc tttgatgcag gagaattttc tctccccacc 1560
tttgattcac tgaatattac tgctgcatct ttaaatgacg atggattgga taatcatact 1620
atactgcttt actactcaac tgctgcctcc agtttggctg taacactgat gatagctatc 1680
tttgttgttt atatggtctc cagagacaat gtttcttgct ccatctgtct ataa 1734

<210> SEQ ID NO 44
<211> LENGTH: 19
<212> TYPE: PRT
<213> ORGANISM: Artificial sequence
<220> FEATURE:
<223> OTHER INFORMATION: H5/Indo cleavage site natural sequence

<400> SEQUENCE: 44

```
Thr Gly Leu Arg Asn Ser Pro Gln Arg Glu Ser Arg Arg Lys Lys Arg
1               5                   10                  15

Gly Leu Phe
```

<210> SEQ ID NO 45
<211> LENGTH: 15
<212> TYPE: PRT
<213> ORGANISM: Artificial sequence
<220> FEATURE:
<223> OTHER INFORMATION: H5/Indo modified cleavage site (TETR)

<400> SEQUENCE: 45

```
Thr Gly Leu Arg Asn Ser Pro Gln Thr Glu Thr Arg Gly Leu Phe
1               5                   10                  15
```

<210> SEQ ID NO 46
<211> LENGTH: 15
<212> TYPE: PRT
<213> ORGANISM: Artificial sequence
<220> FEATURE:
<223> OTHER INFORMATION: H5/Indo modified cleavage site (TETQ)

<400> SEQUENCE: 46

```
Thr Gly Leu Arg Asn Ser Pro Gln Thr Glu Thr Gln Gly Leu Phe
1               5                   10                  15
```

<210> SEQ ID NO 47
<211> LENGTH: 11
<212> TYPE: PRT
<213> ORGANISM: Artificial sequence
<220> FEATURE:
<223> OTHER INFORMATION: H1 cleavage site

<400> SEQUENCE: 47

```
Asn Ile Pro Ser Ile Gln Ser Arg Gly Leu Phe
1               5                   10
```

<210> SEQ ID NO 48
<211> LENGTH: 11
<212> TYPE: PRT
<213> ORGANISM: Artificial sequence
<220> FEATURE:
<223> OTHER INFORMATION: H3 cleavage site

<400> SEQUENCE: 48

```
Asn Val Pro Glu Lys Gln Thr Arg Gly Ile Phe
1               5                   10
```

<210> SEQ ID NO 49
<211> LENGTH: 46
<212> TYPE: PRT
<213> ORGANISM: Artificial sequence
<220> FEATURE:
<223> OTHER INFORMATION: Construct 1462 IF-HAB110.S1+3c

<400> SEQUENCE: 49

```
Ala Ala Ala Thr Thr Thr Gly Thr Cys Gly Gly Gly Cys Cys Cys Ala
1               5                   10                  15

Thr Gly Ala Ala Gly Gly Cys Ala Ala Thr Ala Ala Thr Thr Gly Thr
            20                  25                  30

Ala Cys Thr Ala Cys Thr Cys Ala Thr Gly Gly Thr Ala Gly
        35                  40                  45
```

<210> SEQ ID NO 50
<211> LENGTH: 52

<212> TYPE: DNA
<213> ORGANISM: Artificial sequence
<220> FEATURE:
<223> OTHER INFORMATION: Construct No. 1462 IF-HAB110.s1-4r

<400> SEQUENCE: 50
actaaagaaa ataggccttt atagacagat ggagcatgaa acgttgtctc tg 52

<210> SEQ ID NO 51
<211> LENGTH: 1755
<212> TYPE: DNA
<213> ORGANISM: Influenza HA B wisconsin

<400> SEQUENCE: 51
atgaaggcaa taattgtact actcatggta gtaacatcca atgcagatcg aatctgcact 60
gggataacat cttcaaactc acctcatgtg gtcaaaacag ctactcaagg ggaggtcaat 120
gtgactggcg tgataccact gacaacaaca ccaacaaaat cttattttgc aaatctcaaa 180
ggaacaagga ccagagggaa actatgcccg gactgtctca actgtacaga tctggatgtg 240
gccttgggca ggccaatgtg tgtggggacc acaccttctg ctaaagcttc aatactccac 300
gaggtcagac ctgttacatc cgggtgcttt cctataatgc acgacagaac aaaaatcagg 360
caactaccca atcttctcag aggatatgaa aatatcaggt tatcaaccca aaacgttatc 420
gatgcagaaa aagcaccagg aggaccctac agacttggaa cctcaggatc ttgccctaac 480
gctaccagta aaatcggatt ttttgcaaca atggcttggg ctgtcccaaa ggacaactac 540
aaaaatgcaa cgaacccact aacagtagaa gtaccataca tttgtacaga aggggaagac 600
caaattactg tttgggggtt ccattcagat aacaaaaccc aaatgaagag cctctatgga 660
gactcaaatc ctcaaaagtt cacctcatct gctaatggag taaccacaca ttatgtttct 720
cagattggcg acttcccaga tcaaacagaa gacggaggac taccacaaag cggcagaatt 780
gttgttgatt acatgatgca aaaacctggg aaaacaggaa caattgtcta tcaaagaggt 840
gttttgttgc ctcaaaaggt gtggtgcgcg agtggcagga gcaaagtaat aaaagggtca 900
ttgcctttaa ttggtgaagc agattgcctt catgaaaaat acggtggatt aaacaaaagc 960
aagccttact acacaggaga acatgcaaaa gccataggaa attgcccaat atgggtaaaa 1020
acacctttga agcttgccaa tggaaccaaa tatagacctc ctgcaaaact attgaaggaa 1080
aggggtttct tcggagctat tgctggtttc ctagaaggag gatgggaagg aatgattgca 1140
ggttggcacg gatacacatc tcacggagca catggagtgg cagtggcggc agaccttaag 1200
agtacacaag aagctataaa taagataaca aaaaatctca attctttgag tgagctagaa 1260
gtaaagaacc ttcaaagact aagtggtgcc atggatgaac tccacaacga aatactcgag 1320
ctggatgaga aagtggatga tctcagagct gacactataa gctcacaaat agaacttgca 1380
gtcttgcttt ccaacgaagg aataataaac agtgaagacg agcatctatt ggcacttgag 1440
agaaaactaa agaaaatgct gggtccctct gctgtagaca taggaaacgg atgcttcgaa 1500
accaaacaca aatgcaacca gacctgctta gacaggatag ctgctggcac ctttaatgca 1560
ggagaatttt ctctccccac ttttgattca ttgaacatta ctgctgcatc tttaaatgat 1620
gatggattgg ataaccatac tatactgctc tattactcaa ctgctgcttc tagtttggct 1680
gtaacattaa tgctagctat ttttattgtt tatatggtct ccagagacaa cgtttcatgc 1740
tccatctgtc tataa 1755

<210> SEQ ID NO 52

<211> LENGTH: 6745
<212> TYPE: DNA
<213> ORGANISM: Artificial sequence
<220> FEATURE:
<223> OTHER INFORMATION: Construct 193

<400> SEQUENCE: 52
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860
gtggttaata tagctcaaat atatggtcaa gttcaataga ttaataatgg aaatatcagt 1920
tatcgaaatt cattaacaat caacttaacg ttattaacta ctaattttat atcatcccct 1980
ttgataaatg atagtacacc aattaggaag gagcatgctc gcctaggaga ttgtcgtttc 2040
ccgccttcag tttgcaagct gctctagccg tgtagccaat acgcaaaccg cctctccccg 2100
cgcgttggga attactagcg cgtgtcgaga cgcgttgttg ttgtgactcc gaggggttgc 2160
ctcaaactct atcttataac cggcgtggag gcatggaggc aggggtattt tggtcatttt 2220
aatagatagt ggaaaatgac gtggaattta cttaaagacg aagtctttgc gacaaggggg 2280
ggcccacgcc gaatttaata ttaccggcgt ggcccccct tatcgcgagt gctttagcac 2340
gagcggtcca gatttaaagt agaaaatttc ccgcccacta gggttaaagg tgttcacact 2400
ataaaagcat atacgatgtg atggtatttg gtcgacaagc ttgcatgccg gtcaacatgg 2460
tggagcacga cacacttgtc tactccaaaa atatcaaaga tacagtctca gaagaccaaa 2520
gggcaattga gacttttcaa caaagggtaa tatccggaaa cctcctcgga ttccattgcc 2580
cagctatctg tcactttatt gtgaagatag tggaaaagga aggtggctcc tacaaatgcc 2640
atcattgcga taaaggaaag gccatcgttg aagatgcctc tgccgacagt ggtcccaaag 2700
atggaccccc acccacgagg agcatcgtgg aaaaagaaga cgttccaacc acgtcttcaa 2760
agcaagtgga ttgatgtgat aacatggtgg agcacgacac acttgtctac tccaaaaata 2820
tcaaagatac agtctcagaa gaccaaaggg caattgagac ttttcaacaa agggtaatat 2880
ccggaaacct cctcggattc cattgcccag ctatctgtca ctttattgtg aagatagtgg 2940
aaaaggaagg tggctcctac aaatgccatc attgcgataa aggaaaggcc atcgttgaag 3000
atgcctctgc cgacagtggt cccaaagatg gacccccacc cacgaggagc atcgtggaaa 3060
aagaagacgt tccaaccacg tcttcaaagc aagtggattg atgtgatatc tccactgacg 3120
taagggatga cgcacaatcc cactatcctt cgcaagaccc ttcctctata taaggaagtt 3180
catttcattt ggagaggtat taaaatctta ataggttttg ataaaagcga acgtggggaa 3240
acccgaacca aaccttcttc taaactctct ctcatctctc ttaaagcaaa cttctctctt 3300
gtctttcttg cgtgagcgat cttcaacgtt gtcagatcgt gcttcggcac cagtacaacg 3360
ttttctttca ctgaagcgaa atcaaagatc tctttgtgga cacgtagtgc ggcgccatta 3420
aataacgtgt acttgtccta ttcttgtcgg tgtggtcttg ggaaaagaaa gcttgctgga 3480
ggctgctgtt cagccccata cattacttgt tacgattctg ctgactttcg gcgggtgcaa 3540
tatctctact tctgcttgac gaggtattgt tgcctgtact tctttcttct tcttcttgct 3600
gattggttct ataagaaatc tagtattttc tttgaaacag agttttcccg tggttttcga 3660
acttggagaa agattgttaa gcttctgtat attctgccca aatttgtcgg gcccgcggat 3720
ggcgaaaaac gttgcgattt tcggcttatt gttttctctt cttgtgttgg ttccttctca 3780
gatcttcgcc tgcaggctcc tcagccaaaa cgacaccccc atctgtctat ccactggccc 3840
ctggatctgc tgcccaaact aactccatgg tgaccctggg atgcctggtc aagggctatt 3900
tccctgagcc agtgacagtg acctggaact ctggatccct gtccagcggt gtgcacacct 3960
tcccagctgt cctgcagtct gacctctaca ctctgagcag ctcagtgact gtcccctcca 4020
gcacctggcc cagcgagacc gtcacctgca acgttgccca cccggccagc agcaccaagg 4080
tggacaagaa aattgtgccc agggattgtg gttgtaagcc ttgcatatgt acagtcccag 4140
aagtatcatc tgtcttcatc ttccccccaa agcccaagga tgtgctcacc attactctga 4200
ctcctaaggt cacgtgtgtt gtggtagaca tcagcaagga tgatcccgag gtccagttca 4260
gctggtttgt agatgatgtg gaggtgcaca cagctcagac gcaaccccgg gaggagcagt 4320
tcaacagcac tttccgctca gtcagtgaac ttcccatcat gcaccaggac tggctcaatg 4380
gcaaggagcg atcgctcacc atcaccatca ccatcaccat caccattaaa ggcctatttt 4440
ctttagtttg aatttactgt tattcggtgt gcatttctat gtttggtgag cggttttctg 4500

```
tgctcagagt gtgtttattt tatgtaattt aatttctttg tgagctcctg tttagcaggt   4560
cgtcccttca gcaaggacac aaaaagattt taattttatt aaaaaaaaaa aaaaaaaaga   4620
ccgggaattc gatatcaagc ttatcgacct gcagatcgtt caaacatttg gcaataaagt   4680
ttcttaagat tgaatcctgt tgccggtctt gcgatgatta tcatataatt tctgttgaat   4740
tacgttaagc atgtaataat taacatgtaa tgcatgacgt tatttatgag atgggttttt   4800
atgattagag tcccgcaatt atacatttaa tacgcgatag aaaacaaaat atagcgcgca   4860
aactaggata aattatcgcg cgcggtgtca tctatgttac tagatctcta gagtctcaag   4920
cttggcgcgc cataaaatga ttattttatg aatatatttc attgtgcaag tagatagaaa   4980
ttacatatgt tacataacac acgaaataaa caaaaaaaga caatccaaaa acaaacaccc   5040
caaaaaaaat aatcacttta gataaactcg tatgaggaga ggcacgttca gtgactcgac   5100
gattcccgag caaaaaaagt ctccccgtca cacatatagt gggtgacgca attatcttta   5160
aagtaatcct tctgttgact tgtcattgat aacatccagt cttcgtcagg attgcaaaga   5220
attatagaag ggatcccacc ttttatttc ttctttttc catatttagg gttgacagtg   5280
aaatcagact ggcaacctat taattgcttc cacaatggga cgaacttgaa ggggatgtcg   5340
tcgatgatat tataggtggc gtgttcatcg tagttggtga aatcgatggt accgttccaa   5400
tagttgtgtc gtccgagact tctagcccag gtggtctttc cggtacgagt tggtccgcag   5460
atgtagaggc tggggtgtcg gattccattc cttccattgt cctggttaaa tcggccatcc   5520
attcaaggtc agattgagct tgttggtatg agacaggatg tatgtaagta taagcgtcta   5580
tgcttacatg gtatagatgg gtttccctcc aggagtgtag atcttcgtgg cagcgaagat   5640
ctgattctgt gaagggcgac acatacggtt caggttgtgg agggaataat ttgttggctg   5700
aatattccag ccattgaagt tttgttgccc attcatgagg gaattcttcc ttgatcatgt   5760
caagatattc ctccttagac gttgcagtct ggataatagt tctccatcgt gcgtcagatt   5820
tgcgaggaga gaccttatga tctcggaaat ctcctctggt tttaatatct ccgtcctttg   5880
atatgtaatc aaggacttgt ttagagtttc tagctggctg gatattaggg tgatttcctt   5940
caaaatcgaa aaaagaagga tccctaatac aaggtttttt atcaagctgg agaagagcat   6000
gatagtgggt agtgccatct tgatgaagct cagaagcaac accaaggaag aaaataagaa   6060
aaggtgtgag tttctcccag agaaactgga ataaatcatc tctttgagat gagcacttgg   6120
gataggtaag gaaaacatat ttagattgga gtctgaagtt cttactagca gaaggcatgt   6180
tgttgtgact ccgaggggtt gcctcaaact ctatcttata accggcgtgg aggcatggag   6240
gcaggggtat tttggtcatt ttaatagata gtggaaaatg acgtggaatt tacttaaaga   6300
cgaagtcttt gcgacaaggg ggggcccacg ccgaatttaa tattaccggc gtggcccccc   6360
cttatcgcga gtgctttagc acgagcggtc cagatttaaa gtagaaaatt tcccgcccac   6420
tagggttaaa ggtgttcaca ctataaaagc atatacgatg tgatggtatt tgactagtgg   6480
cactggccgt cgttttacaa cgtcgtgact gggaaaaccc tggcgttacc caacttaatc   6540
gccttgcagc acatccccct ttcgccagct ggcgtaatag cgaagaggcc cgcaccgatc   6600
gcccttccca acagttgcgc agcctgaatg gcgaatgcta gagcagcttg agcttggatc   6660
agattgtcgt ttcccgcctt cagtttaaac tatcagtgtt tgacaggata tattggcggg   6720
taaacctaag agaaaagagc gttta                                         6745
```

<210> SEQ ID NO 53
<211> LENGTH: 3495

```
<212> TYPE: DNA
<213> ORGANISM: Artificial sequence
<220> FEATURE:
<223> OTHER INFORMATION: Cassette 1462

<400> SEQUENCE: 53

gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaacg ttttctttca ctgaagcgaa atcaaagatc tctttgtgga cacgtagtgc    960

ggcgccatta aataacgtgt acttgtccta ttcttgtcgg tgtggtcttg ggaaaagaaa   1020

gcttgctgga ggctgctgtt cagccccata cattacttgt tacgattctg ctgactttcg   1080

gcgggtgcaa tatctctact tctgcttgac gaggtattgt tgcctgtact tctttcttct   1140

tcttcttgct gattggttct ataagaaatc tagtattttc tttgaaacag agttttcccg   1200

tggttttcga acttggagaa agattgttaa gcttctgtat attctgccca aatttgtcgg   1260

gcccatgaag gcaataattg tactactcat ggtagtaaca tccaatgcag atcgaatctg   1320

cactgggata acatcttcaa actcacctca tgtggtcaaa acagctactc aaggggaggt   1380

caatgtgact ggcgtgatac cactgacaac aacaccaaca aaatcttatt ttgcaaatct   1440

caaaggaaca aggaccagag ggaaactatg cccggactgt ctcaactgta cagatctgga   1500

tgtggccttg ggcaggccaa tgtgtgtggg gaccacacct tctgctaaag cttcaatact   1560

ccacgaggtc agacctgtta catccgggtg ctttcctata atgcacgaca gaacaaaaat   1620

caggcaacta cccaatcttc tcagaggata tgaaaatatc aggttatcaa cccaaaacgt   1680

tatcgatgca gaaaaagcac caggaggacc ctacagactt ggaacctcag gatcttgccc   1740

taacgctacc agtaaaatcg gatttttttgc aacaatggct tgggctgtcc caaaggacaa   1800

ctacaaaaat gcaacgaacc cactaacagt agaagtacca tacatttgta cagaaggggga   1860

agaccaaatt actgtttggg ggttccattc agataacaaa acccaaatga agagcctcta   1920

tggagactca aatcctcaaa agttcacctc atctgctaat ggagtaacca cacattatgt   1980

ttctcagatt ggcgacttcc cagatcaaac agaagacgga ggactaccac aaagcggcag   2040

aattgttgtt gattacatga tgcaaaaacc tgggaaaaca ggaacaattg tctatcaaag   2100

aggtgttttg ttgcctcaaa aggtgtggtg cgcgagtggc aggagcaaag taataaaagg   2160
```

```
gtcattgcct ttaattggtg aagcagattg ccttcatgaa aaatacggtg gattaaacaa   2220

aagcaagcct tactacacag gagaacatgc aaaagccata ggaaattgcc caatatgggt   2280

aaaaacacct ttgaagcttg ccaatggaac caaatataga cctcctgcaa aactattgaa   2340

ggaaaggggt ttcttcggag ctattgctgg tttcctagaa ggaggatggg aaggaatgat   2400

tgcaggttgg cacggataca catctcacgg agcacatgga gtggcagtgg cggcagacct   2460

taagagtaca caagaagcta taaataagat aacaaaaaat ctcaattctt tgagtgagct   2520

agaagtaaag aaccttcaaa gactaagtgg tgccatggat gaactccaca acgaaatact   2580

cgagctggat gagaaagtgg atgatctcag agctgacact ataagctcac aaatagaact   2640

tgcagtcttg ctttccaacg aaggaataat aaacagtgaa gacgagcatc tattggcact   2700

tgagagaaaa ctaaagaaaa tgctgggtcc ctctgctgta gacataggaa acggatgctt   2760

cgaaaccaaa cacaaatgca accagacctg cttagacagg atagctgctg gcacctttaa   2820

tgcaggagaa ttttctctcc ccacttttga ttcattgaac attactgctg catctttaaa   2880

tgatgatgga ttggataacc atactatact gctctattac tcaactgctg cttctagttt   2940

ggctgtaaca ttaatgctag ctatttttat tgtttatatg gtctccagag acaacgtttc   3000

atgctccatc tgtctataaa ggcctatttt ctttagtttg aatttactgt tattcggtgt   3060

gcatttctat gtttggtgag cggttttctg tgctcagagt gtgtttattt tatgtaattt   3120

aatttctttg tgagctcctg tttagcaggt cgtcccttca gcaaggacac aaaaagattt   3180

taattttatt aaaaaaaaaa aaaaaaaaga ccgggaattc gatatcaagc ttatcgacct   3240

gcagatcgtt caaacatttg gcaataaagt ttcttaagat tgaatcctgt tgccggtctt   3300

gcgatgatta tcatataatt tctgttgaat tacgttaagc atgtaataat taacatgtaa   3360

tgcatgacgt tatttatgag atgggttttt atgattagag tcccgcaatt atacatttaa   3420

tacgcgatag aaaacaaaat atagcgcgca aactaggata aattatcgcg cgcggtgtca   3480

tctatgttac tagat                                                    3495
```

<210> SEQ ID NO 54
<211> LENGTH: 584
<212> TYPE: PRT
<213> ORGANISM: Influenza B/Wisconsin/1/2010

<400> SEQUENCE: 54

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
```

```
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560
```

Val Thr Leu Met Leu Ala Ile Phe Ile Val Tyr Met Val Ser Arg Asp
565 570 575

Asn Val Ser Cys Ser Ile Cys Leu
580

<210> SEQ ID NO 55
<211> LENGTH: 56
<212> TYPE: DNA
<213> ORGANISM: Artificial sequence
<220> FEATURE:
<223> OTHER INFORMATION: Construct 1467 HAB110(PrL-).r

<400> SEQUENCE: 55
tccttcccat cctccaccag gaggtctata tttggttcca ttggcaagct tcaaag 56

<210> SEQ ID NO 56
<211> LENGTH: 52
<212> TYPE: DNA
<213> ORGANISM: Artificial sequence
<220> FEATURE:
<223> OTHER INFORMATION: Construct 1467 HAB110(PrL-).c

<400> SEQUENCE: 56
atatagacct cctggtggag gatgggaagg aatgattgca ggttggcacg ga 52

<210> SEQ ID NO 57
<211> LENGTH: 3444
<212> TYPE: DNA
<213> ORGANISM: Artificial sequence
<220> FEATURE:
<223> OTHER INFORMATION: Construct 1467

<400> SEQUENCE: 57
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140

```
tcttcttgct gattggttct ataagaaatc tagtattttc tttgaaacag agttttcccg   1200
tggttttcga acttggagaa agattgttaa gcttctgtat attctgccca aatttgtcgg   1260
gcccatgaag gcaataattg tactactcat ggtagtaaca tccaatgcag atcgaatctg   1320
cactgggata acatcttcaa actcacctca tgtggtcaaa acagctactc aaggggaggt   1380
caatgtgact ggcgtgatac cactgacaac aacaccaaca aaatcttatt ttgcaaatct   1440
caaaggaaca aggaccagag ggaaactatg cccggactgt ctcaactgta cagatctgga   1500
tgtggccttg ggcaggccaa tgtgtgtggg gaccacacct tctgctaaag cttcaatact   1560
ccacgaggtc agacctgtta catccgggtg ctttcctata atgcacgaca gaacaaaaat   1620
caggcaacta cccaatcttc tcagaggata tgaaaatatc aggttatcaa cccaaaacgt   1680
tatcgatgca gaaaaagcac caggaggacc ctacagactt ggaacctcag gatcttgccc   1740
taacgctacc agtaaaatcg gatttttgc aacaatggct tgggctgtcc caaaggacaa   1800
ctacaaaaat gcaacgaacc cactaacagt agaagtacca tacatttgta cagaaggga   1860
agaccaaatt actgtttggg ggttccattc agataacaaa acccaaatga agagcctcta   1920
tggagactca aatcctcaaa agttcacctc atctgctaat ggagtaacca cacattatgt   1980
ttctcagatt ggcgacttcc cagatcaaac agaagacgga ggactaccac aaagcggcag   2040
aattgttgtt gattacatga tgcaaaaacc tgggaaaaca ggaacaattg tctatcaaag   2100
aggtgttttg ttgcctcaaa aggtgtggtg cgcgagtggc aggagcaaag taataaaagg   2160
gtcattgcct ttaattggtg aagcagattg ccttcatgaa aaatacggtg gattaaacaa   2220
aagcaagcct tactacacag gagaacatgc aaaagccata ggaaattgcc caatatgggt   2280
aaaaacacct ttgaagcttg ccaatggaac caaatataga cctcctggtg gaggatggga   2340
aggaatgatt gcaggttggc acggatacac atctcacgga gcacatggag tggcagtggc   2400
ggcagacctt aagagtacac aagaagctat aaataagata acaaaaaatc tcaattcttt   2460
gagtgagcta gaagtaaaga accttcaaag actaagtggt gccatggatg aactccacaa   2520
cgaaatactc gagctggatg agaaagtgga tgatctcaga gctgacacta taagctcaca   2580
aatagaactt gcagtcttgc tttccaacga aggaataata aacagtgaag acgagcatct   2640
attggcactt gagagaaaac taaagaaaat gctgggtccc tctgctgtag acataggaaa   2700
cggatgcttc gaaaccaaac acaaatgcaa ccagacctgc ttagacagga tagctgctgg   2760
cacctttaat gcaggagaat ttctctccc cacttttgat tcattgaaca ttactgctgc   2820
atctttaaat gatgatggat tggataacca tactatactg ctctattact caactgctgc   2880
ttctagtttg gctgtaacat taatgctagc tatttttatt gtttatatgg tctccagaga   2940
caacgtttca tgctccatct gtctataaag gcctattttc tttagtttga atttactgtt   3000
attcggtgtg catttctatg tttggtgagc ggttttctgt gctcagagtg tgtttatttt   3060
atgtaattta atttctttgt gagctcctgt ttagcaggtc gtcccttcag caaggacaca   3120
aaaagatttt aattttatta aaaaaaaaaa aaaaaaagac cgggaattcg atatcaagct   3180
tatcgacctg cagatcgttc aaacatttgg caataaagtt tcttaagatt gaatcctgtt   3240
gccggtcttg cgatgattat catataattt ctgttgaatt acgttaagca tgtaataatt   3300
aacatgtaat gcatgacgtt atttatgaga tgggttttta tgattagagt cccgcaatta   3360
tacatttaat acgcgataga aaacaaaata tagcgcgcaa actaggataa attatcgcgc   3420
gcggtgtcat ctatgttact agat                                          3444
```

<210> SEQ ID NO 58
<211> LENGTH: 567
<212> TYPE: PRT
<213> ORGANISM: Artificial sequence
<220> FEATURE:
<223> OTHER INFORMATION: Amino acid sequence HA influenza B/Wisconsin/1/ 2010 (deleted PL)

<400> SEQUENCE: 58

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365
```

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

His Thr Ile Leu Leu Tyr Tyr Ser Thr Ala Ala Ser Ser Leu Ala Val
    530                 535                 540

Thr Leu Met Leu Ala Ile Phe Ile Val Tyr Met Val Ser Arg Asp Asn
545                 550                 555                 560

Val Ser Cys Ser Ile Cys Leu
                565

<210> SEQ ID NO 59
<211> LENGTH: 11
<212> TYPE: PRT
<213> ORGANISM: Artificial sequence
<220> FEATURE:
<223> OTHER INFORMATION: B cleavage site

<400> SEQUENCE: 59

Pro Ala Lys Leu Leu Lys Glu Arg Gly Phe Phe
1               5                   10

<210> SEQ ID NO 60
<211> LENGTH: 19
<212> TYPE: PRT
<213> ORGANISM: Artificial sequence
<220> FEATURE:
<223> OTHER INFORMATION: H5/Indo natural cleavage site

<400> SEQUENCE: 60

Thr Gly Leu Arg Asn Ser Pro Gln Arg Glu Ser Arg Arg Lys Lys Arg
1               5                   10                  15

Gly Leu Phe

<210> SEQ ID NO 61
<211> LENGTH: 15
<212> TYPE: PRT
<213> ORGANISM: Artificial sequence
<220> FEATURE:
<223> OTHER INFORMATION: H5/Indo modified cleavage site

<400> SEQUENCE: 61

Thr Gly Leu Arg Asn Ser Pro Gln Thr Glu Thr Arg Gly Leu Phe
1               5                   10                  15

<210> SEQ ID NO 62
<211> LENGTH: 15
<212> TYPE: PRT
<213> ORGANISM: Artificial sequence
<220> FEATURE:
<223> OTHER INFORMATION: H5/Indo modified cleavage site

<400> SEQUENCE: 62

Thr Gly Leu Arg Asn Ser Pro Gln Thr Glu Thr Gln Gly Leu Phe
1 5 10 15

<210> SEQ ID NO 63
<211> LENGTH: 11
<212> TYPE: PRT
<213> ORGANISM: Artificial sequence
<220> FEATURE:
<223> OTHER INFORMATION: H1/Brisbane modified cleavage site

<400> SEQUENCE: 63

Asn Ile Pro Ser Ile Gln Ser Gln Gly Leu Phe
1 5 10

<210> SEQ ID NO 64
<211> LENGTH: 11
<212> TYPE: PRT
<213> ORGANISM: Artificial sequence
<220> FEATURE:
<223> OTHER INFORMATION: H3/Brisbane modified cleavage site

<400> SEQUENCE: 64

Asn Val Pro Glu Ile Gln Thr Gln Gly Ile Phe
1 5 10

<210> SEQ ID NO 65
<211> LENGTH: 11
<212> TYPE: PRT
<213> ORGANISM: Artificial sequence
<220> FEATURE:
<223> OTHER INFORMATION: B/Florida, B/Brisbane modified cleavage site

<400> SEQUENCE: 65

Pro Ala Ile Leu Leu Asn Ile Gln Gly Phe Phe
1 5 10

<210> SEQ ID NO 66
<211> LENGTH: 19
<212> TYPE: PRT
<213> ORGANISM: Artificial sequence
<220> FEATURE:
<223> OTHER INFORMATION: A/H3/HA0 Consensus

<400> SEQUENCE: 66

Asn Val Pro Glu Lys Gln Thr Arg Gly Ile Phe Gly Ala Ile Ala Gly
1 5 10 15

Phe Ile Glu

<210> SEQ ID NO 67
<211> LENGTH: 19
<212> TYPE: PRT
<213> ORGANISM: Artificial sequence
<220> FEATURE:
<223> OTHER INFORMATION: A/H1/HA0 Consensus

<400> SEQUENCE: 67

Asn Ile Pro Ser Ile Gln Ser Arg Gly Leu Phe Gly Ala Ile Ala Gly 1 5 10 15

Phe Ile Glu

<210> SEQ ID NO 68
<211> LENGTH: 19
<212> TYPE: PRT
<213> ORGANISM: Artificial sequence
<220> FEATURE:
<223> OTHER INFORMATION: B/HA0 Consensus

<400> SEQUENCE: 68

Pro Ala Lys Leu Leu Lys Glu Arg Gly Phe Phe Gly Ala Ile Ala Gly
1 5 10 15

Phe Leu Glu

<210> SEQ ID NO 69
<211> LENGTH: 16
<212> TYPE: PRT
<213> ORGANISM: Artificial sequence
<220> FEATURE:
<223> OTHER INFORMATION: H5 Anhui proteolytic loop deletion

<400> SEQUENCE: 69

Ser Pro Leu Gly Gly Trp Gln Gly Met Val Asp Gly Trp Tyr Gly Tyr
1 5 10 15

<210> SEQ ID NO 70
<211> LENGTH: 16
<212> TYPE: PRT
<213> ORGANISM: Artificial sequence
<220> FEATURE:
<223> OTHER INFORMATION: H5 Indo proteolytic loop deletion

<400> SEQUENCE: 70

Ser Pro Gln Gly Gly Trp Gln Gly Met Val Asp Gly Trp Tyr Gly Tyr
1 5 10 15

<210> SEQ ID NO 71
<211> LENGTH: 16
<212> TYPE: PRT
<213> ORGANISM: Artificial sequence
<220> FEATURE:
<223> OTHER INFORMATION: H5 Vietnam proteolytic loop deletion

<400> SEQUENCE: 71

Ser Pro Gln Gly Gly Trp Gln Gly Met Val Asp Gly Trp Tyr Gly Tyr
1 5 10 15

<210> SEQ ID NO 72
<211> LENGTH: 25
<212> TYPE: PRT
<213> ORGANISM: Artificial sequence
<220> FEATURE:
<223> OTHER INFORMATION: B Florida proteolytic loop deletion

<400> SEQUENCE: 72

Leu Lys Leu Ala Asn Gly Thr Lys Tyr Arg Pro Pro Gly Gly Trp Glu
1 5 10 15

Gly Met Ile Ala Gly Trp His Gly Tyr
20 25

<210> SEQ ID NO 73
<211> LENGTH: 25
<212> TYPE: PRT
<213> ORGANISM: Artificial sequence
<220> FEATURE:
<223> OTHER INFORMATION: B Malaysia proteolytic loop deletion

<400> SEQUENCE: 73

Leu Lys Leu Ala Asn Gly Thr Lys Tyr Arg Pro Pro Gly Gly Trp Glu
1 5 10 15

Gly Met Ile Ala Gly Trp His Gly Tyr
20 25

<210> SEQ ID NO 74
<211> LENGTH: 45
<212> TYPE: DNA
<213> ORGANISM: Artificial sequence
<220> FEATURE:
<223> OTHER INFORMATION: Primer MutCleavage-H5(Indo).r

<400> SEQUENCE: 74
tagtcctctt gtctctgttt gagggctatt tctgagccct gttgc 45

<210> SEQ ID NO 75
<211> LENGTH: 45
<212> TYPE: DNA
<213> ORGANISM: Artificial sequence
<220> FEATURE:
<223> OTHER INFORMATION: Primer MutCleavage-H5(Indo).c

<400> SEQUENCE: 75
tagccctcaa acagagacaa gaggactatt tggagctata gcagg 45

<210> SEQ ID NO 76
<211> LENGTH: 3435
<212> TYPE: DNA
<213> ORGANISM: Artificial sequence
<220> FEATURE:
<223> OTHER INFORMATION: Cassette 676

<400> SEQUENCE: 76
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020

```
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggag aaaatagtgc ttcttcttgc aatagtcagt cttgttaaaa gtgatcagat   1320
ttgcattggt taccatgcaa acaattcaac agagcaggtt gacacaatca tggaaaagaa   1380
cgttactgtt acacatgccc aagacatact ggaaaagaca cacaacggga agctctgcga   1440
tctagatgga gtgaagcctc taattttaag agattgtagt gtagctggat ggctcctcgg   1500
gaacccaatg tgtgacgaat tcatcaatgt accggaatgg tcttacatag tggagaaggc   1560
caatccaacc aatgacctct gttacccagg gagtttcaac gactatgaag aactgaaaca   1620
cctattgagc agaataaacc attttgagaa aattcaaatc atccccaaaa gttcttggtc   1680
cgatcatgaa gcctcatcag gagttagctc agcatgtcca tacctgggaa gtccctcctt   1740
ttttagaaat gtggtatggc ttatcaaaaa gaacagtaca tacccaacaa taaagaaaag   1800
ctacaataat accaaccaag aggatctttt ggtactgtgg ggaattcacc atcctaatga   1860
tgcggcagag cagacaaggc tatatcaaaa cccaaccacc tatatttcca ttgggacatc   1920
aacactaaac cagagattgg taccaaaaat agctactaga tccaaagtaa acgggcaaag   1980
tggaaggatg gagttcttct ggacaatttt aaaacctaat gatgcaatca acttcgagag   2040
taatggaaat ttcattgctc cagaatatgc atacaaaatt gtcaagaaag gggactcagc   2100
aattatgaaa agtgaattgg aatatggtaa ctgcaacacc aagtgtcaaa ctccaatggg   2160
ggcgataaac tctagtatgc cattccacaa catacaccct ctcaccatcg ggaatgcccc   2220
caaatatgtg aaatcaaaca gattagtcct tgcaacaggg ctcagaaata gccctcaaac   2280
agagacaaga ggactatttg gagctatagc aggttttata gagggaggat ggcagggaat   2340
ggtagatggt tggtatgggt accaccatag caatgagcag gggagtgggt acgctgcaga   2400
caaagaatcc actcaaaagg caatagatgg agtcaccaat aaggtcaact caatcattga   2460
caaaatgaac actcagtttg aggccgttgg aagggaattt aataacttag aaaggagaat   2520
agagaattta aacaagaaga tggaagacgg gtttctagat gtctggactt ataatgccga   2580
acttctggtt ctcatggaaa atgagagaac tctagacttt catgactcaa atgttaagaa   2640
cctctacgac aaggtccgac tacagcttag ggataatgca aaggagctgg gtaacggttg   2700
tttcgagttc tatcacaaat gtgataatga atgtatggaa agtataagaa acggaacgta   2760
caactatccg cagtattcag aagaagcaag attaaaaaga gaggaaataa gtggggtaaa   2820
attggaatca ataggaactt accaaatact gtcaatttat tcaacagtgg cgagttccct   2880
agcactggca atcatgatgg ctggtctatc tttatggatg tgctccaatg gatcgttaca   2940
atgcagaatt tgcatttaaa ggcctatttt ctttagtttg aatttactgt tattcggtgt   3000
gcatttctat gtttggtgag cggttttctg tgctcagagt gtgtttattt tatgtaattt   3060
aatttctttg tgagctcctg tttagcaggt cgtcccttca gcaaggacac aaaaagattt   3120
taattttatt aaaaaaaaaa aaaaaaaaga ccgggaattc gatatcaagc ttatcgacct   3180
gcagatcgtt caaacatttg gcaataaagt ttcttaagat tgaatcctgt tgccggtctt   3240
gcgatgatta tcatataatt tctgttgaat tacgttaagc atgtaataat taacatgtaa   3300
tgcatgacgt tatttatgag atgggttttt atgattagag tcccgcaatt atacatttaa   3360
tacgcgatag aaaacaaaat atagcgcgca aactaggata aattatcgcg cgcggtgtca   3420
```

```
tctatgttac tagat                                                     3435


<210> SEQ ID NO 77
<211> LENGTH: 564
<212> TYPE: PRT
<213> ORGANISM: Artificial sequence
<220> FEATURE:
<223> OTHER INFORMATION: Amino acid sequence influenza A/Indonesia/5/
      2005 (H5N1) TETR cleavage site mutant.

<400> SEQUENCE: 77

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Thr Glu Thr Arg Gly Leu Phe Gly Ala Ile Ala Gly Phe Ile
            340                 345                 350
```

```
Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Met Ala Gly Leu Ser Leu Trp Met Cys Ser Asn Gly Ser Leu Gln Cys
545                 550                 555                 560

Arg Ile Cys Ile


<210> SEQ ID NO 78
<211> LENGTH: 48
<212> TYPE: DNA
<213> ORGANISM: Artificial sequence
<220> FEATURE:
<223> OTHER INFORMATION: Primer H5I505_TETQ.r

<400> SEQUENCE: 78

tccaaatagt ccttgtgtct ctgtttgagg gctatttctg agccctgt                  48


<210> SEQ ID NO 79
<211> LENGTH: 48
<212> TYPE: DNA
<213> ORGANISM: Artificial sequence
<220> FEATURE:
<223> OTHER INFORMATION: Primer H5I505_TETQ.c

<400> SEQUENCE: 79

aaatagccct caaacagaga cacaaggact atttggagct atagcagg                  48


<210> SEQ ID NO 80
<211> LENGTH: 3435
<212> TYPE: DNA
<213> ORGANISM: Artificial sequence
<220> FEATURE:
<223> OTHER INFORMATION: Cassette 766

<400> SEQUENCE: 80

gtcaacatgg tggagcacga cacacttgtc tactccaaaa atatcaaaga tacagtctca     60

gaagaccaaa gggcaattga gacttttcaa caaagggtaa tatccggaaa cctcctcgga    120
```

```
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggag aaaatagtgc ttcttcttgc aatagtcagt cttgttaaaa gtgatcagat   1320
ttgcattggt taccatgcaa acaattcaac agagcaggtt gacacaatca tggaaaagaa   1380
cgttactgtt acacatgccc aagacatact ggaaaagaca cacaacggga agctctgcga   1440
tctagatgga gtgaagcctc taattttaag agattgtagt gtagctggat ggctcctcgg   1500
gaacccaatg tgtgacgaat tcatcaatgt accggaatgg tcttacatag tggagaaggc   1560
caatccaacc aatgacctct gttacccagg gagtttcaac gactatgaag aactgaaaca   1620
cctattgagc agaataaacc attttgagaa aattcaaatc atccccaaaa gttcttggtc   1680
cgatcatgaa gcctcatcag gagttagctc agcatgtcca tacctgggaa gtccctcctt   1740
ttttagaaat gtggtatggc ttatcaaaaa gaacagtaca tacccaacaa taaagaaaag   1800
ctacaataat accaaccaag aggatctttt ggtactgtgg ggaattcacc atcctaatga   1860
tgcggcagag cagacaaggc tatatcaaaa cccaaccacc tatatttcca ttgggacatc   1920
aacactaaac cagagattgg taccaaaaat agctactaga tccaaagtaa acgggcaaag   1980
tggaaggatg gagttcttct ggacaatttt aaaacctaat gatgcaatca acttcgagag   2040
taatggaaat ttcattgctc cagaatatgc atacaaaatt gtcaagaaag gggactcagc   2100
aattatgaaa agtgaattgg aatatggtaa ctgcaacacc aagtgtcaaa ctccaatggg   2160
ggcgataaac tctagtatgc cattccacaa catacaccct ctcaccatcg gggaatgccc   2220
caaatatgtg aaatcaaaca gattagtcct tgcaacaggg ctcagaaata gccctcaaac   2280
agagacacaa ggactatttg gagctatagc aggttttata gagggaggat ggcagggaat   2340
ggtagatggt tggtatgggt accaccatag caatgagcag gggagtgggt acgctgcaga   2400
caaagaatcc actcaaaagg caatagatgg agtcaccaat aaggtcaact caatcattga   2460
```

```
caaaatgaac actcagtttg aggccgttgg aagggaattt aataacttag aaaggagaat   2520

agagaattta aacaagaaga tggaagacgg gtttctagat gtctggactt ataatgccga   2580

acttctggtt ctcatggaaa atgagagaac tctagacttt catgactcaa atgttaagaa   2640

cctctacgac aaggtccgac tacagcttag ggataatgca aaggagctgg gtaacggttg   2700

tttcgagttc tatcacaaat gtgataatga atgtatggaa agtataagaa acggaacgta   2760

caactatccg cagtattcag aagaagcaag attaaaaaga gaggaaataa gtggggtaaa   2820

attggaatca ataggaactt accaaatact gtcaatttat tcaacagtgg cgagttccct   2880

agcactggca atcatgatgg ctggtctatc tttatggatg tgctccaatg gatcgttaca   2940

atgcagaatt tgcatttaaa ggcctatttt ctttagtttg aatttactgt tattcggtgt   3000

gcatttctat gtttggtgag cggttttctg tgctcagagt gtgtttattt tatgtaattt   3060

aatttctttg tgagctcctg tttagcaggt cgtcccttca gcaaggacac aaaaagattt   3120

taattttatt aaaaaaaaaa aaaaaaaaga ccgggaattc gatatcaagc ttatcgacct   3180

gcagatcgtt caaacatttg gcaataaagt ttcttaagat tgaatcctgt tgccggtctt   3240

gcgatgatta tcatataatt tctgttgaat tacgttaagc atgtaataat taacatgtaa   3300

tgcatgacgt tatttatgag atgggttttt atgattagag tcccgcaatt atacatttaa   3360

tacgcgatag aaaacaaaat atagcgcgca aactaggata aattatcgcg cgcggtgtca   3420

tctatgttac tagat                                                    3435
```

```
<210> SEQ ID NO 81
<211> LENGTH: 564
<212> TYPE: PRT
<213> ORGANISM: Artificial sequence
<220> FEATURE:
<223> OTHER INFORMATION: Amino acid sequence influenza A/Indonesia/5/
      2005 (H5N1) TETQ cleavage site mutant

<400> SEQUENCE: 81

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
```

```
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Thr Glu Thr Gln Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Met Ala Gly Leu Ser Leu Trp Met Cys Ser Asn Gly Ser Leu Gln Cys
545                 550                 555                 560

Arg Ile Cys Ile


<210> SEQ ID NO 82
<211> LENGTH: 50
<212> TYPE: DNA
<213> ORGANISM: Artificial sequence
<220> FEATURE:
```

<223> OTHER INFORMATION: Primer H5I505(PrL-).r

<400> SEQUENCE: 82
ctgccatcct ccgccagggc tatttctgag ccctgttgca aggactaatc 50

<210> SEQ ID NO 83
<211> LENGTH: 52
<212> TYPE: DNA
<213> ORGANISM: Artificial sequence
<220> FEATURE:
<223> OTHER INFORMATION: Primer H5I505(PrL-).c

<400> SEQUENCE: 83
gaaatagccc tggcggagga tggcagggaa tggtagatgg ttggtatggg ta 52

<210> SEQ ID NO 84
<211> LENGTH: 3390
<212> TYPE: DNA
<213> ORGANISM: Artificial sequence
<220> FEATURE:
<223> OTHER INFORMATION: Cassette 928

<400> SEQUENCE: 84
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccatggag aaaatagtgc ttcttcttgc aatagtcagt cttgttaaaa gtgatcagat 1320
ttgcattggt taccatgcaa acaattcaac agagcaggtt gacacaatca tggaaaagaa 1380
cgttactgtt acacatgccc aagacatact ggaaaagaca cacaacggga agctctgcga 1440
tctagatgga gtgaagcctc taattttaag agattgtagt gtagctggat ggctcctcgg 1500
gaacccaatg tgtgacgaat tcatcaatgt accggaatgg tcttacatag tggagaaggc 1560

-continued

```
caatccaacc aatgacctct gttacccagg gagtttcaac gactatgaag aactgaaaca   1620
cctattgagc agaataaacc attttgagaa aattcaaatc atccccaaaa gttcttggtc   1680
cgatcatgaa gcctcatcag gagttagctc agcatgtcca tacctgggaa gtccctcctt   1740
ttttagaaat gtggtatggc ttatcaaaaa gaacagtaca tacccaacaa taaagaaaag   1800
ctacaataat accaaccaag aggatctttt ggtactgtgg ggaattcacc atcctaatga   1860
tgcggcagag cagacaaggc tatatcaaaa cccaaccacc tatatttcca ttgggacatc   1920
aacactaaac cagagattgg taccaaaaat agctactaga tccaaagtaa acgggcaaag   1980
tggaaggatg gagttcttct ggacaatttt aaaacctaat gatgcaatca acttcgagag   2040
taatggaaat ttcattgctc cagaatatgc atacaaaatt gtcaagaaag ggactcagc   2100
aattatgaaa agtgaattgg aatatggtaa ctgcaacacc aagtgtcaaa ctccaatggg   2160
ggcgataaac tctagtatgc cattccacaa catacaccct ctcaccatcg ggaatgccc   2220
caaatatgtg aaatcaaaca gattagtcct tgcaacaggg ctcagaaata gccctggcgg   2280
aggatggcag ggaatggtag atggttggta tgggtaccac catagcaatg agcaggggag   2340
tgggtacgct gcagacaaag aatccactca aaaggcaata gatggagtca ccaataaggt   2400
caactcaatc attgacaaaa tgaacactca gtttgaggcc gttggaaggg aatttaataa   2460
cttagaaagg agaatagaga atttaaacaa gaagatggaa gacgggtttc tagatgtctg   2520
gacttataat gccgaacttc tggttctcat ggaaaatgag agaactctag actttcatga   2580
ctcaaatgtt aagaacctct acgacaaggt ccgactacag cttagggata atgcaaagga   2640
gctgggtaac ggttgtttcg agttctatca caaatgtgat aatgaatgta tggaaagtat   2700
aagaaacgga acgtacaact atccgcagta ttcagaagaa gcaagattaa aaagagagga   2760
aataagtggg gtaaaattgg aatcaatagg aacttaccaa atactgtcaa tttattcaac   2820
agtggcgagt tccctagcac tggcaatcat gatggctggt ctatctttat ggatgtgctc   2880
caatggatcg ttacaatgca gaatttgcat ttaaaggcct attttcttta gtttgaattt   2940
actgttattc ggtgtgcatt tctatgtttg gtgagcggtt ttctgtgctc agagtgtgtt   3000
tattttatgt aatttaattt ctttgtgagc tcctgtttag caggtcgtcc cttcagcaag   3060
gacacaaaaa gattttaatt ttattaaaaa aaaaaaaaaa aaagaccggg aattcgatat   3120
caagcttatc gacctgcaga tcgttcaaac atttggcaat aaagtttctt aagattgaat   3180
cctgttgccg gtcttgcgat gattatcata taatttctgt tgaattacgt taagcatgta   3240
ataattaaca tgtaatgcat gacgttattt atgagatggg tttttatgat tagagtcccg   3300
caattataca tttaatacgc gatagaaaac aaaatatagc gcgcaaacta ggataaatta   3360
tcgcgcgcgg tgtcatctat gttactagat                                    3390
```

<210> SEQ ID NO 85
<211> LENGTH: 549
<212> TYPE: PRT
<213> ORGANISM: Artificial sequence
<220> FEATURE:
<223> OTHER INFORMATION: Amino acid sequence influenza A/Indonesia/5/
      2005 (H5N1) with deleted proteolytic loop.

<400> SEQUENCE: 85

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30
```

```
Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gly Gly Gly Trp Gln Gly Met Val Asp Gly Trp Tyr Gly Tyr His
            340                 345                 350

His Ser Asn Glu Gln Gly Ser Gly Tyr Ala Ala Asp Lys Glu Ser Thr
        355                 360                 365

Gln Lys Ala Ile Asp Gly Val Thr Asn Lys Val Asn Ser Ile Ile Asp
    370                 375                 380

Lys Met Asn Thr Gln Phe Glu Ala Val Gly Arg Glu Phe Asn Asn Leu
385                 390                 395                 400

Glu Arg Arg Ile Glu Asn Leu Asn Lys Lys Met Glu Asp Gly Phe Leu
                405                 410                 415

Asp Val Trp Thr Tyr Asn Ala Glu Leu Leu Val Leu Met Glu Asn Glu
            420                 425                 430

Arg Thr Leu Asp Phe His Asp Ser Asn Val Lys Asn Leu Tyr Asp Lys
        435                 440                 445
```

```
Val Arg Leu Gln Leu Arg Asp Asn Ala Lys Glu Leu Gly Asn Gly Cys
    450                 455                 460

Phe Glu Phe Tyr His Lys Cys Asp Asn Glu Cys Met Glu Ser Ile Arg
465                 470                 475                 480

Asn Gly Thr Tyr Asn Tyr Pro Gln Tyr Ser Glu Glu Ala Arg Leu Lys
                485                 490                 495

Arg Glu Glu Ile Ser Gly Val Lys Leu Glu Ser Ile Gly Thr Tyr Gln
            500                 505                 510

Ile Leu Ser Ile Tyr Ser Thr Val Ala Ser Ser Leu Ala Leu Ala Ile
        515                 520                 525

Met Met Ala Gly Leu Ser Leu Trp Met Cys Ser Asn Gly Ser Leu Gln
    530                 535                 540

Cys Arg Ile Cys Ile
545


<210> SEQ ID NO 86
<211> LENGTH: 40
<212> TYPE: DNA
<213> ORGANISM: Artificial sequence
<220> FEATURE:
<223> OTHER INFORMATION: Construct 1029 IF-S2+S4-B Bris.c

<400> SEQUENCE: 86

tctcagatct tcgccgatcg aatctgcact ggaataacat                          40


<210> SEQ ID NO 87
<211> LENGTH: 43
<212> TYPE: DNA
<213> ORGANISM: Artificial sequence
<220> FEATURE:
<223> OTHER INFORMATION: Construct 1029 IF-S1a4-B Bris.r

<400> SEQUENCE: 87

actaaagaaa ataggccttt atagacagat ggagcaagaa aca                      43


<210> SEQ ID NO 88
<211> LENGTH: 1758
<212> TYPE: DNA
<213> ORGANISM: Artificial sequence
<220> FEATURE:
<223> OTHER INFORMATION: Synthesized HA B Brisbane gene

<400> SEQUENCE: 88

atgaaggcaa taattgtact actcatggta gtaacatcca atgcagatcg aatctgcact     60

ggaataacat cgtcaaactc accacatgtc gtcaaaactg ctactcaagg ggaggtcaat    120

gtgactggtg taataccact gacaacaaca cccaccaaat ctcattttgc aaatctcaaa    180

ggaacagaaa ccaggggggaa actatgccca aaatgcctca actgcacaga tctggacgta    240

gccttgggca gaccaaaatg cacggggaaa ataccctcgg caagagtttc aatactccat    300

gaagtcagac ctgttacatc tgggtgcttt cctataatgc acgacagaac aaaaattaga    360

cagctgccta accttctccg aggatacgaa catatcaggt tatcaaccca taacgttatc    420

aatgcagaaa atgcaccagg aggaccctac aaaattggaa cctcagggtc ttgccctaac    480

attaccaatg gaaacggatt tttcgcaaca atggcttggg ccgtcccaaa aaacgacaaa    540

aacaaaacag caacaaatcc attaacaata gaagtaccat acatttgtac agaaggagaa    600

gaccaaatta ccgtttgggg gttccactct gacaacgaga cccaaatggc aaagctctat    660

ggggactcaa agccccagaa gttcacctca tctgccaacg gagtgaccac acattacgtt    720
```

-continued

```
tcacagattg gtggcttccc aaatcaaaca gaagacggag gactaccaca aagtggtaga    780
attgttgttg attacatggt gcaaaaatct gggaaaacag gaacaattac ctatcaaagg    840
ggtattttat tgcctcaaaa ggtgtggtgc gcaagtggca ggagcaaggt aataaaagga    900
tccttgcctt taattggaga agcagattgc ctccacgaaa aatacggtgg attaaacaaa    960
agcaagcctt actacacagg ggaacatgca aaggccatag gaaattgccc aatatgggtg   1020
aaaacaccct tgaagctggc caatggaacc aaatatagac ctcctgcaaa actattaaag   1080
gaaaggggtt tcttcggagc tattgctggt ttcttagaag gaggatggga aggaatgatt   1140
gcaggttggc acggatacac atcccatggg gcacatggag tagcggtggc agcagacctt   1200
aagagcactc aagaggccat aaacaagata acaaaaaatc tcaactcttt gagtgagctg   1260
gaagtaaaga atcttcaaag actaagcggt gccatggatg aactccacaa cgaaatacta   1320
gaactagatg agaaagtgga tgatctcaga gctgatacaa taagctcaca aatagaactc   1380
gcagtcctgc tttccaatga aggaataata aacagtgaag atgaacatct cttggcgctt   1440
gaaagaaagc tgaagaaaat gctgggcccc tctgctgtag agatagggaa tggatgcttt   1500
gaaaccaaac acaagtgcaa ccagacctgt ctcgacagaa tagctgctgg tacctttgat   1560
gcaggagaat ttctctccc cacctttgat tcactgaata ttactgctgc atctttaaat   1620
gacgatggat tggataatca tactatactg ctttactact caactgctgc ctccagtttg   1680
gctgtaacac tgatgatagc tatctttgtt gtttatatgg tctccagaga caatgtttct   1740
tgctccatct gtctataa                                                 1758
```

<210> SEQ ID NO 89
<211> LENGTH: 3525
<212> TYPE: DNA
<213> ORGANISM: Artificial sequence
<220> FEATURE:
<223> OTHER INFORMATION: Cassette 1029

<400> SEQUENCE: 89

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
```

-continued

```
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggcg aaaaacgttg cgattttcgg cttattgttt tctcttcttg tgttggttcc   1320
ttctcagatc ttcgccgatc gaatctgcac tggaataaca tcgtcaaact caccacatgt   1380
cgtcaaaact gctactcaag gggaggtcaa tgtgactggt gtaataccac tgacaacaac   1440
acccaccaaa tctcattttg caaatctcaa aggaacagaa accaggggga aactatgccc   1500
aaaatgcctc aactgcacag atctggacgt agccttgggc agaccaaaat gcacggggaa   1560
aataccctcg gcaagagttt caatactcca tgaagtcaga cctgttacat ctgggtgctt   1620
tcctataatg cacgacagaa caaaaattag acagctgcct aaccttctcc gaggatacga   1680
acatatcagg ttatcaaccc ataacgttat caatgcagaa aatgcaccag gaggacccta   1740
caaaattgga acctcagggt cttgccctaa cattaccaat ggaaacggat ttttcgcaac   1800
aatggcttgg gccgtcccaa aaaacgacaa aaacaaaaca gcaacaaatc cattaacaat   1860
agaagtacca tacatttgta cagaaggaga agaccaaatt accgtttggg ggttccactc   1920
tgacaacgag acccaaatgg caaagctcta tggggactca aagccccaga agttcacctc   1980
atctgccaac ggagtgacca cacattacgt ttcacagatt ggtggcttcc caaatcaaac   2040
agaagacgga ggactaccac aaagtggtag aattgttgtt gattacatgg tgcaaaaatc   2100
tgggaaaaca ggaacaatta cctatcaaag ggtattttta ttgcctcaaa aggtgtggtg   2160
cgcaagtggc aggagcaagg taataaaagg atccttgcct ttaattggag aagcagattg   2220
cctccacgaa aaatacggtg gattaaacaa aagcaagcct tactacacag gggaacatgc   2280
aaaggccata ggaaattgcc caatatgggt gaaaacaccc ttgaagctgg ccaatggaac   2340
caaatataga cctcctgcaa aactattaaa ggaaaggggt ttcttcggag ctattgctgg   2400
tttcttagaa ggaggatggg aaggaatgat tgcaggttgg cacggataca catcccatgg   2460
ggcacatgga gtagcggtgg cagcagacct taagagcact caagaggcca taaacaagat   2520
aacaaaaaat ctcaactctt tgagtgagct ggaagtaaag aatcttcaaa gactaagcgg   2580
tgccatggat gaactccaca acgaaatact agaactagat gagaaagtgg atgatctcag   2640
agctgataca ataagctcac aaatagaact cgcagtcctg ctttccaatg aaggaataat   2700
aaacagtgaa gatgaacatc tcttggcgct tgaaagaaag ctgaagaaaa tgctgggccc   2760
ctctgctgta gagataggga atggatgctt tgaaaccaaa cacaagtgca accagacctg   2820
tctcgacaga atagctgctg gtacctttga tgcaggagaa ttttctctcc ccacctttga   2880
ttcactgaat attactgctg catctttaaa tgacgatgga ttggataatc atactatact   2940
gctttactac tcaactgctg cctccagttt ggctgtaaca ctgatgatag ctatctttgt   3000
tgtttatatg gtctccagag acaatgtttc ttgctccatc tgtctataaa ggcctatttt   3060
ctttagtttg aatttactgt tattcggtgt gcatttctat gtttggtgag cggttttctg   3120
tgctcagagt gtgtttattt tatgtaattt aatttctttg tgagctcctg tttagcaggt   3180
cgtcccttca gcaaggacac aaaaagattt taattttatt aaaaaaaaaa aaaaaaaaga   3240
ccgggaattc gatatcaagc ttatcgacct gcagatcgtt caaacatttg gcaataaagt   3300
ttcttaagat tgaatcctgt tgccggtctt gcgatgatta tcatataatt tctgttgaat   3360
```

```
tacgttaagc atgtaataat taacatgtaa tgcatgacgt tatttatgag atgggttttt   3420

atgattagag tcccgcaatt atacatttaa tacgcgatag aaaacaaaat atagcgcgca   3480

aactaggata aattatcgcg cgcggtgtca tctatgttac tagat                   3525


<210> SEQ ID NO 90
<211> LENGTH: 594
<212> TYPE: PRT
<213> ORGANISM: Artificial sequence
<220> FEATURE:
<223> OTHER INFORMATION: Amino acid sequence of PDISP/HA from influenza
      B/Brisbane/60/2008

<400> SEQUENCE: 90

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335
```

```
Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Ala Lys Leu Leu
        355                 360                 365

Lys Glu Arg Gly Phe Phe Gly Ala Ile Ala Gly Phe Leu Glu Gly Gly
    370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
                405                 410                 415

Asn Lys Ile Thr Lys Asn Leu Asn Ser Leu Ser Glu Leu Glu Val Lys
            420                 425                 430

Asn Leu Gln Arg Leu Ser Gly Ala Met Asp Glu Leu His Asn Glu Ile
        435                 440                 445

Leu Glu Leu Asp Glu Lys Val Asp Asp Leu Arg Ala Asp Thr Ile Ser
    450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
                485                 490                 495

Leu Gly Pro Ser Ala Val Glu Ile Gly Asn Gly Cys Phe Glu Thr Lys
            500                 505                 510

His Lys Cys Asn Gln Thr Cys Leu Asp Arg Ile Ala Ala Gly Thr Phe
        515                 520                 525

Asp Ala Gly Glu Phe Ser Leu Pro Thr Phe Asp Ser Leu Asn Ile Thr
    530                 535                 540

Ala Ala Ser Leu Asn Asp Asp Gly Leu Asp Asn His Thr Ile Leu Leu
545                 550                 555                 560

Tyr Tyr Ser Thr Ala Ala Ser Ser Leu Ala Val Thr Leu Met Ile Ala
                565                 570                 575

Ile Phe Val Val Tyr Met Val Ser Arg Asp Asn Val Ser Cys Ser Ile
            580                 585                 590

Cys Leu
```

```
<210> SEQ ID NO 91
<211> LENGTH: 1734
<212> TYPE: DNA
<213> ORGANISM: Artificial sequence
<220> FEATURE:
<223> OTHER INFORMATION: Nucleotide sequence of PDISP/HA B Brisbane
      (PrL-).

<400> SEQUENCE: 91

atggcgaaaa acgttgcgat tttcggctta ttgttttctc ttcttgtgtt ggttccttct      60

cagatcttcg ccgatcgaat ctgcactgga ataacatcgt caaactcacc acatgtcgtc     120

aaaactgcta ctcaagggga ggtcaatgtg actggtgtaa taccactgac aacaacaccc     180

accaaatctc attttgcaaa tctcaaagga acagaaacca gggggaaact atgcccaaaa     240

tgcctcaact gcacagatct ggacgtagcc ttgggcagac caaaatgcac ggggaaaata     300

ccctcggcaa gagtttcaat actccatgaa gtcagacctg ttacatctgg gtgctttcct     360

ataatgcacg acagaacaaa aattagacag ctgcctaacc ttctccgagg atacgaacat     420

atcaggttat caacccataa cgttatcaat gcagaaaatg caccaggagg accctacaaa     480

attggaacct cagggtcttg ccctaacatt accaatggaa acggattttt cgcaacaatg     540
```

```
gcttgggccg tcccaaaaaa cgacaaaaac aaaacagcaa caaatccatt aacaatagaa    600

gtaccataca tttgtacaga aggagaagac caaattaccg tttgggggtt ccactctgac    660

aacgagaccc aaatggcaaa gctctatggg gactcaaagc cccagaagtt cacctcatct    720

gccaacggag tgaccacaca ttacgtttca cagattggtg gcttcccaaa tcaaacagaa    780

gacggaggac taccacaaag tggtagaatt gttgttgatt acatggtgca aaaatctggg    840

aaaacaggaa caattaccta tcaaaggggt attttattgc ctcaaaaggt gtggtgcgca    900

agtggcagga gcaaggtaat aaaaggatcc ttgcctttaa ttggagaagc agattgcctc    960

cacgaaaaat acggtggatt aaacaaaagc aagccttact acacagggga acatgcaaag   1020

gccataggaa attgcccaat atgggtgaaa acacccttga agctggccaa tggaaccaaa   1080

tatagacctc ctggtggagg atgggaagga atgattgcag gttggcacgg atacacatcc   1140

catggggcac atggagtagc ggtggcagca gaccttaaga gcactcaaga ggccataaac   1200

aagataacaa aaaatctcaa ctctttgagt gagctggaag taaagaatct tcaaagacta   1260

agcggtgcca tggatgaact ccacaacgaa atactagaac tagatgagaa agtggatgat   1320

ctcagagctg atacaataag ctcacaaata gaactcgcag tcctgctttc caatgaagga   1380

ataataaaca gtgaagatga acatctcttg gcgcttgaaa gaaagctgaa gaaaatgctg   1440

ggcccctctg ctgtagagat agggaatgga tgctttgaaa ccaaacacaa gtgcaaccag   1500

acctgtctcg acagaatagc tgctggtacc tttgatgcag gagaattttc tctccccacc   1560

tttgattcac tgaatattac tgctgcatct ttaaatgacg atggattgga taatcatact   1620

atactgcttt actactcaac tgctgcctcc agtttggctg taacactgat gatagctatc   1680

tttgttgttt atatggtctc cagagacaat gtttcttgct ccatctgtct ataa          1734
```

```
<210> SEQ ID NO 92
<211> LENGTH: 577
<212> TYPE: PRT
<213> ORGANISM: Artificial sequence
<220> FEATURE:
<223> OTHER INFORMATION: Amino acid sequence of PDISP/HA B Brisbane
      (PrL-)

<400> SEQUENCE: 92

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140
```

-continued

```
Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Ser Ile Cys
```

565 570 575

Leu

<210> SEQ ID NO 93
<211> LENGTH: 160
<212> TYPE: DNA
<213> ORGANISM: Artificial sequence
<220> FEATURE:
<223> OTHER INFORMATION: Expression enhancer CPMVX

<400> SEQUENCE: 93
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagtaca 160

<210> SEQ ID NO 94
<211> LENGTH: 29
<212> TYPE: PRT
<213> ORGANISM: Artificial sequence
<220> FEATURE:
<223> OTHER INFORMATION: Consensus amino acid sequence of transadomain membrane
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 94

Ile Leu Xaa Ile Tyr Tyr Ser Thr Val Ala Ile Ser Ser Leu Xaa Leu
1 5 10 15

Xaa Xaa Met Leu Ala Gly Xaa Ser Xaa Trp Met Cys Ser
20 25

<210> SEQ ID NO 95
<211> LENGTH: 1734
<212> TYPE: DNA
<213> ORGANISM: Artificial sequence
<220> FEATURE:
<223> OTHER INFORMATION: Nucleotide sequence of PDISP/HA B Brisbane (PrL-)+H1 California TMCT.

<400> SEQUENCE: 95
atggcgaaaa acgttgcgat tttcggctta ttgttttctc ttcttgtgtt ggttccttct 60
cagatcttcg ccgatcgaat ctgcactgga ataacatcgt caaactcacc acatgtcgtc 120
aaaactgcta ctcaagggga ggtcaatgtg actggtgtaa taccactgac aacaacaccc 180
accaaatctc attttgcaaa tctcaaagga acagaaacca gggggaaact atgcccaaaa 240
tgcctcaact gcacagatct ggacgtagcc ttgggcagac caaaatgcac ggggaaaata 300
ccctcggcaa gagtttcaat actccatgaa gtcagacctg ttacatctgg gtgctttcct 360

```
ataatgcacg acagaacaaa aattagacag ctgcctaacc ttctccgagg atacgaacat    420

atcaggttat caacccataa cgttatcaat gcagaaaatg caccaggagg accctacaaa    480

attggaacct cagggtcttg ccctaacatt accaatggaa acggattttt cgcaacaatg    540

gcttgggccg tcccaaaaaa cgacaaaaac aaaacagcaa caaatccatt aacaatagaa    600

gtaccataca tttgtacaga aggagaagac caaattaccg tttgggggtt ccactctgac    660

aacgagaccc aaatggcaaa gctctatggg gactcaaagc cccagaagtt cacctcatct    720

gccaacggag tgaccacaca ttacgtttca cagattggtg gcttcccaaa tcaaacagaa    780

gacggaggac taccacaaag tggtagaatt gttgttgatt acatggtgca aaaatctggg    840

aaaacaggaa caattaccta tcaaaggggt attttattgc ctcaaaaggt gtggtgcgca    900

agtggcagga gcaaggtaat aaaaggatcc ttgcctttaa ttggagaagc agattgcctc    960

cacgaaaaat acggtggatt aaacaaaagc aagccttact acacagggga acatgcaaag   1020

gccataggaa attgcccaat atgggtgaaa acacccttga agctggccaa tggaaccaaa   1080

tatagacctc ctggtggagg atgggaagga atgattgcag gttggcacgg atacacatcc   1140

catggggcac atggagtagc ggtggcagca gaccttaaga gcactcaaga ggccataaac   1200

aagataacaa aaaatctcaa ctctttgagt gagctggaag taaagaatct tcaaagacta   1260

agcggtgcca tggatgaact ccacaacgaa atactagaac tagatgagaa agtggatgat   1320

ctcagagctg atacaataag ctcacaaata gaactcgcag tcctgctttc caatgaagga   1380

ataataaaca gtgaagatga acatctcttg gcgcttgaaa gaaagctgaa gaaaatgctg   1440

ggcccctctg ctgtagagat agggaatgga tgctttgaaa ccaaacacaa gtgcaaccag   1500

acctgtctcg acagaatagc tgctggtacc tttgatgcag gagaattttc tctccccacc   1560

tttgattcac tgaatattac tgctgcatct ttaaatgacg atggattgga taattaccag   1620

attttggcga tctattcaac tgtcgccagt tcattggtac tggtagtctc cctgggggca   1680

atcagtttct ggatgtgctc taatgggtct ctacagtgta gaatatgtat ttaa         1734
```

<210> SEQ ID NO 96
<211> LENGTH: 577
<212> TYPE: PRT
<213> ORGANISM: Artificial sequence
<220> FEATURE:
<223> OTHER INFORMATION: Amino acid sequence of PDISP/HA B Brisbane
      (PrL-)+H1 California TMCT

<400> SEQUENCE: 96

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110
```

-continued

```
Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn Tyr Gln Ile Leu Ala Ile
```

```
    530                 535                 540

Tyr Ser Thr Val Ala Ser Ser Leu Val Leu Val Val Ser Leu Gly Ala
545                 550                 555                 560

Ile Ser Phe Trp Met Cys Ser Asn Gly Ser Leu Gln Cys Arg Ile Cys
                565                 570                 575

Ile


<210> SEQ ID NO 97
<211> LENGTH: 1731
<212> TYPE: DNA
<213> ORGANISM: Artificial sequence
<220> FEATURE:
<223> OTHER INFORMATION: Nucleotide sequence of PDISP/HA B
      Massachussetts (PrL-)

<400> SEQUENCE: 97

atggcgaaaa acgttgcgat tttcggctta ttgttttctc ttcttgtgtt ggttccttct     60

cagatcttcg ccgatcgaat ctgcactggg ataacatctt caaactcacc tcatgtggtc    120

aaaacagcta ctcaagggga ggtcaatgtg actggtgtga taccactaac aacaacacca    180

acaaaatctt attttgcaaa tctcaaagga acaaagacca gagggaaact atgcccagac    240

tgtctcaact gtacagatct ggatgtggcc ctgggcaggc caatgtgtgt gggaactaca    300

ccttctgcga aagcttcaat acttcacgaa gtcagacctg ttacatccgg gtgcttccct    360

ataatgcacg acagaacaaa aatcaggcaa ctagccaatc ttctcagagg atatgaaaat    420

atcaggttat caacccaaaa cgttatcgat gcagaaaagg caccaggagg accctacaga    480

cttggaacct caggatcttg ccctaacgct accagtaaaa gcggattttt cgcaacaatg    540

gcttgggctg tcccaaagga caacaacaaa aatgcaacga acccattaac agtagaagta    600

ccatacattt gtgcagaagg ggaagaccaa attactgttt gggggttcca ttcagataac    660

aaaacccaaa tgaagaacct ctatggagac tcaaatcctc aaaagttcac ctcatctgct    720

aatggagtaa ccacacatta tgtttctcag attggcggct tcccagatca aacagaagac    780

ggaggactac cacaaagcgg cagaattgtc gttgattaca tgatgcaaaa acctgggaaa    840

acaggaacaa ttgtctatca aagaggtgtt ttgttgcctc aaaaggtgtg gtgcgcgagt    900

ggcaggagca aagtaataaa agggtccttg cctttaattg gtgaagcaga ttgccttcat    960

gaaaaatacg gtggattaaa caaaagcaag ccttactaca caggagaaca tgcaaaagcc   1020

ataggaaatt gcccaatatg ggtgaaaaca cctttgaagc ttgccaatgg aaccaaatat   1080

agacctcctg gtggaggatg ggaaggaatg attgcaggtt ggcacggata cacatctcac   1140

ggagcacatg gagtggcagt tgctgcagac cttaagagca cacaagaagc tataaacaag   1200

ataacaaaaa atctcaactc tttgagtgag ctagaagtaa agaatcttca aaggctaagt   1260

ggtgccatgg atgaactcca caacgaaata ctcgagctgg atgagaaagt ggatgacctc   1320

agagctgaca ctataagttc acaaatagaa cttgcagtct tgctttccaa cgaaggaata   1380

ataaacagtg aagacgagca tctattggca cttgagagaa aactaaagaa aatgctgggt   1440

ccctctgctg tagacatagg aaatggatgc ttcgaaacca aacacaaatg caaccagacc   1500

tgcttagaca ggatagctgc tggcaccttt aatgcaggag agttttctct ccccactttt   1560

gattcattga acattactgc tgcatcttta aatgatgatg gattggataa ccatactata   1620

ctgctctatt actcaactgc tgcttctagt ttggctgtaa cattgatgct agctattttt   1680

attgtttata tggtctccag agacaacgtt tcatgctcca tctgtctata a            1731
```

<210> SEQ ID NO 98
<211> LENGTH: 576
<212> TYPE: PRT
<213> ORGANISM: Artificial sequence
<220> FEATURE:
<223> OTHER INFORMATION: Amino acid sequence of PDISP/HA B Massachussetts (PrL-)

<400> SEQUENCE: 98

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Lys Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365
```

```
Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn His Thr Ile Leu Leu Tyr Tyr
    530                 535                 540

Ser Thr Ala Ala Ser Ser Leu Ala Val Thr Leu Met Leu Ala Ile Phe
545                 550                 555                 560

Ile Val Tyr Met Val Ser Arg Asp Asn Val Ser Cys Ser Ile Cys Leu
                565                 570                 575
```

<210> SEQ ID NO 99
<211> LENGTH: 1731
<212> TYPE: DNA
<213> ORGANISM: Artificial sequence
<220> FEATURE:
<223> OTHER INFORMATION: Nucleotide sequence of PDISP/HA B Massachussetts (PrL-)+H1 California TMCT

<400> SEQUENCE: 99

```
atggcgaaaa acgttgcgat tttcggctta ttgttttctc ttcttgtgtt ggttccttct      60

cagatcttcg ccgatcgaat ctgcactggg ataacatctt caaactcacc tcatgtggtc     120

aaaacagcta ctcaagggga ggtcaatgtg actggtgtga taccactaac aacaacacca     180

acaaaatctt attttgcaaa tctcaaagga acaaagacca gagggaaact atgcccagac     240

tgtctcaact gtacagatct ggatgtggcc ctgggcaggc caatgtgtgt gggaactaca     300

ccttctgcga aagcttcaat acttcacgaa gtcagacctg ttacatccgg gtgcttccct     360

ataatgcacg acagaacaaa aatcaggcaa ctagccaatc ttctcagagg atatgaaaat     420

atcaggttat caacccaaaa cgttatcgat gcagaaaagg caccaggagg accctacaga     480

cttggaacct caggatcttg ccctaacgct accagtaaaa gcggattttt cgcaacaatg     540

gcttgggctg tcccaaagga caacaacaaa aatgcaacga acccattaac agtagaagta     600

ccatacattt gtgcagaagg ggaagaccaa attactgttt gggggttcca ttcagataac     660

aaaacccaaa tgaagaacct ctatggagac tcaaatcctc aaaagttcac ctcatctgct     720

aatggagtaa ccacacatta tgtttctcag attggcggct tcccagatca aacagaagac     780

ggaggactac cacaaagcgg cagaattgtc gttgattaca tgatgcaaaa acctgggaaa     840
```

```
acaggaacaa ttgtctatca aagaggtgtt ttgttgcctc aaaaggtgtg gtgcgcgagt    900

ggcaggagca aagtaataaa agggtccttg cctttaattg gtgaagcaga ttgccttcat    960

gaaaaatacg gtggattaaa caaaagcaag ccttactaca caggagaaca tgcaaaagcc   1020

ataggaaatt gcccaatatg ggtgaaaaca cctttgaagc ttgccaatgg aaccaaatat   1080

agacctcctg gtggaggatg ggaaggaatg attgcaggtt ggcacggata cacatctcac   1140

ggagcacatg gagtggcagt tgctgcagac cttaagagca cacaagaagc tataaacaag   1200

ataacaaaaa atctcaactc tttgagtgag ctagaagtaa agaatcttca aaggctaagt   1260

ggtgccatgg atgaactcca caacgaaata ctcgagctgg atgagaaagt ggatgacctc   1320

agagctgaca ctataagttc acaaatagaa cttgcagtct tgctttccaa cgaaggaata   1380

ataaacagtg aagacgagca tctattggca cttgagagaa aactaaagaa aatgctgggt   1440

ccctctgctg tagacatagg aaatggatgc ttcgaaacca aacacaaatg caaccagacc   1500

tgcttagaca ggatagctgc tggcaccttt aatgcaggag agttttctct ccccactttt   1560

gattcattga acattactgc tgcatcttta aatgatgatg gattggataa ctaccagatt   1620

ttggcgatct attcaactgt cgccagttca ttggtactgg tagtctccct gggggcaatc   1680

agtttctgga tgtgctctaa tgggtctcta cagtgtagaa tatgtattta a            1731
```

```
<210> SEQ ID NO 100
<211> LENGTH: 576
<212> TYPE: PRT
<213> ORGANISM: Artificial sequence
<220> FEATURE:
<223> OTHER INFORMATION: Amino acid sequence of PDISP/HA B
      Massachussetts (PrL-)+H1 California TMCT

<400> SEQUENCE: 100

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Lys Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205
```

```
Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn Tyr Gln Ile Leu Ala Ile Tyr
    530                 535                 540

Ser Thr Val Ala Ser Ser Leu Val Leu Val Val Ser Leu Gly Ala Ile
545                 550                 555                 560

Ser Phe Trp Met Cys Ser Asn Gly Ser Leu Gln Cys Arg Ile Cys Ile
                565                 570                 575
```

<210> SEQ ID NO 101
<211> LENGTH: 1704
<212> TYPE: DNA
<213> ORGANISM: Artificial sequence
<220> FEATURE:
<223> OTHER INFORMATION: Nucleotide sequence of HA B Wisconsin (PrL-).

<400> SEQUENCE: 101

-continued

```
atgaaggcaa taattgtact actcatggta gtaacatcca atgcagatcg aatctgcact     60
gggataacat cttcaaactc acctcatgtg gtcaaaacag ctactcaagg ggaggtcaat    120
gtgactggcg tgataccact gacaacaaca ccaacaaaat cttattttgc aaatctcaaa    180
ggaacaagga ccagagggaa actatgcccg gactgtctca actgtacaga tctggatgtg    240
gccttgggca ggccaatgtg tgtggggacc acaccttctg ctaaagcttc aatactccac    300
gaggtcagac ctgttacatc cgggtgcttt cctataatgc acgacagaac aaaaatcagg    360
caactaccca atcttctcag aggatatgaa aatatcaggt tatcaaccca aaacgttatc    420
gatgcagaaa aagcaccagg aggaccctac agacttggaa cctcaggatc ttgccctaac    480
gctaccagta aaatcggatt ttttgcaaca atggcttggg ctgtcccaaa ggacaactac    540
aaaaatgcaa cgaacccact aacagtagaa gtaccataca tttgtacaga aggggaagac    600
caaattactg tttgggggtt ccattcagat aacaaaaccc aaatgaagag cctctatgga    660
gactcaaatc ctcaaaagtt cacctcatct gctaatggag taaccacaca ttatgtttct    720
cagattggcg acttcccaga tcaaacagaa gacggaggac taccacaaag cggcagaatt    780
gttgttgatt acatgatgca aaaacctggg aaaacaggaa caattgtcta tcaaagaggt    840
gttttgttgc ctcaaaaggt gtggtgcgcg agtggcagga gcaaagtaat aaaagggtca    900
ttgcctttaa ttggtgaagc agattgcctt catgaaaaat acggtggatt aaacaaaagc    960
aagccttact acacaggaga acatgcaaaa gccataggaa attgcccaat atgggtaaaa   1020
acacctttga agcttgccaa tggaaccaaa tatagacctc ctggtggagg atgggaagga   1080
atgattgcag gttggcacgg atacacatct cacggagcac atggagtggc agtggcggca   1140
gaccttaaga gtacacaaga agctataaat aagataacaa aaaatctcaa ttctttgagt   1200
gagctagaag taaagaacct tcaaagacta agtggtgcca tggatgaact ccacaacgaa   1260
atactcgagc tggatgagaa agtggatgat ctcagagctg acactataag ctcacaaata   1320
gaacttgcag tcttgctttc caacgaagga ataataaaca gtgaagacga gcatctattg   1380
gcacttgaga gaaaactaaa gaaaatgctg ggtccctctg ctgtagacat aggaaacgga   1440
tgcttcgaaa ccaaacacaa atgcaaccag acctgcttag acaggatagc tgctggcacc   1500
tttaatgcag gagaattttc tctccccact tttgattcat tgaacattac tgctgcatct   1560
ttaaatgatg atggattgga taaccatact atactgctct attactcaac tgctgcttct   1620
agtttggctg taacattaat gctagctatt tttattgttt atatggtctc cagagacaac   1680
gtttcatgct ccatctgtct ataa                                          1704
```

<210> SEQ ID NO 102
<211> LENGTH: 567
<212> TYPE: PRT
<213> ORGANISM: Artificial sequence
<220> FEATURE:
<223> OTHER INFORMATION: Amino acid sequence of HA B Wisconsin (PrL-)

<400> SEQUENCE: 102

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
```

```
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480
```

-continued

```
Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

His Thr Ile Leu Leu Tyr Tyr Ser Thr Ala Ala Ser Ser Leu Ala Val
    530                 535                 540

Thr Leu Met Leu Ala Ile Phe Ile Val Tyr Met Val Ser Arg Asp Asn
545                 550                 555                 560

Val Ser Cys Ser Ile Cys Leu
                565
```

<210> SEQ ID NO 103
<211> LENGTH: 1704
<212> TYPE: DNA
<213> ORGANISM: Artificial sequence
<220> FEATURE:
<223> OTHER INFORMATION: Nucleotide sequence of HA B Wisconsin (PrL-)+H1 California TMCT

<400> SEQUENCE: 103

```
atgaaggcaa taattgtact actcatggta gtaacatcca atgcagatcg aatctgcact     60

gggataacat cttcaaactc acctcatgtg gtcaaaacag ctactcaagg ggaggtcaat    120

gtgactggcg tgataccact gacaacaaca ccaacaaaat cttattttgc aaatctcaaa    180

ggaacaagga ccagagggaa actatgcccg gactgtctca actgtacaga tctggatgtg    240

gccttgggca ggccaatgtg tgtggggacc acaccttctg ctaaagcttc aatactccac    300

gaggtcagac ctgttacatc cgggtgcttt cctataatgc acgacagaac aaaaatcagg    360

caactaccca atcttctcag aggatatgaa aatatcaggt tatcaaccca aaacgttatc    420

gatgcagaaa aagcaccagg aggaccctac agacttggaa cctcaggatc ttgccctaac    480

gctaccagta aaatcggatt ttttgcaaca atggcttggg ctgtcccaaa ggacaactac    540

aaaaatgcaa cgaacccact aacagtagaa gtaccataca tttgtacaga aggggaagac    600

caaattactg tttgggggtt ccattcagat aacaaaaccc aaatgaagag cctctatgga    660

gactcaaatc ctcaaaagtt cacctcatct gctaatggag taaccacaca ttatgtttct    720

cagattggcg acttcccaga tcaaacagaa gacggaggac taccacaaag cggcagaatt    780

gttgttgatt acatgatgca aaaacctggg aaaacaggaa caattgtcta tcaaagaggt    840

gttttgttgc ctcaaaaggt gtggtgcgcg agtggcagga gcaaagtaat aaaagggtca    900

ttgcctttaa ttggtgaagc agattgcctt catgaaaaat acggtggatt aaacaaaagc    960

aagccttact acacaggaga acatgcaaaa gccataggaa attgcccaat atgggtaaaa   1020

acacctttga agcttgccaa tggaaccaaa tatagacctc ctggtggagg atgggaagga   1080

atgattgcag gttggcacgg atacacatct cacggagcac atggagtggc agtggcggca   1140

gaccttaaga gtacacaaga agctataaat aagataacaa aaaatctcaa ttctttgagt   1200

gagctagaag taaagaacct tcaaagacta agtggtgcca tggatgaact ccacaacgaa   1260

atactcgagc tggatgagaa agtggatgat ctcagagctg acactataag ctcacaaata   1320

gaacttgcag tcttgctttc caacgaagga ataataaaca gtgaagacga gcatctattg   1380

gcacttgaga gaaaactaaa gaaaatgctg ggtccctctg ctgtagacat aggaaacgga   1440

tgcttcgaaa ccaaacacaa atgcaaccag acctgcttag acaggatagc tgctggcacc   1500
```

```
tttaatgcag gagaattttc tctccccact tttgattcat tgaacattac tgctgcatct   1560

ttaaatgatg atggattgga taactaccag attttggcga tctattcaac tgtcgccagt   1620

tcattggtac tggtagtctc cctgggggca atcagtttct ggatgtgctc taatgggtct   1680

ctacagtgta gaatatgtat ttaa                                          1704


<210> SEQ ID NO 104
<211> LENGTH: 567
<212> TYPE: PRT
<213> ORGANISM: Artificial sequence
<220> FEATURE:
<223> OTHER INFORMATION: Amino acid sequence of HA B Wisconsin (PrL-)+H1
      California TMC

<400> SEQUENCE: 104

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320
```

```
Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

Tyr Gln Ile Leu Ala Ile Tyr Ser Thr Val Ala Ser Ser Leu Val Leu
    530                 535                 540

Val Val Ser Leu Gly Ala Ile Ser Phe Trp Met Cys Ser Asn Gly Ser
545                 550                 555                 560

Leu Gln Cys Arg Ile Cys Ile
                565


<210> SEQ ID NO 105
<211> LENGTH: 1734
<212> TYPE: DNA
<213> ORGANISM: Artificial sequence
<220> FEATURE:
<223> OTHER INFORMATION: Nucleotide sequence of PDISP/HA B Brisbane
      (PrL-)+H1 California TMCT

<400> SEQUENCE: 105

atggcgaaaa acgttgcgat tttcggctta ttgttttctc ttcttgtgtt ggttccttct      60

cagatcttcg ccgatcgaat ctgcactgga ataacatcgt caaactcacc acatgtcgtc     120

aaaactgcta ctcaagggga ggtcaatgtg actggtgtaa taccactgac aacaacaccc     180

accaaatctc attttgcaaa tctcaaagga acagaaacca gggggaaact atgcccaaaa     240

tgcctcaact gcacagatct ggacgtagcc ttgggcagac caaaatgcac ggggaaaata     300

ccctcggcaa gagtttcaat actccatgaa gtcagacctg ttacatctgg gtgctttcct     360

ataatgcacg acagaacaaa aattagacag ctgcctaacc ttctccgagg atacgaacat     420

atcaggttat caacccataa cgttatcaat gcagaaaatg caccaggagg accctacaaa     480

attggaacct cagggtcttg ccctaacatt accaatggaa acggattttt cgcaacaatg     540

gcttgggccg tcccaaaaaa cgacaaaaac aaaacagcaa caaatccatt aacaatagaa     600
```

```
gtaccataca tttgtacaga aggagaagac caaattaccg tttgggggtt ccactctgac    660

aacgagaccc aaatggcaaa gctctatggg gactcaaagc cccagaagtt cacctcatct    720

gccaacggag tgaccacaca ttacgtttca cagattggtg gcttcccaaa tcaaacagaa    780

gacggaggac taccacaaag tggtagaatt gttgttgatt acatggtgca aaaatctggg    840

aaaacaggaa caattaccta tcaaaggggt attttattgc ctcaaaaggt gtggtgcgca    900

agtggcagga gcaaggtaat aaaaggatcc ttgcctttaa ttggagaagc agattgcctc    960

cacgaaaaat acggtggatt aaacaaaagc aagccttact acacagggga acatgcaaag   1020

gccataggaa attgcccaat atgggtgaaa acacccttga agctggccaa tggaaccaaa   1080

tatagacctc ctggtggagg atgggaagga atgattgcag gttggcacgg atacacatcc   1140

catggggcac atggagtagc ggtggcagca gaccttaaga gcactcaaga ggccataaac   1200

aagataacaa aaaatctcaa ctctttgagt gagctggaag taaagaatct tcaaagacta   1260

agcggtgcca tggatgaact ccacaacgaa atactagaac tagatgagaa agtggatgat   1320

ctcagagctg atacaataag ctcacaaata gaactcgcag tcctgctttc caatgaagga   1380

ataataaaca gtgaagatga acatctcttg gcgcttgaaa gaaagctgaa gaaaatgctg   1440

ggcccctctg ctgtagagat agggaatgga tgctttgaaa ccaaacacaa gtgcaaccag   1500

acctgtctcg acagaatagc tgctggtacc tttgatgcag gagaattttc tctccccacc   1560

tttgattcac tgaatattac tgctgcatct ttaaatgacg atggattgga taattaccag   1620

attttggcga tctattcaac tgtcgccagt tcattggtac tggtagtctc cctgggggca   1680

atcagtttct ggatgtgctc taatgggtct ctacagtgta gaatatgtat ttaa         1734
```

<210> SEQ ID NO 106
<211> LENGTH: 577
<212> TYPE: PRT
<213> ORGANISM: Artificial sequence
<220> FEATURE:
<223> OTHER INFORMATION: Amino acid sequence of PDISP/HA B Brisbane (PrL-)+H1 California TMCT

<400> SEQUENCE: 106

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160
```

```
Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn Tyr Gln Ile Leu Ala Ile
    530                 535                 540

Tyr Ser Thr Val Ala Ser Ser Leu Val Leu Val Val Ser Leu Gly Ala
545                 550                 555                 560

Ile Ser Phe Trp Met Cys Ser Asn Gly Ser Leu Gln Cys Arg Ile Cys
                565                 570                 575
```

Ile

<210> SEQ ID NO 107
<211> LENGTH: 1731
<212> TYPE: DNA
<213> ORGANISM: Artificial sequence
<220> FEATURE:
<223> OTHER INFORMATION: Nucleotide sequence of PDISP/HA B
Massachussetts (PrL-)

<400> SEQUENCE: 107
atggcgaaaa acgttgcgat tttcggctta ttgttttctc ttcttgtgtt ggttccttct 60
cagatcttcg ccgatcgaat ctgcactggg ataacatctt caaactcacc tcatgtggtc 120
aaaacagcta ctcaagggga ggtcaatgtg actggtgtga taccactaac aacaacacca 180
acaaaatctt attttgcaaa tctcaaagga acaaagacca gagggaaact atgcccagac 240
tgtctcaact gtacagatct ggatgtggcc ctgggcaggc caatgtgtgt gggaactaca 300
ccttctgcga aagcttcaat acttcacgaa gtcagacctg ttacatccgg gtgcttccct 360
ataatgcacg acagaacaaa aatcaggcaa ctagccaatc ttctcagagg atatgaaaat 420
atcaggttat caacccaaaa cgttatcgat gcagaaaagg caccaggagg accctacaga 480
cttggaacct caggatcttg ccctaacgct accagtaaaa gcggattttt cgcaacaatg 540
gcttgggctg tcccaaagga caacaacaaa aatgcaacga acccattaac agtagaagta 600
ccatacattt gtgcagaagg ggaagaccaa attactgttt gggggttcca ttcagataac 660
aaaacccaaa tgaagaacct ctatggagac tcaaatcctc aaaagttcac ctcatctgct 720
aatggagtaa ccacacatta tgtttctcag attggcggct tcccagatca aacagaagac 780
ggaggactac cacaaagcgg cagaattgtc gttgattaca tgatgcaaaa acctgggaaa 840
acaggaacaa ttgtctatca aagaggtgtt ttgttgcctc aaaaggtgtg gtgcgcgagt 900
ggcaggagca aagtaataaa agggtccttg cctttaattg gtgaagcaga ttgccttcat 960
gaaaaatacg gtggattaaa caaaagcaag ccttactaca caggagaaca tgcaaaagcc 1020
ataggaaatt gcccaatatg ggtgaaaaca cctttgaagc ttgccaatgg aaccaaatat 1080
agacctcctg gtggaggatg ggaaggaatg attgcaggtt ggcacggata cacatctcac 1140
ggagcacatg gagtggcagt tgctgcagac cttaagagca cacaagaagc tataaacaag 1200
ataacaaaaa atctcaactc tttgagtgag ctagaagtaa agaatcttca aaggctaagt 1260
ggtgccatgg atgaactcca caacgaaata ctcgagctgg atgagaaagt ggatgacctc 1320
agagctgaca ctataagttc acaaatagaa cttgcagtct tgctttccaa cgaaggaata 1380
ataaacagtg aagacgagca tctattggca cttgagagaa aactaaagaa aatgctgggt 1440
ccctctgctg tagacatagg aaatggatgc ttcgaaacca aacacaaatg caaccagacc 1500
tgcttagaca ggatagctgc tggcaccttt aatgcaggag agttttctct ccccactttt 1560
gattcattga acattactgc tgcatcttta aatgatgatg gattggataa ccatactata 1620
ctgctctatt actcaactgc tgcttctagt ttggctgtaa cattgatgct agctattttt 1680
attgtttata tggtctccag agacaacgtt tcatgctcca tctgtctata a 1731

<210> SEQ ID NO 108
<211> LENGTH: 576
<212> TYPE: PRT
<213> ORGANISM: Artificial sequence
<220> FEATURE:
<223> OTHER INFORMATION: Amino acid sequence of PDISP/HA B
Massachussetts (PrL-)

<400> SEQUENCE: 108

Met Ala Lys Asn Val Ala Ile Phe Gly Leu Leu Phe Ser Leu Leu Val
1 5 10 15

Leu Val Pro Ser Gln Ile Phe Ala Asp Arg Ile Cys Thr Gly Ile Thr
20 25 30

Ser Ser Asn Ser Pro His Val Val Lys Thr Ala Thr Gln Gly Glu Val
35 40 45

Asn Val Thr Gly Val Ile Pro Leu Thr Thr Thr Pro Thr Lys Ser Tyr
50 55 60

Phe Ala Asn Leu Lys Gly Thr Lys Thr Arg Gly Lys Leu Cys Pro Asp
65 70 75 80

Cys Leu Asn Cys Thr Asp Leu Asp Val Ala Leu Gly Arg Pro Met Cys
85 90 95

Val Gly Thr Thr Pro Ser Ala Lys Ala Ser Ile Leu His Glu Val Arg
100 105 110

Pro Val Thr Ser Gly Cys Phe Pro Ile Met His Asp Arg Thr Lys Ile
115 120 125

Arg Gln Leu Ala Asn Leu Leu Arg Gly Tyr Glu Asn Ile Arg Leu Ser
130 135 140

Thr Gln Asn Val Ile Asp Ala Glu Lys Ala Pro Gly Gly Pro Tyr Arg
145 150 155 160

Leu Gly Thr Ser Gly Ser Cys Pro Asn Ala Thr Ser Lys Ser Gly Phe
165 170 175

Phe Ala Thr Met Ala Trp Ala Val Pro Lys Asp Asn Asn Lys Asn Ala
180 185 190

Thr Asn Pro Leu Thr Val Glu Val Pro Tyr Ile Cys Ala Glu Gly Glu
195 200 205

Asp Gln Ile Thr Val Trp Gly Phe His Ser Asp Asn Lys Thr Gln Met
210 215 220

Lys Asn Leu Tyr Gly Asp Ser Asn Pro Gln Lys Phe Thr Ser Ser Ala
225 230 235 240

Asn Gly Val Thr Thr His Tyr Val Ser Gln Ile Gly Gly Phe Pro Asp
245 250 255

Gln Thr Glu Asp Gly Gly Leu Pro Gln Ser Gly Arg Ile Val Val Asp
260 265 270

Tyr Met Met Gln Lys Pro Gly Lys Thr Gly Thr Ile Val Tyr Gln Arg
275 280 285

Gly Val Leu Leu Pro Gln Lys Val Trp Cys Ala Ser Gly Arg Ser Lys
290 295 300

Val Ile Lys Gly Ser Leu Pro Leu Ile Gly Glu Ala Asp Cys Leu His
305 310 315 320

Glu Lys Tyr Gly Gly Leu Asn Lys Ser Lys Pro Tyr Tyr Thr Gly Glu
325 330 335

His Ala Lys Ala Ile Gly Asn Cys Pro Ile Trp Val Lys Thr Pro Leu
340 345 350

Lys Leu Ala Asn Gly Thr Lys Tyr Arg Pro Pro Gly Gly Gly Trp Glu
355 360 365

Gly Met Ile Ala Gly Trp His Gly Tyr Thr Ser His Gly Ala His Gly
370 375 380

Val Ala Val Ala Ala Asp Leu Lys Ser Thr Gln Glu Ala Ile Asn Lys
385 390 395 400

Ile Thr Lys Asn Leu Asn Ser Leu Ser Glu Leu Glu Val Lys Asn Leu

```
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn His Thr Ile Leu Leu Tyr Tyr
    530                 535                 540

Ser Thr Ala Ala Ser Ser Leu Ala Val Thr Leu Met Leu Ala Ile Phe
545                 550                 555                 560

Ile Val Tyr Met Val Ser Arg Asp Asn Val Ser Cys Ser Ile Cys Leu
                565                 570                 575
```

<210> SEQ ID NO 109
<211> LENGTH: 1731
<212> TYPE: DNA
<213> ORGANISM: Artificial sequence
<220> FEATURE:
<223> OTHER INFORMATION: Nucleotide sequence of PDISP/HA B
      Massachussetts (PrL-)+H1 California TMCT

<400> SEQUENCE: 109

```
atggcgaaaa acgttgcgat tttcggctta ttgttttctc ttcttgtgtt ggttccttct      60

cagatcttcg ccgatcgaat ctgcactggg ataacatctt caaactcacc tcatgtggtc     120

aaaacagcta ctcaagggga ggtcaatgtg actggtgtga taccactaac aacaacacca     180

acaaaatctt attttgcaaa tctcaaagga acaaagacca gagggaaact atgcccagac     240

tgtctcaact gtacagatct ggatgtggcc ctgggcaggc caatgtgtgt gggaactaca     300

ccttctgcga aagcttcaat acttcacgaa gtcagacctg ttacatccgg gtgcttccct     360

ataatgcacg acagaacaaa aatcaggcaa ctagccaatc ttctcagagg atatgaaaat     420

atcaggttat caacccaaaa cgttatcgat gcagaaaagg caccaggagg accctacaga     480

cttggaacct caggatcttg ccctaacgct accagtaaaa gcggattttt cgcaacaatg     540

gcttgggctg tcccaaagga caacaacaaa aatgcaacga acccattaac agtagaagta     600

ccatacattt gtgcagaagg ggaagaccaa attactgttt gggggttcca ttcagataac     660

aaaacccaaa tgaagaacct ctatggagac tcaaatcctc aaaagttcac ctcatctgct     720

aatggagtaa ccacacatta tgtttctcag attggcggct tcccagatca aacagaagac     780

ggaggactac cacaaagcgg cagaattgtc gttgattaca tgatgcaaaa acctgggaaa     840

acaggaacaa ttgtctatca aagaggtgtt ttgttgcctc aaaaggtgtg gtgcgcgagt     900

ggcaggagca aagtaataaa agggtccttg cctttaattg gtgaagcaga ttgccttcat     960

gaaaaatacg gtggattaaa caaaagcaag ccttactaca caggagaaca tgcaaaagcc    1020

ataggaaatt gcccaatatg ggtgaaaaca cctttgaagc ttgccaatgg aaccaaatat    1080
```

```
agacctcctg gtggaggatg ggaaggaatg attgcaggtt ggcacggata cacatctcac   1140

ggagcacatg gagtggcagt tgctgcagac cttaagagca cacaagaagc tataaacaag   1200

ataacaaaaa atctcaactc tttgagtgag ctagaagtaa agaatcttca aaggctaagt   1260

ggtgccatgg atgaactcca caacgaaata ctcgagctgg atgagaaagt ggatgacctc   1320

agagctgaca ctataagttc acaaatagaa cttgcagtct tgctttccaa cgaaggaata   1380

ataaacagtg aagacgagca tctattggca cttgagagaa aactaaagaa aatgctgggt   1440

ccctctgctg tagacatagg aaatggatgc ttcgaaacca aacacaaatg caaccagacc   1500

tgcttagaca ggatagctgc tggcaccttt aatgcaggag agttttctct ccccactttt   1560

gattcattga acattactgc tgcatcttta aatgatgatg gattggataa ctaccagatt   1620

ttggcgatct attcaactgt cgccagttca ttggtactgg tagtctccct gggggcaatc   1680

agtttctgga tgtgctctaa tgggtctcta cagtgtagaa tatgtattta a            1731
```

<210> SEQ ID NO 110
<211> LENGTH: 576
<212> TYPE: PRT
<213> ORGANISM: Artificial sequence
<220> FEATURE:
<223> OTHER INFORMATION: Amino acid sequence of PDISP/HA B
      Massachussetts (PrL-)+H1 California TMCT

<400> SEQUENCE: 110

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Lys Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
```

-continued

```
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn Tyr Gln Ile Leu Ala Ile Tyr
    530                 535                 540

Ser Thr Val Ala Ser Ser Leu Val Leu Val Val Ser Leu Gly Ala Ile
545                 550                 555                 560

Ser Phe Trp Met Cys Ser Asn Gly Ser Leu Gln Cys Arg Ile Cys Ile
                565                 570                 575


<210> SEQ ID NO 111
<211> LENGTH: 1704
<212> TYPE: DNA
<213> ORGANISM: Artificial sequence
<220> FEATURE:
<223> OTHER INFORMATION: Nucleotide sequence of HA B Wisconsin (PrL-)

<400> SEQUENCE: 111

atgaaggcaa taattgtact actcatggta gtaacatcca atgcagatcg aatctgcact      60

gggataacat cttcaaactc acctcatgtg gtcaaaacag ctactcaagg ggaggtcaat     120

gtgactggcg tgataccact gacaacaaca ccaacaaaat cttattttgc aaatctcaaa     180

ggaacaagga ccagagggaa actatgcccg gactgtctca actgtacaga tctggatgtg     240
```

```
gccttgggca ggccaatgtg tgtggggacc acaccttctg ctaaagcttc aatactccac    300

gaggtcagac ctgttacatc cgggtgcttt cctataatgc acgacagaac aaaaatcagg    360

caactaccca atcttctcag aggatatgaa aatatcaggt tatcaaccca aaacgttatc    420

gatgcagaaa aagcaccagg aggaccctac agacttggaa cctcaggatc ttgccctaac    480

gctaccagta aaatcggatt ttttgcaaca atggcttggg ctgtcccaaa ggacaactac    540

aaaaatgcaa cgaacccact aacagtagaa gtaccataca tttgtacaga aggggaagac    600

caaattactg tttgggggtt ccattcagat aacaaaaccc aaatgaagag cctctatgga    660

gactcaaatc ctcaaaagtt cacctcatct gctaatggag taaccacaca ttatgtttct    720

cagattggcg acttcccaga tcaaacagaa gacggaggac taccacaaag cggcagaatt    780

gttgttgatt acatgatgca aaaacctggg aaaacaggaa caattgtcta tcaaagaggt    840

gttttgttgc ctcaaaaggt gtggtgcgcg agtggcagga gcaaagtaat aaaagggtca    900

ttgcctttaa ttggtgaagc agattgcctt catgaaaaat acggtggatt aaacaaaagc    960

aagccttact acacaggaga acatgcaaaa gccataggaa attgcccaat atgggtaaaa   1020

acacctttga agcttgccaa tggaaccaaa tatagacctc ctggtggagg atgggaagga   1080

atgattgcag gttggcacgg atacacatct cacggagcac atggagtggc agtggcggca   1140

gaccttaaga gtacacaaga agctataaat aagataacaa aaaatctcaa ttctttgagt   1200

gagctagaag taaagaacct tcaaagacta agtggtgcca tggatgaact ccacaacgaa   1260

atactcgagc tggatgagaa agtggatgat ctcagagctg acactataag ctcacaaata   1320

gaacttgcag tcttgctttc caacgaagga ataataaaca gtgaagacga gcatctattg   1380

gcacttgaga gaaaactaaa gaaaatgctg ggtccctctg ctgtagacat aggaaacgga   1440

tgcttcgaaa ccaaacacaa atgcaaccag acctgcttag acaggatagc tgctggcacc   1500

tttaatgcag gagaattttc tctccccact tttgattcat tgaacattac tgctgcatct   1560

ttaaatgatg atggattgga taaccatact atactgctct attactcaac tgctgcttct   1620

agtttggctg taacattaat gctagctatt tttattgttt atatggtctc cagagacaac   1680

gtttcatgct ccatctgtct ataa                                          1704
```

<210> SEQ ID NO 112
<211> LENGTH: 567
<212> TYPE: PRT
<213> ORGANISM: Artificial sequence
<220> FEATURE:
<223> OTHER INFORMATION: Amino acid sequence of HA B Wisconsin (PrL-)

<400> SEQUENCE: 112

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95
```

```
Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
```

```
        515                 520                 525

His Thr Ile Leu Leu Tyr Tyr Ser Thr Ala Ala Ser Ser Leu Ala Val
    530                 535                 540

Thr Leu Met Leu Ala Ile Phe Ile Val Tyr Met Val Ser Arg Asp Asn
545                 550                 555                 560

Val Ser Cys Ser Ile Cys Leu
                565


<210> SEQ ID NO 113
<211> LENGTH: 1704
<212> TYPE: DNA
<213> ORGANISM: Artificial sequence
<220> FEATURE:
<223> OTHER INFORMATION: Nucleotide sequence of HA B Wisconsin (PrL-)+H1
      California TMCT

<400> SEQUENCE: 113

atgaaggcaa taattgtact actcatggta gtaacatcca atgcagatcg aatctgcact     60

gggataacat cttcaaactc acctcatgtg gtcaaaacag ctactcaagg ggaggtcaat    120

gtgactggcg tgataccact gacaacaaca ccaacaaaat cttattttgc aaatctcaaa    180

ggaacaagga ccagagggaa actatgcccg gactgtctca actgtacaga tctggatgtg    240

gccttgggca ggccaatgtg tgtggggacc acaccttctg ctaaagcttc aatactccac    300

gaggtcagac ctgttacatc cgggtgcttt cctataatgc acgacagaac aaaaatcagg    360

caactaccca atcttctcag aggatatgaa aatatcaggt tatcaaccca aaacgttatc    420

gatgcagaaa aagcaccagg aggaccctac agacttggaa cctcaggatc ttgccctaac    480

gctaccagta aaatcggatt ttttgcaaca atggcttggg ctgtcccaaa ggacaactac    540

aaaaatgcaa cgaacccact aacagtagaa gtaccataca tttgtacaga aggggaagac    600

caaattactg tttgggggtt ccattcagat aacaaaaccc aaatgaagag cctctatgga    660

gactcaaatc ctcaaaagtt cacctcatct gctaatggag taaccacaca ttatgtttct    720

cagattggcg acttcccaga tcaaacagaa gacggaggac taccacaaag cggcagaatt    780

gttgttgatt acatgatgca aaaacctggg aaaacaggaa caattgtcta tcaaagaggt    840

gttttgttgc ctcaaaaggt gtggtgcgcg agtggcagga gcaaagtaat aaaagggtca    900

ttgcctttaa ttggtgaagc agattgcctt catgaaaaat acggtggatt aaacaaaagc    960

aagccttact acacaggaga acatgcaaaa gccataggaa attgcccaat atgggtaaaa   1020

acacctttga agcttgccaa tggaaccaaa tatagacctc ctggtggagg atgggaagga   1080

atgattgcag gttggcacgg atacacatct cacggagcac atggagtggc agtggcggca   1140

gaccttaaga gtacacaaga agctataaat aagataacaa aaaatctcaa ttctttgagt   1200

gagctagaag taaagaacct tcaaagacta agtggtgcca tggatgaact ccacaacgaa   1260

atactcgagc tggatgagaa agtggatgat ctcagagctg acactataag ctcacaaata   1320

gaacttgcag tcttgctttc caacgaagga ataataaaca gtgaagacga gcatctattg   1380

gcacttgaga gaaaactaaa gaaaatgctg ggtccctctg ctgtagacat aggaaacgga   1440

tgcttcgaaa ccaaacacaa atgcaaccag acctgcttag acaggatagc tgctggcacc   1500

tttaatgcag gagaattttc tctccccact tttgattcat tgaacattac tgctgcatct   1560

ttaaatgatg atggattgga taactaccag attttggcga tctattcaac tgtcgccagt   1620

tcattggtac tggtagtctc cctgggggca atcagtttct ggatgtgctc taatgggtct   1680

ctacagtgta gaatatgtat ttaa                                          1704
```

<210> SEQ ID NO 114
<211> LENGTH: 567
<212> TYPE: PRT
<213> ORGANISM: Artificial sequence
<220> FEATURE:
<223> OTHER INFORMATION: Amino acid sequence of HA B Wisconsin (PrL-)+H1
California TMC.

<400> SEQUENCE: 114

Met Lys Ala Ile Ile Val Leu Leu Met Val Val Thr Ser Asn Ala Asp
1 5 10 15

Arg Ile Cys Thr Gly Ile Thr Ser Ser Asn Ser Pro His Val Val Lys
20 25 30

Thr Ala Thr Gln Gly Glu Val Asn Val Thr Gly Val Ile Pro Leu Thr
35 40 45

Thr Thr Pro Thr Lys Ser Tyr Phe Ala Asn Leu Lys Gly Thr Arg Thr
50 55 60

Arg Gly Lys Leu Cys Pro Asp Cys Leu Asn Cys Thr Asp Leu Asp Val
65 70 75 80

Ala Leu Gly Arg Pro Met Cys Val Gly Thr Thr Pro Ser Ala Lys Ala
85 90 95

Ser Ile Leu His Glu Val Arg Pro Val Thr Ser Gly Cys Phe Pro Ile
100 105 110

Met His Asp Arg Thr Lys Ile Arg Gln Leu Pro Asn Leu Leu Arg Gly
115 120 125

Tyr Glu Asn Ile Arg Leu Ser Thr Gln Asn Val Ile Asp Ala Glu Lys
130 135 140

Ala Pro Gly Gly Pro Tyr Arg Leu Gly Thr Ser Gly Ser Cys Pro Asn
145 150 155 160

Ala Thr Ser Lys Ile Gly Phe Phe Ala Thr Met Ala Trp Ala Val Pro
165 170 175

Lys Asp Asn Tyr Lys Asn Ala Thr Asn Pro Leu Thr Val Glu Val Pro
180 185 190

Tyr Ile Cys Thr Glu Gly Glu Asp Gln Ile Thr Val Trp Gly Phe His
195 200 205

Ser Asp Asn Lys Thr Gln Met Lys Ser Leu Tyr Gly Asp Ser Asn Pro
210 215 220

Gln Lys Phe Thr Ser Ser Ala Asn Gly Val Thr Thr His Tyr Val Ser
225 230 235 240

Gln Ile Gly Asp Phe Pro Asp Gln Thr Glu Asp Gly Gly Leu Pro Gln
245 250 255

Ser Gly Arg Ile Val Val Asp Tyr Met Met Gln Lys Pro Gly Lys Thr
260 265 270

Gly Thr Ile Val Tyr Gln Arg Gly Val Leu Leu Pro Gln Lys Val Trp
275 280 285

Cys Ala Ser Gly Arg Ser Lys Val Ile Lys Gly Ser Leu Pro Leu Ile
290 295 300

Gly Glu Ala Asp Cys Leu His Glu Lys Tyr Gly Gly Leu Asn Lys Ser
305 310 315 320

Lys Pro Tyr Tyr Thr Gly Glu His Ala Lys Ala Ile Gly Asn Cys Pro
325 330 335

Ile Trp Val Lys Thr Pro Leu Lys Leu Ala Asn Gly Thr Lys Tyr Arg
340 345 350

Pro Pro Gly Gly Gly Trp Glu Gly Met Ile Ala Gly Trp His Gly Tyr

```
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

Tyr Gln Ile Leu Ala Ile Tyr Ser Thr Val Ala Ser Ser Leu Val Leu
    530                 535                 540

Val Val Ser Leu Gly Ala Ile Ser Phe Trp Met Cys Ser Asn Gly Ser
545                 550                 555                 560

Leu Gln Cys Arg Ile Cys Ile
                565
```

<210> SEQ ID NO 115
<211> LENGTH: 1707
<212> TYPE: DNA
<213> ORGANISM: Influenza H5 Indonesia

<400> SEQUENCE: 115

```
atggagaaaa tagtgcttct tcttgcaata gtcagtcttg ttaaaagtga tcagatttgc     60

attggttacc atgcaaacaa ttcaacagag caggttgaca caatcatgga aaagaacgtt    120

actgttacac atgcccaaga catactggaa aagacacaca acgggaagct ctgcgatcta    180

gatggagtga agcctctaat tttaagagat tgtagtgtag ctggatggct cctcgggaac    240

ccaatgtgtg acgaattcat caatgtaccg gaatggtctt acatagtgga gaaggccaat    300

ccaaccaatg acctctgtta cccagggagt ttcaacgact atgaagaact gaaacaccta    360

ttgagcagaa taaaccattt tgagaaaatt caaatcatcc ccaaaagttc ttggtccgat    420

catgaagcct catcaggagt tagctcagca tgtccatacc tgggaagtcc ctcctttttt    480

agaaatgtgg tatggcttat caaaaagaac agtacatacc caacaataaa gaaaagctac    540

aataatacca accaagagga tcttttggta ctgtggggaa ttcaccatcc taatgatgcg    600

gcagagcaga caaggctata tcaaaaccca accacctata tttccattgg gacatcaaca    660

ctaaaccaga gattggtacc aaaaatagct actagatcca aagtaaacgg gcaaagtgga    720

aggatggagt tcttctggac aattttaaaa cctaatgatg caatcaactt cgagagtaat    780

ggaaatttca ttgctccaga atatgcatac aaaattgtca agaaagggga ctcagcaatt    840

atgaaaagtg aattggaata tggtaactgc aacaccaagt gtcaaactcc aatgggggcg    900
```

-continued

```
ataaactcta gtatgccatt ccacaacata caccctctca ccatcgggga atgccccaaa    960

tatgtgaaat caaacagatt agtccttgca acagggctca gaaatagccc tcaaagagag   1020

agcagaagaa aaaagagagg actatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactca   1200

atcattgaca aaatgaacac tcagtttgag gccgttggaa gggaatttaa taacttagaa   1260

aggagaatag agaatttaaa caagaagatg gaagacgggt ttctagatgt ctggacttat   1320

aatgccgaac ttctggttct catggaaaat gagagaactc tagactttca tgactcaaat   1380

gttaagaacc tctacgacaa ggtccgacta cagcttaggg ataatgcaaa ggagctgggt   1440

aacggttgtt tcgagttcta tcacaaatgt gataatgaat gtatggaaag tataagaaac   1500

ggaacgtaca actatccgca gtattcagaa gaagcaagat taaaaagaga ggaaataagt   1560

ggggtaaaat tggaatcaat aggaacttac caaatactgt caatttattc aacagtggcg   1620

agttccctag cactggcaat catgatggct ggtctatctt tatggatgtg ctccaatgga   1680

tcgttacaat gcagaatttg catttaa                                       1707
```

```
<210> SEQ ID NO 116
<211> LENGTH: 568
<212> TYPE: PRT
<213> ORGANISM: Influenza H5 Indonesia

<400> SEQUENCE: 116

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
```

-continued

```
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565


<210> SEQ ID NO 117
<211> LENGTH: 52
<212> TYPE: DNA
<213> ORGANISM: Artificial sequence
<220> FEATURE:
<223> OTHER INFORMATION: Construct 1800 IF**(SacII)-PDI.s1+4c

<400> SEQUENCE: 117

acagggccca ataccgcgga gaaaatggcg aaaaacgttg cgattttcgg ct            52


<210> SEQ ID NO 118
```

<211> LENGTH: 51
<212> TYPE: DNA
<213> ORGANISM: Artificial sequence
<220> FEATURE:
<223> OTHER INFORMATION: Construct 1800 IF-H3V36111.s1-4r

<400> SEQUENCE: 118
actaaagaaa ataggccttc aaatgcaaat gttgcaccta atgttgccct t 51

<210> SEQ ID NO 119
<211> LENGTH: 1725
<212> TYPE: DNA
<213> ORGANISM: Artificial sequence
<220> FEATURE:
<223> OTHER INFORMATION: Nucleotide sequence of PDISP/H3 Victoria.

<400> SEQUENCE: 119
atggcgaaaa acgttgcgat tttcggctta ttgttttctc ttcttgtgtt ggttccttct 60
cagatcttcg cccaaaaact tcctggaaat gacaacagca cggcaacgct gtgccttggg 120
caccatgcag taccaaacgg aacgatagtg aaaacaatca cgaatgacca aattgaagtt 180
actaatgcta ctgagctggt tcagaattcc tcaataggtg aaatatgcga cagtcctcat 240
cagatccttg atggagaaaa ctgcacacta atagatgctc tattgggaga ccctcagtgt 300
gatggcttcc aaaataagaa atgggacctt tttgttgaac gaagcaaagc ctacagcaac 360
tgttaccctt atgatgtgcc ggattatgcc tcccttaggt cactagttgc ctcatccggc 420
acactggagt ttaacaatga aagcttcaat tggactggag tcactcaaaa cggaacaagt 480
tctgcttgca taaggagatc taataatagt ttctttagta gattaaattg gttgacccac 540
ttaaacttca aatacccagc attgaacgtg actatgccaa acaatgaaca atttgacaaa 600
ttgtacattt ggggggttca ccacccgggt acggacaagg accaaatctt cctgtatgct 660
caatcatcag gaagaatcac agtatctacc aaaagaagcc aacaagctgt aatcccgaat 720
atcggatcta gacccagaat aaggaatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900
tgcaattctg aatgcatcac tccaaatgga agcattccca atgacaaacc attccaaaat 960
gtaaacagga tcacatacgg ggcctgtccc agatatgtta agcaaagcac tctgaaattg 1020
gcaacaggaa tgcgaaatgt accagagaaa caaactagag gcatatttgg cgcaatagcg 1080
ggtttcatag aaaatggttg ggagggaatg gtggatggtt ggtacggttt caggcatcaa 1140
aattctgagg gaagaggaca agcagcagat ctcaaaagca ctcaagcagc aatcgatcaa 1200
atcaatggga agctgaatcg attgatcggg aaaaccaacg agaaattcca tcagattgaa 1260
aaagaattct cagaagtcga agggagaatt caggaccttg agaaatatgt tgaggacact 1320
aaaatagatc tctggtcata caacgcggag cttcttgttg ccctggagaa ccaacataca 1380
attgatctaa ctgactcaga aatgaacaaa ctgtttgaaa aaacaaagaa gcaactaagg 1440
gaaaatgctg aggatatggg caatggttgt ttcaaaatat accacaaatg tgacaatgcc 1500
tgcataggat caatcagaaa tggaacttat gaccacgatg tatacagaga tgaagcatta 1560
aacaaccggt tccagatcaa gggagttgag ctgaagtcag ggtacaaaga ttggatccta 1620
tggatttcct ttgccatatc atgtttttttg ctttgtgttg ctttgttggg gttcatcatg 1680
tgggcctgcc aaaagggcaa cattaggtgc aacatttgca tttga 1725

<210> SEQ ID NO 120
<211> LENGTH: 4644
<212> TYPE: DNA
<213> ORGANISM: Artificial sequence
<220> FEATURE:
<223> OTHER INFORMATION: Construct 2171

<400> SEQUENCE: 120
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860
gtggttaata tagctcaaat atatggtcaa gttcaataga ttaataatgg aaatatcagt 1920
tatcgaaatt cattaacaat caacttaacg ttattaacta ctaattttat atcatcccct 1980
ttgataaatg atagtacacc aattaggaag gagcatgctc gcctaggaga ttgtcgtttc 2040
ccgccttcag tttgcaagct gctctagccg tgtagccaat acgcaaaccg cctctccccg 2100

-continued

```
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccagtaca gggcccaata   3060
ccgcggagaa aatggcgaaa aacgttgcga ttttcggctt attgttttct cttcttgtgt   3120
tggttccttc tcagatcttc gcgacgtcac tcctcagcca aaacgacacc cccatctgtc   3180
tatccactgg cccctggatc tgctgcccaa actaactcca tggtgaccct gggatgcctg   3240
gtcaagggct atttccctga gccagtgaca gtgacctgga actctggatc cctgtccagc   3300
ggtgtgcaca ccttcccagc tgtcctgcag tctgacctct acactctgag cagctcagtg   3360
actgtcccct ccagcacctg gcccagcgag accgtcacct gcaacgttgc ccacccggcc   3420
agcagcacca aggtggacaa gaaaattgtg cccagggatt gtggttgtaa gccttgcata   3480
tgtacagtcc cagaagtatc atctgtcttc atcttccccc caaagcccaa ggatgtgctc   3540
accattactc tgactcctaa ggtcacgtgt gttgtggtag acatcagcaa ggatgatccc   3600
gaggtccagt tcagctggtt tgtagatgat gtggaggtgc acacagctca gacgcaaccc   3660
cgggaggagc agttcaacag cactttccgc tcagtcagtg aacttcccat catgcaccag   3720
gactggctca atggcaagga gacgtccaga ttttggcgat ctattcaact gtcgccagtt   3780
cattggtact ggtagtctcc ctgggggcaa tcagtttctg gatgtgctct aatgggtctc   3840
tacagtgtag aatatgtatt taaaggccta ttttctttag tttgaattta ctgttattcg   3900
gtgtgcattt ctatgtttgg tgagcggttt tctgtgctca gagtgtgttt attttatgta   3960
atttaatttc tttgtgagct cctgtttagc aggtcgtccc ttcagcaagg acacaaaaag   4020
attttaattt tattaaaaaa aaaaaaaaaa aagaccggga attcgatatc aagcttatcg   4080
acctgcagat cgttcaaaca tttggcaata aagtttctta agattgaatc ctgttgccgg   4140
tcttgcgatg attatcatat aatttctgtt gaattacgtt aagcatgtaa taattaacat   4200
gtaatgcatg acgttattta tgagatgggt ttttatgatt agagtcccgc aattatacat   4260
ttaatacgcg atagaaaaca aaatatagcg cgcaaactag gataaattat cgcgcgcggt   4320
gtcatctatg ttactagatc tctagagtct caagcttggc gcgcccacgt gactagtggc   4380
actggccgtc gttttacaac gtcgtgactg ggaaaaccct ggcgttaccc aacttaatcg   4440
ccttgcagca catccccctt tcgccagctg gcgtaatagc gaagaggccc gcaccgatcg   4500
```

cccttcccaa cagttgcgca gcctgaatgg cgaatgctag agcagcttga gcttggatca 4560
gattgtcgtt tcccgccttc agtttaaact atcagtgttt gacaggatat attggcgggt 4620
aaacctaaga gaaaagagcg ttta 4644

<210> SEQ ID NO 121
<211> LENGTH: 3129
<212> TYPE: DNA
<213> ORGANISM: Artificial sequence
<220> FEATURE:
<223> OTHER INFORMATION: Construct 1800

<400> SEQUENCE: 121
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaggg cccaataccg cggagaaaat ggcgaaaaac gttgcgattt tcggcttatt 960
gttttctctt cttgtgttgg ttccttctca gatcttcgcc caaaaacttc ctggaaatga 1020
caacagcacg gcaacgctgt gccttgggca ccatgcagta ccaaacggaa cgatagtgaa 1080
aacaatcacg aatgaccaaa ttgaagttac taatgctact gagctggttc agaattcctc 1140
aataggtgaa atatgcgaca gtcctcatca gatccttgat ggagaaaact gcacactaat 1200
agatgctcta ttgggagacc ctcagtgtga tggcttccaa aataagaaat gggacctttt 1260
tgttgaacga agcaaagcct acagcaactg ttacccttat gatgtgccgg attatgcctc 1320
ccttaggtca ctagttgcct catccggcac actggagttt aacaatgaaa gcttcaattg 1380
gactggagtc actcaaaacg gaacaagttc tgcttgcata aggagatcta ataatagttt 1440
ctttagtaga ttaaattggt tgacccactt aaacttcaaa tacccagcat tgaacgtgac 1500
tatgccaaac aatgaacaat ttgacaaatt gtacatttgg ggggttcacc acccgggtac 1560
ggacaaggac caaatcttcc tgtatgctca atcatcagga agaatcacag tatctaccaa 1620
aagaagccaa caagctgtaa tcccgaatat cggatctaga cccagaataa ggaatatccc 1680
tagcagaata agcatctatt ggacaatagt aaaaccggga gacatacttt tgattaacag 1740
cacagggaat ctaattgctc ctaggggtta cttcaaaata cgaagtggga aaagctcaat 1800
aatgagatca gatgcaccca ttggcaaatg caattctgaa tgcatcactc caaatggaag 1860

```
cattcccaat gacaaaccat tccaaaatgt aaacaggatc acatacgggg cctgtcccag   1920

atatgttaag caaagcactc tgaaattggc aacaggaatg cgaaatgtac cagagaaaca   1980

aactagaggc atatttggcg caatagcggg tttcatagaa aatggttggg agggaatggt   2040

ggatggttgg tacggtttca ggcatcaaaa ttctgaggga agaggacaag cagcagatct   2100

caaaagcact caagcagcaa tcgatcaaat caatgggaag ctgaatcgat tgatcgggaa   2160

aaccaacgag aaattccatc agattgaaaa agaattctca gaagtcgaag ggagaattca   2220

ggaccttgag aaatatgttg aggacactaa aatagatctc tggtcataca acgcggagct   2280

tcttgttgcc ctggagaacc aacatacaat tgatctaact gactcagaaa tgaacaaact   2340

gtttgaaaaa acaaagaagc aactaaggga aaatgctgag gatatgggca atggttgttt   2400

caaaatatac cacaaatgtg acaatgcctg cataggatca atcagaaatg gaacttatga   2460

ccacgatgta tacagagatg aagcattaaa caaccggttc cagatcaagg gagttgagct   2520

gaagtcaggg tacaaagatt ggatcctatg gatttccttt gccatatcat gtttttttgct   2580

ttgtgttgct ttgttggggt tcatcatgtg ggcctgccaa aagggcaaca ttaggtgcaa   2640

catttgcatt tgaaggccta ttttctttag tttgaattta ctgttattcg gtgtgcattt   2700

ctatgtttgg tgagcggttt tctgtgctca gagtgtgttt attttatgta atttaatttc   2760

tttgtgagct cctgtttagc aggtcgtccc ttcagcaagg acacaaaaag attttaattt   2820

tattaaaaaa aaaaaaaaaa aagaccggga attcgatatc aagcttatcg acctgcagat   2880

cgttcaaaca tttggcaata aagtttctta agattgaatc ctgttgccgg tcttgcgatg   2940

attatcatat aatttctgtt gaattacgtt aagcatgtaa taattaacat gtaatgcatg   3000

acgttattta tgagatgggt ttttatgatt agagtcccgc aattatacat ttaatacgcg   3060

atagaaaaca aaatatagcg cgcaaactag gataaattat cgcgcgcggt gtcatctatg   3120

ttactagat                                                           3129
```

```
<210> SEQ ID NO 122
<211> LENGTH: 574
<212> TYPE: PRT
<213> ORGANISM: Artificial sequence
<220> FEATURE:
<223> OTHER INFORMATION: Amino acid sequence of PDISP/H3 Victoria

<400> SEQUENCE: 122

Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
```

```
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Asn Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560
```

```
Trp Ala Cys Gln Lys Gly Asn Ile Arg Cys Asn Ile Cys Ile
                565                 570


<210> SEQ ID NO 123
<211> LENGTH: 48
<212> TYPE: DNA
<213> ORGANISM: Artificial sequence
<220> FEATURE:
<223> OTHER INFORMATION: Construct 1819 IF(SacII)-Kozac_PDI.c

<400> SEQUENCE: 123

gtcgggccca ataccgcgga gaaaatggcg aaaaacgttg cgattttc                  48


<210> SEQ ID NO 124
<211> LENGTH: 51
<212> TYPE: DNA
<213> ORGANISM: Artificial sequence
<220> FEATURE:
<223> OTHER INFORMATION: Construct 1819 IF-H3V36111.s1-4r

<400> SEQUENCE: 124

actaaagaaa ataggccttc aaatgcaaat gttgcaccta atgttgccct t              51


<210> SEQ ID NO 125
<211> LENGTH: 4914
<212> TYPE: DNA
<213> ORGANISM: Artificial sequence
<220> FEATURE:
<223> OTHER INFORMATION: Construct 2181

<400> SEQUENCE: 125

tggcaggata tattgtggtg taaacaaatt gacgcttaga caacttaata acacattgcg     60

gacgttttta atgtactgaa ttaacgccga atcccgggct ggtatattta tatgttgtca    120

aataactcaa aaaccataaa agtttaagtt agcaagtgtg tacattttta cttgaacaaa    180

aatattcacc tactactgtt ataaatcatt attaaacatt agagtaaaga aatatggatg    240

ataagaacaa gagtagtgat attttgacaa caattttgtt gcaacatttg agaaaatttt    300

gttgttctct cttttcattg gtcaaaaaca atagagagag aaaaaggaag agggagaata    360

aaaacataat gtgagtatga gagagaaagt tgtacaaaag ttgtaccaaa atagttgtac    420

aaatatcatt gaggaatttg acaaaagcta cacaaataag ggttaattgc tgtaaataaa    480

taaggatgac gcattagaga gatgtaccat tagagaattt ttggcaagtc attaaaaaga    540

aagaataaat tatttttaaa attaaaagtt gagtcatttg attaaacatg tgattattta    600

atgaattgat gaaagagttg gattaaagtt gtattagtaa ttagaatttg gtgtcaaatt    660

taatttgaca tttgatcttt tcctatatat tgccccatag agtcagttaa ctcattttta    720

tatttcatag atcaaataag agaaataacg gtatattaat ccctccaaaa aaaaaaaacg    780

gtatatttac taaaaaatct aagccacgta ggaggataac aggatccccg taggaggata    840

acatccaatc caaccaatca caacaatcct gatgagataa cccactttaa gcccacgcat    900

ctgtggcaca tctacattat ctaaatcaca cattcttcca cacatctgag ccacacaaaa    960

accaatccac atctttatca cccattctat aaaaaatcac actttgtgag tctacacttt   1020

gattcccttc aaacacatac aaagagaaga gactaattaa ttaattaatc atcttgagag   1080

aaaatggaac gagctataca aggaaacgac gctagggaac aagctaacag tgaacgttgg   1140

gatggaggat caggaggtac cacttctccc ttcaaacttc ctgacgaaag tccgagttgg   1200

actgagtggc ggctacataa cgatgagacg aattcgaatc aagataatcc ccttggtttc   1260
```

aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860
gtggttaata tagctcaaat atatggtcaa gttcaataga ttaataatgg aaatatcagt 1920
tatcgaaatt cattaacaat caacttaacg ttattaacta ctaattttat atcatcccct 1980
ttgataaatg atagtacacc aattaggaag gagcatgctc gcctaggaga ttgtcgtttc 2040
ccgccttcag tttgcaagct gctctagccg tgtagccaat acgcaaaccg cctctccccg 2100
cgcgttggga attactagcg cgtgtcgaca agcttgcatg ccggtcaaca tggtggagca 2160
cgacacactt gtctactcca aaaatatcaa agatacagtc tcagaagacc aaagggcaat 2220
tgagactttt caacaaaggg taatatccgg aaacctcctc ggattccatt gcccagctat 2280
ctgtcacttt attgtgaaga tagtggaaaa ggaaggtggc tcctacaaat gccatcattg 2340
cgataaagga aaggccatcg ttgaagatgc ctctgccgac agtggtccca aagatggacc 2400
cccacccacg aggagcatcg tggaaaaaga agacgttcca accacgtctt caaagcaagt 2460
ggattgatgt gataacatgg tggagcacga cacacttgtc tactccaaaa atatcaaaga 2520
tacagtctca gaagaccaaa gggcaattga gacttttcaa caaagggtaa tatccggaaa 2580
cctcctcgga ttccattgcc cagctatctg tcactttatt gtgaagatag tggaaaagga 2640
aggtggctcc tacaaatgcc atcattgcga taaaggaaag gccatcgttg aagatgcctc 2700
tgccgacagt ggtcccaaag atggaccccc acccacgagg agcatcgtgg aaaaagaaga 2760
cgttccaacc acgtcttcaa agcaagtgga ttgatgtgat atctccactg acgtaaggga 2820
tgacgcacaa tcccactatc cttcgcaaga cccttcctct atataaggaa gttcatttca 2880
tttggagagg tattaaaatc ttaataggtt ttgataaaag cgaacgtggg gaaacccgaa 2940
ccaaaccttc ttctaaactc tctctcatct ctcttaaagc aaacttctct cttgtctttc 3000
ttgcgtgagc gatcttcaac gttgtcagat cgtgcttcgg caccagtaca acgttttctt 3060
tcactgaagc gaaatcaaag atctctttgt ggacacgtag tgcggcgcca ttaaataacg 3120
tgtacttgtc ctattcttgt cggtgtggtc ttgggaaaag aaagcttgct ggaggctgct 3180
gttcagcccc atacattact tgttacgatt ctgctgactt tcggcgggtg caatatctct 3240
acttctgctt gacgaggtat tgttgcctgt acttctttct tcttcttctt gctgattggt 3300
tctataagaa atctagtatt ttctttgaaa cagagttttc ccgtggtttt cgaacttgga 3360
gaaagattgt taagcttctg tatattctgc ccaaatttgt cgggcccaat accgcggaga 3420
aaatggcgaa aaacgttgcg attttcggct tattgttttc tcttcttgtg ttggttcctt 3480
ctcagatctt cgcgacgtca ctcctcagcc aaaacgacac ccccatctgt ctatccactg 3540
gcccctggat ctgctgccca aactaactcc atggtgaccc tgggatgcct ggtcaagggc 3600

```
tatttccctg agccagtgac agtgacctgg aactctggat ccctgtccag cggtgtgcac   3660

accttcccag ctgtcctgca gtctgacctc tacactctga gcagctcagt gactgtcccc   3720

tccagcacct ggcccagcga gaccgtcacc tgcaacgttg cccacccggc cagcagcacc   3780

aaggtggaca agaaaattgt gcccagggat tgtggttgta agccttgcat atgtacagtc   3840

ccagaagtat catctgtctt catcttcccc ccaaagccca aggatgtgct caccattact   3900

ctgactccta aggtcacgtg tgttgtggta gacatcagca aggatgatcc cgaggtccag   3960

ttcagctggt ttgtagatga tgtggaggtg cacacagctc agacgcaacc ccgggaggag   4020

cagttcaaca gcactttccg ctcagtcagt gaacttccca tcatgcacca ggactggctc   4080

aatggcaagg agcgatcgct caccatcacc atcaccatca ccatcaccat taaaggccta   4140

ttttctttag tttgaattta ctgttattcg gtgtgcattt ctatgtttgg tgagcggttt   4200

tctgtgctca gagtgtgttt attttatgta atttaatttc tttgtgagct cctgtttagc   4260

aggtcgtccc ttcagcaagg acacaaaaag attttaattt tattaaaaaa aaaaaaaaaa   4320

aagaccggga attcgatatc aagcttatcg acctgcagat cgttcaaaca tttggcaata   4380

aagtttctta agattgaatc ctgttgccgg tcttgcgatg attatcatat aatttctgtt   4440

gaattacgtt aagcatgtaa taattaacat gtaatgcatg acgttattta tgagatgggt   4500

ttttatgatt agagtcccgc aattatacat ttaatacgcg atagaaaaca aaatatagcg   4560

cgcaaactag gataaattat cgcgcgcggt gtcatctatg ttactagatc tctagagtct   4620

caagcttggc gcgcccacgt gactagtggc actggccgtc gttttacaac gtcgtgactg   4680

ggaaaaccct ggcgttaccc aacttaatcg ccttgcagca catccccctt tcgccagctg   4740

gcgtaatagc gaagaggccc gcaccgatcg cccttcccaa cagttgcgca gcctgaatgg   4800

cgaatgctag agcagcttga gcttggatca gattgtcgtt tcccgccttc agtttaaact   4860

atcagtgttt gacaggatat attggcgggt aaacctaaga gaaaagagcg ttta         4914
```

<210> SEQ ID NO 126
<211> LENGTH: 3480
<212> TYPE: DNA
<213> ORGANISM: Artificial sequence
<220> FEATURE:
<223> OTHER INFORMATION: Construct 1819

<400> SEQUENCE: 126

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780
```

```
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccaatacc gcggagaaaa tggcgaaaaa cgttgcgatt ttcggcttat tgttttctct   1320
tcttgtgttg gttccttctc agatcttcgc ccaaaaactt cctggaaatg acaacagcac   1380
ggcaacgctg tgccttgggc accatgcagt accaaacgga acgatagtga aaacaatcac   1440
gaatgaccaa attgaagtta ctaatgctac tgagctggtt cagaattcct caataggtga   1500
aatatgcgac agtcctcatc agatccttga tggagaaaac tgcacactaa tagatgctct   1560
attgggagac cctcagtgtg atggcttcca aaataagaaa tgggaccttt ttgttgaacg   1620
aagcaaagcc tacagcaact gttaccctta tgatgtgccg gattatgcct cccttaggtc   1680
actagttgcc tcatccggca cactggagtt taacaatgaa agcttcaatt ggactggagt   1740
cactcaaaac ggaacaagtt ctgcttgcat aaggagatct aataatagtt tctttagtag   1800
attaaattgg ttgacccact taaacttcaa atacccagca ttgaacgtga ctatgccaaa   1860
caatgaacaa tttgacaaat tgtacatttg gggggttcac cacccgggta cggacaagga   1920
ccaaatcttc ctgtatgctc aatcatcagg aagaatcaca gtatctacca aaagaagcca   1980
acaagctgta atcccgaata tcggatctag acccagaata aggaatatcc ctagcagaat   2040
aagcatctat tggacaatag taaaaccggg agacatactt ttgattaaca gcacagggaa   2100
tctaattgct cctaggggtt acttcaaaat acgaagtggg aaaagctcaa taatgagatc   2160
agatgcaccc attggcaaat gcaattctga atgcatcact ccaaatggaa gcattcccaa   2220
tgacaaacca ttccaaaatg taaacaggat cacatacggg gcctgtccca gatatgttaa   2280
gcaaagcact ctgaaattgg caacaggaat gcgaaatgta ccagagaaac aaactagagg   2340
catatttggc gcaatagcgg gtttcataga aaatggttgg gagggaatgg tggatggttg   2400
gtacggtttc aggcatcaaa attctgaggg aagaggacaa gcagcagatc tcaaaagcac   2460
tcaagcagca atcgatcaaa tcaatgggaa gctgaatcga ttgatcggga aaaccaacga   2520
gaaattccat cagattgaaa aagaattctc agaagtcgaa gggagaattc aggaccttga   2580
gaaatatgtt gaggacacta aaatagatct ctggtcatac aacgcggagc ttcttgttgc   2640
cctggagaac caacatacaa ttgatctaac tgactcagaa atgaacaaac tgtttgaaaa   2700
aacaaagaag caactaaggg aaaatgctga ggatatgggc aatggttgtt tcaaaatata   2760
ccacaaatgt gacaatgcct gcataggatc aatcagaaat ggaacttatg accacgatgt   2820
atacagagat gaagcattaa acaaccggtt ccagatcaag ggagttgagc tgaagtcagg   2880
gtacaaagat tggatcctat ggatttcctt tgccatatca tgttttttgc tttgtgttgc   2940
tttgttgggg ttcatcatgt gggcctgcca aaagggcaac attaggtgca acatttgcat   3000
ttgaaggcct attttcttta gtttgaattt actgttattc ggtgtgcatt tctatgtttg   3060
gtgagcggtt ttctgtgctc agagtgtgtt tattttatgt aatttaattt ctttgtgagc   3120
```

-continued tcctgtttag caggtcgtcc cttcagcaag gacacaaaaa gattttaatt ttattaaaaa 3180
aaaaaaaaaa aaagaccggg aattcgatat caagcttatc gacctgcaga tcgttcaaac 3240
atttggcaat aaagtttctt aagattgaat cctgttgccg gtcttgcgat gattatcata 3300
taatttctgt tgaattacgt taagcatgta ataattaaca tgtaatgcat gacgttattt 3360
atgagatggg tttttatgat tagagtcccg caattataca tttaatacgc gatagaaaac 3420
aaaatatagc gcgcaaacta ggataaatta tcgcgcgcgg tgtcatctat gttactagat 3480

<210> SEQ ID NO 127
<211> LENGTH: 50
<212> TYPE: DNA
<213> ORGANISM: Artificial sequence
<220> FEATURE:
<223> OTHER INFORMATION: IF**-H2S157.sl-6r

<400> SEQUENCE: 127
actaaagaaa ataggccttc atatgcagat cctgcactgc agagacccgt 50

<210> SEQ ID NO 128
<211> LENGTH: 1716
<212> TYPE: DNA
<213> ORGANISM: Artificial sequence
<220> FEATURE:
<223> OTHER INFORMATION: Nucleotide sequence of PDISP/H2 Singapore.

<400> SEQUENCE: 128
atggcgaaaa acgttgcgat tttcggctta ttgttttctc ttcttgtgtt ggttccttct 60
cagatcttcg cggaccaaat atgcattgga taccatgcca ataattccac agagaaggtc 120
gacacaattc tagagcggaa cgtcactgtg actcatgcca aggacattct tgagaagacc 180
cataacggaa agttatgcaa actaaacgga atccctccac ttgaactagg ggactgtagc 240
attgccggat ggctccttgg aaatccagaa tgtgataggc ttctaagtgt gccagaatgg 300
tcctatataa tggagaaaga aaacccgaga gacggtttgt gttatccagg cagcttcaat 360
gattatgaag aattgaaaca tctcctcagc agcgtgaaac atttcgagaa agtaaagatt 420
ctgcccaaag atagatggac acagcataca acaactggag gttcacgggc ctgcgcggtg 480
tctggtaatc catcattctt caggaacatg gtctggctga caaagaaaga atcaaattat 540
ccggttgcca aaggatcgta caacaataca agcggagaac aaatgctaat aatttggggg 600
gtgcaccatc ccaatgatga gacagaacaa agaacattgt accagaatgt gggaacctat 660
gtttccgtag gcacatcaac attgaacaaa aggtcaaccc cagacatagc aacaaggcct 720
aaagtgaatg gactaggaag tagaatggag ttctcttgga ccctattgga tatgtgggac 780
accataaatt ttgagagtac tggtaatcta attgcaccag agtatggatt caaaatatcg 840
aaaagaggta gttcagggat catgaaaaca gaaggaacac ttgagaactg tgagaccaaa 900
tgccaaactc ctttgggagc aataaataca acattgcctt ttcacaatgt ccacccactg 960
acaataggtg agtgccccaa atatgtaaaa tcggagaagt tggtcttagc aacaggacta 1020
aggaatgttc cccagattga atcaagagga ttgtttgggg caatagctgg ttttatagaa 1080
ggaggatggc aaggaatggt tgatggttgg tatggatacc atcacagcaa tgaccaggga 1140
tcagggtatg cagcagacaa agaatccact caaaaggcat ttgatggaat caccaacaag 1200
gtaaattctg tgattgaaaa gatgaacacc caatttgaag ctgttgggaa agagttcagt 1260
aacttagaga gaagactgga gaacttgaac aaaaagatgg aagacgggtt tctagatgtg 1320
tggacataca atgctgagct tctagttctg atggaaaatg agaggacact tgactttcat 1380

```
gattctaatg tcaagaatct gtatgataaa gtcagaatgc agctgagaga caacgtcaaa   1440

gaactaggaa atggatgttt tgaattttat cacaaatgtg atgatgaatg catgaatagt   1500

gtgaaaaacg ggacgtatga ttatcccaag tatgaagaag agtctaaact aaatagaaat   1560

gaaatcaaag ggtaaaatt gagcagcatg gggtttatc aaatccttgc catttatgct   1620

acagtagcag gttctctgtc actggcaatc atgatggctg ggatctcttt ctggatgtgc   1680

tccaacgggt ctctgcagtg caggatctgc atatga                              1716
```

<210> SEQ ID NO 129
<211> LENGTH: 3471
<212> TYPE: DNA
<213> ORGANISM: Artificial sequence
<220> FEATURE:
<223> OTHER INFORMATION: Expression cassette number 2220

<400> SEQUENCE: 129

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaacg ttttctttca ctgaagcgaa atcaaagatc tctttgtgga cacgtagtgc    960

ggcgccatta aataacgtgt acttgtccta ttcttgtcgg tgtggtcttg ggaaaagaaa   1020

gcttgctgga ggctgctgtt cagccccata cattacttgt tacgattctg ctgactttcg   1080

gcgggtgcaa tatctctact tctgcttgac gaggtattgt tgcctgtact tctttcttct   1140

tcttcttgct gattggttct ataagaaatc tagtattttc tttgaaacag agttttcccg   1200

tggttttcga acttggagaa agattgttaa gcttctgtat attctgccca aatttgtcgg   1260

gcccaatacc gcggagaaaa tggcgaaaaa cgttgcgatt ttcggcttat tgttttctct   1320

tcttgtgttg gttccttctc agatcttcgc ggaccaaata tgcattggat accatgccaa   1380

taattccaca gagaaggtcg acacaattct agagcggaac gtcactgtga ctcatgccaa   1440

ggacattctt gagaagaccc ataacggaaa gttatgcaaa ctaaacggaa tccctccact   1500

tgaactaggg gactgtagca ttgccggatg gctccttgga aatccagaat gtgataggct   1560

tctaagtgtg ccagaatggt cctatataat ggagaaagaa aacccgagag acggtttgtg   1620

ttatccaggc agcttcaatg attatgaaga attgaaacat ctcctcagca gcgtgaaaca   1680
```

```
tttcgagaaa gtaaagattc tgcccaaaga tagatggaca cagcatacaa caactggagg   1740
ttcacgggcc tgcgcggtgt ctggtaatcc atcattcttc aggaacatgg tctggctgac   1800
aaagaaagaa tcaaattatc cggttgccaa aggatcgtac aacaatacaa gcggagaaca   1860
aatgctaata atttgggggg tgcaccatcc caatgatgag acagaacaaa gaacattgta   1920
ccagaatgtg ggaacctatg tttccgtagg cacatcaaca ttgaacaaaa ggtcaacccc   1980
agacatagca acaaggccta aagtgaatgg actaggaagt agaatggagt tctcttggac   2040
cctattggat atgtgggaca ccataaattt tgagagtact ggtaatctaa ttgcaccaga   2100
gtatggattc aaaatatcga aaagaggtag ttcagggatc atgaaaacag aaggaacact   2160
tgagaactgt gagaccaaat gccaaactcc tttgggagca ataaatacaa cattgccttt   2220
tcacaatgtc cacccactga caataggtga gtgccccaaa tatgtaaaat cggagaagtt   2280
ggtcttagca acaggactaa ggaatgttcc ccagattgaa tcaagaggat tgtttggggc   2340
aatagctggt tttatagaag gaggatggca aggaatggtt gatggttggt atggatacca   2400
tcacagcaat gaccagggat cagggtatgc agcagacaaa gaatccactc aaaaggcatt   2460
tgatggaatc accaacaagg taaattctgt gattgaaaag atgaacaccc aatttgaagc   2520
tgttgggaaa gagttcagta acttagagag aagactggag aacttgaaca aaaagatgga   2580
agacgggttt ctagatgtgt ggacatacaa tgctgagctt ctagttctga tggaaaatga   2640
gaggacactt gactttcatg attctaatgt caagaatctg tatgataaag tcagaatgca   2700
gctgagagac aacgtcaaag aactaggaaa tggatgtttt gaattttatc acaaatgtga   2760
tgatgaatgc atgaatagtg tgaaaaacgg gacgtatgat tatcccaagt atgaagaaga   2820
gtctaaacta aatagaaatg aaatcaaagg ggtaaaattg agcagcatgg gggtttatca   2880
aatccttgcc atttatgcta cagtagcagg ttctctgtca ctggcaatca tgatggctgg   2940
gatctctttc tggatgtgct ccaacgggtc tctgcagtgc aggatctgca tatgaaggcc   3000
tattttcttt agtttgaatt tactgttatt cggtgtgcat ttctatgttt ggtgagcggt   3060
tttctgtgct cagagtgtgt ttattttatg taatttaatt tctttgtgag ctcctgttta   3120
gcaggtcgtc ccttcagcaa ggacacaaaa agattttaat ttattaaaaa aaaaaaaaaa   3180
aaaagaccgg gaattcgata tcaagcttat cgacctgcag atcgttcaaa catttggcaa   3240
taaagtttct taagattgaa tcctgttgcc ggtcttgcga tgattatcat ataatttctg   3300
ttgaattacg ttaagcatgt aataattaac atgtaatgca tgacgttatt tatgagatgg   3360
gtttttatga ttagagtccc gcaattatac atttaatacg cgatagaaaa caaaatatag   3420
cgcgcaaact aggataaatt atcgcgcgcg gtgtcatcta tgttactaga t            3471
```

<210> SEQ ID NO 130
<211> LENGTH: 571
<212> TYPE: PRT
<213> ORGANISM: Artificial sequence
<220> FEATURE:
<223> OTHER INFORMATION: Amino acid sequence of PDISP/H2 Singapore

<400> SEQUENCE: 130

```
Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
            20                  25                  30

Ala Asn Asn Ser Thr Glu Lys Val Asp Thr Ile Leu Glu Arg Asn Val
        35                  40                  45
```

```
Thr Val Thr His Ala Lys Asp Ile Leu Glu Lys Thr His Asn Gly Lys
    50                  55                  60

Leu Cys Lys Leu Asn Gly Ile Pro Pro Leu Glu Leu Gly Asp Cys Ser
65                  70                  75                  80

Ile Ala Gly Trp Leu Leu Gly Asn Pro Glu Cys Asp Arg Leu Leu Ser
                85                  90                  95

Val Pro Glu Trp Ser Tyr Ile Met Glu Lys Glu Asn Pro Arg Asp Gly
            100                 105                 110

Leu Cys Tyr Pro Gly Ser Phe Asn Asp Tyr Glu Glu Leu Lys His Leu
        115                 120                 125

Leu Ser Ser Val Lys His Phe Glu Lys Val Lys Ile Leu Pro Lys Asp
    130                 135                 140

Arg Trp Thr Gln His Thr Thr Thr Gly Gly Ser Arg Ala Cys Ala Val
145                 150                 155                 160

Ser Gly Asn Pro Ser Phe Phe Arg Asn Met Val Trp Leu Thr Lys Lys
                165                 170                 175

Glu Ser Asn Tyr Pro Val Ala Lys Gly Ser Tyr Asn Asn Thr Ser Gly
            180                 185                 190

Glu Gln Met Leu Ile Ile Trp Gly Val His His Pro Asn Asp Glu Thr
        195                 200                 205

Glu Gln Arg Thr Leu Tyr Gln Asn Val Gly Thr Tyr Val Ser Val Gly
    210                 215                 220

Thr Ser Thr Leu Asn Lys Arg Ser Thr Pro Asp Ile Ala Thr Arg Pro
225                 230                 235                 240

Lys Val Asn Gly Leu Gly Ser Arg Met Glu Phe Ser Trp Thr Leu Leu
                245                 250                 255

Asp Met Trp Asp Thr Ile Asn Phe Glu Ser Thr Gly Asn Leu Ile Ala
            260                 265                 270

Pro Glu Tyr Gly Phe Lys Ile Ser Lys Arg Gly Ser Ser Gly Ile Met
        275                 280                 285

Lys Thr Glu Gly Thr Leu Glu Asn Cys Glu Thr Lys Cys Gln Thr Pro
    290                 295                 300

Leu Gly Ala Ile Asn Thr Thr Leu Pro Phe His Asn Val His Pro Leu
305                 310                 315                 320

Thr Ile Gly Glu Cys Pro Lys Tyr Val Lys Ser Glu Lys Leu Val Leu
                325                 330                 335

Ala Thr Gly Leu Arg Asn Val Pro Gln Ile Glu Ser Arg Gly Leu Phe
            340                 345                 350

Gly Ala Ile Ala Gly Phe Ile Glu Gly Gly Trp Gln Gly Met Val Asp
        355                 360                 365

Gly Trp Tyr Gly Tyr His His Ser Asn Asp Gln Gly Ser Gly Tyr Ala
    370                 375                 380

Ala Asp Lys Glu Ser Thr Gln Lys Ala Phe Asp Gly Ile Thr Asn Lys
385                 390                 395                 400

Val Asn Ser Val Ile Glu Lys Met Asn Thr Gln Phe Glu Ala Val Gly
                405                 410                 415

Lys Glu Phe Ser Asn Leu Glu Arg Arg Leu Glu Asn Leu Asn Lys Lys
            420                 425                 430

Met Glu Asp Gly Phe Leu Asp Val Trp Thr Tyr Asn Ala Glu Leu Leu
        435                 440                 445

Val Leu Met Glu Asn Glu Arg Thr Leu Asp Phe His Asp Ser Asn Val
    450                 455                 460

Lys Asn Leu Tyr Asp Lys Val Arg Met Gln Leu Arg Asp Asn Val Lys
```

-continued

```
465                 470                 475                 480

Glu Leu Gly Asn Gly Cys Phe Glu Phe Tyr His Lys Cys Asp Asp Glu
                485                 490                 495

Cys Met Asn Ser Val Lys Asn Gly Thr Tyr Asp Tyr Pro Lys Tyr Glu
            500                 505                 510

Glu Glu Ser Lys Leu Asn Arg Asn Glu Ile Lys Gly Val Lys Leu Ser
        515                 520                 525

Ser Met Gly Val Tyr Gln Ile Leu Ala Ile Tyr Ala Thr Val Ala Gly
    530                 535                 540

Ser Leu Ser Leu Ala Ile Met Met Ala Gly Ile Ser Phe Trp Met Cys
545                 550                 555                 560

Ser Asn Gly Ser Leu Gln Cys Arg Ile Cys Ile
                565                 570


<210> SEQ ID NO 131
<211> LENGTH: 48
<212> TYPE: DNA
<213> ORGANISM: Artificial sequence
<220> FEATURE:
<223> OTHER INFORMATION: H2S157(Prl-).r

<400> SEQUENCE: 131

tgccatcctc cgccgggaac attccttagt cctgttgcta agaccaac                48


<210> SEQ ID NO 132
<211> LENGTH: 50
<212> TYPE: DNA
<213> ORGANISM: Artificial sequence
<220> FEATURE:
<223> OTHER INFORMATION: H2S157(Prl-).c

<400> SEQUENCE: 132

aggaatgttc ccggcggagg atggcaagga atggttgatg gttggtatgg              50


<210> SEQ ID NO 133
<211> LENGTH: 3426
<212> TYPE: DNA
<213> ORGANISM: Artificial sequence
<220> FEATURE:
<223> OTHER INFORMATION: Cassette 2221

<400> SEQUENCE: 133

gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780
```

```
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccaatacc gcggagaaaa tggcgaaaaa cgttgcgatt ttcggcttat tgttttctct   1320
tcttgtgttg gttccttctc agatcttcgc ggaccaaata tgcattggat accatgccaa   1380
taattccaca gagaaggtcg acacaattct agagcggaac gtcactgtga ctcatgccaa   1440
ggacattctt gagaagaccc ataacggaaa gttatgcaaa ctaaacggaa tccctccact   1500
tgaactaggg gactgtagca ttgccggatg gctccttgga aatccagaat gtgataggct   1560
tctaagtgtg ccagaatggt cctatataat ggagaaagaa aacccgagag acggtttgtg   1620
ttatccaggc agcttcaatg attatgaaga attgaaacat ctcctcagca gcgtgaaaca   1680
tttcgagaaa gtaaagattc tgcccaaaga tagatggaca cagcatacaa caactggagg   1740
ttcacgggcc tgcgcggtgt ctggtaatcc atcattcttc aggaacatgg tctggctgac   1800
aaagaaagaa tcaaattatc cggttgccaa aggatcgtac aacaatacaa gcggagaaca   1860
aatgctaata atttgggggg tgcaccatcc caatgatgag acagaacaaa gaacattgta   1920
ccagaatgtg ggaacctatg tttccgtagg cacatcaaca ttgaacaaaa ggtcaacccc   1980
agacatagca acaaggccta aagtgaatgg actaggaagt agaatggagt tctcttggac   2040
cctattggat atgtgggaca ccataaattt tgagagtact ggtaatctaa ttgcaccaga   2100
gtatggattc aaaatatcga aaagaggtag ttcagggatc atgaaaacag aaggaacact   2160
tgagaactgt gagaccaaat gccaaactcc tttgggagca ataaatacaa cattgccttt   2220
tcacaatgtc cacccactga caataggtga gtgccccaaa tatgtaaaat cggagaagtt   2280
ggtcttagca acaggactaa ggaatgttcc cggcggagga tggcaaggaa tggttgatgg   2340
ttggtatgga taccatcaca gcaatgacca gggatcaggg tatgcagcag acaaagaatc   2400
cactcaaaag gcatttgatg gaatcaccaa caaggtaaat tctgtgattg aaaagatgaa   2460
cacccaattt gaagctgttg ggaaagagtt cagtaactta gagagaagac tggagaactt   2520
gaacaaaaag atggaagacg ggtttctaga tgtgtggaca tacaatgctg agcttctagt   2580
tctgatggaa aatgagagga cacttgactt tcatgattct aatgtcaaga atctgtatga   2640
taaagtcaga atgcagctga gagacaacgt caaagaacta ggaaatggat gttttgaatt   2700
ttatcacaaa tgtgatgatg aatgcatgaa tagtgtgaaa aacgggacgt atgattatcc   2760
caagtatgaa gaagagtcta aactaaatag aaatgaaatc aaaggggtaa aattgagcag   2820
catgggggtt tatcaaatcc ttgccattta tgctacagta gcaggttctc tgtcactggc   2880
aatcatgatg gctgggatct ctttctggat gtgctccaac gggtctctgc agtgcaggat   2940
ctgcatatga aggcctattt tctttagttt gaatttactg ttattcggtg tgcatttcta   3000
tgtttggtga gcggttttct gtgctcagag tgtgtttatt ttatgtaatt taatttcttt   3060
gtgagctcct gtttagcagg tcgtcccttc agcaaggaca caaaaagatt ttaattttat   3120
```

```
taaaaaaaaa aaaaaaaaag accgggaatt cgatatcaag cttatcgacc tgcagatcgt   3180

tcaaacattt ggcaataaag tttcttaaga ttgaatcctg ttgccggtct tgcgatgatt   3240

atcatataat ttctgttgaa ttacgttaag catgtaataa ttaacatgta atgcatgacg   3300

ttatttatga gatgggtttt tatgattaga gtcccgcaat tatacattta atacgcgata   3360

gaaaacaaaa tatagcgcgc aaactaggat aaattatcgc gcgcggtgtc atctatgtta   3420

ctagat                                                              3426
```

<210> SEQ ID NO 134
<211> LENGTH: 556
<212> TYPE: PRT
<213> ORGANISM: Artificial sequence
<220> FEATURE:
<223> OTHER INFORMATION: Amino acid sequence of PDISP/H2 Singapore with deleted proteolytic loop

<400> SEQUENCE: 134

```
Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
            20                  25                  30

Ala Asn Asn Ser Thr Glu Lys Val Asp Thr Ile Leu Glu Arg Asn Val
        35                  40                  45

Thr Val Thr His Ala Lys Asp Ile Leu Glu Lys Thr His Asn Gly Lys
    50                  55                  60

Leu Cys Lys Leu Asn Gly Ile Pro Pro Leu Glu Leu Gly Asp Cys Ser
65                  70                  75                  80

Ile Ala Gly Trp Leu Leu Gly Asn Pro Glu Cys Asp Arg Leu Leu Ser
                85                  90                  95

Val Pro Glu Trp Ser Tyr Ile Met Glu Lys Glu Asn Pro Arg Asp Gly
            100                 105                 110

Leu Cys Tyr Pro Gly Ser Phe Asn Asp Tyr Glu Glu Leu Lys His Leu
        115                 120                 125

Leu Ser Ser Val Lys His Phe Glu Lys Val Lys Ile Leu Pro Lys Asp
    130                 135                 140

Arg Trp Thr Gln His Thr Thr Thr Gly Gly Ser Arg Ala Cys Ala Val
145                 150                 155                 160

Ser Gly Asn Pro Ser Phe Phe Arg Asn Met Val Trp Leu Thr Lys Lys
                165                 170                 175

Glu Ser Asn Tyr Pro Val Ala Lys Gly Ser Tyr Asn Asn Thr Ser Gly
            180                 185                 190

Glu Gln Met Leu Ile Ile Trp Gly Val His His Pro Asn Asp Glu Thr
        195                 200                 205

Glu Gln Arg Thr Leu Tyr Gln Asn Val Gly Thr Tyr Val Ser Val Gly
    210                 215                 220

Thr Ser Thr Leu Asn Lys Arg Ser Thr Pro Asp Ile Ala Thr Arg Pro
225                 230                 235                 240

Lys Val Asn Gly Leu Gly Ser Arg Met Glu Phe Ser Trp Thr Leu Leu
                245                 250                 255

Asp Met Trp Asp Thr Ile Asn Phe Glu Ser Thr Gly Asn Leu Ile Ala
            260                 265                 270

Pro Glu Tyr Gly Phe Lys Ile Ser Lys Arg Gly Ser Ser Gly Ile Met
        275                 280                 285

Lys Thr Glu Gly Thr Leu Glu Asn Cys Glu Thr Lys Cys Gln Thr Pro
    290                 295                 300
```

```
Leu Gly Ala Ile Asn Thr Thr Leu Pro Phe His Asn Val His Pro Leu
305                 310                 315                 320

Thr Ile Gly Glu Cys Pro Lys Tyr Val Lys Ser Glu Lys Leu Val Leu
                325                 330                 335

Ala Thr Gly Leu Arg Asn Val Pro Gly Gly Gly Trp Gln Gly Met Val
            340                 345                 350

Asp Gly Trp Tyr Gly Tyr His His Ser Asn Asp Gln Gly Ser Gly Tyr
        355                 360                 365

Ala Ala Asp Lys Glu Ser Thr Gln Lys Ala Phe Asp Gly Ile Thr Asn
    370                 375                 380

Lys Val Asn Ser Val Ile Glu Lys Met Asn Thr Gln Phe Glu Ala Val
385                 390                 395                 400

Gly Lys Glu Phe Ser Asn Leu Glu Arg Arg Leu Glu Asn Leu Asn Lys
                405                 410                 415

Lys Met Glu Asp Gly Phe Leu Asp Val Trp Thr Tyr Asn Ala Glu Leu
            420                 425                 430

Leu Val Leu Met Glu Asn Glu Arg Thr Leu Asp Phe His Asp Ser Asn
        435                 440                 445

Val Lys Asn Leu Tyr Asp Lys Val Arg Met Gln Leu Arg Asp Asn Val
    450                 455                 460

Lys Glu Leu Gly Asn Gly Cys Phe Glu Phe Tyr His Lys Cys Asp Asp
465                 470                 475                 480

Glu Cys Met Asn Ser Val Lys Asn Gly Thr Tyr Asp Tyr Pro Lys Tyr
                485                 490                 495

Glu Glu Glu Ser Lys Leu Asn Arg Asn Glu Ile Lys Gly Val Lys Leu
            500                 505                 510

Ser Ser Met Gly Val Tyr Gln Ile Leu Ala Ile Tyr Ala Thr Val Ala
        515                 520                 525

Gly Ser Leu Ser Leu Ala Ile Met Met Ala Gly Ile Ser Phe Trp Met
    530                 535                 540

Cys Ser Asn Gly Ser Leu Gln Cys Arg Ile Cys Ile
545                 550                 555


<210> SEQ ID NO 135
<211> LENGTH: 3120
<212> TYPE: DNA
<213> ORGANISM: Artificial sequence
<220> FEATURE:
<223> OTHER INFORMATION: Cassette 2222

<400> SEQUENCE: 135

gtcaacatgg tggagcacga cacacttgtc tactccaaaa atatcaaaga tacagtctca      60

gaagaccaaa gggcaattga gacttttcaa caaagggtaa tatccggaaa cctcctcgga     120

ttccattgcc cagctatctg tcactttatt gtgaagatag tggaaaagga aggtggctcc     180

tacaaatgcc atcattgcga taaaggaaag gccatcgttg aagatgcctc tgccgacagt     240

ggtcccaaag atggaccccc acccacgagg agcatcgtgg aaaaagaaga cgttccaacc     300

acgtcttcaa agcaagtgga ttgatgtgat aacatggtgg agcacgacac acttgtctac     360

tccaaaaata tcaaagatac agtctcagaa gaccaaaggg caattgagac ttttcaacaa     420

agggtaatat ccggaaacct cctcggattc cattgcccag ctatctgtca ctttattgtg     480

aagatagtgg aaaaggaagg tggctcctac aaatgccatc attgcgataa aggaaaggcc     540

atcgttgaag atgcctctgc cgacagtggt cccaaagatg gacccccacc cacgaggagc     600
```

-continued

```
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaggg cccaataccg cggagaaaat ggcgaaaaac gttgcgattt tcggcttatt    960
gttttctctt cttgtgttgg ttccttctca gatcttcgcg gaccaaatat gcattggata   1020
ccatgccaat aattccacag agaaggtcga cacaattcta gagcggaacg tcactgtgac   1080
tcatgccaag gacattcttg agaagaccca taacggaaag ttatgcaaac taaacggaat   1140
ccctccactt gaactagggg actgtagcat tgccggatgg ctccttggaa atccagaatg   1200
tgataggctt ctaagtgtgc cagaatggtc ctatataatg gagaaagaaa acccgagaga   1260
cggtttgtgt tatccaggca gcttcaatga ttatgaagaa ttgaaacatc tcctcagcag   1320
cgtgaaacat ttcgagaaag taaagattct gcccaaagat agatggacac agcatacaac   1380
aactggaggt tcacgggcct gcgcggtgtc tggtaatcca tcattcttca ggaacatggt   1440
ctggctgaca aagaaagaat caaattatcc ggttgccaaa ggatcgtaca acaatacaag   1500
cggagaacaa atgctaataa tttggggggt gcaccatccc aatgatgaga cagaacaaag   1560
aacattgtac cagaatgtgg gaacctatgt ttccgtaggc acatcaacat tgaacaaaag   1620
gtcaacccca gacatagcaa caaggcctaa agtgaatgga ctaggaagta gaatggagtt   1680
ctcttggacc ctattggata tgtgggacac cataaatttt gagagtactg gtaatctaat   1740
tgcaccagag tatggattca aaatatcgaa aagaggtagt tcagggatca tgaaaacaga   1800
aggaacactt gagaactgtg agaccaaatg ccaaactcct ttgggagcaa taaatacaac   1860
attgcctttt cacaatgtcc acccactgac aataggtgag tgccccaaat atgtaaaatc   1920
ggagaagttg gtcttagcaa caggactaag gaatgttccc cagattgaat caagaggatt   1980
gtttggggca atagctggtt ttatagaagg aggatggcaa ggaatggttg atggttggta   2040
tggataccat cacagcaatg accagggatc agggtatgca gcagacaaag aatccactca   2100
aaaggcattt gatggaatca ccaacaaggt aaattctgtg attgaaaaga tgaacaccca   2160
atttgaagct gttgggaaag agttcagtaa cttagagaga agactggaga acttgaacaa   2220
aaagatggaa gacgggtttc tagatgtgtg gacatacaat gctgagcttc tagttctgat   2280
ggaaaatgag aggacacttg actttcatga ttctaatgtc aagaatctgt atgataaagt   2340
cagaatgcag ctgagagaca acgtcaaaga actaggaaat ggatgttttg aattttatca   2400
caaatgtgat gatgaatgca tgaatagtgt gaaaaacggg acgtatgatt atcccaagta   2460
tgaagaagag tctaaactaa atagaaatga aatcaaaggg gtaaaattga gcagcatggg   2520
ggtttatcaa atccttgcca tttatgctac agtagcaggt tctctgtcac tggcaatcat   2580
gatggctggg atctctttct ggatgtgctc caacgggtct ctgcagtgca ggatctgcat   2640
atgaaggcct attttcttta gtttgaattt actgttattc ggtgtgcatt tctatgtttg   2700
gtgagcggtt ttctgtgctc agagtgtgtt tattttatgt aatttaattt ctttgtgagc   2760
tcctgtttag caggtcgtcc cttcagcaag gacacaaaaa gattttaatt ttattaaaaa   2820
aaaaaaaaaa aaagaccggg aattcgatat caagcttatc gacctgcaga tcgttcaaac   2880
atttggcaat aaagtttctt aagattgaat cctgttgccg gtcttgcgat gattatcata   2940
taatttctgt tgaattacgt taagcatgta ataattaaca tgtaatgcat gacgttattt   3000
```

atgagatggg tttttatgat tagagtcccg caattataca tttaatacgc gatagaaaac 3060
aaaatatagc gcgcaaacta ggataaatta tcgcgcgcgg tgtcatctat gttactagat 3120

<210> SEQ ID NO 136
<211> LENGTH: 3075
<212> TYPE: DNA
<213> ORGANISM: Artificial sequence
<220> FEATURE:
<223> OTHER INFORMATION: Cassette 2223

<400> SEQUENCE: 136
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaggg cccaataccg cggagaaaat ggcgaaaaac gttgcgattt tcggcttatt 960
gttttctctt cttgtgttgg ttccttctca gatcttcgcg gaccaaatat gcattggata 1020
ccatgccaat aattccacag agaaggtcga cacaattcta gagcggaacg tcactgtgac 1080
tcatgccaag gacattcttg agaagaccca taacggaaag ttatgcaaac taaacggaat 1140
ccctccactt gaactagggg actgtagcat tgccggatgg ctccttggaa atccagaatg 1200
tgataggctt ctaagtgtgc cagaatggtc ctatataatg gagaaagaaa acccgagaga 1260
cggtttgtgt tatccaggca gcttcaatga ttatgaagaa ttgaaacatc tcctcagcag 1320
cgtgaaacat ttcgagaaag taaagattct gcccaaagat agatggacac agcatacaac 1380
aactggaggt tcacgggcct gcgcggtgtc tggtaatcca tcattcttca ggaacatggt 1440
ctggctgaca aagaaagaat caaattatcc ggttgccaaa ggatcgtaca acaatacaag 1500
cggagaacaa atgctaataa tttgggggt gcaccatccc aatgatgaga cagaacaaag 1560
aacattgtac cagaatgtgg gaacctatgt ttccgtaggc acatcaacat tgaacaaaag 1620
gtcaacccca gacatagcaa caaggcctaa agtgaatgga ctaggaagta gaatggagtt 1680
ctcttggacc ctattggata tgtgggacac cataaatttt gagagtactg gtaatctaat 1740
tgcaccagag tatggattca aaatatcgaa aagaggtagt tcagggatca tgaaaacaga 1800
aggaacactt gagaactgtg agaccaaatg ccaaactcct ttgggagcaa taaatacaac 1860
attgcctttt cacaatgtcc acccactgac aataggtgag tgccccaaat atgtaaaatc 1920
ggagaagttg gtcttagcaa caggactaag gaatgttccc ggcggaggat ggcaaggaat 1980
ggttgatggt tggtatggat accatcacag caatgaccag ggatcagggt atgcagcaga 2040
caaagaatcc actcaaaagg catttgatgg aatcaccaac aaggtaaatt ctgtgattga 2100
aaagatgaac acccaatttg aagctgttgg gaaagagttc agtaacttag agagaagact 2160
ggagaacttg aacaaaaaga tggaagacgg gtttctagat gtgtggacat acaatgctga 2220
gcttctagtt ctgatggaaa atgagaggac acttgacttt catgattcta atgtcaagaa 2280
tctgtatgat aaagtcagaa tgcagctgag agacaacgtc aaagaactag gaaatggatg 2340
ttttgaattt tatcacaaat gtgatgatga atgcatgaat agtgtgaaaa acgggacgta 2400
tgattatccc aagtatgaag aagagtctaa actaaataga aatgaaatca aaggggtaaa 2460
attgagcagc atgggggttt atcaaatcct tgccatttat gctacagtag caggttctct 2520
gtcactggca atcatgatgg ctgggatctc tttctggatg tgctccaacg ggtctctgca 2580
gtgcaggatc tgcatatgaa ggcctatttt ctttagtttg aatttactgt tattcggtgt 2640
gcatttctat gtttggtgag cggttttctg tgctcagagt gtgtttattt tatgtaattt 2700
aatttctttg tgagctcctg tttagcaggt cgtcccttca gcaaggacac aaaaagattt 2760
taattttatt aaaaaaaaaa aaaaaaaaga ccgggaattc gatatcaagc ttatcgacct 2820
gcagatcgtt caaacatttg gcaataaagt ttcttaagat tgaatcctgt tgccggtctt 2880
gcgatgatta tcatataatt tctgttgaat tacgttaagc atgtaataat taacatgtaa 2940
tgcatgacgt tatttatgag atgggttttt atgattagag tcccgcaatt atacatttaa 3000
tacgcgatag aaaacaaaat atagcgcgca aactaggata aattatcgcg cgcggtgtca 3060
tctatgttac tagat 3075

<210> SEQ ID NO 137
<211> LENGTH: 1725
<212> TYPE: DNA
<213> ORGANISM: Artificial sequence
<220> FEATURE:
<223> OTHER INFORMATION: Nucleotide sequence of PDISP/H3 Perth

<400> SEQUENCE: 137
atggcgaaaa acgttgcgat tttcggctta ttgttttctc ttcttgtgtt ggttccttct 60
cagatcttcg cgcaaaaact tcctggaaat gacaacagca cggcaacgct gtgccttggg 120
caccatgcag taccaaacgg aacgatagtg aaaacaatca cgaatgacca aattgaagtt 180
actaatgcta ctgagctggt tcagagttcc tcaacaggtg aaatatgcga cagtcctcat 240
cagatccttg atggaaaaaa ctgcacacta atagatgctc tattgggaga ccctcagtgt 300
gatggcttcc aaaataagaa atgggacctt tttgttgaac gcagcaaagc ctacagcaac 360
tgttaccctt atgatgtgcc ggattatgcc tcccttaggt cactagttgc ctcatccggc 420
acactggagt ttaacaatga aagcttcaat tggactggag tcactcaaaa cggaacaagc 480
tctgcttgca taaggagatc taaaaacagt ttctttagta gattgaattg gttgacccac 540
ttaaacttca aatacccagc attgaacgtg actatgccaa acaatgaaca atttgacaaa 600
ttgtacattt ggggggttca ccacccgggt acggacaaag accaaatctt cctgtatgct 660
caagcatcag gaagaatcac agtctctacc aaaagaagcc aacaaaccgt aagcccgaat 720
atcggatcta gacccagagt aaggaatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900

```
tgcaattctg aatgcatcac tccaaatgga agcattccca atgacaaacc attccaaaat    960

gtaaacagga tcacatacgg ggcctgtccc agatatgtta agcaaaacac tctgaaattg   1020

gcaacaggga tgcgaaatgt accagagaaa caaactagag gcatatttgg cgcaatcgcg   1080

ggtttcatag aaaatggttg ggagggaatg gtggatggtt ggtacggttt caggcatcaa   1140

aattctgagg gaagaggaca agcagcagat ctcaaaagca ctcaagcagc aatcgatcaa   1200

atcaatggga agctgaatag attgatcggg aaaaccaacg agaaattcca tcagattgaa   1260

aaagaattct cagaagtcga agggagaatt caggaccttg agaaatatgt tgaggacact   1320

aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg caatggttgt ttcaaaatat accacaaatg tgacaatgcc   1500

tgcataggat caatcagaaa tggaacttat gaccacgatg tatacagaga tgaagcatta   1560

aacaaccggt ttcagatcaa gggagttgag ctgaagtcag ggtacaaaga ttggatccta   1620

tggatttcct ttgccatatc atgtttttttg ctttgtgttg ctttgttggg gttcatcatg   1680

tgggcctgcc aaaaaggcaa cattaggtgc aacatttgca tttga                   1725
```

<210> SEQ ID NO 138
<211> LENGTH: 50
<212> TYPE: DNA
<213> ORGANISM: Artificial sequence
<220> FEATURE:
<223> OTHER INFORMATION: IF**-H3P1609.S1-6r

<400> SEQUENCE: 138

```
actaaagaaa ataggccttc aaatgcaaat gttgcaccta atgttgcctt                 50
```

<210> SEQ ID NO 139
<211> LENGTH: 574
<212> TYPE: PRT
<213> ORGANISM: Artificial sequence
<220> FEATURE:
<223> OTHER INFORMATION: Amino acid sequence of PDISP/H3 Perth

<400> SEQUENCE: 139

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60

Glu Leu Val Gln Ser Ser Ser Thr Gly Glu Ile Cys Asp Ser Pro His
65                  70                  75                  80

Gln Ile Leu Asp Gly Lys Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
```

```
145                 150                 155                 160

Ser Ala Cys Ile Arg Arg Ser Lys Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ala Ser Gly
    210                 215                 220

Arg Ile Thr Val Ser Thr Lys Arg Ser Gln Gln Thr Val Ser Pro Asn
225                 230                 235                 240

Ile Gly Ser Arg Pro Arg Val Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Asn
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 140
<211> LENGTH: 1680
<212> TYPE: DNA
<213> ORGANISM: Artificial sequence
<220> FEATURE:
<223> OTHER INFORMATION: Nucleotide sequence of PDISP/H3 Perth with deleted proteolytic loop

<400> SEQUENCE: 140
atggcgaaaa acgttgcgat tttcggctta ttgttttctc ttcttgtgtt ggttccttct 60
cagatcttcg cgcaaaaact tcctggaaat gacaacagca cggcaacgct gtgccttggg 120
caccatgcag taccaaacgg aacgatagtg aaaacaatca cgaatgacca aattgaagtt 180
actaatgcta ctgagctggt tcagagttcc tcaacaggtg aaatatgcga cagtcctcat 240
cagatccttg atggaaaaaa ctgcacacta atagatgctc tattgggaga ccctcagtgt 300
gatggcttcc aaaataagaa atgggacctt tttgttgaac gcagcaaagc ctacagcaac 360
tgttaccctt atgatgtgcc ggattatgcc tcccttaggt cactagttgc ctcatccggc 420
acactggagt ttaacaatga aagcttcaat tggactggag tcactcaaaa cggaacaagc 480
tctgcttgca taaggagatc taaaaacagt ttctttagta gattgaattg gttgacccac 540
ttaaacttca aatacccagc attgaacgtg actatgccaa acaatgaaca atttgacaaa 600
ttgtacattt gggggttca ccacccgggt acggacaaag accaaatctt cctgtatgct 660
caagcatcag gaagaatcac agtctctacc aaaagaagcc aacaaaccgt aagcccgaat 720
atcggatcta gacccagagt aaggaatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900
tgcaattctg aatgcatcac tccaaatgga agcattccca atgacaaacc attccaaaat 960
gtaaacagga tcacatacgg ggcctgtccc agatatgtta agcaaaacac tctgaaattg 1020
gcaacaggga tgcgaaatgt accaggcgga ggttgggagg gaatggtgga tggttggtac 1080
ggtttcaggc atcaaaattc tgagggaaga ggacaagcag cagatctcaa aagcactcaa 1140
gcagcaatcg atcaaatcaa tgggaagctg aatagattga tcgggaaaac caacgagaaa 1200
ttccatcaga ttgaaaaaga attctcagaa gtcgaaggga gaattcagga ccttgagaaa 1260
tatgttgagg acactaaaat agatctctgg tcatacaacg cggagcttct tgttgccctg 1320
gagaaccaac atacaattga tctaactgac tcagaaatga acaaactgtt tgaaaaaaca 1380
aagaagcaac tgagggaaaa tgctgaggat atgggcaatg gttgtttcaa aatataccac 1440
aaatgtgaca atgcctgcat aggatcaatc agaaatggaa cttatgacca cgatgtatac 1500
agagatgaag cattaaacaa ccggtttcag atcaagggag ttgagctgaa gtcagggtac 1560
aaagattgga tcctatggat ttcctttgcc atatcatgtt ttttgctttg tgttgctttg 1620
ttggggttca tcatgtgggc ctgccaaaaa ggcaacatta ggtgcaacat ttgcatttga 1680

<210> SEQ ID NO 141
<211> LENGTH: 48
<212> TYPE: DNA
<213> ORGANISM: Artificial sequence
<220> FEATURE:
<223> OTHER INFORMATION: H3P1609(Prl-)#2.r

<400> SEQUENCE: 141
ccctcccaac ctccgcctgg tacatttcgc atccctgttg ccaatttc 48

<210> SEQ ID NO 142
<211> LENGTH: 48
<212> TYPE: DNA
<213> ORGANISM: Artificial sequence
<220> FEATURE:
<223> OTHER INFORMATION: H3P1609(Prl-)#2.c

<400> SEQUENCE: 142
aatgtaccag gcggaggttg ggagggaatg gtggatggtt ggtacggt 48

<210> SEQ ID NO 143
<211> LENGTH: 559
<212> TYPE: PRT
<213> ORGANISM: Artificial sequence
<220> FEATURE:
<223> OTHER INFORMATION: Amino acid sequence of PDISP/H3 Perth with deleted proteolytic loop

<400> SEQUENCE: 143

Met Ala Lys Asn Val Ala Ile Phe Gly Leu Leu Phe Ser Leu Leu Val
1 5 10 15

Leu Val Pro Ser Gln Ile Phe Ala Gln Lys Leu Pro Gly Asn Asp Asn
20 25 30

Ser Thr Ala Thr Leu Cys Leu Gly His His Ala Val Pro Asn Gly Thr
35 40 45

Ile Val Lys Thr Ile Thr Asn Asp Gln Ile Glu Val Thr Asn Ala Thr
50 55 60

Glu Leu Val Gln Ser Ser Ser Thr Gly Glu Ile Cys Asp Ser Pro His
65 70 75 80

Gln Ile Leu Asp Gly Lys Asn Cys Thr Leu Ile Asp Ala Leu Leu Gly
85 90 95

Asp Pro Gln Cys Asp Gly Phe Gln Asn Lys Lys Trp Asp Leu Phe Val
100 105 110

Glu Arg Ser Lys Ala Tyr Ser Asn Cys Tyr Pro Tyr Asp Val Pro Asp
115 120 125

Tyr Ala Ser Leu Arg Ser Leu Val Ala Ser Ser Gly Thr Leu Glu Phe
130 135 140

Asn Asn Glu Ser Phe Asn Trp Thr Gly Val Thr Gln Asn Gly Thr Ser
145 150 155 160

Ser Ala Cys Ile Arg Arg Ser Lys Asn Ser Phe Phe Ser Arg Leu Asn
165 170 175

Trp Leu Thr His Leu Asn Phe Lys Tyr Pro Ala Leu Asn Val Thr Met
180 185 190

Pro Asn Asn Glu Gln Phe Asp Lys Leu Tyr Ile Trp Gly Val His His
195 200 205

Pro Gly Thr Asp Lys Asp Gln Ile Phe Leu Tyr Ala Gln Ala Ser Gly
210 215 220

Arg Ile Thr Val Ser Thr Lys Arg Ser Gln Gln Thr Val Ser Pro Asn
225 230 235 240

Ile Gly Ser Arg Pro Arg Val Arg Asn Ile Pro Ser Arg Ile Ser Ile
245 250 255

Tyr Trp Thr Ile Val Lys Pro Gly Asp Ile Leu Leu Ile Asn Ser Thr
260 265 270

Gly Asn Leu Ile Ala Pro Arg Gly Tyr Phe Lys Ile Arg Ser Gly Lys
275 280 285

Ser Ser Ile Met Arg Ser Asp Ala Pro Ile Gly Lys Cys Asn Ser Glu

```
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Asn
                325                 330                 335

Thr Leu Lys Leu Ala Thr Gly Met Arg Asn Val Pro Gly Gly Gly Trp
            340                 345                 350

Glu Gly Met Val Asp Gly Trp Tyr Gly Phe Arg His Gln Asn Ser Glu
        355                 360                 365

Gly Arg Gly Gln Ala Ala Asp Leu Lys Ser Thr Gln Ala Ala Ile Asp
    370                 375                 380

Gln Ile Asn Gly Lys Leu Asn Arg Leu Ile Gly Lys Thr Asn Glu Lys
385                 390                 395                 400

Phe His Gln Ile Glu Lys Glu Phe Ser Glu Val Glu Gly Arg Ile Gln
                405                 410                 415

Asp Leu Glu Lys Tyr Val Glu Asp Thr Lys Ile Asp Leu Trp Ser Tyr
            420                 425                 430

Asn Ala Glu Leu Leu Val Ala Leu Glu Asn Gln His Thr Ile Asp Leu
        435                 440                 445

Thr Asp Ser Glu Met Asn Lys Leu Phe Glu Lys Thr Lys Lys Gln Leu
    450                 455                 460

Arg Glu Asn Ala Glu Asp Met Gly Asn Gly Cys Phe Lys Ile Tyr His
465                 470                 475                 480

Lys Cys Asp Asn Ala Cys Ile Gly Ser Ile Arg Asn Gly Thr Tyr Asp
                485                 490                 495

His Asp Val Tyr Arg Asp Glu Ala Leu Asn Asn Arg Phe Gln Ile Lys
            500                 505                 510

Gly Val Glu Leu Lys Ser Gly Tyr Lys Asp Trp Ile Leu Trp Ile Ser
        515                 520                 525

Phe Ala Ile Ser Cys Phe Leu Leu Cys Val Ala Leu Leu Gly Phe Ile
    530                 535                 540

Met Trp Ala Cys Gln Lys Gly Asn Ile Arg Cys Asn Ile Cys Ile
545                 550                 555
```

<210> SEQ ID NO 144
<211> LENGTH: 1680
<212> TYPE: DNA
<213> ORGANISM: Artificial sequence
<220> FEATURE:
<223> OTHER INFORMATION: Nucleotide sequence of PDISP/H3 Victoria with deleted proteolytic loop

<400> SEQUENCE: 144

```
atggcgaaaa acgttgcgat tttcggctta ttgttttctc ttcttgtgtt ggttccttct      60

cagatcttcg cgcaaaaact tcctggaaat gacaacagca cggcaacgct gtgccttggg     120

caccatgcag taccaaacgg aacgatagtg aaaacaatca cgaatgacca aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggcttcc aaaataagaa atgggacctt tttgttgaac gaagcaaagc ctacagcaac     360

tgttaccctt atgatgtgcc ggattatgcc tcccttaggt cactagttgc ctcatccggc     420

acactggagt ttaacaatga aagcttcaat tggactggag tcactcaaaa cggaacaagt     480

tctgcttgca taaggagatc taataatagt ttctttagta gattaaattg gttgacccac     540
```

```
ttaaacttca aatacccagc attgaacgtg actatgccaa acaatgaaca atttgacaaa    600

ttgtacattt gggggttca ccacccgggt acggacaagg accaaatctt cctgtatgct    660

caatcatcag gaagaatcac agtatctacc aaaagaagcc aacaagctgt aatcccgaat    720

atcggatcta gacccagaat aaggaatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaattctg aatgcatcac tccaaatgga agcattccca atgacaaacc attccaaaat    960

gtaaacagga tcacatacgg ggcctgtccc agatatgtta agcaaagcac tctgaaattg   1020

gcaacaggaa tgcgaaatgt accaggcgga ggttgggagg gaatggtgga tggttggtac   1080

ggtttcaggc atcaaaattc tgagggaaga ggacaagcag cagatctcaa aagcactcaa   1140

gcagcaatcg atcaaatcaa tgggaagctg aatcgattga tcgggaaaac caacgagaaa   1200

ttccatcaga ttgaaaaaga attctcagaa gtcgaaggga gaattcagga ccttgagaaa   1260

tatgttgagg acactaaaat agatctctgg tcatacaacg cggagcttct tgttgccctg   1320

gagaaccaac atacaattga tctaactgac tcagaaatga acaaactgtt tgaaaaaaca   1380

aagaagcaac taagggaaaa tgctgaggat atgggcaatg gttgtttcaa aatataccac   1440

aaatgtgaca atgcctgcat aggatcaatc agaaatggaa cttatgacca cgatgtatac   1500

agagatgaag cattaaacaa ccggttccag atcaagggag ttgagctgaa gtcagggtac   1560

aaagattgga tcctatggat ttcctttgcc atatcatgtt ttttgctttg tgttgctttg   1620

ttggggttca tcatgtgggc ctgccaaaag ggcaacatta ggtgcaacat ttgcatttga   1680
```

```
<210> SEQ ID NO 145
<211> LENGTH: 48
<212> TYPE: DNA
<213> ORGANISM: Artificial sequence
<220> FEATURE:
<223> OTHER INFORMATION: H3V36111(Prl-).r

<400> SEQUENCE: 145

ccctcccaac ctccgcctgg tacatttcgc attcctgttg ccaatttc                 48


<210> SEQ ID NO 146
<211> LENGTH: 48
<212> TYPE: DNA
<213> ORGANISM: Artificial sequence
<220> FEATURE:
<223> OTHER INFORMATION: H3V36111(Prl-).c

<400> SEQUENCE: 146

aatgtaccag gcggaggttg ggagggaatg gtggatggtt ggtacggt                 48


<210> SEQ ID NO 147
<211> LENGTH: 559
<212> TYPE: PRT
<213> ORGANISM: Artificial sequence
<220> FEATURE:
<223> OTHER INFORMATION: Amino acid sequence of PDISP/H3 Victoria with
      deleted proteolytic loop

<400> SEQUENCE: 147

Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30
```

```
Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Asn Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Gly Gly Gly Trp
            340                 345                 350

Glu Gly Met Val Asp Gly Trp Tyr Gly Phe Arg His Gln Asn Ser Glu
        355                 360                 365

Gly Arg Gly Gln Ala Ala Asp Leu Lys Ser Thr Gln Ala Ala Ile Asp
    370                 375                 380

Gln Ile Asn Gly Lys Leu Asn Arg Leu Ile Gly Lys Thr Asn Glu Lys
385                 390                 395                 400

Phe His Gln Ile Glu Lys Glu Phe Ser Glu Val Glu Gly Arg Ile Gln
                405                 410                 415

Asp Leu Glu Lys Tyr Val Glu Asp Thr Lys Ile Asp Leu Trp Ser Tyr
            420                 425                 430

Asn Ala Glu Leu Leu Val Ala Leu Glu Asn Gln His Thr Ile Asp Leu
        435                 440                 445

Thr Asp Ser Glu Met Asn Lys Leu Phe Glu Lys Thr Lys Lys Gln Leu
```

```
    450                 455                 460

Arg Glu Asn Ala Glu Asp Met Gly Asn Gly Cys Phe Lys Ile Tyr His
465                 470                 475                 480

Lys Cys Asp Asn Ala Cys Ile Gly Ser Ile Arg Asn Gly Thr Tyr Asp
                485                 490                 495

His Asp Val Tyr Arg Asp Glu Ala Leu Asn Asn Arg Phe Gln Ile Lys
            500                 505                 510

Gly Val Glu Leu Lys Ser Gly Tyr Lys Asp Trp Ile Leu Trp Ile Ser
        515                 520                 525

Phe Ala Ile Ser Cys Phe Leu Leu Cys Val Ala Leu Leu Gly Phe Ile
    530                 535                 540

Met Trp Ala Cys Gln Lys Gly Asn Ile Arg Cys Asn Ile Cys Ile
545                 550                 555

<210> SEQ ID NO 148
<211> LENGTH: 1701
<212> TYPE: DNA
<213> ORGANISM: Artificial sequence
<220> FEATURE:
<223> OTHER INFORMATION: Nucleotide sequence of PDISP/H7 Hangzhou

<400> SEQUENCE: 148
atggcgaaaa acgttgcgat tttcggctta ttgttttctc ttcttgtgtt ggttccttct      60
cagatcttcg cggacaaaat ctgcctcgga catcatgccg tgtcaaacgg aaccaaagta     120
aacacattaa ctgaaagagg agtggaagtc gtcaatgcaa ctgaaacagt ggaacgaaca     180
aacatcccca ggatctgctc aaaagggaaa aggacagttg acctcggtca atgtggactc     240
ctggggacaa tcactggacc acctcaatgt gaccaattcc tagaattttc agccgattta     300
attattgaga ggcgagaagg aagtgatgtc tgttatcctg ggaaattcgt gaatgaagaa     360
gctctgaggc aaattctcag agaatcaggc ggaattgaca aggaagcaat gggattcaca     420
tacagtggaa taagaactaa tggagcaacc agtgcatgta ggagatcagg atcttcattc     480
tatgcagaaa tgaaatggct cctgtcaaac acagataatg ctgcattccc gcagatgact     540
aagtcatata aaaatacaag aaaaagccca gctctaatag tatgggggat ccatcattcc     600
gtatcaactg cagagcaaac caagctatat gggagtggaa acaaactggt gacagttggg     660
agttctaatt atcaacaatc ttttgtaccg agtccaggag cgagaccaca agttaatggt     720
atatctggaa gaattgactt tcattggcta atgctaaatc ccaatgatac agtcactttc     780
agtttcaatg gggctttcat agctccagac cgtgcaagct tcctgagagg aaaatctatg     840
ggaatccaga gtggagtaca ggttgatgcc aattgtgaag gggactgcta tcatagtgga     900
gggacaataa taagtaactt gccatttcag aacatagata gcagggcagt tggaaaatgt     960
ccgagatatg ttaagcaaag gagtctgctg ctagcaacag ggatgaagaa tgttcctgag    1020
attccaaagg gaagaggcct atttggtgct atagcgggtt tcattgaaaa tggatgggaa    1080
ggcctaattg atggttggta tggtttcaga caccagaatg cacagggaga gggaactgct    1140
gcagattaca aaagcactca atcggcaatt gatcaaataa caggaaaatt aaaccggctt    1200
atagaaaaaa ccaaccaaca atttgagttg atcgacaatg aattcaatga ggtagagaag    1260
caaatcggta atgtgataaa ttggaccaga gattctataa cagaagtgtg gtcatacaat    1320
gctgaactct tggtagcaat ggagaaccag catacaattg atctggctga ttcagaaatg    1380
gacaaactgt acgaacgagt gaaaagacag ctgagagaga atgctgaaga agatggcact    1440
ggttgctttg aaatatttca caagtgtgat gatgactgta tggccagtat tagaaataac    1500
```

acctatgatc acagcaaata cagggaagag gcaatgcaaa atagaataca gattgaccca 1560
gtcaaactaa gcagcggcta caaagatgtg atactttggt ttagcttcgg ggcatcatgt 1620
ttcatacttc tagccattgt aatgggcctt gtcttcatat gtgtaaagaa tggaaacatg 1680
cggtgcacta tttgtatata a 1701

<210> SEQ ID NO 149
<211> LENGTH: 50
<212> TYPE: DNA
<213> ORGANISM: Artificial sequence
<220> FEATURE:
<223> OTHER INFORMATION: IF*-H7H113.s1-6r

<400> SEQUENCE: 149
actaaagaaa ataggccttt atatacaaat agtgcaccgc atgtttccat 50

<210> SEQ ID NO 150
<211> LENGTH: 566
<212> TYPE: PRT
<213> ORGANISM: Artificial sequence
<220> FEATURE:
<223> OTHER INFORMATION: Amino acid sequence of PDISP/H7 Hangzhou

<400> SEQUENCE: 150

Met Ala Lys Asn Val Ala Ile Phe Gly Leu Leu Phe Ser Leu Leu Val
1 5 10 15

Leu Val Pro Ser Gln Ile Phe Ala Asp Lys Ile Cys Leu Gly His His
20 25 30

Ala Val Ser Asn Gly Thr Lys Val Asn Thr Leu Thr Glu Arg Gly Val
35 40 45

Glu Val Val Asn Ala Thr Glu Thr Val Glu Arg Thr Asn Ile Pro Arg
50 55 60

Ile Cys Ser Lys Gly Lys Arg Thr Val Asp Leu Gly Gln Cys Gly Leu
65 70 75 80

Leu Gly Thr Ile Thr Gly Pro Pro Gln Cys Asp Gln Phe Leu Glu Phe
85 90 95

Ser Ala Asp Leu Ile Ile Glu Arg Arg Glu Gly Ser Asp Val Cys Tyr
100 105 110

Pro Gly Lys Phe Val Asn Glu Glu Ala Leu Arg Gln Ile Leu Arg Glu
115 120 125

Ser Gly Gly Ile Asp Lys Glu Ala Met Gly Phe Thr Tyr Ser Gly Ile
130 135 140

Arg Thr Asn Gly Ala Thr Ser Ala Cys Arg Arg Ser Gly Ser Ser Phe
145 150 155 160

Tyr Ala Glu Met Lys Trp Leu Leu Ser Asn Thr Asp Asn Ala Ala Phe
165 170 175

Pro Gln Met Thr Lys Ser Tyr Lys Asn Thr Arg Lys Ser Pro Ala Leu
180 185 190

Ile Val Trp Gly Ile His His Ser Val Ser Thr Ala Glu Gln Thr Lys
195 200 205

Leu Tyr Gly Ser Gly Asn Lys Leu Val Thr Val Gly Ser Ser Asn Tyr
210 215 220

Gln Gln Ser Phe Val Pro Ser Pro Gly Ala Arg Pro Gln Val Asn Gly
225 230 235 240

Ile Ser Gly Arg Ile Asp Phe His Trp Leu Met Leu Asn Pro Asn Asp
245 250 255

```
Thr Val Thr Phe Ser Phe Asn Gly Ala Phe Ile Ala Pro Asp Arg Ala
            260                 265                 270

Ser Phe Leu Arg Gly Lys Ser Met Gly Ile Gln Ser Gly Val Gln Val
        275                 280                 285

Asp Ala Asn Cys Glu Gly Asp Cys Tyr His Ser Gly Gly Thr Ile Ile
    290                 295                 300

Ser Asn Leu Pro Phe Gln Asn Ile Asp Ser Arg Ala Val Gly Lys Cys
305                 310                 315                 320

Pro Arg Tyr Val Lys Gln Arg Ser Leu Leu Leu Ala Thr Gly Met Lys
                325                 330                 335

Asn Val Pro Glu Ile Pro Lys Gly Arg Gly Leu Phe Gly Ala Ile Ala
            340                 345                 350

Gly Phe Ile Glu Asn Gly Trp Glu Gly Leu Ile Asp Gly Trp Tyr Gly
        355                 360                 365

Phe Arg His Gln Asn Ala Gln Gly Glu Gly Thr Ala Ala Asp Tyr Lys
    370                 375                 380

Ser Thr Gln Ser Ala Ile Asp Gln Ile Thr Gly Lys Leu Asn Arg Leu
385                 390                 395                 400

Ile Glu Lys Thr Asn Gln Gln Phe Glu Leu Ile Asp Asn Glu Phe Asn
                405                 410                 415

Glu Val Glu Lys Gln Ile Gly Asn Val Ile Asn Trp Thr Arg Asp Ser
            420                 425                 430

Ile Thr Glu Val Trp Ser Tyr Asn Ala Glu Leu Leu Val Ala Met Glu
        435                 440                 445

Asn Gln His Thr Ile Asp Leu Ala Asp Ser Glu Met Asp Lys Leu Tyr
    450                 455                 460

Glu Arg Val Lys Arg Gln Leu Arg Glu Asn Ala Glu Glu Asp Gly Thr
465                 470                 475                 480

Gly Cys Phe Glu Ile Phe His Lys Cys Asp Asp Asp Cys Met Ala Ser
                485                 490                 495

Ile Arg Asn Asn Thr Tyr Asp His Ser Lys Tyr Arg Glu Glu Ala Met
            500                 505                 510

Gln Asn Arg Ile Gln Ile Asp Pro Val Lys Leu Ser Ser Gly Tyr Lys
        515                 520                 525

Asp Val Ile Leu Trp Phe Ser Phe Gly Ala Ser Cys Phe Ile Leu Leu
    530                 535                 540

Ala Ile Val Met Gly Leu Val Phe Ile Cys Val Lys Asn Gly Asn Met
545                 550                 555                 560

Arg Cys Thr Ile Cys Ile
                565


<210> SEQ ID NO 151
<211> LENGTH: 1650
<212> TYPE: DNA
<213> ORGANISM: Artificial sequence
<220> FEATURE:
<223> OTHER INFORMATION: Nucleotide sequence of PDISP/H7 Hangzhou with
      deleted proteolytic loop

<400> SEQUENCE: 151

atggcgaaaa acgttgcgat tttcggctta ttgttttctc ttcttgtgtt ggttccttct      60

cagatcttcg cggacaaaat ctgcctcgga catcatgccg tgtcaaacgg aaccaaagta     120

aacacattaa ctgaaagagg agtggaagtc gtcaatgcaa ctgaaacagt ggaacgaaca     180

aacatcccca ggatctgctc aaaagggaaa aggacagttg acctcggtca atgtggactc     240
```

ctggggacaa tcactggacc acctcaatgt gaccaattcc tagaattttc agccgattta 300
attattgaga ggcgagaagg aagtgatgtc tgttatcctg ggaaattcgt gaatgaagaa 360
gctctgaggc aaattctcag agaatcaggc ggaattgaca aggaagcaat gggattcaca 420
tacagtggaa taagaactaa tggagcaacc agtgcatgta ggagatcagg atcttcattc 480
tatgcagaaa tgaaatggct cctgtcaaac acagataatg ctgcattccc gcagatgact 540
aagtcatata aaaatacaag aaaaagccca gctctaatag tatgggggat ccatcattcc 600
gtatcaactg cagagcaaac caagctatat gggagtggaa acaaactggt gacagttggg 660
agttctaatt atcaacaatc ttttgtaccg agtccaggag cgagaccaca agttaatggt 720
atatctggaa gaattgactt tcattggcta atgctaaatc ccaatgatac agtcactttc 780
agtttcaatg gggctttcat agctccagac cgtgcaagct tcctgagagg aaaatctatg 840
ggaatccaga gtggagtaca ggttgatgcc aattgtgaag gggactgcta tcatagtgga 900
gggacaataa taagtaactt gccatttcag aacatagata gcagggcagt tggaaaatgt 960
ccgagatatg ttaagcaaag gagtctgctg ctagcaacag ggatgaagaa tgttcctggc 1020
ggatgggaag gcctaattga tggttggtat ggtttcagac accagaatgc acagggagag 1080
ggaactgctg cagattacaa aagcactcaa tcggcaattg atcaaataac aggaaaatta 1140
aaccggctta tagaaaaaac caaccaacaa tttgagttga tcgacaatga attcaatgag 1200
gtagagaagc aaatcggtaa tgtgataaat tggaccagag attctataac agaagtgtgg 1260
tcatacaatg ctgaactctt ggtagcaatg gagaaccagc atacaattga tctggctgat 1320
tcagaaatgg acaaactgta cgaacgagtg aaaagacagc tgagagagaa tgctgaagaa 1380
gatggcactg gttgctttga aatatttcac aagtgtgatg atgactgtat ggccagtatt 1440
agaaataaca cctatgatca cagcaaatac agggaagagg caatgcaaaa tagaatacag 1500
attgacccag tcaaactaag cagcggctac aaagatgtga tactttggtt tagcttcggg 1560
gcatcatgtt tcatacttct agccattgta atgggccttg tcttcatatg tgtaaagaat 1620
ggaaacatgc ggtgcactat ttgtatataa 1650

<210> SEQ ID NO 152
<211> LENGTH: 49
<212> TYPE: DNA
<213> ORGANISM: Artificial sequence
<220> FEATURE:
<223> OTHER INFORMATION: H7H113(PrL-).r

<400> SEQUENCE: 152
ccttcccatc cgccaggaac attcttcatc cctgttgcta gcagcagac 49

<210> SEQ ID NO 153
<211> LENGTH: 48
<212> TYPE: DNA
<213> ORGANISM: Artificial sequence
<220> FEATURE:
<223> OTHER INFORMATION: H7H113(PrL-).c

<400> SEQUENCE: 153
agaatgttcc tggcggatgg gaaggcctaa ttgatggttg gtatggtt 48

<210> SEQ ID NO 154
<211> LENGTH: 549
<212> TYPE: PRT
<213> ORGANISM: Artificial sequence
<220> FEATURE:
<223> OTHER INFORMATION: Amino acid sequence of PDISP/H7 Hangzhou with deleted proteolytic loop

<400> SEQUENCE: 154

```
Met Ala Lys Asn Val Ala Ile Phe Gly Leu Leu Phe Ser Leu Leu Val
1               5                   10                  15

Leu Val Pro Ser Gln Ile Phe Ala Asp Lys Ile Cys Leu Gly His His
            20                  25                  30

Ala Val Ser Asn Gly Thr Lys Val Asn Thr Leu Thr Glu Arg Gly Val
        35                  40                  45

Glu Val Val Asn Ala Thr Glu Thr Val Glu Arg Thr Asn Ile Pro Arg
    50                  55                  60

Ile Cys Ser Lys Gly Lys Arg Thr Val Asp Leu Gly Gln Cys Gly Leu
65                  70                  75                  80

Leu Gly Thr Ile Thr Gly Pro Pro Gln Cys Asp Gln Phe Leu Glu Phe
                85                  90                  95

Ser Ala Asp Leu Ile Ile Glu Arg Arg Glu Gly Ser Asp Val Cys Tyr
            100                 105                 110

Pro Gly Lys Phe Val Asn Glu Glu Ala Leu Arg Gln Ile Leu Arg Glu
        115                 120                 125

Ser Gly Gly Ile Asp Lys Glu Ala Met Gly Phe Thr Tyr Ser Gly Ile
    130                 135                 140

Arg Thr Asn Gly Ala Thr Ser Ala Cys Arg Arg Ser Gly Ser Ser Phe
145                 150                 155                 160

Tyr Ala Glu Met Lys Trp Leu Leu Ser Asn Thr Asp Asn Ala Ala Phe
                165                 170                 175

Pro Gln Met Thr Lys Ser Tyr Lys Asn Thr Arg Lys Ser Pro Ala Leu
            180                 185                 190

Ile Val Trp Gly Ile His His Ser Val Ser Thr Ala Glu Gln Thr Lys
        195                 200                 205

Leu Tyr Gly Ser Gly Asn Lys Leu Val Thr Val Gly Ser Ser Asn Tyr
    210                 215                 220

Gln Gln Ser Phe Val Pro Ser Pro Gly Ala Arg Pro Gln Val Asn Gly
225                 230                 235                 240

Ile Ser Gly Arg Ile Asp Phe His Trp Leu Met Leu Asn Pro Asn Asp
                245                 250                 255

Thr Val Thr Phe Ser Phe Asn Gly Ala Phe Ile Ala Pro Asp Arg Ala
            260                 265                 270

Ser Phe Leu Arg Gly Lys Ser Met Gly Ile Gln Ser Gly Val Gln Val
        275                 280                 285

Asp Ala Asn Cys Glu Gly Asp Cys Tyr His Ser Gly Gly Thr Ile Ile
    290                 295                 300

Ser Asn Leu Pro Phe Gln Asn Ile Asp Ser Arg Ala Val Gly Lys Cys
305                 310                 315                 320

Pro Arg Tyr Val Lys Gln Arg Ser Leu Leu Leu Ala Thr Gly Met Lys
                325                 330                 335

Asn Val Pro Gly Gly Trp Glu Gly Leu Ile Asp Gly Trp Tyr Gly Phe
            340                 345                 350

Arg His Gln Asn Ala Gln Gly Glu Gly Thr Ala Ala Asp Tyr Lys Ser
        355                 360                 365

Thr Gln Ser Ala Ile Asp Gln Ile Thr Gly Lys Leu Asn Arg Leu Ile
    370                 375                 380

Glu Lys Thr Asn Gln Gln Phe Glu Leu Ile Asp Asn Glu Phe Asn Glu
385                 390                 395                 400
```

-continued

```
Val Glu Lys Gln Ile Gly Asn Val Ile Asn Trp Thr Arg Asp Ser Ile
                405                 410                 415

Thr Glu Val Trp Ser Tyr Asn Ala Glu Leu Leu Val Ala Met Glu Asn
            420                 425                 430

Gln His Thr Ile Asp Leu Ala Asp Ser Glu Met Asp Lys Leu Tyr Glu
        435                 440                 445

Arg Val Lys Arg Gln Leu Arg Glu Asn Ala Glu Glu Asp Gly Thr Gly
    450                 455                 460

Cys Phe Glu Ile Phe His Lys Cys Asp Asp Asp Cys Met Ala Ser Ile
465                 470                 475                 480

Arg Asn Asn Thr Tyr Asp His Ser Lys Tyr Arg Glu Glu Ala Met Gln
                485                 490                 495

Asn Arg Ile Gln Ile Asp Pro Val Lys Leu Ser Ser Gly Tyr Lys Asp
            500                 505                 510

Val Ile Leu Trp Phe Ser Phe Gly Ala Ser Cys Phe Ile Leu Leu Ala
        515                 520                 525

Ile Val Met Gly Leu Val Phe Ile Cys Val Lys Asn Gly Asn Met Arg
    530                 535                 540

Cys Thr Ile Cys Ile
545


<210> SEQ ID NO 155
<211> LENGTH: 1701
<212> TYPE: DNA
<213> ORGANISM: Artificial sequence
<220> FEATURE:
<223> OTHER INFORMATION: Nucleotide sequence of PDISP/H9 Hong Kong

<400> SEQUENCE: 155

atggcgaaaa acgttgcgat tttcggctta ttgttttctc ttcttgtgtt ggttccttct     60

cagatcttcg cggataaaat ctgcatcggc caccagtcaa caaactccac agaaactgtg    120

gacacgctaa cagaaaccaa tgttcctgtg acacatgcca aagaattgct ccacacagag    180

cataatggaa tgctgtgtgc aacaagcctg ggacatcccc tcattctaga cacatgcact    240

attgaaggac tagtctatgg caacccttct tgtgacctgc tgttgggagg aagagaatgg    300

tcctacatcg tcgaaagatc atcagctgta aatggaacgt gttaccctgg gaatgtagaa    360

aacctagagg aactcaggac actttttagt tccgctagtt cctaccaaag aatccaaatc    420

ttcccagaca caacctggaa tgtgacttac actggaacaa gcagagcatg ttcaggttca    480

ttctacagga gtatgagatg gctgactcaa aagagcggtt tttaccctgt tcaagacgcc    540

caatacacaa ataacagggg aaagagcatt cttttcgtgt ggggcataca tcacccaccc    600

acctataccg agcaaacaaa tttgtacata agaaacgaca caacaacaag cgtgacaaca    660

gaagatttga ataggacctt caaaccagtg atagggccaa ggccccttgt caatggtctg    720

cagggaagaa ttgattatta ttggtcggta ctaaaaccag gccaaacatt gcgagtacga    780

tccaatggga atctaattgc tccatggtat ggacacgttc tttcaggagg gagccatgga    840

agaatcctga agactgattt aaaaggtggt aattgtgtag tgcaatgtca gactgaaaaa    900

ggtggcttaa acagtacatt gccattccac aatatcagta aatatgcatt tggaacctgc    960

cccaaatatg taagagttaa tagtctcaaa ctggcagtcg gtctgaggaa cgtgcctgct   1020

agatcaagta gaggactatt tggagccata gctggattca tagaaggagg ttggccagga   1080

ctagtcgctg gctggtatgg tttccagcat tcaaatgatc aaggggttgg tatggctgca   1140

gatagggatt caactcaaaa ggcaattgat aaaataacat ccaaggtgaa taatatagtc   1200
```

gacaagatga acaagcaata tgaaataatt gatcatgaat ttagtgaggt tgaaactaga 1260
ctcaatatga tcaataataa gattgatgac caaatacaag acgtatgggc atataatgca 1320
gaattgctag tactacttga aaatcaaaaa acactcgatg agcatgatgc gaacgtgaac 1380
aatctatata acaaggtgaa gagggcactg ggctccaatg ctatggaaga tgggaaaggc 1440
tgtttcgagc tataccataa atgtgatgat cagtgcatgg aaacaattcg gaacgggacc 1500
tataatagga gaaagtatag agaggaatca agactagaaa ggcagaaaat agagggggtt 1560
aagctggaat ctgagggaac ttacaaaatc ctcaccattt attcgactgt cgcctcatct 1620
cttgtgcttg caatggggtt tgctgccttc ctgttctggg ccatgtccaa tggatcttgc 1680
agatgcaaca tttgtatata a 1701

<210> SEQ ID NO 156
<211> LENGTH: 50
<212> TYPE: DNA
<213> ORGANISM: Artificial sequence
<220> FEATURE:
<223> OTHER INFORMATION: IF**-H9HK107399.S1-6r

<400> SEQUENCE: 156
actaaagaaa ataggccttt atatacaaat gttgcatctg caagatccat 50

<210> SEQ ID NO 157
<211> LENGTH: 566
<212> TYPE: PRT
<213> ORGANISM: Artificial sequence
<220> FEATURE:
<223> OTHER INFORMATION: Amino acid sequence of PDISP/H9 Hong Kong

<400> SEQUENCE: 157

Met Ala Lys Asn Val Ala Ile Phe Gly Leu Leu Phe Ser Leu Leu Val
1 5 10 15

Leu Val Pro Ser Gln Ile Phe Ala Asp Lys Ile Cys Ile Gly His Gln
20 25 30

Ser Thr Asn Ser Thr Glu Thr Val Asp Thr Leu Thr Glu Thr Asn Val
35 40 45

Pro Val Thr His Ala Lys Glu Leu Leu His Thr Glu His Asn Gly Met
50 55 60

Leu Cys Ala Thr Ser Leu Gly His Pro Leu Ile Leu Asp Thr Cys Thr
65 70 75 80

Ile Glu Gly Leu Val Tyr Gly Asn Pro Ser Cys Asp Leu Leu Leu Gly
85 90 95

Gly Arg Glu Trp Ser Tyr Ile Val Glu Arg Ser Ser Ala Val Asn Gly
100 105 110

Thr Cys Tyr Pro Gly Asn Val Glu Asn Leu Glu Glu Leu Arg Thr Leu
115 120 125

Phe Ser Ser Ala Ser Ser Tyr Gln Arg Ile Gln Ile Phe Pro Asp Thr
130 135 140

Thr Trp Asn Val Thr Tyr Thr Gly Thr Ser Arg Ala Cys Ser Gly Ser
145 150 155 160

Phe Tyr Arg Ser Met Arg Trp Leu Thr Gln Lys Ser Gly Phe Tyr Pro
165 170 175

Val Gln Asp Ala Gln Tyr Thr Asn Asn Arg Gly Lys Ser Ile Leu Phe
180 185 190

Val Trp Gly Ile His His Pro Pro Thr Tyr Thr Glu Gln Thr Asn Leu
195 200 205

```
Tyr Ile Arg Asn Asp Thr Thr Thr Ser Val Thr Thr Glu Asp Leu Asn
    210                 215                 220

Arg Thr Phe Lys Pro Val Ile Gly Pro Arg Pro Leu Val Asn Gly Leu
225                 230                 235                 240

Gln Gly Arg Ile Asp Tyr Tyr Trp Ser Val Leu Lys Pro Gly Gln Thr
                245                 250                 255

Leu Arg Val Arg Ser Asn Gly Asn Leu Ile Ala Pro Trp Tyr Gly His
            260                 265                 270

Val Leu Ser Gly Gly Ser His Gly Arg Ile Leu Lys Thr Asp Leu Lys
        275                 280                 285

Gly Gly Asn Cys Val Val Gln Cys Gln Thr Glu Lys Gly Gly Leu Asn
    290                 295                 300

Ser Thr Leu Pro Phe His Asn Ile Ser Lys Tyr Ala Phe Gly Thr Cys
305                 310                 315                 320

Pro Lys Tyr Val Arg Val Asn Ser Leu Lys Leu Ala Val Gly Leu Arg
                325                 330                 335

Asn Val Pro Ala Arg Ser Ser Arg Gly Leu Phe Gly Ala Ile Ala Gly
            340                 345                 350

Phe Ile Glu Gly Gly Trp Pro Gly Leu Val Ala Gly Trp Tyr Gly Phe
        355                 360                 365

Gln His Ser Asn Asp Gln Gly Val Gly Met Ala Ala Asp Arg Asp Ser
    370                 375                 380

Thr Gln Lys Ala Ile Asp Lys Ile Thr Ser Lys Val Asn Asn Ile Val
385                 390                 395                 400

Asp Lys Met Asn Lys Gln Tyr Glu Ile Ile Asp His Glu Phe Ser Glu
                405                 410                 415

Val Glu Thr Arg Leu Asn Met Ile Asn Asn Lys Ile Asp Asp Gln Ile
            420                 425                 430

Gln Asp Val Trp Ala Tyr Asn Ala Glu Leu Leu Val Leu Leu Glu Asn
        435                 440                 445

Gln Lys Thr Leu Asp Glu His Asp Ala Asn Val Asn Asn Leu Tyr Asn
    450                 455                 460

Lys Val Lys Arg Ala Leu Gly Ser Asn Ala Met Glu Asp Gly Lys Gly
465                 470                 475                 480

Cys Phe Glu Leu Tyr His Lys Cys Asp Asp Gln Cys Met Glu Thr Ile
                485                 490                 495

Arg Asn Gly Thr Tyr Asn Arg Arg Lys Tyr Arg Glu Glu Ser Arg Leu
            500                 505                 510

Glu Arg Gln Lys Ile Glu Gly Val Lys Leu Glu Ser Glu Gly Thr Tyr
        515                 520                 525

Lys Ile Leu Thr Ile Tyr Ser Thr Val Ala Ser Ser Leu Val Leu Ala
    530                 535                 540

Met Gly Phe Ala Ala Phe Leu Phe Trp Ala Met Ser Asn Gly Ser Cys
545                 550                 555                 560

Arg Cys Asn Ile Cys Ile
                565
```

<210> SEQ ID NO 158
<211> LENGTH: 1656
<212> TYPE: DNA
<213> ORGANISM: Artificial sequence
<220> FEATURE:
<223> OTHER INFORMATION: Nucleotide sequence of PDISP/H9 Hong Kong with deleted proteolytic loop -continued

<400> SEQUENCE: 158

```
atggcgaaaa acgttgcgat tttcggctta ttgttttctc ttcttgtgtt ggttccttct     60
cagatcttcg cggataaaat ctgcatcggc caccagtcaa caaactccac agaaactgtg    120
gacacgctaa cagaaaccaa tgttcctgtg acacatgcca aagaattgct ccacacagag    180
cataatggaa tgctgtgtgc aacaagcctg ggacatcccc tcattctaga cacatgcact    240
attgaaggac tagtctatgg caacccttct tgtgacctgc tgttgggagg aagagaatgg    300
tcctacatcg tcgaaagatc atcagctgta aatggaacgt gttaccctgg gaatgtagaa    360
aacctagagg aactcaggac actttttagt tccgctagtt cctaccaaag aatccaaatc    420
ttcccagaca caacctggaa tgtgacttac actggaacaa gcagagcatg ttcaggttca    480
ttctacagga gtatgagatg gctgactcaa aagagcggtt tttaccctgt tcaagacgcc    540
caatacacaa ataacagggg aaagagcatt cttttcgtgt ggggcataca tcacccaccc    600
acctataccg agcaaacaaa tttgtacata agaaacgaca caacaacaag cgtgacaaca    660
gaagatttga ataggacctt caaaccagtg atagggccaa ggccccttgt caatggtctg    720
cagggaagaa ttgattatta ttggtcggta ctaaaaccag gccaaacatt gcgagtacga    780
tccaatggga atctaattgc tccatggtat ggacacgttc tttcaggagg gagccatgga    840
agaatcctga agactgattt aaaaggtggt aattgtgtag tgcaatgtca gactgaaaaa    900
ggtggcttaa acagtacatt gccattccac aatatcagta aatatgcatt tggaacctgc    960
cccaaatatg taagagttaa tagtctcaaa ctggcagtcg gtctgaggaa cgtgcctggc   1020
ggaggttggc caggactagt cgctggctgg tatggtttcc agcattcaaa tgatcaaggg   1080
gttggtatgg ctgcagatag ggattcaact caaaaggcaa ttgataaaat aacatccaag   1140
gtgaataata tagtcgacaa gatgaacaag caatatgaaa taattgatca tgaatttagt   1200
gaggttgaaa ctagactcaa tatgatcaat aataagattg atgaccaaat acaagacgta   1260
tgggcatata atgcagaatt gctagtacta cttgaaaatc aaaaaacact cgatgagcat   1320
gatgcgaacg tgaacaatct atataacaag gtgaagaggg cactgggctc caatgctatg   1380
gaagatggga aaggctgttt cgagctatac cataaatgtg atgatcagtg catggaaaca   1440
attcggaacg ggacctataa taggagaaag tatagagagg aatcaagact agaaaggcag   1500
aaaatagagg gggttaagct ggaatctgag ggaacttaca aaatcctcac catttattcg   1560
actgtcgcct catctcttgt gcttgcaatg gggtttgctg ccttcctgtt ctgggccatg   1620
tccaatggat cttgcagatg caacatttgt atataa                              1656
```

<210> SEQ ID NO 159
<211> LENGTH: 48
<212> TYPE: DNA
<213> ORGANISM: Artificial sequence
<220> FEATURE:
<223> OTHER INFORMATION: H9HK107399(Prl-).r

<400> SEQUENCE: 159

```
gtcctggcca acctccgcca ggcacgttcc tcagaccgac tgccagtt                  48
```

<210> SEQ ID NO 160
<211> LENGTH: 48
<212> TYPE: DNA
<213> ORGANISM: Artificial sequence
<220> FEATURE:
<223> OTHER INFORMATION: H9HK107399(Prl-).c

<400> SEQUENCE: 160
ggaacgtgcc tggcggaggt tggccaggac tagtcgctgg ctggtatg 48

<210> SEQ ID NO 161
<211> LENGTH: 551
<212> TYPE: PRT
<213> ORGANISM: Artificial sequence
<220> FEATURE:
<223> OTHER INFORMATION: Amino acid sequence of PDISP/H9 Hong Kong with deleted proteolytic loop

<400> SEQUENCE: 161

Met Ala Lys Asn Val Ala Ile Phe Gly Leu Leu Phe Ser Leu Leu Val
1 5 10 15

Leu Val Pro Ser Gln Ile Phe Ala Asp Lys Ile Cys Ile Gly His Gln
20 25 30

Ser Thr Asn Ser Thr Glu Thr Val Asp Thr Leu Thr Glu Thr Asn Val
35 40 45

Pro Val Thr His Ala Lys Glu Leu Leu His Thr Glu His Asn Gly Met
50 55 60

Leu Cys Ala Thr Ser Leu Gly His Pro Leu Ile Leu Asp Thr Cys Thr
65 70 75 80

Ile Glu Gly Leu Val Tyr Gly Asn Pro Ser Cys Asp Leu Leu Leu Gly
85 90 95

Gly Arg Glu Trp Ser Tyr Ile Val Glu Arg Ser Ser Ala Val Asn Gly
100 105 110

Thr Cys Tyr Pro Gly Asn Val Glu Asn Leu Glu Glu Leu Arg Thr Leu
115 120 125

Phe Ser Ser Ala Ser Ser Tyr Gln Arg Ile Gln Ile Phe Pro Asp Thr
130 135 140

Thr Trp Asn Val Thr Tyr Thr Gly Thr Ser Arg Ala Cys Ser Gly Ser
145 150 155 160

Phe Tyr Arg Ser Met Arg Trp Leu Thr Gln Lys Ser Gly Phe Tyr Pro
165 170 175

Val Gln Asp Ala Gln Tyr Thr Asn Asn Arg Gly Lys Ser Ile Leu Phe
180 185 190

Val Trp Gly Ile His His Pro Pro Thr Tyr Thr Glu Gln Thr Asn Leu
195 200 205

Tyr Ile Arg Asn Asp Thr Thr Thr Ser Val Thr Thr Glu Asp Leu Asn
210 215 220

Arg Thr Phe Lys Pro Val Ile Gly Pro Arg Pro Leu Val Asn Gly Leu
225 230 235 240

Gln Gly Arg Ile Asp Tyr Tyr Trp Ser Val Leu Lys Pro Gly Gln Thr
245 250 255

Leu Arg Val Arg Ser Asn Gly Asn Leu Ile Ala Pro Trp Tyr Gly His
260 265 270

Val Leu Ser Gly Gly Ser His Gly Arg Ile Leu Lys Thr Asp Leu Lys
275 280 285

Gly Gly Asn Cys Val Val Gln Cys Gln Thr Glu Lys Gly Gly Leu Asn
290 295 300

Ser Thr Leu Pro Phe His Asn Ile Ser Lys Tyr Ala Phe Gly Thr Cys
305 310 315 320

Pro Lys Tyr Val Arg Val Asn Ser Leu Lys Leu Ala Val Gly Leu Arg
325 330 335

Asn Val Pro Gly Gly Gly Trp Pro Gly Leu Val Ala Gly Trp Tyr Gly
340 345 350

```
Phe Gln His Ser Asn Asp Gln Gly Val Gly Met Ala Ala Asp Arg Asp
        355                 360                 365

Ser Thr Gln Lys Ala Ile Asp Lys Ile Thr Ser Lys Val Asn Asn Ile
    370                 375                 380

Val Asp Lys Met Asn Lys Gln Tyr Glu Ile Ile Asp His Glu Phe Ser
385                 390                 395                 400

Glu Val Glu Thr Arg Leu Asn Met Ile Asn Asn Lys Ile Asp Asp Gln
                405                 410                 415

Ile Gln Asp Val Trp Ala Tyr Asn Ala Glu Leu Leu Val Leu Leu Glu
            420                 425                 430

Asn Gln Lys Thr Leu Asp Glu His Asp Ala Asn Val Asn Asn Leu Tyr
        435                 440                 445

Asn Lys Val Lys Arg Ala Leu Gly Ser Asn Ala Met Glu Asp Gly Lys
    450                 455                 460

Gly Cys Phe Glu Leu Tyr His Lys Cys Asp Asp Gln Cys Met Glu Thr
465                 470                 475                 480

Ile Arg Asn Gly Thr Tyr Asn Arg Arg Lys Tyr Arg Glu Glu Ser Arg
                485                 490                 495

Leu Glu Arg Gln Lys Ile Glu Gly Val Lys Leu Glu Ser Glu Gly Thr
            500                 505                 510

Tyr Lys Ile Leu Thr Ile Tyr Ser Thr Val Ala Ser Ser Leu Val Leu
        515                 520                 525

Ala Met Gly Phe Ala Ala Phe Leu Phe Trp Ala Met Ser Asn Gly Ser
    530                 535                 540

Cys Arg Cys Asn Ile Cys Ile
545                 550
```

<210> SEQ ID NO 162
<211> LENGTH: 1785
<212> TYPE: DNA
<213> ORGANISM: Artificial sequence
<220> FEATURE:
<223> OTHER INFORMATION: Nucleotide sequence of PDISP/HA B Malaysia

<400> SEQUENCE: 162

```
atggcgaaaa acgttgcgat tttcggctta ttgttttctc ttcttgtgtt ggttccttct      60

cagatcttcg cggatcgaat ctgcactggg ataacatcgt caaactcacc acatgttgtc     120

aaaactgcta ctcaagggga ggtcaatgtg actggtgtaa taccactgac aacaacaccc     180

accaaatctc attttgcaaa tctcaaagga acagaaacca gagggaaact atgcccaaaa     240

tgcctcaact gcacagatct ggacgtggcc ttgggcagac caaaatgcac ggggaacata     300

ccctcggcaa gagtttcaat actccatgaa gtcagacctg ttacatctgg gtgctttcct     360

ataatgcacg acagaacaaa aattagacag ctgcctaaac ttctcagagg atacgaacat     420

atcaggttat caactcataa cgttatcaat gcagaaaatg caccaggagg accctacaaa     480

attggaacct cagggtcttg ccctaacgtt accaatggaa acggattttt cgcaacaatg     540

gcttgggccg tcccaaaaaa cgacaacaac aaaacagcaa caaattcatt aacaatagaa     600

gtaccataca tttgtacaga aggagaagac caaattaccg tttgggggtt ccactctgat     660

aacgaaaccc aaatggcaaa gctctatggg gactcaaagc cccagaagtt cacctcatct     720

gccaacggag tgaccacaca ttacgtttca cagattggtg gcttcccaaa tcaaacagaa     780

gacggaggac taccacaaag cggtagaatt gttgttgatt acatggtgca aaaatctggg     840

aaaacaggaa caattaccta tcaaagaggt attttattgc ctcaaaaagt gtggtgcgca     900
```

agtggcagga gcaaggtaat aaaaggatcg ttgcctttaa ttggagaagc agattgcctc 960
cacgaaaaat acggtggatt aaacaaaagc aagccttact acacagggga acatgcaaag 1020
gccataggaa attgcccaat atgggtgaaa acacccttga agctggccaa tggaaccaaa 1080
tatagacctc ctgcaaaact attaaaggaa aggggtttct tcggagctat tgctggtttc 1140
ttagaaggag gatgggaagg aatgattgca ggttggcacg gatacacatc ccatggggca 1200
catggagtag cggtggcagc agaccttaag agcactcaag aggccataaa caagataaca 1260
aaaaatctca actctttgag tgagctggaa gtaaagaatc ttcaaagact aagcggtgcc 1320
atggatgaac tccacaacga aatactagaa ctagacgaga aagtggatga tctcagagct 1380
gatacaataa gctcacaaat agaactcgca gtcctgcttt ccaatgaagg aataataaac 1440
agtgaagatg agcatctctt ggcgcttgaa agaaagctga agaaaatgct gggcccctct 1500
gctgtagaga tagggaatgg atgctttgaa accaaacaca agtgcaacca gacctgtctc 1560
gacagaatag ctgctggtac ctttgatgca ggagaatttt ctctccccac ttttgattca 1620
ctgaatatta ctgctgcatc tttaaatgac gatggattgg ataatcatac tatactgctt 1680
tactactcaa ctgctgcctc cagtttggct gtaacattga tgatagctat ctttgttgtt 1740
tatatggtct ccagagacaa tgtttcttgc tccatctgtc tataa 1785

<210> SEQ ID NO 163
<211> LENGTH: 50
<212> TYPE: DNA
<213> ORGANISM: Artificial sequence
<220> FEATURE:
<223> OTHER INFORMATION: IF**-HBM250604.S1-6r

<400> SEQUENCE: 163
actaaagaaa ataggccttt atagacagat ggagcaagaa acattgtctc 50

<210> SEQ ID NO 164
<211> LENGTH: 594
<212> TYPE: PRT
<213> ORGANISM: Artificial sequence
<220> FEATURE:
<223> OTHER INFORMATION: Amino acid sequence of PDISP/HA B Malaysia

<400> SEQUENCE: 164

Met Ala Lys Asn Val Ala Ile Phe Gly Leu Leu Phe Ser Leu Leu Val
1 5 10 15

Leu Val Pro Ser Gln Ile Phe Ala Asp Arg Ile Cys Thr Gly Ile Thr
20 25 30

Ser Ser Asn Ser Pro His Val Val Lys Thr Ala Thr Gln Gly Glu Val
35 40 45

Asn Val Thr Gly Val Ile Pro Leu Thr Thr Thr Pro Thr Lys Ser His
50 55 60

Phe Ala Asn Leu Lys Gly Thr Glu Thr Arg Gly Lys Leu Cys Pro Lys
65 70 75 80

Cys Leu Asn Cys Thr Asp Leu Asp Val Ala Leu Gly Arg Pro Lys Cys
85 90 95

Thr Gly Asn Ile Pro Ser Ala Arg Val Ser Ile Leu His Glu Val Arg
100 105 110

Pro Val Thr Ser Gly Cys Phe Pro Ile Met His Asp Arg Thr Lys Ile
115 120 125

Arg Gln Leu Pro Lys Leu Leu Arg Gly Tyr Glu His Ile Arg Leu Ser
130 135 140

```
Thr His Asn Val Ile Asn Ala Glu Asn Ala Pro Gly Gly Pro Tyr Lys
145                 150                 155                 160

Ile Gly Thr Ser Gly Ser Cys Pro Asn Val Thr Asn Gly Asn Gly Phe
                165                 170                 175

Phe Ala Thr Met Ala Trp Ala Val Pro Lys Asn Asp Asn Asn Lys Thr
            180                 185                 190

Ala Thr Asn Ser Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Ala Lys Leu Leu
        355                 360                 365

Lys Glu Arg Gly Phe Phe Gly Ala Ile Ala Gly Phe Leu Glu Gly Gly
    370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
                405                 410                 415

Asn Lys Ile Thr Lys Asn Leu Asn Ser Leu Ser Glu Leu Glu Val Lys
            420                 425                 430

Asn Leu Gln Arg Leu Ser Gly Ala Met Asp Glu Leu His Asn Glu Ile
        435                 440                 445

Leu Glu Leu Asp Glu Lys Val Asp Asp Leu Arg Ala Asp Thr Ile Ser
    450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
                485                 490                 495

Leu Gly Pro Ser Ala Val Glu Ile Gly Asn Gly Cys Phe Glu Thr Lys
            500                 505                 510

His Lys Cys Asn Gln Thr Cys Leu Asp Arg Ile Ala Ala Gly Thr Phe
        515                 520                 525

Asp Ala Gly Glu Phe Ser Leu Pro Thr Phe Asp Ser Leu Asn Ile Thr
    530                 535                 540

Ala Ala Ser Leu Asn Asp Asp Gly Leu Asp Asn His Thr Ile Leu Leu
545                 550                 555                 560
```

```
Tyr Tyr Ser Thr Ala Ala Ser Ser Leu Ala Val Thr Leu Met Ile Ala
                565                 570                 575

Ile Phe Val Val Tyr Met Val Ser Arg Asp Asn Val Ser Cys Ser Ile
            580                 585                 590

Cys Leu


<210> SEQ ID NO 165
<211> LENGTH: 1734
<212> TYPE: DNA
<213> ORGANISM: Artificial sequence
<220> FEATURE:
<223> OTHER INFORMATION: Nucleotide sequence of PDISP/HA B Malaysia with
      deleted proteolytic loop

<400> SEQUENCE: 165

atggcgaaaa acgttgcgat tttcggctta ttgttttctc ttcttgtgtt ggttccttct     60

cagatcttcg cggatcgaat ctgcactggg ataacatcgt caaactcacc acatgttgtc    120

aaaactgcta ctcaagggga ggtcaatgtg actggtgtaa taccactgac aacaacaccc    180

accaaatctc attttgcaaa tctcaaagga acagaaacca gagggaaact atgcccaaaa    240

tgcctcaact gcacagatct ggacgtggcc ttgggcagac caaaatgcac ggggaacata    300

ccctcggcaa gagtttcaat actccatgaa gtcagacctg ttacatctgg gtgctttcct    360

ataatgcacg acagaacaaa aattagacag ctgcctaaac ttctcagagg atacgaacat    420

atcaggttat caactcataa cgttatcaat gcagaaaatg caccaggagg accctacaaa    480

attggaacct cagggtcttg ccctaacgtt accaatggaa acggattttt cgcaacaatg    540

gcttgggccg tcccaaaaaa cgacaacaac aaaacagcaa caaattcatt aacaatagaa    600

gtaccataca tttgtacaga aggagaagac caaattaccg tttgggggtt ccactctgat    660

aacgaaaccc aaatggcaaa gctctatggg gactcaaagc cccagaagtt cacctcatct    720

gccaacggag tgaccacaca ttacgtttca cagattggtg gcttcccaaa tcaaacagaa    780

gacggaggac taccacaaag cggtagaatt gttgttgatt acatggtgca aaaatctggg    840

aaaacaggaa caattaccta tcaaagaggt attttattgc ctcaaaaagt gtggtgcgca    900

agtggcagga gcaaggtaat aaaaggatcg ttgcctttaa ttggagaagc agattgcctc    960

cacgaaaaat acggtggatt aaacaaaagc aagccttact acacagggga acatgcaaag   1020

gccataggaa attgcccaat atgggtgaaa acacccttga agctggccaa tggaaccaaa   1080

tatagacctc ctggtggagg atgggaagga atgattgcag gttggcacgg atacacatcc   1140

catggggcac atggagtagc ggtggcagca gaccttaaga gcactcaaga ggccataaac   1200

aagataacaa aaaatctcaa ctctttgagt gagctggaag taaagaatct tcaaagacta   1260

agcggtgcca tggatgaact ccacaacgaa atactagaac tagacgagaa agtggatgat   1320

ctcagagctg atacaataag ctcacaaata gaactcgcag tcctgctttc caatgaagga   1380

ataataaaca gtgaagatga gcatctcttg gcgcttgaaa gaaagctgaa gaaaatgctg   1440

ggcccctctg ctgtagagat agggaatgga tgctttgaaa ccaaacacaa gtgcaaccag   1500

acctgtctcg acagaatagc tgctggtacc tttgatgcag gagaattttc tctccccact   1560

tttgattcac tgaatattac tgctgcatct ttaaatgacg atggattgga taatcatact   1620

atactgcttt actactcaac tgctgcctcc agtttggctg taacattgat gatagctatc   1680

tttgttgttt atatggtctc cagagacaat gtttcttgct ccatctgtct ataa          1734


<210> SEQ ID NO 166
```

```
<211> LENGTH: 48
<212> TYPE: DNA
<213> ORGANISM: Artificial sequence
<220> FEATURE:
<223> OTHER INFORMATION: HBM250604(PrL-).r

<400> SEQUENCE: 166

cattccttcc catcctccac caggaggtct atatttggtt ccattggc                48


<210> SEQ ID NO 167
<211> LENGTH: 48
<212> TYPE: DNA
<213> ORGANISM: Artificial sequence
<220> FEATURE:
<223> OTHER INFORMATION: HBM250604(PrL-).c

<400> SEQUENCE: 167

agacctcctg gtggaggatg ggaaggaatg attgcaggtt ggcacgga                48


<210> SEQ ID NO 168
<211> LENGTH: 577
<212> TYPE: PRT
<213> ORGANISM: Artificial sequence
<220> FEATURE:
<223> OTHER INFORMATION: Amino acid sequence of PDISP/HA B Malaysia with
      deleted proteolytic loop

<400> SEQUENCE: 168

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Asn Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Lys Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Val Thr Asn Gly Asn Gly Phe
                165                 170                 175

Phe Ala Thr Met Ala Trp Ala Val Pro Lys Asn Asp Asn Asn Lys Thr
            180                 185                 190

Ala Thr Asn Ser Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
```

```
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Ser Ile Cys
                565                 570                 575

Leu
```

<210> SEQ ID NO 169
<211> LENGTH: 1782
<212> TYPE: DNA
<213> ORGANISM: Artificial sequence
<220> FEATURE:
<223> OTHER INFORMATION: Nucleotide sequence of PDISP/HA B Massachusetts

<400> SEQUENCE: 169

```
atggcgaaaa acgttgcgat tttcggctta ttgttttctc ttcttgtgtt ggttccttct      60

cagatcttcg ccgatcgaat ctgcactggg ataacatctt caaactcacc tcatgtggtc     120

aaaacagcta ctcaagggga ggtcaatgtg actggtgtga taccactaac aacaacacca     180
```

```
acaaaatctt attttgcaaa tctcaaagga acaaagacca gagggaaact atgcccagac    240

tgtctcaact gtacagatct ggatgtggcc ctgggcaggc caatgtgtgt gggaactaca    300

ccttctgcga aagcttcaat acttcacgaa gtcagacctg ttacatccgg gtgcttccct    360

ataatgcacg acagaacaaa aatcaggcaa ctagccaatc ttctcagagg atatgaaaat    420

atcaggttat caacccaaaa cgttatcgat gcagaaaagg caccaggagg accctacaga    480

cttggaacct caggatcttg ccctaacgct accagtaaaa gcggattttt cgcaacaatg    540

gcttgggctg tcccaaagga caacaacaaa aatgcaacga acccattaac agtagaagta    600

ccatacattt gtgcagaagg ggaagaccaa attactgttt gggggttcca ttcagataac    660

aaaacccaaa tgaagaacct ctatggagac tcaaatcctc aaaagttcac ctcatctgct    720

aatggagtaa ccacacatta tgtttctcag attggcggct tcccagatca aacagaagac    780

ggaggactac cacaaagcgg cagaattgtc gttgattaca tgatgcaaaa acctgggaaa    840

acaggaacaa ttgtctatca aagaggtgtt ttgttgcctc aaaaggtgtg gtgcgcgagt    900

ggcaggagca aagtaataaa agggtccttg cctttaattg gtgaagcaga ttgccttcat    960

gaaaaatacg gtggattaaa caaaagcaag ccttactaca caggagaaca tgcaaaagcc   1020

ataggaaatt gcccaatatg ggtgaaaaca cctttgaagc ttgccaatgg aaccaaatat   1080

agacctcctg caaaactatt aaaggaaagg ggtttcttcg gagctattgc tggtttccta   1140

gaaggaggat gggaaggaat gattgcaggt tggcacggat acacatctca cggagcacat   1200

ggagtggcag ttgctgcaga ccttaagagc acacaagaag ctataaacaa gataacaaaa   1260

aatctcaact ctttgagtga gctagaagta aagaatcttc aaaggctaag tggtgccatg   1320

gatgaactcc acaacgaaat actcgagctg gatgagaaag tggatgacct cagagctgac   1380

actataagtt cacaaataga acttgcagtc ttgctttcca acgaaggaat aataaacagt   1440

gaagacgagc atctattggc acttgagaga aaactaaaga aaatgctggg tccctctgct   1500

gtagacatag gaaatggatg cttcgaaacc aaacacaaat gcaaccagac ctgcttagac   1560

aggatagctg ctggcacctt taatgcagga gagttttctc tccccacttt tgattcattg   1620

aacattactg ctgcatcttt aaatgatgat ggattggata accatactat actgctctat   1680

tactcaactg ctgcttctag tttggctgta acattgatgc tagctatttt tattgtttat   1740

atggtctcca gagacaacgt ttcatgctcc atctgtctat aa                      1782
```

<210> SEQ ID NO 170
<211> LENGTH: 593
<212> TYPE: PRT
<213> ORGANISM: Artificial sequence
<220> FEATURE:
<223> OTHER INFORMATION: Amino acid sequence of PDISP/HA B Massachusetts

<400> SEQUENCE: 170

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Lys Thr Arg Gly Lys Leu Cys Pro Asp
65                  70                  75                  80
```

```
Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Ala Lys Leu Leu Lys
        355                 360                 365

Glu Arg Gly Phe Phe Gly Ala Ile Ala Gly Phe Leu Glu Gly Gly Trp
    370                 375                 380

Glu Gly Met Ile Ala Gly Trp His Gly Tyr Thr Ser His Gly Ala His
385                 390                 395                 400

Gly Val Ala Val Ala Ala Asp Leu Lys Ser Thr Gln Glu Ala Ile Asn
                405                 410                 415

Lys Ile Thr Lys Asn Leu Asn Ser Leu Ser Glu Leu Glu Val Lys Asn
            420                 425                 430

Leu Gln Arg Leu Ser Gly Ala Met Asp Glu Leu His Asn Glu Ile Leu
        435                 440                 445

Glu Leu Asp Glu Lys Val Asp Asp Leu Arg Ala Asp Thr Ile Ser Ser
    450                 455                 460

Gln Ile Glu Leu Ala Val Leu Leu Ser Asn Glu Gly Ile Ile Asn Ser
465                 470                 475                 480

Glu Asp Glu His Leu Leu Ala Leu Glu Arg Lys Leu Lys Lys Met Leu
                485                 490                 495
```

```
Gly Pro Ser Ala Val Asp Ile Gly Asn Gly Cys Phe Glu Thr Lys His
            500                 505                 510

Lys Cys Asn Gln Thr Cys Leu Asp Arg Ile Ala Ala Gly Thr Phe Asn
        515                 520                 525

Ala Gly Glu Phe Ser Leu Pro Thr Phe Asp Ser Leu Asn Ile Thr Ala
    530                 535                 540

Ala Ser Leu Asn Asp Asp Gly Leu Asp Asn His Thr Ile Leu Leu Tyr
545                 550                 555                 560

Tyr Ser Thr Ala Ala Ser Ser Leu Ala Val Thr Leu Met Leu Ala Ile
                565                 570                 575

Phe Ile Val Tyr Met Val Ser Arg Asp Asn Val Ser Cys Ser Ile Cys
            580                 585                 590

Leu


<210> SEQ ID NO 171
<211> LENGTH: 63
<212> TYPE: DNA
<213> ORGANISM: Artificial sequence
<220> FEATURE:
<223> OTHER INFORMATION: Nucleotide sequence of patatin A signal peptide

<400> SEQUENCE: 171

atggcaacta ctaaaacttt tttaatttta ttttttatga tattagcaac tactagttca      60

aca                                                                    63


<210> SEQ ID NO 172
<211> LENGTH: 23
<212> TYPE: PRT
<213> ORGANISM: Artificial sequence
<220> FEATURE:
<223> OTHER INFORMATION: Amino acid sequence of patatin A signal peptide

<400> SEQUENCE: 172

Met Ala Thr Thr Lys Thr Phe Leu Ile Leu Phe Phe Met Ile Leu Ala
1               5                   10                  15

Thr Thr Ser Ser Thr Cys Ala
            20


<210> SEQ ID NO 173
<211> LENGTH: 517
<212> TYPE: DNA
<213> ORGANISM: Artificial sequence
<220> FEATURE:
<223> OTHER INFORMATION: CMPV HT sequence

<400> SEQUENCE: 173

tattaaaatc ttaataggtt ttgataaaag cgaacgtggg gaaacccgaa ccaaaccttc      60

ttctaaactc tctctcatct ctcttaaagc aaacttctct cttgtctttc ttgcgtgagc     120

gatcttcaac gttgtcagat cgtgcttcgg caccagtaca acgttttctt tcactgaagc     180

gaaatcaaag atctctttgt ggacacgtag tgcggcgcca ttaaataacg tgtacttgtc     240

ctattcttgt cggtgtggtc ttgggaaaag aaagcttgct ggaggctgct gttcagcccc     300

atacattact tgttacgatt ctgctgactt tcggcgggtg caatatctct acttctgctt     360

gacgaggtat tgttgcctgt acttctttct tcttcttctt gctgattggt tctataagaa     420

atctagtatt ttctttgaaa cagagttttc ccgtggtttt cgaacttgga gaaagattgt     480

taagcttctg tatattctgc ccaaatttgt cgggccc                             517
```

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187
<211> LENGTH: 528
<212> TYPE: DNA
<213> ORGANISM: Artificial sequence
<220> FEATURE:
<223> OTHER INFORMATION: [00173] CPMV HT+ with a plant kozak consensus sequence

<400> SEQUENCE: 187

```
tattaaaatc ttaataggtt ttgataaaag cgaacgtggg gaaacccgaa ccaaaccttc     60

ttctaaactc tctctcatct ctcttaaagc aaacttctct cttgtctttc ttgcgtgagc    120

gatcttcaac gttgtcagat cgtgcttcgg caccagtaca acgttttctt tcactgaagc    180

gaaatcaaag atctctttgt ggacacgtag tgcggcgcca ttaaataacg tgtacttgtc    240

ctattcttgt cggtgtggtc ttgggaaaag aaagcttgct ggaggctgct gttcagcccc    300

atacattact tgttacgatt ctgctgactt tcggcgggtg caatatctct acttctgctt    360

gacgaggtat tgttgcctgt acttctttct tcttcttctt gctgattggt tctataagaa    420

atctagtatt ttctttgaaa cagagttttc ccgtggtttt cgaacttgga gaaagattgt    480

taagcttctg tatattctgc ccaaatttgt tcgggcccaa taccgcgg                 528
```

<210> SEQ ID NO 188
<211> LENGTH: 511
<212> TYPE: DNA
<213> ORGANISM: Artificial sequence
<220> FEATURE:
<223> OTHER INFORMATION: Nucleotide sequence of CPMV HT+ 511

<400> SEQUENCE: 188

```
tattaaaatc ttaataggtt ttgataaaag cgaacgtggg gaaacccgaa ccaaaccttc     60

ttctaaactc tctctcatct ctcttaaagc aaacttctct cttgtctttc ttgcgtgagc    120

gatcttcaac gttgtcagat cgtgcttcgg caccagtaca acgttttctt tcactgaagc    180

gaaatcaaag atctctttgt ggacacgtag tgcggcgcca ttaaataacg tgtacttgtc    240

ctattcttgt cggtgtggtc ttgggaaaag aaagcttgct ggaggctgct gttcagcccc    300

atacattact tgttacgatt ctgctgactt tcggcgggtg caatatctct acttctgctt    360

gacgaggtat tgttgcctgt acttctttct tcttcttctt gctgattggt tctataagaa    420

atctagtatt ttctttgaaa cagagttttc ccgtggtttt cgaacttgga gaaagattgt    480

taagcttctg tatattctgc ccaaatttga a                                   511
```

<210> SEQ ID NO 189
<211> LENGTH: 534
<212> TYPE: DNA
<213> ORGANISM: Artificial sequence
<220> FEATURE:
<223> OTHER INFORMATION: Nucleotide sequence of CPMV HT+ [WT115]

<400> SEQUENCE: 189

```
tattaaaatc ttaataggtt ttgataaaag cgaacgtggg gaaacccgaa ccaaaccttc     60
```

ttctaaactc tctctcatct ctcttaaagc aaacttctct cttgtctttc ttgcatgagc 120
gatcttcaac gttgtcagat cgtgcttcgg caccagtaca acgttttctt tcactgaagc 180
gaaatcaaag atctctttgt ggacacgtag tgcggcgcca ttaaataacg tgtacttgtc 240
ctattcttgt cggtgtggtc ttgggaaaag aaagcttgct ggaggctgct gttcagcccc 300
atacattact tgttacgatt ctgctgactt tcggcgggtg caatatctct acttctgctt 360
gacgaggtat tgttgcctgt acttctttct tcttcttctt gctgattggt tctataagaa 420
atctagtatt ttctttgaaa cagagttttc ccgtggtttt cgaacttgga gaaagattgt 480
taagcttctg tatattctgc ccaaatttgt tcgggcccaa taccgcggag aaaa 534

<210> SEQ ID NO 190
<211> LENGTH: 56
<212> TYPE: DNA
<213> ORGANISM: Artificial Sequence
<220> FEATURE:
<223> OTHER INFORMATION: HBF406(PrL-).r (construct 2102 and 2104)

<400> SEQUENCE: 190
tccttcccat cctccaccag gaggtctata tttggttcca ttggcgagct tcaaag 56

<210> SEQ ID NO 191
<211> LENGTH: 52
<212> TYPE: DNA
<213> ORGANISM: Artificial sequence
<220> FEATURE:
<223> OTHER INFORMATION: HBF406(PrL-).c (construct 2102 and 2104)

<400> SEQUENCE: 191
atatagacct cctggtggag gatgggaagg aatgattgca ggctggcacg ga 52

<210> SEQ ID NO 192
<211> LENGTH: 50
<212> TYPE: DNA
<213> ORGANISM: Artificial sequence
<220> FEATURE:
<223> OTHER INFORMATION: IF*-HBF406.s1-6r (construct 2102 and 2104)

<400> SEQUENCE: 192
actaaagaaa ataggccttt atagacagat ggagcatgaa acgttgtctc 50

<210> SEQ ID NO 193
<211> LENGTH: 1731
<212> TYPE: DNA
<213> ORGANISM: Artificial sequence
<220> FEATURE:
<223> OTHER INFORMATION: Nucleotide sequence of PDISP/HA B Florida with
deleted proteolytic loop (construct 2102 and 2104)

<400> SEQUENCE: 193
atggcgaaaa acgttgcgat tttcggctta ttgttttctc ttcttgtgtt ggttccttct 60
cagatcttcg cggatcgaat ctgcactgga ataacatctt caaactcacc tcatgtggtc 120
aaaacagcca ctcaagggga ggtcaatgtg actggtgtga taccactaac aacaacacca 180
acaaaatctt attttgcaaa tctcaaagga acaaggacca gagggaaact atgcccagac 240
tgtctcaact gcacagatct ggatgtggct ttgggcagac caatgtgtgt ggggaccaca 300
ccttcggcga aggcttcaat actccacgaa gtcaaacctg ttacatccgg gtgctttcct 360
ataatgcacg acagaacaaa aatcaggcaa ctacccaatc ttctcagagg atatgaaaat 420
atcaggctat caacccaaaa cgtcatcgat gcggaaaagg caccaggagg accctacaga 480

```
cttggaacct caggatcttg ccctaacgct accagtaaga gcggattttt cgcaacaatg    540

gcttgggctg tcccaaagga caacaacaaa aatgcaacga acccactaac agtagaagta    600

ccatacattt gtacagaagg ggaagaccaa atcactgttt gggggttcca ttcagataac    660

aaaacccaaa tgaagaacct ctatggagac tcaaatcctc aaaagttcac ctcatctgct    720

aatggagtaa ccacacacta tgtttctcag attggcagct tcccagatca aacagaagac    780

ggaggactac cacaaagcgg caggattgtt gttgattaca tgatgcaaaa acctgggaaa    840

acaggaacaa ttgtctacca aagaggtgtt ttgttgcctc aaaaggtgtg gtgcgcgagt    900

ggcaggagca aagtaataaa agggtccttg cctttaattg gtgaagcaga ttgccttcat    960

gaaaaatacg gtggattaaa caaaagcaag ccttactaca caggagaaca tgcaaaagcc   1020

ataggaaatt gcccaatatg ggtgaaaaca cctttgaagc tcgccaatgg aaccaaatat   1080

agacctcctg gtggaggatg ggaaggaatg attgcaggct ggcacggata cacatctcac   1140

ggagcacatg gagtggcagt ggcggcggac cttaagagta cgcaagaagc tataaacaag   1200

ataacaaaaa atctcaattc tttgagtgag ctagaagtaa agaatcttca aagactaagt   1260

ggtgccatgg atgaactcca caacgaaata ctcgagctgg atgagaaagt ggatgatctc   1320

agagctgaca ctataagctc gcaaatagaa cttgcagtct tgctttccaa cgaaggaata   1380

ataaacagtg aagatgagca tctattggca cttgagagaa aactaaagaa aatgctgggt   1440

ccctctgctg tagagatagg aaatggatgc ttcgaaacca aacacaagtg caaccagacc   1500

tgcttagaca ggatagctgc tggcaccttt aatgcaggag aattttctct ccccactttt   1560

gattcactga acattactgc tgcatcttta aatgatgatg gattggataa ccatactata   1620

ctgctctatt actcaactgc tgcttctagt ttggctgtaa cattgatgct agctattttt   1680

attgtttata tggtctccag agacaacgtt tcatgctcca tctgtctata a            1731
```

```
<210> SEQ ID NO 194
<211> LENGTH: 576
<212> TYPE: PRT
<213> ORGANISM: Artificial sequence
<220> FEATURE:
<223> OTHER INFORMATION: Amino acid sequence of PDISP/HA B Florida with
      deleted proteolytic loop (construct 2102 and 2104)

<400> SEQUENCE: 194

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Arg Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Lys
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu Asn Ile Arg Leu Ser
```

```
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Thr Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Ser Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Glu Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn His Thr Ile Leu Leu Tyr Tyr
    530                 535                 540

Ser Thr Ala Ala Ser Ser Leu Ala Val Thr Leu Met Leu Ala Ile Phe
545                 550                 555                 560
```

```
Ile Val Tyr Met Val Ser Arg Asp Asn Val Ser Cys Ser Ile Cys Leu
                565                 570                 575
```

<210> SEQ ID NO 195
<211> LENGTH: 3486
<212> TYPE: DNA
<213> ORGANISM: Artificial sequence
<220> FEATURE:
<223> OTHER INFORMATION: Cassette 2102

<400> SEQUENCE: 195

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccaatacc gcggagaaaa tggcgaaaaa cgttgcgatt ttcggcttat tgttttctct   1320
tcttgtgttg gttccttctc agatcttcgc ggatcgaatc tgcactggaa taacatcttc   1380
aaactcacct catgtggtca aaacagccac tcaaggggag gtcaatgtga ctggtgtgat   1440
accactaaca acaacaccaa caaaatctta ttttgcaaat ctcaaaggaa caaggaccag   1500
agggaaacta tgcccagact gtctcaactg cacagatctg gatgtggctt tgggcagacc   1560
aatgtgtgtg gggaccacac cttcggcgaa ggcttcaata ctccacgaag tcaaacctgt   1620
tacatccggg tgctttccta taatgcacga cagaacaaaa atcaggcaac tacccaatct   1680
tctcagagga tatgaaaata tcaggctatc aacccaaaac gtcatcgatg cggaaaaggc   1740
accaggagga ccctacagac ttggaacctc aggatcttgc cctaacgcta ccagtaagag   1800
cggatttttc gcaacaatgg cttgggctgt cccaaaggac aacaacaaaa atgcaacgaa   1860
cccactaaca gtagaagtac catacatttg tacagaaggg gaagaccaaa tcactgtttg   1920
gggttccat tcagataaca aaacccaaat gaagaacctc tatggagact caaatcctca    1980
```

```
aaagttcacc tcatctgcta atggagtaac cacacactat gtttctcaga ttggcagctt   2040

cccagatcaa acagaagacg gaggactacc acaaagcggc aggattgttg ttgattacat   2100

gatgcaaaaa cctgggaaaa caggaacaat tgtctaccaa agaggtgttt tgttgcctca   2160

aaaggtgtgg tgcgcgagtg gcaggagcaa agtaataaaa gggtccttgc ctttaattgg   2220

tgaagcagat tgccttcatg aaaaatacgg tggattaaac aaaagcaagc cttactacac   2280

aggagaacat gcaaaagcca taggaaattg cccaatatgg gtgaaaacac ctttgaagct   2340

cgccaatgga accaaatata gacctcctgg tggaggatgg gaaggaatga ttgcaggctg   2400

gcacggatac acatctcacg gagcacatgg agtggcagtg gcggcggacc ttaagagtac   2460

gcaagaagct ataaacaaga taacaaaaaa tctcaattct ttgagtgagc tagaagtaaa   2520

gaatcttcaa agactaagtg gtgccatgga tgaactccac aacgaaatac tcgagctgga   2580

tgagaaagtg gatgatctca gagctgacac tataagctcg caaatagaac ttgcagtctt   2640

gctttccaac gaaggaataa taaacagtga agatgagcat ctattggcac ttgagagaaa   2700

actaaagaaa atgctgggtc cctctgctgt agagatagga aatggatgct tcgaaaccaa   2760

acacaagtgc aaccagacct gcttagacag gatagctgct ggcaccttta atgcaggaga   2820

attttctctc cccactttg attcactgaa cattactgct gcatctttaa atgatgatgg   2880

attggataac catactatac tgctctatta ctcaactgct gcttctagtt tggctgtaac   2940

attgatgcta gctattttta ttgtttatat ggtctccaga gacaacgttt catgctccat   3000

ctgtctataa aggcctattt tctttagttt gaatttactg ttattcggtg tgcatttcta   3060

tgtttggtga gcggttttct gtgctcagag tgtgtttatt ttatgtaatt taatttcttt   3120

gtgagctcct gtttagcagg tcgtcccttc agcaaggaca caaaaagatt ttaattttat   3180

taaaaaaaaa aaaaaaaaag accgggaatt cgatatcaag cttatcgacc tgcagatcgt   3240

tcaaacattt ggcaataaag tttcttaaga ttgaatcctg ttgccggtct tgcgatgatt   3300

atcatataat ttctgttgaa ttacgttaag catgtaataa ttaacatgta atgcatgacg   3360

ttatttatga gatgggtttt tatgattaga gtcccgcaat tatacattta atacgcgata   3420

gaaaacaaaa tatagcgcgc aaactaggat aaattatcgc gcgcggtgtc atctatgtta   3480

ctagat                                                              3486
```

<210> SEQ ID NO 196
<211> LENGTH: 5368
<212> TYPE: DNA
<213> ORGANISM: Artificial sequence
<220> FEATURE:
<223> OTHER INFORMATION: Cassette 2104

<400> SEQUENCE: 196

```
tgttgttgtg actccgaggg gttgcctcaa actctatctt ataaccggcg tggaggcatg     60

gaggcagggg tattttggtc attttaatag atagtggaaa atgacgtgga atttacttaa    120

agacgaagtc tttgcgacaa gggggggccc acgccgaatt taatattacc ggcgtggccc    180

ccccttatcg cgagtgcttt agcacgagcg gtccagattt aaagtagaaa atttcccgcc    240

cactagggtt aaaggtgttc acactataaa agcatatacg atgtgatggt atttggtcga    300

caagcttgca tgccggtcaa catggtggag cacgacacac ttgtctactc caaaaatatc    360

aaagatacag tctcagaaga ccaaagggca attgagactt ttcaacaaag ggtaatatcc    420

ggaaacctcc tcggattcca ttgcccagct atctgtcact ttattgtgaa gatagtggaa    480
```

```
aaggaaggtg gctcctacaa atgccatcat tgcgataaag gaaaggccat cgttgaagat    540
gcctctgccg acagtggtcc caaagatgga cccccaccca cgaggagcat cgtggaaaaa    600
gaagacgttc caaccacgtc ttcaaagcaa gtggattgat gtgataacat ggtggagcac    660
gacacacttg tctactccaa aaatatcaaa gatacagtct cagaagacca aagggcaatt    720
gagacttttc aacaaagggt aatatccgga aacctcctcg gattccattg cccagctatc    780
tgtcacttta ttgtgaagat agtggaaaag gaaggtggct cctacaaatg ccatcattgc    840
gataaaggaa aggccatcgt tgaagatgcc tctgccgaca gtggtcccaa agatggaccc    900
ccacccacga ggagcatcgt ggaaaaagaa gacgttccaa ccacgtcttc aaagcaagtg    960
gattgatgtg atatctccac tgacgtaagg gatgacgcac aatcccacta tccttcgcaa   1020
gacccttcct ctatataagg aagttcattt catttggaga ggtattaaaa tcttaatagg   1080
ttttgataaa agcgaacgtg gggaaacccg aaccaaacct tcttctaaac tctctctcat   1140
ctctcttaaa gcaaacttct ctcttgtctt tcttgcgtga gcgatcttca acgttgtcag   1200
atcgtgcttc ggcaccagta caacgttttc tttcactgaa gcgaaatcaa agatctcttt   1260
gtggacacgt agtgcggcgc cattaaataa cgtgtacttg tcctattctt gtcggtgtgg   1320
tcttgggaaa agaaagcttg ctggaggctg ctgttcagcc ccatacatta cttgttacga   1380
ttctgctgac tttcggcggg tgcaatatct ctacttctgc ttgacgaggt attgttgcct   1440
gtacttcttt cttcttcttc ttgctgattg gttctataag aaatctagta ttttctttga   1500
aacagagttt tcccgtggtt ttcgaacttg gagaaagatt gttaagcttc tgtatattct   1560
gcccaaattt gtcgggccca ataccgcgga gaaaatggcg aaaaacgttg cgattttcgg   1620
cttattgttt tctcttcttg tgttggttcc ttctcagatc ttcgcggatc gaatctgcac   1680
tggaataaca tcttcaaact cacctcatgt ggtcaaaaca gccactcaag gggaggtcaa   1740
tgtgactggt gtgataccac taacaacaac accaacaaaa tcttattttg caaatctcaa   1800
aggaacaagg accagaggga aactatgccc agactgtctc aactgcacag atctggatgt   1860
ggctttgggc agaccaatgt gtgtggggac cacaccttcg gcgaaggctt caatactcca   1920
cgaagtcaaa cctgttacat ccgggtgctt tcctataatg cacgacagaa caaaaatcag   1980
gcaactaccc aatcttctca gaggatatga aaatatcagg ctatcaaccc aaaacgtcat   2040
cgatgcggaa aaggcaccag gaggacccta cagacttgga acctcaggat cttgccctaa   2100
cgctaccagt aagagcggat ttttcgcaac aatggcttgg gctgtcccaa aggacaacaa   2160
caaaaatgca acgaacccac taacagtaga agtaccatac atttgtacag aaggggaaga   2220
ccaaatcact gtttgggggt tccattcaga taacaaaacc caaatgaaga acctctatgg   2280
agactcaaat cctcaaaagt tcacctcatc tgctaatgga gtaaccacac actatgtttc   2340
tcagattggc agcttcccag atcaaacaga agacggagga ctaccacaaa gcggcaggat   2400
tgttgttgat tacatgatgc aaaaacctgg gaaaacagga acaattgtct accaaagagg   2460
tgttttgttg cctcaaaagg tgtggtgcgc gagtggcagg agcaaagtaa taaaagggtc   2520
cttgccttta attggtgaag cagattgcct tcatgaaaaa tacggtggat taaacaaaag   2580
caagccttac tacacaggag aacatgcaaa agccatagga aattgcccaa tatgggtgaa   2640
aacacctttg aagctcgcca atggaaccaa atatagacct cctggtggag gatgggaagg   2700
aatgattgca ggctggcacg gatacacatc tcacggagca catggagtgg cagtggcggc   2760
ggaccttaag agtacgcaag aagctataaa caagataaca aaaaatctca attctttgag   2820
tgagctagaa gtaaagaatc ttcaaagact aagtggtgcc atggatgaac tccacaacga   2880
```

aatactcgag ctggatgaga aagtggatga tctcagagct gacactataa gctcgcaaat 2940
agaacttgca gtcttgcttt ccaacgaagg aataataaac agtgaagatg agcatctatt 3000
ggcacttgag agaaaactaa agaaaatgct gggtccctct gctgtagaga taggaaatgg 3060
atgcttcgaa accaaacaca agtgcaacca gacctgctta gacaggatag ctgctggcac 3120
ctttaatgca ggagaatttt ctctccccac ttttgattca ctgaacatta ctgctgcatc 3180
tttaaatgat gatggattgg ataaccatac tatactgctc tattactcaa ctgctgcttc 3240
tagtttggct gtaacattga tgctagctat ttttattgtt tatatggtct ccagagacaa 3300
cgtttcatgc tccatctgtc tataaaggcc tatttttcttt agtttgaatt tactgttatt 3360
cggtgtgcat ttctatgttt ggtgagcggt tttctgtgct cagagtgtgt ttattttatg 3420
taatttaatt tctttgtgag ctcctgttta gcaggtcgtc ccttcagcaa ggacacaaaa 3480
agattttaat tttattaaaa aaaaaaaaaa aaaagaccgg gaattcgata tcaagcttat 3540
cgacctgcag atcgttcaaa catttggcaa taaagtttct taagattgaa tcctgttgcc 3600
ggtcttgcga tgattatcat ataatttctg ttgaattacg ttaagcatgt aataattaac 3660
atgtaatgca tgacgttatt tatgagatgg gtttttatga ttagagtccc gcaattatac 3720
atttaatacg cgatagaaaa caaaatatag cgcgcaaact aggataaatt atcgcgcgcg 3780
gtgtcatcta tgttactaga tctctagagt ctcaagcttg gcgcgccata aaatgattat 3840
tttatgaata tatttcattg tgcaagtaga tagaaattac atatgttaca taacacacga 3900
aataaacaaa aaaagacaat ccaaaaacaa acaccccaaa aaaaataatc actttagata 3960
aactcgtatg aggagaggca cgttcagtga ctcgacgatt cccgagcaaa aaaagtctcc 4020
ccgtcacaca tatagtgggt gacgcaatta tctttaaagt aatccttctg ttgacttgtc 4080
attgataaca tccagtcttc gtcaggattg caaagaatta tagaagggat cccacctttt 4140
attttcttct tttttccata tttagggttg acagtgaaat cagactggca acctattaat 4200
tgcttccaca atgggacgaa cttgaagggg atgtcgtcga tgatattata ggtggcgtgt 4260
tcatcgtagt tggtgaaatc gatggtaccg ttccaatagt tgtgtcgtcc gagacttcta 4320
gcccaggtgg tctttccggt acgagttggt ccgcagatgt agaggctggg gtgtcggatt 4380
ccattccttc cattgtcctg gttaaatcgg ccatccattc aaggtcagat tgagcttgtt 4440
ggtatgagac aggatgtatg taagtataag cgtctatgct tacatggtat agatgggttt 4500
ccctccagga gtgtagatct tcgtggcagc gaagatctga ttctgtgaag ggcgacacat 4560
acggttcagg ttgtggaggg aataatttgt tggctgaata ttccagccat tgaagttttg 4620
ttgcccattc atgagggaat tcttccttga tcatgtcaag atattcctcc ttagacgttg 4680
cagtctggat aatagttctc catcgtgcgt cagatttgcg aggagagacc ttatgatctc 4740
ggaaatctcc tctggtttta atatctccgt cctttgatat gtaatcaagg acttgtttag 4800
agtttctagc tggctggata ttagggtgat ttccttcaaa atcgaaaaaa gaaggatccc 4860
taatacaagg ttttttatca agctggagaa gagcatgata gtgggtagtg ccatcttgat 4920
gaagctcaga agcaacacca aggaagaaaa taagaaaagg tgtgagtttc tcccagagaa 4980
actggaataa atcatctctt tgagatgagc acttgggata ggtaaggaaa acatatttag 5040
attggagtct gaagttctta ctagcagaag gcatgttgtt gtgactccga ggggttgcct 5100
caaactctat cttataaccg gcgtggaggc atggaggcag ggtattttg gtcattttaa 5160 tagatagtgg aaaatgacgt ggaatttact taaagacgaa gtctttgcga caaggggggg 5220
cccacgccga atttaatatt accggcgtgg ccccccctta tcgcgagtgc tttagcacga 5280
gcggtccaga tttaaagtag aaaatttccc gcccactagg gttaaaggtg ttcacactat 5340
aaaagcatat acgatgtgat ggtatttg 5368

<210> SEQ ID NO 197
<211> LENGTH: 46
<212> TYPE: DNA
<213> ORGANISM: Artificial sequence
<220> FEATURE:
<223> OTHER INFORMATION: IF-H1cTMCT.S1-4r

<400> SEQUENCE: 197
actaaagaaa ataggccttt aaatacatat tctacactgt agagac 46

<210> SEQ ID NO 198
<211> LENGTH: 1731
<212> TYPE: DNA
<213> ORGANISM: Artificial sequence
<220> FEATURE:
<223> OTHER INFORMATION: Nucleotide sequence of PDISP/HA B Florida+H1Cal
TMCT with deleted proteolytic loop (construct 2106 and 2108)

<400> SEQUENCE: 198
atggcgaaaa acgttgcgat ttcggctta ttgttttctc ttcttgtgtt ggttccttct 60
cagatcttcg cggatcgaat ctgcactgga ataacatctt caaactcacc tcatgtggtc 120
aaaacagcca ctcaagggga ggtcaatgtg actggtgtga taccactaac aacaacacca 180
acaaaatctt attttgcaaa tctcaaagga acaaggacca gagggaaact atgcccagac 240
tgtctcaact gcacagatct ggatgtggct ttgggcagac caatgtgtgt ggggaccaca 300
ccttcggcga aggcttcaat actccacgaa gtcaaacctg ttacatccgg gtgctttcct 360
ataatgcacg acagaacaaa aatcaggcaa ctacccaatc ttctcagagg atatgaaaat 420
atcaggctat caacccaaaa cgtcatcgat gcggaaaagg caccaggagg accctacaga 480
cttggaacct caggatcttg ccctaacgct accagtaaga gcggattttt cgcaacaatg 540
gcttgggctg tcccaaagga caacaacaaa aatgcaacga acccactaac agtagaagta 600
ccatacattt gtacagaagg ggaagaccaa atcactgttt gggggttcca ttcagataac 660
aaaacccaaa tgaagaacct ctatggagac tcaaatcctc aaaagttcac ctcatctgct 720
aatggagtaa ccacacacta tgtttctcag attggcagct tcccagatca aacagaagac 780
ggaggactac cacaaagcgg caggattgtt gttgattaca tgatgcaaaa acctgggaaa 840
acaggaacaa ttgtctacca aagaggtgtt ttgttgcctc aaaaggtgtg gtgcgcgagt 900
ggcaggagca aagtaataaa agggtccttg cctttaattg gtgaagcaga ttgccttcat 960
gaaaaatacg gtggattaaa caaaagcaag ccttactaca caggagaaca tgcaaaagcc 1020
ataggaaatt gcccaatatg ggtgaaaaca cctttgaagc tcgccaatgg aaccaaatat 1080
agacctcctg gtggaggatg ggaaggaatg attgcaggct ggcacggata cacatctcac 1140
ggagcacatg gagtggcagt ggcggcggac cttaagagta cgcaagaagc tataaacaag 1200
ataacaaaaa atctcaattc tttgagtgag ctagaagtaa agaatcttca aagactaagt 1260
ggtgccatgg atgaactcca caacgaaata ctcgagctgg atgagaaagt ggatgatctc 1320
agagctgaca ctataagctc gcaaatagaa cttgcagtct tgctttccaa cgaaggaata 1380
ataaacagtg aagatgagca tctattggca cttgagagaa aactaaagaa aatgctgggt 1440
ccctctgctg tagagatagg aaatggatgc ttcgaaacca aacacaagtg caaccagacc 1500

```
tgcttagaca ggatagctgc tggcaccttt aatgcaggag aattttctct ccccactttt   1560

gattcactga acattactgc tgcatcttta aatgatgatg gattggataa ctaccagatt   1620

ttggcgatct attcaactgt cgccagttca ttggtactgg tagtctccct gggggcaatc   1680

agtttctgga tgtgctctaa tgggtctcta cagtgtagaa tatgtattta a            1731


<210> SEQ ID NO 199
<211> LENGTH: 576
<212> TYPE: PRT
<213> ORGANISM: Artificial sequence
<220> FEATURE:
<223> OTHER INFORMATION: Amino acid sequence of PDISP/HA B Florida+H1Cal
      TMCT with deleted proteolytic loop (construct 2106 and 2108)

<400> SEQUENCE: 199

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Arg Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Lys
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Thr Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Ser Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320
```

-continued

```
Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Glu Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn Tyr Gln Ile Leu Ala Ile Tyr
    530                 535                 540

Ser Thr Val Ala Ser Ser Leu Val Leu Val Val Ser Leu Gly Ala Ile
545                 550                 555                 560

Ser Phe Trp Met Cys Ser Asn Gly Ser Leu Gln Cys Arg Ile Cys Ile
                565                 570                 575
```

<210> SEQ ID NO 200
<211> LENGTH: 3486
<212> TYPE: DNA
<213> ORGANISM: Artificial sequence
<220> FEATURE:
<223> OTHER INFORMATION: Cassette 2106

<400> SEQUENCE: 200

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660
```

tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccaatacc gcggagaaaa tggcgaaaaa cgttgcgatt ttcggcttat tgttttctct 1320
tcttgtgttg gttccttctc agatcttcgc ggatcgaatc tgcactggaa taacatcttc 1380
aaactcacct catgtggtca aaacagccac tcaaggggag gtcaatgtga ctggtgtgat 1440
accactaaca acaacaccaa caaaatctta ttttgcaaat ctcaaaggaa caaggaccag 1500
agggaaacta tgcccagact gtctcaactg cacagatctg gatgtggctt tgggcagacc 1560
aatgtgtgtg gggaccacac cttcggcgaa ggcttcaata ctccacgaag tcaaacctgt 1620
tacatccggg tgctttccta taatgcacga cagaacaaaa atcaggcaac tacccaatct 1680
tctcagagga tatgaaaata tcaggctatc aacccaaaac gtcatcgatg cggaaaaggc 1740
accaggagga ccctacagac ttggaacctc aggatcttgc cctaacgcta ccagtaagag 1800
cggatttttc gcaacaatgg cttgggctgt cccaaaggac aacaacaaaa atgcaacgaa 1860
cccactaaca gtagaagtac catacatttg tacagaaggg gaagaccaaa tcactgtttg 1920
ggggttccat tcagataaca aaacccaaat gaagaacctc tatggagact caaatcctca 1980
aaagttcacc tcatctgcta atggagtaac cacacactat gtttctcaga ttggcagctt 2040
cccagatcaa acagaagacg gaggactacc acaaagcggc aggattgttg ttgattacat 2100
gatgcaaaaa cctgggaaaa caggaacaat tgtctaccaa agaggtgttt tgttgcctca 2160
aaaggtgtgg tgcgcgagtg gcaggagcaa agtaataaaa gggtccttgc ctttaattgg 2220
tgaagcagat tgccttcatg aaaaatacgg tggattaaac aaaagcaagc cttactacac 2280
aggagaacat gcaaaagcca taggaaattg cccaatatgg gtgaaaacac ctttgaagct 2340
cgccaatgga accaaatata gacctcctgg tggaggatgg gaaggaatga ttgcaggctg 2400
gcacggatac acatctcacg gagcacatgg agtggcagtg gcggcggacc ttaagagtac 2460
gcaagaagct ataaacaaga taacaaaaaa tctcaattct ttgagtgagc tagaagtaaa 2520
gaatcttcaa agactaagtg gtgccatgga tgaactccac aacgaaatac tcgagctgga 2580
tgagaaagtg gatgatctca gagctgacac tataagctcg caaatagaac ttgcagtctt 2640
gctttccaac gaaggaataa taaacagtga agatgagcat ctattggcac ttgagagaaa 2700
actaaagaaa atgctgggtc cctctgctgt agagatagga aatggatgct tcgaaaccaa 2760
acacaagtgc aaccagacct gcttagacag gatagctgct ggcaccttta atgcaggaga 2820
attttctctc cccacttttg attcactgaa cattactgct gcatctttaa atgatgatgg 2880
attggataac taccagattt tggcgatcta ttcaactgtc gccagttcat tggtactggt 2940
agtctccctg gggggcaatca gtttctggat gtgctctaat gggtctctac agtgtagaat 3000
atgtatttaa aggcctattt tctttagttt gaatttactg ttattcggtg tgcatttcta 3060
tgtttggtga gcggttttct gtgctcagag tgtgtttatt ttatgtaatt taatttcttt 3120
gtgagctcct gtttagcagg tcgtcccttc agcaaggaca caaaaagatt ttaattttat 3180
taaaaaaaaa aaaaaaaaag accgggaatt cgatatcaag cttatcgacc tgcagatcgt 3240
tcaaacattt ggcaataaag tttcttaaga ttgaatcctg ttgccggtct tgcgatgatt 3300
atcatataat ttctgttgaa ttacgttaag catgtaataa ttaacatgta atgcatgacg 3360
ttatttatga gatgggtttt tatgattaga gtcccgcaat tatacattta atacgcgata 3420
gaaaacaaaa tatagcgcgc aaactaggat aaattatcgc gcgcggtgtc atctatgtta 3480
ctagat 3486

<210> SEQ ID NO 201
<211> LENGTH: 5368
<212> TYPE: DNA
<213> ORGANISM: Artificial sequence
<220> FEATURE:
<223> OTHER INFORMATION: Cassette 2108

<400> SEQUENCE: 201
tgttgttgtg actccgaggg gttgcctcaa actctatctt ataaccggcg tggaggcatg 60
gaggcagggg tattttggtc attttaatag atagtggaaa atgacgtgga atttacttaa 120
agacgaagtc tttgcgacaa ggggggggcc acgccgaatt taatattacc ggcgtggccc 180
ccccttatcg cgagtgcttt agcacgagcg gtccagattt aaagtagaaa atttcccgcc 240
cactagggtt aaaggtgttc acactataaa agcatatacg atgtgatggt atttggtcga 300
caagcttgca tgccggtcaa catggtggag cacgacacac ttgtctactc caaaaatatc 360
aaagatacag tctcagaaga ccaaagggca attgagactt ttcaacaaag ggtaatatcc 420
ggaaacctcc tcggattcca ttgcccagct atctgtcact ttattgtgaa gatagtggaa 480
aaggaaggtg gctcctacaa atgccatcat tgcgataaag gaaaggccat cgttgaagat 540
gcctctgccg acagtggtcc caaagatgga cccccaccca cgaggagcat cgtggaaaaa 600
gaagacgttc caaccacgtc ttcaaagcaa gtggattgat gtgataacat ggtggagcac 660
gacacacttg tctactccaa aaatatcaaa gatacagtct cagaagacca aagggcaatt 720
gagacttttc aacaaagggt aatatccgga aacctcctcg gattccattg cccagctatc 780
tgtcacttta ttgtgaagat agtggaaaag gaaggtggct cctacaaatg ccatcattgc 840
gataaaggaa aggccatcgt tgaagatgcc tctgccgaca gtggtcccaa agatggaccc 900
ccacccacga ggagcatcgt ggaaaaagaa gacgttccaa ccacgtcttc aaagcaagtg 960
gattgatgtg atatctccac tgacgtaagg gatgacgcac aatcccacta tccttcgcaa 1020
gacccttcct ctatataagg aagttcattt catttggaga ggtattaaaa tcttaatagg 1080
ttttgataaa agcgaacgtg gggaaacccg aaccaaacct tcttctaaac tctctctcat 1140
ctctcttaaa gcaaacttct ctcttgtctt tcttgcgtga gcgatcttca acgttgtcag 1200
atcgtgcttc ggcaccagta caacgttttc tttcactgaa gcgaaatcaa agatctcttt 1260
gtggacacgt agtgcggcgc cattaaataa cgtgtacttg tcctattctt gtcggtgtgg 1320
tcttgggaaa agaaagcttg ctggaggctg ctgttcagcc ccatacatta cttgttacga 1380
ttctgctgac tttcggcggg tgcaatatct ctacttctgc ttgacgaggt attgttgcct 1440
gtacttcttt cttcttcttc ttgctgattg gttctataag aaatctagta ttttctttga 1500
aacagagttt tcccgtggtt ttcgaacttg gagaaagatt gttaagcttc tgtatattct 1560

-continued

```
gcccaaattt gtcgggccca ataccgcgga gaaaatggcg aaaaacgttg cgattttcgg   1620
cttattgttt tctcttcttg tgttggttcc ttctcagatc ttcgcggatc gaatctgcac   1680
tggaataaca tcttcaaact cacctcatgt ggtcaaaaca gccactcaag gggaggtcaa   1740
tgtgactggt gtgataccac taacaacaac accaacaaaa tcttattttg caaatctcaa   1800
aggaacaagg accagaggga aactatgccc agactgtctc aactgcacag atctggatgt   1860
ggctttgggc agaccaatgt gtgtggggac cacaccttcg gcgaaggctt caatactcca   1920
cgaagtcaaa cctgttacat ccgggtgctt tcctataatg cacgacagaa caaaaatcag   1980
gcaactaccc aatcttctca gaggatatga aaatatcagg ctatcaaccc aaaacgtcat   2040
cgatgcggaa aaggcaccag gaggacccta cagacttgga acctcaggat cttgccctaa   2100
cgctaccagt aagagcggat ttttcgcaac aatggcttgg gctgtcccaa aggacaacaa   2160
caaaaatgca acgaacccac taacagtaga agtaccatac atttgtacag aaggggaaga   2220
ccaaatcact gtttgggggt tccattcaga taacaaaacc caaatgaaga acctctatgg   2280
agactcaaat cctcaaaagt tcacctcatc tgctaatgga gtaaccacac actatgtttc   2340
tcagattggc agcttcccag atcaaacaga agacggagga ctaccacaaa gcggcaggat   2400
tgttgttgat tacatgatgc aaaaacctgg gaaaacagga acaattgtct accaaagagg   2460
tgttttgttg cctcaaaagg tgtggtgcgc gagtggcagg agcaaagtaa taaaagggtc   2520
cttgccttta attggtgaag cagattgcct tcatgaaaaa tacggtggat taaacaaaag   2580
caagccttac tacacaggag aacatgcaaa agccatagga aattgcccaa tatgggtgaa   2640
aacacctttg aagctcgcca atggaaccaa atatagacct cctggtggag gatgggaagg   2700
aatgattgca ggctggcacg gatacacatc tcacggagca catggagtgg cagtggcggc   2760
ggaccttaag agtacgcaag aagctataaa caagataaca aaaaatctca attctttgag   2820
tgagctagaa gtaaagaatc ttcaaagact aagtggtgcc atggatgaac tccacaacga   2880
aatactcgag ctggatgaga aagtggatga tctcagagct gacactataa gctcgcaaat   2940
agaacttgca gtcttgcttt ccaacgaagg aataataaac agtgaagatg agcatctatt   3000
ggcacttgag agaaaactaa agaaaatgct gggtccctct gctgtagaga taggaaatgg   3060
atgcttcgaa accaaacaca agtgcaacca gacctgctta gacaggatag ctgctggcac   3120
ctttaatgca ggagaatttt ctctccccac ttttgattca ctgaacatta ctgctgcatc   3180
tttaaatgat gatggattgg ataactacca gattttggcg atctattcaa ctgtcgccag   3240
ttcattggta ctggtagtct ccctgggggc aatcagtttc tggatgtgct ctaatgggtc   3300
tctacagtgt agaatatgta tttaaaggcc tattttcttt agtttgaatt tactgttatt   3360
cggtgtgcat ttctatgttt ggtgagcggt tttctgtgct cagagtgtgt ttattttatg   3420
taatttaatt tctttgtgag ctcctgttta gcaggtcgtc ccttcagcaa ggacacaaaa   3480
agattttaat tttattaaaa aaaaaaaaaa aaaagaccgg gaattcgata tcaagcttat   3540
cgacctgcag atcgttcaaa catttggcaa taaagtttct taagattgaa tcctgttgcc   3600
ggtcttgcga tgattatcat ataatttctg ttgaattacg ttaagcatgt aataattaac   3660
atgtaatgca tgacgttatt tatgagatgg gtttttatga ttagagtccc gcaattatac   3720
atttaatacg cgatagaaaa caaaatatag cgcgcaaact aggataaatt atcgcgcgcg   3780
gtgtcatcta tgttactaga tctctagagt ctcaagcttg gcgcgccata aaatgattat   3840
tttatgaata tatttcattg tgcaagtaga tagaaattac atatgttaca taacacacga   3900
```

-continued

```
aataaacaaa aaaagacaat ccaaaaacaa acaccccaaa aaaaataatc actttagata    3960

aactcgtatg aggagaggca cgttcagtga ctcgacgatt cccgagcaaa aaaagtctcc    4020

ccgtcacaca tatagtgggt gacgcaatta tctttaaagt aatccttctg ttgacttgtc    4080

attgataaca tccagtcttc gtcaggattg caaagaatta tagaagggat cccacctttt    4140

attttcttct ttttccata tttagggttg acagtgaaat cagactggca acctattaat    4200

tgcttccaca atgggacgaa cttgaagggg atgtcgtcga tgatattata ggtggcgtgt    4260

tcatcgtagt tggtgaaatc gatggtaccg ttccaatagt tgtgtcgtcc gagacttcta    4320

gcccaggtgg tctttccggt acgagttggt ccgcagatgt agaggctggg gtgtcggatt    4380

ccattccttc cattgtcctg gttaaatcgg ccatccattc aaggtcagat tgagcttgtt    4440

ggtatgagac aggatgtatg taagtataag cgtctatgct tacatggtat agatgggttt    4500

ccctccagga gtgtagatct tcgtggcagc gaagatctga ttctgtgaag ggcgacacat    4560

acggttcagg ttgtggaggg aataatttgt tggctgaata ttccagccat tgaagttttg    4620

ttgcccattc atgagggaat tcttccttga tcatgtcaag atattcctcc ttagacgttg    4680

cagtctggat aatagttctc catcgtgcgt cagatttgcg aggagagacc ttatgatctc    4740

ggaaatctcc tctggtttta atatctccgt cctttgatat gtaatcaagg acttgtttag    4800

agtttctagc tggctggata ttagggtgat ttccttcaaa atcgaaaaaa gaaggatccc    4860

taatacaagg ttttttatca agctggagaa gagcatgata gtgggtagtg ccatcttgat    4920

gaagctcaga agcaacacca aggaagaaaa taagaaaagg tgtgagtttc tcccagagaa    4980

actggaataa atcatctctt tgagatgagc acttgggata ggtaaggaaa acatatttag    5040

attggagtct gaagttctta ctagcagaag gcatgttgtt gtgactccga ggggttgcct    5100

caaactctat cttataaccg gcgtggaggc atggaggcag gggtattttg gtcattttaa    5160

tagatagtgg aaaatgacgt ggaatttact taaagacgaa gtctttgcga caaggggggg    5220

cccacgccga atttaatatt accggcgtgg ccccccctta tcgcgagtgc tttagcacga    5280

gcggtccaga tttaaagtag aaaatttccc gcccactagg gttaaaggtg ttcacactat    5340

aaaagcatat acgatgtgat ggtatttg                                       5368
```

INFLUENZA VIRUS-LIKE PARTICLE PRODUCTION IN PLANTS

CROSS-REFERENCE TO RELATED APPLICATION

This application is a Continuation of U.S. application Ser. No. 14/779,423, filed Sep. 23, 2015; which claims priority to PCT International Application No. PCT/CA2014/050326, filed Mar. 28, 2014; which claims the benefit of U.S. Provisional Application Nos. 61/806,227, filed Mar. 28, 2013; 61/925,852, filed Jan. 10, 2014; and 61/971,274, filed Mar. 27, 2014, which applications are incorporated herein by reference.

FIELD OF INVENTION

This invention relates to producing virus like particles in plants.

BACKGROUND OF THE INVENTION

Influenza is caused by an RNA virus of the orthomyxoviridae family. There are three types of these viruses and they cause three different types of influenza: type A, B and C. Influenza virus type A viruses infect mammals (humans, pigs, ferrets, horses) and birds. This is very important to mankind, as this is the type of virus that has caused worldwide pandemics. Influenza virus type B (also known simply as influenza B) infects only humans. It occasionally causes local outbreaks of flu. Influenza C viruses also infect only humans. They infect most people when they are young and rarely causes serious illness.

Vaccination provides protection against disease caused by a like agent by inducing a subject to mount a defense prior to infection. Conventionally, this has been accomplished through the use of live attenuated or whole inactivated forms of the infectious agents as immunogens. To avoid the danger of using the whole virus (such as killed or attenuated viruses) as a vaccine, recombinant viral proteins, for example subunits, have been pursued as vaccines. Both peptide and subunit vaccines are subject to a number of potential limitations. Subunit vaccines may exhibit poor immunogenicity, owing to incorrect folding or poor antigen presentation. A major problem is the difficulty of ensuring that the conformation of the engineered proteins mimics that of the antigens in their natural environment. Suitable adjuvants and, in the case of peptides, carrier proteins, must be used to boost the immune response. In addition these vaccines elicit primarily humoral responses, and thus may fail to evoke effective immunity. Subunit vaccines are often ineffective for diseases in which whole inactivated virus can be demonstrated to provide protection.

Virus-like particles (VLPs) are potential candidates for inclusion in immunogenic compositions. VLPs closely resemble mature virions, but they do not contain viral genomic material. Therefore, VLPs are nonreplicative in nature, which make them safe for administration as a vaccine. In addition, VLPs can be engineered to express viral glycoproteins on the surface of the VLP, which is their most native physiological configuration. Moreover, since VLPs resemble intact virions and are multivalent particulate structures, VLPs may be more effective in inducing neutralizing antibodies to the glycoprotein than soluble envelope protein antigens.

VLPs have been produced in plants (WO2009/009876; WO 2009/076778; WO 2010/003225; WO 2010/003235; WO 2011/03522; WO 2010/148511; which are incorporated herein by reference), and in insect and mammalian systems (Noad, R. and Roy, P., 2003, *Trends Microbiol* 11: 438-44; Neumann et al., 2000, J. Virol., 74, 547-551). Latham and Galarza (2001, J. Virol., 75, 6154-6165) reported the formation of influenza VLPs in insect cells infected with recombinant baculovirus co-expressing hemagglutinin (HA), neuramindase (NA), M1, and M2 genes. This study demonstrated that influenza virion proteins self-assemble upon co-expression in eukaryotic cells and that the M1 matrix protein was required for VLP production. Gomez-Puertas et al., (1999, J. Gen. Virol, 80, 1635-1645) showed that overexpression of M2 completely blocked CAT RNA transmission to MDCK cultures.

The spike glycoprotein hemagglutinin (HA) of influenza viruses is of great importance for the uptake of virus particles by the host cell. It is responsible for their attachment to sialic acid-containing cellular receptors, and it is involved in virus penetration through fusion of the virus envelope with cellular membranes. Fusion activity and consequently virus infectivity depend on cleavage of the HA precursor molecule, HA0, into the disulfide-linked polypeptide chains, HA1 and HA2. Cleavage a subsequent pH-dependent conformational change result in the exposure and relocation of a highly conserved hydrophobic peptide at the amino terminus of the transmembrane polypeptide HA2, which mediates membrane fusion.

HA is synthesised as a precursor protein HA0, which undergoes proteolytic processing into two subunits (HA1 and HA2) linked together by a disulfide bridge. Two structural features are thought to be involved in HA cleavability: in HAs of restricted cleavability, the linker usually consists of a single arginine, whereas HAs cleavable in a broad range of different cell types have an insertion of a series of multiple basic residues in this position with the main enzyme recognition motif Arg-X-Lys/Arg-Arg, whereby X is a nonbasic amino acid. HAs with a multiple basic cleavage site are cleaved on the exocytic transport route before they reach the budding site on the cell surface, in contrast to HAs with a monobasic linker that are activated on virus particles either in the extracellular space or, as shown for the WSN strain, at the stage of virus entry. A second determinant of HA cleavage appears to be a carbohydrate side chain that is present in close vicinity of the cleavage site and interferes with protease accessibility. Loss of this carbohydrate resulted in enhanced HA cleavability and viral pathogenicity.

Mammalian and apathogenic avian influenza virus strains cause anatomically localized infections as a result of the restricted range of cells secreting a protease that can cleave the HA0 precursor extracellularly (Chen J, et. al. 1998, Cell. Vol 95:409-417). The proteases responsible for cleavage of HA0 in influenza infections of humans, are secreted by cells of the respiratory tract, or by coinfecting bacteria or mycoplasma, or they may be produced in inflammatory responses to infections. A major protease candidate is the tryptase Clara, which is produced by Clara cells of the bronchiolar epithelium, and has limited tissue distribution (upper respiratory tract). The protease is specific for the monobasic sequence Q/E-X-R found at the cleavage site of the H1, H2, H3, and H6. HA from H9 and B strains show a slightly different monobasic cleavage site with SSR and KER sequence respectively. No protease has been identified for the majority of influenza viruses that cause enteric and respiratory infection seen in aquatic birds. Most cell lines do not support multi-cycle replication unless exogenous protease (usually trypsin) is added.

In highly pathogenic avian strains, however, HA0 are cleaved by a family of more widespread intracellular proteases, resulting in systemic flu infections. This difference in pathogenicity correlates with structural differences at the HA0 cleavage site. Pathogenic strains have inserts of polybasic amino acids within, or next to, the monobasic site. Cleavage in this case occurs intracellularly and the proteases involved have been identified as furin, and other subtilisin-like enzymes, found in the Golgi and involved in the post-translational processing of hormone and growth factor precursors. The furin recognition sequence R-X-R/K-R is a frequent insertion amino acid at the HA0 cleavage sites of H5 and H7. The wide tissue distribution of the enzyme, and the efficiency of intracellular cleavage, contribute to the wide-spread and virulent systemic infection caused by these viruses.

The HA cleavage site is a target for virus attenuation, since activation cleavage of the HA0 precursor into the HA1 and HA2 fragments by host proteases is a step in the replication cycle of all influenza A and B virus strains. Only the cleaved HA can undergo a conformational change in the acidic milieu of the endosome after receptor-mediated endocytosis to expose the hydrophobic N terminus of the HA2 fragment for mediating fusion between endosomal and virion membranes.

Horimoto T, et. al. (2006, Vaccine, Vol 24: 3669-3676) describes the abolition of the polybasic cleavage site of H5 (RERRRKKR↓G) in H5. Selected mutants were submitted to immunogenicity study in mice, including a mutant with a deletion of the 4 first charged amino acids (RERR) and a modification to inactivate the polybasic cleavage site (RKKR with TETR). Abolition of the cleavage site did not affect the immunogenic properties of the mutant H5. Abolition the polybasic site (GERRRKKR↓G replaced by RETR) to produce mutant NIBSC 05/240 NIBSC influenza reference virus NIBG-23, has also been reported. Hoffman et. al. (2002, 2002, Vaccine, Vol 20:3165-3170) replaced the polybasic cleavage site of a H5 HA with the monobasic site of H6 in order to boost the expression in eggs. The first 4 residues were deleted and replaced the four last amino acids of the polybasic site by IETR (replacement of RERRRKKR↓G with IETR↓G). This mutant H5 showed a high expression level, potential proteolysis and conformational change at low pH required for viral replication and production in the host cell, immunogenicity data were not reported. These studies show that modification of the cleavage site can be employed to diminishes the virulence of the viral particle (in cases where the true viruses is replicated), allowing the virus to replicate without killing the host egg. Without such mutations, viruses kill the egg before reaching high titers.

WO2013043067 by Sirko et al. describe a DNA vaccine for chicken which contains the cDNA encoding a modified H5 haemagluttinin (HA) protein wherein the proteolytic cleavage site between HA subunits is deleted. Sirko et al. state that this provides for greater safety of the vaccines and the expression of a “super antigen” in the form of a long, non-processed polypeptide. Sirko et al. further state that the encoding region of the HA is modified in such a way that protein production in bird cells achieves maximal yield. The main modification is codon optimisation for chicken and deletion of the proteolysis sensitive region of HA.

WO 2013/044390 describes a method of producing a virus like particle (VLP) in a plant with modified hemagglutinin (HA) wherein the modified HA protein comprises a modified proteolytic loop. The modified HA is expressed in the presence of the regulatory region Cowpea mosaic virus (CPMV) HT and the geminivirus amplification element from Bean Yellow Dwarf Virus (BeYDV).

US 2008/0069821 by Yang et al. discloses polypeptides and polynucleotides variants of influenza HA for use in the production of influenza viruses as vaccines. Reassortant influenza viruses are obtained by introducing a subset of vectors corresponding to genomic segments of a master influenza virus, in combination with complementary segments derived from the variants of influenza HA. Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity.

SUMMARY OF THE INVENTION

This invention relates to producing virus like particles and modified HA proteins in plants.

It is an object of the invention to provide an improved production of virus like particles and HA proteins in plants.

Described herein is a nucleic acid comprising an expression enhancer active in a plant and operatively linked to a nucleotide sequence encoding a modified influenza hemagglutinin (HA) comprising a modified proteolytic loop.

Furthermore described herein is a method (A) of producing a virus like particle (VLP) in a plant comprising, a) introducing a nucleic acid comprising an expression enhancer active in a plant and operatively linked to a nucleotide sequence encoding a modified influenza hemagglutinin (HA) comprising a modified proteolytic loop into the plant, or portion of the plant;

b) incubating the plant or portion of the plant under conditions that permit the expression of the nucleic acid, thereby producing the VLP.

In addition, described herein is a method (B) for producing influenza virus like particles (VLPs) in a plant comprising:

a) providing a plant, or a portion of a plant, comprising a nucleic acid comprising an expression enhancer active in a plant and operatively linked to a nucleotide sequence encoding a modified influenza hemagglutinin (HA) comprising a modified proteolytic loop, and b) incubating the plant or portion of the plant under conditions that permit the expression of the nucleic acid, thereby producing the VLPs Furthermore described herein is a method (C) of producing a modified HA protein comprising a modified proteolytic loop comprising one or more protease cleavage sites exhibiting reduced or abolished cleavage in a plant comprising, a) introducing a nucleic acid comprising an expression enhancer active in a plant and operatively linked to a nucleotide sequence encoding a modified influenza hemagglutinin (HA) comprising a modified proteolytic loop into the plant, or portion of the plant;

b) incubating the plant or portion of the plant under conditions that permit the expression of the HA protein, thereby producing the modified HA protein, c) harvesting the plant and purifying the modified HA protein.

The methods (A), (B) or (C) as described above may further comprising the steps of c) harvesting the plant, and d) purifying the VLPs, wherein the VLPs range in size from 80-300 nm.

Furthermore, described herein is a method (D) of increasing the product yield of a HA protein in a plant, comprising, a) introducing a nucleic acid comprising an expression enhancer active in a plant and operatively linked to a nucleotide sequence encoding a modified influenza hemagglutinin (HA) comprising a modified proteolytic loop into the plant, or portion of the plant;

b) incubating the plant or portion of the plant under conditions that permit the expression of the HA protein, thereby producing the modified HA protein, c) harvesting the plant and purifying the HA protein.

The expression enhancer may be CPMVX, CPMVX+ or CPMV-HT+. Furthermore, the nucleotide acid may not comprise a geminivirus amplification element. The nucleotide acid therefore may not comprise a Bean Yellow Dwarf Virus long intergenic region (BeYDV LIR), and a BeYDV short intergenic region (BeYDV SIR). The modified proteolytic loop may comprises one or more protease cleavage sites exhibiting reduced or abolished cleavage by a protease. The protease may be Clara-like or Furin-like. Furthermore the modified proteolytic loop may comprises a linker sequence and the linker sequence may have the amino acid sequence GG, TETQ or TETR. The modified HA may comprise a native or a non-native signal peptide. Furthermore the nucleotide sequence encoding the modified HA may comprise a chimeric nucleotide sequence encoding, in series, a modified HA ectodomain comprising a modified proteolytic loop, an influenza transmembrane domain, and a cytoplasmic tail, wherein the modified HA ectodomain is from a first influenza strain and the transmembrane domain and the cytoplasmic tail are from a second influenza strain.

The modified proteolytic loop may comprise one or more protease cleavage sites exhibiting reduced or abolished cleavage by a protease. Furthermore, the nucleotide sequence encoding the HA is selected from the group consisting of B HA, C, H1, H2, H3, H4, H5, H6, H7, H8, H9, H10, H11, H12, H13, H14, H15, and H16. Also described herein is a virus like particle (VLP) produced by the method (A). The virus like particle (VLP) may comprise plant-specific N-glycans, or modified N-glycans.

The present disclosure also provides a composition comprising an effective dose of the VLP for inducing an immune response, and a pharmaceutically acceptable carrier.

Also described herein is a nucleic acid comprising a nucleotide sequence encoding an influenza hemagglutinin (HA), the nucleotide sequence operatively linked with a regulatory region that is active in a plant, wherein the HA comprises a modified proteolytic loop sequence. The nucleic acid may encode an HA comprising a modified proteolytic loop, where in the protein has hemagglutinin (HA) activity. A plant comprising the nucleic acid is also provided. Also included is a virus like particle (VLP) produced in a plant, the VLP comprising an influenza virus hemagglutinin (HA) encoded by the nucleic acid and one or more than one lipid derived from a plant.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows components used to prepare A-2X35S/CPMV-HT/H5 Indonesia/NOS (Construct number 489). FIG. 1A shows primer IF-H5A-I-05.s1+3c (SEQ ID NO: 2). FIG. 1B shows primer IF-H5dTm.r (SEQ ID NO: 3). FIG. 1D shows Construct 1191 (SEQ ID NO 4). FIG. 1E shows expression cassette number 489 (SEQ ID NO 5). FIG. 1F shows amino acid sequence of H5 from influenza A/Indonesia/5/2005 (H5N1) (SEQ ID NO: 6). FIG. 1G shows a nucleotide sequence encoding H5 from influenza A/Indonesia/5/2005 (H5N1) (SEQ ID NO: 42).

FIG. 2 shows components used to prepare B-2X35S/CPMV HT/M2 New Caledonia/NOS (Construct number 1261). FIG. 2A shows primer IF-S1-M1+M2ANC.c (SEQ ID NO:7). FIG. 2B shows primer IF-S1-4-M2ANC.r (SEQ ID NO: 8). FIG. 2C shows the nucleotide sequence for the synthesized M2 gene (corresponding to nt 1-26 joined to 715-982 from Genbank accession number DQ508860) (SEQ ID NO: 9). FIG. 2D shows the expression cassette number 1261 from 2X35S promoter to NOS terminator. M2 from influenza A/New Caledonia/20/1999 (H1N1) is underlined. (SEQ ID NO: 10). FIG. 2E shows the amino acid sequence of M2 from influenza A/New Caledonia/20/1999 (H1N1) (SEQ ID NO: 11).

FIG. 3 shows components used to prepare C-2X35S/CPMV-HT/M2 Puerto Rico/NOS (Construct number 859). FIG. 3A shows the nucleotide sequence of the synthesized M2 gene (corresponding to nt 26-51 joined to nt 740-1007 from Genebank accession number EF467824) (SEQ ID NO: 12). FIG. 3B shows the expression cassette number 859 from 2X35S promoter to NOS terminator. M2 from Influenza A/Puerto Rico/8/1934 (H1N1) is underlined. (SEQ ID NO: 13). FIG. 3C shows the amino acid sequence of M2 from influenza A/Puerto Rico/8/1934 (H1N1) (SEQ ID NO: 14).

FIG. 4 shows components used to prepare G-2X35S/CPMV-HT/PDISP/HA B Brisbane/NOS into BeYDV+Replicase amplification system (Construct number 1008). FIG. 4A shows a schematic representation of construct 1194. SacII and StuI restriction enzyme sites used for plasmid linearization are annotated on the representation. FIG. 4B shows construct 1194 from left to right t-DNA borders (underlined). 2X35S/CPMV-HT/PDISP/NOS into BeYDV+Replicase amplification system with Plastocyanine-P19-Plastocyanine silencing inhibitor expression cassette (SEQ ID NO: 31). FIG. 4C shows expression cassette number 1008 from BeYDV left LIR to BeYDV right LIR. PDISP/HA from influenza B/Brisbane/60/2008 is underlined. (SEQ ID NO: 32).

FIG. 5 shows components used to prepare I-2X35S/CPMV-HT/PDISP/HA B Brisbane with deleted proteolytic loop/NOS into BeYDV+Replicase amplification system (Construct number 1059). FIG. 5A shows primer 1039+1059.r (SEQ ID NO: 38). FIG. 5B shows primer 1039+1059.c (SEQ ID NO: 39). FIG. 5C shows expression cassette number 1059 from BeYDV left LIR to BeYDV right LIR. PDISP/HA from influenza B/Brisbane/60/2008 with deleted proteolytic loop is underlined (SEQ ID NO: 40). FIG. 5D shows amino acid sequence of PDISP/HA from influenza B/Brisbane/60/2008 with deleted proteolytic loop (SEQ ID NO: 41). FIG. 5E shows nucleotide sequence of PDISP/HA from influenza B/Brisbane/60/2008 with deleted proteolytic loop (SEQ ID NO: 43).

FIG. 61H shows a schematic representation of construct 1462.

FIG. 7 shows components used to prepare C-2X35S/CPMV-HT/HA B Wisconsin with deleted proteolytic loop/NOS into BeYDV(m)+Replicase amplification system (Construct number 1467). FIG. 7A shows primer HAB110 (PrL-).r (SEQ ID NO: 55). FIG. 7B shows primer HAB110 (PrL-).c (SEQ ID NO: 56). FIG. 7C shows the nucleotide sequence of expression cassette number 1467 from 2X35S promoter to NOS terminator. HA from influenza B/Wisconsin/1/2010 with deleted proteolytic loop is underlined (SEQ ID NO: 57). FIG. 7D shows the amino acid sequence of influenza B/Wisconsin/1/2010 with deleted proteolytic loop (SEQ ID NO: 58).

FIG. 8 shows components used to prepare A-2X35S/CPMV-HT/PDISP/HA B Brisbane with deleted proteolytic loop/NOS (Construct number 1039). FIG. 8A shows the nucleotide sequence of expression cassette number 1039 from 2X35S promoter to NOS terminator. HA from influenza B/Brisbane/60/2008 with deleted proteolytic loop is underlined (SEQ ID NO: 15). FIG. 8B shows a schematic representation of construct 1039.

FIG. 15 shows the amino acid sequence alignment of the region surrounding the linker of HAs from several strains of influenza: H1 New Cal (SEQ ID NO:22); H1 Brisbane (SEQ ID NO:23); H1 Sol Islands (SEQ ID NO:24); H2A Singapore (SEQ ID NO:25); H3A Brisbane (SEQ ID NO:26); H3A WCN (SEQ ID NO:27); H5 Anhui (SEQ ID NO:28); H5 Indo (SEQ ID NO:29); H5 Vietnam (SEQ ID NO:30); H6 Teal HK (SEQ ID NO:33); H7 Eq Prague (SEQ ID NO:34); H9A HK (SEQ ID NO:35); B Florida (SEQ ID NO:36); B Malaysia (SEQ ID NO:37). The cleavage site of the precursor HA0 is indicated by an arrow.

FIG. 18A shows the schematic representation of the cleavage of the HA0 by Clara-like and/or Furin like protease into HA1 and HA2. FIG. 18B shows the sequence alignment of HAs from several strains of influenza: H1 New Cal (SEQ ID NO:22); H1 Brisbane (SEQ ID NO:23); H1 Sol Islands (SEQ ID NO:24); H2A Singapore (SEQ ID NO:25); H3A Brisbane (SEQ ID NO:26); H3A WCN (SEQ ID NO:27); H5

Anhui (SEQ ID NO:28); H5 Indo (SEQ ID NO:29); H5 Vietnam (SEQ ID NO:30); H6 Teal HK (SEQ ID NO:33); H7 Eq Prague (SEQ ID NO:34); H9A HK (SEQ ID NO:35); B Florida (SEQ ID NO:36); B Malaysia (SEQ ID NO:37). FIG. 18C shows deletion of part of the cleavage site in H5 strains, A/Anhui/1/2005 (H5N1) SEQ ID NO: 69, A/Indonesia/5/2005 (H5N1) SEQ ID NO: 70, A/Vietnam/1194/2004 (H5N1) SEQ ID NO: 71, and type B strains, B/Florida/4/2006 SEQ ID NO: 72, and B/Malaysia/2506/2004 SEQ ID NO:73.

FIG. 21 shows various approaches for modifying the proteolytic loop of type B HA. FIG. 21A shows the amino acid sequence of native B/Brisbane/60/2008 (SEQ ID NO: 16). The underlined portion is the proteolytic loop and the HA2 domain. FIG. 21B shows the amino acid sequence of B/Brisbane/60/2008 with the proteolytic loop modified (SEQ ID NO: 17), wherein 19 amino acid residues comprising the sequence AKLLKERGFFGAIAGFLEG have been replaced with a GG linker (italics). FIG. 21 C shows the amino acid sequence of B/Brisbane/60/2008 (SEQ ID NO: 18), wherein 9 amino acid comprising the sequence PPAKLLKER has been replaced with a -GSSSGSSSG- linker (italics). FIG. 21 D shows the amino acid sequence of native H3 A/Perth/16/2009 (SEQ ID NO: 19). FIG. 21 E shows the amino acid sequence of H3 A/Perth/16/2009 (SEQ ID NO: 20) with 12 amino acid residues comprising the sequence RNVPEKQTRGIF replaced by a GS linker (italics). FIG. 21 F shows the amino acid sequence of H3 A/Perth/16/2009 (SEQ ID NO: 21) with 9 amino acid residues comprising the sequence RNVPEKQTR replaced by a GSSGSSGSS- linker (italics).

FIG. 23 shows components used to prepare B-2X35S/CPMV-HT/H5 from A/Indonesia/5/2005 with TETR cleavage site mutation (Construct number 676). FIG. 23A shows primer sequence MutCleavage-H5(Indo).r (SEQ ID NO:74). FIG. 23B shows primer sequence MutCleavage-H5(Indo).c (SEQ ID NO:75). FIG. 23C shows the nucleotide sequence (SEQ ID NO: 76) for expression cassette 676 from the 2X35S promoter to NOS terminator. H5 from influenza A/Indonesia/5/2005 (H5N1) TETR cleavage site mutant is underlined. FIG. 23D shows the amino acid sequence (SEQ ID NO:77) of a TETR cleavage site mutant of H5 from influenza A/Indonesia/5/2005 (H5N1). FIG. 23E shows a schematic representation of construct number 676.

FIG. 24 shows components used to prepare B-2X35S/CPMV-HT/H5 from A/Indonesia/5/2005 with TETQ cleavage site mutation (Construct number 766). FIG. 24A shows primer sequence H5I505_TETQ.r (SEQ ID NO:78). FIG. 24B shows primer sequence H5I505_TETQ.c (SEQ ID NO:79). FIG. 24C shows the nucleotide sequence (SEQ ID NO: 80) for expression cassette 766 from the 2X35S promoter to NOS terminator. H5 from influenza A/Indonesia/5/2005 (H5N1) TETQ cleavage site mutant is underlined.

FIG. 24D shows the amino acid sequence (SEQ ID NO:81) of a TETQ cleavage site mutant of H5 from influenza A/Indonesia/5/2005 (H5N1). FIG. 24E shows a schematic representation of construct number 766.

FIG. 25 shows components used to prepare B-2X35S/CPMV-HT/H5 from A/Indonesia/5/2005 with a deleted proteolytic loop (Construct number 928). FIG. 25A shows primer sequence H5I505(PrL-).r (SEQ ID NO: 82). FIG. 25B shows primer sequence H5I505(PrL-).c (SEQ ID NO: 83). FIG. 25C shows the nucleotide sequence (SEQ ID NO:84) for expression cassette 928 from the 2X35S promoter to NOS terminator. H5 from influenza A/Indonesia/5/2005 (H5N1) the deleted proteolytic loop is underlined.

FIG. 25D shows the amino acid sequence (SEQ ID NO:85) of a mutant of H5 from influenza A/Indonesia/5/2005 (H5N1) comprising a deleted proteolytic loop. FIG. 25E shows a schematic representation of construct number 928.

FIG. 30 shows sequence components used to prepare Construct number 1029 (F-2X35S/CPMV-HT/PDISP/HA B Brisbane/NOS; see Example 5.11). FIG. 30A shows primer IF-S2+S4-B Bris.c (SEQ ID NO: 86). FIG. 30B shows primer IF-S1a4-B Bris.r (SEQ ID NO: 87). FIG. 30C shows the nucleotide sequence of synthesized HA B Brisbane gene (corresponding to nt 34-1791 from Genbank accession number FJ766840) (SEQ ID NO: 88). FIG. 30D shows the nucleotide sequence of expression cassette number 1029 from 2X35S promoter to NOS terminator. PDISP/HA from influenza B/Brisbane/60/2008 is underlined. (SEQ ID NO: 89). FIG. 30E shows the amino acid sequence of PDISP/HA from influenza B/Brisbane/60/2008 (SEQ ID NO: 90).

FIG. 31 shows sequence components used to prepare construct numbers 1039 and 1829 (2X35S/CPMV HT PDISP/HA B Brisbane (PrL-) NOS and 2X35S/CPMV HT+ PDISP/HA B Brisbane (PrL-) NOS, respectively; see Example 5.12). Construct number 1039 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)). Construct number 1829 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop. FIG. 31A shows the nucleotide sequence of PDISP/HA B Brisbane (PrL-) (SEQ ID NO: 91). FIG. 31B shows the amino acid sequence of PDISP/HA B Brisbane (PrL-); SEQ ID NO: 92). FIG. 31C shows a schematic representation of construct number 1829 (2X35S/CPMV HT+).

FIG. 33 shows sequence components used to prepare construct numbers 1067 and 1977 (2X35S/CPMV HT PDISP/HA B Brisbane (Prl-)+H1 California TMCT NOS and 2X35S/CPMV160+ PDISP/HA B Brisbane (PrL-)+H1 California TMCT NOS, respectively; see Example 5.14). Construct number 1067 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)+H1 California TMCT). Construct number 1977 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. PDISP: protein disulfide isomerase signal peptide; NOS: nopaline synthase terminator; PrL-: deleted proteolytic loop; TMCT: transmembrane domain cytoplasmic tail. FIG. 33A shows the nucleotide sequence of PDISP/HA B Brisbane (PrL-)+H1 California TMCT (SEQ ID NO: 95). FIG. 33B shows the amino acid sequence of PDISP/HA B Brisbane (PrL-)+H1 California TMCT (SEQ ID NO: 96).

FIG. 34 shows sequence components used to prepare construct numbers 2072 and 2050 (2X35S/CPMV HT PDISP/HA B Massachusetts (PrL-) NOS and 2X35S/CPMV160+ PDISP/HA B Massachusetts (PrL-) NOS, respectively; see Example 5.15). Construct number 2072 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)). Construct number 2050 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. PDISP: protein disulfide isomerase signal peptide; NOS: nopaline synthase terminator; PrL-: deleted proteolytic loop. FIG. 34A shows the nucleotide sequence of PDISP/HA B Massachusetts (PrL-) (SEQ ID NO: 97). FIG. 34B shows the amino acid sequence of PDISP/HA B Massachusetts (PrL-) (SEQ ID NO: 98).

FIG. 35 shows sequence components used to prepare construct numbers 2074 and 2060 (2X35S/CPMV HT PDISP/HA B Massachusetts (PrL-)+H1 California TMCT NOS and 2X35S/CPMV160+ PDISP/HA B Massachusetts (PrL-)+H1 California TMCT NOS, respectively; see Example 5.16). Construct number 2074 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)+ H1 California TMCT). Construct number 2060 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. PDISP: protein disulfide isomerase signal peptide; NOS: nopaline synthase terminator; PrL-: deleted proteolytic loop; TMCT: transmembrane domain cytoplasmic tail. FIG. 35A shows the nucleotide sequence of PDISP/HA B Massachusetts (PrL-)+ H1 California TMCT (SEQ ID NO: 99). FIG. 35B shows the amino acid sequence of PDISP/HA B Massachusetts (PrL-)+ H1 California TMCT (SEQ ID NO: 100).

FIG. 36 shows sequence components used to prepare construct numbers 1445, 1820 and 1975 (2X35S/CPMV HT HA B Wisconsin (PrL-) NOS, 2X35S/CPMV160+HA B Wisconsin (PrL-) NOS and 2X35S/CPMV160 HA B Wisconsin (PrL-) NOS, respectively; see Example 15.17). Construct number 1445 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)). Construct number 1820 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. Construct number 1975 includes a CPMV 5'UTR comprising 160 nucleotides, and does not include a stuffer fragment (multiple cloning site), or a plant kozak sequence (this construct also does not comprise a sequence encoding an incomplete M protein) and is an example of a “CPMV160” (CPMVX) based construct. PrL-: deleted proteolytic loop; NOS: nopaline synthase terminator. FIG. 36A shows the nucleotide sequence of HA B Wisconsin (PrL-) (SEQ ID NO: 101). FIG. 36B shows the amino acid sequence of HA B Wisconsin (PrL-) (SEQ ID NO: 102).

FIG. 37 shows sequence components used to prepare construct numbers 1454 and 1893 (2X35S/CPMV HT HA B Wisconsin (PrL-)+H1 California TMCT NOS and 2X35S/CPMV160+HA B Wisconsin (PrL-)+H1 California TMCT NOS, respectively; see Example 5.18). Construct number 1454 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)+H1 California TMCT). Construct number 1893 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. NOS: nopaline synthase terminator; PrL-: deleted proteolytic loop; TMCT: transmembrane domain cytoplasmic tail. FIG. 37A shows the nucleotide sequence of HA B Wisconsin (PrL-)+H1 California TMCT (SEQ ID NO: 103). FIG. 37B shows the amino acid sequence of PDISP/HA B Wisconsin (PrL-)+H1 California TMCT (SEQ ID NO: 104).

FIG. 38 shows sequence components used to prepare construct numbers 1067 and 1875 (2X35S/CPMV HT PDISP/HA B Brisbane (Prl-)+H1 California TMCT NOS and 2X35S/CPMV HT+ PDISP/HA B Brisbane (PrL-)+H1 California TMCT NOS, respectively; see Example 5.19). Construct number 1067 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)+H1 California TMCT). Construct number 1875 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop; TMCT: transmembrane domain cytoplasmic tail. FIG. 38A shows the nucleotide sequence of PDISP/HA B Brisbane (PrL-)+H1 California TMCT (SEQ ID NO: 105). FIG. 38B shows the amino acid sequence of PDISP/HA B Brisbane (PrL-)+H1 California TMCT (SEQ ID NO: 106).

FIG. 39 shows sequence components used to prepare construct numbers 2072 and 2052 (2X35S/CPMV HT PDISP/HA B Massachusetts (PrL-) NOS and 2X35S/CPMV HT+ PDISP/HA B Massachusetts (PrL-) NOS, respectively; see Example 5.20). Construct number 2072 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)). Construct number 2052 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop. FIG. 39A shows the nucleotide sequence of PDISP/HA B Massachusetts (PrL-) (SEQ ID NO: 107). FIG. 39B shows the amino acid sequence of PDISP/HA B Massachusetts (PrL-) (SEQ ID NO: 108).

FIG. 40 shows sequence components used to prepare construct numbers 2074 and 2062 (2X35S/CPMV HT PDISP/HA B Massachusetts (PrL-)+H1 California TMCT NOS and 2X35S/CPMV HT+ PDISP/HA B Massachusetts (PrL-)+H1 California TMCT NOS, respectively; see Example 5.21). Construct number 2074 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)+H1 California TMCT). Construct number 2062 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop; TMCT: transmembrane domain cytoplasmic tail. FIG. 40A shows the nucleotide sequence of PDISP/HA B Massachusetts (PrL-)+H1 California TMCT (SEQ ID NO: 109). FIG. 40B shows the amino acid sequence of PDISP/HA B Massachusetts (PrL-)+H1 California TMCT (SEQ ID NO: 110). FIG. 40C shows a schematic representation of construct number 2062 (2X35S/CPMV HT+).

FIG. 41 shows sequence components used to prepare construct numbers 1445 and 1839 (2X35S/CPMV HT HA B Wisconsin (PrL-) NOS, and 2X35S/CPMV HT+HA B Wisconsin (PrL-) NOS, respectively; see Example 5.22). Construct number 1445 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)). Construct number 1839 includes a CPMV 5'UTR comprising 160 nucleotides, a stuffer fragment comprising an incomplete M protein, a multiple cloning site, and a plant kozak sequence and is an example of a CPMV HT+ based construct. PrL-: deleted proteolytic loop; NOS: nopaline synthase terminator. FIG. 41A shows the nucleotide sequence of HA B Wisconsin (PrL-) (SEQ ID NO: 111). FIG. 41B shows the amino acid sequence of HA B Wisconsin (PrL-) (SEQ ID NO: 112).

FIG. 42 shows sequence components used to prepare construct numbers 1454 and 1860 (2X35S/CPMV HT HA B Wisconsin (PrL-)+H1 California TMCT NOS and 2X35S/CPMV HT+HA B Wisconsin (PrL-)+H1 California TMCT NOS, respectively; see Example 5.23). Construct number 1454 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)+H1 California TMCT). Construct number 1860 includes a CPMV 5'UTR comprising 160 nucleotides, a stuffer fragment comprising n incomplete M protein, a multiple cloning site, and a plant kozak sequence and is an example of a CPMV HT+ based construct. NOS: nopaline synthase terminator; PrL-: deleted proteolytic loop; TMCT: transmembrane domain cytoplasmic tail. FIG. 42A shows the nucleotide sequence of HA B Wisconsin (PrL-)+H1 California TMCT (SEQ ID NO: 113). FIG. 42B shows the amino acid sequence of PDISP/HA B Wisconsin (PrL-)+H1 California TMCT (SEQ ID NO: 114).

FIG. 43 shows sequence components used to prepare construct numbers 489 (2X35S/CPMV HT H5 Indonesia NOS see Example 5.24). Construct number 489 incorporates a CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/H1 California). FIG. 43A shows the nucleotide sequence of native H5 Indonesia (SEQ ID NO: 115). FIG. 43B shows the amino acid sequence of native H5 Indonesia (SEQ ID NO: 116).

FIG. 44 shows the sequence components used to prepare construct number 1800 (A-2X35S CPMV160+ PDISP H3Victoria NOS; see example 5.25). Construct number 1800 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. PDISP: protein disulfide isomerase signal peptide. NOS: nopaline synthase terminator. FIG. 44A shows primer sequence IF(SacII)-PDI.s1+4c (SEQ ID NO:117). FIG. 44**B shows primer sequence IF-H3V36111.s1-4r (SEQ ID NO: 118).

FIG. 44C shows the sequence of PDISP/H3 Victoria (SEQ ID NO:119). FIG. 44E shows construct 2171 from left to right t-DNA borders (underlined), 2X35S/CPMV160+/NOS with Plastocyanine-P19-Plastocyanine silencing inhibitor expression cassette, an H1 California transmembrane cytoplasmic tail, and the CPMV3'UTR (SEQ ID NO: 120). FIG. 44F shows expression cassette number 1800 from 2X35S promoter to NOS terminator. PDISP/H3 Victoria nucleotide sequence is underlined; 5'UTR is shown in bold; plant kozak sequence double underline; a stuffer fragment (multiple cloning site) of 16 base pairs is positioned between the 5'UTR and plant kozak sequence (SEQ ID NO:121). FIG. 44G shows the amino acid sequence of PDISP/H3 Victoria (SEQ ID NO:122).

FIG. 45 shows the sequence components used to prepare construct number 1819 (2X35S CPMV-HT+ PDISP H3Victoria NOS). Construct number 1819 incorporates a CPMV-HT+ sequence (CMPV 5'UTR with mutated start codon at position 161 fused to a stuffer fragment encoding an incomplete M protein, a multiple cloning site, and comprises a plant kozak sequence between the multiple cloning site and the nucleotide sequence of interest (PDISP/H3 Victoria)). PDISP: protein disulfide isomerase signal peptide. NOS: nopaline synthase terminator. FIG. 45A shows primer sequence IF(SacII)-Kozac_PDI.c (SEQ ID NO: 123). FIG. 45B shows primer sequence IF-H3V36111.s1-4r (SEQ ID NO:124). FIG. 45C shows a schematic representation of construct 2181. FIG. 45D shows the sequence for construct 2181 (from left to right t-DNA borders, underlined; 2X35S/CPMV-HT+/NOS with Plastocyanine-P19-Plastocyanine silencing inhibitor expression cassette; SEQ ID NO:126). FIG. 45E shows expression cassette number 1819 from 2X35S promoter to NOS terminator. The PDISP/H3 Victoria nucleotide sequence is underlined (SEQ ID NO:127).

FIG. 46A shows the relative hemagglutination activity of native H7 Hangzhou HA and modified H7 Hangzhou HA, with the proteolytic loop deleted when co-expressed with M2. Native and modified H7 Hangzhou HA (constructs #2142 and 2152, see Examples 5.33 and 5.34) were expressed in the presence of M2 (construct #1261 see Example 5.1) and purified from plants. FIG. 46B shows the protein yield of native H7 Hangzhou HA (construct #2142) and modified H7 Hangzhou HA, with the proteolytic loop deleted (construct #2152). FIG. 46C shows an SDS-PAGE analysis, with lane 2 showing purified modified H7 Hangzhou HA with a removed proteolytic loop (construct #2152) and lane 3 showing the purified native H7 Hangzhou HA (construct #2142). For each lane, 2 g of total protein were loaded on the gel. The purity of the proteins profiles are similar for both constructs.

FIG. 48 shows sequence components used to prepare construct numbers 2220 (2X35S/CPMV HT+/PDISP/H2 Singapore/NOS see Example 5.27). FIG. 48A shows the nucleotide sequence of primer IF-H2S157.s1-6r (SEQ ID NO: 127). FIG. 48B shows the nucleotide sequence of PDISP/H2 Singapore (SEQ ID NO: 128) FIG. 48C shows the nucleotide sequence of expression cassette number 2220 from 2X35S promoter to NOS terminator. PDISP/H2 Singapore nucleotide sequence is underlined. FIG. 48D shows the Amino acid sequence of PDISP/H2 Singapore. FIG. 48**E shows a schematic representation of construct number 2220.

FIG. 49 shows sequence components used to prepare construct numbers 2221 (2X35S/CPMV HT+/PDISP/H2 Singapore with deleted proteolytic loop/NOS see Example 5.28). FIG. 49A shows the nucleotide sequence of primer H2S157(Prl-).r (SEQ ID NO: 131). FIG. 49B shows the nucleotide sequence of primer H2S157(Prl-).c (SEQ ID NO: 132) FIG. 49C shows the nucleotide sequence of expression cassette number 2221 from 2X35S promoter to NOS terminator. PDISP/H2 Singapore nucleotide sequence is underlined (SEQ ID NO: 133). FIG. 49D shows the Amino acid sequence of PDISP/H2 Singapore with deleted proteolytic loop (SEQ ID NO:134). FIG. 49E shows a schematic representation of construct number 2221.

FIG. 51**E shows a schematic representation of construct number 2139.

FIG. 52 shows sequence components used to prepare construct numbers 2039 (2X35S/CPMV HT+ PDISP/H3 Perth with deleted proteolytic loop) and 2159 (2X35S/CPMV 160+ PDISP/H3 Perth with deleted proteolytic loop) see Example 5.31). FIG. 52A shows the nucleotide sequence of PDISP/H3 Perth with deleted proteolytic loop (SEQ ID NO: 140). FIG. 52B shows the nucleotide sequence of primer H3P1609(Prl-)#2.r (SEQ ID NO: 141). FIG. 52C shows the nucleotide sequence of primer H3P1609(Prl-)#2.c (SEQ ID NO: 142). FIG. 52D shows the amino acid sequence of PDISP/H3 Perth with deleted proteolytic loop (SEQ ID NO: 143).

FIG. 53 shows sequence components used to prepare construct numbers 2230 (2X35S/CPMV HT+ PDISP/H3 Victoria with deleted proteolytic loop) and 2250 (2X35S/CPMV 160+ PDISP/H3 Victoria with deleted proteolytic loop) see Example 5.32). FIG. 53A shows the nucleotide sequence of nucleotide sequence of PDISP/H3 Victoria with deleted proteolytic loop (SEQ ID NO: 144). FIG. 53B shows the nucleotide sequence of primer H3V36111(Prl-).r (SEQ ID NO: 145). FIG. 53C shows the nucleotide sequence of primer H3V36111(Prl-).c (SEQ ID NO: 146). FIG. 53D shows the amino acid sequence of PDISP/H3 Victoria with deleted proteolytic loop (SEQ ID NO: 147).

FIG. 54 shows sequence components used to prepare construct number 2142 (2X35S/CPMV HT+/PDISP/H7 Hangzhou/NOS) see Example 5.33). FIG. 54A shows the nucleotide sequence of PDISP/H7 Hangzhou (SEQ ID NO: 148). FIG. 54B shows the nucleotide sequence of primer IF*-H7H113.s1-6r (SEQ ID NO: 149). FIG. 54C shows the amino acid sequence of PDISP/H7 Hangzhou (SEQ ID NO: 150). FIG. 53D shows a schematic representation of construct number 2142.

FIG. 55 shows sequence components used to prepare construct number 2152 (2X35S/CPMV HT+/PDISP/H7 Hangzhou with deleted proteolytic loop/NOS) see Example 5.34). FIG. 55A shows the nucleotide sequence of PDISP/H7 Hangzhou with deleted proteolytic loop (SEQ ID NO: 151). FIG. 55B shows the nucleotide sequence of primer H7H113(PrL-).r (SEQ ID NO: 152). FIG. 55C shows the nucleotide sequence of primer H7H113(PrL-).c (SEQ ID NO: 153). FIG. 55D shows the amino acid sequence of PDISP/H7 Hangzhou with deleted proteolytic loop (SEQ ID NO: 154).

FIG. 56**E shows a schematic representation of construct number 2226.

FIG. 57 shows sequence components used to prepare construct numbers 2225 (2X35S/CPMV HT+ PDISP/H9 Hong Kong with deleted proteolytic loop) and 2227 (2X35S/CPMV 160+ PDISP/H9 Hong Kong with deleted proteolytic loop) see Example 5.36. FIG. 57A shows the nucleotide sequence of PDISP/H9 Hong Kong with deleted proteolytic loop (SEQ ID NO: 158). FIG. 57B shows the nucleotide sequence of primer H9HK107399(Prl-).r (SEQ ID NO: 159). FIG. 57C shows the nucleotide sequence of primer H9HK107399(Prl-).c (SEQ ID NO: 160). FIG. 57D shows the amino acid sequence of PDISP/H9 Hong Kong with deleted proteolytic loop (SEQ ID NO: 161).

FIG. 58 shows sequence components used to prepare construct number 2013 (2X35S/CPMV 160+/PDISP/HA B Malaysia/NOS) see Example 5.37. FIG. 58A shows the nucleotide sequence of PDISP/HA B Malaysia (SEQ ID NO: 162). FIG. 58B shows the nucleotide sequence of primer IF-HBM250604.S1-6r (SEQ ID NO: 163). FIG. 58C shows the amino acid sequence of PDISP/HA B Malaysia (SEQ ID NO: 164). FIG. 58**D shows a schematic representation of construct number 2013.

FIG. 59 shows sequence components used to prepare construct number 2014 (2X35S/CPMV 160+/PDISP/HA B Malaysia with deleted proteolytic loop/NOS) see Example 5.38. FIG. 59A shows the nucleotide sequence of PDISP/HA B Malaysia with deleted proteolytic loop (SEQ ID NO: 165). FIG. 59B shows the nucleotide sequence of primer HBM250604(PrL-).r (SEQ ID NO: 166). FIG. 59C shows the nucleotide sequence of primer HBM250604(PrL-).c (SEQ ID NO: 167). FIG. 59D shows the amino acid sequence of PDISP/HA B Malaysia with deleted proteolytic loop (SEQ ID NO: 168). FIG. 59E shows a schematic representation of construct number 2014.

FIG. 60 shows sequence components used to prepare construct numbers 2070 (2X35S/CPMV HT PDISP/HA B Massachusetts), 2080 (2X35S/CPMV HT+ PDISP/HA B Massachusetts) and 2090 (2X35S/CPMV 160+ PDISP/HA B Massachusetts) see Example 5.39. FIG. 60A shows the nucleotide sequence of PDISP/HA B Massachusetts (SEQ ID NO: 169). FIG. 60B shows amino acid sequence of PDISP/HA B Massachusetts (SEQ ID NO: 170).

FIG. 61 shows sequence components used to prepare construct numbers 2102 (2X35S/CPMV HT PDISP/HA B Florida with proteolytic loop deleted) and 2104 (2X35S/CPMV HT+/BeYDV/PDISP/HA B Florida with proteolytic loop deleted) see Example 5.40. FIG. 61A shows the nucleotide sequence of primer HBF406(PrL-).r (SEQ ID NO: 190). FIG. 61B shows the nucleotide sequence of primer HBF406 (PrL-).c (SEQ ID NO: 191). FIG. 61C shows the nucleotide sequence of primer IF*-HBF406.s1-6r (SEQ ID NO: 192). FIG. 61D shows the nucleotide sequence of PDISP/HA B Florida with deleted proteolytic loop. FIG. 61E shows the amino acid sequence of PDISP/HA B Florida with deleted proteolytic loop. FIG. 61F shows the nucleotide sequence of expression cassette number 2102. FIG. 61H shows the nucleotide sequence of expression cassette number 2104. FIG. 61I shows the schematic representation of construct number 2104.

FIG. 62 shows sequence components used to prepare construct numbers 2106 (2X35S/CPMV HT+/PDISP/B Florida +H1 California TMCT with proteolytic loop deleted/NOS) and 2108 (2X35S/CPMV HT+/BeYDV/PDISP/B Florida +H1 California TMCT with proteolytic loop deleted/NOS) see Example 5.41. FIG. 62A shows the nucleotide sequence of primer IF-H1cTMCT.S1-4r (SEQ ID NO: 197). FIG. 62B shows the nucleotide sequence of PDISP/HA B Florida+H1Cal TMCT with deleted proteolytic loop (SEQ ID NO: 198). FIG. 62C shows the amino acid sequence of PDISP/HA B Florida+H1Cal TMCT with deleted proteolytic loop. FIG. 62D shows the nucleotide sequence of expression cassette number 2106. FIG. 62F shows the nucleotide sequence of expression cassette number 2108.

DETAILED DESCRIPTION

Figure 1C:
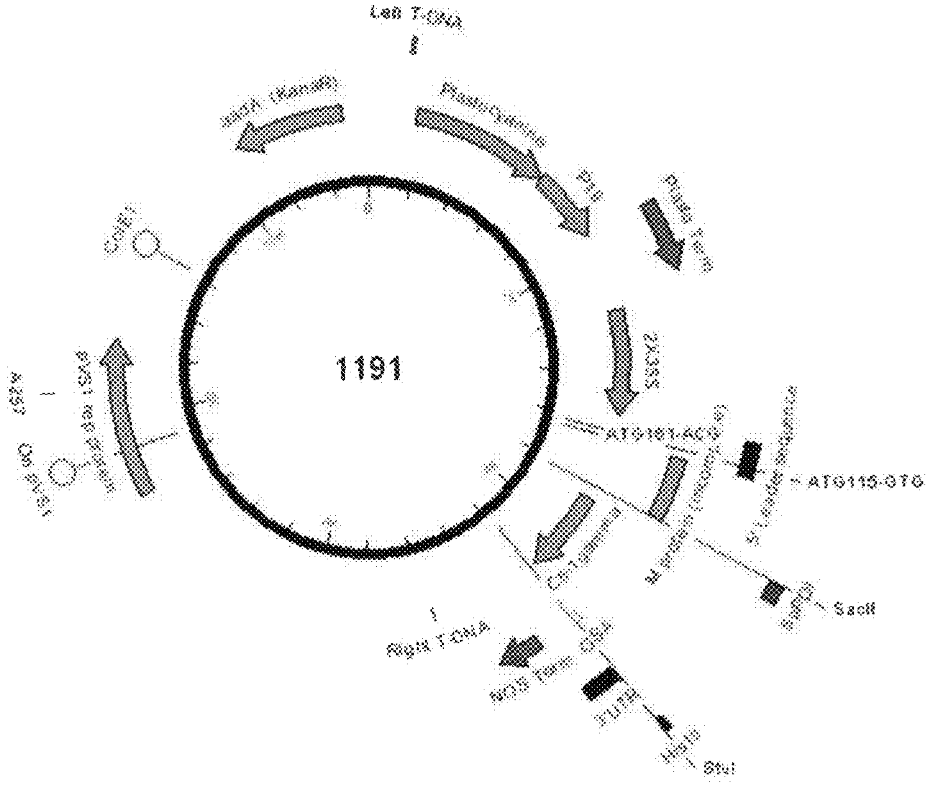
FIG. 1C shows a schematic representation of construct 1191.

The following description is of a preferred embodiment.

The present invention relates to virus-like particles (VLPs) and methods of producing and increasing VLP yield, accumulation and production in plants.

The present invention provides, in part, a method of producing a virus like particle (VLP) in a plant, or portion of the plant. The method involves introducing a nucleic acid into the plant or portion of the plant. The nucleic acid comprises comprising a regulatory region active in the plant and operatively linked to a nucleotide sequence encoding an influenza hemagglutinin (HA). The HA comprises a modified proteolytic loop or cleavage site. The plant or portion of the plant is incubated under conditions that permit the expression of the nucleic acid, thereby producing the VLP. If desired, the plant or portion of the plant may be harvested and the VLP purified.

The present invention also provides a VLP produced by this method. The VLP may comprise one or more than one lipid derived from a plant.

The VLP may be used to prepare a composition comprising an effective dose of the VLP for inducing an immune response, and a pharmaceutically acceptable carrier.

Also provided herein is a modified hemagglutinin, wherein the proteolytic loop or cleavage site has been modified.

The present invention also provides plant matter comprising the VLP produced by expressing the nucleic acids described above. The plant matter may be used in inducing immunity to an influenza virus infection in a subject. The plant matter may also be admixed as a food supplement.

The VLP of the present invention may also be produced by providing a plant or portion of the plant comprising a nucleic acid as defined above, and incubating the plant or portion of the plant under conditions that permit the expression of the nucleic acid, thereby producing the VLP. The VLP may comprise one or more than one lipid derived from a plant. The VLP may be used to prepare a composition comprising an effective dose of the VLP for inducing an immune response, and a pharmaceutically acceptable carrier. The present invention also provides plant matter comprising the VLP produced by expressing the first and second nucleic acids. The plant matter may be used in inducing immunity to an influenza virus infection in a subject. The plant matter may also be admixed as a food supplement.

The VLP of the present invention comprises one or more modified influenza hemagglutinin (HA). The modified HA may be derived from any HA, for example an H1, H2, H3, H4, H5, H6, H7, H8, H9, H10, H11, H12, H13, H14, H15, H16 or type B HA as described in WO 2009/009876; WO 2009/076778; WO 2010/003225; WO 2010/003235; WO 2011/03522; which are incorporated herein by reference).

The current invention includes VLPs comprising HA sequences of influenza strains, where the HA sequences comprise modified polybasic cleavage sites including for example, the modifications as described herein.

HA Protein

The term "hemagglutinin" or "HA" as used herein refers to a glycoprotein found on the outside of influenza viral particles. HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available—see, for example, the BioDefence Public Health base (Influenza Virus; see URL: biohealthbase.org) or National Center for Biotechnology Information (see URL: ncbi.nlm.nih.gov), both of which are incorporated herein by reference. HA may include any HA, for example an H1, H2, H3, H4, H5, H6, H7, H8, H9, H10, H11, H12, H13, H14, H15, H16 or type B HA as described in WO 2009/009876; WO 2009/076778; WO 2010/003225; WO 2010/003235; WO 2011/03522; which are incorporated herein by reference). Furthermore, the HA may be based on the sequence of a hemagglutinin that is isolated from one or more emerging or newly-identified influenza viruses. The present invention also includes VLPs that comprise modified HAs obtained from one or more than one influenza subtype.

The HA monomer may be subdivided in three functional domains—a stem domain, or stem domain cluster (SDC), a globular head domain, or head domain cluster (HDC) and a transmembrane domain cluster (TDC). The SDC and HDC may be collectively referred to as the 'ectodomain'. A publication by Ha et al. 2002 (EMBO J. 21:865-875; which is incorporated herein by reference) illustrates the relative orientation of the various subdomains of the SDC and HDC in several influenza subtypes, based on Xray crystallographic structures.

HA protein is synthesized as a precursor protein (HA0) of about 75 kDa, which assembles at the surface into an elongated trimeric protein. The precursor protein is cleaved at a conserved activation cleavage site into 2 polypeptide chains, HA1 and HA2 (comprising the transmembrane region), linked by a disulfide bond. FIG. 15 provides non-limiting examples of amino acid sequences of the linker region for several HAs.

The term "homotrimer" or "homotrimeric" indicates that an oligomer is formed by three HA protein molecules. Without wishing to be bound by theory, HA protein is synthesized as monomeric precursor protein (HA0) of about 75 kDa, which assembles at the surface into an elongated trimeric protein. Before trimerization occurs, the precursor protein is cleaved at a conserved activation cleavage site (also referred to as fusion peptide) into 2 polypeptide chains, HA1 and HA2 (comprising the transmembrane region), linked by a disulfide bond. The HA1 segment may be 328 amino acids in length, and the HA2 segment may be 221 amino acids in length. Although this cleavage may be important for virus infectivity, it may not be essential for the trimerization of the protein or for immunogenicity. Insertion of HA within the endoplasmic reticulum (ER) membrane of the host cell, signal peptide cleavage and protein glycosylation are co-translational events. Correct refolding of HA requires glycosylation of the protein and formation of 5-6 intra-chain disulfide bonds. The HA trimer assembles within the cis- and trans-Golgi complex, the transmembrane domain playing a role in the trimerization process. The crystal structures of bromelain-treated HA proteins, which lack the transmembrane domain, have shown a highly conserved structure amongst influenza strains. It has also been established that HA undergoes major conformational changes during the infection process, which requires the precursor HA0 to be cleaved into the 2 polypeptide chains HA1 and HA2. The HA protein may be processed (i.e., comprise HA1 and HA2 domains), or may be unprocessed (i.e. comprise the HA0 domain). The unprocessed precursor protein of HA is synthesized as a precursor protein (HA0) of about 75 kDa, which assembles at the surface into an elongated trimeric protein. The precursor protein is cleaved at a conserved cleavage site (also known as a proteolytic loop) into 2 polypeptide chains, HA1 and HA2 (comprising the transmembrane region), linked by a disulfide bond.

The HA protein as described herein may further be a modified HA (also referred to as "mutant HA") protein, for example a modified precursor protein (HA0), in which the proteolytic loop or cleavage site is modified.

Modified HA/Cleavage Site

Following cleavage of HA0, HA becomes sensitive to pH, undergoing irreversible conformational change at the pH of endosome (<pH 6.0). The conformation of the precursor HA0 is stable at low pH, but the cleaved HA1-HA2 form, is metastable (Bullough P A et. al., 1994, Nature. Vol 371:37-43). The pH threshold that induce conformational change in different HA's is approximately pH 5.8-5.9 for the B strains, whereas it is more acidic, pH 5.1 to 5.8, for type A HA's (Beyer W E P et al, 1986, Archives Virol, vol 90: 173). Following cleavage, the amino terminal of HA2 is a non-polar sequence of 23 amino acids that then become a transmembrane domain spraining cross the host cell membrane (called the fusion peptide; FIG. 15). The cleavage site of an HA is located on a protruding loop at the surface of the HA, and this site is accessible by proteases.

In order to optimize the production of vaccine in eggs and maintain an active but attenuated virus, modification of the polybasic cleavage site of H5 (RERRRKKR↓G) has been studied (Horimoto T, et. al, 2006, Vaccine, Vol 24: 3669-3676). Mutants of interest contained a deletion of the 4 first charged amino acids (RERR) and a replacement of amino acids RKKR with TETR that inactivate the polybasic cleavage site but maintained the possibility to process HA0 to HA1-HA2 through the Arginin residue of the TETR motif (see FIG. 19). A similar strategy to produce attenuated virus is employed by NIBSC to abolish the polybasic site allowing producing at high yields the A/Turkey/Turkey/1/2005 H5N1 strain without killing the eggs. The polybasic site sequence (GERRRKKR↓G) is replaced by RETR in their mutant (NIBSC 05/240 NIBSC influenza reference virus NIBG-23). The polybasic cleavage site of a H5 HA has also been replaced by the monobasic site of H6 for expression in eggs. In this example, the first 4 residues and the four last amino acids of the polybasic site are replaced by IETR (replacement of RERRRKKR↓G with IETR↓G; Hoffman E, et. al., 2002, Vaccine, Vol 20:3165-3170). In each of the examples provided above, the modification was performed to attenuate the virus while maintaining production of the HA within eggs. That is, the cleavage of HA0 precursor was not totally inactivated in order to allow the HA0 to be processed to HA1-HA2 and undergo pH conformational change, thereby permitting virus replication in the host cell.

As used herein, the term "modified hemagglutinin" or "modified HA", "mutated hemagglutinin" or "mutated HA" refers to an HA in which the HA has a modification or mutation, for example a substitution, insertion, deletion, or a combination thereof, that results in an altered amino acid sequence in the proteolytic loop or cleavage site of the HA protein.

The crystal structure of HA0 from A/Hong Kong/68 has been determined (Chen, J., 1998. Cell 95:409-417; incorporated herein by reference). Residues that are exposed to solvent are generally thought of being part of the cleavage site which forms an extended, highly exposed surface loop. A consensus sequence may be determined in this chosen region for example, but not limited to:

```
A/H3/HA0 Consensus:
                                  (SEQ ID NO: 66)
NVPEKQTR/GIFGAIAGFIE

A/H1/HA0 Consensus:
                                  (SEQ ID NO: 67)
NIPSIQSR/GLFGAIAGFIE

Avian H5 Consensus
                                   (SEQ ID NO: 1)
QRESRRKKR/GLFGAIAGFIEG

B/HA0 Consensus:
                                  (SEQ ID NO: 68)
PAKLLKER/GFFGAIAGFLE
```

Where the cleavage between HA1 and HA2 is indicated by "/" (see Bianchi et al., 2005, Journal of Virology, 79:7380-7388; incorporated herein by reference), and also FIGS. 15 and 18A.

The HA protein may be an influenza type B hemagglutinin or Influenza type A hemagglutinin protein with a modification in the proteolytic loop region, for example a deletion, insertion, substitution or a combination thereof of the proteolytic loop (cleavage site). Without wishing to be bound by theory, modification of the proteolytic loop may ensures that the HA molecule is maintained as an HA0 precursor. Thereby producing a more homogenous and consistent VLP comprising HA0 proteins.

By "proteolytic loop" or "cleavage site" is meant the consensus sequence of the proteolytic site that is involved in precursor HA0 cleavage. "Consensus" or "consensus sequence" as used herein means a sequence (either amino acid or nucleotide sequence) that comprises the sequence variability of related sequences based on analysis of alignment of multiple sequences, for example, subtypes of a particular influenza HA0 sequence. Consensus sequence of the influenza HA0 cleavage site may include influenza A consensus hemagglutinin amino acid sequences, including for example consensus H1, consensus H3, consensus H5, or influenza B consensus hemagglutinin amino acid sequences, for example but not limited to B Florida and B Malaysia. Non limiting examples of sequences of the proteolytic loop region are shown in FIGS. 15 and 18B (and see Bianchi et al., 2005, Journal of Virology, 79:7380-7388; incorporated herein by reference).

Residues in the proteolytic loop or cleavage site might be either mutated, for example but not limited to point mutation, substitution, insertion, or deletion. The term "amino acid mutation" or "amino acid modification" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced or abolished cleavage of the proteolytic loop or cleavage site by a protease.

By "modified proteolytic loop" it is meant that the proteolytic loop may include one or more point mutations, be partially deleted, fully deleted, partially replaced with a linker sequence, fully replaced by a linker sequence, comprise a partial or complete replacement of amino acids within the cleavage site with one or more non-protein amino acids, or a combination thereof. Similarly, by "modified cleavage site", it is meant that the cleavage site within the proteolytic loop may include one or more point mutations, be partially deleted, fully deleted, partially replaced with a linker sequence, fully replaced by a linker sequence, comprising a partial or complete replacement of amino acids within the cleavage site with one or more non-protein amino acids, or a combination thereof. Modifications to the proteolytic loop, cleavage site, or both, may also involve the deletion, replacement, or substitution of one or more amino acids that are located outside of, or adjacent to, the proteolytic loop or cleavage site sequence. By "linker" it is meant an amino acid sequence comprising one or more amino acids that may be introduced within a proteolytic loop or a cleavage site, or that may replace some or all of the amino acids with the proteolytic loop or cleavage site. A linker may be designed to ensure that any amino acids deletions within the proteolytic loop or cleavage site do not disrupt the expression or subsequent activity of the modified HA.

By stabilizing the HA protein by modifying or deleting the proteolytic loop increased product or protein yields may be achieved, when expressing the modified HA in a plant, when compared to a native HA expressed in a plant under the same conditions. Furthermore, by modifying or deleting the proteolytic loop the variability of expression of the expressed modified HA is reduced and the consistency of the produced modified HA is increased, when compared to a native HA expressed in a plant under the same conditions.

Therefore, the present invention also includes a method of increasing the product yield of a HA protein in a plant. Without wishing to be bound by theory, it is believed that by modifying or deleting the proteolytic loop in an HA protein, improved stability against proteolytic degradation in the plant, stabilization during passage of the HA in the golgi apparatus secretion process, and during the purification process is provided.

Furthermore, the present invention also includes a method of increasing the product quality of an HA protein expressed in a plant. By product quality, it is meant for example an increased product yield of an HA expressed in a plant, stability of the product for example increased stability of the HA expressed in a plant, consistency of the product for example the production of a homogenous product for example HA0 or a combination thereof.

By an increase in product or protein yield, it is meant an increase in relative protein yield by about 20% to about 100%, or any amount therebetween as determined using standard techniques in the art, for example, from about 40% to about 70% or any value therebetween for example about 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, or 100%, or any amount therebetween, when compared to the product or protein yield of the same HA protein that does not have its proteolytic loop removed.

Figures 13A, 13B:
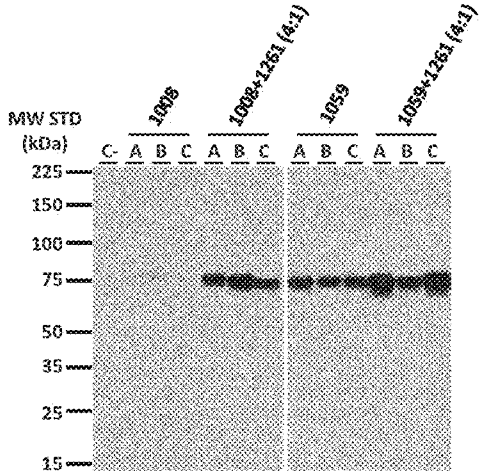
FIG. 13A shows a Western blot analysis of HA protein expression in agroinfiltrated *Nicotiana benthamiana* leaves. “1008”: expression of wild-type HA from B/Brisbane/60/2008 in the presence of amplification elements (BeYDV); “1008+1261”: co-expression of wild-type HA from B/Brisbane/60/2008 in the presence of amplification elements (BeYDV) with M2 from A/New Caledonia/20/99; “1059”: expression of mutant HA from B/Brisbane/60/2008 in the presence of amplification elements (BeYDV); “1059+1261”: co-expression of mutant HA from B/Brisbane/60/2008 in the presence of amplification elements (BeYDV) with M2 from A/New Caledonia/20/99. Plants from three separate infiltrations were analyzed (A, B and C). Ratios indicate the proportion of *Agrobacterium* cultures used in co-expression experiments.
FIG. 13B shows a comparison of hemagglutination capacity of crude protein extracts from HA-producing plants.
Figure 14:
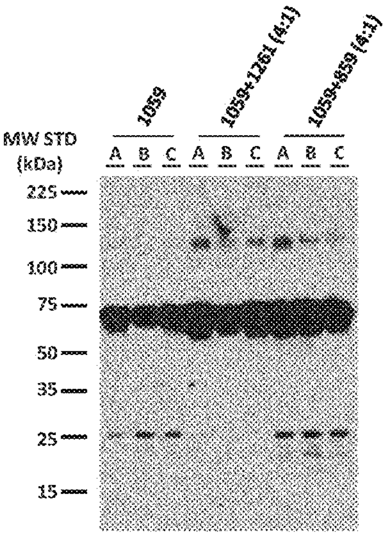
FIG. 14 shows a Western blot analysis of HA protein expression in agroinfiltrated *Nicotiana benthamiana* leaves. “1059”: expression of mutant HA from B/Brisbane/60/2008 in the presence of amplification elements (BeYDV); “1059+1261”: co-expression of mutant HA from B/Brisbane/60/2008 in the presence of amplification elements (BeYDV) with M2 from A/New Caledonia/20/99. “1059+859”: co-expression of mutant HA from B/Brisbane/60/2008 in the presence of amplification elements (BeYDV) with M2 from A/Puerto Rico/8/34. Plants from three separate infiltrations were analyzed (A, B and C). Ratios indicate the proportion of *Agrobacterium* cultures used in co-expression experiments.

As shown in FIGS. 13A and 14, HA from B/Brisbane/60/2008 is poorly expressed in agroinfiltrated *Nicotiana benthamiana* leaves (see lane 1008). However, expression of HA type B that has been modified to delete the proteolytic loop (see lane 1059, FIG. 13A, FIG. 14) resulted in increased expression. Furthermore, co-expression of HA-type B with M2 from A/New Caledonia/20/99, results in an increase in HA expression (see lanes "1008+1261"; and 1059+1261"). Co-expression of HA type B comprising a deletion in the proteolytic loop, with a M2 from A/Puerto Rico/8/34 also resulted in increased expression (1059+859; FIG. 14).

As further shown in FIG. 46B, protein yield of HA protein from H7 A/Hangzhou/1/13 expressed in agroinfiltrated *Nicotiana benthamiana* is increased in HA that has been modified to delete or modify the proteolytic loop. Co-expression of native (wildtype) HA H7 A/Hangzhou/1/13 with M2 from A/New Caledonia/20/99 lead to a 100% relative protein yield, whereas co-expression of HA H7 A/Hangzhou/1/13 comprising a deletion in the proteolytic loop, with M2 from A/New Caledonia/20/99, lead to a 182% relative protein yield (FIG. 46B). The increase of relative protein yield of HA comprising a deletion in the proteolytic loop is, however, not dependent on M2. As for example shown in FIG. 29A, H7 A/Hangzhou/1/13 comprising a deletion in the proteolytic loop showed increased expression (as measure by the relative HA titer) when compared to native H7 A/Hangzhou/1/13.

Several strategies were evaluated in order to inactivate the cleavage of HA0 for both A and B strains. The consensus sequence that is recognized by proteases is enclosed on a extended loop, exposed to the solvent, and closed to the membrane distal part to the protein. In the B strain, this loop contains 2 sequence motifs recognized by proteases and the first N-terminal amino acids of the HA2 domain. A point mutation approach (for examples see Table 2, below) to inactivate the cleavage of HA0 precursor resulted in HA0 production, without an increase accumulation of B strain VLP. Deletion of the sequence motifs comprising the 2 protease cleavage motifs (7 amino acids) abolished the accumulation of the B HA. Remove the entire 18-amino acid loop from the HA protein of the B strain and inserting a linker to conserve structural features (beta strands) of the protein structure was effective (see below; FIGS. 13A, 14, 16A, 17B). Removal or replacement of the proteolytic loop in HA protein of A strains was also effective (see FIGS. 20, 22).

Figure 7E:
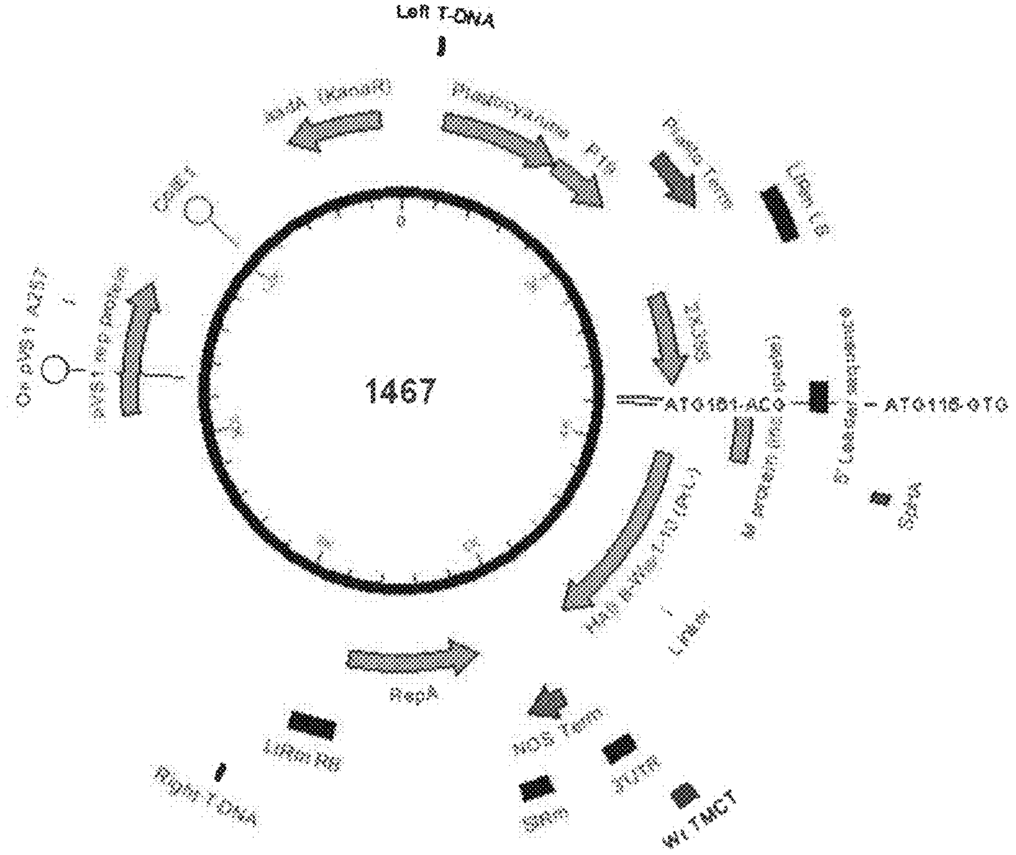
FIG. 7E shows a schematic representation of construct 1467.
Figure 10:
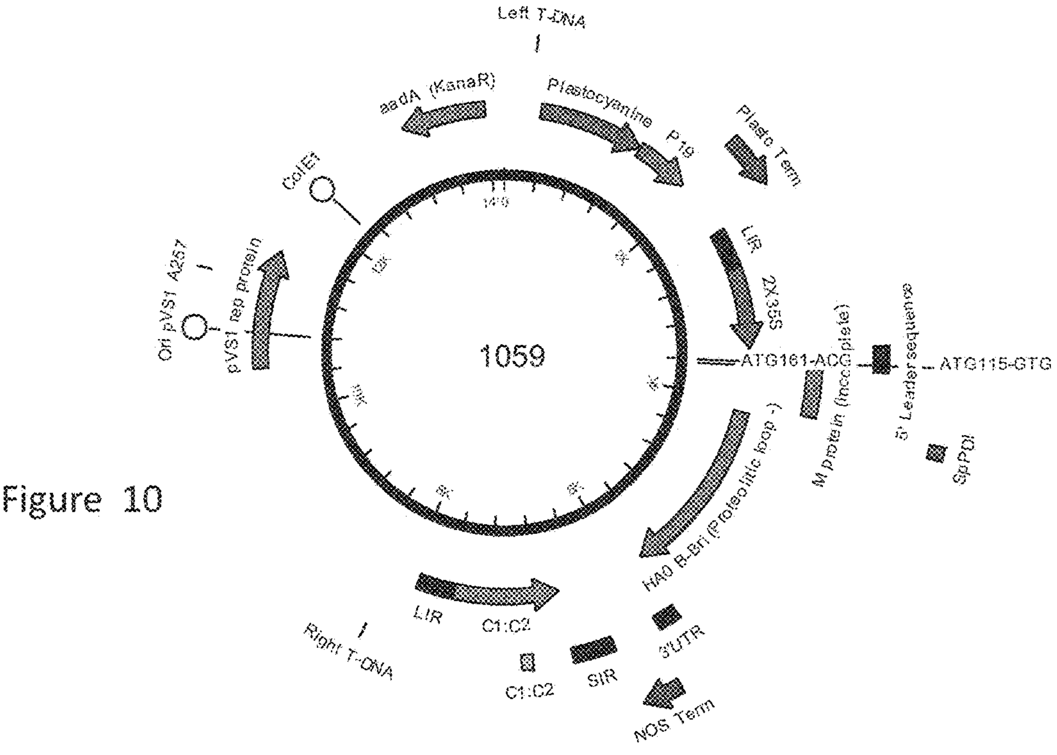
FIG. 10 shows the plasmid map of construct number 1059. Construct number 1059 directs the expression of a mutant HA from influenza strain B/Brisbane/60/2008 with deleted proteolytic loop. This construct comprises BeYDV-derived elements for DNA amplification.
Figure 19:
FIG. 19 shows the mutation of the cleavage site in H5/Indo. Native sequence (SEQ ID NO: 44); H5/Indo modified cleavage site comprising TETR (SEQ ID NO:45); H5/Indo modified cleavage site comprising TETQ (SEQ ID NO:46).

Amino acid sequence deletions and insertions include amino acid deletions and insertions of amino acids. A non-limiting example of a deletion in influenza B is the deletion of 17 amino acids (AKLLKERGFFGAIAGFLE) from position 340 to 357 of mature HA protein for example as shown in FIG. 18C for influenza B Florida and B Malaysia. This deletion may be replaced by an appropriate linker to link the polypeptide chains for proper expression, for example but not limited to, using the sequence "GG", as shown in FIG. 21B (SEQ ID NO:17; modified B/Brisbane/60/2008; replacing AKLLKERGFFGAIAGFLEG with GG; e.g. Construct 1059, FIG. 5D, 10; Construct 1039, FIG. 8B, or Construct 1467; FIG. 7D, 7E). An alternate replacement make comprise replacing "PPAKLLKER" with "GSSSGSSSG", as shown in FIG. 21C (SEQ ID NO: 18). Furthermore, the sequence "RESRRKKR" may be replaced with "TETR" or "TETQ", as shown in FIG. 19 for influenza H5/Indonesia.

Alternate amino acid mutations for HA from the A strain include amino acid substitutions, insertions and deletions, for example but not limited to a deletion in the proteolytic loop region of H5 Anhui of the amino acid sequence "RERRRKRGLFGAIAGFIE", a deletion of the amino acid sequence of the proteolytic loop region of H5 Indo comprising "RESRRKKRGLFGAIAGFIE" or a deletion of the amino acid sequence of the proteolytic loop region of H5 Vietnam "RERRRKKRGLFGAIAGFIE". For H3, the sequence "RNVPEKQTRGIF" may be deleted and replaced by an appropriate linker sequence, for example but not limited to "GS" as shown in FIG. 21E (SEQ ID NO:20). Alternatively, the sequence "RNVPEKQTR" in H3 may be replaced by "GSSGSSGSS" as shown in FIG. 21F (SEQ ID NO: 21; modified H3 A/Perth/16/2009).

Furthermore, modifying or altering the proteolytic loop or cleavage site of a HA to reduce or abolish cleavage of the proteolytic loop or cleavage site by a protease, may also comprise non-conservative amino acid substitutions, i.e. replacing one amino acid with another amino acid having different structural and/or chemical properties. Non-protein amino acids may also be used for substitution. For example, amino acid substitutions may include replacing a hydrophobic by a hydrophilic amino acid. Amino acid substitutions may include replacement by non-naturally occurring amino acids or by naturally occurring amino acid derivatives of the protein amino acids.

Amino acid mutations for HA from the B strain and/or A strains may include amino acid deletions. For example in order to reduce or abolish cleavage of the proteolytic loop or cleavage site by a protease, one or more amino acid are deletion or removal within the proteolytic loop or cleavage site sequence. Non-limiting examples of deletions include removal of amino acids 323 to 341 of native HA H5 protein, for example H5 Anhui (RERRRKRGLFGAIAGFIE), H5 Indo (RESRRKKRGLFGAIAGFIE), or H5 Vietnam (RERRRKKRGLFGAIAGFIE), as shown in FIG. 18C. For H3, the sequence "RNVPEKQTRGIF" may be replaced by "GS" (FIG. 21E; SEQ ID NO:20), or the H3 sequence "RNVPEKQTR" may be replaced by "GSSGSSGSS" (FIG. 21F; SEQ ID NO: 21). For B strains, the sequence "AKLLKERGFFGAIAGFLE" may be deleted and/or replaced by the sequence "GG", as shown in FIG. 21B (SEQ ID NO:17), the sequence "AKLLKERGFFGAIAGFLEG" may be replaced with "GG"), or the sequence "PPAKLLKER" replaced with "GSSSGSSSG" (FIG. 21C; SEQ ID NO: 18).

Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

Therefore the hemagglutinin (HA) sequences of the invention may comprise modified proteolytic loop sequences or cleavage sites, thereby having reduced or abolished cleavage of the proteolytic loop or cleavage site by a protease. The hemagglutinin polypeptide sequences may comprise modified proteolytic loop or modified cleavage site sequences as, for example, set forth in FIGS. 5D, 7D, 8A, 18C, 19, 21B, 21C, 21E, 21F, 24D, 25D, and 26D. The cleavage sites of any hemagglutinin polypeptide sequence of any influenza strain can be determined or predicted using any number of methods known in the art, including sequence alignment (see for example FIG. 15).

Analysis of sequence from H1, H3 and B HAs reveals that H1 possess one monobasic proteolytic site (Clara type monobasic: Q/EXR) that directly precedes the fusion peptide, whereas H3 and B HAs have 2 proteolytic sites, one that is recognized by Clara-like proteases (as found in H1), and another site recognized by trypsine and chymotrypsine-like proteases (P-E/A-K). The consensus sequence for cleavage of these HA is presented in Table 1.

TABLE 1

Consensus sequence of the proteolytic site for precursor $HA_0$ cleavage. The sequences recognized by Clara tryptases or trypsine/chimotrypsine are italicized, and bolded respectively. Several HA strains comprise polybasic Furin type cleavage sites (RKKR; plain text, underlined).

| | | |
|---|---|---|
| H1 | NIPSI*QSR*↓GLF | SEQ ID NO: 47 |
| H3 | NV**PEK***QTR*↓GIF | SEQ ID NO: 48 |
| H5 | TGLRNSPQRESRRKKR↓GLF | SEQ ID NO: 60 |
| B | **PAK**LL*KER*↓GFF | SEQ ID NO: 59 |

In order to avoid a potential proteolytic cleavage of HA0 precursor of the HA, only one proteolytic site may need to be modified from the sequence of H1, whereas, in the case of H3 and B, two monobasic sites may need to be modified.

For example, a first cleavage site of $HA_0$ of B/Florida and B/Brisbane may for example be eliminated by replacing the Lys 341 (mature protein numbering) with an Ile (see Table 2). The second monobasic site may be abolished by replacing three amino acids prior to the fusion peptide, KER (344-346), with NIQ. Sequences of several modified proteolytic loops of HA are provided in Table 2.

TABLE 2

Illustration of examples of mutations to destroy the cleavage of the precursor $HA_0$. The monobasic site are italicized (Clara-like recognition) and in bold (no underlining; trypsine/chymotrypsine-like). The mutation are shown as bolded and underlined. The arrow represents the site for cleavage for conversion of $HA_0$ into HA1-HA2.

| Strain | Natural sequence | Abolition of precursor cleavage site |
|---|---|---|
| H5/Indo | TGLRNSPQ**RESRRKKR**↓GLF SEQ ID NO: 60 | TGLRNSPQ***TETR***GLF SEQ ID NO: 61 |
| | | TGLRNSPQ***TETQ***GLF SEQ ID NO: 62 |
| H1/Brisbane | NIPSI*QSR*↓GLF SEQ ID NO: 47 | NIPSIQS***Q***GLF SEQ ID NO: 63 |
| H3/Brisbane | NV**PEK***QTR*↓GIF SEQ ID NO: 48 | NVPE***I***QT***Q***GIF SEQ ID NO: 64 |
| B/Florida, B/Brisbane | **PAK**LL*KER*↓GFF SEQ ID NO: 59 | PA***I***LL***NIQ***GFF SEQ ID NO: 65 |

In further examples, the sequences comprising the proteolytic loop in HA0 may be replaced or deleted. For example, an H3 variant containing a deletion of the sequence RNVPEKQT at the C-terminus of HA1 in addition of deletion of the N-terminus amino acids GIFGIA of HA2 is provided in FIG. 21 E. The shortened HA1-HA2 may be linked together by a GS linker.

In another example, the loop contain the proteolytic cleavage site in, for example H3, may have been replaced by a flexible linker, and the HA2 part may be left intact. A (GSS)3 linker may be designed in order to accommodate the shortened HA1 to HA2. (see FIG. 21F).

In another example, HA from influenza B may contain a deletion of sequence ALKLLKER at the C-terminus of HA1 in addition of deletion of the N-terminus amino acids GFFGAIAGFLEG of HA2. The shortened HA1-HA2 may be linked together by a GG linker (see for example FIG. 21B; Construct 1008). The expression of this construct is shown in FIGS. 13A and B.

In another example, HA from influenza B the loop containing the proteolytic site may have been replaced by a flexible linker, and the HA2 part was left intact. A longer GSSS linker may be designed in order to accommodate the shortened HA1 to HA2. (see for example FIG. 21 C).

As shown in FIGS. 13A and 14, HA from B/Brisbane/60/2008 is poorly expressed in agroinfiltrated *Nicotiana benthamiana* leaves (see lane 1008). However, expression of HA type B that has been modified to delete the proteolytic loop (see lane 1059, FIG. 13A, FIG. 14) resulted in increased expression. Furthermore, co-expression of HA-type B with M2 from A/New Caledonia/20/99, results in an increase in HA expression (see lanes "1008+1261"; and 1059+1261"). Co-expression of HA type B comprising a deletion in the proteolytic loop, with a M2 from A/Puerto Rico/8/34 also resulted in increased expression (1059+859; FIG. 14).

Figure 20:
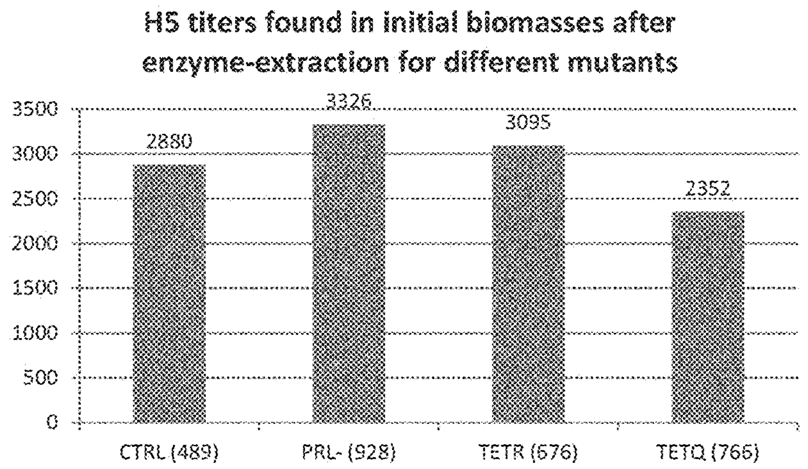
FIG. 20 shows the titers found in initial biomasses after enzyme-extraction of different modified H5/Indo HA's comprising mutations within the proteolytic loop. H5/Indo control (construct 489); H5/Indo proteolytic loop replaced with GG linker (construct 928); H5/Indo proteolytic loop replaced with TETR linker (construct 676); H5/Indo proteolytic loop replaced with TETQ linker (construct 766).

In a similar manner, deletion of the proteolytic loop in H5/Indo, and replacement with either a "GG" (Construct 928; see FIG. 46D), "TETR" (Construct 676; also see FIGS. 19, 24D) or "TETQ" (Construct 766; also see FIGS. 19, 25D) sequence resulted in expression levels that matched or increased over the level of expression observed with native H5/Indo (Construct 489; see FIGS. 20 and 23).

As show in FIG. 13B, by deleting the proteolytic loop of HA0 (sequence shown in FIG. 21B), the resultant HA0 protein exhibits an increased activity as shown by a greater hemagglutination capacity, when compared to a HA protein that does not have its proteolytic loop removed.

By an increase in activity, it is meant an increase in hemagglutination capacity by about 2% to about 100%, or any amount therebetween as determined using standard techniques in the art, for example, from about 10% to about 50% or any value therebetween for example about 2, 5, 8, 10, 12, 15, 18, 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, or 100%, or any amount therebetween, when compared to the activity of the same HA protein that does not have its proteolytic loop removed.

The present invention also includes nucleotide sequences encoding modified HA from for example modified H1, H2, H3, H4, H5, H6, H7, H8, H9, H10, H11, H12, H13, H14, H15, H16 or type B HA, or any nucleotide sequences that hybridize to H1, H2, H3, H4, H5, H6, H7, H8, H9, H10, H11, H12, H13, H14, H15, H16 or type B HA under stringent conditions, or a nucleotide sequence that hybridizes under stringent hybridisation conditions to a compliment of H1, H2, H3, H4, H5, H6, H7, H8, H9, H10, H11, H12, H13, H14, H15, H16 or type B HA, wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA from B or H3. The VLP, when administered to a subject, induces an immune response. Preferably, the VLP induces the production of an antibody and the VLP, when administered to a subject, induces an immune response.

For example, expression of the nucleotide sequence within a plant cell forms a VLP, and the VLP may be used to produce an antibody that is capable of binding a virus protein such for example HA, including but not limited to HA0, HA0 protein with its proteolytic loop deleted or modified, HA1 or HA2 of one or more influenza types or subtypes, such for example but not limited to subtypes H1, H2, H3, H4, H5, H6, H7, H8, H9, H10, H11, H12, H13, H14, H15, H16, type B HA. The VLP, when administered to a subject, induces an immune response.

Hybridization under stringent hybridization conditions is known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, $3^{rd}$ edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence encoding H1, H2, H3, H4, H5, H6, H7, H8, H9, H10, H11, H12, H13, H14, H15, H16 or type B HA, wherein the nucleotide sequence encodes a hemagglutinin protein (modified HA) with a modified proteolytic loop sequences or cleavage sites which has reduced or abolished cleavage of the proteolytic loop or cleavage site by a protease. When nucleotide sequence encoding the modified HA is expressed it forms a VLP, and the VLP induces the production of an antibody. For example, expression of the nucleotide sequence within a plant cell forms a VLP, and the VLP may be used to produce an antibody that is capable of binding HA, including unprocessed HA (HA0) or unprocessed wherein the proteolytic loop has been deleted. The VLP, when administered to a subject, induces an immune response.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 43, 91, 95, 97, 99, 101, 103, 105, 107, 109, 111, 113, 137, 140, 144, 151, 158, 165, wherein the nucleotide sequence encodes a modified HA protein that when expressed forms a VLP, and that the VLP induces the production of an antibody that is capable of binding HA, including unprocessed HA (HA0) or unprocessed wherein the proteolytic loop has been deleted or modified. The VLP, when administered to a subject, induces an immune response.

Furthermore, the present invention includes amino acid sequences that are characterized as having about 70, 75, 80, 85, 87, 90, 91, 92, 93 94, 95, 96, 97, 98, 99, 100% or any amount therebetween, sequence identity, or sequence similarity, with the amino acid sequences of SEQ ID NO: 17, 18, 20, 21, 41, 58, 77, 81, 85, 92, 96, 98, 100, 102, 104, 106, 108, 110, 112, 114, 134, 143, 147, 154, 161, 168, 194 and 199. wherein the amino acid sequence encodes a modified HA protein that when expressed forms a VLP, and that the VLP induces the production of an antibody that is capable of binding HA, including unprocessed HA (HA0) or unprocessed wherein the proteolytic loop has been deleted or modified. The VLP, when administered to a subject, induces an immune response.

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST), or by manual alignment and visual inspection. An example of sequence alignment of HAs from different strains of influenza can be found in FIG. 24.

For example, but is not limited to, nucleotide sequences encoding:

- a type B HA with a modified proteolytic loop as defined by SEQ ID NO:17, SEQ ID NO:18, SEQ ID NO: 41, SEQ ID NO: 43, SEQ ID NO: 58, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114 and SEQ ID NO: 168, or nucleotide sequences encoding type B HAs comprising modified proteolytic loop regions as defined in SEQ ID NO: 65, SEQ ID NO: 72, SEQ ID NO:73, SEQ ID NO:95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113 and SE ID NO: 165.

an H1 with a modified proteolytic loop include sequences comprising a modified cleavage site as defined by SEQ ID NO: 63.

an H2 with a modified proteolytic loop include sequences comprising a modified cleavage site as defined by SEQ ID NO: 134.

an H3 with a modified proteolytic loop include sequences defined by SEQ ID NO: 20, SEQ ID NO: 21, SEQ ID NO 143, SEQ ID NO: 147 or comprising a modified cleavage site as defined by SEQ ID NO: 64.

an H5 with a deleted proteolytic loop include sequences comprising a modified cleavage site as defined by SEQ ID NO: 61, SEQ ID NO:62, SEQ ID NO: 69, SEQ ID NO: 70, SEQ ID NO: 71.

an H7 with a modified proteolytic loop include sequences comprising a modified cleavage site as defined by SEQ ID NO: 154 or nucleotide sequences encoding type H7 HAs comprising modified proteolytic loop regions as defined in SEQ ID NO: 151.

an H9 with a modified proteolytic loop include sequences comprising a modified cleavage site as defined by SEQ ID NO: 161 or nucleotide sequences encoding type H9 HAs comprising modified proteolytic loop regions as defined in SEQ ID NO: 158.

The present invention pertains to the use of an HA protein comprising the transmembrane domain and includes HA1 and HA2 domains, for example the HA protein may be HA0, or processed HA comprising HA1 and HA2. The HA protein may be used in the production or formation of VLPs using a plant, or plant cell, expression system.

Amplification Elements and Enhancer Elements/Regulatory Elements

In another example the modified HA protein may be expressed in an expression system that comprises amplification elements and/or regulatory elements or regions (also referred to herein as enhancer elements). For example an amplification element from a geminivirus such as for example, an amplification element from the bean yellow dwarf virus (BeYDV) may be used to express the modified HA. BeYDV belongs to the Mastreviruses genus adapted to dicotyledonous plants. BeYDV is monopartite having a single-strand circular DNA genome and can replicate to very high copy numbers by a rolling circle mechanism. BeYDV-derived DNA replicon vector systems have been used for rapid high-yield protein production in plants.

As used herein, the phrase "amplification elements" refers to a nucleic acid segment comprising at least a portion of one or more long intergenic regions (LIR) of a geminivirus genome. As used herein, "long intergenic region" refers to a region of a long intergenic region that contains a rep binding site capable of mediating excision and replication by a geminivirus Rep protein. In some aspects, the nucleic acid segment comprising one or more LIRs, may further comprises a short intergenic region (SIR) of a geminivirus genome. As used herein, "short intergenic region" refers to the complementary strand (the short IR (SIR) of a Mastreviruses). Any suitable geminivirus-derived amplification element may be used herein. See, for example, WO2000/20557; WO2010/025285; Zhang X. et al. (2005, *Biotechnology and Bioengineering*, Vol. 93, 271-279), Huang Z. et al. (2009, *Biotechnology and Bioengineering*, Vol. 103, 706-714), Huang Z. et al. (2009, *Biotechnology and Bioengineering*, Vol. 106, 9-17); which are herein incorporated by reference). If more than one LIR is used in the construct, for example two LIRs, then the promoter, CMPV-HT regions and the nucleic acid sequence of interest and the terminator are bracketed by each of the two LIRs.

As described herein, co-delivery of bean yellow dwarf virus (BeYDV)-derived vector and a Rep/RepA-supplying vector, by agroinfiltration of *Nicotiana benthamiana* leaves results in efficient replicon amplification and robust protein production. Western blot analysis of protein extracts from plants transformed with gene constructs driving the expression of modified influenza B HA (from B/Brisbane/60/2008) with or without the proteolytic loop removed (see FIG. 17A for constructs) and in the presence or absence of the amplification element BeYDV (construct no. 1059 and 1039) showed that in the absence of BeYDV no accumulation of influenza B HA could be detected (FIG. 17B), when the regulatory element was CPMV-HT.

Figures 17A, 17B:
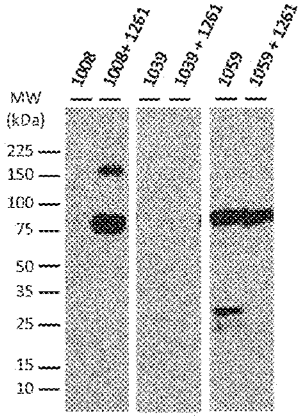
FIGS. 17A and 17B shows a Western blot analysis of HA protein expression in agroinfiltrated *Nicotiana benthamiana* leaves. “1008”: expression of wild-type HA from B/Brisbane/60/2008 in the presence of amplification elements (BeYDV); “1008+1261”: co-expression of wild-type HA from B/Brisbane/60/2008 in the presence of amplification elements (BeYDV) with M2 from A/New Caledonia/20/99; “1039”: expression of mutant HA from B/Brisbane/60/2008 in the absence of amplification elements (BeYDV). “1039+1261”: co-expression of mutant HA from B/Brisbane/60/2008 in the absence of amplification elements (BeYDV) with M2 from A/New Caledonia/20/99.HA from A/Brisbane/59/2007 (H1N1). “1059”: expression of mutant HA from B/Brisbane/60/2008 in the presence of amplification elements (BeYDV); “1059+1261”: co-expression of mutant HA from B/Brisbane/60/2008 in the presence of amplification elements (BeYDV) with M2 from A/New Caledonia/20/99.

As shown in FIG. 17B, expression of HA from B/Brisbane/60/2008 with the proteolytic loop removed in the absence of BeYDV does not lead to detectable expression by Western Blot analysis (see lane 1039 in FIG. 17B). However, expression of HA type B with the proteolytic loop removed in the presence of amplification element BeYDV, results in increased expression (see lane 1059). Similarly, in the absence of BeYDV, co-expression of mutant HA-type B comprising a deletion in the proteolytic loop, with M2 from A/New Caledonia/20/99, does not result in detectable HA expression (see lanes "1039+1261" in FIG. 17B). Co-expression of mutant HA type B comprising a deletion in the proteolytic loop in the presence of BeYDV, with a M2 from A/New Caledonia/20/99 on the other hand resulted in increased expression (see lane "1059+1261"; FIG. 17B).

However, the presence of BeyDV is not required when an enhancer element is present in the expression system and when the enhance element is not CPMV-HT. As for example shown in FIG. 29A, expression of various B HA strains under the control of an enhancer element, such for example CPMV 160, CPMV160+ or CPMV HT+, leads to the production of HA proteins that show increased hemagglutination titre (HMG) in the absence of BeYDV.

Therefore, the mutant (modified) HA protein may be expressed in the absence of an amplification element, such as a geminivirus-based amplification element for example BeYDV, but in the presence of an enhancer element, such for example CPMV 160, CPMV160+ or CPMV HT+.

The mutant (modified HA) may be expressed in the presence of an enhancer element, such for example CPMV 160, CPMV160+ or CPMV HT+, but in the absence or presence of an amplification element, such for example BeYDV. As shown in FIGS. 28B, 28C and 28F mutant (modified) HA may be expressed in the presence of an enhancer element, with or without the presence of an amplification element. Therefore the present invention is also directed to the expression of a mutant (modified) HA in the presence of an enhancer element and optionally an amplification element.

Figure 28A:
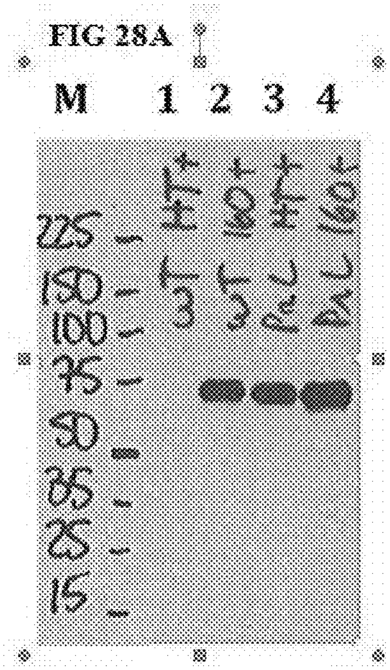
FIG. 28A shows a Western blot analysis of H3 Perth protein expression in agroinfiltrated *Nicotiana benthamiana* leaves. Lane 1: (2019+1261) co-expression of native (wildtype) HA from H3 Perth-16-09 in the presence of expression enhancer (CPMV-HT+) with M2 from A/New Caledonia/20/99; Lane 2: (2139+1261) co-expression of native (wildtype) HA from H3 Perth-16-09 in the presence of expression enhancer (CPMV 160+) with M2 from A/New Caledonia/20/99; Lane 3 (2039+1261) co-expression of mutant (modified) HA from H3 Perth-16-09 in the presence of expression enhancer (CPMV HT+) with M2 from A/New Caledonia/20/99; Lane 4: (2159+1261) co-expression of mutant (modified) HA from H3 Perth-16-09 in the presence of expression enhancer (CPMV 160+) with M2 from A/New Caledonia/20/99.
Figure 28B:
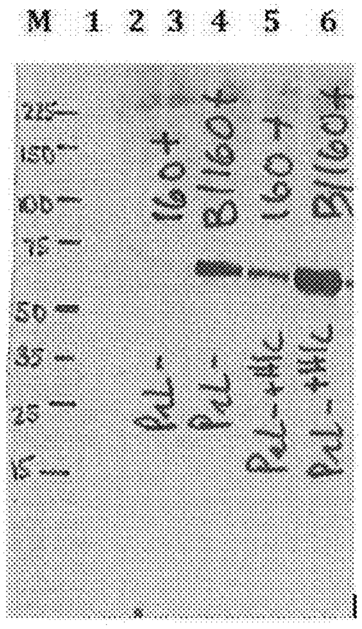
FIG. 28B shows a Western blot analysis of B Malaysia protein expression in agroinfiltrated *Nicotiana benthamiana* leaves. Lane 2: (2013+1261) co-expression of native (wildtype) HA from B Malaysia 2506-04 in the presence of expression enhancer (CPMV-160+) with M2 from A/New Caledonia/20/99; Lane 2: (2014+1261) co-expression of mutant (modified) HA from B Malaysia 2506-04 in the presence of expression enhancer (CPMV 160+) with M2 from A/New Caledonia/20/99.
Figure 28C:
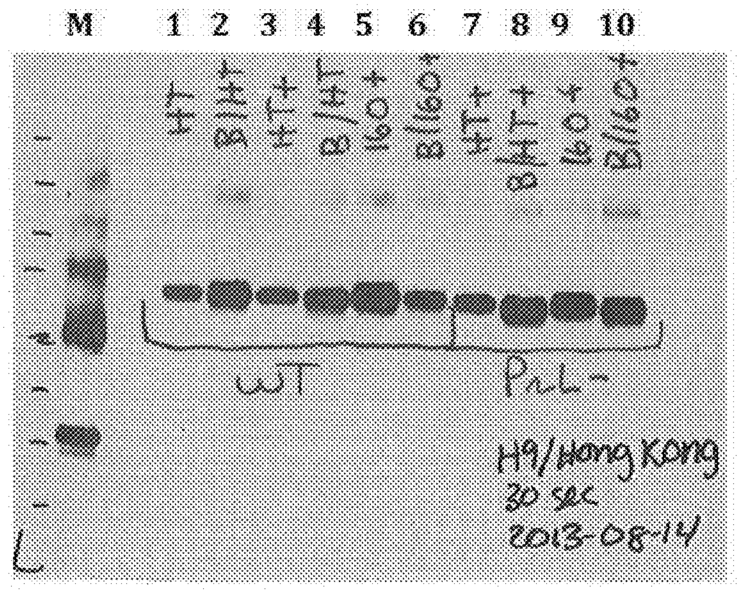
FIG. 28C shows a Western blot analysis of H9 Hong Kong protein expression in agroinfiltrated *Nicotiana benthamiana* leaves. Lane 1: (1610+1261) co-expression of native (wildtype) HA from H9 Hong Kong-1037-99 in the presence of expression enhancer (CPMV-HT) with M2 from A/New Caledonia/20/99; Lane 2: (1630+1261) co-expression of native (wildtype) HA from H9 Hong Kong-1037-99 in the presence of expression enhancer (CPMV-HT+) and amplification element BEYDV with M2 from A/New Caledonia/20/99; Lane 3: (2244+1261) co-expression of native (wildtype) HA from H9 Hong Kong-1037-99 in the presence of expression enhancer (CPMV-HT+) with M2 from A/New Caledonia/20/99; Lane 4: (2226+1261): co-expression of native (wildtype) HA from H9 Hong Kong-1037-99 in the presence of expression enhancer (CPMV 160+) with M2 from A/New Caledonia/20/99. Lane 6: (2246+1261) co-expression of native (wildtype) HA from H9 Hong Kong-1037-99 in the presence of expression enhancer (CPMV-160+) and amplification element BeYDV with M2 from A/New Caledonia/20/99; Lane 7: (2225+1261) co-expression of mutant (modified) HA from H9 Hong Kong-1037-99 in the presence of expression enhancer (CPMV-HT+) with M2 from A/New Caledonia/20/99; Lane 8: (2245+1261) co-expression of mutant (modified) HA from H9 Hong Kong-1037-99 in the presence of expression enhancer (CPMV HT+) and amplification element BeYDV with M2 from A/New Caledonia/20/99. Lane 9: (2227+1261) co-expression of mutant (modified) HA from H9 Hong Kong-1037-99 in the presence of expression enhancer (CPMV 160+) with M2 from A/New Caledonia/20/99. Lane 10: (2247+1261) co-expression of mutant (modified) HA from H9 Hong Kong-1037-99 in the presence of expression enhancer (CPMV 160+) and amplification element BeYDV with M2 from A/New Caledonia/20/99.
Figure 28D:
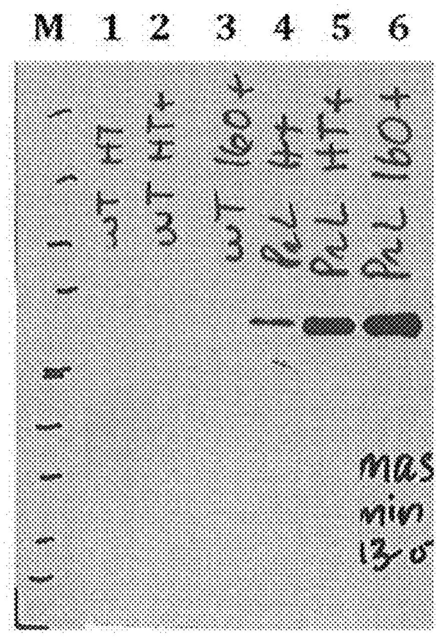
FIG. 28D shows a Western blot analysis of B Massachusetts protein expression in agroinfiltrated *Nicotiana benthamiana* leaves. Lane 1: (2070+1261) co-expression of native (wildtype) HA from B Massachusetts-2-12 in the presence of expression enhancer (CPMV-HT) with M2 from A/New Caledonia/20/99; Lane 2: (2080+1261) co-expression of native (wildtype) HA from B Massachusetts-2-12 in the presence of expression enhancer (CPMV-HT+) with M2 from A/New Caledonia/20/99; Lane 3: (2090+1261) co-expression of native (wildtype) HA from B Massachusetts-2-12 in the presence of expression enhancer (CPMV-160+) with M2 from A/New Caledonia/20/99; Lane 4: (2072+1261) co-expression of mutant (modified) HA from B Massachusetts-2-12 in the presence of expression enhancer (CPMV HT) with M2 from A/New Caledonia/20/99; Lane 5: (2052+1261) co-expression of mutant (modified) HA from B Massachusetts-2-12 in the presence of expression enhancer (CPMV HT+) with M2 from A/New Caledonia/20/99; Lane 6: (2050+1261) co-expression of mutant (modified) HA from B Massachusetts-2-12 in the presence of expression enhancer (CPMV 160+) with M2 from A/New Caledonia/20/99.
Figure 28E:
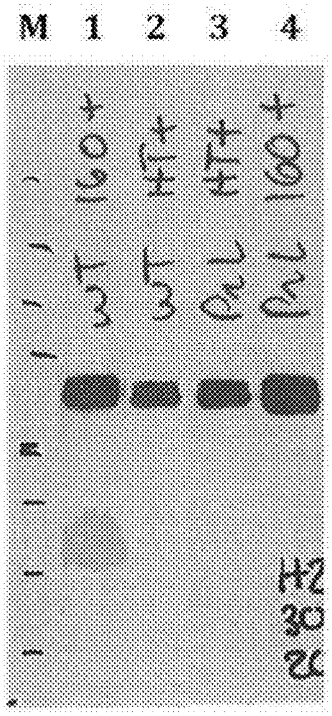
FIG. 28E shows a Western blot analysis of H2 Sin protein expression in agroinfiltrated *Nicotiana benthamiana* leaves. Lane 1: (2220+1261) co-expression of native (wildtype) HA from H2 Singapore-1-57 in the presence of expression enhancer (CPMV-HT+) with M2 from A/New Caledonia/20/99; Lane 2: (2222+1261) co-expression of native (wildtype) HA from H2 Singapore-1-57 in the presence of expression enhancer (CPMV 160+) with M2 from A/New Caledonia/20/99. Lane 3: (2221+1261) co-expression of mutant (modified) HA from H2 Singapore-1-57 in the presence of expression enhancer (CPMV-HT+) with M2 from A/New Caledonia/20/99; Lane 4: (2223+1261) co-expression of mutant (modified) HA from H2 Singapore-1-57 in the presence of expression enhancer (CPMV 160+) with M2 from A/New Caledonia/20/99.
Figure 28F:
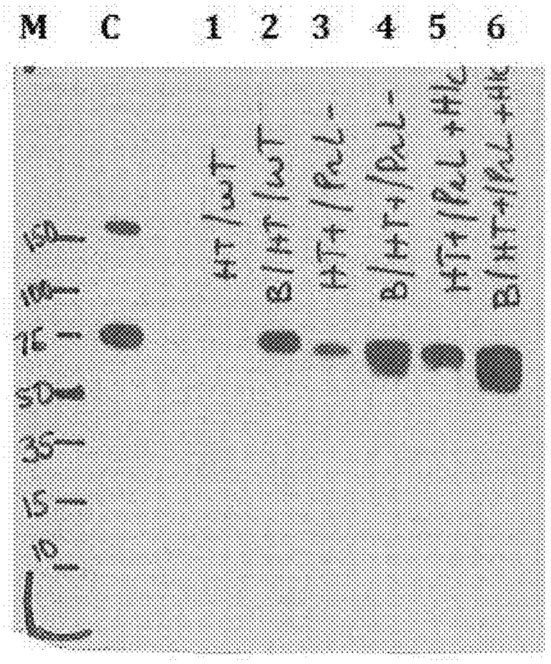
FIG. 28F shows a Western blot analysis of B/Florida protein expression in agroinfiltrated *Nicotiana benthamiana* leaves. Lane 1: (1004+1261) co-expression of native (wildtype) HA from B/Florida in the presence of expression enhancer (CPMV-HT) with M2 from A/New Caledonia/20/99; Lane 2: (1003+1261) co-expression of native (wildtype) HA from B/Florida in the presence of expression enhancer (CPMV HT) and amplification element BeYDV with M2 from A/New Caledonia/20/99. Lane 3: (2102+1261) co-expression of mutant (modified) HA from B/Florida in the presence of expression enhancer (CPMV-HT+) with M2 from A/New Caledonia/20/99; Lane 4: (2104+1261) co-expression of mutant (modified) HA from B/Florida in the presence of expression enhancer (CPMV HT+) and amplification element BeYDV with M2 from A/New Caledonia/20/99. Lane 5: (2106+1261) co-expression of mutant (modified) HA from B/Florida+H1 California TMCT in the presence of expression enhancer (CPMV HT+) with M2 from A/New Caledonia/20/99. Lane 6: (2108+1261) co-expression of mutant (modified) HA from B/Florida+H1 California TMCT in the presence of expression enhancer (CPMV HT+) and amplification element BeYDV with M2 from A/New Caledonia/20/99.

HA constructs comprising an enhancer element (either CMPV HT+ or CMPV 160+) and a proteolytic loop replaced with a GG linker (deleted proteolytic loop) exhibit increased expression when compared to wild type or HA constructs comprising CPMV HT (FIG. 28A, H3 Per; FIG. 28B, B Malaysia; FIG. 28C, H9 HK; FIG. 29D, B Mass; FIG. 28E, H2 Sin).

Figure 29A:
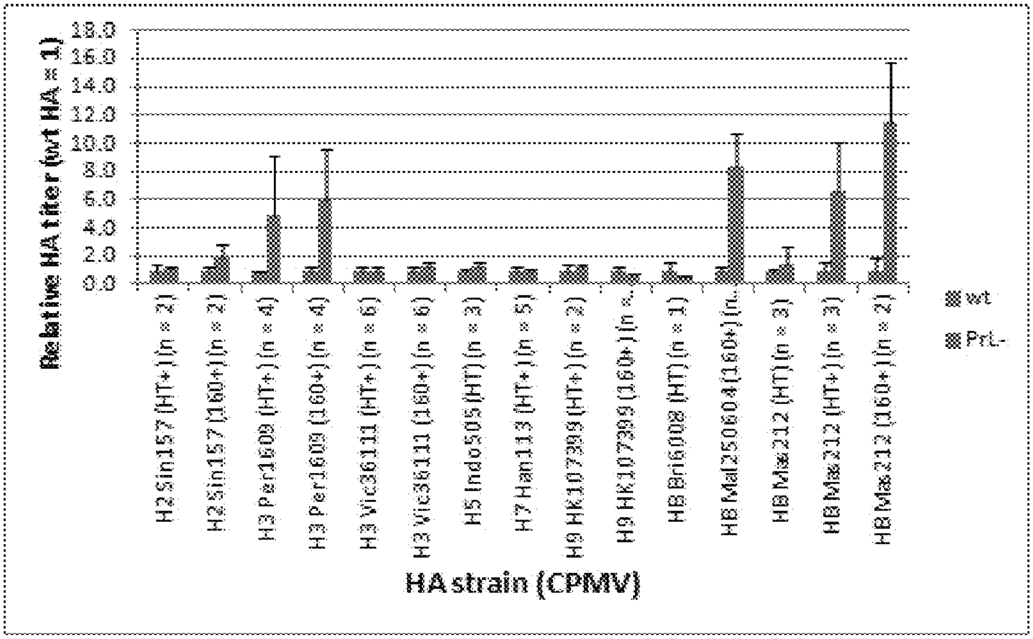
FIG. 29A shows the relative HA titer of modified HA from various influenza strains that were expressed in the presence of enhancer element CPMV HT, CPMV HT+ or CPMV 160+. Activity is compared to the native HA protein expressed with the same enhancer element. H3 A Perth/16/09 (H3 Per1609), H3 Victoria/361/11 (H3 Vic26111), B Brisbane 60/2008 (HB Bris60008), B Malaysia 2506/04 (HB Mal 250604) and B Massachusetts 2/12 (Ma212) were co-expressed with influenza M2 protein.

FIG. 29A present summary data for hemagglutination titre of modified HA proteins produced in plants comprising CPMV HT, CPMV HT+, CPMV 160 or CPMV160+, based enhancer elements operatively linked with a nucleotide sequence encoding either modified HA with a deleted proteolytic loop (GG linker) or a native HA. In most cases, the expression (determined as hemagglutination titer) were higher for the CPMV HT+, CPMV 160 or CPMV160+ based construct demonstrates significant expression levels.

Enhancer elements may be used to achieve high level of transient expression of mutant (modified) HA proteins with modified proteolytic loops. Enhancer elements may be based on RNA plant viruses, including comoviruses, such as Cowpea mosaic virus (CPMV; see, for example, WO2007/135480; WO2009/087391; US 2010/0287670, Sainsbury F. et al., 2008, *Plant Physiology;* 148: 121-1218; Sainsbury F. et al., 2008, *Plant Biotechnology Journal,* 6: 82-92; Sainsbury F. et al., 2009, *Plant Biotechnology Journal,* 7: 682-693; Sainsbury F. et al. 2009, Methods in Molecular Biology, *Recombinant Proteins From Plants*, vol. 483: 25-39).

CPMV 160 (CPMVX) and CPMV 160+ (CPMVX+)

In one embodiment the Enhancer Elements are “CPMVX” (also referred as “CPMV 160”) and/or “CPMVX+” (also referred to as “CPMV 160+”) as described in U.S. 61/925,852, which is incorporated herein by reference.

Expression enhancer “CPMVX” comprises a comovirus cowpea mosaic virus (CPMV) 5' untranslated region (UTR). The 5'UTR from nucleotides 1-160 of the CPMV RNA-2 sequence (SEQ ID NO: 93), starts at the transcription start site to the first in frame initiation start codon (at position 161), which serve as the initiation site for the production of the longer of two carboxy coterminal proteins encoded by a wild-type comovirus genome segment. Furthermore a ‘third’ initiation site at (or corresponding to) position 115 in the CPMV RNA-2 genomic sequence may also be mutated, deleted or otherwise altered. It has been shown that removal of AUG 115 in addition to the removal of AUG 161 enhances expression when combined with an incomplete M protein (Sainsbury and Lomonossoff, 2008, *Plant Physiology;* 148: 1212-1218; WO 2009/087391; which are incorporated herein by reference).

CPMVX comprises X nucleotides of SEQ ID NO:93, where X=160, 155, 150, or 114 of SEQ ID NO:93, or a sequence that comprises between 80% to 100% sequence similarity with CPMVX, where X=160, 155, 150, or 114 of SEQ ID NO:93. This expression enhancer is generally referred to as CPMVX (see FIG. 26A).

The expression enhancer CPMVX, where X=160, consists of nucleotides 1-160 of SEQ ID NO: 93:

```
                                                (SEQ ID NO: 93)
  1  tattaaaatc ttaataggtt ttgataaaag cgaacgtggg gaaacccgaa ccaaaccttc

 61  ttctaaactc tctctcatct ctcttaaagc aaacttctct cttgtctttc ttgcgtgagc

121  gatcttcaac gttgtcagat cgtgcttcgg caccagtaca
```

The CPMVX enhancer sequence may further be fused to a stuffer sequence, wherein the CMPVX comprises X nucleotides of SEQ ID NO:1, where X=160, 155, 150, or 114 of SEQ ID NO:1, or a sequence that comprises between 80 to 100% sequence similarity with CPMVX, where X=160, 155, 150, or 114 of SEQ ID NO:93, and the stuffer sequence comprises from 1-100 nucleotides fused to the 3' end of the CMPVX sequence. For example, the stuffer sequence may comprise from about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 nucleotides, or any number of nucleotides therebetween.

If the CMPVX sequence comprises a stuffer fragment, then this expression enhancer may be referred to as CPMVX+ (see FIG. 26A), where X=160, 155, 150, 114 of SEQ ID NO:1, it may also be referred to as CMPVX comprising a stuffer sequence, or it may be referred to as CPMV160+; CPMV155+; CPMV150+; CPMV114+, when X-160, 155, 150, or 114, respectively. Constructs comprising CPMVX that do not comprise a stuffer sequence may be termed CPMVX+, where X=160, 155, 150, 114 of SEQ ID NO:93, and where the stuffer sequence is of 0 nucleotides in length.

The stuffer sequence may be modified by truncation, deletion, or replacement of the native CMPV5'UTR sequence that is located 3' to nucleotide 160. The modified stuffer sequence may be removed, replaced, truncated or shortened when compared to the initial or unmodified (i.e. native) stuffer sequence associated with the 5'UTR (as described in Sainsbury F., and Lomonossoff G. P., 2008, Plant Physiol. 148: pp. 1212-1218). The stuffer sequence may comprise a one or more restriction sites (polylinker, multiple cloning site, one or more cloning sites), one or more plant kozak sequences, one or more linker sequences, one or more recombination sites, or a combination thereof. For example, which is not to be considered limiting, a stuffer sequence may comprise in series, a multiple cloning site of a desired length fused to a plant kozak sequence. The stuffer sequence does not comprise a nucleotide sequence from the native 5'UTR sequence that is positioned 3' to nucleotide 160 of the native CPMV 5'UTR, for example nucleotides 161 to 512 as shown in FIG. 1 of Sainsbury F., and Lomonossoff G. P. (2008, Plant Physiol. 148: pp. 1212-1218; which is incorporated herein by reference), or nucleotides 161-509 of SEQ ID NO:4. That is, the incomplete M protein present in the prior art CPMV HT sequence (FIG. 1; of Sainsbury F., and Lomonossoff G. P., 2008) is removed from the 5'UTR in the present invention.

Plant Kozak consensus sequences are known in the art (see for example Rangan et al. Mol. Biotechnol., 2008, July 39(3), pp. 207-213). Both naturally occurring and synthetic Kozak sequences may be used in the expression enhancer or may be fused to the nucleotide sequence of interest as described herein.

The plant kozak sequence may be any known plant kozak sequences (see for example L. Rangan et. al. Mol. Biotechnol. 2008), including, but not limited to the following plant consensus sequences:

```
                 (SEQ ID NO: 174; plant kingdom)
caA(A/C)a

                        (SEQ ID NO: 175; dicots)
aaA(A/C)a

                  (SEQ ID NO: 176; arabidopsis)
aa(A/G)(A/C)a
```

The plant kozak sequence may also be selected from the group of:

(SEQ ID NO: 177)
AGAAA (SEQ ID NO: 178)
AGACA (SEQ ID NO: 179)
AGGAA (SEQ ID NO: 180)
AAAAA (SEQ ID NO: 181)
AAACA (SEQ ID NO: 182)
AAGCA (SEQ ID NO: 183)
AAGAA (SEQ ID NO: 184)
AAAGAA (SEQ ID NO: 185)
AAAGAA (SEQ ID NO: 186; Consensus sequence)
(A/-)A(A/G)(A/G)(A/C)A.

The expression enhancer CPMVX, or CPMVX+, may be operatively linked at the 5'-end of the enhancer sequence with a regulatory region that is active in a plant, and operatively linked to a nucleotide sequence of interest at the 3'-end of the expression enhancer (FIG. 26A), in order to drive expression of the nucleotide sequence of interest within a plant host.

CPMV HT+, CPMV HT+ [WT115], CPMV HT+ [511]

Figure 27A:
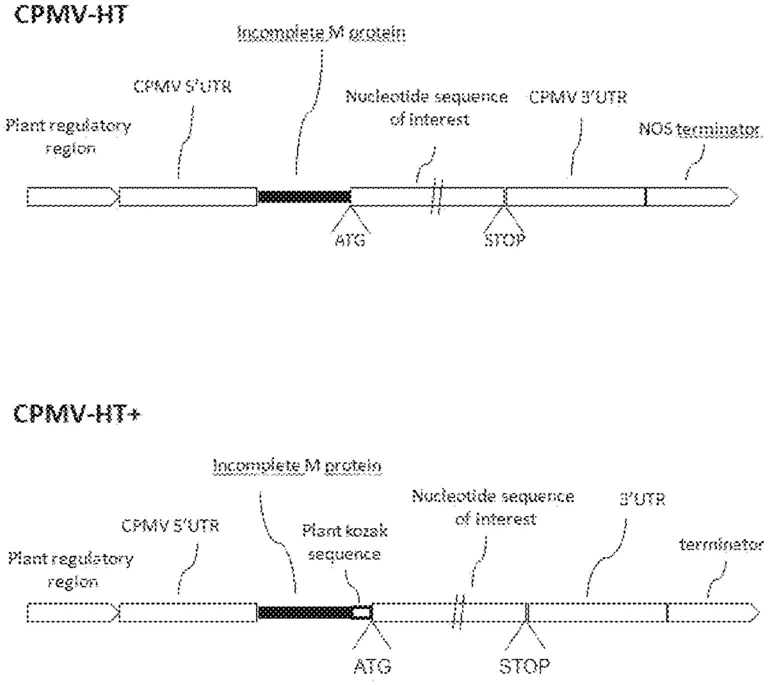
FIG. 27A shows a general schematic of the enhancer sequence of the CPMV HT and CPMV HT+ fused to a nucleotide sequence of interest. Not all of the elements shown in this figure may be required within the enhancer sequence. Additional elements may be included at the 3'-end of the nucleotide sequence of interest (not shown) including a sequence encoding a comovirus 3' untranslated region (UTR), a plastocyanin 3' UTR, or a combination of the comovirus 3' UTR and the plastocyanin 3' UTR.

In another embodiment the Enhancer Elements is "CPMV HT+" as described in U.S. 61/971,274, which is incorporated herein by reference. Expression enhancer "CPMV HT+" (see FIG. 27A) comprises a comovirus 5' untranslated region (UTR) and a modified, lengthened, or truncated stuffer sequence.

A plant expression system comprising a first nucleic acid sequence comprising a regulatory region, operatively linked with one or more than one expression enhancer as described herein (e.g. CPMV HT+, CPMV HT+[WT115], CPMV HT+[511]), and a nucleotide sequence encoding a modified HA is also provided. Furthermore, a nucleic acid comprising a promoter (regulatory region) sequence, an expression enhancer (e.g. CPMV HT+ or CPMV HT+[WT115]) comprising a comovirus 5'UTR and a stuffer sequence with a plant kozak sequence fused to one or more nucleic acid sequences encoding a modified HA are described. The nucleic acid may further comprise a sequence comprising a comovirus 3' untranslated region (UTR), for example, a plastocyanin 3' UTR, or other 3'UTR active in a plant, and a terminator sequence, for example a NOS terminator, operatively linked to the 3'-end of the nucleotide sequence encoding a modified HA (referred to as nucleotide of interest in FIG. 27A), so that the nucleotide sequence encoding the modified HA is inserted upstream from the comovirus 3' untranslated region (UTR), plastocyanin 3' UTR, or other 3'UTR sequence.

SEQ ID NO:173 comprises a "CPMV HT" expression enhancer as known in the prior art (e.g. FIG. 1 of Sainsbury and Lomonossoff 2008, Plant Physiol. 148: pp. 1212-1218; which is incorporated herein by reference). CPMV HT includes the 5'UTR sequence from nucleotides 1-160 of SEQ ID NO:173 with modified nucleotides at position 115 (cgt), and an incomplete M protein with a modified nucleotide at position 162 (acg), and lacks a plant kozak sequence (5'UTR: nucleotides 1-160; incomplete M protein underlined, nucleotides 161-509). SEQ ID NO:173 also includes a multiple cloning site (italics, nucleotides 510-528) which is not present in the prior art CPMV HT sequence:

SEQ ID NO: 173

1 tattaaaatc ttaataggtt ttgataaaag cgaacgtggg gaaacccgaa ccaaaccttc 61 ttctaaactc tctctcatct ctcttaaagc aaacttctct cttgtctttc ttgcgtgagc 121 gatcttcaac gttgtcagat cgtgcttcgg caccagtaca *acg*ttttctt tcactgaagc 181 gaaatcaaag atctctttgt ggacacgtag tgcggcgcca ttaaataacg tgtacttgtc 241 ctattcttgt cggtgtggtc ttgggaaaag aaagcttgct ggaggctgct gttcagcccc 301 atacattact tgttacgatt ctgctgactt tcggcgggtg caatatctct acttctgctt 361 gacgaggtat tgttgcctgt acttctttct tcttcttctt gctgattggt tctataagaa 421 atctagtatt ttctttgaaa cagagttttc ccgtggtttt cgaacttgga gaaagattgt 481 taagcttctg tatattctgc ccaaatttg*t cgggccc*

CPMV HT+ with a plant kozak consensus sequence is provided in SEQ ID NO:187 (nucleotide 1-160, 5'UTR, including modified ATG at positions 115 (GTG) lower case bold and italics; stuffer fragment comprising: an incomplete M protein underlined, nucleotides 161-509, with modified nucleotide at 162 (ACG); a multiple cloning site, italics, nucleotides 510-528; and a consensus plant kozak sequence, caps and bold, nucleotides 529-534).

(SEQ ID NO: 187)

```
1   tattaaaatc ttaataggtt ttgataaaag cgaacgtggg gaaacccgaa ccaaaccttc
61  ttctaaactc tctctcatct ctcttaaagc aaacttctct cttgtctttc ttgcgtgagc
121 gatcttcaac gttgtcagat cgtgcttcgg caccagtaca acgttttctt tcactgaagc
181 gaaatcaaag atctctttgt ggacacgtag tgcggcgcca ttaaataacg tgtacttgtc
241 ctattcttgt cggtgtggtc ttgggaaaag aaagcttgct ggaggctgct gttcagcccc
301 atacattact tgttacgatt ctgctgactt tcggcgggtg caatatctct acttctgctt
361 gacgaggtat tgttgcctgt acttctttct tcttcttctt gctgattggt tctataagaa
421 atctagtatt ttctttgaaa cagagttttc ccgtggtttt cgaacttgga gaaagattgt
481 taagcttctg tatattctgc ccaaatttgt tcgggcccaa taccgcgg(A/-)A(A/G)
    (A/G)(A/C)A
```

SEQ ID NO:188 ("CPMV HT+ 511") comprises a segment of the native sequence of the CPMV RNA 2 genome from nucleotides 1-154. The 5'UTR sequence from nucleotides 1-511 of SEQ ID NO:188 comprises modified "atg" sequences at positions 115 ("g" in place of "a"; italics bold) and 162 ("c" in place of "t"; italics bold), and an incomplete M protein (underlined) from nucleotides 161-511. CPMV HT+ 511 comprises a native M protein kozak consensus sequence (nucleotides 508-511; bold):

SEQ ID NO: 188

```
1   tattaaaatc ttaataggtt ttgataaaag cgaacgtggg gaaacccgaa ccaaaccttc
61  ttctaaactc tctctcatct ctcttaaagc aaacttctct cttgtctttc ttgcgtgagc
121 gatcttcaac gttgtcagat cgtgcttcgg caccagtaca acgttttctt tcactgaagc
181 gaaatcaaag atctctttgt ggacacgtag tgcggcgcca ttaaataacg tgtacttgtc
241 ctattcttgt cggtgtggtc ttgggaaaag aaagcttgct ggaggctgct gttcagcccc
301 atacattact tgttacgatt ctgctgactt tcggcgggtg caatatctct acttctgctt
361 gacgaggtat tgttgcctgt acttctttct tcttcttctt gctgattggt tctataagaa
421 atctagtatt ttctttgaaa cagagttttc ccgtggtttt cgaacttgga gaaagattgt
481 taagcttctg tatattctgc ccaaatttga a...
```

Another non-limiting example of a CPMV HT+ enhancer sequence is provided by the sequence of SEQ ID NO:189 (CPMV HT+[WT115]). Expression cassettes or vectors comprising CPMV HT+ and including a plant regulatory region in operative association with the expression enhancer sequence of SEQ ID NO: 189, and the transcriptional start site (ATG) at the 3' end fused to a nucleotide sequence encoding modified HA are also part of the present invention.

SEQ ID NO: 189 (CPMV HT+[WT115]) nucleotide 1-160, 5'UTR, with an ATG at position 115-117, lower case bold; stuffer fragment comprising: an incomplete M protein underlined, nucleotides 161-509; with a modified ATG at position 161-153 lower case bold, and underlined, a multiple cloning site, italics, nucleotides 510-528; and a plant kozak sequence, caps and bold, nucleotides 529-534).

(SEQ ID NO: 189)

```
1   tattaaaatc ttaataggtt ttgataaaag cgaacgtggg gaaacccgaa ccaaaccttc
61  ttctaaactc tctctcatct ctcttaaagc aaacttctct cttgtctttc ttgcatgagc
121 gatcttcaac gttgtcagat cgtgcttcgg caccagtaca acgttttctt tcactgaagc
181 gaaatcaaag atctctttgt ggacacgtag tgcggcgcca ttaaataacg tgtacttgtc
241 ctattcttgt cggtgtggtc ttgggaaaag aaagcttgct ggaggctgct gttcagcccc
301 atacattact tgttacgatt ctgctgactt tcggcgggtg caatatctct acttctgctt
```

-continued

```
361  gacgaggtat tgttgcctgt acttctttct tcttcttctt gctgattggt tctataagaa

421  atctagtatt ttctttgaaa cagagttttc ccgtggtttt cgaacttgga gaaagattgt

481  taagcttctg tatattctgc ccaaatttgt tcgggcccaa taccgcggAG AAAA
```

The plant kozak sequence of SEQ ID NO:189 may be any plant kozak sequence, including but not limited, to one of the sequences of SEQ ID NO's: 174-186.

"Chimeric Protein"

The modified HA might further be a chimeric protein. By "chimeric virus protein" or "chimeric virus polypeptide", also referred to as "chimeric protein" or "chimeric polypeptide", or "chimeric HA" it is meant a protein or polypeptide that comprises amino acid sequences from two or more than two sources, for example but not limited to, two or more influenza types or subtypes, or influenza's of a different origin, that are fused as a single polypeptide. The chimeric protein or polypeptide may include a signal peptide that is the same as, or heterologous with, the remainder of the polypeptide or protein. The chimeric protein or chimeric polypeptide may be produced as a transcript from a chimeric nucleotide sequence, and following synthesis, and as required, may associate to form a multimeric protein. Therefore, a chimeric protein or a chimeric polypeptide also includes a protein or polypeptide comprising subunits that are associated via disulphide bridges (i.e. a multimeric protein). For example, a chimeric polypeptide comprising amino acid sequences from two or more than two sources may be processed into subunits, and the subunits associated via disulphide bridges to produce a chimeric protein or chimeric polypeptide. A chimeric HA protein may also comprises an antigenic protein or a fragment thereof of a first influenza virus, and a transmembrane domain complex (TDC) from an second virus influenza HA, including a transmembrane domain and cytosolic tail domains (TM/CT). The polypeptide may be a modified HA, and each of the two or more than two amino acid sequences that make up the polypeptide may be obtained from different HA's to produce a chimeric HA, chimeric influenza HA, chimeric modified HA or chimeric modified influenza HA. A chimeric HA may also include an amino acid sequence comprising heterologous signal peptide (a chimeric HA preprotein) that is cleaved after or during protein synthesis. Preferably, the chimeric polypeptide, or chimeric influenza HA is not naturally occurring. A nucleic acid encoding a chimeric polypeptide may be described as a "chimeric nucleic acid", or a "chimeric nucleotide sequence". For example a chimeric nucleic acid may comprise a nucleotide sequence encoding the modified HA comprises a chimeric nucleotide sequence encoding, in series, a modified HA ectodomain comprising a modified proteolytic loop, an influenza transmembrane domain, and a cytoplasmic tail, wherein the modified HA ectodomain is from a first influenza strain and the transmembrane domain and the cytoplasmic tail are from a second influenza strain. Examples of chimeric nucleotide acids, wherein the modified HA ectodomain is from a first influenza strain and the transmembrane domain and the cytoplasmic tail are from a second influenza strain are given in Examples 5.14, 5.16, 5.18, 5.19, 5. 21 and 5.23. A virus-like particle comprised of chimeric HA may be described as a "chimeric VLP".

As described above, the chimeric protein, chimeric polypeptide, or chimeric HA may include a signal peptide that is the same as, or heterologous with, the remainder of the polypeptide or protein. The term "signal peptide" is well known in the art and refers generally to a short (about 5-30 amino acids) sequence of amino acids, found generally at the N-terminus of a polypeptide that may direct translocation of the newly-translated polypeptide to a particular organelle, or aid in positioning of specific domains of the polypeptide chain relative to others. As a non-limiting example, the signal peptide may target the translocation of the protein into the endoplasmic reticulum and/or aid in positioning of the N-terminus proximal domain relative to a membrane-anchor domain of the nascent polypeptide to aid in cleavage and folding of the mature protein, for example a modified HA or chimeric modified HA.

The HA may also be a chimeric HA or chimeric modified HA, wherein a native transmembrane domain of the HA or modified HA is replaced with a heterologous transmembrane domain. The transmembrane domain of HA proteins is highly conserved (see for example FIG. 1C of WO 2010/148511; which is incorporated herein by reference). The heterologous transmembrane domain may be obtained from any HA transmembrane domain, for example but not limited to the transmembrane domain from H1 California, B/Florida/4/2006 (GenBank Accession No. ACA33493.1), B/Malaysia/2506/2004 (GenBank Accession No. ABU99194.1), H1/Bri (GenBank Accession No. ADE28750.1), H1 A/Solomon Islands/3/2006 (GenBank Accession No. ABU99109.1), H1/NC (GenBank Accession No. AAP34324.1), H2 A/Singapore/1/1957 (GenBank Accession No. AAA64366.1), H3 A/Brisbane/10/2007 (GenBank Accession No. AC 126318.1), H3 A/Wisconsin/67/2005 (GenBank Accession No. ABO37599.1), H5 A/Anhui/1/2005 (GenBank Accession No. ABD28180.1), H5 A/Vietnam/1194/2004 (GenBank Accession No. ACR48874.1), H5-Indo (GenBank Accession No. ABW06108.1). The transmembrane domain may also be defined by the following consensus amino acid sequence:

(SEQ ID NO: 94)
iLXiYystvAiSslXlXXmlagXsXwmcs

Figure 26A:
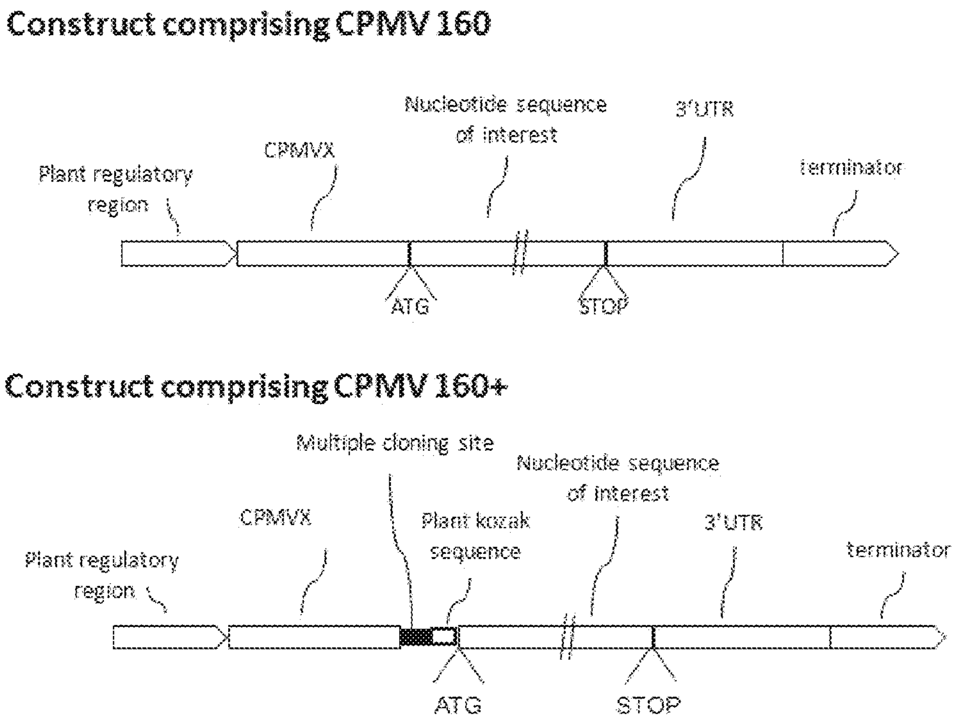
FIG. 26A shows a general schematic of an example of several enhancer sequences, CPMVX, and CPMVX+ (comprising CPMVX, and a stuffer fragment, which in this non-limiting example, comprises a multiple cloning site and plant kozak sequence), as described herein. CPMCX and CPMVX+ are each shown as operatively linked to plant regulatory region at their 5'-ends, and at their 3' ends, in series, a nucleotide sequence of interest (including an ATG initiation site and STOP site), a 3'UTR, and a terminator sequence. An example of construct CPMVX as described herein, is CPMV160. An example of construct CPMVX+ as described herein, is CPMV160+.
Figure 26B:
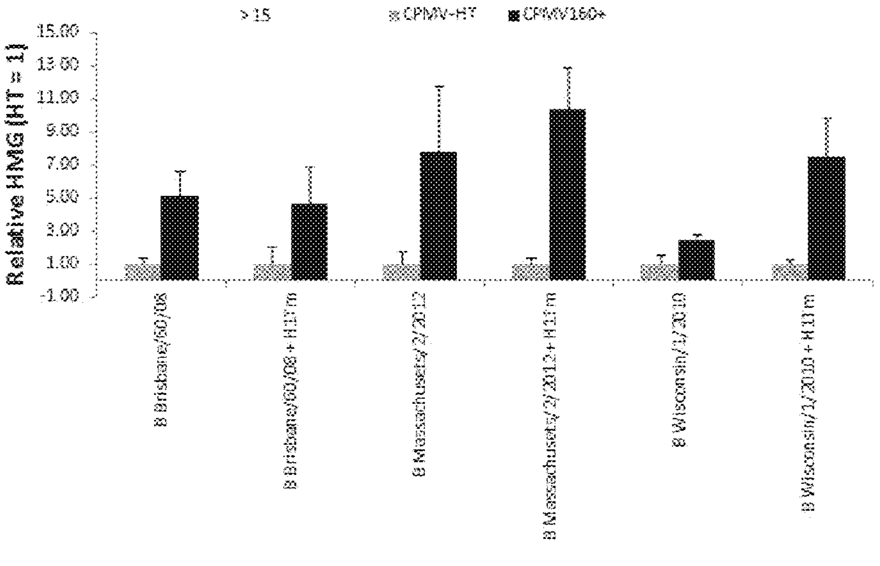
FIG. 26B shows the relative hemagglutination titres (HMG) in crude protein extracts of modified HA proteins produced in plants comprising CPMV-HT expression constructs, and CPMV160+ based expression constructs. Data for the expression of HA B Brisbane/60/08 with deleted proteolytic loop and with a PDI signal peptide (construct number 1039, 5'UTR: CMPV HT; and construct number 1937, 5'UTR: CMPV160+; see Example 5.7), B Brisbane/60/08+H1Tm, with deleted proteolytic loop, with transmembrane domain and cytoplasmic tail replaced by those of H1, B Massachusetts/2/2012 2012 with deleted proteolytic loop and with a PDI signal peptide (construct number 2072, 5'UTR: CMPV HT; and construct number 2050, 5'UTR: CMPV160+; see Example 5.14), B Massachusetts/2/2012+H1Tm with deleted proteolytic loop, with transmembrane domain and cytoplasmic tail replaced by those of H1 A/California/07/2009 and with a PDI signal peptide (construct number 2074, 5'UTR: CMPV HT; and construct number 2060, 5'UTR: CMPV160+; see Example 5.15), B Wisconsin/1/2010 with deleted proteolytic loop and with the native signal peptide (construct number 1445, 5'UTR: CMPV HT; and construct number 1975, 5'UTR: CMPV160+; see Example 5.16), and B Wisconsin/1/2010+H1Tm with deleted proteolytic loop, with transmembrane domain and cytoplasmic tail replaced by those of H1 A/California/07/2009 and with the native signal peptide (construct number 1454, 5'UTR: CMPV HT; and construct number 1893, 5'UTR: CMPV160+; see Example 5.18), are shown.
Figure 27B:
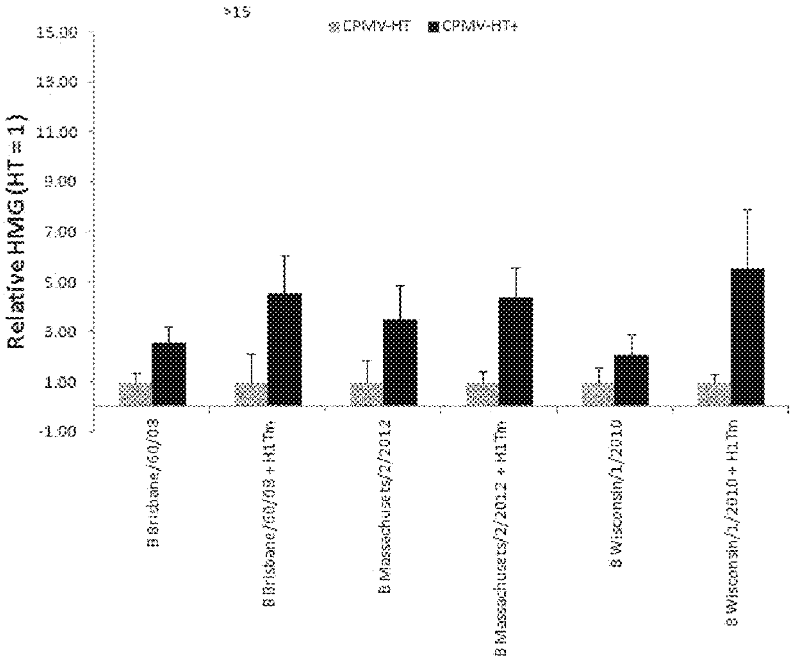
FIG. 27B shows the relative hemagglutination titre (HMG) in crude protein extracts of proteins produced in plants comprising CPMV-HT expression constructs, and CPMV HT+ based expression constructs, operatively linked with a nucleotide sequence of interest. Data for the expression of HA B Brisbane/60/08 with deleted proteolytic loop and with a PDI signal peptide (construct number 1039: CPMV HT; see Example 5.7 and construct number 1829: CPMV HT+; see example 5.12), B Brisbane/60/08+H1TM with deleted proteolytic loop, with transmembrane domain and cytoplasmic tail replaced by those of H A/California/07/2009, and with a PDI signal peptide (construct number 1067: CPMV HT; see Example 5.14 and construct number 1875: CPMV HT+; see example 5.19), B Massachusetts/2/2012 with deleted proteolytic loop, and with a PDI signal peptide (construct number 2072: CMPV HT; see Example 5.15 and construct number 2052: CMPV HT+; see Example 5.20), B Massachusetts/2/2012+H1Tm with deleted proteolytic loop, with transmembrane domain and cytoplasmic tail replaced by those of H1 A/California/07/2009 and with a PDI signal peptide (construct number 2074: CMPV HT; see Example 5.16 and construct number 2062: CMPV HT+; see Example 5.21), B Wisconsin/1/2010 with deleted proteolytic loop and with the native signal peptide (construct number 1445: CMPV HT; see Example 5.17 and construct number 1839: CMPV HT+; see Example 5.22), and B Wisconsin/1/2010+H1Tm with deleted proteolytic loop, with transmembrane domain and cytoplasmic tail replaced by those of H1 A/California/07/2009 and with the native signal peptide (construct number 1454: CMPV HT; see Example 5.18 and construct number 1860: CMPV HT+; see Example 5.23), are shown.

Examples of constructs comprising a chimeric HA with a heterologous trans-membrane domain include: construct number 1875 (CPMV-HT+ B Brisbane/60/08 with deleted proteolytic loop+H1TM, with trans-membrane domain and cytoplasmic tail replaced by H1 A/California/07/2009; see example 5.19), construct number 1977 (CPMV-160+ B Brisbane/60/08 with deleted proteolytic loop+H1TM, with trans-membrane domain and cytoplasmic tail replaced by H1 A/California/07/2009; see example 5.14), construct number 1067 (CPMV-HT B Brisbane/60/08 with deleted proteolytic loop+H1TM, with trans-membrane domain and cytoplasmic tail replaced by H1 A/California/07/2009; see example 5.14), construct number 2074 (CPMV HT B Massachusetts/2/2012+H1Tm, with trans-membrane domain and cytoplasmic tail replaced by those of H1 A/California/07/2009; see Example 5.16), construct number 2060 (CPMV HT160+ Massachusetts/2/2012+H1Tm, with trans-membrane domain and cytoplasmic tail replaced by those of H1 A/California/07/2009; see Example 5.16), construct number 2062 (CPMV 160+ B Massachusetts/2/2012+H1Tm, with trans-membrane domain and cytoplasmic tail replaced by those of H1 A/California/07/2009; see Example 5.21), construct number 1860 (CPMV HT+ B Wisconsin/1/2010+H1Tm with trans-membrane domain and cytoplasmic tail replaced by those of H1 A/California/07/2009; see Example 5.23), construct number 1454 (CPMV HT B Wisconsin/1/2010+H1Tm with trans-membrane domain and cytoplasmic tail replaced by those of H1 A/California/07/2009, see Example 5.18) and construct number 1893 (CPMV 160+ B Wisconsin/1/2010+H1Tm with trans-membrane domain and cytoplasmic tail replaced by those of H1 A/California/07/2009) see Example 5.18. Activity of these chimeric modified HA's is shown in FIGS. 26B and 27B.

Signal Peptide

A signal peptide (SP) may be native to the modified HA or chimeric modified HA, or a signal peptide may be heterologous with respect to the primary sequence of the modified HA being expressed. The modified HA may comprise a signal peptide from a first influenza type, subtype or strain with the balance of the HA from one or more than one different influenza type, subtype or strain. For example the native signal peptide of HA subtypes H1, H2, H3, H5, H6, H7, H9 or influenza type B may be used to express the modified HA in a plant system. In some embodiments of the invention, the SP may be of an influenza type B, H1, H3 or H5; or of the subtype H1/Bri, H1/NC, H5/Indo, H3/Bri or B/Flo.

Furthermore, the modified HA or chimeric modified HA may comprise a native, or a non-native signal peptide; the non-native signal peptide may be of plant origin or obtained from an animal or bacterial polypeptide. The native signal peptide may correspond to that of the HA or modified HA being expressed, additionally, the signal peptide may be from a structural protein or hemagglutinin of a virus other than influenza. Non-limiting examples of a signal peptide that may be used is that of alfalfa protein disulfide isomerase (PDI SP; nucleotides 32-103 of Accession No. Z 1499 also see WO 2009/076778; WO 2010/148511, or WO 2010/003235), or the patatin signal peptide (PatA SP; located nucleotides 1738-1806 of GenBank Accession number A08215). The nucleotide sequence of PatA SP for this accession number is:

(SEQ ID NO: 171)
ATGGCAACTACTAAAACTTTTTTAATTTTATTTTTTATGATATTAGCAAC
TACTAGTTCAACATGTGCT the amino acid sequence of patatin A signal peptide is:

(SEQ ID NO: 172)
MATTKTFLILFFMILATTSSTCA

The present invention therefore provides for a modified HA or chimeric modified HA comprising a native, or a non-native signal peptide, and nucleic acids encoding such chimeric modified HA proteins.

Co-Expression with Channel Protein

The mutant (modified) HA may be produced in a plant by co-expressing a first nucleic acid encoding the modified HA with a second nucleic acid encoding a channel protein, for example but not limited to a proton channel protein. The first and second nucleic acids may be introduced to the plant in the same step, or they may be introduced to the plant sequentially. The first and second nucleic acids may be introduced in the plant in a transient manner, or in a stably manner. Furthermore, a plant that expresses a first nucleic acid encoding the modified HA may transformed with a channel protein, for example but not limited to a proton channel protein, (second nucleic acid) so that both the first and the second nucleic acids are co-expressed in the plant. Alternatively, a plant that expresses a channel protein, for example but not limited to a proton channel protein, (second nucleic acid) may transformed with a first nucleic acid encoding the modified HA so that both the first and the second nucleic acids are co-expressed in the plant. Additionally, a first plant expressing the first nucleic acid encoding modified HA, may be crossed with a second plant expressing the second nucleic acid encoding the channel protein for example but not limited to a proton channel protein, to produce a progeny plant that co-expresses the first and second nucleic acids encoding the modified HA and the channel protein, for example but not limited to a proton channel protein, respectively.

Without wishing to be bound by theory, the pH of a cellular compartment comprising modified HA, including the Golgi apparatus, may be important for the folding, stability and/or proteolysis of HA. Proton channel proteins, such as for example influenza M2 and BM2 protein may regulate the pH in cellular compartments. For example, M2 regulates the potentiation of membrane fusion by buffering intracellular compartments both in late and early stages of influenza viral replication.

By co-expressing a channel protein, for example but not limited to a proton channel protein, along with a modified HA, the pH within the Golgi apparatus may increase, and result in an increase in stability, reduction of degradation, or a combination thereof, and increase expression levels and yield of modified HA and/or VLPs.

By co-expressing a modified HA along with a channel protein, for example but not limited to a proton channel protein, in a plant, increased yield of HA and/or VLPs are observed, when compared to a plant that expressed the modified without co-expression of the channel protein, for example but not limited to a proton channel protein (see FIGS. 13A and 14). As shown for example in FIG. 13A, the co-expression of M2 with the modified influenza B HA increased HA accumulation level (FIG. 13A, 1059 vs 1059+1261).

Furthermore, the efficacy of M2 from influenza A/Puerto Rico/8/1934 to increase accumulation of the modified influenza B HA and H3 was compared to that of M2 from influenza A/New Caledonia/20/1999. For the modified influenza B HA, the comparison was undertaken by western blot analysis of protein extracts from plants transformed with constructs 1059, 1059+1261 and 1059+859. The results obtained demonstrated that the co-expression of M2 from influenza A/Puerto Rico/8/1934 (encoded by construct no. 859) was as efficient as the co-expression of M2 from influenza A/New Caledonia/20/1999 (encoded by construct no. 1261) for increasing accumulation of the modified influenza B HA (FIG. 14).

As used herein, the terms "M2," "M2 protein," "M2 sequence" and "M2 domain" refer to all or a portion of an M2 protein sequence isolated from, based upon or present in any naturally occurring or artificially produced influenza virus strain or isolate. Thus, the term M2 and the like include naturally occurring M2 sequence variants produced by mutation during the virus life-cycle or produced in response to a selective pressure (e.g., drug therapy, expansion of host cell tropism or infectivity, etc.), as well as recombinantly or synthetically produced M2 sequences. Non-limiting example of sequences that may be used with the present invention include M2 from A/Puerto Rico/8/1934 and M2 from A/New Caledonia/20/1999.

Immune Response

An "immune response" generally refers to a response of the adaptive immune system. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity is of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cross-reactivity HAI titres may also be used to demonstrate the efficacy of an immune response to other strains of virus related to the vaccine subtype. For example, serum from a subject immunized with a vaccine composition of a first strain (e.g. VLPs of A/Indonesia 5/05) may be used in an HAI assay with a second strain of whole virus or virus particles (e.g. A/Vietnam/1194/2004), and the HAI titer determined.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be obtained several ways, including: 1) enumeration of lysis plaques (plaque assay) following crystal violet fixation/coloration of cells; 2) microscopic observation of cell lysis in culture; 3) ELISA and spectrophotometric detection of NP virus protein (correlate with virus infection of host cells).

The term "virus like particle" (VLP), or "virus-like particles" or "VLPs" refers to structures that self-assemble and comprise virus proteins for example an influenza HA protein or modified HA protein such for example an HA0 protein, wherein the proteolytic loop has been modified. VLPs are generally morphologically and antigenically similar to virions produced in an infection, but lack genetic information sufficient to replicate and thus are non-infectious. In some examples, VLPs may comprise a single protein species, or more than one protein species. For VLPs comprising more than one protein species, the protein species may be from the same species of virus, or may comprise a protein from a different species, genus, subfamily or family of virus (as designated by the ICTV nomenclature). In other examples, one or more of the protein species comprising a VLP may be modified from the naturally occurring sequence, such for example a modified HA as described herein. VLPs may be produced in suitable host cells including plant and insect host cells. Following extraction from the host cell and upon isolation and further purification under suitable conditions, VLPs may be purified as intact structures.

Furthermore, VLPs may be produced that comprise a combination of HA subtypes. For example, VLPs may comprise one or more than one HA or one or more than one modified HA from the subtype H1, H2, H3, H4, H5, H6, H7, H8, H9, H10, H11, H12, H13, H14, H15, H16, subtype B HA or a combination thereof. Selection of the combination of HAs or modified HAs may be determined by the intended use of the vaccine prepared from the VLP. For example a vaccine for use in inoculating birds may comprise any combination of HA subtypes or modified HA subtypes, while VLPs useful for inoculating humans may comprise subtypes one or more than one of subtypes or modified subtype of H1, H2, H3, H4, H5, H6, H7, H8, H9, H10, H11, H12, H13, H14, H15, H16, subtype B HA. However, other HA subtype or modified HA subtype combinations may be prepared depending upon the use of the VLP. In order to produce VLPs comprising combinations of HA subtypes or modified subtype HAs, the desired HA subtype or modified HA subtype may be co-expressed within the same cell, for example a plant cell.

The VLPs produced from influenza derived proteins, in accordance with the present invention do not comprise M1 protein. The M1 protein is known to bind RNA (Wakefield and Brownlee, 1989) which is a contaminant of the VLP preparation. The presence of RNA is undesired when obtaining regulatory approval for the VLP product, therefore a VLP preparation lacking RNA may be advantageous.

The VLPs produced as described herein do not typically comprise neuramindase (NA). However, NA may be co-expressed with HA should VLPs comprising HA and NA be desired.

The invention also includes, but is not limited to, virus derived VLPs that obtain a lipid envelope from the plasma membrane of the cell in which the VLP proteins are expressed. For example, if the VLP is expressed in a plant-based system, the VLP may obtain a lipid envelope from the plasma membrane of the cell.

Generally, the term "lipid" refers to a fat-soluble (lipophilic), naturally-occurring molecules. The term is also used more specifically to refer to fatty-acids and their derivatives (including tri-, di-, and monoglycerides and phospholipids), as well as other fat-soluble sterol-containing metabolites or sterols. Phospholipids are a major component of all biological membranes, along with glycolipids, sterols and proteins. Examples of phospholipids include phosphatidylethanolamine, phosphatidylcholine, phosphatidylinositol, phosphatidylserine, and the like. Examples of sterols include zoosterols (e.g., cholesterol) and phytosterols. Over 200 phytosterols have been identified in various plant species, the most common being campesterol, stigmasterol, ergosterol, brassicasterol, delta-7-stigmasterol, delta-7-avenasterol, daunosterol, sitosterol, 24-methylcholesterol, cholesterol or beta-sitosterol. As one of skill in the art would understand, the lipid composition of the plasma membrane of a cell may vary with the culture or growth conditions of the cell or organism from which the cell is obtained.

Cell membranes generally comprise lipid bilayers, as well as proteins for various functions. Localized concentrations of particular lipids may be found in the lipid bilayer, referred to as 'lipid rafts'. Without wishing to be bound by theory, lipid rafts may have significant roles in endo and exocytosis, entry or egress of viruses or other infectious agents, intercell signal transduction, interaction with other structural components of the cell or organism, such as intracellular and extracellular matrices.

In plants, influenza VLPs bud from the plasma membrane therefore the lipid composition of the VLPs reflects their origin. The VLPs produced according to the present invention comprise HA of one or more than one type or subtype of influenza, complexed with plant derived lipids. Plant lipids can stimulate specific immune cells and enhance the immune response induced. Plant membranes are made of lipids, phosphatidylcholine (PC) and phosphatidylethanolamine (PE), and also contain glycosphingolipids, saponins, and phytosterols. Additionally, lipid rafts are also found in plant plasma membranes—these microdomains are enriched in sphingolipids and sterols. In plants, a variety of phytosterols are known to occur, including stigmasterol, sitosterol, 24-methylcholesterol and cholesterol (Mongrand et al., 2004).

PC and PE, as well as glycosphingolipids can bind to CD1 molecules expressed by mammalian immune cells such as antigen-presenting cells (APCs) like dendritic cells and macrophages and other cells including B and T lymphocytes in the thymus and liver (Tsuji M., 2006). CD1 molecules are structurally similar to major histocompatibility complex (MHC) molecules of class I and their role is to present glycolipid antigens to NKT cells (Natural Killer T cells). Upon activation, NKT cells activate innate immune cells such as NK cells and dendritic cells and also activate adaptive immune cells like the antibody-producing B cells and T-cells.

A variety of phytosterols may be found in a plasma membrane—the specific complement may vary depending on the species, growth conditions, nutrient resources or pathogen state, to name a few factors. Generally, beta-sitosterol is the most abundant phytosterol.

The phytosterols present in an influenza VLP complexed with a lipid bilayer, such as an plasma-membrane derived envelope may provide for an advantageous vaccine composition. Without wishing to be bound by theory, plant-made VLPs complexed with a lipid bilayer, such as a plasma-membrane derived envelope, may induce a stronger immune reaction than VLPs made in other expression systems, and may be similar to the immune reaction induced by live or attenuated whole virus vaccines.

The VLP as described herein may be complexed with a plant-derived lipid bilayer. In some embodiments the plant-derived lipid bilayer may comprise the envelope of the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a 'plant lipid'. Examples of phytosterols are known in the art, and include, for example, stigmasterol, sitosterol, 24-methylcholesterol and cholesterol—see, for example, Mongrand et al., 2004.

VLPs may be assessed for structure and size by, for example, hemagglutination assay, electron microscopy, or by size exclusion chromatography.

For size exclusion chromatography, total soluble proteins may be extracted from plant tissue by homogenizing (Polytron) sample of frozen-crushed plant material in extraction buffer, and insoluble material removed by centrifugation. Precipitation with PEG may be used. The soluble protein is quantified, and the extract passed through a size exclusion matrix, for example but not limited to Sephacryl™. Following chromatography, fractions may be further analyzed by immunoblot to determine the protein complement of the fraction.

Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guinea pigs, humans and sheep (see also Ito T. et al, 1997, Virology, vol 227, p 493-499; and Medeiros R et al, 2001, Virology, vol 289 p. 74-85).

Correct folding of the expressed virus protein may be important for stability of the protein, formation of multimers, formation of VLPs, function of the virus protein and recognition of the virus protein by an antibody, among other characteristics. Folding and accumulation of a protein may be influenced by one or more factors, including, but not limited to, the sequence of the protein, the relative abundance of the protein, the degree of intracellular crowding, the pH in a cell compartment, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, ClpP, GrpE, ubiquitin, calnexin, and protein disulfide isomerases (see, for example, Macario, A. J. L., *Cold Spring Harbor Laboratory Res.* 25:59-70. 1995; Parsell, D. A. & Lindquist, S. *Ann. Rev. Genet.* 27:437-496 (1993); U.S. Pat. No. 5,232,833). As described herein, chaperone proteins, for example but not limited to Hsp40 and Hsp70 may be used to ensure folding of a virus protein.

Examples of Hsp70 include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin: referred to herein as Hsp71). DnaK from *Escherichia coli*, yeast and other prokaryotes, and BiP and Grp78 from eukaryotes, such as *A. thaliana* (Lin et al. 2001 (Cell Stress and Chaperones 6:201-208). A particular example of an Hsp70 is *A. thaliana* Hsp70 (encoded by Genbank ref: AY120747.1). Hsp70 is capable of specifically binding ATP as well as unfolded polypeptides and peptides, thereby participating in protein folding and unfolding as well as in the assembly and disassembly of protein complexes.

Examples of Hsp40 include DnaJ from prokaryotes such as *E. coli* and mycobacteria and HSJ1, HDJ1 and Hsp40 from eukaryotes, such as alfalfa (Frugis et al., 1999. Plant Molecular Biology 40:397-408). A particular example of an Hsp40 is *M. sativa* MsJ1 (Genbank ref: AJ000995.1). Hsp40 plays a role as a molecular chaperone in protein folding, thermotolerance and DNA replication, among other cellular activities.

Among Hsps, Hsp70 and its co-chaperone, Hsp40, are involved in the stabilization of translating and newly synthesized polypeptides before the synthesis is complete. Without wishing to be bound by theory, Hsp40 binds to the hydrophobic patches of unfolded (nascent or newly transferred) polypeptides, thus facilitating the interaction of Hsp70-ATP complex with the polypeptide. ATP hydrolysis leads to the formation of a stable complex between the polypeptide, Hsp70 and ADP, and release of Hsp40. The association of Hsp70-ADP complex with the hydrophobic patches of the polypeptide prevents their interaction with other hydrophobic patches, preventing the incorrect folding and the formation of aggregates with other proteins (reviewed in Hartl, F U. 1996. Nature 381:571-579).

Native chaperone proteins may be able to facilitate correct folding of low levels of recombinant protein, but as the expression levels increase, the abundance of native chaperones may become a limiting factor. High levels of expression of virus protein in the agroinfiltrated leaves may lead to the accumulation of virus protein in the cytosol, and co-expression of one or more than one chaperone proteins such as Hsp70, Hsp40 or both Hsp70 and Hsp40 may reduce the level of misfolded or aggregated proteins, and increase the number of proteins exhibiting tertiary and quaternary structural characteristics that allow for formation of virus-like particles.

Therefore, the present invention also provides for a method of producing virus protein VLPs in a plant, wherein a first nucleic acid encoding a virus protein is co-expressed with a second nucleic acid encoding a channel protein, for example but not limited to a proton channel protein, and a third nucleic acid encoding a chaperone. The first, second and third nucleic acids may be introduced to the plant in the same step, or may be introduced to the plant sequentially.

The VLP produced within a plant may induce an virus protein comprising plant-specific N-glycans. Therefore, this invention also provides for a VLP comprising virus protein having plant specific N-glycans.

Furthermore, modification of N-glycan in plants is known (see for example WO 2008/151440; WO 2010/006452; or U.S. 60/944,344; which are incorporated herein by reference) and virus protein having modified N-glycans may be produced. Virus protein comprising a modified glycosylation pattern, for example with reduced fucosylated, xylosylated, or both, fucosylated and xylosylated, N-glycans may be obtained, or virus protein having a modified glycosylation pattern may be obtained, wherein the protein lacks fucosylation, xylosylation, or both, and comprises increased galatosylation. Furthermore, modulation of post-translational modifications, for example, the addition of terminal galactose may result in a reduction of fucosylation and xylosylation of the expressed virus protein when compared to a wild-type plant expressing virus protein.

For example, which is not to be considered limiting, the synthesis of virus protein having a modified glycosylation pattern may be achieved by co-expressing the protein of interest along with a nucleotide sequence encoding beta-1.4galactosyltransferase (GalT), for example, but not limited to mammalian GalT, or human GalT however GalT from another sources may also be used. The catalytic domain of GalT may also be fused to a CTS domain (i.e. the cytoplasmic tail, transmembrane domain, stem region) of N-acetylglucosaminyl transferase (GNT1), to produce a GNT1-GalT hybrid enzyme, and the hybrid enzyme may be co-expressed with virus protein. The virus protein may also be co-expressed along with a nucleotide sequence encoding N-acetylglucosaminyltrasnferase III (GnT-III), for example but not limited to mammalian GnT-III or human GnT-III, GnT-III from other sources may also be used. Additionally, a GNT1-GnT-III hybrid enzyme, comprising the CTS of GNT1 fused to GnT-III may also be used.

Therefore the present invention also includes VLP's comprising one or more virus protein having modified N-glycans.

Non-limiting example of sequences that may be used with the present invention to produce modified HA's also include those described in WO 2009/009876; WO 2009/076778; WO 2010/003225; WO 2010/148511; WO 2010/003235; WO 2010/006452 (which are herein incorporated by reference), for example, but not limited to:

H1 protein encoded by the nucleic acid molecule for example from A/Brisbane/59/2007 (H1N1), A/New Caledonia/20/99 (H1N1), A/Solomon Islands 3/2006 (H1N1), /PuertoRico/8/34 (H1N1), A/Brisbane/59/2007 (H1N1), strain;

H2 protein encoded by the nucleic acid molecule may be from the A/Singapore/1/57 (H2N2) strain;

H3 protein encoded by the nucleic acid molecule may be from the A/Brisbane 10/2007 (H3N2), A/Wisconsin/67/2005 (H3N2) strain, A/Victoria/361/2011 (H3N2) or A/Perth/16/2009 (H3N2);

H5 protein encoded by the nucleic acid molecule may be from the A/Anhui/1/2005 (H5N1), A/Indonesia/5/2005 (H5N1), A/Vietnam/1194/2004 (H5N1)

H6 protein encoded by the nucleic acid molecule may be from the A/Teal/HongKong/W312/97 (H6N1) strain;

H7 protein encoded by the nucleic acid molecule may also be from the A/Hangzhou/1/13 (H7N9), A/Equine/Prague/56 (H7N7) strain;

H9 protein encoded by the nucleic acid molecule may be from the A/HongKong/1073/99 (H9N2) strain; HA protein from B subtype encoded by the nucleic acid may be from the B/Florida/4/2006, B/Massachusetts/2/12, B/Malaysia/2506/2004, B/Wisconsin/1/2010, or B/Brisbane/60/2008 strain.

TABLE 3

Examples of constructs that have been prepared as described herein:

| Constr. # | Expression Enhancer | Ampl. Element | Description | Example |
|---|---|---|---|---|
| 1261 | CPMV-HT | | A/New Caledonia/20/1999 (H1N1) | Example 5.1 |
| 859 | CPMV-HT | | A/Puerto Rico/8/1934 (H1N1) | Example 5.2 |

TABLE 3-continued

Examples of constructs that have been prepared as described herein:

| Constr. # | Expression Enhancer | Ampl. Element | Description | Example |
|---|---|---|---|---|
| 1008 | CPMV-HT | BeYDV | B/Brisbane/60/2008 | Example 5.3 |
| 1059 | CPMV-HT | BeYDV | B/Brisbane/60/2008 with deleted proteolytic loop | Example 5.4 |
| 1462 | CPMV-HT | BeYDV | B/Wisconsin/1/2010 | Example 5.5 |
| 1467 | CPMV-HT | BeYDV | B/Wisconsin/1/2010 with deleted proteolytic loop | Example 5.6 |
| 1039 | CPMV-HT | | B/Brisbane/60/2008 with deleted proteolytic loop | Example 5.7 |
| 1029 | CPMV-HT | | B/Brisbane/60/2008 | Example 5.11 |
| 1829 | CPMV-HT+ | | B/Brisbane/60/2008 with deleted proteolytic loop | Example 5.12 |
| 1937 | CPMV-160+ | | B/Brisbane/60/2008 with deleted proteolytic loop | Example 5.13 |
| 1067 | CPMV-HT | | B/Brisbane/60/2008 with deleted proteolytic loop + H1 California TMCT | Example 5.14 |
| 1977 | CPMV-160+ | | B/Brisbane/60/2008 with deleted proteolytic loop + H1 California TMCT | Example 5.14 |
| 1875 | CPMV-HT+ | | B/Brisbane/60/2008 with deleted proteolytic loop + H1 California TMCT | Example 5.19 |
| 676 | CPMV-HT | | H5 A/Indonesia/5/2005 with TETR cleavage site | Example 5.8 |
| 766 | CPMV-HT | | H5 A/Indonesia/5/2005 with TETQ cleavage site | Example 5.9 |
| 928 | CPMV-HT | | H5 A/Indonesia/5/2005 with deleted proteolytic loop | Example 5.10 |
| 489 | CPMV-HT | | H5 A/Indonesia/5/2005 (native) | Example 5.24 |
| 2220 | CPMV-HT+ | | H2 A/Singapore/1/57 (native) | Example 5.27 |
| 2221 | CPMV-HT+ | | H2 A/Singapore/1/57 with deleted proteolytic loop | Example 5.28 |
| 2222 | CPMV-160+ | | H2 A/Singapore/1/57 (native) | Example 5.29 |
| 2223 | CPMV-160+ | | H2 A/Singapore/1/57 with deleted proteolytic loop | Example 5.29 |
| 2019 | CPMV-HT+ | | H3 A/Perth/16/09 (native) | Example 5.30 |
| 2039 | CPMV-HT+ | | H3 A/Perth/16/09 with deleted proteolytic loop | Example 5.31 |
| 2139 | CPMV-160+ | | H3 A/Perth/16/09 (native) | Example 5.30 |
| 2159 | CPMV-160+ | | H3 A/Perth/16/09 with deleted proteolytic loop | Example 5.31 |
| 1819 | CPMV-HT+ | | H3 A/Victoria /361/11 (native) | Example 5.26 |
| 2230 | CPMV-HT+ | | H3 A/Victoria /361/11 with deleted proteolytic loop | Example 5.32 |
| 1800 | CPMV-160+ | | H3 A/Victoria /361/11 (native) | Example 5.25 |
| 2250 | CPMV-160+ | | H3 A/Victoria /361/11 with deleted proteolytic loop | Example 5.32 |
| 2142 | CPMV-HT+ | | H7 A/Hangzhou/1/13 (native) | Example 5.33 |
| 2152 | CPMV-HT+ | | H7 A/Hangzhou/1/13 with deleted proteolytic loop | Example 5.34 |
| 2224 | CPMV-HT+ | | H9 A/Hong Kong/1073/99 (native) | Example 5.35 |
| 2225 | CPMV-HT+ | | H9 A/Hong Kong/1073/99 with deleted proteolytic loop | Example 5.36 |
| 2226 | CPMV-160+ | | H9 A/Hong Kong/1073/99 (native) | Example 5.35 |
| 2227 | CPMV-160+ | | H9 A/Hong Kong/1073/99 with deleted proteolytic loop | Example 5.36 |
| 2013 | CPMV-160+ | | B/Malaysia/2506/04 (native) | Example 5.37 |
| 2014 | CPMV-160+ | | B/Malaysia/2506/04 with deleted proteolytic loop | Example 5.38 |
| 2070 | CPMV-HT | | B/Massachusetts/2/12 (native) | Example 5.39 |
| 2072 | CPMV-HT | | B/Massachusetts/2/12 with deleted proteolytic loop | Example 5.15 |
| 2080 | CPMV-HT+ | | B/Massachusetts/2/12 (native) | Example 5.39 |
| 2052 | CPMV-HT+ | | B/Massachusetts/2/12 with deleted proteolytic loop | Example 5.20 |
| 2090 | CPMV-160+ | | B/Massachusetts/2/12 (native) | Example 5.39 |
| 2050 | CPMV-160+ | | B/Massachusetts/2/12 with deleted proteolytic loop | Example 5.15 |
| 2074 | CPMV HT | | HA B/Massachusetts/2/12 (PrL−) + H1 California TMCT | Example 5.16 |
| 2060 | CPMV-160+ | | HA B/Massachusetts/2/12 (PrL−) + H1 California TMCT | Example 5.16 |
| 2062 | CPMV-HT+ | | HA B/Massachusetts/2/12 (PrL−) + H1 California TMCT | Example 5.21 |
| 1445 | CPMV HT | | B/Wisconsin/1/2010 with deleted proteolytic loop (PrL−) | Example 5.17 |
| 1839 | CPMV-HT+ | | B/Wisconsin/1/2010 with deleted proteolytic loop (PrL−) | Example 5.22 |

TABLE 3-continued

Examples of constructs that have been prepared as described herein:

| Constr. # | Expression Enhancer | Ampl. Element | Description | Example |
|---|---|---|---|---|
| 1820 | CPMV160+ | | B/Wisconsin/1/2010 with deleted proteolytic loop (PrL−) | Example 5.17 |
| 1975 | CPMV160 | | B/Wisconsin/1/2010 with deleted proteolytic loop (PrL−) | Example 5.17 |
| 1454 | CPMV-HT | | HA B Wisconsin with deleted proteolytic loop (PrL−) + H1 California TMCT | Example 5.18 |
| 1893 | CPMV-160+ | | HA B Wisconsin with deleted proteolytic loop (PrL−) + H1 California TMCT | Example 5.18 |
| 1860 | CPMV-HT+ | | HA B Wisconsin with deleted proteolytic loop (PrL−) + H1 California TMCT | Example 5.23 |
| 2102 | CPMV-HT+ | | B Florida with deleted proteolytic loop (PrL−) | Example 5.40 |
| 2104 | CPMV-HT+ | BeYDV | B Florida with deleted proteolytic loop (PrL−) | Example 5.40 |
| 2016 | CPMV-HT+ | | B Florida + H1 California TMCT with deleted proteolytic loop (PrL−) | Example 5.41 |
| 2108 | CPMV-HT+ | BeYDV | B Florida + H1 California TMCT with deleted proteolytic loop (PrL−) | Example 5.41 |

TABLE 4

Description of sequences

| SEQ ID NO: | Description | FIG. |
|---|---|---|
| 1 | Avian H5 proteolytic loop consensus sequence | |
| 2 | IF-HSA-I-05.si + 3c | 1A |
| 3 | IF-H5dTm.r | 1B |
| 4 | Construct 1191 | 1D |
| 5 | Cassette 489 | 1E |
| 6 | Amino acid sequence H5 A/Indonesia/5/2005 (H5N1) | 1F |
| 7 | IF-S1-M1 + M2ANC.c | 2A |
| 8 | IF-S1-4 − M2ANC.r | 2B |
| 9 | Synthetic M2 (nt 1-26 joined to 715-982 from DQ508860) | 2C |
| 10 | Cassette 1261 | 2D |
| 11 | M2 from influenza A/ New Caledonia/20/1999 (H1N1) | 2E |
| 12 | Synthetic M2 (nt 26-51 joined to nt 740-1007 from EF467824) | 3A |
| 13 | Cassette 859 | 3B |
| 14 | Amino acid sequence M2 influenza A/ Puerto Rico/8/1934 (H1N1) | 3C |
| 15 | Cassette 1039 | 8A |
| 16 | Amino acid sequence B/Brisbane/60/2008 | 21A |
| 17 | Amino acid sequence delta-proteolytic loop of type B HA (with linker GG) | 21B |
| 18 | Amino acid sequence replacing cleavage site of B HA with linker | 21C |
| 19 | Amino acid sequence H3 A/Perth/16/2009 | 21D |
| 20 | Aminoa cid sequence delta-proteolytic loop H3 (with linker GS) | 21E |
| 21 | Amino acid sequence Replacing cleavage site of H3 with linker | 21F |

TABLE 4-continued

Description of sequences

| SEQ ID NO: | Description | FIG. |
|---|---|---|
| 22 | H1 New Cal linker region | 15 |
| 23 | H1 Brisbane linker region | 15 |
| 24 | H1 Sol Islands linker region | 15 |
| 25 | H2A Singapore linker region | 15 |
| 26 | H3A Brisbane linker region | 15 |
| 27 | H3A WCN linker region | 15 |
| 28 | H5 Anhui linker region | 15 |
| 29 | H5 Indo linker region | 15 |
| 30 | H5 Vietnam linker region | 15 |
| 31 | Construct 1194 | 4B |
| 32 | Cassette 1008 | 4C |
| 33 | H6 Teal HK linker region | 15 |
| 34 | H7 Eq Prague linker region | 15 |
| 35 | H9A HK linker region | 15 |
| 36 | B Florida linker region | 15 |
| 37 | B Malaysia | 15 |
| 38 | 1039 + 1059.r | 5A |
| 39 | 1039 + 1059.c | 5B |
| 40 | Cassette 1059 | 5C |
| 41 | Amino acid sequence PDISP/HA influenza B/Brisbane/60/2008 (deleted proteolytic loop) | 5D |
| 42 | Nucleotide sequence H5 A/Indonesia/5/2005 (H5N1) | 1G |
| 43 | nucleotide sequence PDISP/HA influenza B/ Brisbane/60/2008 (deleted proteolytic loop) | 5E |
| 44 | H5/Indo cleavage site natural sequence | 19 |
| 45 | H5/Indo modified cleavage site (TETR) | 19 |
| 46 | H5/Indo modified cleavage site (TETQ) | 19 |
| 47 | H1 cleavage site | Table 1 |
| 48 | H3 cleavage site | Table 1 |
| 49 | IF-HAB110.S1 + 3c | 6A |
| 50 | IF-HAB110.s1 − 4r | 6B |
| 51 | Synthetic HA B Wisconsin | 6C |
| 52 | Construct 193 | 6E |
| 53 | Cassette 1462 | 6F |

TABLE 4-continued

Description of sequences

| SEQ ID NO: | Description | FIG. |
|---|---|---|
| 54 | Amino acid sequence HA influenza B/ Wisconsin/1/2010 | 6G |
| 55 | HAB110(PrL−).r | 7A |
| 56 | HAB110(PrL−).c | 7B |
| 57 | Cassette 1467 | 7C |
| 58 | Amino acid sequence HA influenza B/ Wisconsin/1/2010 (deleted PL) | 7D |
| 59 | B cleavage site | Table 1 |
| 60 | H5/Indo natural cleavage site | Table 2 |
| 61 | H5/Indo modified cleavage site | Table 2 |
| 62 | H5/Indo modified cleavage site | Table 2 |
| 63 | H1/Brisbane modified cleavage site | Table 2 |
| 64 | H3/Brisbane modified cleavage site | Table 2 |
| 65 | B/Florida, B/Brisbane modified cleavage site | Table 2 |
| 66 | A/H3/HA0 Consensus | |
| 67 | A/H1/HA0 Consensus | |
| 68 | B/HA0 Consensus | |
| 69 | H5 Anhui proteolytic loop deletion | 18C |
| 70 | H5 Indo proteolytic loop deletion | 18C |
| 71 | H5 Vietnam proteolytic loop deletion | 18C |
| 72 | B Florida proteolytic loop deletion | 18C |
| 73 | B Malaysia proteolytic loop deletion | 18C |
| 74 | MutCleavage-H5(Indo).r | 23A |
| 75 | MutCleavage-H5(Indo).c | 23B |
| 76 | Cassette 676 | 23C |
| 77 | Amino acid sequence influenza A/ Indonesia/5/2005 (H5N1) TETR cleavage site mutant. | 23D |
| 78 | H5I505_TETQ.r | 24A |
| 79 | H5I505_TETQ.c | 24B |
| 80 | Cassette 766 | 25C |
| 81 | Amino acid sequence influenza A/ Indonesia/5/2005 (H5N1) TETQ cleavage site mutant. | 25D |
| 82 | H5I505(PrL−).r | 26A |
| 83 | H5I505(PrL−).c | 26B |
| 84 | Cassette 928 | 26C |
| 85 | Amino acid sequence influenza A/ Indonesia/5/2005 (H5N1) with deleted proteolytic loop. | 26D |
| 86 | IF-S2 + S4-B Bris.c | 30A |
| 87 | IF-S1a4-B Bris.r | 30B |
| 88 | Synthesized HA B Brisbane gene | 30C |
| 89 | Construct 1029 | 30D |
| 90 | Amino acid sequence of PDISP/HA from influenza B/ Brisbane/60/2008 | 30E |
| 91 | Nucleotide sequence of PDISP/HA B Brisbane (PrL−). | 31A |
| 92 | Amino acid sequence of PDISP/HA B Brisbane (PrL−) | 31B |
| 93 | Nucleotide sequence of CPMVX/CPMVX+ | |
| 94 | consensus amino acid sequence of transmembrane domain | |
| 95 | Nucleotide sequence of PDISP/HA B Brisbane (PrL−) + H1 California TMCT. | 33A |
| 96 | Amino acid sequence of PDISP/HA B Brisbane (PrL−) + H1 California TMCT. | 33B |
| 97 | Nucleotide sequence of PDISP/HA B Massachussetts (PrL) | 34A |
| 98 | Amino acid sequence of PDISP/HA B Massachussetts (PrL) | 34B |
| 99 | Nucleotide sequence of PDISP/HA B Massachussetts (PrL) + H1 California TMCT. | 35A |
| 100 | Amino acid sequence of PDISP/HA B Massachussetts (PrL−) + H1 California TMCT. | 35B |
| 101 | Nucleotide sequence of HA B Wisconsin (PrL−). | 36A |
| 102 | Amino acid sequence of HA B Wisconsin (PrL−). | 36B |
| 103 | Nucleotide sequence of HA B Wisconsin (PrL−) + H1 California TMCT | 37A |
| 104 | Amino acid sequence of HA B Wisconsin (PrL−) + H1 California TMC. | 37B |
| 105 | Nucleotide sequence of PDISP/HA B Brisbane (PrL−) + H1 California TMCT. | 38A |
| 106 | Amino acid sequence of PDISP/HA B Brisbane (PrL−) + H1 California TMCT. | 38B |
| 107 | Nucleotide sequence of PDISP/HA B Massachussetts (PrL−). | 39A |
| 108 | Amino acid sequence of PDISP/HA B Massachussetts (PrL−). | 39B |
| 109 | Nucleotide sequence of PDISP/HA B Massachussetts (PrL−) + H1 California TMCT. | 40A |
| 110 | Amino acid sequence of PDISP/HA B Massachussetts (PrL−) + H1 California TMCT. | 40B |
| 111 | Nucleotide sequence of HA B Wisconsin (PrL−). | 41A |
| 112 | Amino acid sequence of HA B Wisconsin (PrL−). | 41B |
| 113 | Nucleotide sequence of HA B Wisconsin (PrL−) + H1 California TMCT | 42A |
| 114 | Amino acid sequence of HA B Wisconsin (PrL−) + H1 California TMC. | 42B |
| 115 | Nucleotide sequence of native H5 Indonesia. | 43A |

TABLE 4-continued

Description of sequences

| SEQ ID NO: | Description | FIG. |
|---|---|---|
| 116 | Amino acid sequence of native H5 Indonesia | 43B |
| 117 | IF**(SacII)-PDI.s1 + 4c | 44A |
| 118 | IF-H3V36111.s1 − 4r | 44B |
| 119 | Nucleotide sequence of PDISP/H3 Victoria. | 44C |
| 120 | Construct 2171 | 44E |
| 121 | Construct 1800 | 44F |
| 122 | Amino acid sequence of PDISP/H3 Victoria | 44G |
| 123 | IF(SacID-Kozac_PDI.c | 45A |
| 124 | IF-H3V36111.s1 − 4r | 45B |
| 125 | Construct 2181 | 45D |
| 126 | Construct 1819 | 45E |
| 127 | IF**-H2S157.s1 − 6r | 48A |
| 128 | Nucleotide sequence of PDISP/H2 Singapore. | 48B |
| 129 | Expression cassette number 2220 | 48C |
| 130 | Amino acid sequence of PDISP/H2 Singapore | 48D |
| 131 | H2S157(Prl−).r | 49A |
| 132 | H2S157(Prl−).c | 49B |
| 133 | Expression cassette number 2221 | 49C |
| 134 | Amino acid sequence of PDISP/H2 Singapore with deleted proteolytic loop | 49D |
| 135 | Expression cassette number 2222 | 50A |
| 136 | Expression cassette number 2223 | 50B |
| 137 | Nucleotide sequence of PDISP/H3 Perth | 51A |
| 138 | IF**-H3P1609.S1 − 6r | 51B |
| 139 | Amino acid sequence of PDISP/H3 Perth | 51C |
| 140 | Nucleotide sequence of PDISP/H3 Perth with deleted proteolytic loop | 52A |
| 141 | H3P1609(Prl−)#2.r | 52B |
| 142 | H3P1609(Prl−)#2.c | 52C |
| 143 | Amino acid sequence of PDISP/H3 Perth with deleted proteolytic loop | 52D |
| 144 | Nucleotide sequence of PDISP/H3 Victoria with deleted proteolytic loop | 53A |
| 145 | H3V36111(Prl−).r | 53B |
| 146 | H3V36111(Prl−).c | 53C |
| 147 | Amino acid sequence of PDISP/H3 Victoria with deleted proteolytic loop | 53D |
| 148 | Nucleotide sequence of PDISP/H7 Hangzhou | 54A |
| 149 | IF*-H7H113.s1 − 6r | 54B |
| 150 | Amino acid sequence of PDISP/H7 Hangzhou | 54C |
| 151 | Nucleotide sequence of PDISP/H7 Hangzhou with deleted proteolytic loop | 55A |
| 152 | H7H113(PrL−).r | 55B |
| 153 | H7H113(PrL−).c | 55C |
| 154 | Amino acid sequence of PDISP/H7 Hangzhou with deleted proteolytic loop | 55D |
| 155 | Nucleotide sequence of PDISP/H9 Hong Kong | 56A |
| 156 | IF* *-H9HK107399. S1 − 6r | 56B |
| 157 | Amino acid sequence of PDISP/H9 Hong Kong | 56C |
| 158 | Nucleotide sequence of PDISP/H9 Hong Kong with deleted proteolytic loop | 57A |

TABLE 4-continued

Description of sequences

| SEQ ID NO: | Description | FIG. |
|---|---|---|
| 159 | H9HK107399(Prl−).r | 57B |
| 160 | H9HK107399(Prl−).c | 57C |
| 161 | Amino acid sequence of PDISP/H9 Hong Kong with deleted proteolytic loop | 57D |
| 162 | Nucleotide sequence of PDISP/HA B Malaysia | 58A |
| 163 | IF**-HBM250604.S1 − 6r | 58B |
| 164 | Amino acid sequence of PDISP/HA B Malaysia | 58C |
| 165 | Nucleotide sequence of PDISP/HA B Malaysia with deleted proteolytic loop | 59A |
| 166 | HBM250604(PrL−).r | 59B |
| 167 | HBM250604(PrL−).c | 59C |
| 168 | Amino acid sequence of PDISP/HA B Malaysia with deleted proteolytic loop | 59D |
| 169 | Nucleotide sequence of PDISP/HA B Massachusetts | 60A |
| 170 | Amino acid sequence of PDISP/HA B Massachusetts | 60B |
| 171 | nucleotide sequence of PatA SP | |
| 172 | amino acid sequence of patatin A signal peptide | |
| 173 | CPMV HT sequence | |
| 174 | Plant consensus kozak sequence-plant kingdom | |
| 175 | Plant consensus kozak sequence-dicots | |
| 176 | Plant consensus kozak sequence-arabidopsis | |
| 177 | Plant consensus kozak sequence | |
| 178 | Plant consensus kozak sequence | |
| 179 | Plant consensus kozak sequence | |
| 180 | Plant consensus kozak sequence | |
| 181 | Plant consensus kozak sequence | |
| 182 | Plant consensus kozak sequence | |
| 183 | Plant consensus kozak sequence | |
| 184 | Plant consensus kozak sequence | |
| 185 | Plant consensus kozak sequence | |
| 186 | Kozak consensus sequence | |
| 187 | Nucleotide sequence of CPMV HT+ | |
| 188 | Nucleotide sequence of CPMV HT + 511 | |
| 189 | Nucleotide sequence ofCPMV HT + [WT115] | |
| 190 | HBF406(PrL−).r | 61A |
| 191 | HBF406(PrL−).c | 61B |
| 192 | IF*-HBF406.s1 − 6r | 61C |
| 193 | Nucleotide sequence of PDISP/HA B Florida with deleted proteolytic loop | 61D |
| 194 | Amino acid sequence of PDISP/HA B Florida with deleted proteolytic loop | 61E |
| 195 | Expression cassette number 2102 | 61F |
| 196 | Expression cassette number 2104 | 61H |
| 197 | IF-H1cTMCT.S1 − 4r | 62A |
| 198 | Nucleotide sequence of PDISP/HA B Florida + H1Cal | 62B |

TABLE 4-continued

| Description of sequences | | |
|---|---|---|
| SEQ ID NO: | Description | FIG. |
| | TMCT with deleted proteolytic loop | |
| 199 | Amino acid sequence of PDISP/HA B Florida + H1Cal TMCT with deleted proteolytic loop | 62C |
| 200 | Expression cassette number 2106 | 62D |
| 201 | Expression cassette number 2108 | 62F |

EXAMPLES

Example 1

*Agrobacterium* Transfection

*Agrobacterium* strain AGL1 was transfected by electroporation with the DNA constructs using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

The terms "biomass" and "plant matter" as used herein are meant to reflect any material derived from a plant. Biomass or plant matter may comprise an entire plant, tissue, cells, or any fraction thereof. Further, biomass or plant matter may comprise intracellular plant components, extracellular plant components, liquid or solid extracts of plants, or a combination thereof. Further, biomass or plant matter may comprise plants, plant cells, tissue, a liquid extract, or a combination thereof, from plant leaves, stems, fruit, roots or a combination thereof. A portion of a plant may comprise plant matter or biomass.

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

*Agrobacteria* transfected with each construct were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 2-6 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 3 volumes of cold 50 mM Tris pH 8.0, 0.5 M NaCl, 0.1% Triton X-100 and 1 mM phenylmethanesulfonyl fluoride. After homogenization, the slurries were centrifuged at 10,000 g for 10 min at 4° C. and these clarified crude extracts (supernatant) kept for analyses.

Protein Analysis and Immunoblotting

The total protein content of clarified crude extracts was determined by the Bradford assay (Bio-Rad, Hercules, Calif.) using bovine serum albumin as the reference standard. Proteins were separated by SDS-PAGE and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Immunoblotting was performed with a first incubation with a primary antibody (Table 4 presents the antibodies and conditions used for the detection of each HA), in 2 μg/ml in 2% skim milk in TBS-Tween 20 0.1%. Secondary antibodies used for chemiluminescence detection were as indicated in Table 4, diluted as indicated in 2% skim milk in TBS-Tween 20 0.1%. Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

TABLE 4

Electrophoresis conditions, antibodies, and dilutions for immunoblotting of expressed proteins.

| HA subtype | Influenza strain | Electrophoresis condition | Primary antibody | Dilution | Secondary antibody | Dilution |
|---|---|---|---|---|---|---|
| B | B/Brisbane/60/2008 | Non-reducing | TGA, AS397 | 1:20000 | Rabbit anti-sheep (JIR 313-035-045) | 1:10 000 |
| B | B/Wisconsin/1/2010 | Non-reducing | NIBSC 07/356 | 1:2000 | Rabbit anti-sheep (JIR 313-035-045) | 1:10 000 |
| B | B/Malaysia/2506/2004 | Non-reducing | NIBSC 07/184 | 1:2000 | Rabbit anti-sheep (JIR 313-035-045) | 1:10 000 |
| H3 | A/Perth/16/2009 (H3N2) | Non-reducing | TGA, AS400 | 1:20000 | Rabbit anti-sheep (JIR 313-035-045) | 1:10 000 |
| H3 | A/Victoria/361/2011 | Non-reducing | TGA, AS400 | 1:20000 | Rabbit anti-sheep (JIR 313-035-045) | 1:10 000 |

TABLE 4-continued

Electrophoresis conditions, antibodies, and dilutions for immunoblotting of expressed proteins.

| HA subtype | Influenza strain | Electro-phoresis condition | Primary antibody | Dilution | Secondary antibody | Dilution |
|---|---|---|---|---|---|---|
| H1 | A/California/07/2009 (H1N1) | Reducing | Sino, 11055-MMO1 | 1 μg/ml | Goat anti-mouse (JIR 115-035-146) | 1:7 500 |
| H5 | A/Indonesia/05/2005 (H5N1) | Reducing | CBER, S-7858 | 1:4000 | Rabbit anti-sheep (JIR 313-035-045) | 1:10 000 |

JIR: Jackson ImmunoResearch, West Grove, PA, USA;
CBER: Center for Biologics Evaluation and Research, Rockville, MD, USA.
Sino: Sino Biological inc., Beijing, China.
TGA: Therapeutic Goods Administration, Australia.
NIBSC: National Institute for Biological Standards and Control, United Kingdom Hemagglutination Assay Hemagglutination assay was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as HA activity. In parallel, a recombinant HA standard (A/Vietnam/1203/2004 H5N1) (Protein Science Corporation, Meriden, Conn.) was diluted in PBS and run as a control on each plate.

VLP Extraction by Cell Wall Digestion

Leaf tissue was collected from the *Nicotiana benthamiana* plants and cut into ~1 $cm^2$ pieces. The leaf pieces were soaked in 500 mM mannitol for 30 minutes at room temperature (RT). The mannitol solution was then removed and changed with the enzyme mix (mixture of cellulases from *Trichoderma viride* (Onozuka R-10; 3% v/v) and a mixture of pectinases from *Rhizopus* sp. (MACEROZYME™; 0.75% v/v; both from Yakult Pharmaceuticals) in protoplasting solution (500 mM mannitol, 10 mM $CaCl_2$ and 5 mM MES/KOH (pH 5.6)). The ratio used was 20 g of leaf pieces per 100 mL solution. This preparation was spread evenly into a shallow vessel (~11×18 cm) and incubated for 16 hours on a rotary shaker at 40 rpm and 26° C.

Alternately, VLP extraction may be performed as follows: plants were agroinfiltrated with AGL1/#489, 928, 676 and 766. Leaf tissue was collected from the *N. benthamiana* plants at day 7 post-infiltration and cut into ~1 $cm^2$ pieces. Pectinase 162 L (Biocatalysts), Multifect CX CG and Multifect CX B (Genencor) were added to a 200 mM Mannitol, 75 mM Citrate, 0.04% sodium bisulfite pH 6.0 buffer; digestion buffer. The biomasses were digested in duplicate overnight at room temperature in an orbital shaker.

Following enzyme-assisted extraction, leaf debris was removed by filtration (nylon filter of 250 or 400 μm mesh). The coarse filtered extract was centrifuged at 5000×g for 5 minutes. Supernatant was submitted to detection of HA expression (hemagglutination activity (see FIG. 20) and Western blotting (see FIG. 22).

Example 2

Effect of Modified Proteolytic Loop on Accumulation of HA

As shown in FIG. 13A, expression of native B/Brisbane (Construct No: 1008) was lower than the expression of B/Brisbane comprising a modified proteolytic loop (Construct No: 1059). Increased hemagglutination activity was also observed with B/Brisbane comprising a modified proteolytic loop (Construct No: 1059) when compared to the native B/Brisbane HA (Construct No: 1008; FIG. 13B).

Figures 16A, 16B:
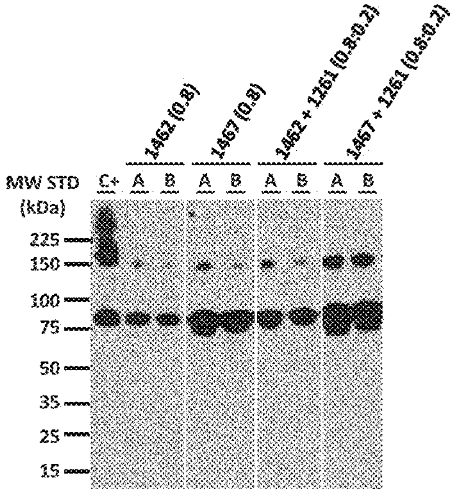
FIG. 16A shows a Western blot analysis of HA protein expression in agroinfiltrated *Nicotiana benthamiana* leaves. HA from B/Wisconsin/1/2010 is co-expressed with M2 from A/New Caledonia/20/99. Ten micrograms of protein extract were loaded per lane. “C+”: positive control, semi-purified B/Wisconsin/1/2010 virus from the National Institute for Biological Standards and Control, United Kingdom; “1462”: expression of wild-type HA from B/Wisconsin/1/2010 in the presence of amplification elements (BeYDV); “1467”: expression of the mutant HA from B/Wisconsin/1/2010 in the presence of amplification elements (BeYDV); “1462+1261”: co-expression of wild-type HA from B/Wisconsin/1/2010 in the presence of amplification elements (BeYDV) with M2; “1467+1261”: co-expression of the mutant HA from B/Wisconsin/1/2010 in the presence of amplification elements (BeYDV) with M2. Ratios indicate the optical density for each *Agrobacterium* culture used in expression and co-expression experiments.
FIG. 16B shows a comparison of hemagglutination capacity of crude protein extracts from plants transformed with AGL1/1462, AGL1/1467, AGL1/1462+AGL1/1261 and AGL1/1467+AGL1/1261.

Similar results were observed in the accumulation level of B/Wisconsin comprising a modified proteolytic loop (Construct No: 1467), which is greater than that observed for the native B/Wisconsin HA (Construct No: 1462; FIG. 16A). Increased hemagglutination activity was also observed with B/Wisconsin comprising a modified proteolytic loop (Construct No: 1467) when compared to the native B/Wisconsin HA (Construct No: 1462; FIG. 16B) indicating a greater accumulation for the mutant protein.

Figure 22:
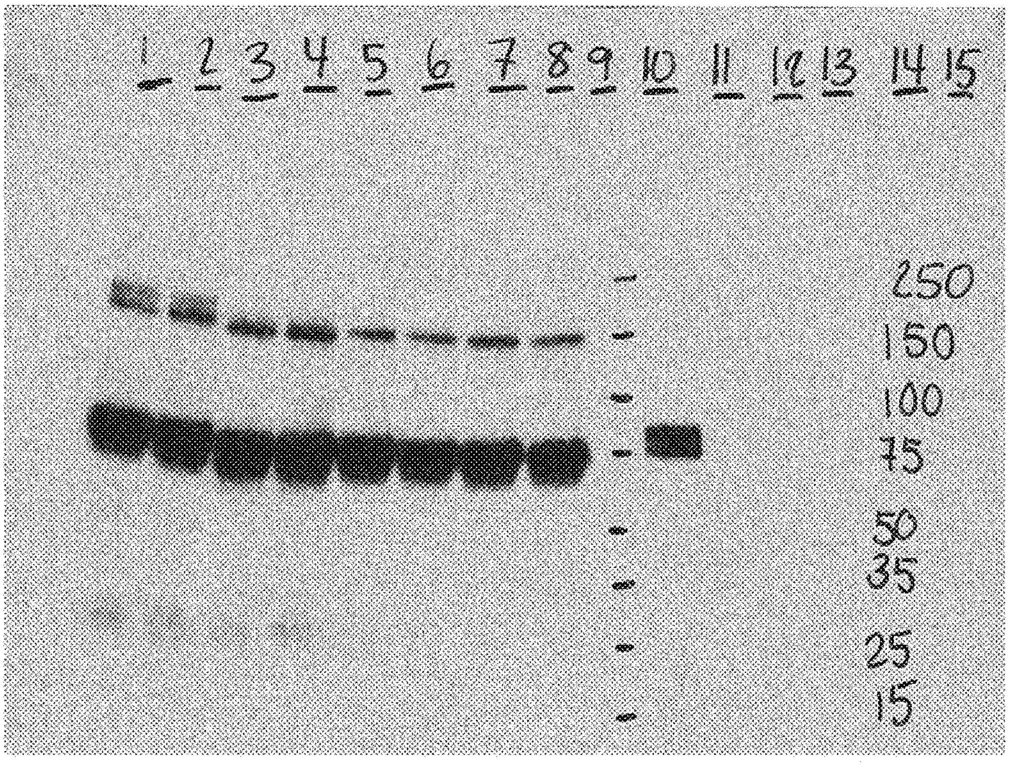
FIG. 22 shows a Western blot analysis of HA protein expression in agroinfiltrated *Nicotiana benthamiana* leaves. HA from H5/Indo. Upper panel listing of components loaded in each lane; lower panel Western blot. C: Recombinant H5 Indonesia/5/05 S-STD-0002; primary antibody: Anti-HA A/Indonesia/05/2005 CBER #S-BIO-0003 1/50 000; blot. Lanes 1 and 2: H5/Indo control (construct 489); lanes 3 and 4 H5/Indo proteolytic loop replaced with GG linker (construct 928); lanes 5 and 6 H5/Indo proteolytic loop replaced with TETR linker (construct 676); lanes 7 and 8 H5/Indo proteolytic loop replaced with TETQ linker (construct 766); lane 9 MW marker; lane 10 H5 control.

Expression of H5/Indo comprising a modified proteolytic loop was also observed with modifications including a proteolytic loop comprising a GG linker (Construct No: 928; SEQ ID NO:85), a TETR linker (Construct No: 676; SEQ ID NO:77), or a TETQ linker (Construct No: 766; SEQ ID NO: 8; FIG. 22).

Effect of Influenza M2 Co-Expression on the Accumulation Level of HA

The co-expression of M2 was evaluated for its impact on the accumulation level of a modified influenza B HA. Construct no. 1059 encodes an influenza B HA in which the proteolytic loop is replaced by a 2 amino acid linker (GG in place of aa 341-359). The results from western blot analysis presented in FIG. 13A show that the removal of the proteolytic loop resulted in increased influenza B HA accumulation level (compare 1008 with 1059) and that the co-expression of M2 with the modified influenza B HA also increased HA accumulation level (FIG. 13A, 1059 vs 1059+1261). An analysis of hemagglutination activity on crude protein extracts from plants transformed with influenza B HA with or without modification and with or without co-expression of M2 confirmed the positive effect of M2 co-expression on the accumulation level of the native influenza B HA (FIG. 13B, 1008 vs 1008+1261) and the modified influenza B HA (FIG. 13B, 1059 vs 1059+1261).

Co-expression of M2 with type A HA comprising a modified proteolytic loop also resulted in HA expression. For example, co-expression of modified H3, with the proteolytic loop replaced with a GS linker or a $(GSS)_3$ linker (see FIG. 21E, 21F), along with M2 may also result in HA accumulation in a plant.

The efficacy of M2 from influenza A/Puerto Rico/8/1934 to increase accumulation of the modified influenza B HA and H3 was compared to that of M2 from influenza A/New Caledonia/20/1999. For the modified influenza B HA, the comparison was undertaken by western blot analysis of protein extracts from plants transformed with constructs 1059, 1059+1261 and 1059+859. The results obtained demonstrated that the co-expression of M2 from influenza A/Puerto Rico/8/1934 (encoded by construct no. 859) was as efficient as the co-expression of M2 from influenza A/New Caledonia/20/1999 (encoded by construct no. 1261) for increasing accumulation of the modified influenza B HA (FIG. 14).

Effect of Influenza M2 Co-Expression on the Accumulation Level of Different Strains of B HA Western blot analysis of protein extracts from plants transformed with gene constructs driving the expression of influenza B HA (from B/Wisconsin/1/2010) (constructs no. 1462) in the presence or absence of M2-expression construct (construct no. 1261) showed that M2 co-expression results in increased accumulation of influenza B HA (FIG. 16A).

The co-expression of M2 was also evaluated for its impact on the accumulation level of a modified influenza B HA. Construct no. 1467 encodes an influenza B HA in which the proteolytic loop is replaced by a 2 amino acid linker (GG in place of aa 341-359). The results from western blot analysis presented in FIG. 16A show that the removal of the proteolytic loop resulted in increased influenza B HA accumulation level (compare 1462 with 1467) and that the co-expression of M2 with the modified influenza B HA also increased HA accumulation level (FIG. 16A, 1467 vs 1467+1261). An analysis of hemagglutination activity on crude protein extracts from plants transformed with influenza B HA with or without modification and with or without co-expression of M2 confirmed the positive effect of M2 co-expression on the accumulation level of the native influenza B HA (FIG. 16B, 1462 vs 1462+1261) and the modified influenza B HA (FIG. 16B, 1467 vs 1467+1261).

Effect of Amplification Element BeYDV and Modified Proteolytic Loop on Accumulation of HA Western blot analysis of protein extracts from plants transformed with gene constructs driving the expression of modified influenza B HA (from B/Brisbane/60/2008) with or without the proteolytic loop removed (see FIG. 17A for constructs) and in the presence or absence of the amplification element BeYDV (construct no. 1059 and 1039) showed that in the absence of BeYDV no accumulation of influenza B HA could be detected (FIG. 17B), when the regulatory element was CPMV-HT.

Effect of Modified Proteolytic Loop on Relative HA Titer and Hemagglutination

With reference to FIG. 29A, there is shown a comparison of the activity of modified HA proteins produced in plants comprising CPMV HT, CPMV HT+, CPMV 160 or CPMV160+, based enhancer elements operatively linked with a nucleotide sequence encoding either modified HA with the proteolytic loop deleted (replaced with a GG linker) or a native HA. In most cases, the expression (determined as hemagglutination titrer or activity) were higher for the CPMV HT+, CPMV 160 or CPMV160+ based construct demonstrates significant expression levels.

TABLE 5a

Relative HA titer (wt HA = 1) (see FIG. 29A)

| | Fct = 1 | | | | | |
|---|---|---|---|---|---|---|
| | wt | | | PrL− | | |
| Description (n=) | GM | MD | n= | GM | MD | n= |
| H2 Sin157 (HT+) (n = 2) | 1.0 | 0.4 | 2 | 1.2 | 0.1 | 2 |
| H2 Sin157 (160+) (n = 2) | 1.0 | 0.3 | 2 | 1.9 | 0.9 | 2 |

TABLE 5a-continued

Relative HA titer (wt HA = 1) (see FIG. 29A)

| | Fct = 1 | | | | | |
|---|---|---|---|---|---|---|
| | wt | | | PrL− | | |
| Description (n=) | GM | MD | n= | GM | MD | n= |
| H3 Per1609 (HT+) (n = 4) | 1.0 | 0.0 | 4 | 4.9 | 4.2 | 4 |
| H3 Per1609 (160+) (n = 4) | 1.0 | 0.3 | 4 | 6.1 | 3.6 | 4 |
| H3 Vic36111 (HT+) (n = 6) | 1.0 | 0.3 | 6 | 0.9 | 0.3 | 6 |
| H3 Vic36111 (160+) (n = 6) | 1.0 | 0.3 | 6 | 1.2 | 0.4 | 6 |
| H5 Indo505 (HT) (n = 3) | 1.0 | 0.1 | 3 | 1.2 | 0.3 | 3 |
| H7 Han113 (HT+) (n = 5) | 1.0 | 0.2 | 5 | 1.0 | 0.1 | 5 |
| H9 HK107399 (HT+) (n = 2) | 1.0 | 0.4 | 2 | 1.2 | 0.2 | 2 |
| H9 HK107399 (160+) (n = 2) | 1.0 | 0.2 | 2 | 0.7 | 0.1 | 2 |
| HB Bri6008 (HT) (n =1) | 1.0 | 0.6 | 1 | 0.6 | 0.1 | 1 |
| HB Mal250604 (160+) (n = 2) | 1.0 | 0.3 | 2 | 8.4 | 2.4 | 2 |
| HB Mas212 (HT) (n = 3) | 1.0 | 0.1 | 3 | 1.4 | 1.3 | 3 |
| HB Mas212 (HT+) (n = 3) | 1.0 | 0.6 | 3 | 6.7 | 3.5 | 3 |
| HB Mas212 (160+) (n = 2) | 1.0 | 0.8 | 2 | 11.5 | 4.2 | 2 |

Example 3

Increased H7 Hangzhou HA VLP Yields when the Proteolytic Loop is Removed (PrL-) Compared to the Native Construct.

*N. benthamiana* plants were infiltrated with AGL1/#2142+1261 and #2152+1261 and the leaves were harvested after a seven-day incubation period. Leaf tissue was collected and cut into ~1 $cm^2$ pieces. Pectinase 162 L and Pectinase 444 L (Biocatalysts), Multifect CX CG and Multifect CX B (Genencor) were added in a 200 mM Mannitol, 125 mM Citrate, 0.04% sodium bisulfite pH 6.0 buffer. The biomass was digested overnight at room temperature in an orbital shaker.

Following digestion, the apoplastic fraction was filtered through a 400 μm nylon filter to remove coarse undigested vegetal tissue (<5% of starting biomass). The filtered extract was then centrifuged at room temperature for 15 min at 5000×g to remove protoplasts and intracellular contaminants (proteins, DNA, membranes, vesicles, pigments, etc). Next, the supernatant was depth-filtered (for clarification) using a 1.2 μm glass fiber filter (Sartopore GF plus/Sartorius Stedim), and a 0.45/0.2 μm filter (Sartopore 2/Sartorius Stedim), before being subjected to chromatography.

The clarified apoplastic fraction was loaded over a cation exchange column (Poros HS Applied Biosystems) equilibrated with an equilibration/elution buffer (50 mM NaPO4, 100 mM NaCl, 0.005% Tween 80 pH 6.0). Once the UV was back to zero, the extract was step-eluted with the equilibration/elution buffer containing increasing concentrations of NaCl (500 mM). The purified VLPs were concentrated by TFF, diafiltered against formulation buffer (100 mM PO4, 150 mM NaCl, 0.01% Tween 80 at pH 7.4) and passed through a 0.22 μm filter.

Hemagglutination assay for H7 was performed based on a method described by Nayak and Reichl (2004). Briefly, successive double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as hemagglutination activity.

Total protein content of clarified crude extracts was determined using bovine serum albumin as the reference standard. Relative yields were obtained by comparing the PrL-construct to the native construct used as control. Separation by SDS-PAGE, with denaturing sample loading buffer (0.1M Tris pH 6.8, 0.05% bromophenol blue, 12.5% glycerol, 4% SDS and 5% beta-mercaptoethanol), was performed under reducing conditions and Coomassie Brillant Blue R-250 was used for protein staining.

FIG. 46A shows that the hemagglutination activity in plant extracts is greater for the H7 Hangzhou construct where the proteolytic loop is removed (#2152+#1261, see Example 5.34) compared to the native construct (#2142+#1261, see Example 5.33).

FIG. 46B shows that the relative total protein yield in purified VLP is greater for the H7 Hangzhou construct where the proteolytic loop is removed (#2152+#1261) compared to the native construct (#2142+#1261). This example demonstrate a good correlation between the improvement in the VLP accumulated in plants vs the final yields when performing the complete process.

FIG. 46C shows a SDS-PAGE analysis, with lane 2 showing the purified H7 Hangzhou construct with a removed proteolytic loop and lane 3 showing the purified native H7 Hangzhou construct. For each lane, 2 g of total protein were loaded on the gel. The purity of the proteins profiles is similar for both constructs and greater than 90%.

Example 4.1

Trypsin Resistance of Mutants H5 Indonesia VLP where the Proteolytic Loop is Modified or Removed is Greater than Native H5 Indonesia.

*N. benthamiana* plants were agroinfiltrated with AGL1/#489, #928, #766 and #676 as described in Example 1 (above). Leaves were collected from the plants 7 days post-infiltration, cut into ~1 cm2 pieces. Pectinase 162 L (Biocatalysts), Multifect CX CG and Multifect CX B (Genencor) were added in a 200 mM Mannitol, 75 mM Citrate, 0.04% sodium bisulfite pH 6.0 buffer. The biomass was digested overnight at room temperature in an orbital shaker. The digested extracts were coarse-filtered, centrifuged, clarified and purified as described in Example 3 (H7 Hangzhou).

For each of the native (#489), PRL- (#928), TETQ (#766) and TETR (#676), H5 Indonesia HA VLP extracts, two samples of HA VLPs were resuspended in buffer (100 mM Na/$KPO_4$, 150 mM NaCl, 0.01% TWEEN 80) at pH 7.4. Trypsin was added in a 1:100 protein ratio. Samples were grabbed after 30, 60 and 120 minutes of incubation at room temperature, then boiled in sample loading buffer to stop the reaction. The non-digested extracts (control) and the trypsin-digested extracts analysed by SDS-PAGE gel as described in Example 3.

Figure 47A:
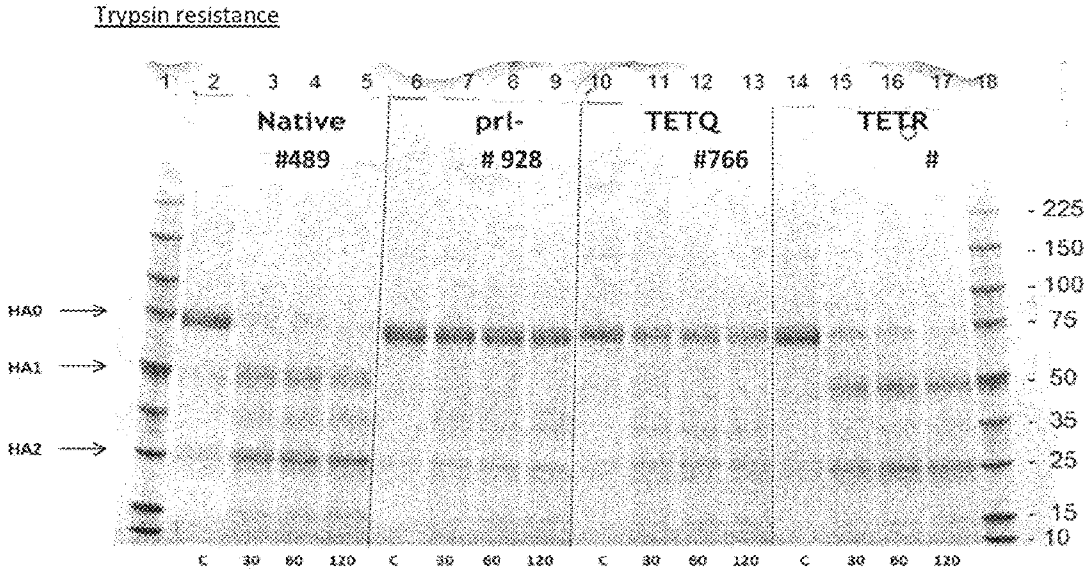
FIG. 47A shows the Trypsin resistance between native HA protein and modified HA with the proteolytic loop replaced with a GG liker (prl-), modified HA with the proteolytic loop replaced with a TETQ liker (TETQ) and modified HA with the proteolytic loop replaced with a TETR liker (TETR). Native (#489), PRL- (#928), TETQ (#766) and TETR (#676) H5 Indonesia HA VLP constructs were purified. For each lot, two samples of HA VLPs were resuspended in buffer (100 mM $Na/KP_{O4}$, 150 mM NaCl, 0.01% TWEEN 80) at pH 7.4 at a target concentration of 150 g/mL. Trypsin was added in a 1:100 protein ratio to one resuspended sample. Samples were incubated for 30, 60 and 120 minutes at room temperature. 30 μL of the non-digested extract (control) and 30 μL of the digested extracts were loaded on SDS-PAGE gel, which was stained with Coomassie blue.

FIG. 47A shows an SDS-PAGE analysis of trypsin-digested samples, with lanes 2 through 5 showing the native H5 Indonesia VLP (#489), with lanes 6 through 9 showing PrL- H5 Indonesia VLP (#928), with lanes 10 through 13 showing TETQ H5 Indonesia VLP (#766) and with lanes 14 through 17 showing the TETR H5 Indonesia VLP (#676) at different time points in the digestion (0, 30, 60, and 120 minutes). The native H5 Indonesia VPL, with a band corresponding to the HA0 monomer being detectable at approximately 75 kDa in the non-digested extract in lane 2, was rapidly processed into HA1 and HA2 bands through addition of trypsine, detectable at approximately 50 and 25 kDa respectively during the trypsin digestion in lanes 3 through 5. Both the PrL- and the TETQ H5 Indonesia VLPs, stabilized by the removal or modification of the proteolytic site, showed trypsin resistance as the HA0 band did not cleave into HA1 and HA2 bands. The TETR H5 Indonesia VLPs were partially stabilized by the modification of the proteolytic site and HA0 monomers were cleaved into HA1 and HA2 slower than in the native H5 Indonesia VLPS.

These data demonstrate the successful protection of the HA0 protein at its proteolytic site within HA1-HA2, by either deleting the proteolytic loop (prl-) or replacing the proteolytic loop with a linker sequence (TETQ) approach.

Example 4.2. Immunogenicity of Native H5 Indonesia VLPs is Similar to its Mutant Counterparts (PrL-, TETQ and TETR) in Mice The native, PrL-, TETR and TETQ H5 Indonesia VLPs extracts were purified as described in Example 4.1 (above).

Figure 47B:
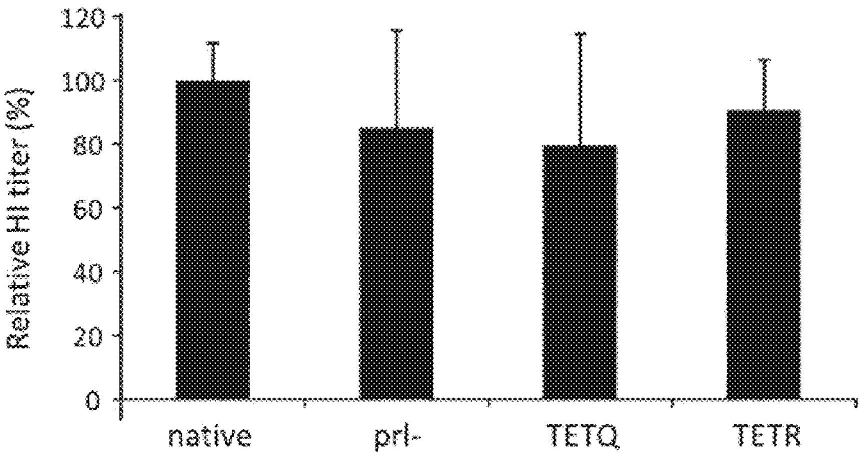
FIG. 47B shows immunogenicity (HI titer) of native H5 VLP and its mutant counterparts (prl-, TETQ and TETR) in mice after two doses. Bars represent relative (%) HI titers comparison of each H5 mutants VLP with the native H5 VLP.

FIG. 47B shows immunogenicity (HI titer) of native H5 VLP and its mutant counterparts (prl-, TETQ and TETR) in mice after two doses. BALB/c mice (n=8/group)/were injected twice intramuscularly, 21 days apart, with 10 ug dose of plant based H5 VLP vaccines (native, prl-, TETQ or TETR) based on its HA content. HI titers analysis was done from sera of each animal, 42 dpv (21 days after de 2nd dose) and H5 VLP A/Indonesia/5/2005 (H5N1) was used as antigen. Bars represent relative (%) HI titers comparison of each H5 mutants VLP with the H5 VLP native (calculated with the log 2 of the HI titer GMT and 95% CI). Statistical differences between groups for each dose were compared by using a one-way ANOVA followed by a Tukey's post-hoc analysis on Log 2-transformed data (assuming a normal distribution of them). *$p<0.05$ was considered significant. No difference between groups for each dose was observed.

Example 5.1: B-2X35S/CPMV-HT/M2 New Caledonia/NOS (Construct Number 1261)

Figure 11:
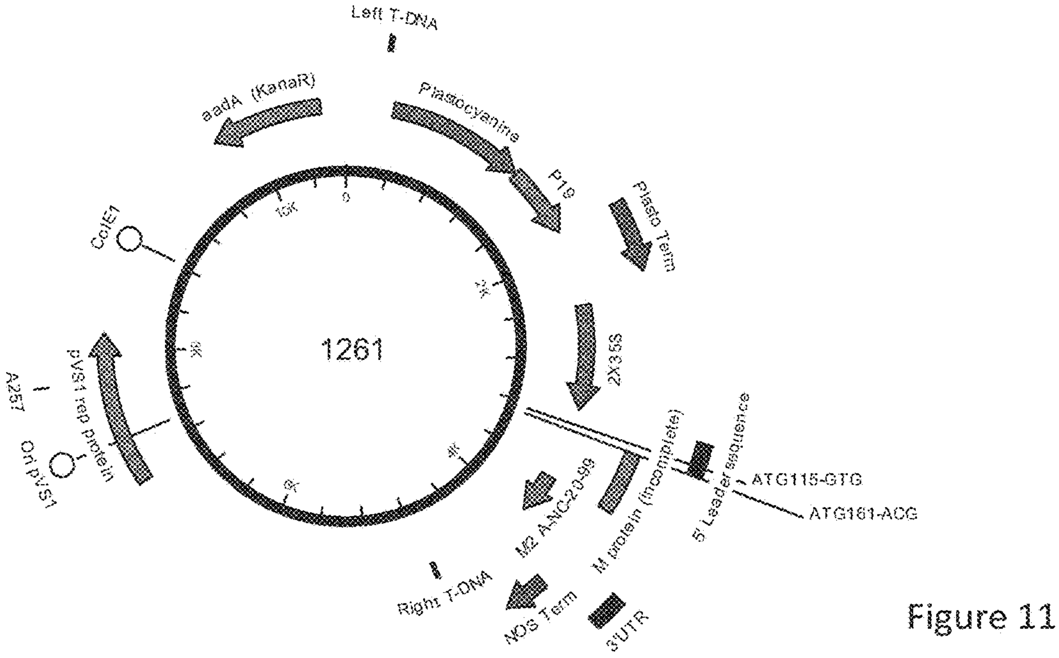
FIG. 11 shows the plasmid map of construct number 1261. Construct number 1261 directs the expression of wild-type M2 from influenza strain A/New Caledonia/20/99 (H1N1).
Figure 12:
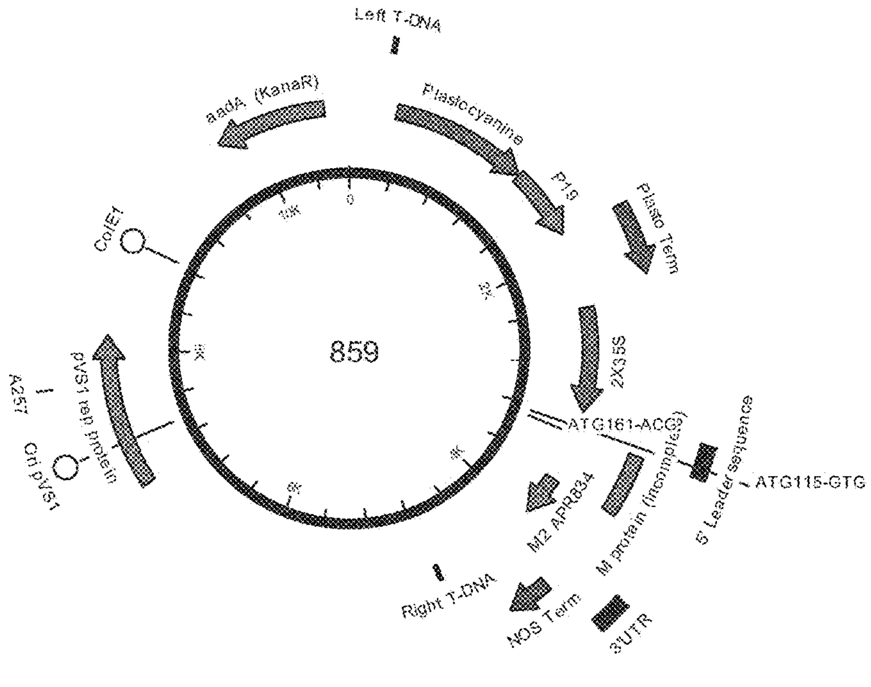
FIG. 12 shows the plasmid map of construct number 859. Construct number 859 directs the expression of wild-type M2 from influenza strain A/Puerto Rico/8/34 (H1N1).

A sequence encoding M2 from influenza A/New Caledonia/20/1999 (H1N1) was cloned into 2X35S/CPMV-HT/NOS expression system in a plasmid containing Plasto_pro/P19/Plasto_ter expression cassette using the following PCR-based method. A fragment containing the complete M2 coding sequence was amplified using primers IF-S1-M1+M2ANC.c (FIG. 2A, SEQ ID NO: 7) and IF-S1-4-M2ANC.r (FIG. 2B, SEQ ID NO: 8) using synthesized M2 gene (corresponding to nt 1-26 joined to nt 715-982 from GenBank accession number DQ508860; FIG. 2C, SEQ ID NO: 9) as template. The PCR product was cloned in 2X35S/CPMV-HT/NOS expression system using In-Fusion cloning system (Clontech, Mountain View, Calif.). Construct 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 1261 (FIG. 2D, SEQ ID NO: 10). The amino acid sequence of M2 from influenza A/New Caledonia/20/1999 (H1N1) is presented in FIG. 2E (SEQ ID NO: 11). A representation of plasmid 1261 is presented in FIG. 11.

Example 5.2: C-2X35S/CPMV-HT/M2 Puerto Rico/NOS (Construct Number 859)

A sequence encoding M2 from influenza A/Puerto Rico/8/1934 (H1N1) was cloned into 2X35S/CPMV-HT/NOS expression system in a plasmid containing Plasto_pro/P19/Plasto_ter expression cassette using the following PCR-based method. A fragment containing the complete M2 coding sequence was amplified using primers IF-S1-M1+M2ANC.c (FIG. 2A, SEQ ID NO: 7) and IF-S1-4-M2ANC.r (FIG. 2B, SEQ ID NO: 8), using synthesized M2 gene (corresponding to nt 26-51 joined to nt 740-1007 from Genbank accession number EF467824) (FIG. 3A, SEQ ID NO: 12) as template. The PCR product was cloned in 2X35S/CPMV-HT/NOS expression system using In-Fusion cloning system (Clontech, Mountain View, Calif.). Construct 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The vector is a pCAMBIA binary plasmid and the sequence from left to right t-DNA borders is presented in FIG. 1D (SEQ ID NO: 4). The resulting construct was given number 859 (FIG. 3B, SEQ ID NO: 13). The amino acid sequence of M2 from influenza A/Puerto Rico/8/1934 (H1N1) is presented in FIG. 3C (SEQ ID NO: 14). A representation of plasmid 859 is presented in FIG. 17.

Example 5.3: G-2X35S/CPMV-HT/PDISP/HA B Brisbane/NOS into BeYDV+Replicase Amplification System (Construct Number 1008)

Figure 9:
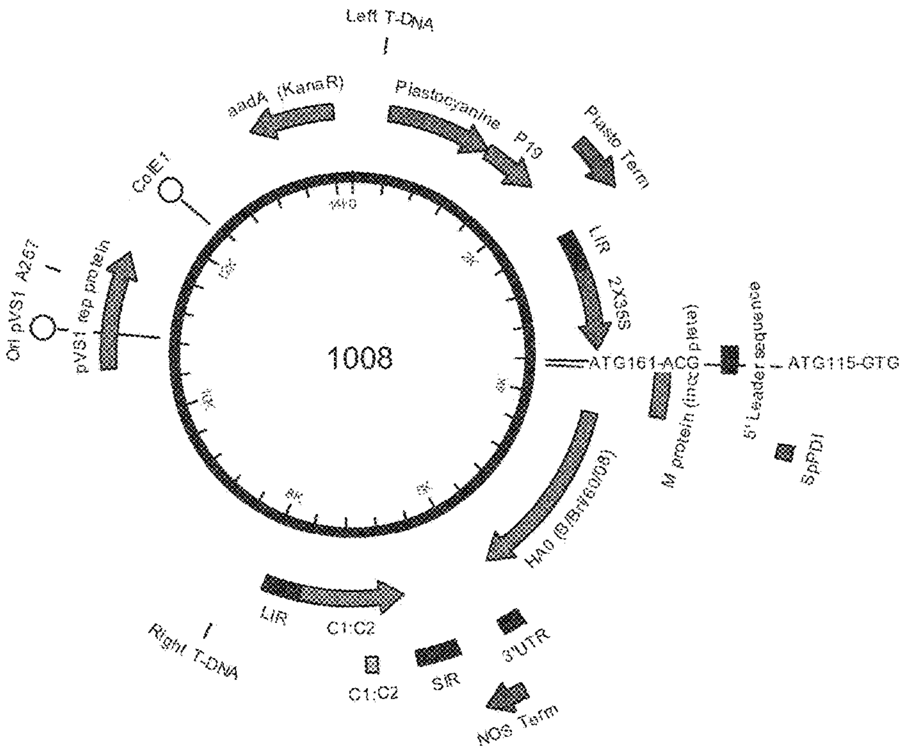
FIG. 9 shows the plasmid map of construct number 1008. Construct number 1008 directs the expression of wild-type HA from influenza strain B/Brisbane/60/2008. This construct comprises BeYDV-derived elements for DNA amplification.

The preparation of construct 1008 is described in U.S. 61/541,780. Briefly, a sequence encoding HA from influenza B/Brisbane/60/2008 was cloned into 2X35S/CPMV-HT/PDISP/NOS comprising the BeYDV+replicase amplification system in a plasmid containing Plasto_pro/P19/Plasto_ter expression cassette using a PCR-based method using synthesized HA B Brisbane gene (corresponding to nt 34-1791 from Genbank accession number FJ766840). The PCR product was cloned in-frame with alfalfa PDI signal peptide in 2X35S/CPMV-HT/NOS expression cassette into the BeYDV amplification system. Construct 1194 (see FIGS. 4A, 4B) was digested with SacII and StuI restriction enzyme and the linearized plasmid was used for an assembly reaction to produce construct number 1008 (FIG. 4C, FIG. 9; SEQ ID NO: 32).

Construct number 1194 (FIG. 4A) is an acceptor plasmid intended for "In Fusion" cloning of genes of interest in frame with an alfalfa PDI signal peptide in a CPMV-HT-based expression cassette into the BeYDV amplification system. It also incorporates a gene construct for the co-expression of the TBSV P19 suppressor of silencing under the alfalfa Plastocyanin gene promoter and terminator. The backbone is a pCAMBIA binary plasmid.

Example 5.4: I-2X35S/CPMV-HT/PDISP-HA B Brisbane with Deleted Proteolytic Loop into BeYDV+Replicase Amplification System (Construct Number 1059)

The preparation of construct 1059 is described in U.S. 61/541,780. Briefly, a sequence encoding HA from influenza B/Brisbane/60/2008 with deleted proteolytic loop was cloned into 2X35S/CPMV-HT/PDISP/NOS comprising the BeYDV+replicase amplification system in a plasmid containing Plasto_pro/P19/Plasto_ter expression cassette using the a PCR-based ligation method (Darveau et al., 1995, Methods in Neuroscience 26: 77-85). In a first round of PCR, a fragment containing HA B Brisbane coding sequence from nt 46 to nt 1065 was amplified using synthesized HA B Brisbane gene (corresponding to nt 34-1791 from Genebank accession number FJ766840) as template. A second fragment, containing HA B Brisbane coding sequence from nt 1123 to nt 1758, was amplified using synthesized HA B Brisbane gene (corresponding to nt 34-1791 from Genbank accession number FJ766840) as template. The PCR products from both amplifications were then mixed and used as template for a second round of amplification. The resulting fragment (encoding HA B/Brisbane/60/2008 Δa.a. 356-374 with a GG linker between fragments; see FIG. 21B) was cloned in-frame with alfalfa PDI signal peptide in 2X35S/CPMV-HT/NOS expression cassette comprising the BeYDV amplification system to produce construct 1194 (FIGS. 4A, 4B) was digested with SacII and StuI restriction enzyme and the linearized plasmid was used for an assembly reaction. The resulting construct was given number 1059 (FIG. 5C; SEQ ID NO: 40).

The amino acid sequence of PDISP-HA B/Brisbane/60/2008 with deleted proteolytic loop is presented in FIG. 5D (SEQ ID NO: 41).

Example 5.5: B-2X35S/CPMV-HT/HA B Wisconsin/NOS into BeYDV(m)+Replicase Amplification System (Construct Number 1462)

The preparation of construct 1462 is described in U.S. 61/541,780. Briefly, a sequence encoding HA from influenza B/Wisconsin/1/2010 was cloned into 2X35S/CPMV-HT/NOS comprising the BeYDV(m)+replicase amplification system in a plasmid containing Plasto_pro/P19/Plasto_ter expression cassette using a PCR-based method. A fragment containing the complete HA B Wisconsin coding sequence was amplified using synthesized HA B Wisconsin gene (Genbank accession number JN993010) as template. The PCR product was cloned in 2X35S/CPMV-HT/NOS expression cassette into the BeYDV(m) amplification system. Construct 193 (FIG. 6D) was digested with SacII and StuI restriction enzyme and the linearized plasmid was used for an assembly reaction.

Figure 6D:
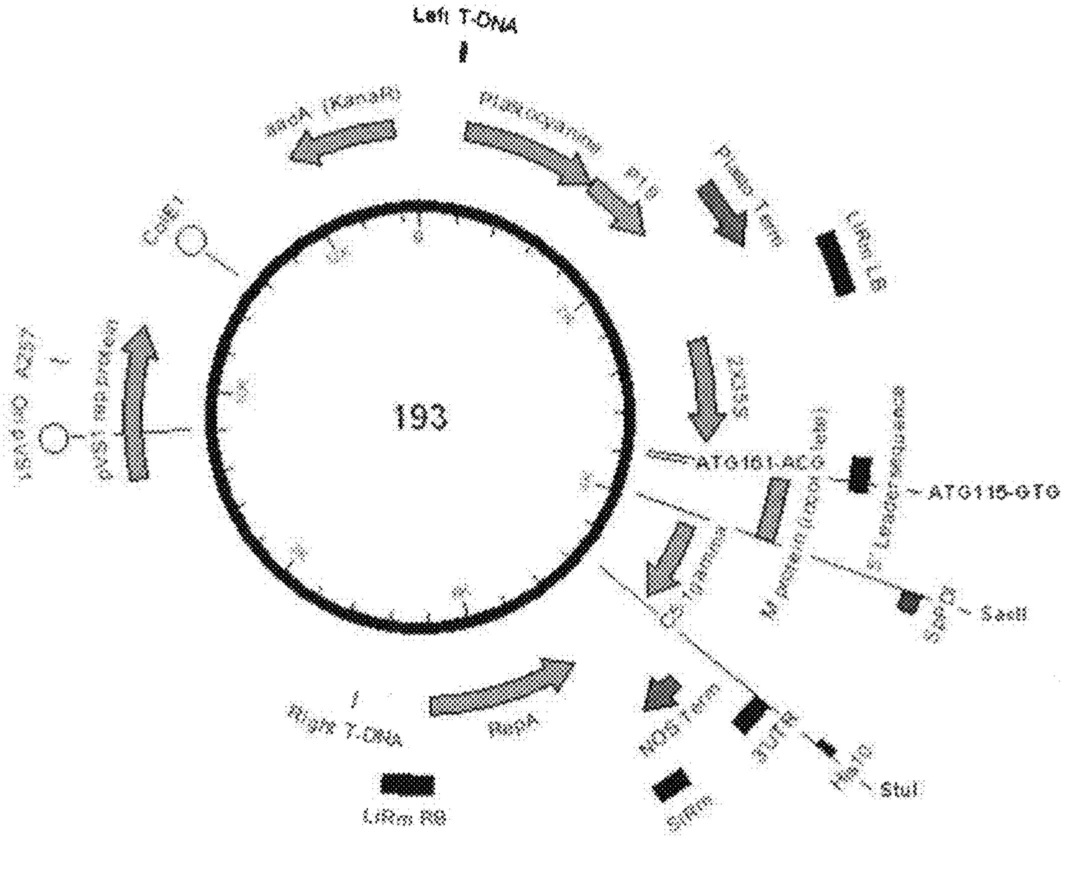
FIG. 6D shows a schematic representation of construct 193.
Figure 6H:
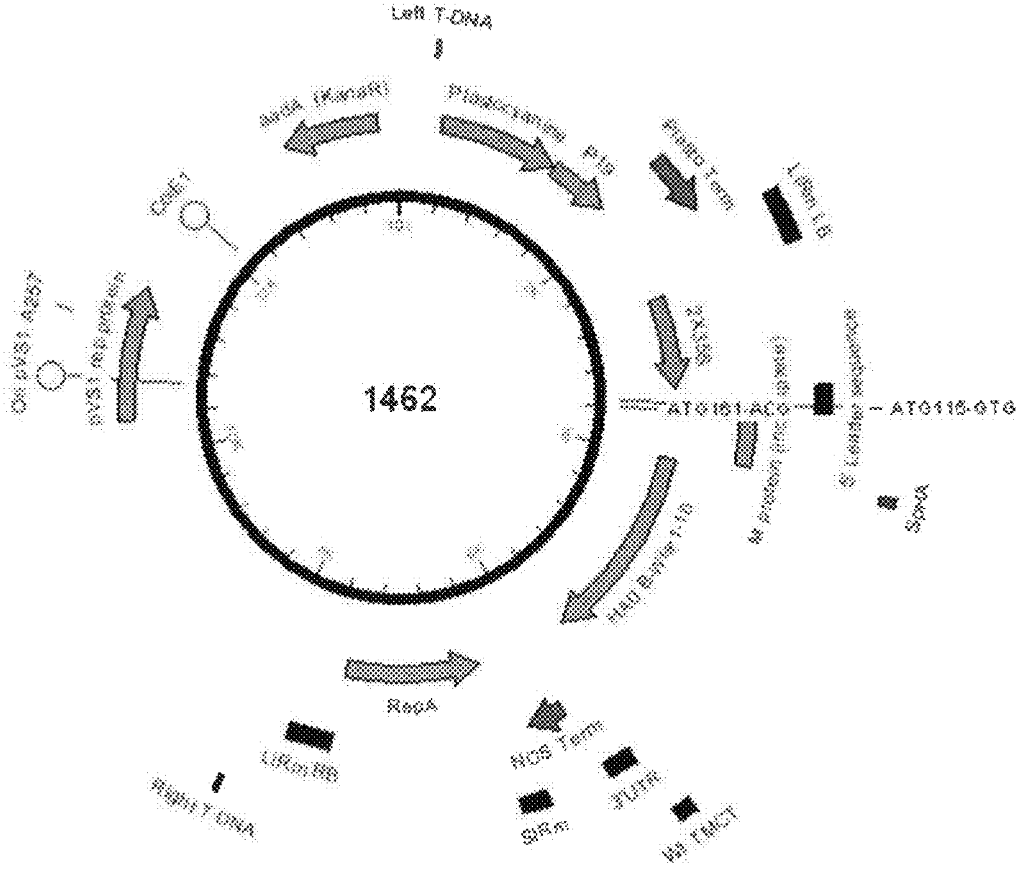
FIG. 6 shows components used to prepare B-2X35S/CPMV-HT/HA B Wisconsin/NOS into BeYDV(m)+Replicase amplification system (Construct number 1462).
FIG. 6A shows primer IF-HAB110.S1+3c (SEQ ID NO: 49).
FIG. 6B shows primer IF-HAB110.s1-4r (SEQ ID NO: 50).
FIG. 6C shows the nucleotide sequence of synthesized HA B Wisconsin (Genbank accession number JN993010) (SEQ ID NO: 51).
FIG. 6E shows construct 193 from left to right t-DNA borders (underlined). 2X35S/CPMV-HT/NOS into BeYDV(m)+Replicase amplification system with Plastocyanine-P19-Plastocyanine silencing inhibitor expression cassette (SEQ ID NO: 52).
FIG. 6F shows the nucleotide sequence of expression cassette number 1462 from 2X35S promoter to NOS terminator. HA from influenza B/Wisconsin/1/2010 is underlined (SEQ ID NO: 53).
FIG. 6G shows the amino acid sequence of HA from influenza B/Wisconsin/1/2010 (SEQ ID NO: 54).

Construct number 193 (FIG. 6D, 6E) is an acceptor plasmid intended for "In Fusion" cloning of genes of interest in a CPMV-HT-based expression cassette into the BeYDV (m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6E (SEQ ID NO: 52). The resulting construct was given number 1462 (FIG. 6F, SEQ ID NO: 53). The amino acid sequence of PDISP/HA from Influenza B/Wisconsin/1/2010 is presented in FIG. 6G (SEQ ID NO: 54). A representation of plasmid 1462 is presented in FIG. 6H.

Example 5.6: C-2X35S/CPMV-HT/HA B Wisconsin with Deleted Proteolytic Loop into BeYDV(m)+Replicase Amplification System (Construct Number 1467)

The preparation of construct 1467 is described in U.S. 61/541,780. Briefly, a sequence encoding HA from influenza B/Wisconsin/1/2010 with deleted proteolytic loop was cloned into 2X35S/CPMV-HT/NOS comprising the BeYDV (m)+replicase amplification system in a plasmid containing Plasto_pro/P19/Plasto_ter expression cassette using a PCR-based ligation method (Darveau et al. 1995, Methods in Neuroscience 26: 77-85). In a first round of PCR, a fragment containing HA B Wisconsin coding sequence from nt 1 to nt 1062 was amplified using primers IF-HAB110.S1+3c (FIG. 6A, SEQ ID NO: 49) and HAB110(PrL-).r (FIG. 7A, SEQ ID NO: 55), using synthesized HA B Wisconsin gene (Genbank accession number JN993010) (FIG. 6C, SEQ ID NO: 51) as template. A second fragment, containing HA B Wisconsin coding sequence from nt 1120 to nt 1755, was amplified using primers HAB110(PrL-).c (FIG. 7B, SEQ ID NO: 56) and IF-HAB110.s1-4r (FIG. 6B, SEQ ID NO: 50), using synthesized HA B Wisconsin gene (Genbank accession number JN993010) (FIG. 6C, SEQ ID NO: 51) as template. The PCR products from both amplifications were then mixed and used as template for a second round of amplification using IF-HAB110.S1+3c (FIG. 6A, SEQ ID NO: 49) and IF-HAB110.s1-4r (FIG. 6B, SEQ ID NO: 50) as primers. The resulting fragment (encoding HA B/Wisconsin/1/2010 Δa.a. 340-358 with a GG linker between fragments) was cloned in 2X35S/CPMV-HT/NOS expression cassette comprising the BeYDV(m) amplification system using In-Fusion cloning system (Clontech, Mountain View, Calif.). Construct 193 (FIG. 6D) was digested with SacII and StuI restriction enzyme and the linearized plasmid was used for the In-Fusion assembly reaction.

Construct number 193 is an acceptor plasmid intended for "In Fusion" cloning of genes of interest in a CPMV-HT-based expression cassette into the BeYDV(m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6E (SEQ ID NO: 52). The resulting construct was given number 1467 (FIG. 7C, SEQ ID NO: 57). The amino acid sequence of HA from Influenza B/Wisconsin/1/2010 with deleted proteolytic loop is presented in FIG. 7D (SEQ ID NO: 58). A representation of plasmid 1467 is presented in FIG. 7E.

Example 5.7: A-2X35S/CPMV-HT/PDISP-HA B Brisbane with Deleted Proteolytic Loop (Construct Number 1039)

The preparation of construct 1192 is described in U.S. 61/541,780. Briefly, a sequence encoding HA from influenza B/Brisbane/60/2008 with deleted proteolytic loop was cloned into 2X35S/CPMV-HT/PDISP/NOS in a plasmid containing Plasto_pro/P19/Plasto_ter expression cassette using the following PCR-based ligation method (Darveau et al., 1995, Methods in Neuroscience 26: 77-85). In a first round of PCR, a fragment containing HA B Brisbane coding sequence from nt 46 to nt 1065 was amplified using synthesized HA B Brisbane gene (corresponding to nt 34-1791 from Genebank accession number FJ766840) as template. A second fragment, containing HA B Brisbane coding sequence from nt 1123 to nt 1758, was amplified using synthesized HA B Brisbane gene (corresponding to nt 34-1791 from Genbank accession number FJ766840) as template. The PCR products from both amplifications were then mixed and used as template for a second round of amplification. The resulting fragment (encoding HA B/Brisbane/60/2008 Δa.a. 356-374 with a GG linker between fragments) was cloned in-frame with alfalfa PDI signal peptide in 2X35S/CPMV-HT/NOS expression cassette. Construct 1192 was digested with SacII and StuI restriction enzyme and the linearized plasmid was used for the In-Fusion assembly reaction.

Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid The resulting construct was given number 1039 (FIG. 8B). The amino acid sequence of PDISP-HA B/Brisbane/60/2008 with deleted proteolytic loop is presented in FIG. 5D (SEQ ID NO: 41). A representation of plasmid 1039 is presented in FIG. 8A (SEQ ID NO: 15).

Example 5.8: A-2X35S/CPMV-HT/H5 from A/Indonesia/5/2005 with TETR Cleavage Site Mutation (Construct Number 676)

A sequence encoding H5 from A/Indonesia/5/2005 with TETR cleavage site mutation was cloned into 2X35S/CPMV-HT/NOS in a plasmid containing Plasto_pro/P19/Plasto_ter expression cassette using the following PCR-based ligation method (Darveau et al., 1995, Methods in Neuroscience 26: 77-85). In a first round of PCR, a fragment containing H5 from A/Indonesia/5/2005 coding sequence from nt 1 to nt 1015 was amplified using primers IF-H5A-I-05.s1+3c (FIG. 1A, SEQ ID NO: 2) and MutCleavage-H5 (Indo).r (FIG. 23A, SEQ ID NO: 74), using synthesized H5 from A/Indonesia/5/2005 (FIG. 1G, SEQ ID NO: 42) as template. A second fragment, containing H5 from A/Indonesia/5/2005 coding sequence from nt 1038 to nt 1707, was amplified using primers MutCleavage-H5(Indo).c (FIG. 23B, SEQ ID NO: 75) and IF-H5dTm.r (FIG. 1B, SEQ ID NO: 3), using synthesized H5 from A/Indonesia/5/2005 (FIG. 1G, SEQ ID NO: 42) as template. The PCR products from both amplifications were then mixed and used as template for a second round of amplification using IF-H5A-I-05.s1+3c (FIG. 1A, SEQ ID NO: 2) and IF-H5dTm.r (FIG. 1B, SEQ ID NO: 3) as primers. The resulting fragment (encoding H5 from A/Indonesia/5/2005 Δa.a. 339-346 with a TETR linker between fragments) was cloned in 2X35S/CPMV-HT/NOS expression cassette using In-Fusion cloning system (Clontech, Mountain View, Calif.). Construct 1191 (FIG. 1D) was digested with SacII and StuI restriction enzyme and the linearized plasmid was used for the In-Fusion assembly reaction. Construct number 1191 is an acceptor plasmid intended for "In Fusion" cloning of genes of interest in frame in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 676 (FIG. 23C, SEQ ID NO: 76). The amino acid sequence of H5 from A/Indonesia/5/2005 TETR cleavage site mutant is presented in FIG. 23D (SEQ ID NO: 77). A schematic representation of plasmid 676 is presented in FIG. 23E.

Example 5.9: B-2X35S/CPMV-HT/H5 from A/Indonesia/5/2005 with TETO Cleavage Site Mutation (Construct Number 766)

A sequence encoding H5 from A/Indonesia/5/2005 with TETQ cleavage site mutation was cloned into 2X35S/

CPMV-HT/NOS in a plasmid containing Plasto_pro/P19/Plasto_ter expression cassette using the following PCR-based ligation method (Darveau et al., 1995, Methods in Neuroscience 26: 77-85). In a first round of PCR, a fragment containing H5 from A/Indonesia/5/2005 coding sequence from nt 1 to nt 1015 was amplified using primers IF-H5A-I-05.s1+3c (FIG. 1A, SEQ ID NO: 2) and H5I505_TETQ.r (FIG. 24A, SEQ ID NO: 78), using synthesized H5 from A/Indonesia/5/2005 (FIG. 1G, SEQ ID NO: 42) as template. A second fragment, containing H5 from A/Indonesia/5/2005 coding sequence from nt 1038 to nt 1707, was amplified using primers H5I505_TETQ.c (FIG. 24B, SEQ ID NO: 79) and IF-H5dTm.r (FIG. 1B, SEQ ID NO: 3), using synthesized H5 from A/Indonesia/5/2005 (FIG. 1G, SEQ ID NO: 42) as template. The PCR products from both amplifications were then mixed and used as template for a second round of amplification using IF-H5A-I-05.s1+3c (FIG. 1A, SEQ ID NO: 2) and IF-H5dTm.r (FIG. 1B, SEQ ID NO: 3) as primers. The resulting fragment (encoding H5 from A/Indonesia/5/2005 Δa.a. 339-346 with a TETQ linker between fragments) was cloned in 2X35S/CPMV-HT/NOS expression cassette using In-Fusion cloning system (Clontech, Mountain View, Calif.). Construct 1191 (FIG. 1D) was digested with SacII and StuI restriction enzyme and the linearized plasmid was used for the In-Fusion assembly reaction. Construct number 1191 is an acceptor plasmid intended for “In Fusion” cloning of genes of interest in frame in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 766 (FIG. 24C, SEQ ID NO: 80). The amino acid sequence of H5 from A/Indonesia/5/2005 TETQ cleavage site mutant is presented in FIG. 24D (SEQ ID NO: 81). A schematic representation of plasmid 766 is presented in FIG. 24E.

Example 5.10: C-2X35S/CPMV-HT/H5 from A/Indonesia/5/2005 with Deleted Proteolytic Loop (Construct Number 928)

A sequence encoding H5 from A/Indonesia/5/2005 with deleted proteolytic loop was cloned into 2X35S/CPMV-HT/NOS in a plasmid containing Plasto_pro/P19/Plasto_ter expression cassette using the following PCR-based ligation method presented by Darveau et al. (Methods in Neuroscience 26: 77-85 (1995)). In a first round of PCR, a fragment containing H5 from A/Indonesia/5/2005 coding sequence from nt 1 to nt 1011 was amplified using primers IF-H5A-I-05.s1+3c (FIG. 1A, SEQ ID NO: 2) and H5I505(PrL-).r (FIG. 25A, SEQ ID NO: 82), using synthesized H5 from A/Indonesia/5/2005 (FIG. 1G, SEQ ID NO: 42) as template. A second fragment, containing H5 from A/Indonesia/5/2005 coding sequence from nt 1075 to nt 1707, was amplified using primers H5I505(PrL-).c (FIG. 25B, SEQ ID NO: 83) and IF-H5dTm.r (FIG. 1B, SEQ ID NO: 3), using synthesized H5 from A/Indonesia/5/2005 (FIG. 1G, SEQ ID NO: 42) as template. The PCR products from both amplifications were then mixed and used as template for a second round of amplification using IF-H5A-I-05.s1+3c (FIG. 1A, SEQ ID NO: 2) and IF-H5dTm.r (FIG. 1B, SEQ ID NO: 3) as primers. The resulting fragment (encoding H5 from A/Indonesia/5/2005 Δa.a. 338-358 with a GG linker between fragments) was cloned in 2X35S/CPMV-HT/NOS expression cassette using In-Fusion cloning system (Clontech, Mountain View, Calif.). Construct 1191 (FIG. 1D) was digested with SacII and StuI restriction enzyme and the linearized plasmid was used for the In-Fusion assembly reaction. Construct number 1191 is an acceptor plasmid intended for “In Fusion” cloning of genes of interest in frame in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 928 (FIG. 25C, SEQ ID NO: 84). The amino acid sequence of H5 from A/Indonesia/5/2005 with deleted proteolytic loop is presented in FIG. 25D (SEQ ID NO: 85). A representation of plasmid 928 is presented in FIG. 25E.

Example 5.11—F-2X35S/CPMV-HT/PDISP/HA B Brisbane/NOS (Construct Number 1029)

Figure 30F:
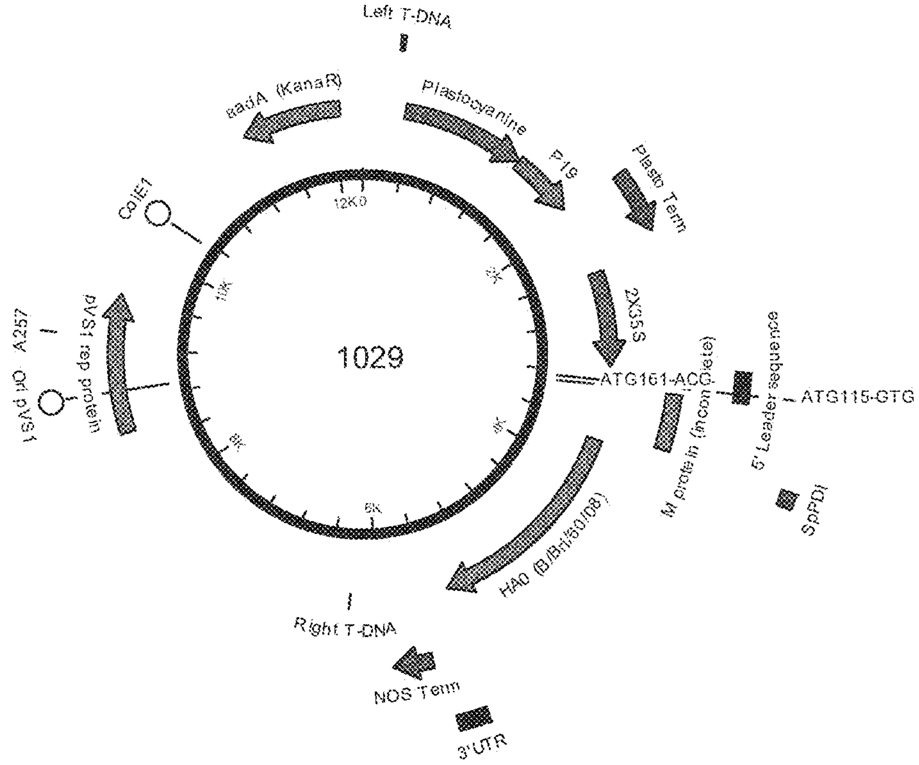
FIG. 30F shows a schematic representation of construct 1029. SacII and StuI restriction enzyme sites used for plasmid linearization are annotated on the representation.

A sequence encoding HA from influenza B/Brisbane/60/2008 was cloned into 2X35S/CPMV-HT/PDISP/NOS expression system in a plasmid containing Plasto_pro/P19/Plasto_ter expression cassette using the following PCR-based method. A fragment containing HA B Brisbane coding sequence without his wild type signal peptide was amplified using primers IF-S2+S4-B Bris.c (FIG. 30A, SEQ ID NO: 86) and IF-S1a4-B Bris.r (FIG. 30B, SEQ ID NO: 87), using synthesized HA B Brisbane gene (corresponding to nt 34-1791 from Genbank accession number FJ766840) (FIG. 30C, SEQ ID NO: 88) as template. The PCR product was cloned in-frame with alfalfa PDI signal peptide in 2X35S/CPMV-HT/NOS expression system using In-Fusion cloning system (Clontech, Mountain View, Calif.). Construct 1192 was digested with SacII and StuI restriction enzyme and the linearized plasmid was used for the In-Fusion assembly reaction. Construct number 1192 is an acceptor plasmid intended for “In Fusion” cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders. The resulting construct was given number 1029 (FIG. 30D, SEQ ID NO: 89). The amino acid sequence of PDISP/HA from influenza B/Brisbane/60/2008 is presented in FIG. 30E (SEQ ID NO: 90). A representation of plasmid 1029 is presented in FIG. 30F.

Example 5.12-2X35S/CPMV HT (Construct No 1039) and HT+ (Construct No 1829) for PDISP/HA B Brisbane (PrL-)

A coding sequence corresponding to HA from Influenza B/Brisbane/60/2008 with deleted proteolytic loop (PrL-) in which the native signal peptide has been replaced by that of alfalfa protein disulfide isomerase (PDISP/HA B Brisbane (PrL-; FIG. 31A, SEQ ID NO: 91) was cloned into original HT and modified HT+ using the same PCR-based method described in Examples 5.7 and 5.11, but with modified PCR primers specifically designed for PDISP/HA B Brisbane (PrL-). The amino acid sequence of mature HA B Brisbane (PrL-) fused with PDISP is presented in FIG. 31B (SEQ ID NO: 92). Representations of plasmid 1039 and 1829 are presented in FIGS. 8B and 31D.

Example 5.13-2X35S/CPMV HT (Construct No 1039) and 2X35S/CPMV160+ (Construct No 1937) for PDISP/HA B Brisbane (PrL-)

Figures 32, 32A:
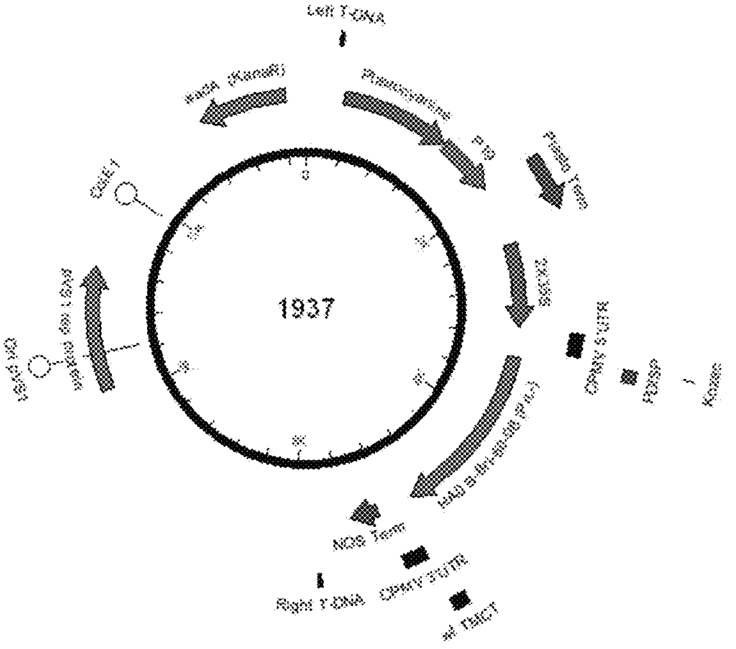
FIG. 32 shows sequence components used to prepare construct numbers 1039 and 1937 (2X35S/CPMV HT PDISP/HA B Brisbane (PrL-) NOS and 2X35S/CPMV160+ PDISP/HA B Brisbane (PrL-) NOS, respectively; see Example 5.7). Construct number 1039 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)). Construct number 1937 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. PDISP: protein disulfide isomerase signal peptide; NOS: nopaline synthase terminator; PrL-: deleted proteolytic loop.
FIG. 32A shows a schematic representation of construct number 1937 (2X35S/CPMV160+; a CPMVX+ based construct, where X=160).

A coding sequence corresponding to HA from Influenza B/Brisbane/60/2008 with deleted proteolytic loop (PrL-) (see U.S. provisional application No. 61/806,227 Filed Mar. 28, 2013, which is incorporated herein by reference, for additional information re: deleted proteolytic loop regions in HA sequences) in which the native signal peptide has been replaced by that of alfalfa protein disulfide isomerase (PDISP/HA B Brisbane (PrL-)) (FIG. 32A, SEQ ID NO: 93) was cloned into original CPMV-HT and CPMV160+ using the same PCR-based method as described in Example 5.7 and in Example 5.11, but with modified PCR primers specifically designed for PDISP/HA B Brisbane (PrL-). The amino acid sequence of mature HA B Brisbane (PrL-) fused with PDISP is presented in FIG. 31B (SEQ ID NO: 92). Representations of plasmid 1039 and 1937 are presented in FIG. 8B and FIG. 32C.

Figure 33C:
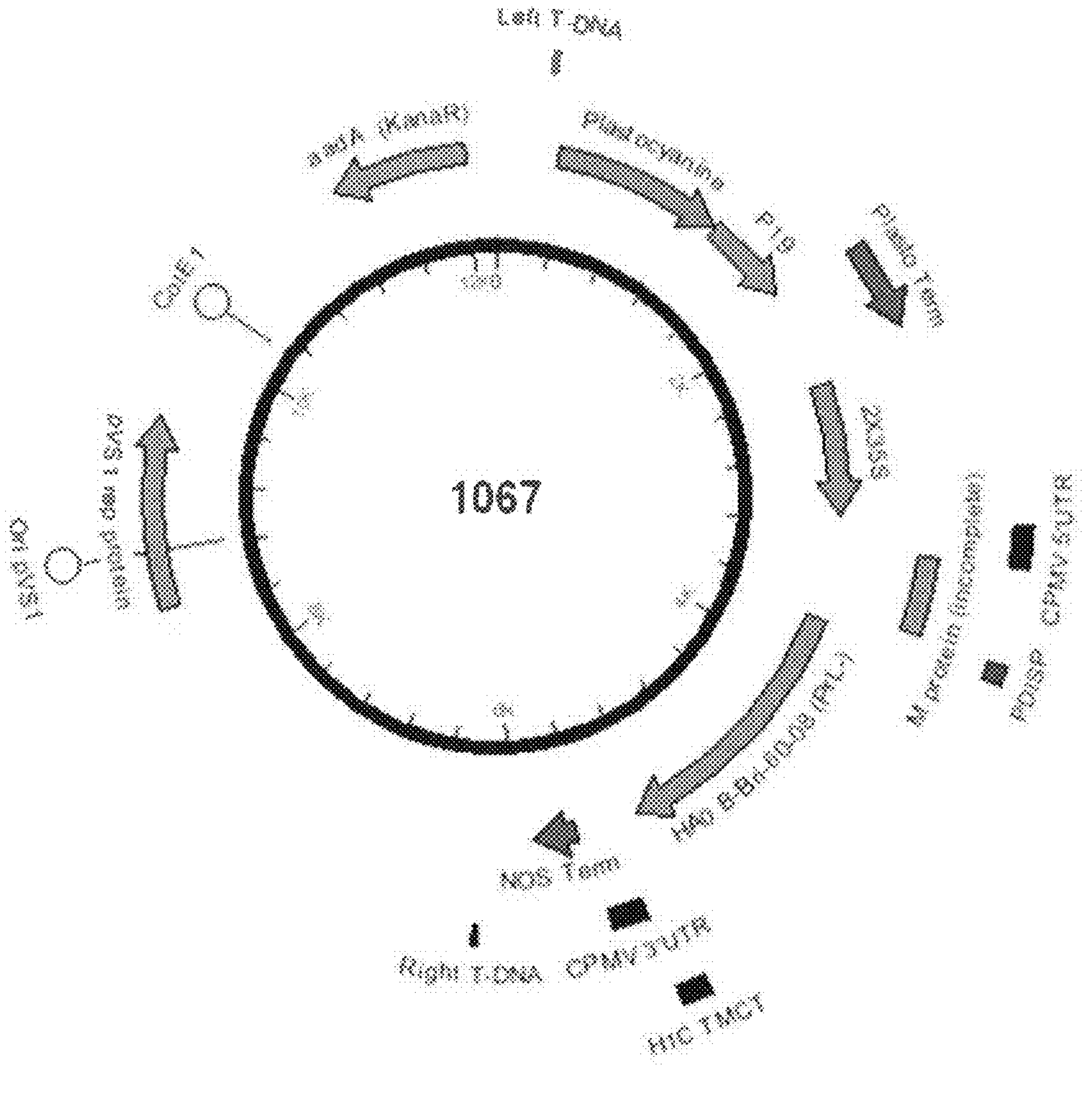
FIG. 33C shows a schematic representation of construct number 1067 (2X35S/CPMV HT; reference construct).
Figure 33D:
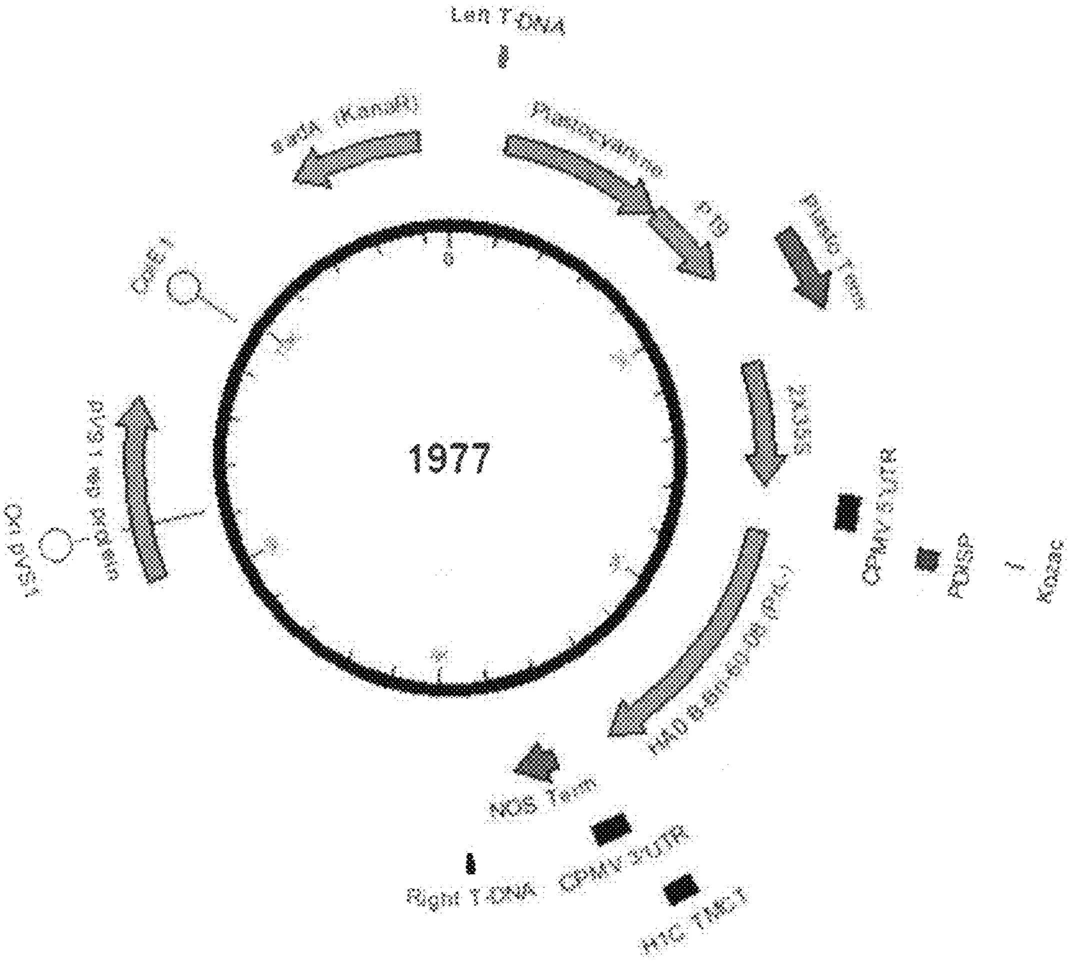
FIG. 33D shows a schematic representation of construct number 1977 (2X35S/CPMV160+; a CPMVX+ based construct, where X=160).

Example 15.14-2X35S/CPMV HT (Construct No 1067) and 2X35S/CPMV160+ (Construct No 1977) for PDISP/HA B Brisbane (PrL-)+H1 California TMCT A chimer hemagglutinin coding sequence corresponding to the ectodomain of HA from Influenza B/Brisbane/60/08 with deleted proteolytic loop (PrL-) (see U.S. provisional application No. 61/806,227 Filed Mar. 28, 2013, which is incorporated herein by reference, for additional information re: deleted proteolytic loop regions in HA sequences) fused to the transmembrane domain and cytoplasmic tail (TMCT) of H1 from influenza A/California/7/2009 and with the signal peptide of alfalfa protein disulfide isomerase (PDISP/HA B Brisbane (PrL-)+H1 California TMCT) (FIG. 33A, SEQ ID NO: 95) was cloned into original CPMV-HT and CPMV160+ using the same PCR-based method as described in Examples 5.7 and 5.11, but with modified PCR primers specifically designed for PDISP/HA B Brisbane (PrL-)+H1 California TMCT. The amino acid sequence of mature HA B Brisbane (PrL-)+H1 California TMCT fused with PDISP is presented in FIG. 33B (SEQ ID NO: 96). Representations of plasmid 1067 and 1977 are presented in FIG. 33C and FIG. 33D.

Example 5.15-2X35S/CPMV HT (Construct No 2072) and 2X35S/CPMV160+ (Construct No 2050) for PDISP/HA B Massachusetts (PrL-)

Figure 34C:
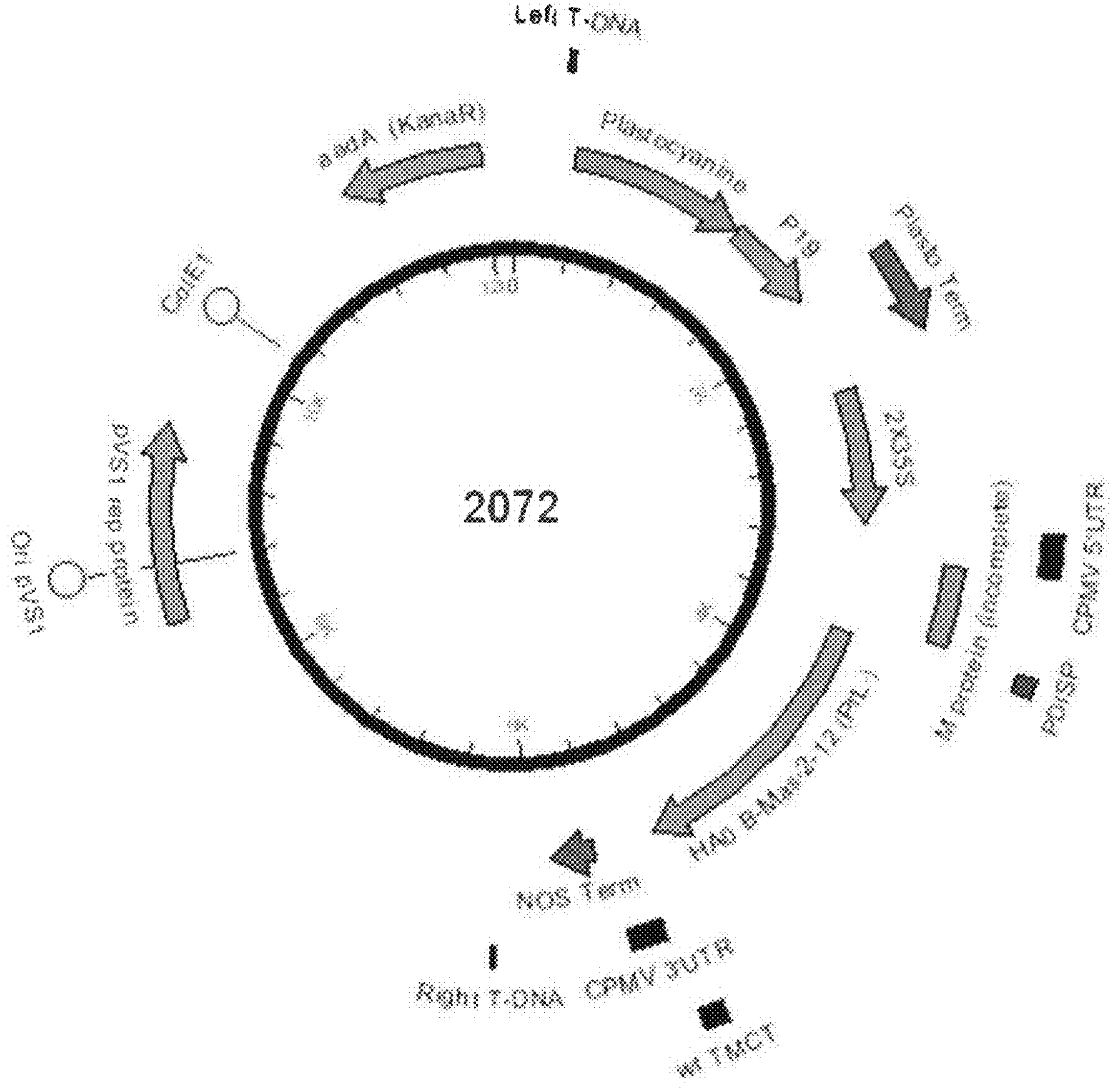
FIG. 34C shows a schematic representation of construct number 2072 (2X35S/CPMV HT; reference construct).
Figure 34D:
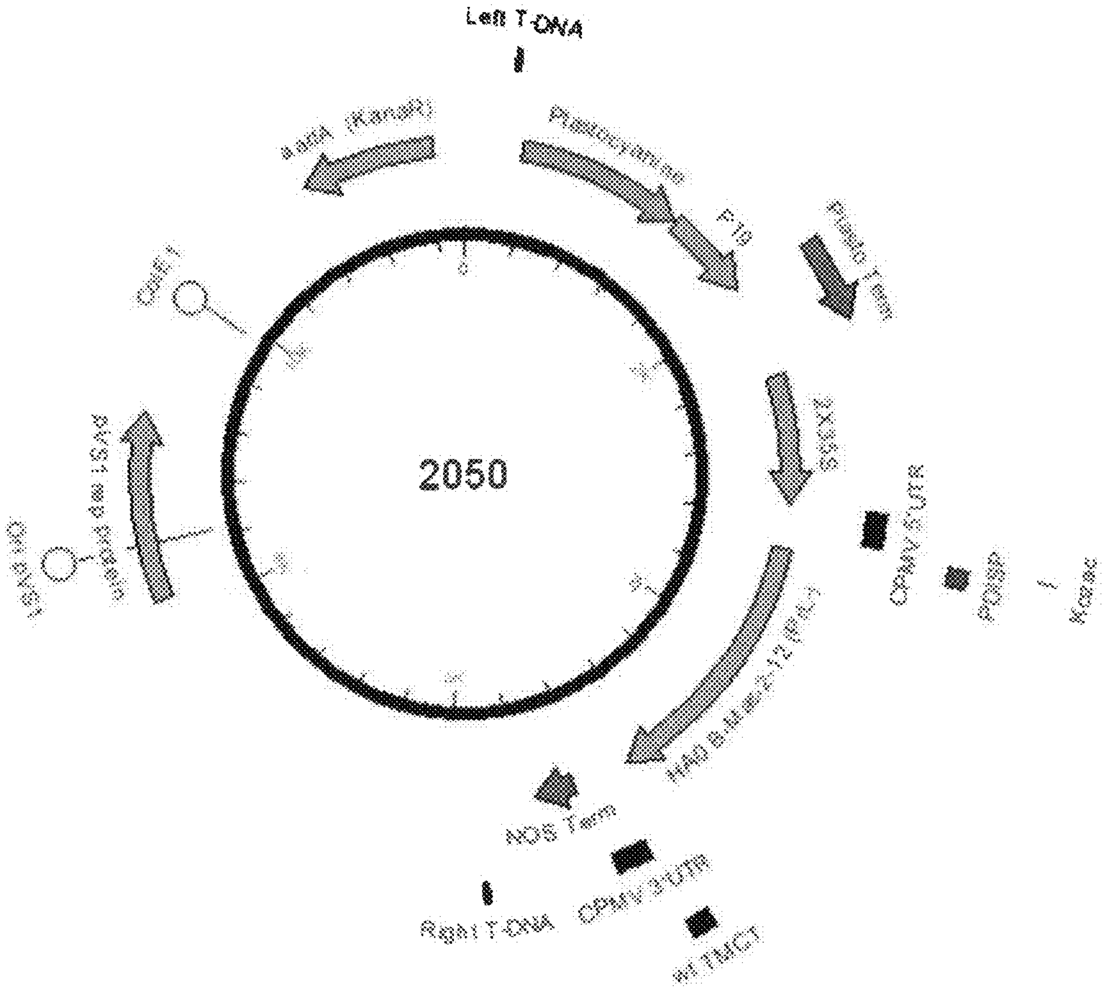
FIG. 34D shows a schematic representation of construct number 2050 (2X35S/CPMV160+; a CPMVX+ based construct, where X=160).

A coding sequence corresponding to HA from Influenza B/Massachusetts/2/2012 with deleted proteolytic loop (PrL-) (see U.S. provisional application No. 61/806,227 Filed Mar. 28, 2013 for additional information re: deleted proteolytic loop regions in HA sequences, which is incorporated herein by reference) in which the native signal peptide has been replaced by that of alfalfa protein disulfide isomerase (PDISP/HA B Massachusetts (PrL-)) (FIG. 34A, SEQ ID NO: 97) was cloned into original CPMV-HT and CPMV160+ using the same PCR-based method as described in Examples 5.7 and 5.11, but with modified PCR primers specifically designed for PDISP/HA B Massachusetts (PrL-). The amino acid sequence of mature HA B Massachusetts (PrL-) fused with PDISP is presented in FIG. 34B (SEQ ID NO: 98). Representations of plasmid 2072 and 2050 are presented in FIG. 34C and FIG. 34D.

Figure 35C:
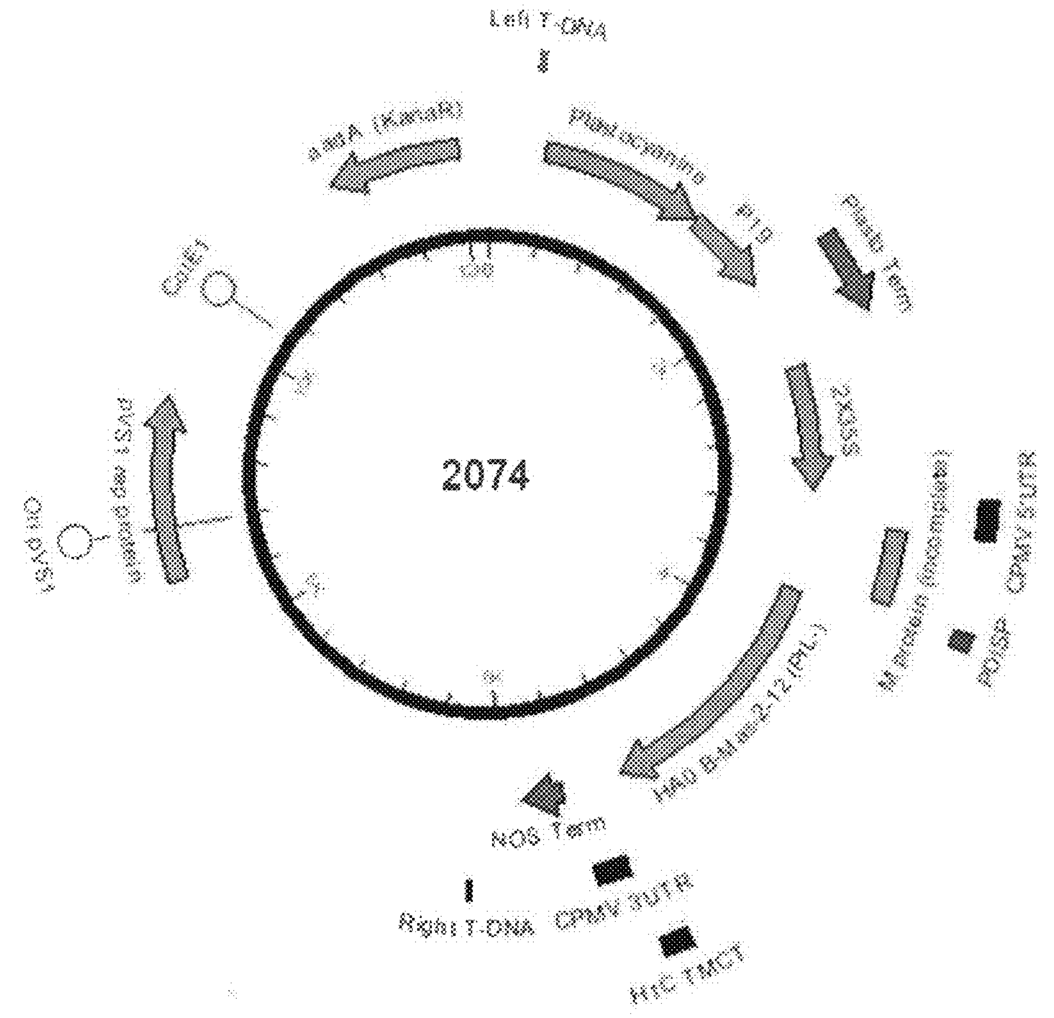
FIG. 35C shows a schematic representation of construct number 2074 (2X35S/CPMV HT; reference construct).
Figure 35D:
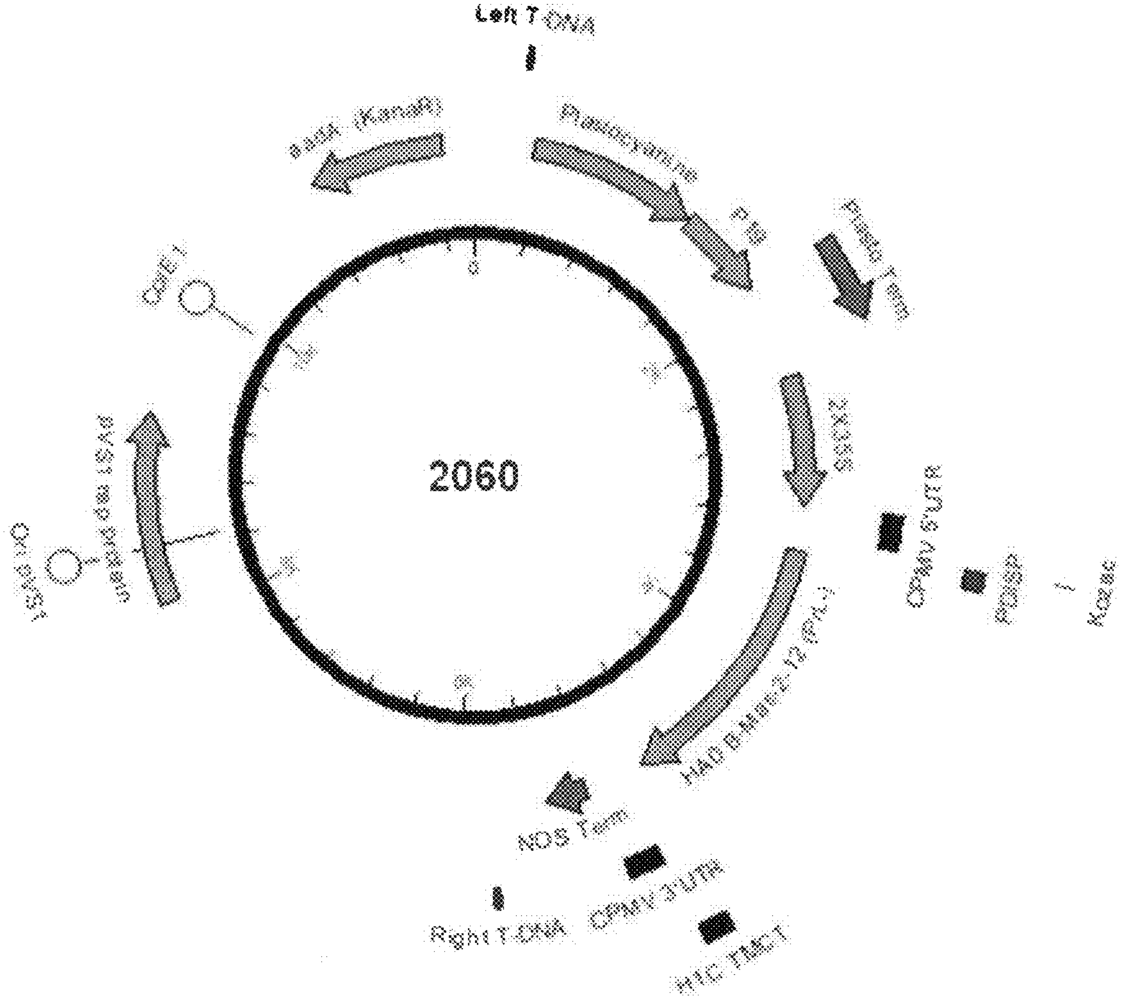
FIG. 35D shows a schematic representation of construct number 2060 (2X35S/CPMV160+; a CPMVX+ based construct, where X=160).

Example 5.16-2X35S/CPMV HT (Construct No 2074) and 2X35S/CPMV160+ (Construct No 2060) for PDISP/HA B Massachusetts (PrL-)+H1 California TMCT A chimer hemagglutinin coding sequence corresponding to the ectodomain of HA from Influenza B/Massachusetts/2/2012 with deleted proteolytic loop (PrL-) (see U.S. provisional application No. 61/806,227 Filed Mar. 28, 2013 for additional information re: deleted proteolytic loop regions in HA sequences, which is incorporated herein by reference) fused to the transmembrane domain and cytoplasmic tail (TMCT) of H1 from influenza A/California/7/2009 and with the signal peptide of alfalfa protein disulfide isomerase (PDISP/HA B Massachusetts (PrL-)+H1 California TMCT) (FIG. 35A, SEQ ID NO: 99) was cloned into original CPMV-HT and CPMV160+ using the same PCR-based method as described in Examples 5.7 and 5.11, but with modified PCR primers specifically designed for PDISP/HA B Massachusetts (PrL-)+H1 California TMCT. The amino acid sequence of mature HA B Massachusetts (PrL-)+H1 California TMCT fused with PDISP is presented in FIG. 35B (SEQ ID NO: 100). Representations of plasmid 2074 and 2060 are presented in FIGS. 35C and 35D.

Example 5.17-2X35S/CPMV HT (Construct No 1445), 2X35S/CPMVHT+ (Construct No 1820) and CPMV160+ (Construct No 1975) for HA B Wisconsin (PrL-)

Figure 36C:
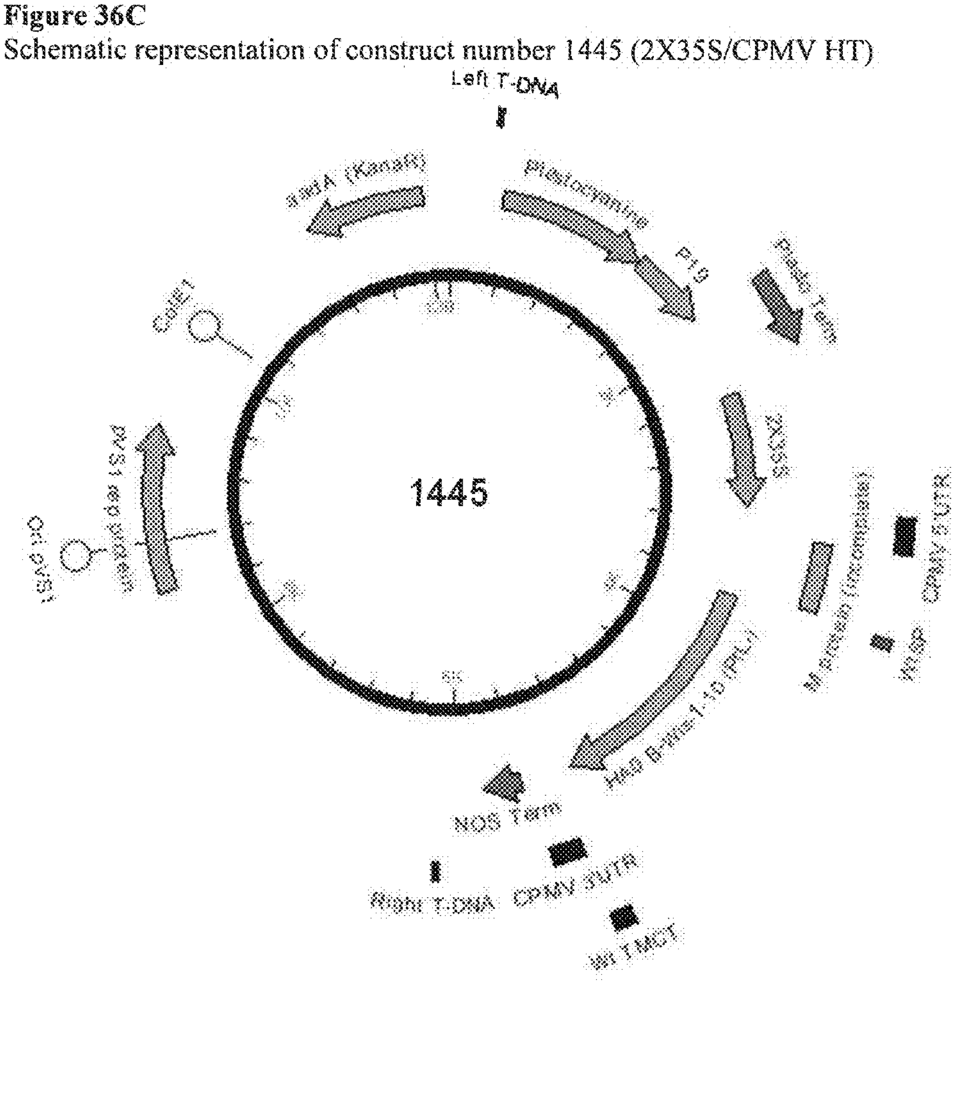
FIG. 36C shows a schematic representation of construct number 1445 (2X35S/CPMV HT; reference construct).
Figure 36D:
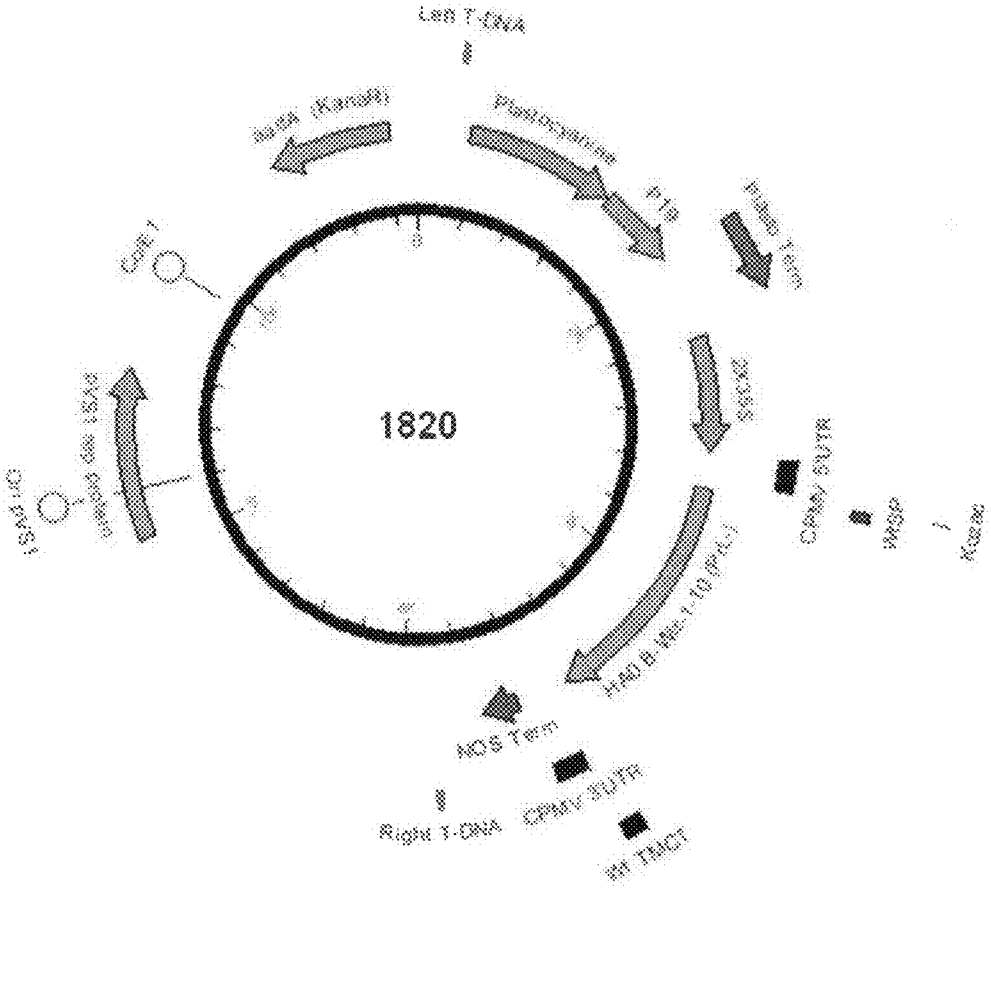
FIG. 36D shows a schematic representation of construct number 1820 (2X35S/CPMV160+; a CPMVX+ based construct).
Figure 36E:
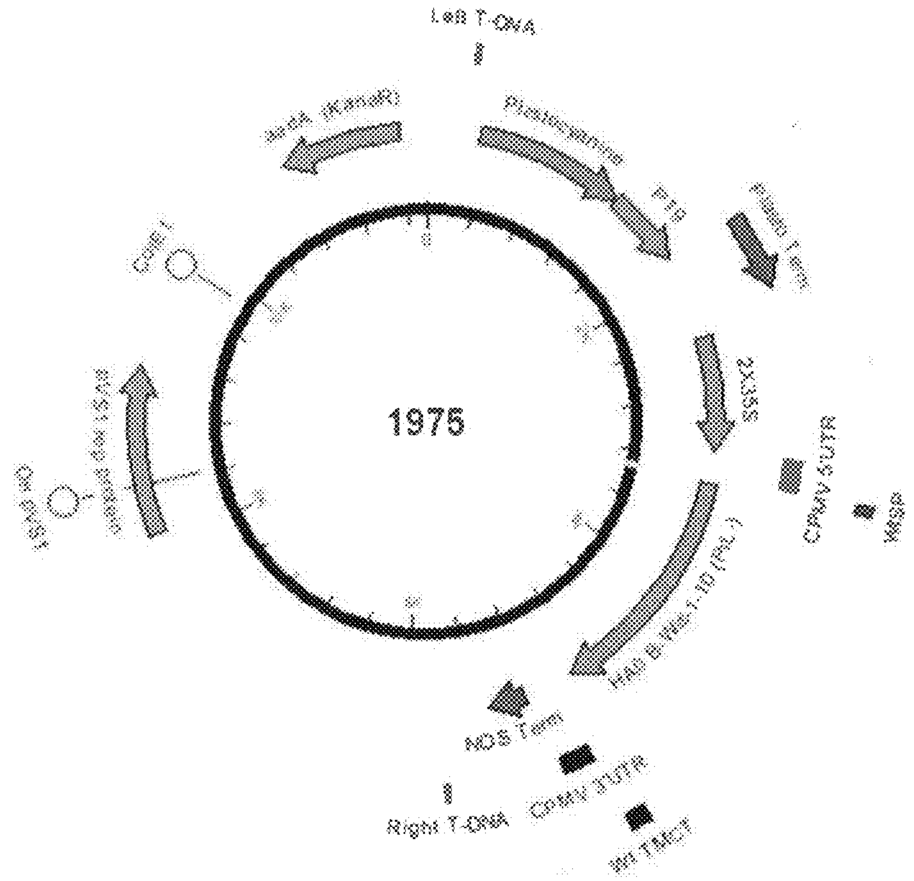
FIG. 36E shows a schematic representation of construct number 1975 (2X35S/CPMV160; a CPMVX based construct, where X=160).

A coding sequence corresponding to HA from Influenza B/Wisconsin/1/2010 with deleted proteolytic loop (PrL-) (see U.S. provisional application No. 61/806,227 Filed Mar. 28, 2013 for additional information re: deleted proteolytic loop regions in HA sequences, which is incorporated herein by reference) with his native signal peptide (HA B Wisconsin (PrL-)) (FIG. 36AA, SEQ ID NO: 101) was cloned into original CPMV-HT, CPMVHT+, and CPMV160 using the same PCR-based method as described in Examples 5.7 and 5.11, but with modified PCR primers specifically designed for HA B Wisconsin (PrL-). The amino acid sequence of HA B Wisconsin (PrL-) with his native signal peptide is presented in FIG. 36B (SEQ ID NO: 102). Representations of plasmid 1445, 1820 and 1975 are presented in FIGS. 36C, 36D and 36E, respectively.

Figure 37C:
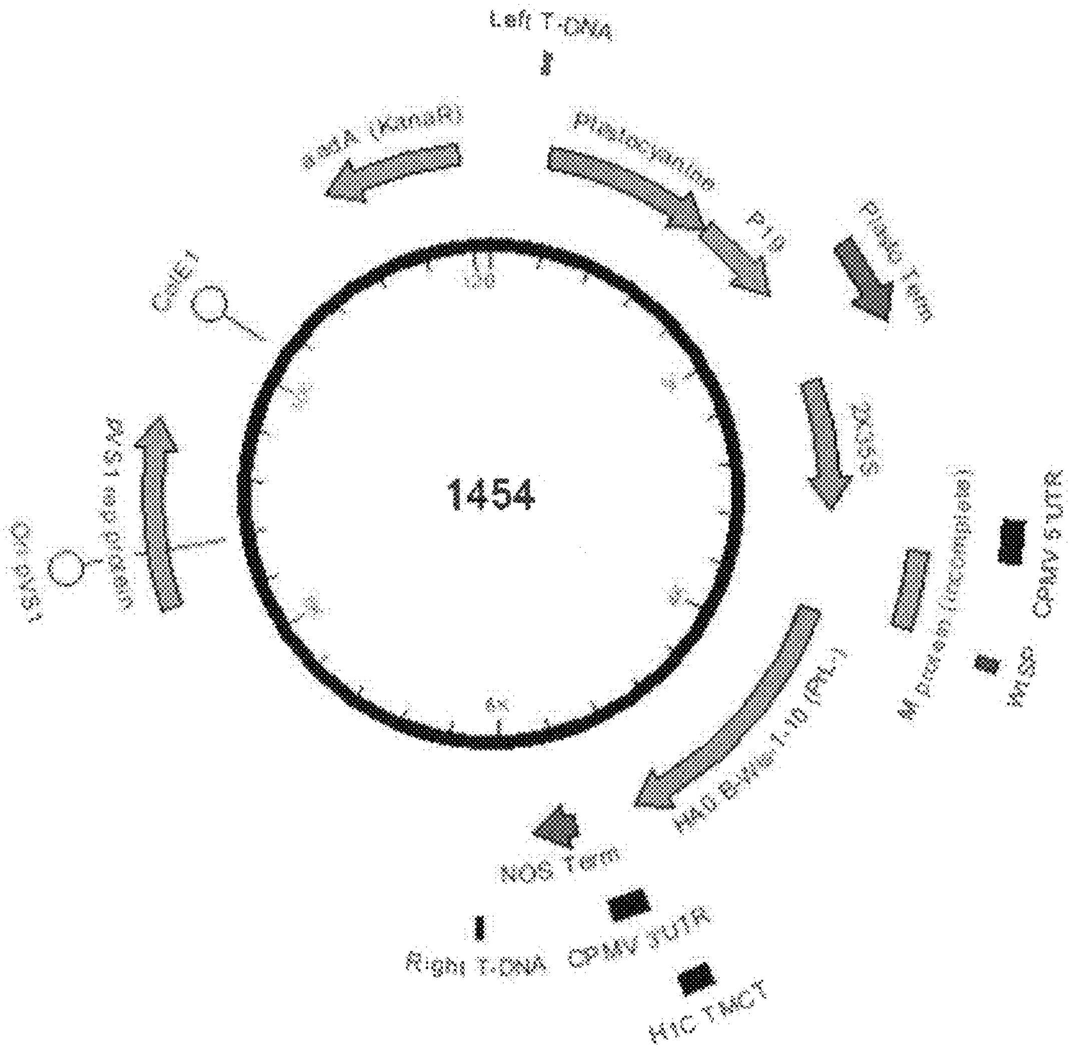
FIG. 37C shows a schematic representation of construct number 1454 (2X35S/CPMV HT; reference construct).
Figure 37D:
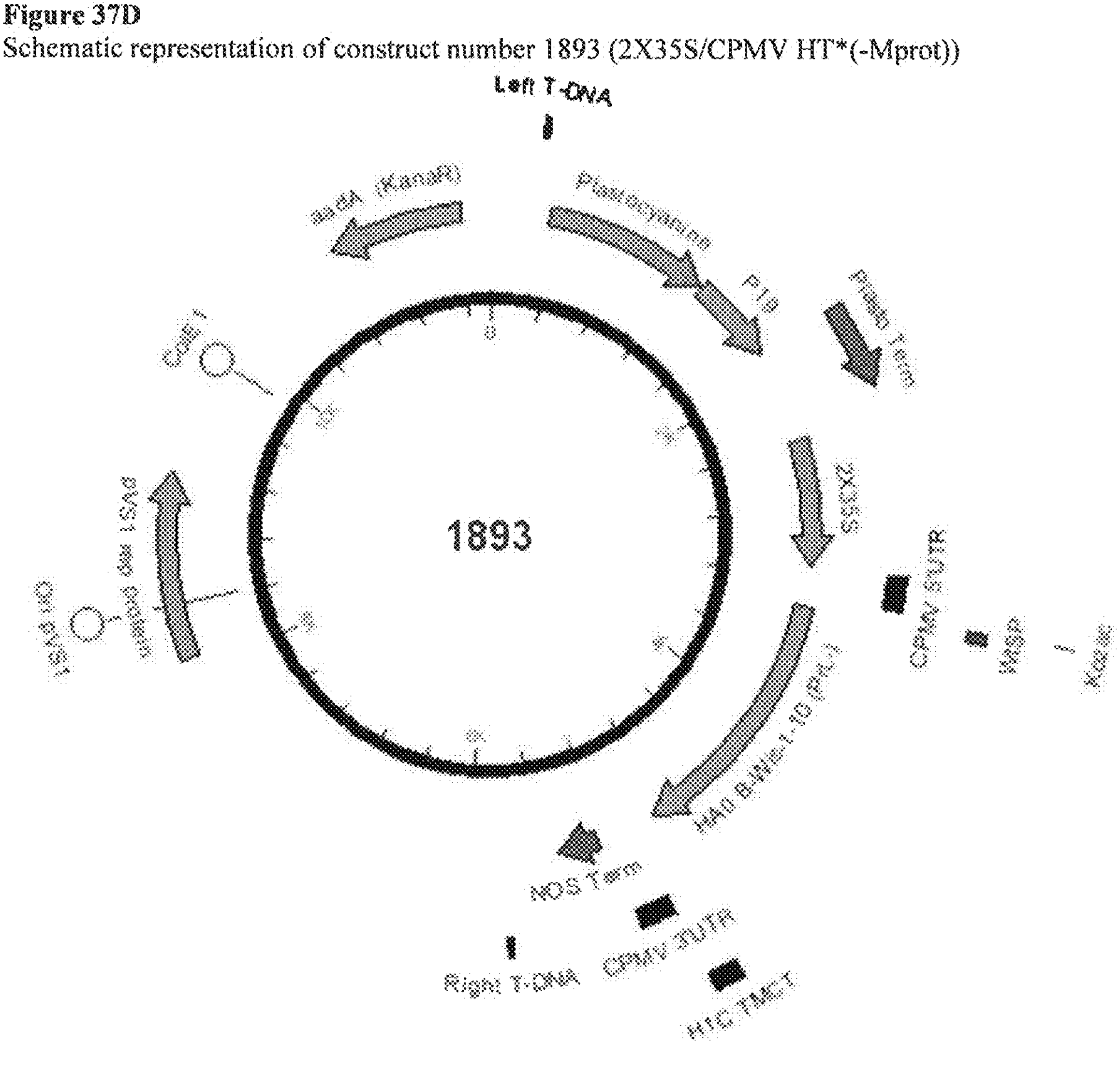
FIG. 37D shows a schematic representation of construct number 1893 (2X35S/CPMV160+; a CPMVX+ based construct, where X=160).

Example 5.18-2X35S/CPMV HT (Construct No 1454) and 2X35S/CPMV160+ (Construct No 1893) for HA B Wisconsin (PrL-)+H1 California TMCT A chimer hemagglutinin coding sequence corresponding to the ectodomain of HA from Influenza B/Wisconsin/2/2012 with deleted proteolytic loop (PrL-) (see U.S. provisional application No. 61/806,227 Filed Mar. 28, 2013 for additional information re: deleted proteolytic loop regions in HA sequences, which is incorporated herein by reference) fused to the transmembrane domain and cytoplasmic tail (TMCT) of H1 from influenza A/California/7/2009 with the native signal peptide of HA B Wisconsin (HA B Wisconsin (PrL-)+H1 California TMCT) (FIG. 37A, SEQ ID NO: 103) was cloned into original CPMV-HT and CPMV160+ using the same PCR-based method as described in Examples 5.7 and 5.11, but with modified PCR primers specifically designed for HA B Wisconsin (PrL-)+H1 California TMCT. The amino acid sequence of HA B Wisconsin (PrL-)+H1 California TMCT is presented in FIG. 37 (SEQ ID NO:

104). Representations of plasmid 1454 and 1893 are presented in FIGS. 37C and 37D.

Figure 38C:
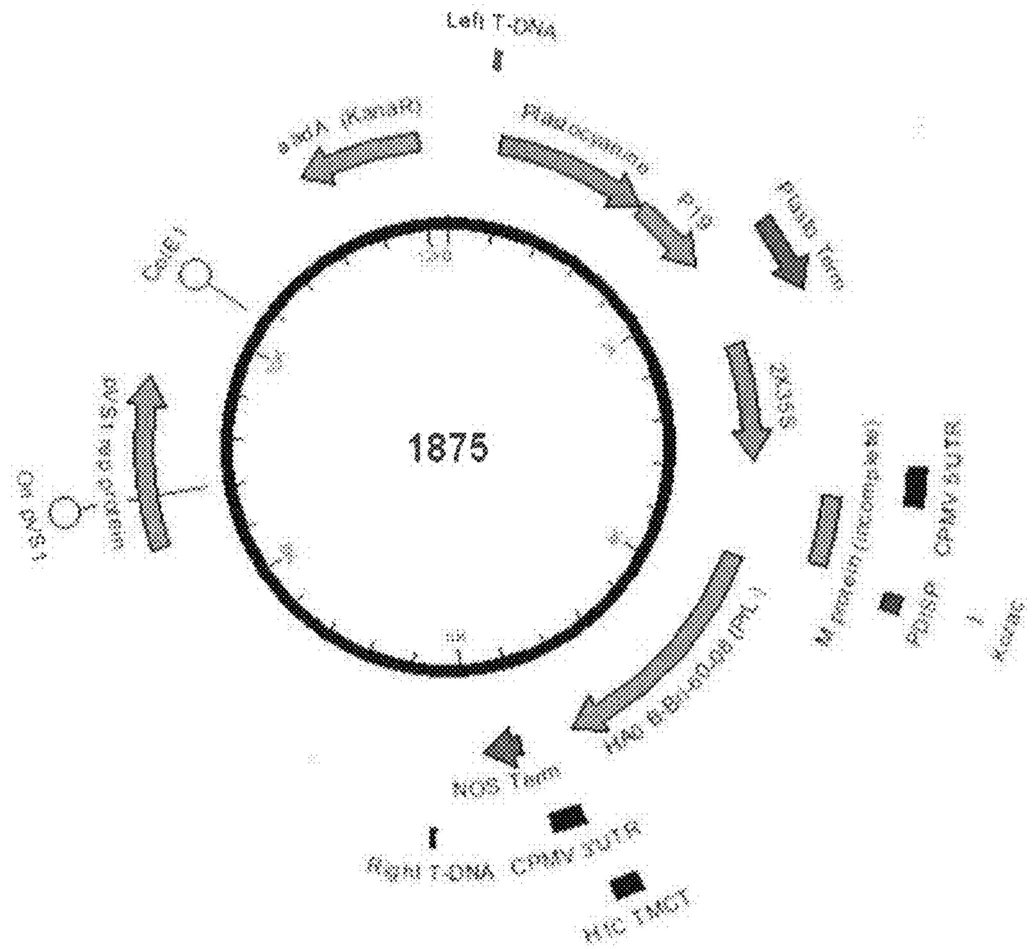
FIG. 38C shows a schematic representation of construct number 1875 (2X35S/CPMV160+).
Figure 39C:
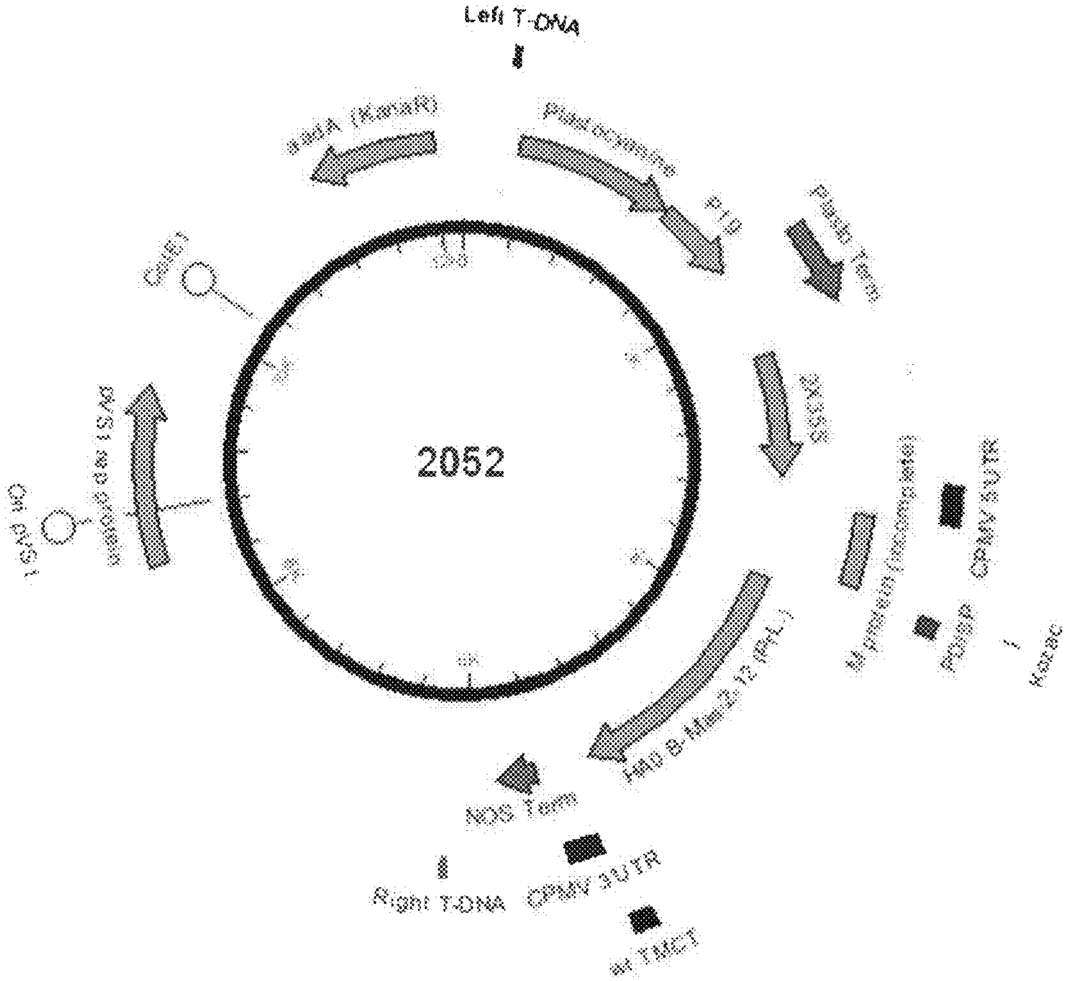
FIG. 39C shows a schematic representation of construct number 2052 (2X35S/CPMV HT+).

Example 5.19: 2X35S/CPMV HT (Construct No 1067) and HT+ (Construct No 1875) for PDISP/HA B Brisbane (PrL-)+H1 California TMCT A chimer hemagglutinin coding sequence corresponding to the ectodomain of HA from Influenza B/Brisbane/60/08 with deleted proteolytic loop (PrL-) fused to the transmembrane domain and cytoplasmic tail (TMCT) of H1 from influenza A/California/7/2009 and with the signal peptide of alfalfa protein disulfide isomerase (PDISP/HA B Brisbane (PrL-)+H1 California TMCT) (FIG. 38A, SEQ ID NO: 105) was cloned into original HT and modified HT+ using the same PCR-based method as described in Example 5.26, but with modified PCR primers specifically designed for PDISP/HA B Brisbane (PrL-)+H1 California TMCT. The amino acid sequence of mature HA B Brisbane (PrL-)+H1 California TMCT fused with PDISP is presented in FIG. 38B (SEQ ID NO: 106). Representations of plasmid 1067 and 1875 are presented in FIGS. 33C and 39C.

Example 5.20: 2X35S/CPMV HT (Construct No 2072) and HT+ (Construct No 2052) for PDISP/HA B Massachusetts (PrL-)

A coding sequence corresponding to HA from Influenza B/Massachusetts/2/2012 with deleted proteolytic loop (PrL-) in which the native signal peptide has been replaced by that of alfalfa protein disulfide isomerase (PDISP/HA B Massachusetts (PrL-)) (FIG. 39A, SEQ ID NO: 107) was cloned into original HT and modified HT+ using the same PCR-based method as described in Example 5.26, but with modified PCR primers specifically designed for PDISP/HA B Massachusetts (PrL-). The amino acid sequence of mature HA B Massachusetts (PrL-) fused with PDISP is presented in FIG. 39B (SEQ ID NO: 108). Representations of plasmid 2072 and 2052 are presented in FIG. 34C and FIG. 39C.

Example 5.21: 2X35S/CPMV HT (Construct No 2074) and HT+ (Construct No 2062) for PDISP/HA B Massachusetts (PrL-)+H1 California TMCT A chimer hemagglutinin coding sequence corresponding to the ectodomain of HA from Influenza B/Massachusetts/2/2012 with deleted proteolytic loop (PrL-) fused to the transmembrane domain and cytoplasmic tail (TMCT) of H1 from influenza A/California/7/2009 and with the signal peptide of alfalfa protein disulfide isomerase (PDISP/HA B Massachusetts (PrL-)+H1 California TMCT) (FIG. 40A, SEQ ID NO: 109) was cloned into original HT and modified HT+ using the same PCR-based method as described in Example 5.26, but with modified PCR primers specifically designed for PDISP/HA B Massachusetts (PrL-)+H1 California TMCT. The amino acid sequence of mature HA B Massachusetts (PrL-)+H1 California TMCT fused with PDISP is presented in FIG. 40B (SEQ ID NO: 110). Representations of plasmid 2074 and 2062 are presented in FIG. 35C and FIG. 40C.

Example 5.22: 2X35S/CPMV HT (Construct No 1445) and HT+ (Construct No 1839) for HA B Wisconsin (PrL-)

Figure 41C:
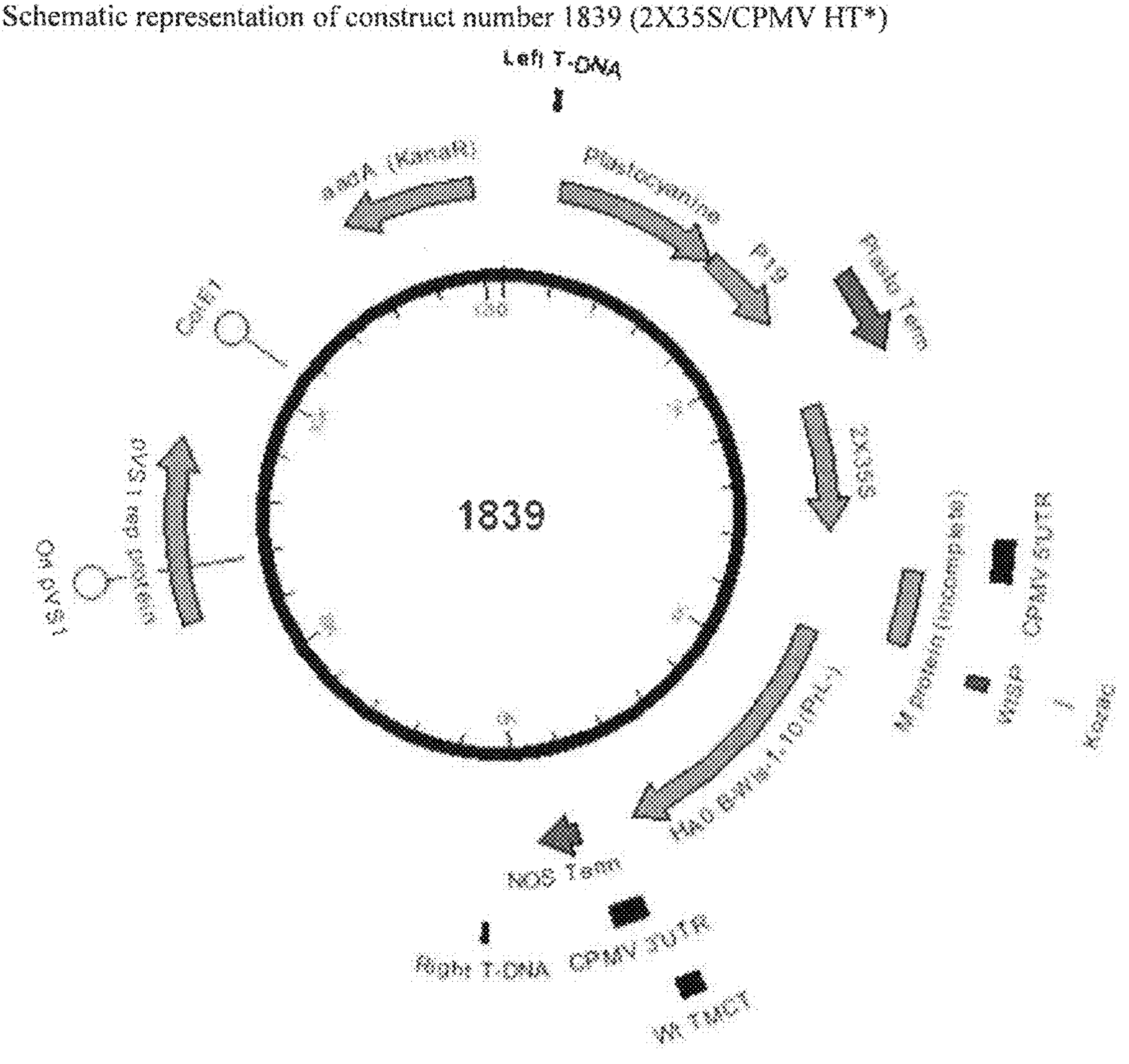
FIG. 41C shows a schematic representation of construct number 1839 (2X35S/CPMV HT+).

A coding sequence corresponding to HA from Influenza B/Wisconsin/1/2010 with deleted proteolytic loop (PrL-) with his native signal peptide (HA B Wisconsin (PrL-)) (FIG. 41A, SEQ ID NO: 111) was cloned into original HT and modified HT+ using the same PCR-based method as described in Example 5.26, but with modified PCR primers specifically designed for HA B Wisconsin (PrL-). The amino acid sequence of HA B Wisconsin (PrL-) with his native signal peptide is presented in FIG. 41B (SEQ ID NO: 112). Representations of plasmid 1445 and 1839 are presented in FIGS. 36C and 41C.

Figure 42C:
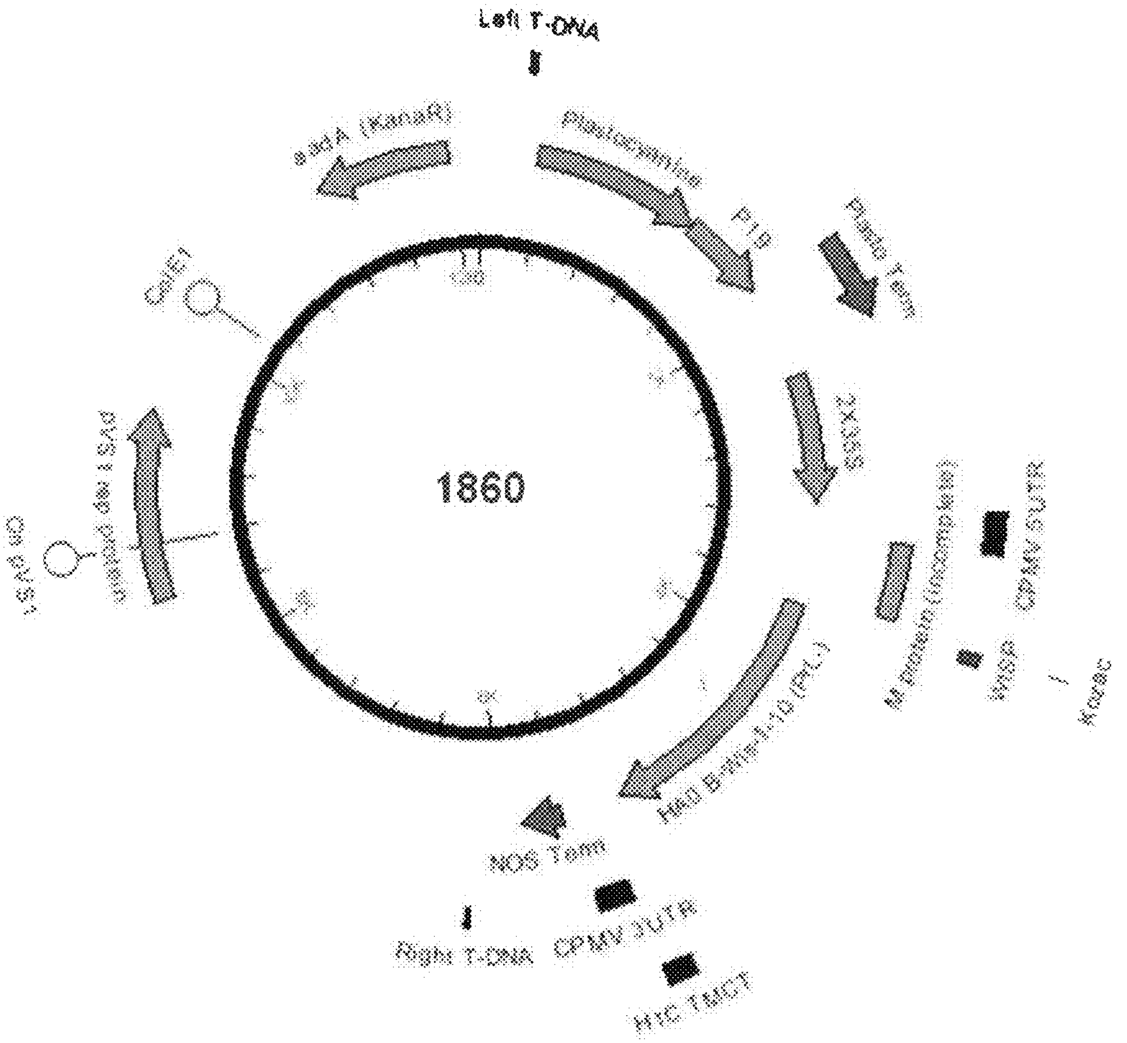
FIG. 42C shows a schematic representation of construct number 1893 (2X35S/CPMV HT+).

Example 5.23: 2X35S/CPMV HT (Construct No 1454) and HT+ (Construct No 1860) for HA B Wisconsin (PrL-)+H1 California TMCT A chimer hemagglutinin coding sequence corresponding to the ectodomain of HA from Influenza B/Wisconsin/2/2012 with deleted proteolytic loop (PrL-) fused to the transmembrane domain and cytoplasmic tail (TMCT) of H1 from influenza A/California/7/2009 with the native signal peptide of HA B Wisconsin (HA B Wisconsin (PrL-)+H1 California TMCT) (FIG. 42A, SEQ ID NO: 113) was cloned into original HT and modified HT+ using the same PCR-based method as described in Example 5.26 but with modified PCR primers specifically designed for HA B Wisconsin (PrL-)+H1 California TMCT. The amino acid sequence of HA B Wisconsin (PrL-)+H1 California TMCT is presented in FIG. 42B (SEQ ID NO: 114). Representations of plasmid 1454 and 1860 are presented in FIGS. 37C and 42C.

Figure 43C:
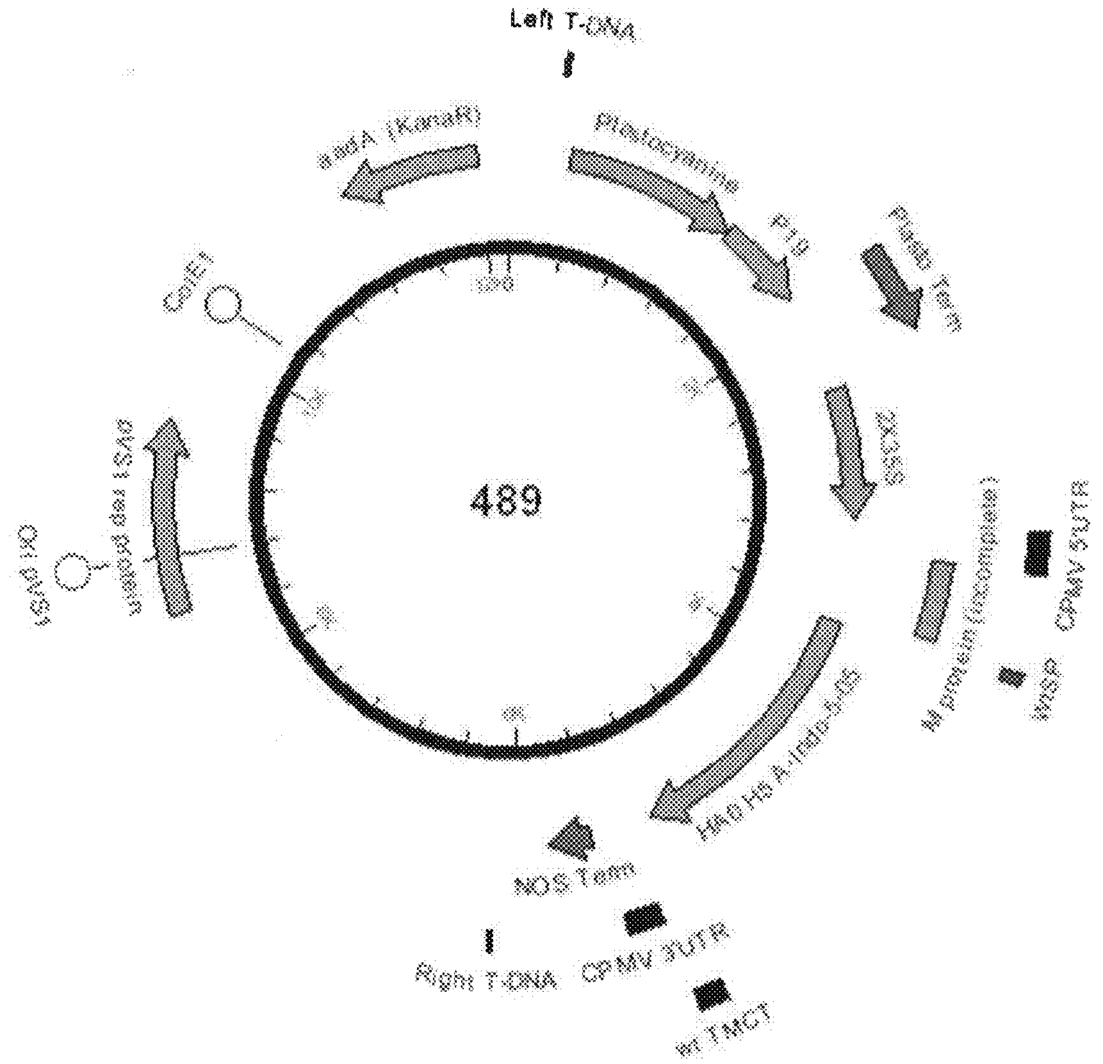
FIG. 43C shows a schematic representation of construct number 489 (2X35S/CPMV HT; reference construct).

Example 5.24-2X35S/CPMV HT (Construct No 489), 2X35S/CPMV160+ (Construct No 1880) and 2X35S/CPMV160 (Construct No 1885) for H5 Indonesia A coding sequence corresponding to native H5 from Influenza A/Indonesia/5/2005 (FIG. 43A, SEQ ID NO: 115) was cloned into original CPMV-HT, CPMV160+ and CPMV160 using the same PCR-based method as described in Example 5.25 but with modified PCR primers specifically designed for H5 Indonesia. The amino acid sequence of native H5 from Influenza A/Indonesia/5/2005 is presented in FIG. 43B (SEQ ID NO: 116). Representation of plasmid 489 is presented in FIG. 43C.

Example 5.25-2X35S/CPMV160+/PDISP/H3 Victoria/NOS (Construct Number 1800)

Figure 44D:
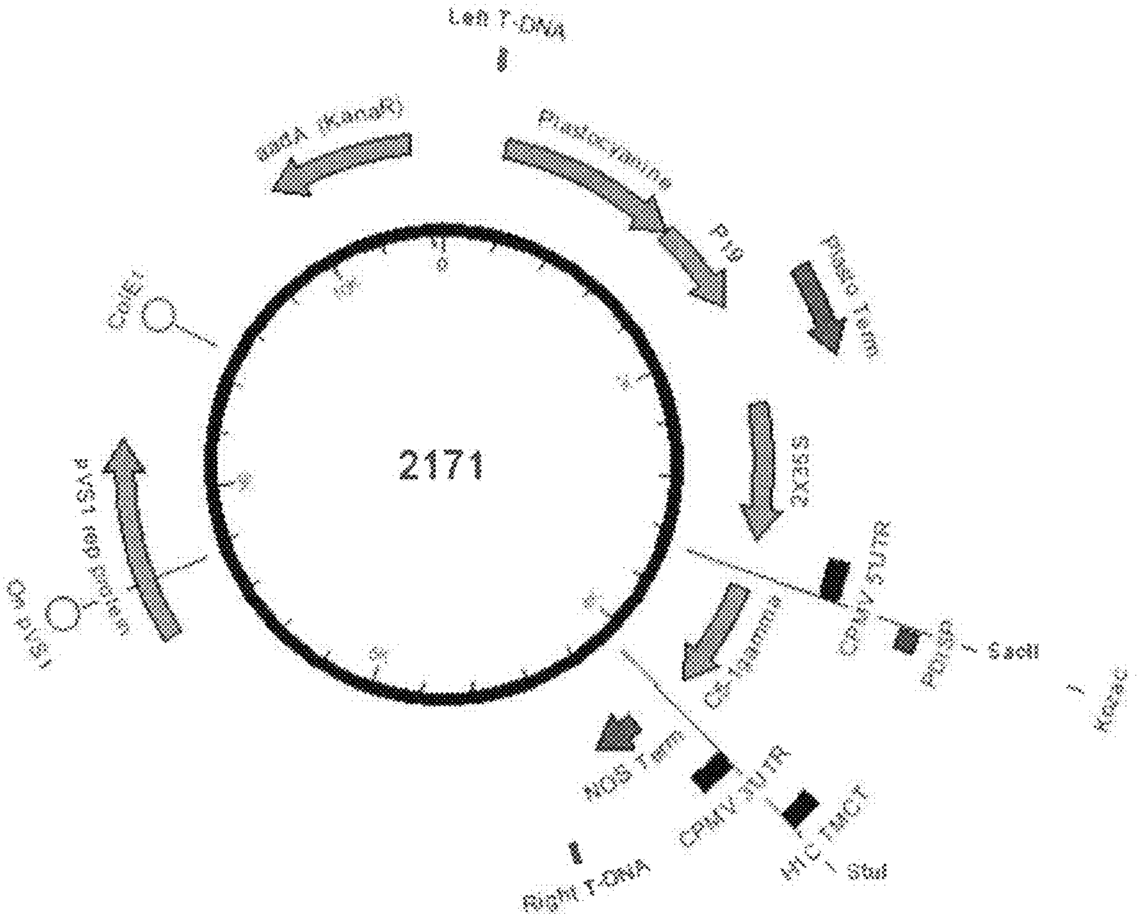
FIG. 44D shows a schematic representation of construct 2171 (SacII and StuI restriction enzyme sites used for plasmid linearization are indicated).
Figure 44H:
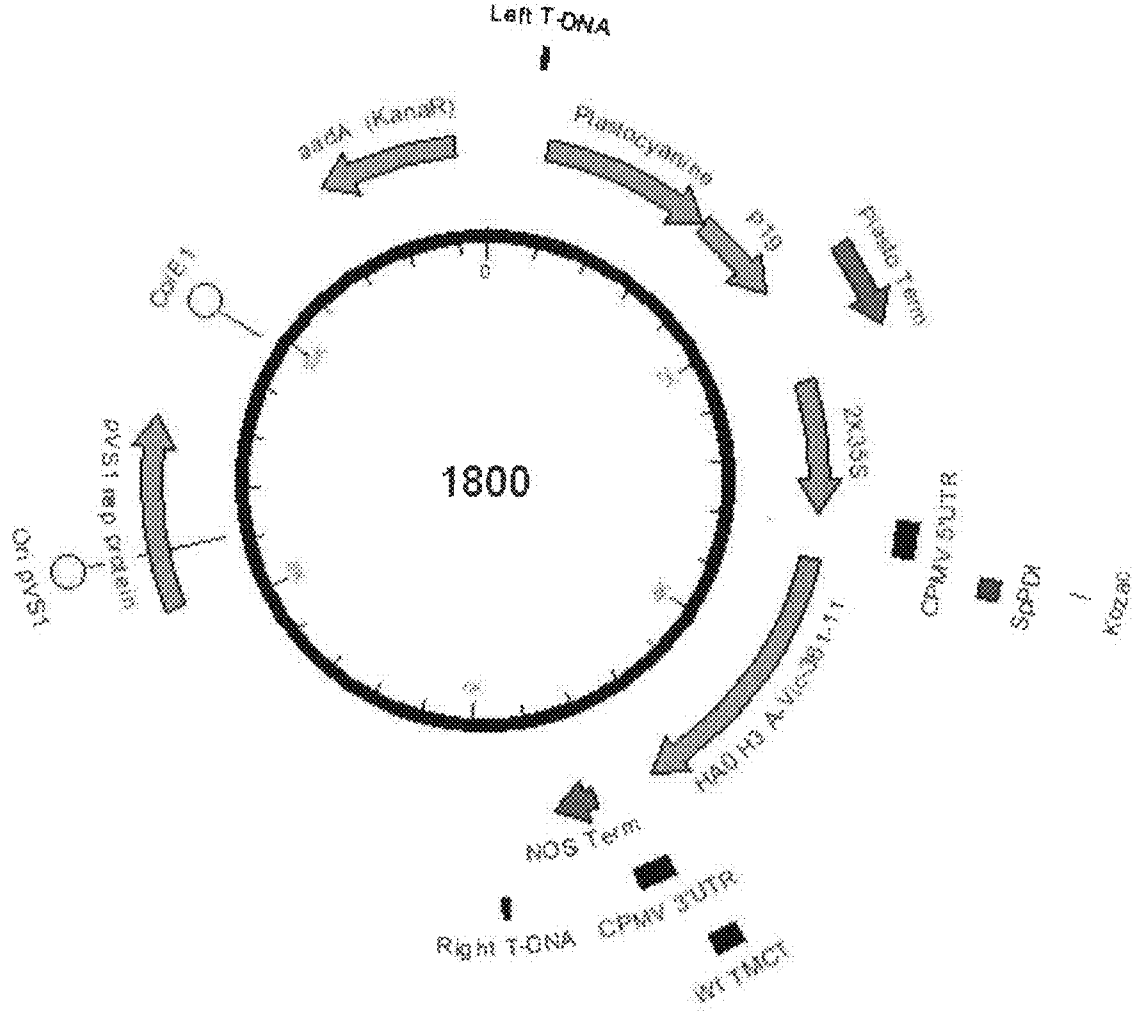
FIG. 44H shows a schematic representation of construct number 1800 (a CPMVX+ based construct, where X=160).

A sequence encoding H3 from Influenza A/Victoria/361/2011 in which the native signal peptide has been replaced by that of alfalfa protein disulfide isomerase (PDISP/H3 Victoria) was cloned into 2X35S/CPMV160+/NOS expression system (CPMV160+) using the following PCR-based method. A fragment containing the PDISP/H3 Victoria coding sequence was amplified using primers IF(SacII)-PDI.s1+4c (FIG. 44A, SEQ ID NO: 117) and IF-H3V36111.s1-4r (FIG. 44B, SEQ ID NO: 118), using PDISP/H3 Victoria sequence (FIG. 44C, SEQ ID NO: 119) as template. The PCR product was cloned in 2X35S/CPMV160+/NOS expression system using In-Fusion cloning system (Clontech, Mountain View, Calif.). Construct number 2171 (FIG. 44D) was digested with SacII and StuI restriction enzyme and the linearized plasmid was used for the In-Fusion assembly reaction. Construct number 2171 is an acceptor plasmid intended for "In Fusion" cloning of genes of interest in a CPMV160+ based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 44E (SEQ ID NO: 120). The resulting construct was given number 1800 (FIG. 44F, SEQ ID NO: 121). The amino acid sequence of mature H3 from Influenza A/Victoria/361/2011 fused with PDISP is presented in FIG. 44G (SEQ ID NO: 122). A representation of plasmid 1800 is presented in FIG. 44**H.

Example 5.26: 2X35S/CPMV-HT+/PDISP/H3 Victoria/NOS (Construct Number 1819)

Figure 45F:
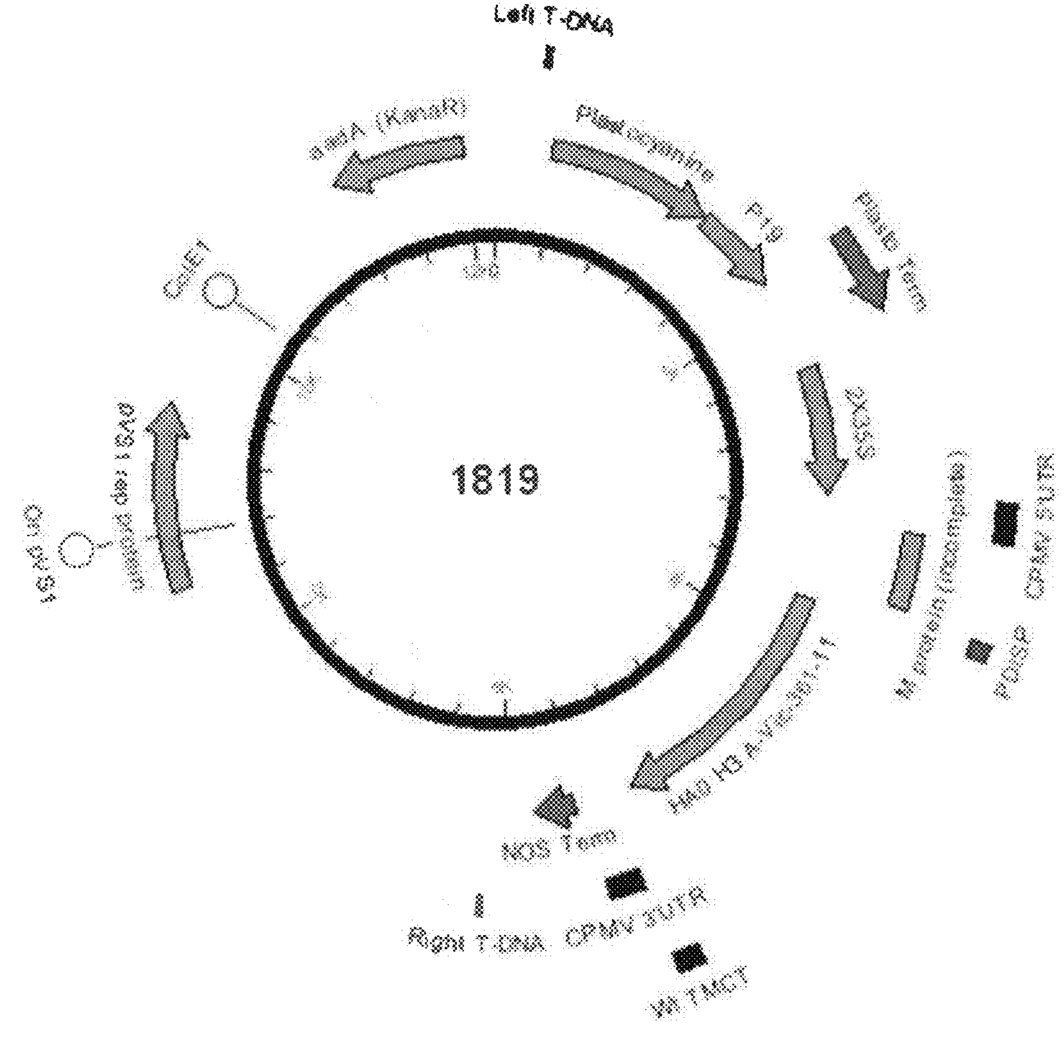
FIG. 45F shows a schematic representation of construct 1819.

A sequence encoding H3 from Influenza A/Victoria/361/2011 in which the native signal peptide has been replaced by that of alfalfa protein disulfide isomerase (PDISP/H3 Victoria) was cloned into 2X35S-CPMV-HT+/NOS expression using the following PCR-based method. A fragment containing the PDISP/H3 Victoria coding sequence was amplified using primers IF(SacII)-Kozac_PDI.c (FIG. 45A, SEQ ID NO: 123) and IF-H3V36111.s1-4r (FIG. 45B, SEQ ID NO: 124), using PDISP/H3 Victoria sequence (FIG. 44C, SEQ ID NO: 119) as template. The PCR product was cloned in 2X35S/CPMV-HT+/NOS expression system using In-Fusion cloning system (Clontech, Mountain View, Calif.). Construct number 2181 (FIG. 45D) was digested with SacII and StuI restriction enzyme and the linearized plasmid was used for the In-Fusion assembly reaction. Construct number 2181 is an acceptor plasmid intended for "In Fusion" cloning of genes of interest in a CPMV-HT+ based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 45E (SEQ ID NO: 125). The resulting construct was given number 1819 (FIG. 45E, SEQ ID NO: 126). The amino acid sequence of mature H3 from Influenza A/Victoria/361/2011 fused with PDISP is presented in FIG. 44G (SEQ ID NO: 122). A representation of plasmid 1819 is presented in FIG. 45F.

Example 5.27 2X35S/CPMV HT+/PDISP/H2 Singapore/NOS (Construct Number 2220)

A sequence encoding H2 from Influenza A/Singapore/1/1957 in which the native signal peptide has been replaced by that of alfalfa protein disulfide isomerase (PDISP/H2 Singapore) was cloned into 2X35S/CPMV HT+/NOS expression system using the following PCR-based method. A fragment containing the PDISP/H2 Singapore coding sequence was amplified using primers IF(SacII)-Kozac_PDI.c (described for construct 1819 in Example 5.26) and IF-H2S157.s1-6r (FIG. 48A, SEQ ID NO: 127), using PDISP/H2 Singapore sequence (FIG. 48B, SEQ ID NO: 128) as template. The PCR product was cloned in 2X35S/CPMV HT+/NOS expression system using In-Fusion cloning system (Clontech, Mountain View, Calif.). Construct number 2181 (described for construct 1819 in Example 5.26) was digested with SacII and StuI restriction enzyme and the linearized plasmid was used for the In-Fusion assembly reaction. Construct number 2181 is an acceptor plasmid intended for "In Fusion" cloning of genes of interest in a CPMV HT+ based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 45D. The resulting construct was given number 2220 (FIG. 48C, SEQ ID NO: 129). The amino acid sequence of mature H2 from Influenza A/Singapore/1/1957 fused with PDISP is presented in FIG. 48D (SEQ ID NO: 130). A representation of plasmid 2220 is presented in FIG. 48**E.

Example 5.28 2X35S/CPMV HT+/PDISP/H2 Singapore with Deleted Proteolytic Loop/NOS (Construct Number 2221)

A sequence encoding H2 from Influenza A/Singapore/1/1957 with deleted proteolytic loop in which the native signal peptide has been replaced by that of alfalfa protein disulfide isomerase (PDISP/H2 Singapore with deleted proteolytic loop) was cloned into 2X35S/CPMV HT+/NOS expression system using the following PCR-based ligation method presented by Darveau et al. (Methods in Neuroscience 26: 77-85 (1995)). In a first round of PCR, a fragment containing H2 from Influenza A/Singapore/1/1957 coding sequence from nt 1 to nt 1032 was amplified with primers IF(SacII)-Kozac_PDI.c (described for construct 1819 in Example 5.26) and H2S157(Prl-).r (FIG. 49A, SEQ ID NO: 131), using PDISP/H2 Singapore sequence (FIG. 48B, SEQ ID NO: 128) as template. A second fragment, containing H2 from Influenza A/Singapore/1/1957 coding sequence from nt 1084 to nt 1716, was amplified with primers H2S157 (Prl-).c (FIG. 49B, SEQ ID NO: 132) and IF-H2S157.s1-6r (FIG. 48A, SEQ ID NO: 127) using PDISP/H2 Singapore sequence (FIG. 48B, SEQ ID NO:128) as template. The PCR products from both amplifications were then mixed and used as template for a second round of amplification using IF(SacII)-Kozac_PDI.c (described for construct 1819 in Example 5.26) and IF-H2S157.s1-6r (FIG. 48A, SEQ ID NO: 127) as primers. The PCR product (comprising PDISP/H2 Singapore coding sequence with aa 321 to 337 replaced by a GG linker) was cloned in 2X35S/CPMV HT+/NOS expression system using In-Fusion cloning system (Clontech, Mountain View, Calif.). Construct number 2181 (described for construct 1819 in Example 5.26) was digested with SacII and StuI restriction enzyme and the linearized plasmid was used for the In-Fusion assembly reaction. Construct number 2181 is an acceptor plasmid intended for "In Fusion" cloning of genes of interest in a CPMV HT+ based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 45D (described for construct 1819, in Example 5.26). The resulting construct was given number 2221 (FIG. 49C, SEQ ID NO: 133). The amino acid sequence of mature H2 from Influenza A/Singapore/1/1957 with deleted proteolytic loop fused with PDISP is presented in FIG. 49D (SEQ ID NO: 134). A representation of plasmid 2221 is presented in FIG. 49E.

Figure 50C:
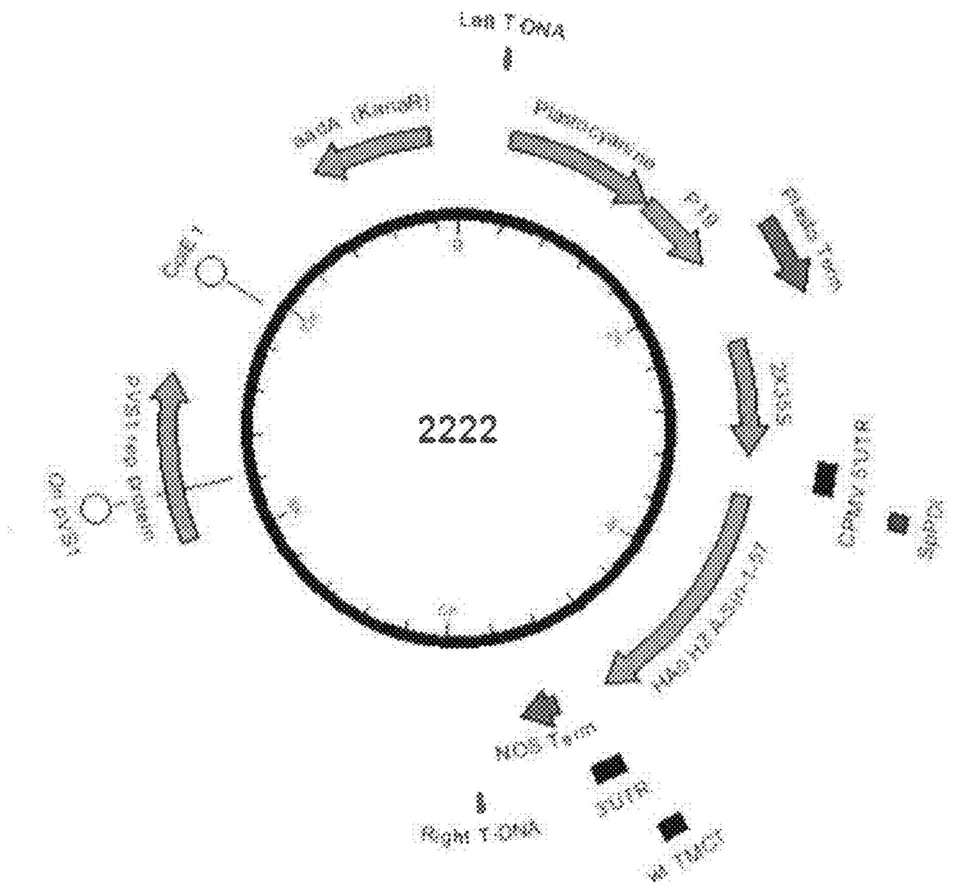
FIG. 50C a schematic representation of construct number 2222 FIG. 50D a schematic representation of construct number 2223.
Figure 50D:
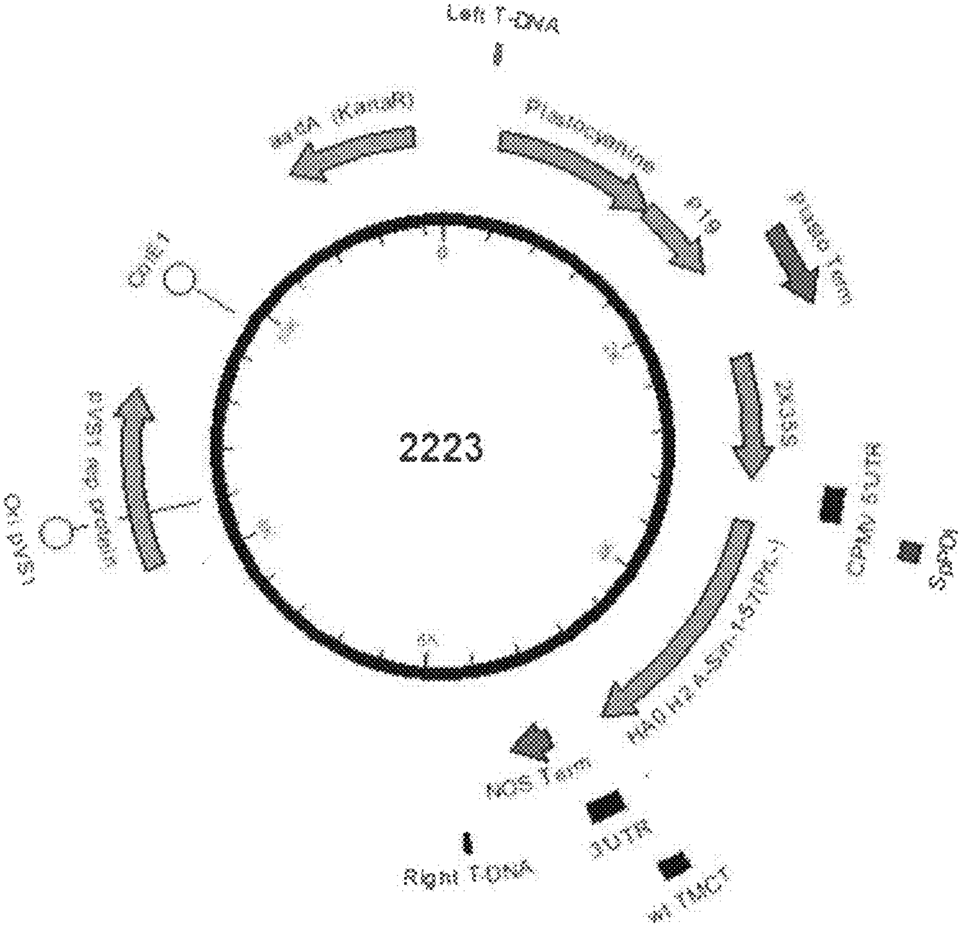
FIG. 50 shows sequence components used to prepare construct numbers 2222 (2X35S/CPMV 160+/PDISP/H2 Singapore) and 2223 (2X35S/CPMV 160+/PDISP/H2 Singapore with deleted proteolytic loop/NOS) see Example 5.29).
FIG. 50A shows the nucleotide sequence of expression cassette number 2222 from 2X35S promoter to NOS terminator. PDISP/H2 Singapore nucleotide sequence is underlined (SEQ ID NO:135).
FIG. 50B shows the nucleotide sequence of expression cassette number 2223 from 2X35S promoter to NOS terminator. PDISP/H2 Singapore with deleted proteolytic loop nucleotide sequence is underlined (SEQ ID NO: 136).

Example 5.29 PDISP/H2 Singapore (Construct Number 2222) and PDISP/H2 Singapore with Deleted Proteolytic Loop (Construct Number 2223) in 2X35S/CPMV 160+/NOS Expression System Sequences encoding H2 from Influenza A/Singapore/1/1957 with or without proteolytic loop in which the native signal peptide has been replaced by that of alfalfa protein disulfide isomerase (PDISP/H2 Singapore and PDISP/H2 Singapore with deleted proteolytic loop) were cloned into 2X35S/CPMV 160+/NOS expression system using the same PCR-based method as construct 2220 and 2221, respectively, but using modified forward primer IF(SacII)-PDI.s1+4c (described for construct 1800 in Example 5.25) for amplification and a different acceptor plasmid. Resulting PCR products were cloned in 2X35S/CPMV 160+/NOS expression system using In-Fusion cloning system (Clontech, Mountain View, Calif.). Construct number 2171 (described for construct 1800 in Example 5.25) was digested with SacII and StuI restriction enzyme and the linearized plasmid was used for the In-Fusion assembly reaction. Construct number 2171 is an acceptor plasmid intended for "In Fusion" cloning of genes of interest in a CPMV 160+ based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in (described for construct 1800 in Example 5.25). The resulting constructs were given number 2222 for PDISP/H2 Singapore (FIG. 50A, SEQ ID NO: 135) and 2223 for PDISP/H2 Singapore with deleted proteolytic loop (FIG. 50B, SEQ ID NO: 136). Representations of plasmid 2222 and 2223 are presented in FIGS. 50C and 50**D respectively.

Figure 51D:
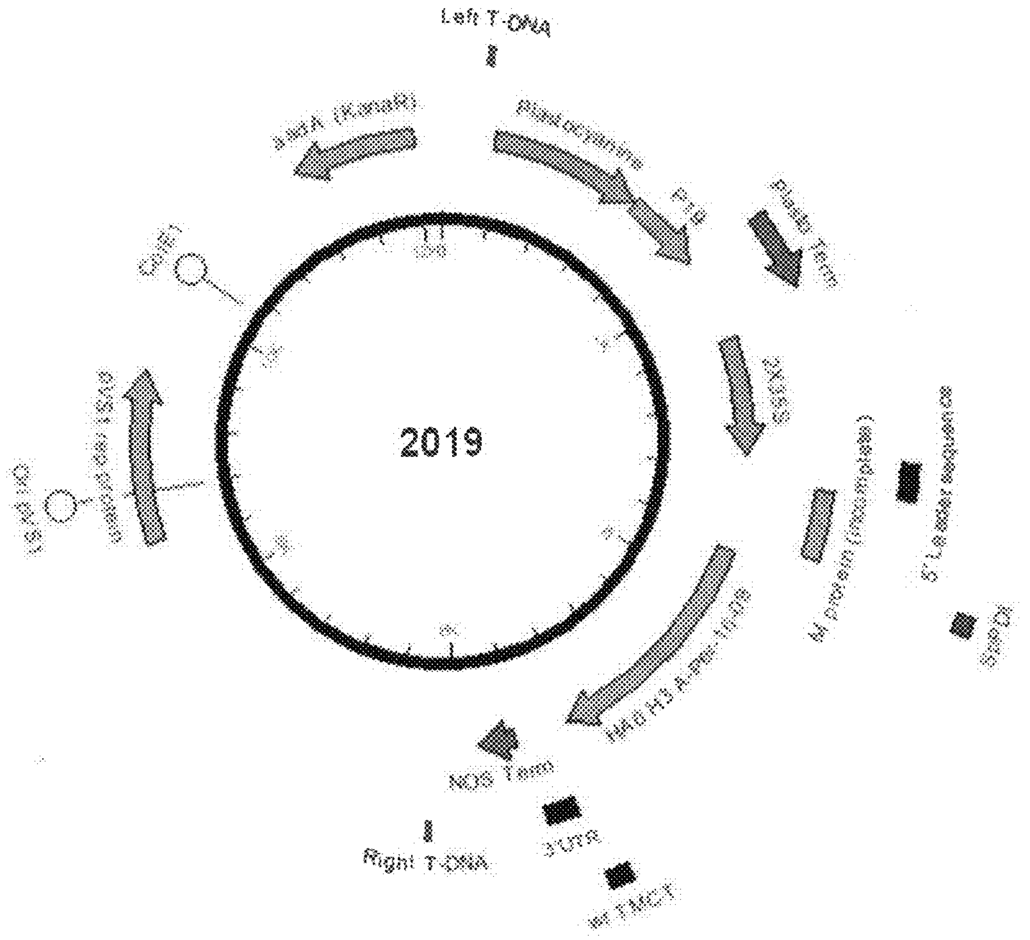
FIG. 51D shows a schematic representation of construct number 2219.
Figure 51E:
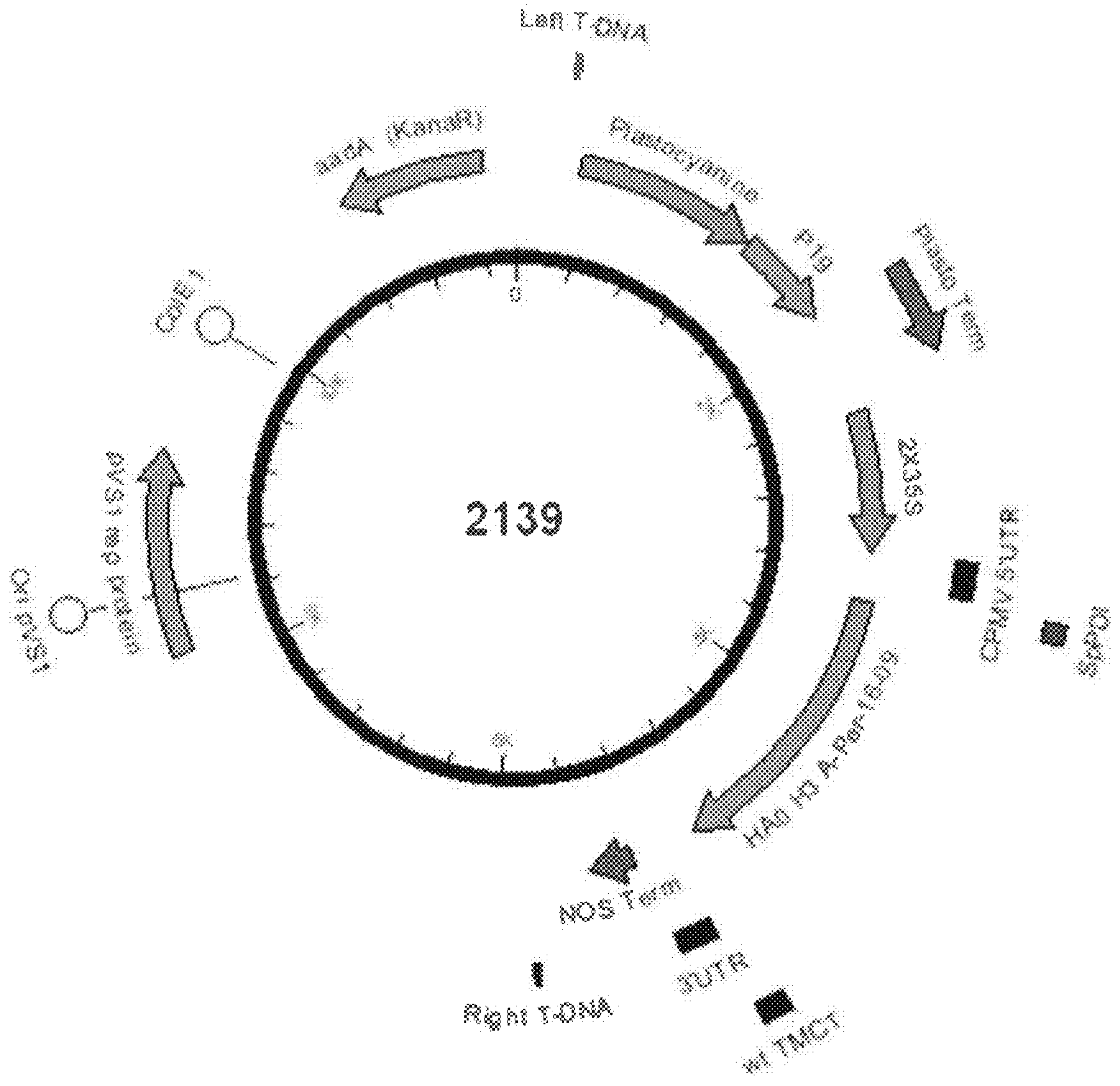
FIG. 51 shows sequence components used to prepare construct numbers 2219 (2X35S/CPMV HT+ PDISP/H3 Perth) and 2139 (2X35S/CPMV 160+/PDISP/H3 Perth) see Example 5.30).
FIG. 51A shows the nucleotide sequence of PDISP/H3 Perth (SEQ ID NO: 137).
FIG. 51B shows the nucleotide sequence of primer IF-H3P1609.S1-6r (SEQ ID NO: 138).
FIG. 51C shows the Amino acid sequence of PDISP/H3 Perth (SEQ ID NO: 139).

Example 5.30 2X35S/CPMV HT+ (Construct No 2019) and 160+ (Construct No 2139) for PDISP/H3 Perth A coding sequence corresponding to H3 from Influenza A/Perth/16/2009 in which the native signal peptide has been replaced by that of alfalfa protein disulfide isomerase (PDISP/H3 Perth) (FIG. 51A, SEQ ID NO: 137) was cloned into modified CPMV HT+ and 160+ using the same In Fusion-based approach as construct 2220 and 2222, respectively, but with modified PCR primer specifically designed for PDISP/H3 Perth (FIG. 51B, SEQ ID NO: 138). The amino acid sequence of mature H3 from Influenza A/Perth/16/2009 fused with PDISP is presented in FIG. 51C (SEQ ID NO: 139). Representations of plasmid 2019 and 2139 are presented in FIG. 51D and FIG. 51E.

Figure 52E:
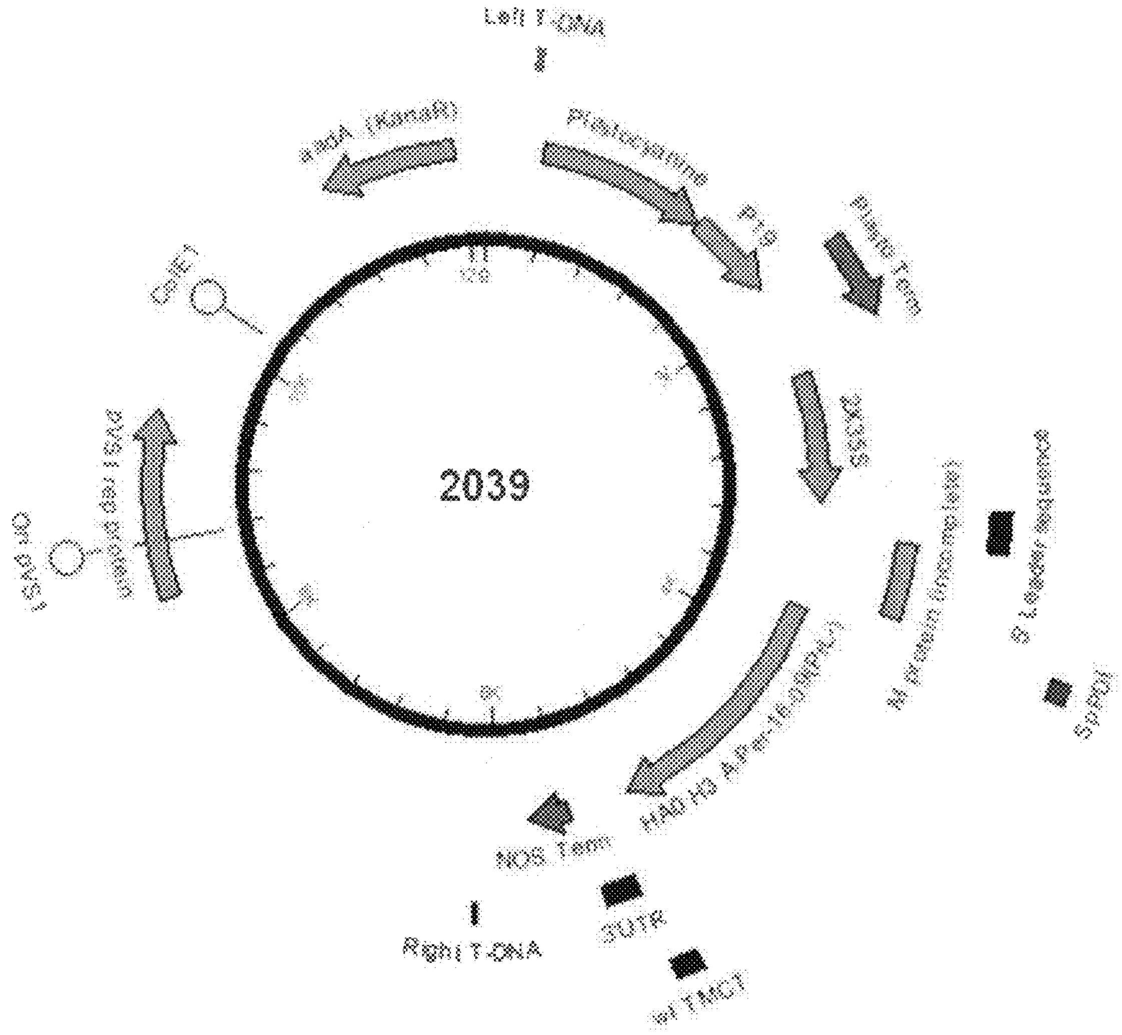
FIG. 52E shows a schematic representation of construct number 2039.
Figure 52F:
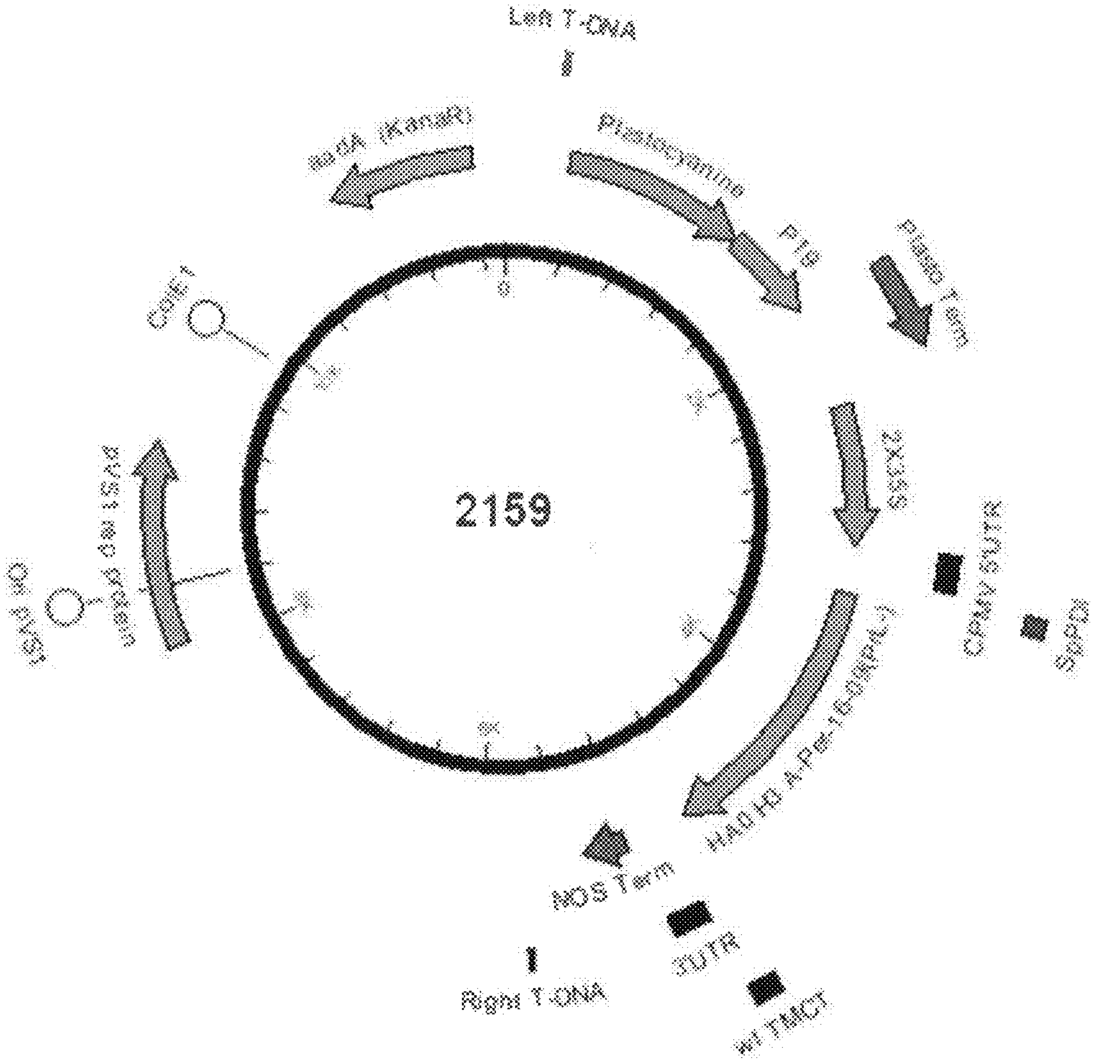
FIG. 52F shows a schematic representation of construct number 2159.

Example 5.31 2X35S/CPMV HT+ (Construct No 2039) and 160+ (Construct No 2159) for PDISP/H3 Perth with Deleted Proteolytic Loop A coding sequence corresponding to H3 from Influenza A/Perth/16/2009 with deleted proteolytic loop in which the native signal peptide has been replaced by that of alfalfa protein disulfide isomerase (PDISP/H3 Perth with deleted proteolytic loop) (FIG. 52, SEQ ID NO: 140) was cloned into modified CPMV HT+ and 160+ using the same In Fusion-based approach as construct 2221 and 2223, respectively, but with modified PCR primers specifically designed for PDISP/H3 Perth with deleted proteolytic loop (FIGS. 51B (SEQ ID NO: 138), 52B (SEQ ID NO: 141) and 53C (SEQ ID NO: 142). The amino acid sequence of mature H3 from Influenza A/Perth/16/2009 with deleted proteolytic loop fused with PDISP is presented in FIG. 52D (SEQ ID NO: 143). Representations of plasmid 2039 and 2159 are presented in FIG. 52E and FIG. 52F.

Figure 53E:
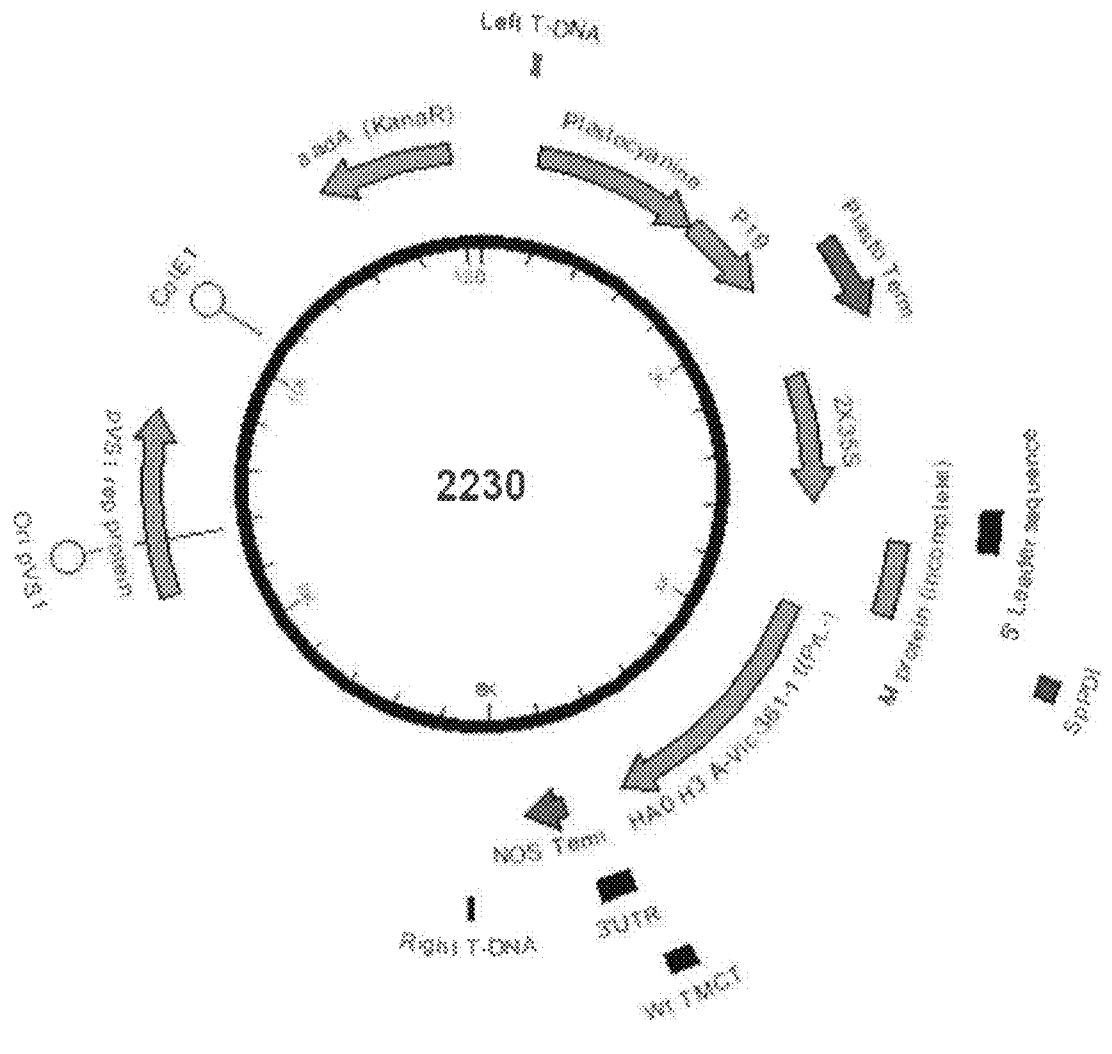
FIG. 53E shows a schematic representation of construct number 2230.
Figure 53F:
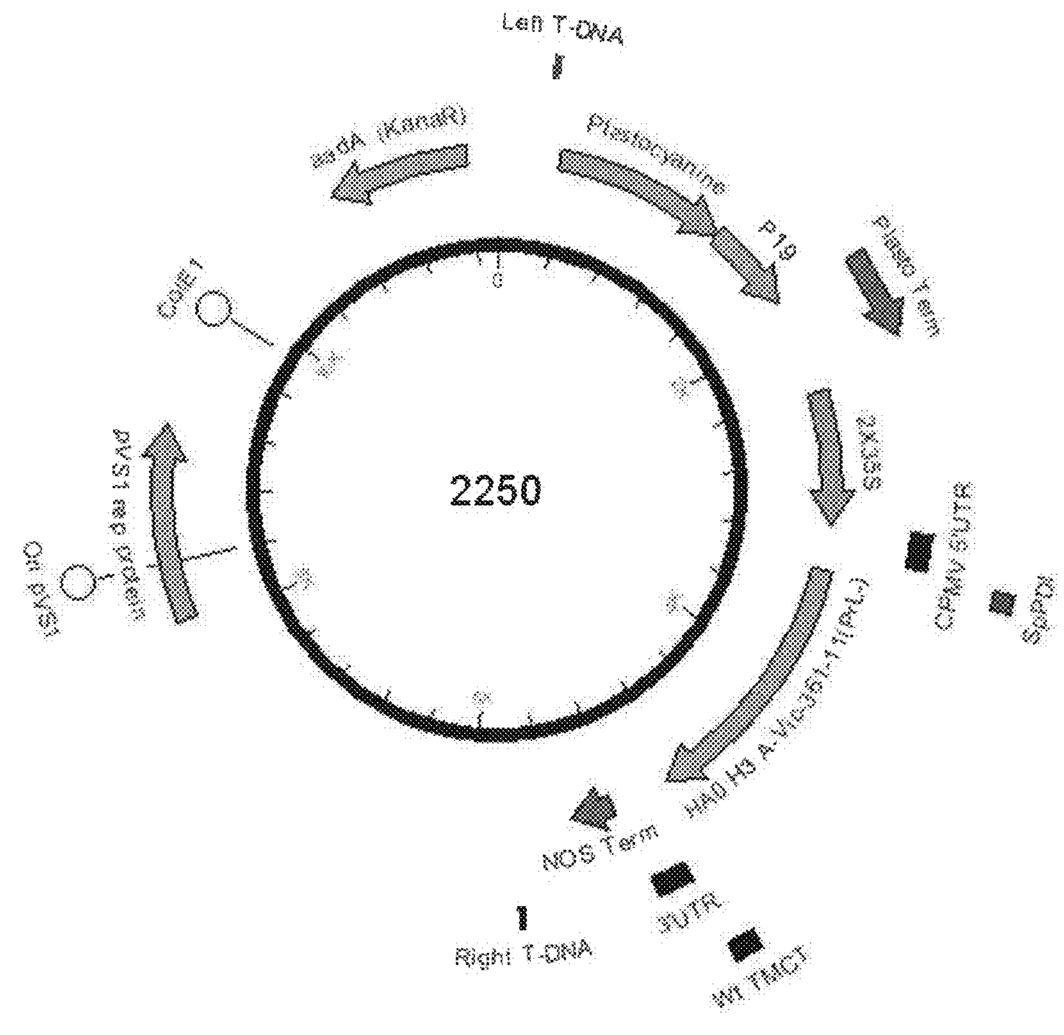
FIG. 53F shows a schematic representation of construct number 2250.

Example 5.32 2X35S/CPMV HT+ (Construct No 2230) and 160+ (Construct No 2250) for PDISP/H3 Victoria with Deleted Proteolytic Loop A coding sequence corresponding to H3 from Influenza A/Victoria/361/2011 with deleted proteolytic loop in which the native signal peptide has been replaced by that of alfalfa protein disulfide isomerase (PDISP/H3 Victoria with deleted proteolytic loop) (FIG. 53, SEQ ID NO: 144) was cloned into modified CPMV HT+ and 160+ using the same In Fusion-based approach as construct 2221 and 2223 (see Examples 5.28 and 5.29), respectively, but with modified PCR primer specifically designed for PDISP/H3 Victoria with deleted proteolytic loop (FIGS. 53B (SEQ ID NO: 145) and 53C (SEQ ID NO: 146). The amino acid sequence of mature H3 from Influenza A/Victoria/361/2011 with deleted proteolytic loop fused with PDISP is presented in FIG. 53D (SEQ ID NO: 147). Representations of plasmid 2230 and 2250 are presented in FIG. 53E and FIG. 53F.

Example 5.33 2X35S/CPMV HT+/PDISP/H7 Hangzhou/NOS (Construct No 2142)

A coding sequence corresponding to H7 from Influenza A/Hangzhou/1/2013 in which the native signal peptide has been replaced by that of alfalfa protein disulfide isomerase (PDISP/H7 Hangzhou) (FIG. 54A, SEQ ID NO: 148) was cloned into modified CPMV HT+ using the same In Fusion-based approach as construct 2220 but with modified PCR primer specifically designed for PDISP/H7 Hangzhou (FIG. 54B, SEQ ID NO: 149). The amino acid sequence of mature H7 from Influenza A/Hangzhou/1/2013 fused with PDISP is presented in FIG. 54C (SEQ ID NO: 150). Representation of plasmid 2142 is presented in FIG. 54E.

Example 5.34 2X35S/CPMV HT+/PDISP/H7 Hangzhou with Deleted Proteolytic Loop/NOS (Construct No 2152)

Figure 55E:
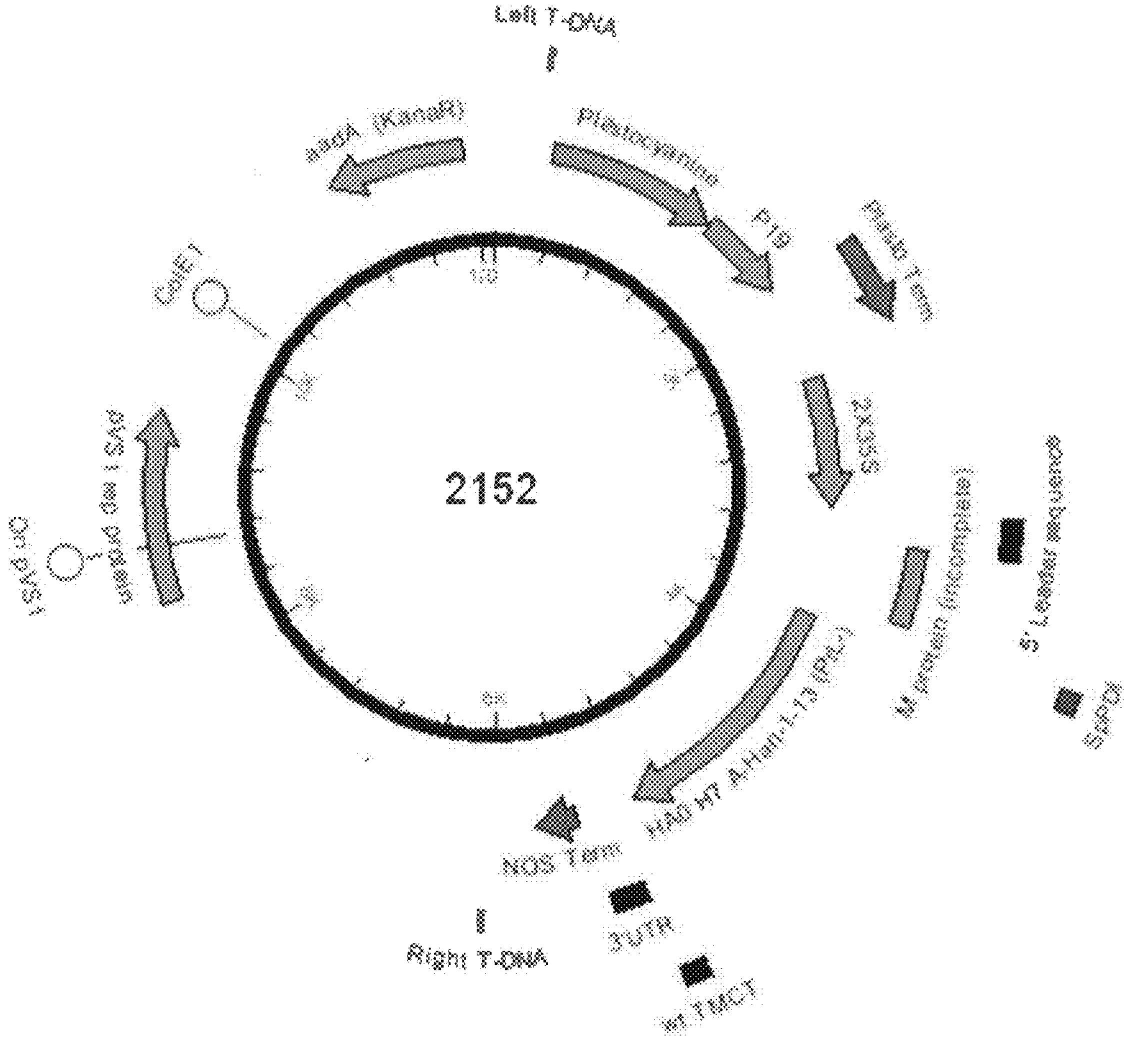
FIG. 55E shows a schematic representation of construct number 2152.

A coding sequence corresponding to H7 from Influenza A/Hangzhou/1/2013 with deleted proteolytic loop in which the native signal peptide has been replaced by that of alfalfa protein disulfide isomerase (PDISP/H7 Hangzhou with deleted proteolytic loop) (FIG. 55A, SEQ ID NO: 151) was cloned into modified CPMV HT+ using the same In Fusion-based approach as construct 2221 but with modified PCR primers specifically designed for PDISP/H7 Hangzhou with deleted proteolytic loop (FIG. 54B (SEQ ID NO: 149), FIG. 55B (SEQ ID NO: 152) and FIG. 55C (SEQ ID NO: 153)). The amino acid sequence of mature H7 from Influenza A/Hangzhou/1/2013 with deleted proteolytic loop fused with PDISP is presented in FIG. 55D (SEQ ID NO: 154). Representation of plasmid 2152 is presented in FIG. 55E.

Figure 56D:
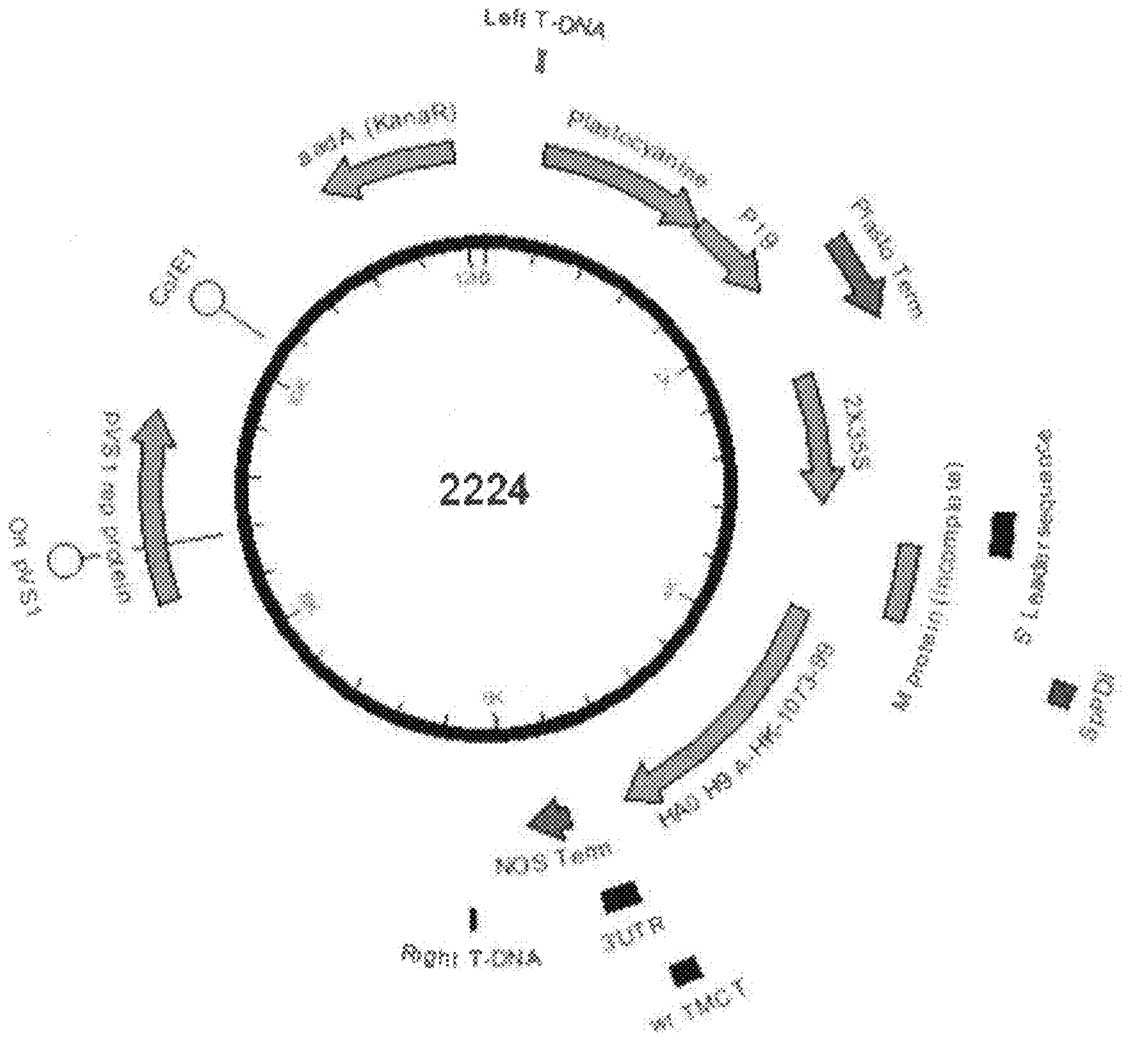
FIG. 56D shows a schematic representation of construct number 2224.
Figure 56E:
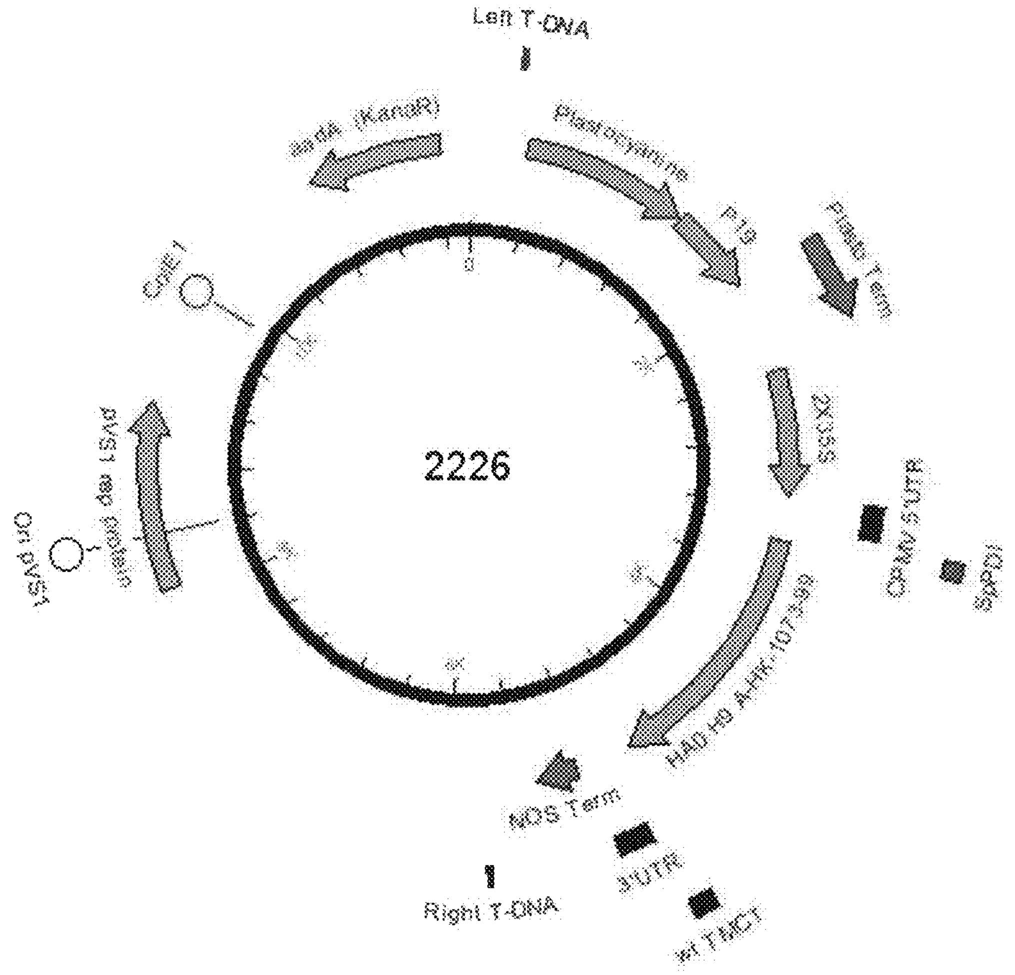
FIG. 56 shows sequence components used to prepare construct numbers 2224 (2X35S/CPMV HT+ PDISP/H9 Hong Kong) and 2226 (2X35S/CPMV 160+ PDISP/H9 Hong Kong) see Example 5.35).
FIG. 56A shows the nucleotide sequence of PDISP/H9 Hong Kong (SEQ ID NO: 155).
FIG. 56B shows the nucleotide sequence of primer IF-H9HK107399.S1-6r (SEQ ID NO: 156).
FIG. 56C shows the amino acid sequence of PDISP/H9 Hong Kong (SEQ ID NO: 157).

Example 5.35 2X35S/CPMV HT+ (Construct No 2224) and 160+ (Construct No 2226) for PDISP/H9 Hong Kong A coding sequence corresponding to H9 from Influenza A/Hong Kong/1073/1999 in which the native signal peptide has been replaced by that of alfalfa protein disulfide isomerase (PDISP/H9 Hong Kong) (FIG. 56A, SEQ ID NO: 155) was cloned into modified CPMV HT+ and 160+ using the same In Fusion-based approach as construct 2220 and 2222, respectively, but with modified PCR primer specifically designed for PDISP/H9 Hong Kong (FIG. 56B, SEQ ID NO: 156). The amino acid sequence of mature H9 from Influenza A/Hong Kong/1073/1999 fused with PDISP is presented in FIG. 56C (SEQ ID NO: 157). Representations of plasmid 2224 and 2226 are presented in FIG. 56D and FIG. 56E.

Figure 57E:
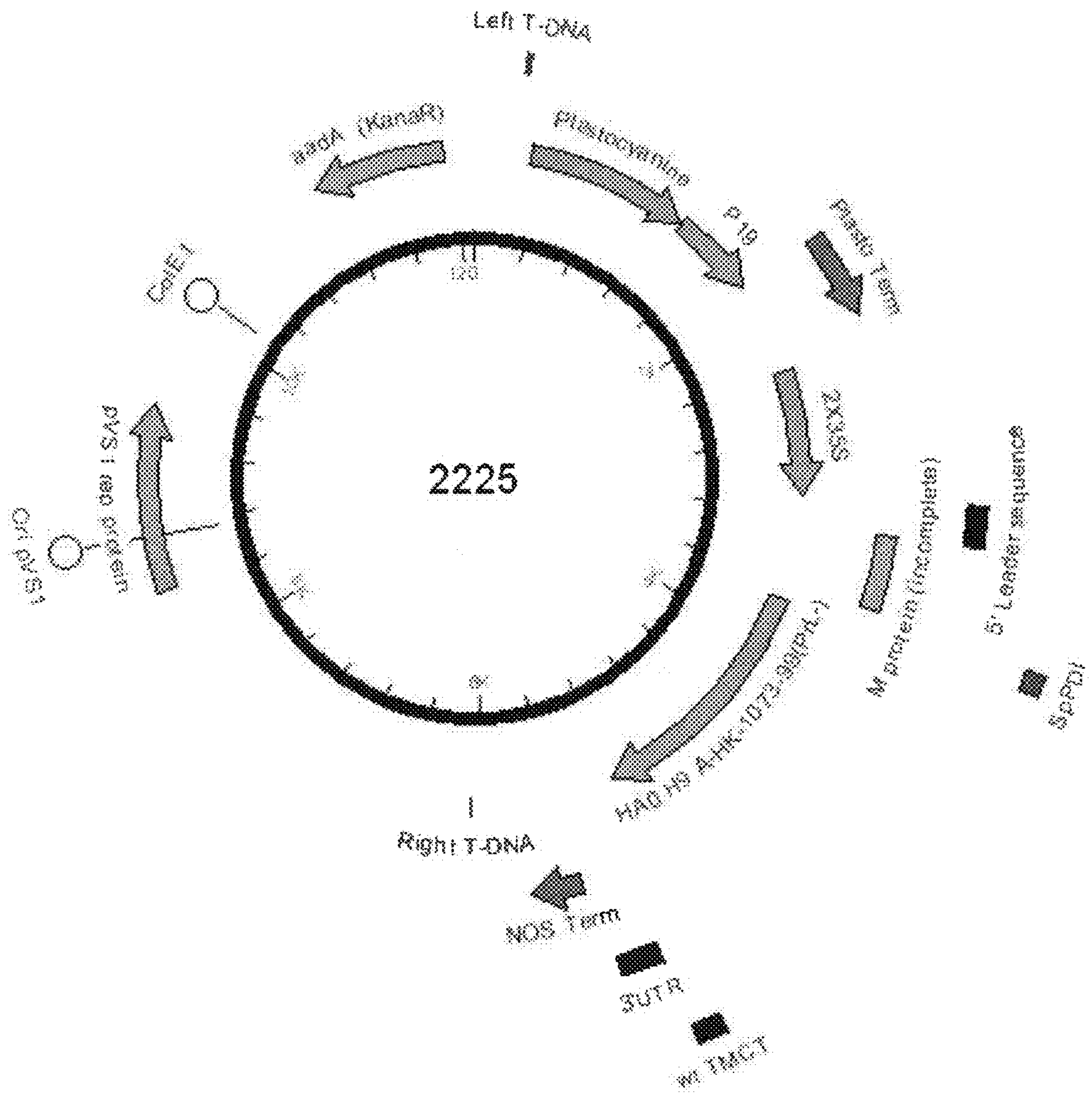
FIG. 57E shows a schematic representation of construct number 2225.
Figure 57F:
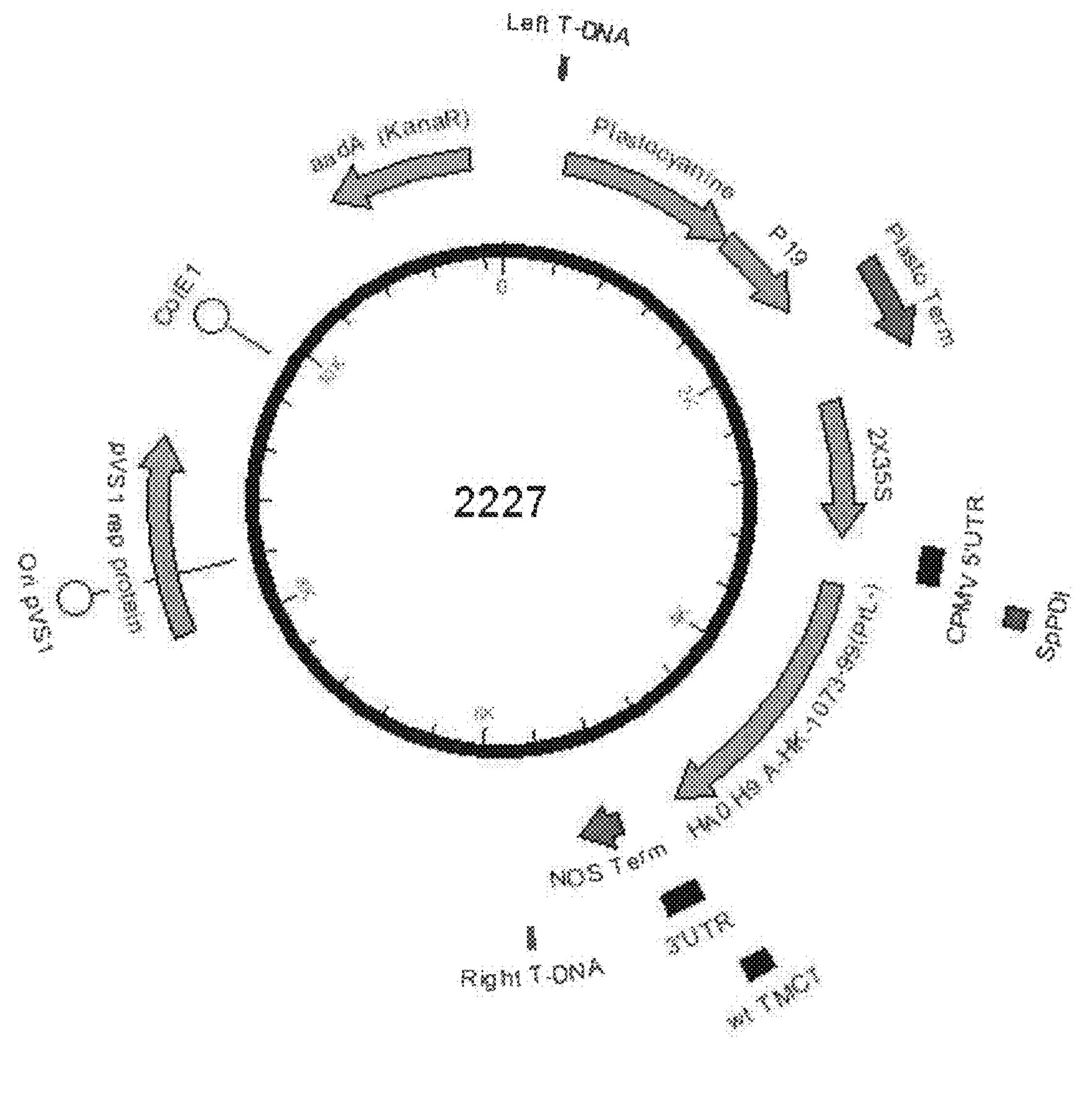
FIG. 57F shows a schematic representation of construct number 2227.

Example 5.36 2X35S/CPMV HT+ (Construct No 2225) and 160+ (Construct No 2227) for PDISP/H9 Hong Kong with Deleted Proteolytic Loop A coding sequence corresponding to H9 from Influenza A/Hong Kong/1073/1999 with deleted proteolytic loop in which the native signal peptide has been replaced by that of alfalfa protein disulfide isomerase (PDISP/H9 Hong Kong with deleted proteolytic loop) (FIG. 57A, SEQ ID NO: 158) was cloned into modified CPMV HT+ and 160+ using the same In Fusion-based approach as construct 2221 and 2223, respectively, but with modified PCR primers specifically designed for PDISP/H9 Hong Kong with deleted proteolytic loop (FIG. 56B (SEQ ID NO: 156), FIG. 57B (SEQ ID NO: 159) and FIG. 57C (SEQ ID NO: 160)). The amino acid sequence of mature H9 from Influenza A/Hong Kong/1073/1999 with deleted proteolytic loop fused with PDISP is presented in FIG. 57D (SEQ ID NO: 161). Representations of plasmid 2225 and 2227 are presented in FIG. 57E and FIG. 57F.

Example 5.37 2X35S/CPMV 160+/PDISP/HA B Malaysia/NOS (Construct No 2013)

A coding sequence corresponding to HA from Influenza B/Malaysia/2506/2004 in which the native signal peptide has been replaced by that of alfalfa protein disulfide isomerase (PDISP/HA B Malaysia) (FIG. 58A, SEQ ID NO: 162) was cloned into modified CPMV 160+ using the same In Fusion-based approach as construct 2222 but with modified PCR primer specifically designed for PDISP/HA B Malaysia (FIG. 58B, SEQ ID NO: 163). The amino acid sequence of mature HA from Influenza B/Malaysia/2506/2004 fused with PDISP is presented in FIG. 58C (SEQ ID NO: 164). Representation of plasmid 2013 is presented in FIG. 58D.

Example 5.38 2X35S/CPMV 160+/PDISP/HA B Malaysia with Deleted Proteolytic Loop/NOS (Construct No 2014)

A coding sequence corresponding to HA from Influenza B/Malaysia/2506/2004 with deleted proteolytic loop in which the native signal peptide has been replaced by that of alfalfa protein disulfide isomerase (PDISP/HA B Malaysia with deleted proteolytic loop) (FIG. 59A, SEQ ID NO: 165) was cloned into modified CPMV 160+ using the same In Fusion-based approach as construct 2223 but with modified PCR primers specifically designed for PDISP/HA B Malaysia with deleted proteolytic loop (FIG. 58B (SEQ ID NO: 163), FIG. 59B (SEQ ID NO: 166), FIG. 59C (SEQ ID NO: 167). The amino acid sequence of mature HA from Influenza B/Malaysia/2506/2004 with deleted proteolytic loop fused with PDISP is presented in FIG. 59D (SEQ ID NO: 168). Representation of plasmid 2014 is presented in FIG. 59E.

Figure 60C:
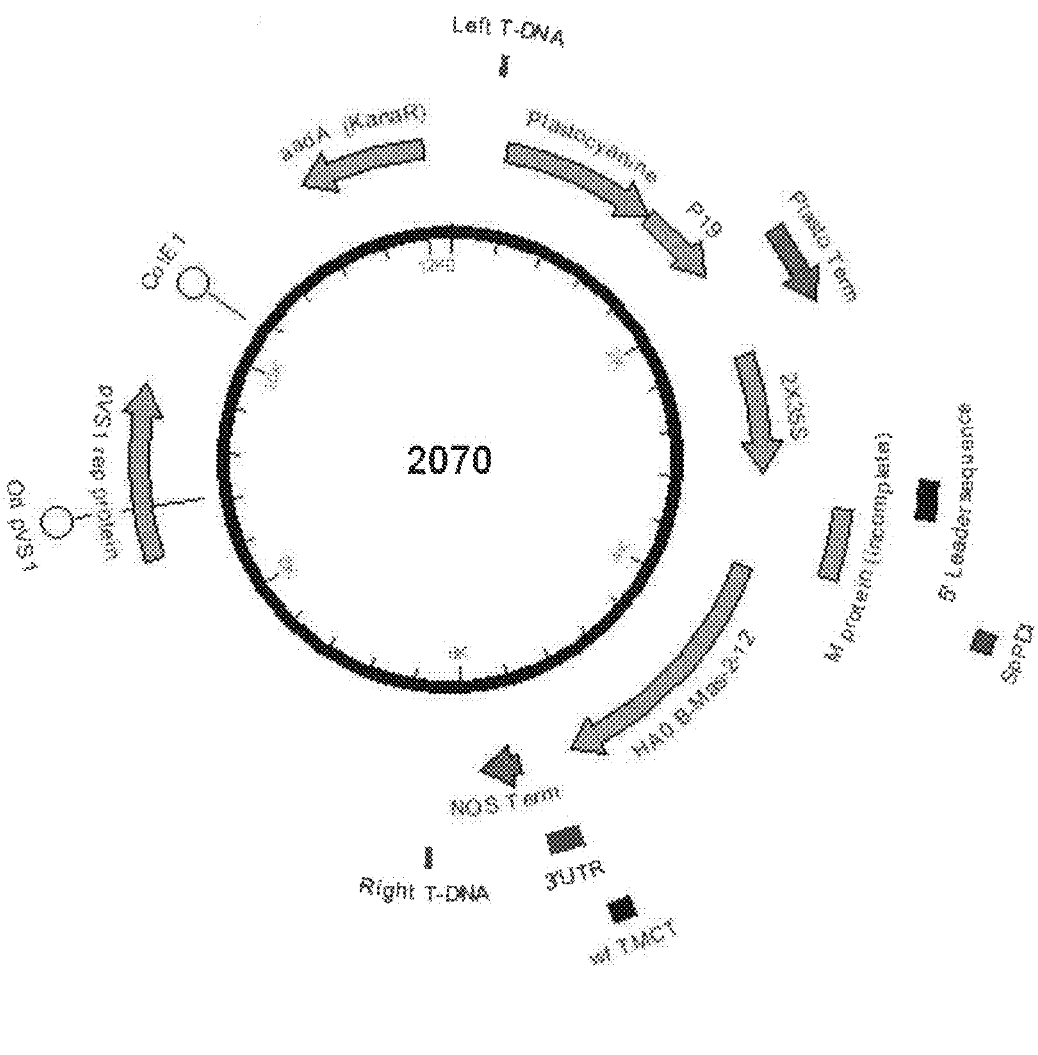
FIG. 60C shows a schematic representation of construct number 2070.
Figure 60D:
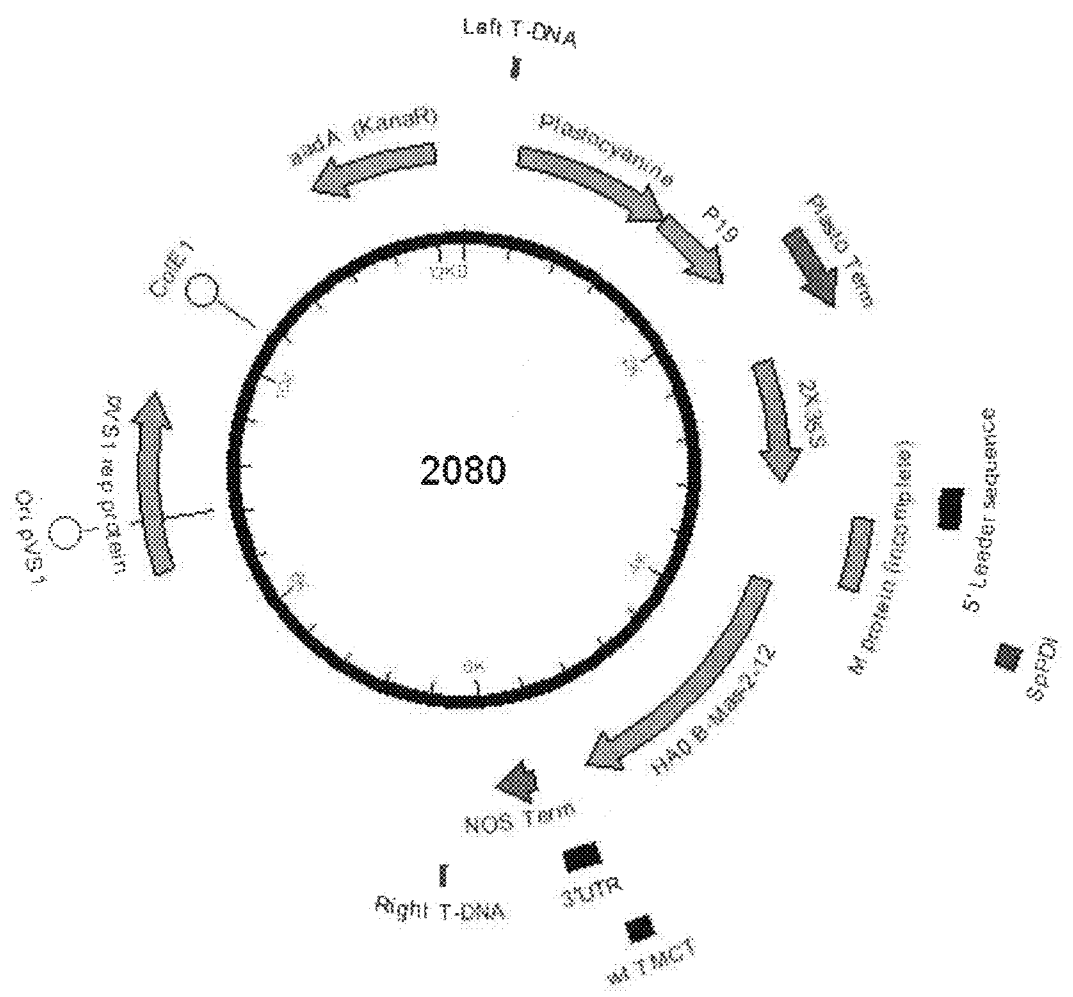
FIG. 60D shows a schematic representation of construct number 2080.
Figure 60E:
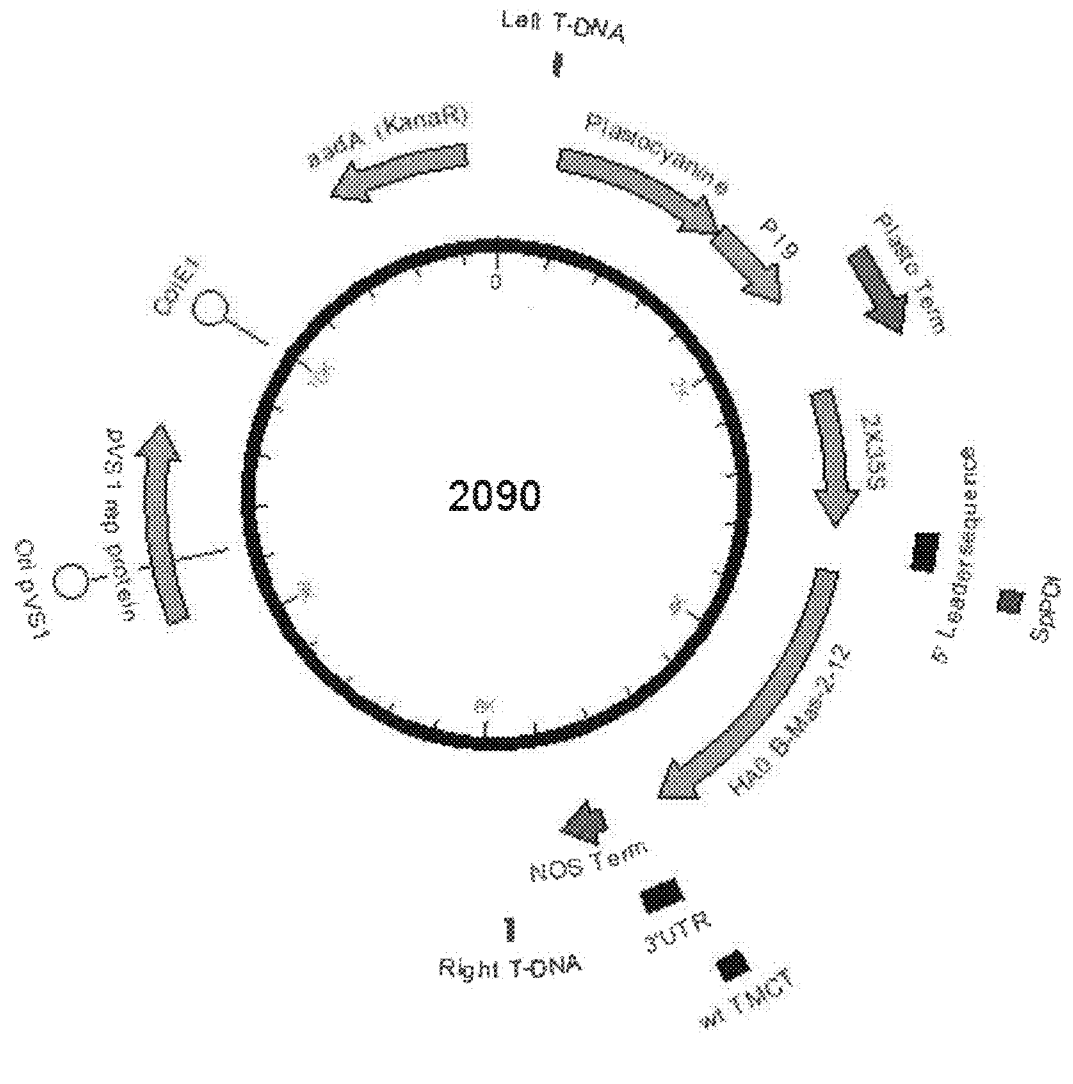
FIG. 60E shows a schematic representation of construct number 2090.

Example 5.39 2X35S/CPMV HT (Construct No 2070), HT+ (Construct No 2080) and 160+ (-Mprot) (Construct No 2090) for PDISP/HA B Massachusetts A coding sequence corresponding to HA from Influenza B/Massachusetts/2/2012 in which the native signal peptide has been replaced by that of alfalfa protein disulfide isomerase (PDISP/HA B Massachusetts) (FIG. 60A, SEQ ID NO: 169) was cloned into original HT, modified HT+ and 160+ using the same In Fusion-based approach as construct 2072, 2220 and 2222, respectively, but with modified PCR primers specifically designed for PDISP/HA B Massachusetts. The amino acid sequence of mature HA from Influenza B/Massachusetts/2/2012 fused with PDISP is presented in FIG. 60B (SEQ ID NO: 170). Representations of plasmid 2070, 2080 and 2090 are presented in FIG. 60C, FIG. 60D and FIG. 60E.

Figure 61G:
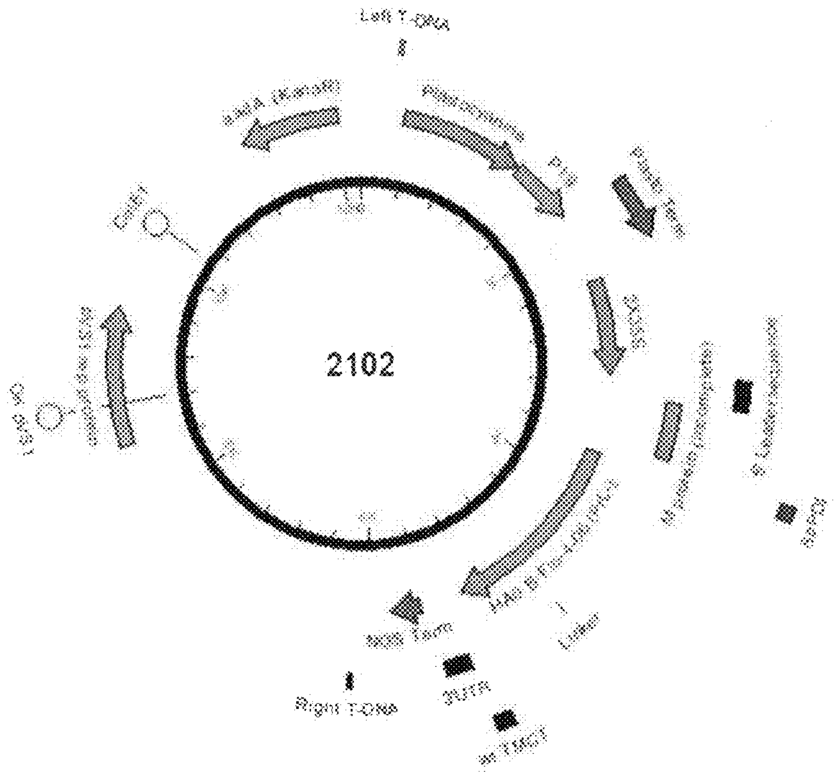
FIG. 61G shows the schematic representation of construct number 2102.

Example 5.40 2X35S/CPMV HT+ (Construct No 2102), HT+ with BeYDV (Construct No 2104) for PDISP/HA B Florida with Deleted Proteolytic Loop A coding sequence corresponding to HA from Influenza B/Florida with the proteolytic loop deleted and in which the native signal peptide has been replaced by that of alfalfa protein disulfide isomerase (PDISP/HA B Florida) (FIG. 61D, SEQ ID NO: 193) was cloned into modified HT+ the same In Fusion-based approach as described above, but with modified PCR primers specifically designed for PDISP/HA B/Florida (see Figures FIG. 61A (SEQ ID No: 190), FIG. 61B (SEQ ID NO: 191) and FIG. 61C (SEQ ID NO: 192). The nucleotide sequence of the resulting expression cassette 2102 is given in FIG. 61F (SEQ ID NO: 195). Similarly, a coding sequence corresponding to HA from Influenza B/Florida with the proteolytic loop deleted and in which the native signal peptide has been replaced by that of alfalfa protein disulfide isomerase was cloned into modified HT+ together with amplification element BeYDV. The nucleotide sequence of the resulting expression cassette 2104 is given in FIG. 61F (SEQ ID NO: 196). The amino acid sequence of mature HA from Influenza B/Florida with deleted proteolytic loop fused with PDISP is presented in FIG. 61E (SEQ ID NO: 194). Representations of plasmid 2102 and 2104 are presented in FIGS. 61G and 61I.

Figure 62E:
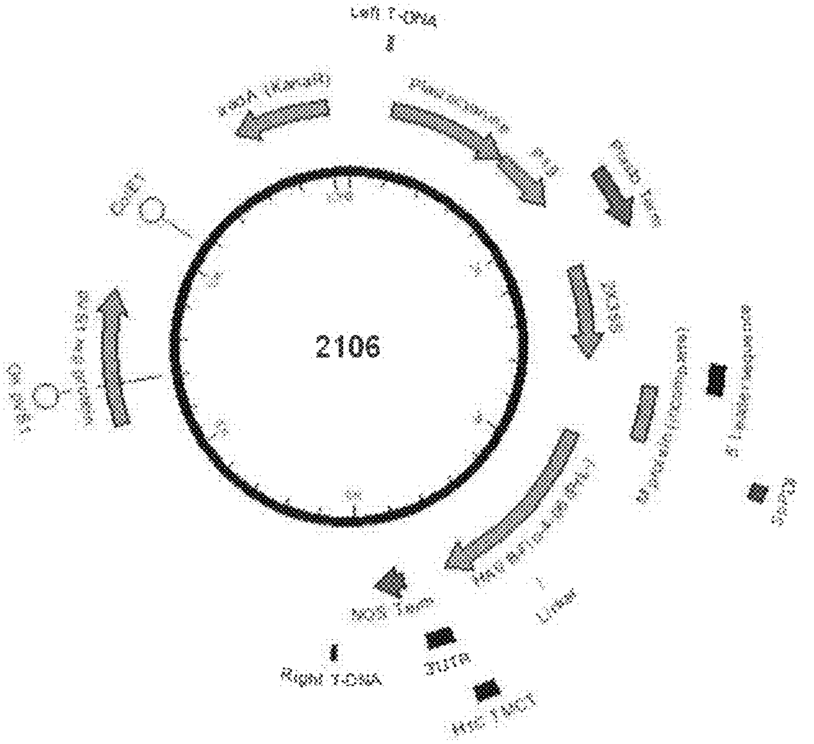
FIG. 62E shows the schematic representation of construct number 2106.
Figure 62G:
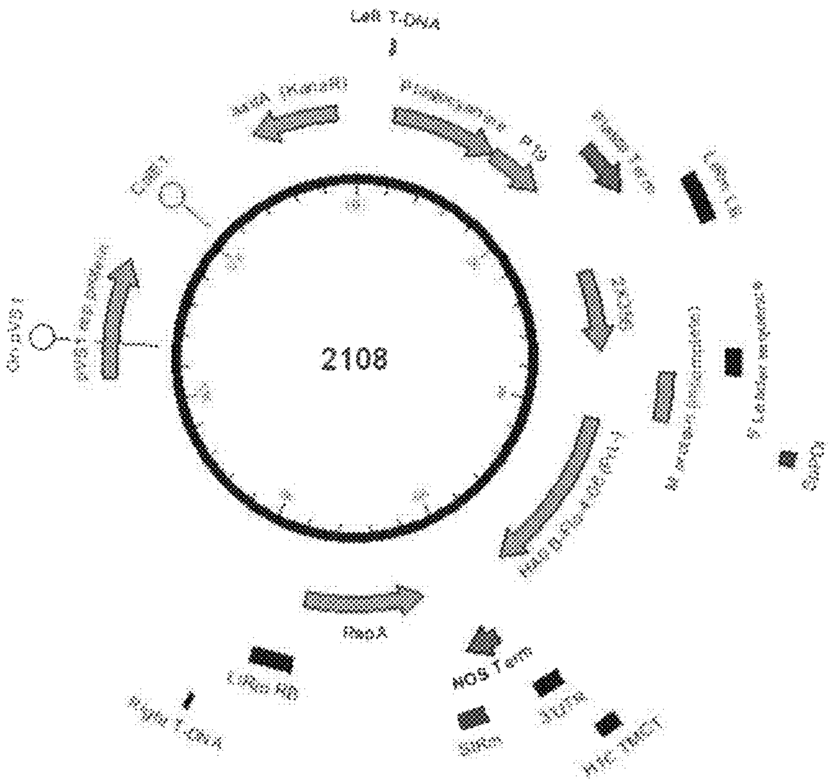
FIG. 62G shows the schematic representation of construct number 2108.

Example 5.41 2X35S/CPMV HT+ (Construct No 2106), HT+ with BeYDV (Construct No 2108) for PDISP/HA B Florida +H1 California TMCT with Deleted Proteolytic Loop A coding sequence corresponding to HA from Influenza B/Florida +H1 California TMCT with the proteolytic loop deleted and in which the native signal peptide has been replaced by that of alfalfa protein disulfide isomerase (PDISP/HA B Florida +H1 California TMCT) (FIG. 62B, SEQ ID NO: 198) was cloned into modified HT+ the same In Fusion-based approach as described above, but with modified PCR primers specifically designed for PDISP/HA B/Florida+H1 California TMCT (see Figures FIG. 61A (SEQ ID No: 197). The nucleotide sequence of the resulting expression cassette 2106 is given in FIG. 62D (SEQ ID NO: 200). Similarly, a coding sequence corresponding to HA from Influenza B/Florida +H1 California TMCT with the proteolytic loop deleted and in which the native signal peptide has been replaced by that of alfalfa protein disulfide isomerase was cloned into modified HT+ together with amplification element BeYDV. The nucleotide sequence of the resulting expression cassette 2108 is given in FIG. 62F (SEQ ID NO: 201). The amino acid sequence of mature HA from Influenza B/Florida+H1 California TMCT with deleted proteolytic loop fused with PDISP is presented in FIG. 62C (SEQ ID NO: 199). Representations of plasmid 2106 and 2108 are presented in FIGS. 62E and 62G.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A modified influenza type B hemagglutinin (HA) comprising a fully deleted proteolytic loop between subunits HA1 and HA2, the fully deleted proteolytic loop characterized as comprising a monobasic cleavage site, wherein the modified influenza type B HA does not comprise the B/Brisbane/60/2008 strain.

2. The modified influenza HA of claim 1, wherein the modified influenza HA is derived from an unmodified B HA comprising 90-100% sequence identity to a sequence defined by SEQ ID NO:54.

3. The modified influenza HA of claim 1, wherein the monobasic cleavage site is recognized by a Clara-like protease.

4. The modified influenza HA of claim 3, wherein the Clara-like protease is tryptase Clara or trypsin/chymotrypsin.

5. The modified influenza HA of claim 1, wherein the monobasic cleavage site comprises amino acid sequence KER, PAK or a combination thereof.

6. The modified influenza HA of claim 1, wherein the proteolytic loop is fully replaced by a linker sequence.

7. A virus like particle (VLP) comprising the modified influenza HA defined in claim 1.

8. A virus like particle (VLP) comprising the modified influenza HA defined in claim 2.

9. A plant comprising the modified influenza HA of claim 1.

10. A plant comprising the VLP of claim 7.

11. A plant comprising the VLP of claim 8.

12. A composition comprising an effective dose of the VLP of claim 7 for inducing an immune response, and a pharmaceutically acceptable carrier.

13. A vaccine comprising an effective dose of the composition of claim 12 for inducing an immune response.

14. A method of inducing immunity to an influenza virus infection in a subject, comprising administering the composition of claim 12.

15. The method of claim 14, wherein the composition is administered to a subject orally, intradermally, intranasally, intramuscularly, intraperitoneally, intravenously, or subcutaneously.

* * * * *